(12) United States Patent
Domenyuk et al.

(10) Patent No.: US 11,332,748 B2
(45) Date of Patent: May 17, 2022

(54) OLIGONUCLEOTIDE PROBES AND USES THEREOF

(71) Applicant: Caris Science, Inc., Irving, TX (US)

(72) Inventors: Valeriy Domenyuk, Phoenix, AZ (US); Tassilo Hornung, Phoenix, AZ (US); Heather O'Neill, Mesa, AZ (US); Mark Miglarese, Phoenix, AZ (US); David Spetzler, Paradise Valley, AZ (US)

(73) Assignee: Caris Science, Inc., Irving, TX (US)

( * ) Notice: Subject to any disclaimer, the term of this patent is extended or adjusted under 35 U.S.C. 154(b) by 0 days.

(21) Appl. No.: 16/897,976

(22) Filed: Jun. 10, 2020

(65) Prior Publication Data

US 2021/0062191 A1 Mar. 4, 2021

Related U.S. Application Data

(63) Continuation of application No. 16/084,504, filed as application No. PCT/US2017/023108 on Mar. 18, 2017, now Pat. No. 10,731,166.

(60) Provisional application No. 62/472,953, filed on Mar. 17, 2017, provisional application No. 62/457,691, filed on Feb. 10, 2017, provisional application No. 62/432,561, filed on Dec. 9, 2016, provisional application No. 62/420,497, filed on Nov. 10, 2016, provisional application No. 62/413,361, filed on Oct. 26, 2016, provisional application No. 62/310,665, filed on Mar. 18, 2016.

(51) Int. Cl.
| | |
|---|---|
| C12N 15/115 | (2010.01) |
| C12N 15/10 | (2006.01) |
| C12Q 1/6883 | (2018.01) |
| C12Q 1/6886 | (2018.01) |

(52) U.S. Cl.
CPC ............ *C12N 15/115* (2013.01); *C12N 15/10* (2013.01); *C12Q 1/6883* (2013.01); *C12Q 1/6886* (2013.01); *C12N 2310/16* (2013.01); *C12N 2330/31* (2013.01); *C12Q 2600/106* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 3,687,808 A | 8/1972 | Merigan et al. | |
| 4,016,043 A | 4/1977 | Schuurs et al. | |
| 4,018,653 A | 4/1977 | Mennen | |
| 4,275,149 A | 6/1981 | Litman et al. | |
| 4,376,110 A | 3/1983 | David et al. | |
| 4,424,279 A | 1/1984 | Bohn et al. | |
| 4,469,863 A | 9/1984 | Ts'o et al. | |
| 4,476,301 A | 10/1984 | Imbach et al. | |
| 4,486,530 A | 12/1984 | David et al. | |
| 4,551,435 A | 11/1985 | Liberti et al. | |
| 4,587,044 A | 5/1986 | Miller et al. | |
| 4,605,735 A | 8/1986 | Miyoshi et al. | |
| 4,667,025 A | 5/1987 | Miyoshi et al. | |
| 4,737,456 A | 4/1988 | Weng et al. | |
| 4,762,779 A | 8/1988 | Snitman et al. | |
| 4,789,737 A | 12/1988 | Miyoshi et al. | |
| 4,795,698 A | 1/1989 | Owen et al. | |
| 4,824,941 A | 4/1989 | Gordon et al. | |
| 4,828,979 A | 5/1989 | Klevan et al. | |
| 4,835,263 A | 5/1989 | Nguyen et al. | |
| 4,845,205 A | 7/1989 | Dinh et al. | |
| 4,876,335 A | 10/1989 | Yamane et al. | |
| 4,904,582 A | 2/1990 | Tullis | |
| 4,925,788 A | 5/1990 | Liberti | |
| 4,948,882 A | 8/1990 | Ruth | |
| 4,958,013 A | 9/1990 | Letsinger | |
| 5,013,830 A | 5/1991 | Ohtsuka et al. | |
| 5,023,243 A | 6/1991 | Tullis | |
| 5,034,506 A | 7/1991 | Summerton et al. | |
| 5,082,830 A | 1/1992 | Brakel et al. | |
| 5,108,933 A | 4/1992 | Liberti et al. | |
| 5,109,124 A | 4/1992 | Ramachandran et al. | |
| 5,112,963 A | 5/1992 | Pieles et al. | |
| 5,118,802 A | 6/1992 | Smith et al. | |
| 5,130,302 A | 7/1992 | Spielvogel et al. | |
| 5,134,066 A | 7/1992 | Rogers et al. | |
| 5,138,045 A | 8/1992 | Cook et al. | |
| 5,149,797 A | 9/1992 | Pederson et al. | |
| 5,158,871 A | 10/1992 | Rossomando et al. | |
| 5,166,315 A | 11/1992 | Summerton et al. | |
| 5,175,273 A | 12/1992 | Bischofberger et al. | |

(Continued)

FOREIGN PATENT DOCUMENTS

| | | |
|---|---|---|
| CN | 104498500 | 4/2015 |
| EP | 0527905 | 2/1993 |

(Continued)

OTHER PUBLICATIONS

US 5,756,703 A, 04/1982, Horumeru (withdrawn)
Shi et al. (he Journal of Histochemistry and Cytochemistry, vol. 39, pp. 741-748 (Year: 1991).*
Extended European Search Report in European Application No. 20213211.4, dated Apr. 19, 2021, 9 pages.
JP Office Action in Japanese Application No. 2018-568182, dated Apr. 19, 2021, 15 pages (with English translation).
EP Office Action in European Appln. No. 17803629.9, dated Jan. 12, 2021, 6 pages.

(Continued)

*Primary Examiner* — Brian Whiteman
(74) *Attorney, Agent, or Firm* — Fish & Richardson P.C.

(57) ABSTRACT

Methods and compositions are provided to identify oligonucleotides that bind targets of interest. The targets include tissues, cells, circulating biomarkers such as microvesicles, including those derived from various diseases. The oligonucleotides can be used in diagnostic and therapeutic applications.

19 Claims, 100 Drawing Sheets
Specification includes a Sequence Listing.

(56) References Cited

U.S. PATENT DOCUMENTS

| | | |
|---|---|---|
| 5,177,196 A | 1/1993 | Meyer, Jr. et al. |
| 5,185,444 A | 2/1993 | Summerton et al. |
| 5,186,827 A | 2/1993 | Liberti et al. |
| 5,188,897 A | 2/1993 | Suhadolnik et al. |
| 5,200,084 A | 4/1993 | Liberti et al. |
| 5,214,134 A | 5/1993 | Weis et al. |
| 5,214,136 A | 5/1993 | Lin et al. |
| 5,216,141 A | 6/1993 | Benner |
| 5,218,105 A | 6/1993 | Cook et al. |
| 5,220,007 A | 6/1993 | Pederson et al. |
| 5,235,033 A | 8/1993 | Summerton et al. |
| 5,245,022 A | 9/1993 | Weis et al. |
| 5,254,469 A | 10/1993 | Warren, III et al. |
| 5,256,775 A | 10/1993 | Froehler |
| 5,258,506 A | 11/1993 | Urdea et al. |
| 5,262,536 A | 11/1993 | Hobbs, Jr. |
| 5,264,423 A | 11/1993 | Cohen et al. |
| 5,264,562 A | 11/1993 | Matteucci |
| 5,264,564 A | 11/1993 | Matteucci |
| 5,270,163 A | 12/1993 | Gold et al. |
| 5,272,250 A | 12/1993 | Spielvogel et al. |
| 5,276,019 A | 1/1994 | Cohen et al. |
| 5,278,302 A | 1/1994 | Caruthers et al. |
| 5,286,717 A | 2/1994 | Cohen et al. |
| 5,292,873 A | 3/1994 | Rokita et al. |
| 5,317,098 A | 5/1994 | Shizuya et al. |
| 5,321,131 A | 6/1994 | Agrawal et al. |
| 5,366,878 A | 11/1994 | Pederson et al. |
| 5,367,066 A | 11/1994 | Urdea et al. |
| 5,371,241 A | 12/1994 | Brush |
| 5,376,252 A | 12/1994 | Eksrom et al. |
| 5,391,723 A | 2/1995 | Priest |
| 5,399,676 A | 3/1995 | Froehler |
| 5,403,711 A | 4/1995 | Walder et al. |
| 5,405,938 A | 4/1995 | Summerton et al. |
| 5,405,939 A | 4/1995 | Suhadolnik et al. |
| 5,414,077 A | 5/1995 | Lin et al. |
| 5,416,203 A | 5/1995 | Letsinger |
| 5,432,272 A | 7/1995 | Benner |
| 5,434,257 A | 7/1995 | Matteucci |
| 5,451,463 A | 9/1995 | Nelson et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,470,967 A | 11/1995 | Huie et al. |
| 5,475,096 A | 12/1995 | Gold et al. |
| 5,476,925 A | 12/1995 | Letsinger et al. |
| 5,484,908 A | 1/1996 | Froehler et al. |
| 5,486,603 A | 1/1996 | Buhr |
| 5,489,677 A | 2/1996 | Sanghvi et al. |
| 5,491,133 A | 2/1996 | Walder et al. |
| 5,496,938 A | 3/1996 | Gold et al. |
| 5,502,177 A | 3/1996 | Matteucci et al. |
| 5,510,475 A | 4/1996 | Agrawal et al. |
| 5,512,439 A | 4/1996 | Hornes et al. |
| 5,512,667 A | 4/1996 | Reed et al. |
| 5,514,785 A | 5/1996 | Van Ness et al. |
| 5,519,126 A | 5/1996 | Hecht |
| 5,525,465 A | 6/1996 | Haralambidis et al. |
| 5,525,711 A | 6/1996 | Hawkins et al. |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,541,313 A | 7/1996 | Ruth |
| 5,545,730 A | 8/1996 | Urdea et al. |
| 5,550,111 A | 8/1996 | Suhadolnik et al. |
| 5,552,538 A | 9/1996 | Urdea et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,552 A | 10/1996 | Magda et al. |
| 5,567,588 A | 10/1996 | Gold et al. |
| 5,567,810 A | 10/1996 | Weis et al. |
| 5,571,799 A | 11/1996 | Tkachuk et al. |
| 5,574,142 A | 11/1996 | Meyer, Jr. et al. |
| 5,578,717 A | 11/1996 | Urdea et al. |
| 5,578,718 A | 11/1996 | Cook et al. |
| 5,580,731 A | 12/1996 | Chang et al. |
| 5,580,737 A | 12/1996 | Polinsky et al. |
| 5,585,481 A | 12/1996 | Arnold, Jr. et al. |
| 5,587,361 A | 12/1996 | Cook et al. |
| 5,587,371 A | 12/1996 | Sessler et al. |
| 5,587,469 A | 12/1996 | Cook et al. |
| 5,591,584 A | 1/1997 | Chang et al. |
| 5,595,726 A | 1/1997 | Magda et al. |
| 5,596,086 A | 1/1997 | Matteucci et al. |
| 5,596,091 A | 1/1997 | Switzer |
| 5,597,696 A | 1/1997 | Linn et al. |
| 5,599,923 A | 2/1997 | Sessler et al. |
| 5,599,928 A | 2/1997 | Hemmi et al. |
| 5,602,240 A | 2/1997 | Mesmaeker et al. |
| 5,608,046 A | 3/1997 | Cook et al. |
| 5,610,289 A | 3/1997 | Cook et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,633,360 A | 5/1997 | Bischofberger et al. |
| 5,637,459 A | 6/1997 | Burke et al. |
| 5,648,214 A | 7/1997 | Nieuwlandt et al. |
| 5,652,355 A | 7/1997 | Metelev et al. |
| 5,652,356 A | 7/1997 | Agrawal et al. |
| 5,660,985 A | 8/1997 | Pieken et al. |
| 5,663,312 A | 9/1997 | Chaturvedula et al. |
| 5,672,695 A | 9/1997 | Eckstein et al. |
| 5,677,437 A | 10/1997 | Teng et al. |
| 5,677,439 A | 10/1997 | Weis et al. |
| 5,681,941 A | 10/1997 | Cook et al. |
| 5,683,867 A | 11/1997 | Biesecker et al. |
| 5,688,941 A | 11/1997 | Cook et al. |
| 5,698,687 A | 12/1997 | Eckstein et al. |
| 5,700,922 A | 12/1997 | Cook |
| 5,705,337 A | 1/1998 | Gold et al. |
| 5,707,796 A | 1/1998 | Gold et al. |
| 5,714,331 A | 2/1998 | Buchardt et al. |
| 5,719,262 A | 2/1998 | Buchardt et al. |
| 5,736,330 A | 4/1998 | Fulton |
| 5,750,692 A | 5/1998 | Cook et al. |
| 5,763,177 A | 6/1998 | Gold et al. |
| 5,817,635 A | 10/1998 | Eckstein et al. |
| 5,858,731 A | 1/1999 | Sorge et al. |
| 5,861,254 A | 1/1999 | Schneider et al. |
| 5,958,691 A | 9/1999 | Pieken et al. |
| 6,011,020 A | 1/2000 | Gold et al. |
| 6,051,698 A | 4/2000 | Janjic et al. |
| 6,057,107 A | 5/2000 | Fulton |
| 6,329,209 B1 | 12/2001 | Wagner et al. |
| 6,365,418 B1 | 4/2002 | Wagner et al. |
| 6,406,921 B1 | 6/2002 | Wagner et al. |
| 6,408,878 B2 | 6/2002 | Unger et al. |
| 6,475,808 B1 | 11/2002 | Wagner et al. |
| 6,475,809 B1 | 11/2002 | Wagner et al. |
| 6,599,331 B2 | 7/2003 | Chandler et al. |
| 6,623,526 B1 | 9/2003 | Lloyd |
| 6,645,432 B1 | 11/2003 | Anderson et al. |
| 6,719,868 B1 | 4/2004 | Schueller et al. |
| 6,773,812 B2 | 8/2004 | Chandler et al. |
| 6,793,753 B2 | 9/2004 | Unger et al. |
| 6,899,137 B2 | 5/2005 | Unger et al. |
| 6,929,030 B2 | 8/2005 | Unger et al. |
| 7,040,338 B2 | 5/2006 | Unger et al. |
| 7,118,661 B2 | 10/2006 | Surh et al. |
| 7,118,910 B2 | 10/2006 | Unger et al. |
| 7,125,711 B2 | 10/2006 | Pugia et al. |
| 7,135,147 B2 | 11/2006 | Cox et al. |
| 7,138,062 B2 | 11/2006 | Yin et al. |
| 7,141,978 B2 | 11/2006 | Peck et al. |
| 7,144,616 B1 | 12/2006 | Unger et al. |
| 7,189,368 B2 | 3/2007 | Andersson et al. |

(56) References Cited

U.S. PATENT DOCUMENTS

| | | |
|---|---|---|
| 7,189,580 B2 | 3/2007 | Beebe et al. |
| 7,189,581 B2 | 3/2007 | Beebe et al. |
| 7,195,986 B1 | 3/2007 | Bousse et al. |
| 7,201,881 B2 | 4/2007 | Cox et al. |
| 7,216,671 B2 | 5/2007 | Unger et al. |
| 7,229,538 B2 | 6/2007 | Tseng et al. |
| 7,233,865 B2 | 6/2007 | Chien |
| 7,238,255 B2 | 7/2007 | Derand et al. |
| 7,238,324 B2 | 7/2007 | Ko et al. |
| 7,250,128 B2 | 7/2007 | Unger et al. |
| 7,253,003 B2 | 8/2007 | Beebe et al. |
| 7,258,837 B2 | 8/2007 | Yager et al. |
| 7,261,824 B2 | 8/2007 | Schlautmann et al. |
| 7,274,316 B2 | 9/2007 | Moore |
| 7,323,140 B2 | 1/2008 | Handique et al. |
| 7,329,391 B2 | 2/2008 | Cox |
| 7,338,637 B2 | 3/2008 | Pease et al. |
| 7,351,380 B2 | 4/2008 | Simmons et al. |
| 7,351,592 B2 | 4/2008 | Storek et al. |
| 7,357,864 B2 | 4/2008 | Takada et al. |
| 7,381,471 B2 | 6/2008 | Augustine et al. |
| 7,390,463 B2 | 6/2008 | He et al. |
| 7,399,600 B2 | 7/2008 | Carr |
| 7,399,632 B2 | 7/2008 | Simmons et al. |
| 7,402,229 B2 | 7/2008 | Sibbett et al. |
| 7,411,184 B2 | 8/2008 | Sarrut |
| 7,413,709 B2 | 8/2008 | Roitman et al. |
| 7,419,639 B2 | 9/2008 | Osterfeld et al. |
| 7,419,822 B2 | 9/2008 | Jeon et al. |
| 7,422,669 B2 | 9/2008 | Jacobson et al. |
| 7,422,725 B2 | 9/2008 | Kimizuka |
| 7,431,887 B2 | 10/2008 | Storek et al. |
| 7,445,844 B2 | 11/2008 | Chandler et al. |
| 7,449,096 B2 | 11/2008 | Berndt et al. |
| 7,452,509 B2 | 11/2008 | Cox et al. |
| 7,452,713 B2 | 11/2008 | Barlocchi et al. |
| 7,467,928 B2 | 12/2008 | Fakunle et al. |
| 7,485,214 B2 | 2/2009 | Palmieri |
| 7,488,596 B2 | 2/2009 | Palmieri |
| 7,494,555 B2 | 2/2009 | Unger et al. |
| 7,501,245 B2 | 3/2009 | Quake et al. |
| 7,518,726 B2 | 4/2009 | Rulison et al. |
| 7,541,578 B2 | 6/2009 | Weng |
| 7,544,506 B2 | 6/2009 | Breidford et al. |
| 7,552,741 B2 | 6/2009 | Yamada et al. |
| 7,568,399 B2 | 8/2009 | Sparks et al. |
| 7,575,722 B2 | 8/2009 | Arnold |
| 7,579,136 B2 | 8/2009 | Shim et al. |
| 7,581,429 B2 | 9/2009 | Sparks et al. |
| 7,591,936 B2 | 9/2009 | Sarrut |
| 7,601,270 B1 | 10/2009 | Unger et al. |
| 7,640,947 B2 | 1/2010 | Fernandes et al. |
| 7,666,361 B2 | 2/2010 | McBride et al. |
| 7,691,333 B2 | 4/2010 | McBride et al. |
| 7,704,735 B2 | 4/2010 | Facer et al. |
| 7,751,053 B2 | 7/2010 | Carr |
| 7,754,010 B2 | 7/2010 | Unger et al. |
| 7,837,946 B2 | 11/2010 | McBride et al. |
| 7,955,802 B2 | 6/2011 | Whitman et al. |
| 8,008,019 B2 | 8/2011 | Merante et al. |
| 8,124,015 B2 | 2/2012 | Diercks et al. |
| 10,731,166 B2 | 8/2020 | Domenyuk et al. |
| 2003/0061687 A1 | 4/2003 | Hansen et al. |
| 2005/0084421 A1 | 4/2005 | Unger et al. |
| 2005/0112882 A1 | 5/2005 | Unger et al. |
| 2005/0129581 A1 | 6/2005 | McBride et al. |
| 2005/0145496 A1 | 7/2005 | Goodsaid et al. |
| 2005/0201901 A1 | 9/2005 | Grossman et al. |
| 2005/0214173 A1 | 9/2005 | Facer et al. |
| 2005/0252773 A1 | 11/2005 | McBride et al. |
| 2006/0006067 A1 | 1/2006 | Unger |
| 2006/0257900 A1 | 11/2006 | Hudson et al. |
| 2009/0264508 A1 | 10/2009 | Sullenger et al. |
| 2012/0258870 A1 | 10/2012 | Schwartz et al. |
| 2012/0328607 A1 | 12/2012 | Hicks et al. |
| 2013/0017837 A1 | 1/2013 | Hakola et al. |
| 2013/0065778 A1 | 3/2013 | Weidhaas |
| 2013/0217582 A1 | 8/2013 | Borer et al. |
| 2014/0094383 A1 | 4/2014 | Lee et al. |
| 2014/0371088 A1 | 12/2014 | Webster |
| 2019/0367903 A1 | 12/2019 | Domenyuk et al. |

FOREIGN PATENT DOCUMENTS

| | | |
|---|---|---|
| EP | 1065378 | 1/2001 |
| EP | 2703488 | 3/2014 |
| JP | 2008-535482 | 9/2008 |
| WO | WO 1991/19813 | 12/1991 |
| WO | WO 1992/07065 | 4/1992 |
| WO | WO 1993/022684 | 11/1993 |
| WO | WO 1998/18480 | 5/1998 |
| WO | WO 2007/137187 | 11/2007 |
| WO | WO 2009/015357 | 1/2009 |
| WO | WO 2009/036236 | 3/2009 |
| WO | WO 2010/045318 | 4/2010 |
| WO | WO 2010/056337 | 5/2010 |
| WO | WO 2010/062706 | 6/2010 |
| WO | WO 2010/072410 | 7/2010 |
| WO | WO 2010/093465 | 8/2010 |
| WO | WO 2011/056688 | 5/2011 |
| WO | WO 2011/066589 | 6/2011 |
| WO | WO 2011/088226 | 7/2011 |
| WO | WO 2011/109440 | 9/2011 |
| WO | WO 2011/127219 | 10/2011 |
| WO | WO 2012/024543 | 2/2012 |
| WO | WO 2012/092336 | 7/2012 |
| WO | WO 2012/115885 | 8/2012 |
| WO | WO 2012/147800 | 11/2012 |
| WO | WO 2012/170711 | 12/2012 |
| WO | WO 2012/170715 | 12/2012 |
| WO | WO 2012/174282 | 12/2012 |
| WO | WO 2013/022995 | 2/2013 |
| WO | WO 2013/134786 | 9/2013 |
| WO | WO 2013/022786 | 2/2014 |
| WO | WO 2014/068408 | 5/2014 |
| WO | WO 2014/082083 | 5/2014 |
| WO | WO 2014/089241 | 6/2014 |
| WO | WO 2014/100434 | 6/2014 |
| WO | WO 2015/031694 | 3/2015 |
| WO | WO 2015/116868 | 8/2015 |
| WO | WO 2015/164238 | 10/2015 |
| WO | WO 2016/018934 | 2/2016 |
| WO | WO 2016/081941 | 5/2016 |
| WO | WO 2016/141169 | 9/2016 |
| WO | WO 2016/145128 | 9/2016 |
| WO | WO 2017/004243 | 1/2017 |
| WO | WO 2017/019918 | 2/2017 |
| WO | WO 2017/205686 | 11/2017 |

OTHER PUBLICATIONS

[No Author Listed] "Guidance for industry: clinical trial endpoints for the approval of cancer drugs and biologics," Washington, DC, US Food and Drug Administration, May 2007, 19 pages.

Altschul et al., "Basic local alignment search tool," Journal of molecular biology, Oct. 5, 1990, 215(3):403-10.

Altschul et al., "Gapped BLAST and PSI-BLAST: a new generation of protein database search programs," Nucleic Acids Research Sep. 1, 1997, 25(17):3389-402.

Avci-Adali et al., "Upgrading SELEX technology by using lambda exonuclease digestion for single-stranded DNA generation," Molecules, Jan. 2010, 15(1): 11 Pages.

Bartsch et al., "Trastuzumab in the management of early and advanced stage breast cancer," Biologics: Targets & Therapy, Mar. 2007, 1(1):19-31.

Bonotto et al., "Treatment of metastatic breast cancer in a real-world scenario: is progression-free survival with first line predictive of benefit from second and later lines?," The Oncologist, Jul. 1, 2015, 20(7):719-24.

Braasch et al., "Novel antisense and peptide nucleic acid strategies for controlling gene expression," Biochemistry, Apr. 9, 2002, 41(14):4503-10.

(56) References Cited

OTHER PUBLICATIONS

Brody et al., "Aptamers as therapeutic and diagnostic agents," Reviews in Molecular Biotechnology, Mar. 1, 2000, 74(1):5-13.
Badayeva et al., "A mass spectrometry view of stable and transient protein interactions," Advancements of Mass Spectrometry in Biomedical Research, Springer, Cham, 2014, 263-282.
Burstein, "The distinctive nature of HER2-positive breast cancers," New England Journal of Medicine, Oct. 20, 2005, 353(16):1652-4.
Chang et al., "Combination therapy targeting ectopic ATP synthase and 26S proteasome induces ER stress in breast cancer cells," Cell Death & Disease, Nov. 5, 2014, (11):e1540, 12 pages.
Charras et al., "Blebs lead the way: how to migrate without lamellipodia," Nature Reviews Molecular Cell Biology, Sep. 2008, 9(9):730-6.
Chen et al., "Aptamer microarray as a novel bioassay for protein-protein interaction discovery and analysis," Biosensors and Bioelectronics, Apr. 15, 2013, 42:248-55.
Chen et al., "Microfluidic isolation and transcriptome analysis of serum microvesicles," Lab on a Chip, 2010, 10(4):505-11.
ClinicalTrials.gov, "Chemotherapy With or Without Trastuzumab After Surgery in Treating Women With Invasive Breast Cancer," Jan. 12, 2011, retreived from URL <https://clinicaltrials.gov/ct2/show/NCT01275677?term=NSABP+B01275647&rank=01275671>, 20 pages.
Colcher et al., "Effects of genetic engineering on the pharmacokinetics of antibodies," The Quarterly Journal of Nuclear Medicine and Molecular Imaging.Jun. 1, 1999;43(2):132-9.
Cotten et al., "2'-O-methyl, 2'-O-ethyl oligoribonucleotides and phosphorothioate oligodeoxyribonucleotides as inhibitors of the in vitro U7 snRNP-dependent mRNA processing event," Nucleic Acids Research, May 25, 1991, 19(10):2629-35.
Crooke et al., "Pharmacokinetic properties of several novel oligonucleotide analogs in mice," Journal of Pharmacology and Experimental Therapeutics, May 1, 1996, 277(2):923-37.
Cutillas et al., "Proteomic analysis of plasma membrane vesicles isolated from the rat renal cortex," Proteomics, Jan. 2005, 5(1):101-12.
Cutillas et al., "Quantification of gel-separated proteins and their phosphorylation sites by LC-MS using unlabeled internal standards: analysis of phosphoprotein dynamics in a B cell lymphoma cell line," Molecular & Cellular Proteomics, Aug. 1, 2005, 4(8):1038-51.
De Mesmaeker et al., "Antisense oligonucleotides," Accounts of Chemical Research, Sep. 1, 1995, 28(9):366-74.
DNA Replication, 2nd Ed., 1980, Chapter 2, 47 pages.
Domenyuk et al., "Plasma exosome profiling of cancer patients by a next generation systems biology approach," Scientific Reports, Feb. 20, 2017, 7:42741.
Duffy et al., "Companion biomarkers: paving the pathway to personalized treatment for cancer," Clinical Chemistry, Oct. 1, 2013, 59(10):1447-56.
EP extended European Search Report in EP Appln. No. 17803629.9, dated Feb. 14, 2020, 10 Pages.
EP Search Report in International Appln. 17767690.5, dated Oct. 9, 2019, 41 Pages.
Epelbaum et al., Molecular profiling-selected therapy for treatment of advanced pancreaticobiliary cancer: a retrospective multicenter study, BioMed Research International, 2015, 2015, 9 pages.
Espelund et al., "A simple method for generating single-stranded DNA probes labeled to high activities," Nucleic Acids Research, Oct. 25, 1990, 18(20):6157-8.
Eswarakumar et al., "Cellular signaling by fibroblast growth factor receptors," Cytokine & Growth Factor Reviews, Apr. 1, 2005, 16(2):139-49.
Famulok et al., "Aptamer modules as sensors and detectors," Accounts of Chemical Research, Aug. 5, 2011, 44(12):1349-58.
Famulok et al., "Functional aptamers and aptazymes in biotechnology, diagnostics, and therapy," Chemical Reviews, Sep. 12, 2007, 107(9):3715-43.

Faoro et al., "Ribonomic approaches to study the RNA-binding proteome," FEBS Letters, Oct. 16, 2014, 588(20):3649-64.
Fouz et al., "Gene expression analysis in MCF-7 breast cancer cells treated with recombinant bromelain," Applied Biochemistry and Biotechnology, Aug. 1, 2014, 173(7):1618-39.
Froehler et al., "Synthesis of DNA via deoxynudeoside H-phosphonate intermediates," Nucleic Acids Research, Jul. 11, 1986, 5399-407.
Froehler, "Deoxynucleoside H-phosphonate diester intermediates in the synthesis of internucleotide phosphate analogues," Tetrahedron Letters, Jan. 1, 1986, 27(46):5575-8.
Garraway et al., "Lessons from the cancer genome," Cell, Mar. 28, 2013, 153(1):17-37.
Gatalica et al., "The expression of Fhit protein is related inversely to disease progression in patients with breast carcinoma," Cancer, Mar. 15, 2000, 88(6):1378-83.
Gerlinger et al., "Intratumor heterogeneity and branched evolution revealed by multiregion sequencing," New England Journal of Medicine, Mar. 8, 2012, 366(10):883-92.
Gyllenstenet al., "Generation of single-stranded DNA by the polymerase chain reaction and its application to direct sequencing of the HLA-DQA locus," Proceedings of the National Academy of Sciences, Oct. 1, 1988,85(20):76520-6.
Hanahan et al., "Hallmarks of cancer: the next generation," Cell, Mar. 4, 2011, 144(5):646-74.
Heasman, "Morpholino oligos: making sense of antisense?," Developmental Biology, Mar. 15, 2002, 243(2):209-14.
Herzog et al., "Impact of molecular profiling on overall survival of patients with advanced ovarian cancer," Oncotarget, Apr. 12, 2016, 7(15):19840-9.
Hicke et al., "Escort aptamers: a delivery service for diagnosis and therapy," The Journal of Clinical Investigation, Oct. 15, 2000, 106(8):923-8.
Higuchi et al., "Production of single-stranded DNA templates by exonuclease digestion following the polymerase chain reaction," Nucleic Acids Research, Jul. 25, 1989, 17(14):5865, 1 Page.
Hirose et al. "Rapid synthesis of trideoxyribonucleotide blocks," Tetrahedron Letters, Jan. 1, 1978, 19(28):2449-52.
Hobbs et al., "Polynucleotides containing 2'-amino-2'-deoxyribose and 2'-azido-2'-deoxyribose," Biochemistry, Dec. 1, 1973, 12(25):5138-45.
Hofacker et al., "Fast folding and comparison of RNA secondary structures," Monatshefte für Chemie/Chemical Monthly, Feb. 1, 1994, 125(2):167-88.
Hofacker, "Vienna RNA secondary structure server," Nucleic Acids Research, Jul. 1, 2003,31(13):3429-31.
Hoopmann et al., "Tumor M2 pyruvate kinase-determination in breast cancer patients receiving trastuzumab therapy," Cancer Letters, Dec. 10, 2002, 187(1-2):223-8.
Horton, "Trastuzumab use in breast cancer: clinical issues," Cancer Control, Nov. 2002, 9(6):499-507.
Hurley et al., "Membrane budding and scission by the ESCRT machinery: it's all in the neck," Nature Reviews Molecular Cell Biology, Aug. 2010 Aug, 11(8):556-566.
International Preliminary Report on Patentability in International Application No. PCT/US2017/23108, dated Sep. 18, 2018, 7 pages.
International Preliminary Report on Patentability in International Application No. PCT/US2017/34567, dated Nov. 27, 2018, 7 pages.
International Search Report and Written Opinion in International Application No. PCT/US2017/23108, dated Jul. 7, 2017, 11 pages.
International Search Report and Written Opinion in International Application No. PCT/US2017/34567, dated Aug. 25, 2017, 11 pages.
Ithimakin et al., "HER2 drives luminal breast cancer stem cells in the absence of HER2 amplification: implications for efficacy of adjuvant trastuzumab," Cancer Research, Mar. 1, 2013, 73(5):1635-46.
Jain, "Integrative omics, pharmacoproteomics, and human body fluids," Proteomics of Human Body Fluids, Humana Press, 2007, 175-192.
Jameson et al., "A pilot study utilizing multi-omic molecular profiling to find potential targets and select individualized treat-

(56) References Cited

OTHER PUBLICATIONS ments for patients with previously treated metastatic breast cancer," Breast Cancer Research and Treatment, Oct. 1, 2014, 147(3):579-88.

Jeong et al., "PMCA2 regulates HER2 protein kinase localization and signaling and promotes HER2-mediated breast cancer," Proceedings of the National Academy of Sciences, Jan. 19, 2016, 113(3):E282-90.

Jones et al., "High-affinity aptamers to subtype 3a hepatitis C virus polymerase display genotypic specificity," Antimicrobial Agents and Chemotherapy, Sep. 1, 2006, 50(9):3019-27.

Jorgensen et al., "Extracellular Vesicle (EV) Array: microarray capturing of exsomes and other extracellular vesicles for multiplexed phenotyping," Journal of Extracellular Vesicles, Jun. 2013; 2(1):1-9.

Kabanov et al., "A new class of antivirals: antisense oligonucleotides combined with a hydrophobic substituent effectively inhibit influenza virus reproduction and synthesis of virus-specific proteins in MDCK cells," FEBS Letters, Jan. 1, 1990, 259(2):327-30.

Kärkkäinen et al., "POSH2 is a RING finger E3 ligase with Rac 1 binding activity through a partial CRIB domain," FEBS Letters, Sep. 24, 2010, 584(18):3867-72.

Kartalov et al., "High-throughput multi-antigen microfluidic fluorescence immunoassays," BioTechniques, Jan. 2006, 40(1):85-90.

Keller et al., "Exosomes: from biogenesis and secretion to biological function," Immunology Letters, Nov. 2006, 107(2):102-8.

Klement et al., "Future paradigms for precision oncology," Oncotarget, Jul. 19, 2016, 7(29):46813.

Kowal et al., "Biogenesis and secretion of exosomes," Current Opinion in Cell Biology, Aug. 1, 2014, 29:116-25.

Kurzrock et al., "Precision oncology for patients with advanced cancer: the challenges of malignant snowflakes," Cell Cycle, Jul. 18, 2015, 14(14):2219-21.

Kuypers et al., "On-line melting of double-stranded DNA for analysis of single-stranded DNA using capillary electrophoresis," Journal of Chromatography B: Biomedical Sciences and Applications, Jan. 26, 1996, 675(2):205-11.

Lacerra et al., "Restoration of hemoglobin A synthesis in erythroid cells from peripheral blood of thalassemic patients," Proceedings of the National Academy of Sciences, Aug. 15, 2000, 97(17):9591-6.

Letsinger et al., "Cholesteryl-conjugated oligonucleotides: synthesis, properties, and activity as inhibitors of replication of human immunodeficiency virus in cell culture," Proceedings of the National Academy of Sciences, Sep. 1, 1989, 86(17):6553-6.

Li et al., "Identification of an aptamer targeting hnRNP A1 by tissue slide-based SELEX," The Journal of Pathology: A Journal of the Pathological Society of Great Britain and Ireland, Jul. 2009, 218(3):327-36.

Li et al., "The oral fluid MEMS/NEMS chip (OFMNC): diagnostic & translational applications," Advances in Dental Research, Jun. 2005, 18(1):3-5.

Liu et al, Comprehensive Proteomics Analysis Reveals Metabolic Reprogramming of Tumor-Associated Macrophages Stimulated by the Tumor Microenvironment. J Proteome Res. Jan. 6, 2017;16(1):288-297.

Liu et al., "High plasma fibrinogen is correlated with poor response to trastuzumab treatment in HER2 positive breast cancer," Medicine, Feb. 2015, 94(5).

Liu et al., "TiGER: a database for tissue-specific gene expression and regulation," BMC Bioinformatics, Dec. 2008, 9(1):271, 7 pages.

Loi et al., "Effects of estrogen receptor and human epidermal growth factor receptor-2 levels on the efficacy of trastuzumab: a secondary analysis of the HERA trial," JAMA Oncology, Aug. 1, 2016, 2(8):1040-7.

Lousberg et al., "Resistance to therapy in estrogen receptor positive and human epidermal growth factor 2 positive breast cancers: progress with latest therapeutic strategies," Therapeutic Advances in Medical Oncology, Nov. 2016, 8(6):429-49.

Manoharan et al., "Chemical modifications to improve uptake and bioavailability of antisense oligonucleotides," Annals of the New York Academy of Sciences, Oct. 1992, 660(1):306-9.

Manoharan et al., "Cholic acid-oligonucleotide conjugates for antisense applications," Bioorganic & Medicinal Chemistry Letters, Apr. 21, 1994, 4(8):1053-60.

Manoharan et al., "Introduction of a lipophilic thioether tether in the minor groove of nucleic acids for antisense applications," Bioorganic & Medicinal Chemistry Letters, Dec. 1, 1993, 3(12):2765-70.

Manoharan et al., "Lipidic nucleic acids," Tetrahedron Letters, May 22, 1995, 36(21):3651-4.

Manoharan et al., "Oligonucleotide conjugates: alteration of the pharmacokinetic properties of antisense agents," Nucleosides, Nucleotides & Nucleic Acids, May 1, 1995, 14(3-5):969-73.

Mathews et al., "Expanded sequence dependence of thermodynamic parameters provides robust prediction of RNA secondary structure," Journal of Molecular Biology, 1999, 288, 911-940.

Mere et al., "Miniaturized FRET assays and microfluidics: key components for ultra-high-throughput screening," Drug Discovery Today, Aug. 1, 1999, 4(8):363-9.

Mishra et al., "Improved leishmanicidal effect of phosphorotioate antisense oligonucleotides by LDL-mediated delivery," Biochimica et Biophysica Acta (BBA)-Gene Structure and Expression, Nov. 7, 1995, 1264(2):229-37.

Mitri et al., "The HER2 receptor in breast cancer: pathophysiology, clinical use, and new advances in therapy," Chemotherapy Research and Practice. Dec. 20, 2012, 2012, 8 pages.

Moosavian et al., "Development of RNA aptamers as molecular probes for HER2+ breast cancer study using cell-SELEX," Iranian Journal of Basic Medical Sciences, Jun. 2015, 18(6):576-86.

Nasevicius et al., "Effective targeted gene 'knockdown' in zebrafish," Nature Genetics, Oct. 2000, 26(2):216-20.

Nida et al., "Fluorescent nanocrystals for use in early cervical cancer detection," Gynecologic Oncology, Dec. 1, 2005, 99(3):S89-94.

Nielsen et al., "Sequence-selective recognition of DNA by strand displacement with a thymine-substituted polyamide," Science, Dec. 6, 1991, 254(5037):1497-500.

Oberhauser et al., "Effective incorporation of 2'-O-methyl-oligoribonuclectides into liposomes and enhanced cell association through modification with thiocholesterol," Nucleic Acids Research, Feb. 11, 1992, 20(3):533-8.

Oh et al., "Rapid, Efficient Aptamer Generation: Kinetic-Challenge Microfluidic SELEX," 12th Annual UC Systemwide Bioengineering Symposium, Jun. 13, 2011.

Ormerod, Flow Cytometry 2nd ed., Chapter 3, Springer-Verlag, New York (1999), 7 pages.

Ormerod, Flow Cytometry 2nd ed., Chapter 4, Springer-Verlag, New York (1999), 9 pages.

Paik et al., "HER2 status and benefit from adjuvant trastuzumab in breast cancer," New England Journal of Medicine, Mar. 27, 2008, 358(13):1409-11.

Pan et al., "ATP synthase ecto-α-subunit: a novel therapeutic target for breast cancer," Journal of Translational Medicine, Dec. 2011, 9(1):211, 15 Pages.

Paul et al., "Streptavidin-coated magnetic beads for DNA strand separation implicate a multitude of problems during cell-SELEX," Oligonucleotides, Sep. 1, 2009, 19(3):243-54.

Pei et al., "Clinical applications of nucleic acid aptamers in cancer," Molecular and Clinical Oncology, May 1, 2014 May, 2(3):341-8.

Peták et al., "Integrating molecular diagnostics into anticancer drug discovery," Nature Reviews Drug Discovery, Jul. 2010, 9(7):523.

Pipper et al., "Clockwork PCR including sample preparation," Angewandte Chemie International Edition, May 13, 2008 May, 47(21):3900-4.

Prasad et al., "Precision oncology: origins, optimism, and potential," The Lancet Oncologym, Feb. 1, 2016, 17(2):e81-6.

Prasad, "Perspective: the precision-oncology illusion," Nature, Sep. 7, 2016, 537(7619):S63.

Raiborg et al., "The ESCRT machinery in endosomal sorting of ubiquitylated membrane proteins," Nature, Mar. 25, 2009, 458(7237):445-52.

(56) References Cited

OTHER PUBLICATIONS

Reff et al., "A review of modifications to recombinant antibodies: attempt to increase efficacy in oncology applications," Critical Reviews in Oncology/Hematology, Oct. 1, 2001, 40(1):25-35.

Santangelo et al., "The RNA-binding protein SYNCRIP is a component of the hepatocyte exosomal machinery controlling microRNA sorting," Cell Reports, Oct. 11, 2016, 17(3):799-808.

Sayers et al., "Vaxjo: a web-based vaccine adjuvant database and its application for analysis of vaccine adjuvants and their uses in vaccine development," BioMed Research International, Mar. 13, 2012, 2012, 13 Pages.

Shea et al., "Synthesis, hybridization properties and antiviral activity of lipid-oligodeoxynucleotide conjugates," Nucleic Acids Research, Jul. 11, 1990, 18(13):3777-83.

Shrager et al., "Rapid learning for precision oncology," Nature Reviews Clinical oncology, Feb. 2014, 11(2):109.

Slamon et al., Human breast cancer: correlation of relapse and survival with amplification of the HER-2/neu oncogene, Science, Jan. 9, 1987, 235(4785):177-82.

Sood et al., "A rapid and convenient synthesis of poly-thymidylic acid by the modified triester approach," Nucleic Acids Research, Aug. 1, 1977, 4(8):2757-65.

Sproat et al., "New synthetic routes to synthons suitable for 2'-O-allyloligoribonucleotide assembly," Nucleic Acids Research, Feb. 25, 1991, 19(4):733-8.

Srinivas et al., "Aptamer-functionalized microgel particles for protein detection," Analytical Chemistry, Nov. 7, 2011, 83(23):9138-45.

Stumpf et al., "Estimating the size of the human interactome," Proceedings of the National Academy of Sciences, May 13, 2008, 105(19):6959-64.

Suchanek et al., "Photo-leucine and photo-methionine allow identification of protein-protein interactions in living cells," Nature Methods, Apr. 2005, 2(4):261.

Svinarchuk et al., "Inhibition of HIV proliferation in MT-4 cells by antisense oligonucleotide conjugated to lipophilic groups," Biochimie, Jan. 1, 1993, 75(1-2):49-54.

Svobodová et al., "Comparison of different methods for generation of single-stranded DNA for SELEX processes," Analytical and Bioanalytical Chemistry, Aug. 1, 2012, 404(3):835-42.

Swoboda et al., "Shared MHC class II-dependent melanoma ribosomal protein 18 identified by phage display," Cancer Research, Apr. 15, 2007, 67(8):3555-9.

Tacheny et al., "Mass spectrometry-based identification of proteins interacting with nucleic acids," Journal of Proteomics, Dec. 6, 2013, 94:89-109.

Tang et al., "Chip-based genotyping by mass spectrometry," Proceedings of the National Academy of Sciences, Aug. 31, 1999, 96(18):10016-20.

Théry et al., "Membrane vesicles as conveyors of immune responses," Nature Reviews Immunology, Aug. 2009, 9(8):581-93.

Unger et al., "Single-molecule fluorescence observed with mercury lamp illumination," Biotechniques, Nov. 1999, 27(5):1008-14.

Vinkenborg et al., "Aptamer-Based Affinity Labeling of Proteins," Angewandte Chemie International Edition, Sep. 3, 2012, 51(36):9176-80.

Von Hoff et al., "Pilot study using molecular profiling of patients' tumors to find potential targets and select treatments for their refractory cancers," Journal of Clinical Oncology, Nov. 20, 2010, 28(33):4877-83.

Wang et al., "Cyclohexene nucleic acids (CeNA): serum stable oligonucleotides that activate RNase H and increase duplex stability with complementary RNA," Journal of the American Chemical Society, Sep. 13, 2000, 122(36):8595-602.

Wang et al., "Integrative exploration of genomic profiles for triple negative breast cancer identifies potential drug targets," Medicine, Jul. 2016, 95(30).

Wang et al., "Morph-X-Select: Morphology-based tissue aptamer selection for ovarian cancer biomarker discovery," Biotechniques, Nov. 2016, 61(5):249-59.

Wilbur et al., "Rapid similarity searches of nucleic acid and protein data banks," Proceedings of the National Academy of Sciences, Feb. 1, 1983, 80(3):726-30.

Wilhelm et al., "Sh3rf2/POSHER protein promotes cell survival by ring-mediated proteasomal degradation of the c-Jun N-terminal kinase scaffold POSH (Plenty of SH3s) protein," Journal of Biological Chemistry, Jan. 13, 2012, 287(3):2247-56.

Williams et al., "PCR product with strands of unequal length," Nucleic Acids Research, Oct. 25, 1995, 23(20):4220-1.

Wolff et al., "Recommendations for human epidermal growth factor receptor 2 testing in breast cancer: American Society of Clinical Oncology/College of American Pathologists clinical practice guideline update," Archives of Pathology and Laboratory Medicine, Oct. 7, 2013 ,38(2):241-56.

Wu et al., "An allosteric synthetic DNA," Nucleic Acids Research, Mar. 1, 1999, 27(6):1512-6.

Xu et al, "Direct removal in the mouse of a floxed neo gene from a three-loxp conditional knockout allele by two novel approaches," Genesis, May 2001, 30(1):1-6.

Zhang et al., "Indirect purification method provides high yield and quality ssDNA sublibrary for potential aptamer selection," Analytical Biochemistry, May 1, 2015, 476:84-90.

Zhou et al., Cell-type-specific, aptamer-functionalized agents for targeted disease therapy, Molecular Therapy-Nucleic Acids, Jan. 1, 2014, 3:e169, 17 pages.

Zong et al., "Forward-phase and reverse-phase protein microarray," Microarrays, Humana Press, 2007, 363-73.

* cited by examiner

SEQ ID NO. 2

SEQ ID NO. 1

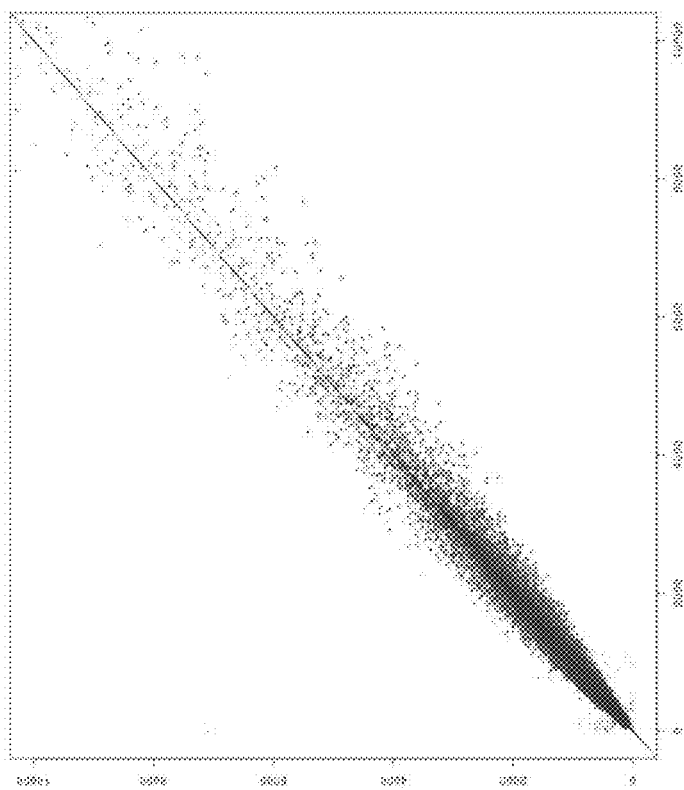
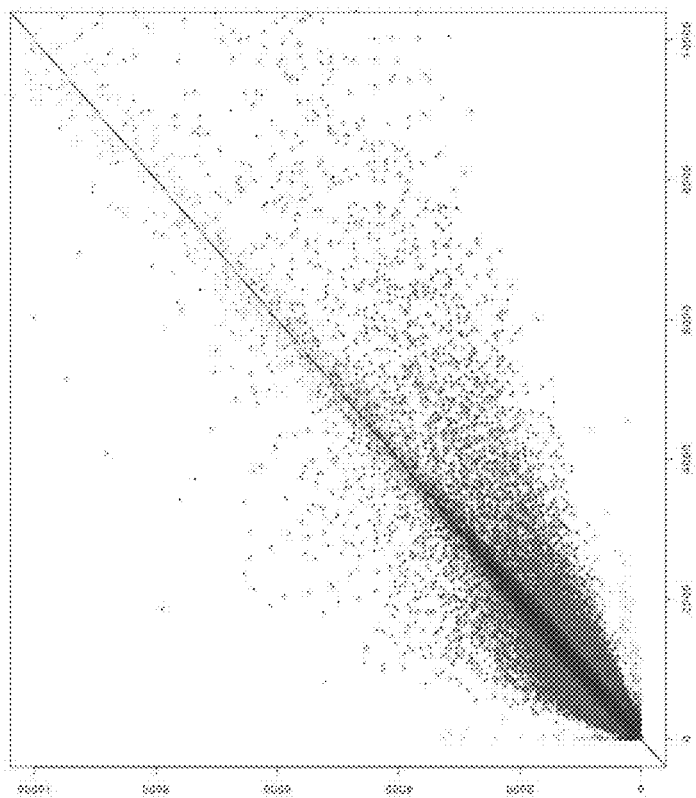
FIG. 5C

| Cancer v Non-Cancer | |
|---|---|
| P-0.005 | 2471 |
| d-50 | 1615 |
| d-100 | 914 |
| d-200 | 315 |
| d-500 | |

| | |
|---|---|
| P-0.005 | 2.95% |
| d-50 | 3.07% |
| d-100 | 3.18% |
| d-200 | 3.10% |
| d-500 | |
| Random | 0.50% |

| Random | |
|---|---|
| P-0.005 | 49 |
| d-50 | 27 |
| d-100 | 17 |
| d-200 | 5 |
| d-500 | |

| | |
|---|---|
| P-0.005 | 0.06% |
| d-50 | 0.05% |
| d-100 | 0.06% |
| d-200 | 0.05% |
| d-500 | |
| Random | 0.50% |

FIG. 5E

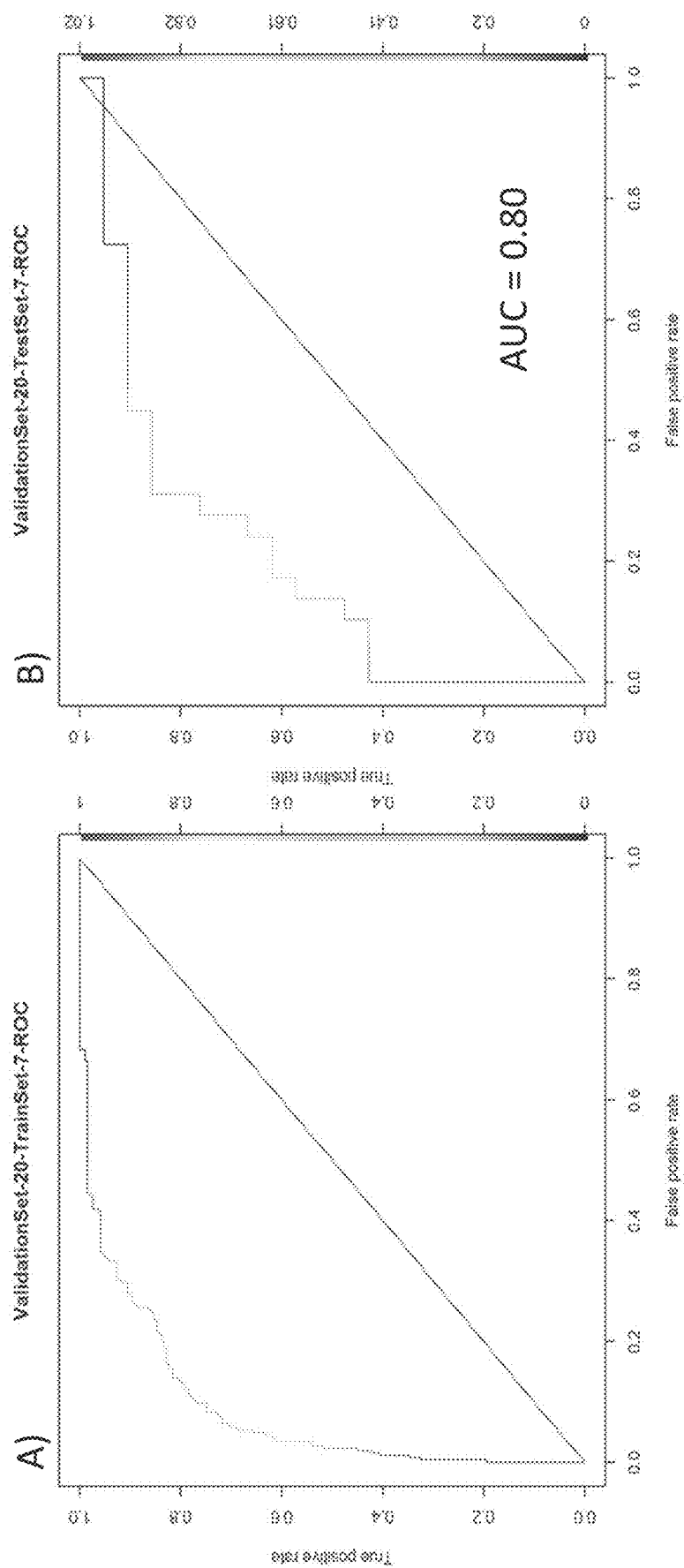
FIG. 7A-B

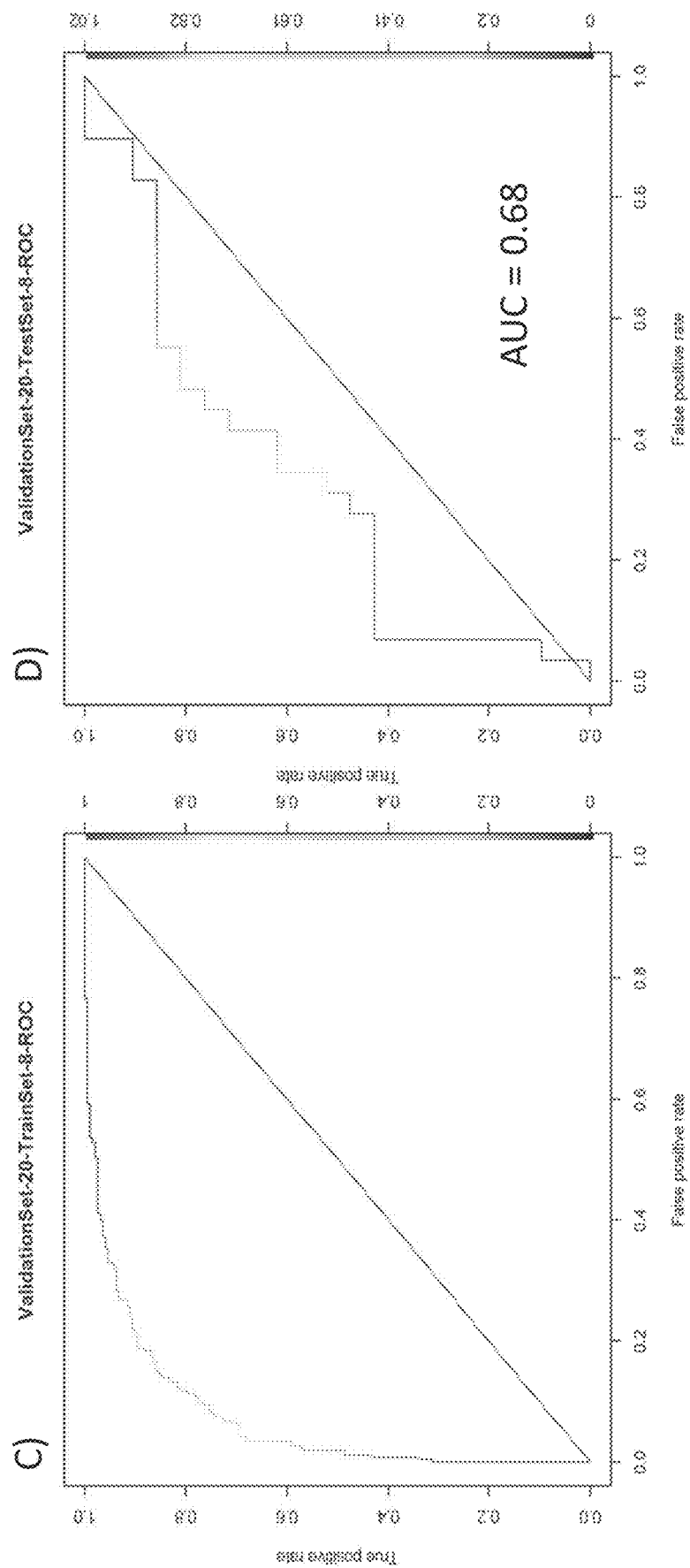
FIG. 7C-D

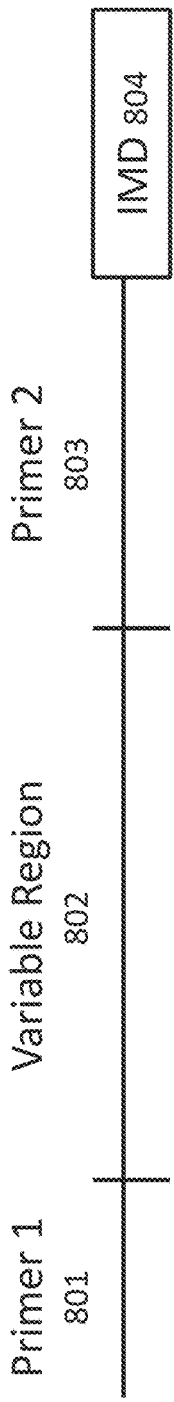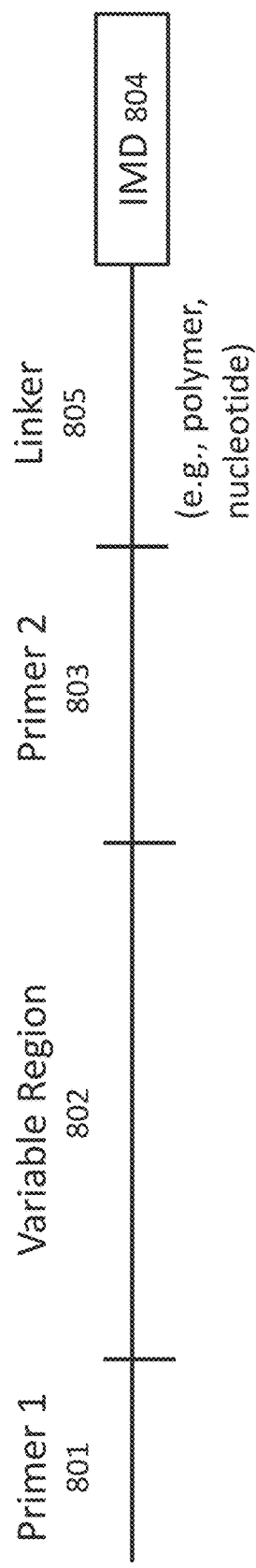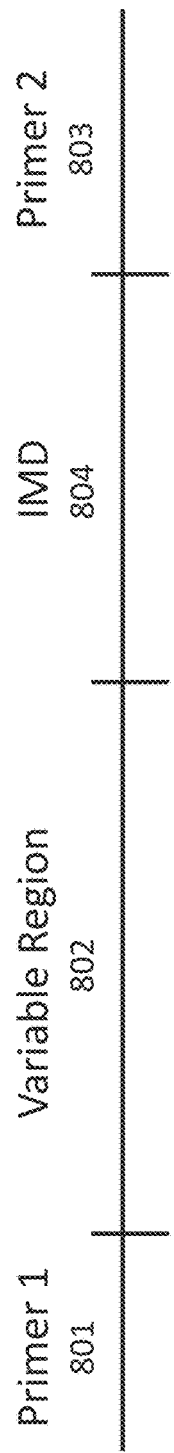
FIG. 8

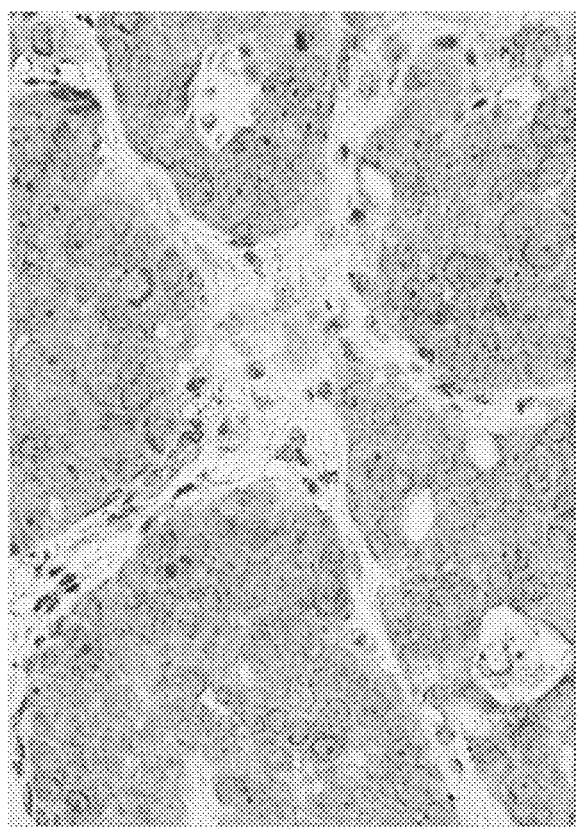
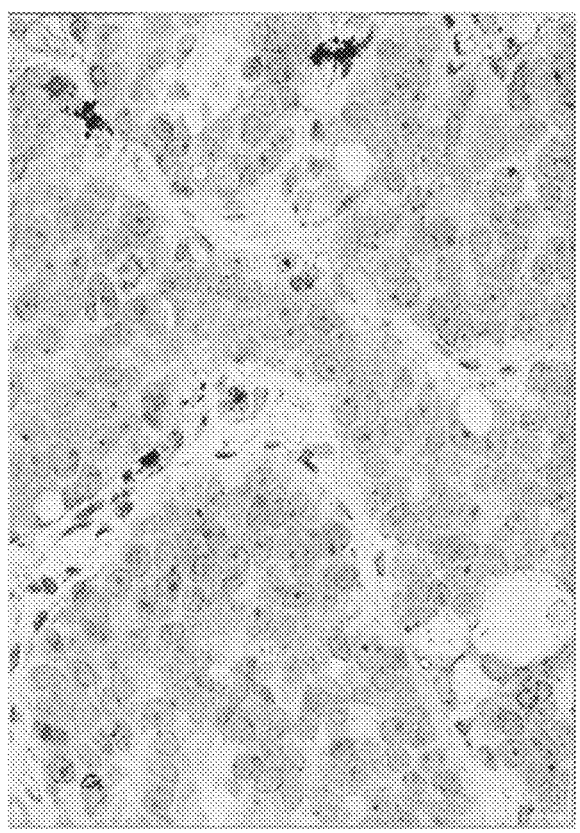
FIG. 15C

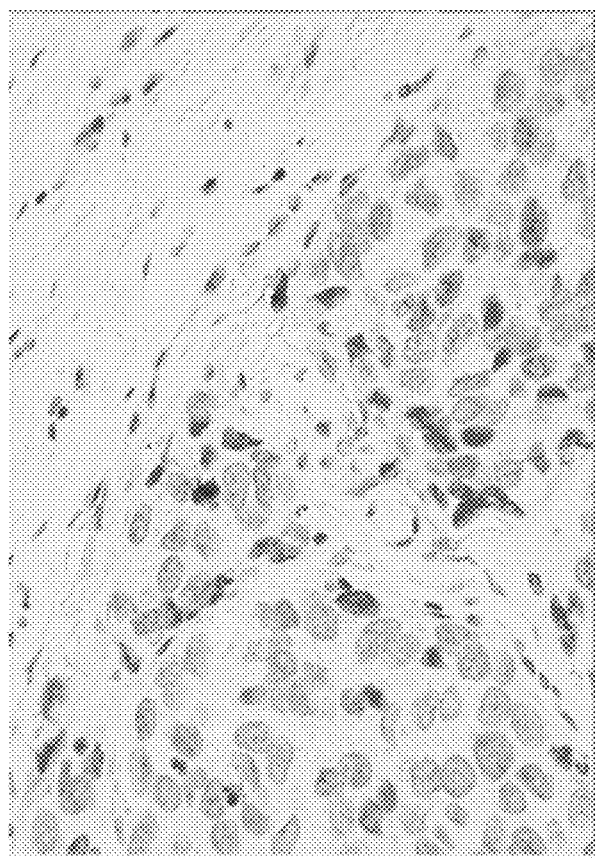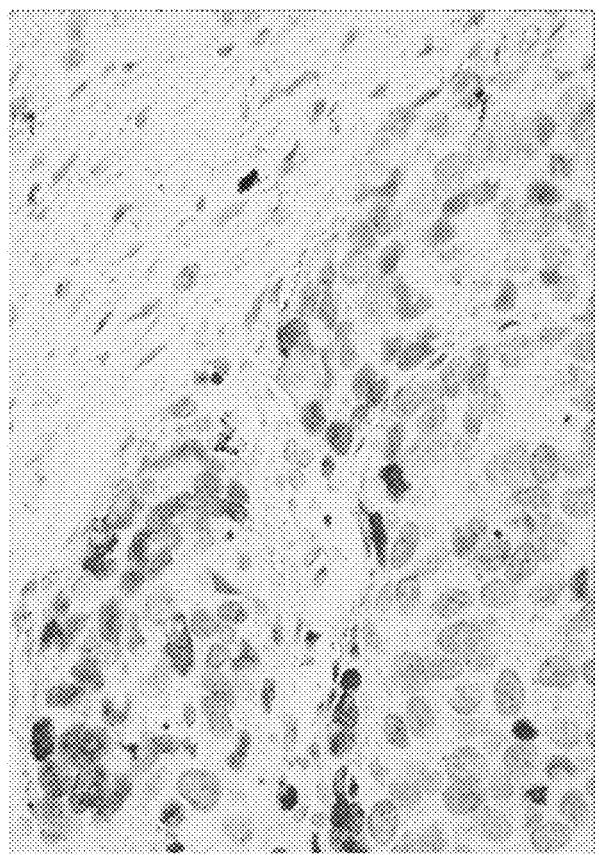
FIG. 15D

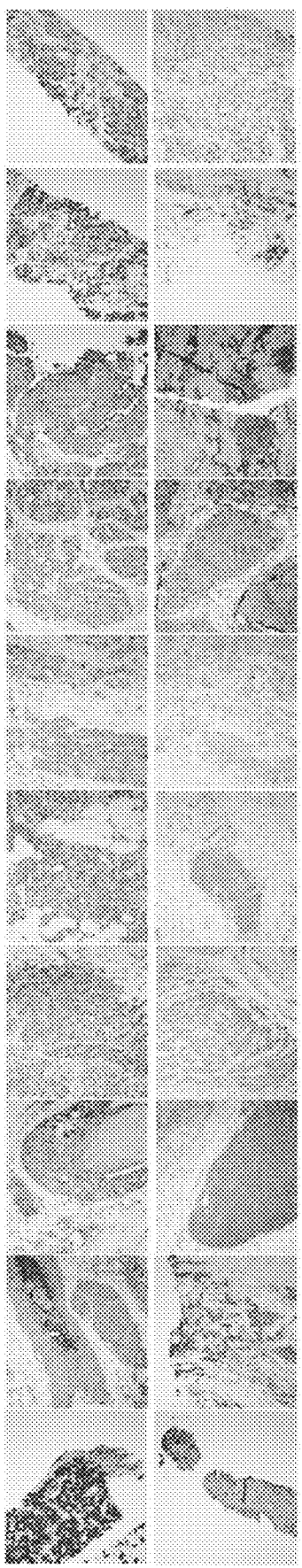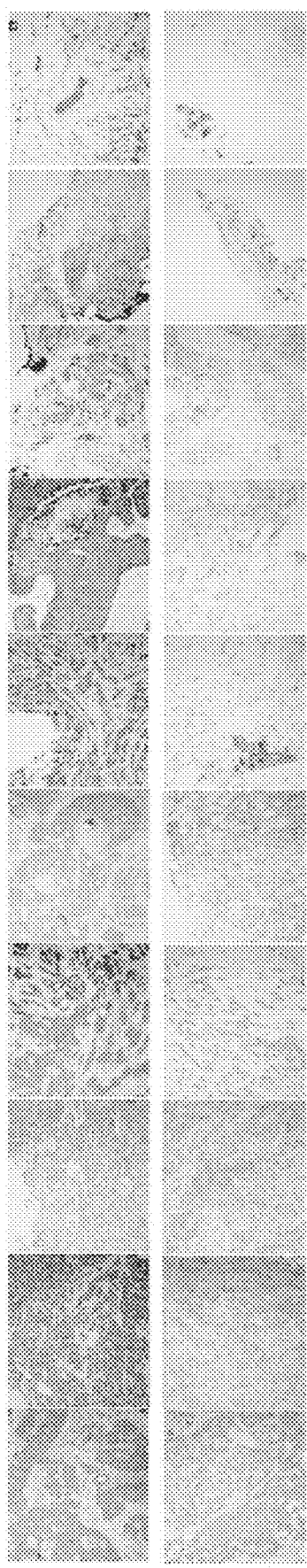
FIG. 16C

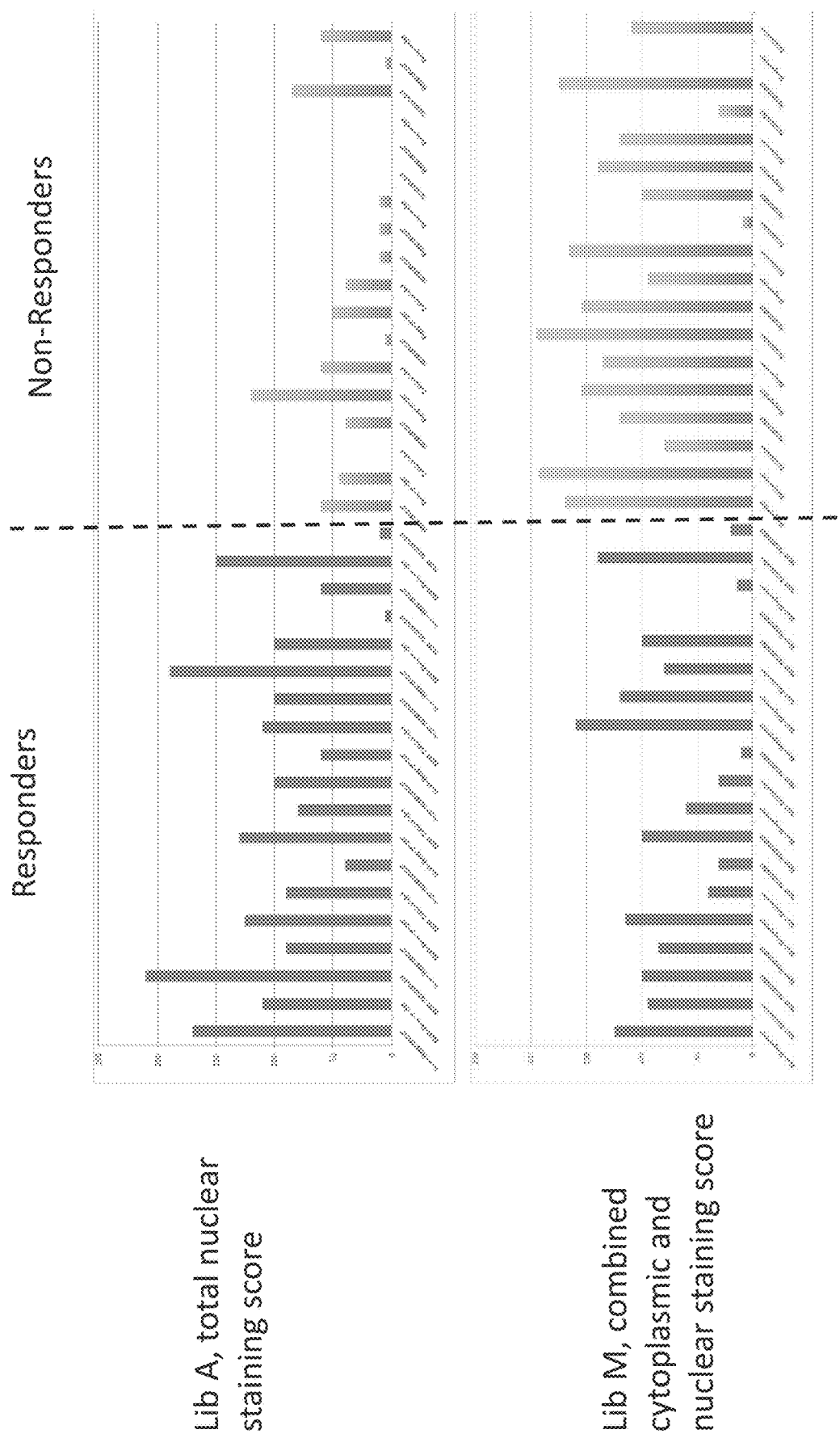

i) B case, not used for enrichment
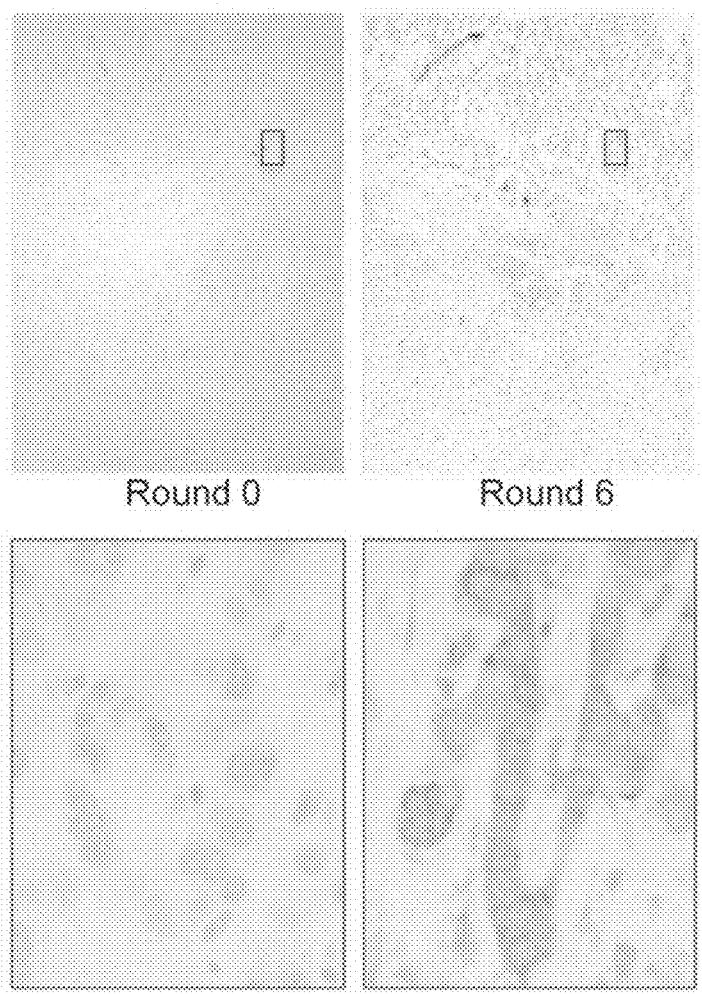
NB-case
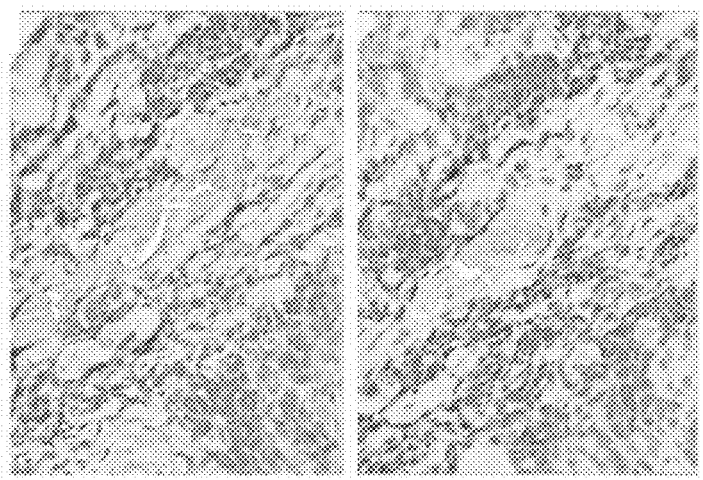
FIG. 17E

| Compartment | % stained cells at: | | | | Histological score |
|---|---|---|---|---|---|
| | 0 | 1 | 2 | 3 Total | |
| Red area Cytoplasm | 0 | 25 | 75 | 0 | |
| Nucleus | 15 | 10 | 75 | 0 | |
| Blue area Cytoplasm | 18 | 46 | 36 | 0 | |
| Nucleus | 27 | 27 | 46 | 0 | |
| Total Cytoplasm | 7 | 32 | 61 | 0 154 | 300 |
| Nucleus | 19 | 16 | 65 | 0 146 | |

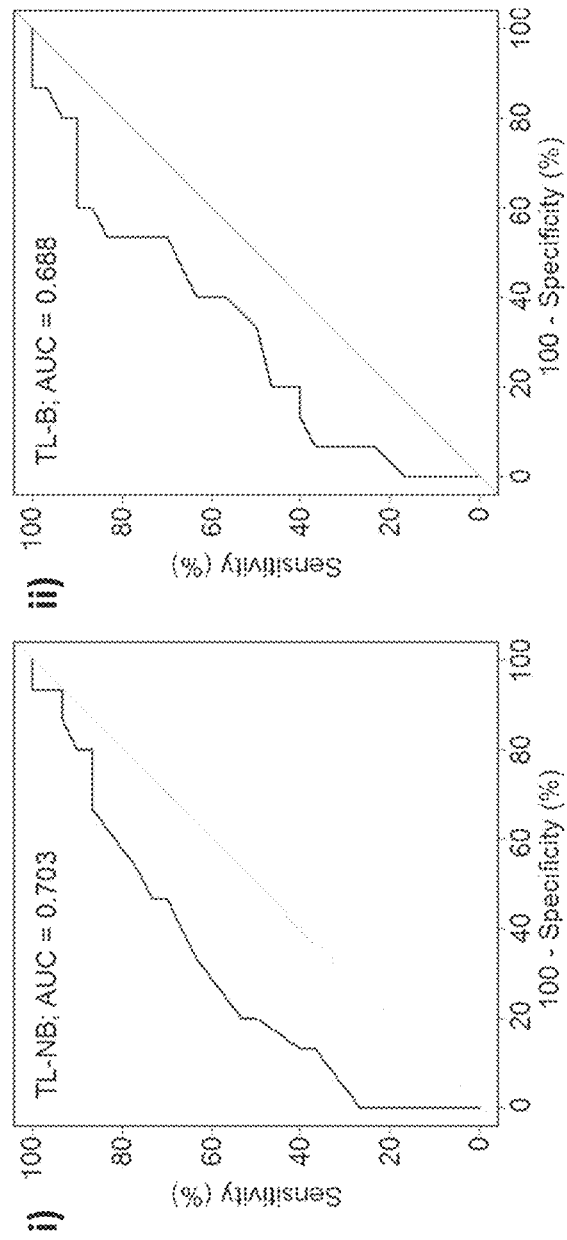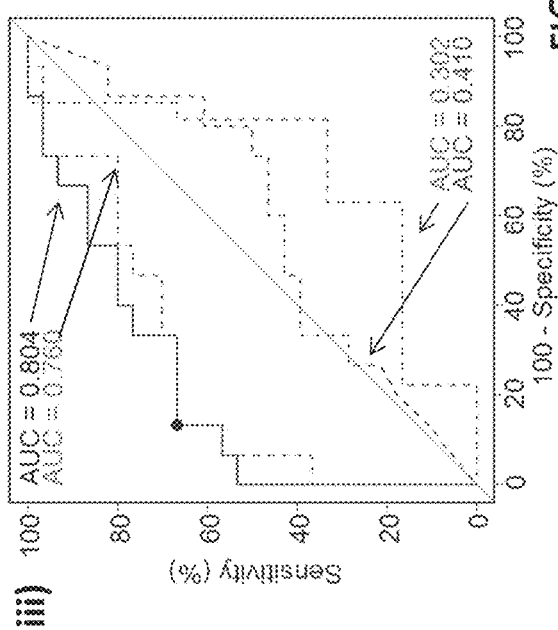
FIG. 17M

Enrichment scheme

Round 1: positive selection → PCR

Round 2: positive selection → PCR

Round 3: positive selection → PCR

Round 4: negative selection → negative selection → positive selection → PCR

Round 5: negative selection → negative selection → positive selection → PCR

Round 6: negative selection → negative selection → positive selection → PCR

FIG. 18A

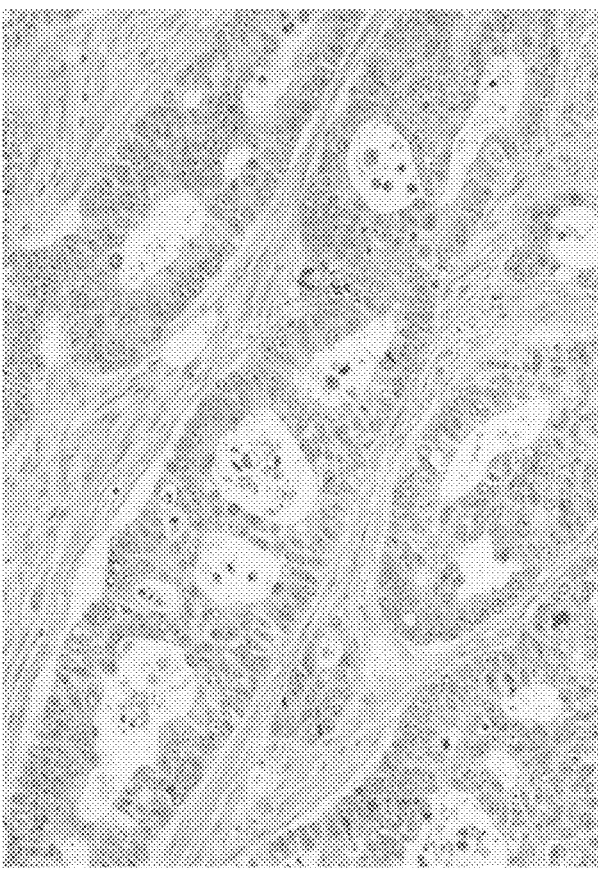
FIGs. 18D-E

| | Round 0 | Round 1-Pos | Round 2-Pos | Round 3-Pos | Round 4-N-P | Round 5-N-P | Round 6-Neg | Round 6-Pos | Round 7-Pos |
|---|---|---|---|---|---|---|---|---|---|
| Permeabilization | NA | ✓ | ✓ | ✓ | ✓ | ✓ | ✓ | ✓ | ✓ |
| Epitope retrieval | NA | ✓ | ✓ | ✓ | ✓ | ✓ | ✓ | ✓ | ✓ |
| Library input, ng | NA | 500 | 250 | 100 | 100 | 1 | 0.002 | 100 | 100 |
| Binding (-/+ reaction buffer) | NA | off line, 150ul | off line, 150ul | off line, 150ul | N/P-offline | N/P-offline | off line, 150+50ul | auto | auto |
| Binding cocktail: Triton x100 | NA | 0% | 0% | 0.005% | 0% | 0.01% | 0.005% | 0.01% | 0.01% |
| Binding cocktail: BlockAid | NA | 5% | 10% | 15% | 20% | 20% | 15% | 25% | 25% |
| Post AL Binding Rinses | NA | 1 dip | 1 dip | 1 rinse | 4 rinses | 4 rinses | NA | 4 rinses | 4 rinses |
| Enrichment staining | NA | NA | NA | ✓ | ✓ | ✓ | NA | ✓ | ✓ |
| Pre/Post-Enrichment staining | ✓ | NA | NA | | | | ✓ | | |

FIG. 20A

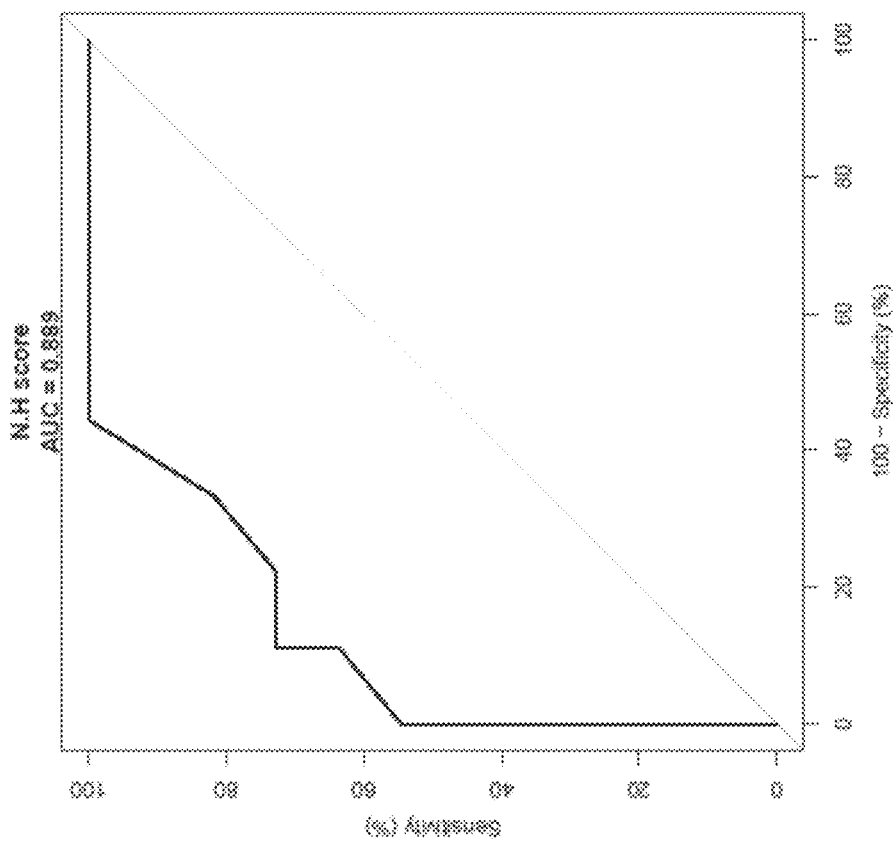
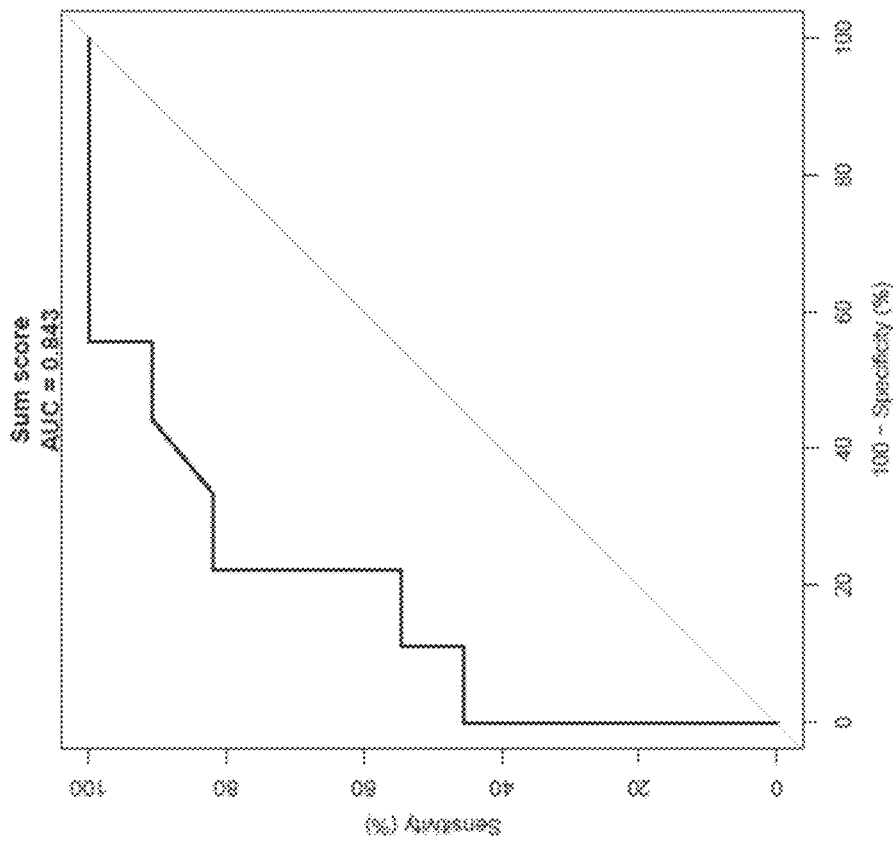
FIG. 20D

| Conditions | Round 0 | Round 1 Pos | Round 2 Pos | Round 3 Pos | Round 4 Neg | Round 4 Pos | Round 5 Neg | Round 5 Pos | Round 4 Neg->Pos | Round 5 Neg->Pos | Round 6 Neg->Pos | R6 staining |
|---|---|---|---|---|---|---|---|---|---|---|---|---|
| Permeabilization | NA | ✓ | ✓ | ✓ | ✓ | ✓ | ✓ | ✓ | ✓ | ✓ | ✓ | ✓ |
| Epitope retrieval | NA | ✓ | ✓ | ✓ | ✓ | ✓ | ✓ | ✓ | ✓ | ✓ | ✓ | ✓ |
| Library input, ng | NA | 500 | 80% of Rd 1 recovery | 200 | 0.1 | 100 | 0.075 | 100 | 100 | 100 | 100 | 100 |
| Binding (-/+ reaction buffer) | NA | auto | auto | auto | auto | auto | auto | auto | auto | auto | auto | auto |
| Binding cocktail: Triton x100 | NA | 0% | 0% | 0.005% | 0.005% | 0.01% | 0.01% | 0.01% | 0.005% | 0.01% | 0.01% | 0.01% |
| BlockAid: Binding cocktail | NA | 5% | 10% | 15% | 15% | 20% | 20% | 25% | 15% | 20% | 25% | 25% |
| BlockAid: Streptavidin | NA | 0% | 0% | 0% | NA | 0% | NA | 20% | NA | 0% | 20% | 20% |
| Post Al Binding Rinses | NA | 1 rinse | 1 rinse | 1 rinse | NA | 4 rinses | NA | 4 rinses | NA->4 rinses | NA->4 rinses | NA->4 rinses | 4 rinses |
| Enrichment staining | NA | NA | NA | | NA | ✓ | NA | ✓ | NA | ✓ | ✓ | NA |
| Post-Enrichment staining | ✓ N and P | NA | NA | ✓ | ✓ | | ✓ | | | | ✓ | ✓ |

FIG. 21A

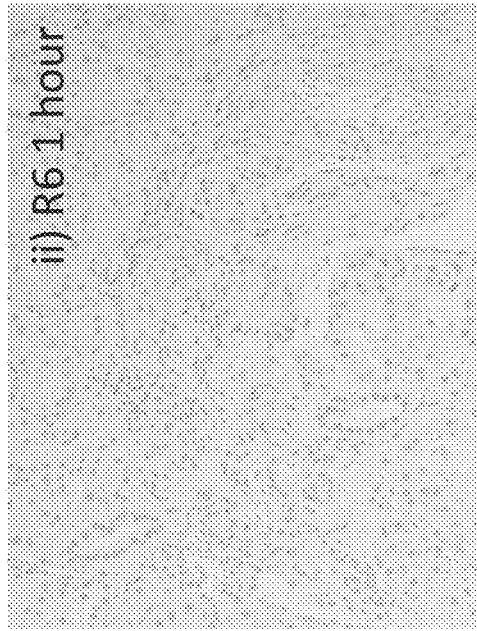
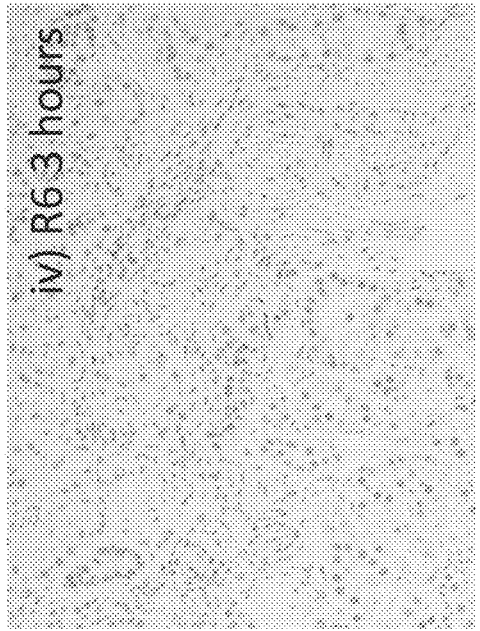
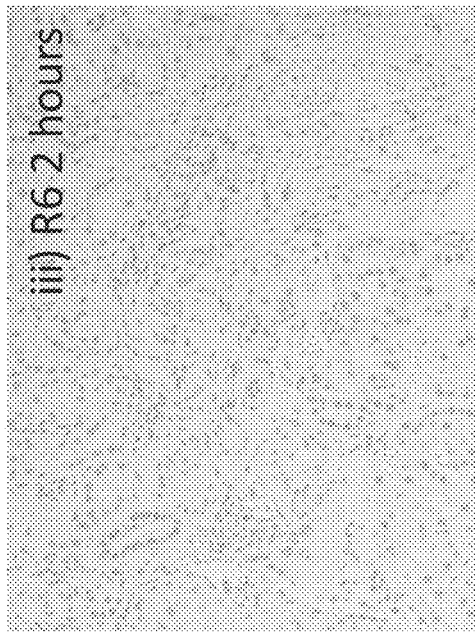
FIG. 22B

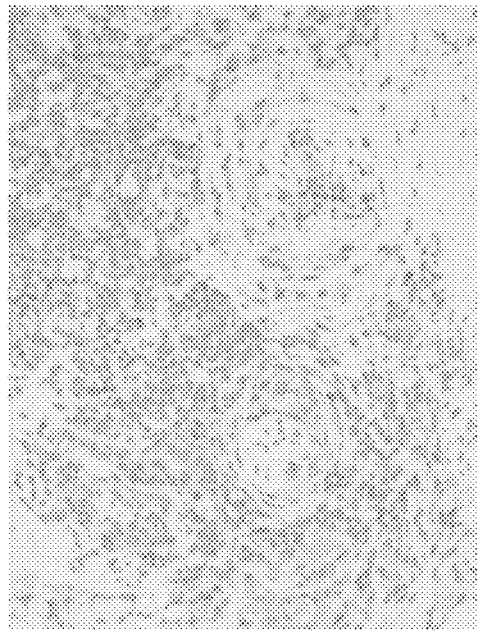
FIG. 23C

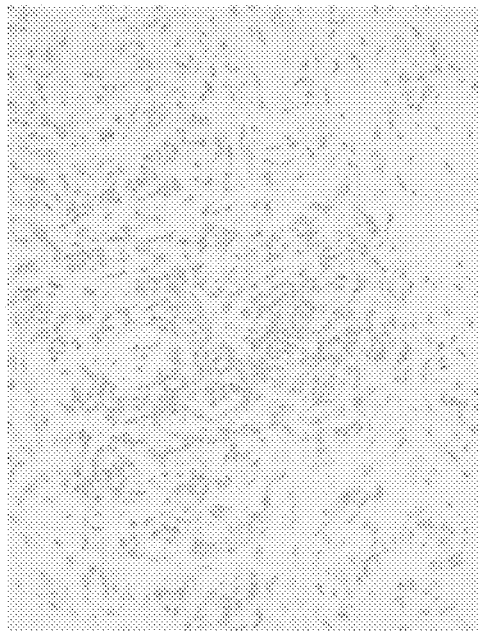
FIG. 23D

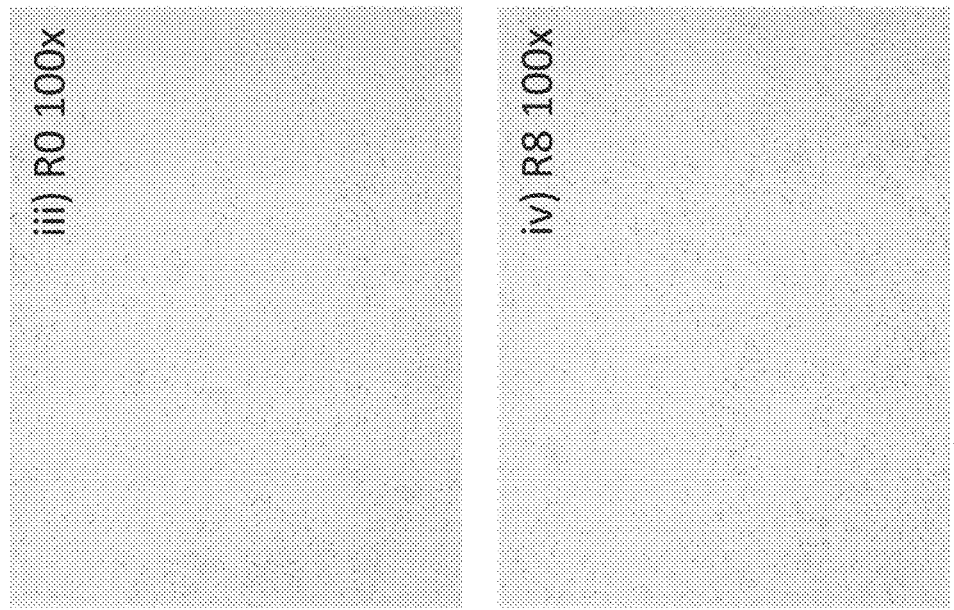
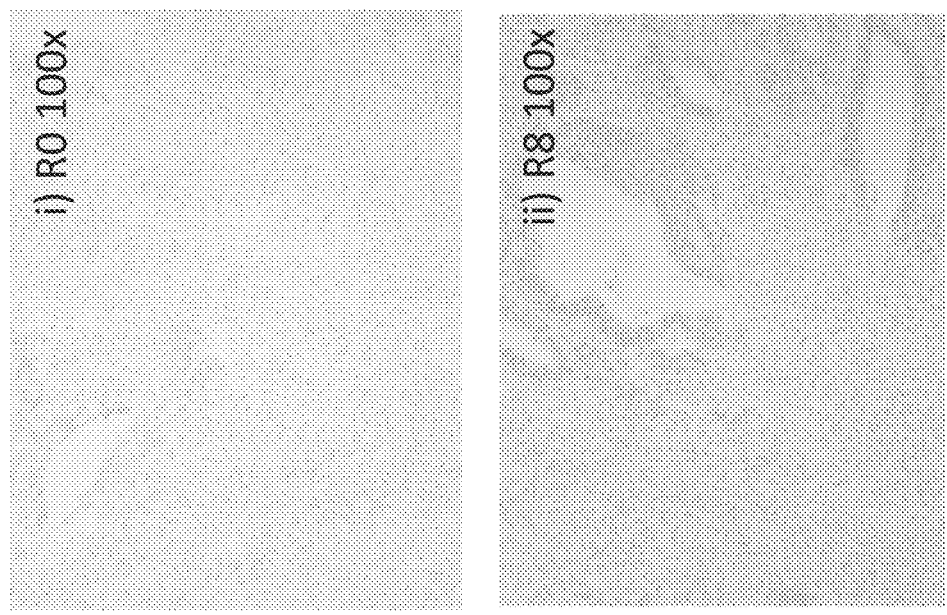
FIG. 24A

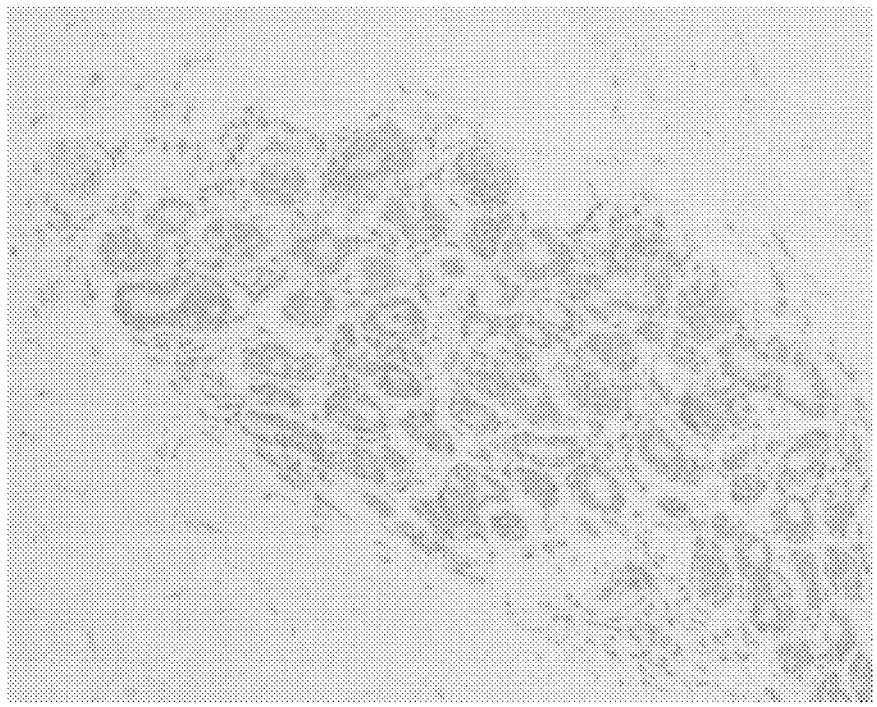
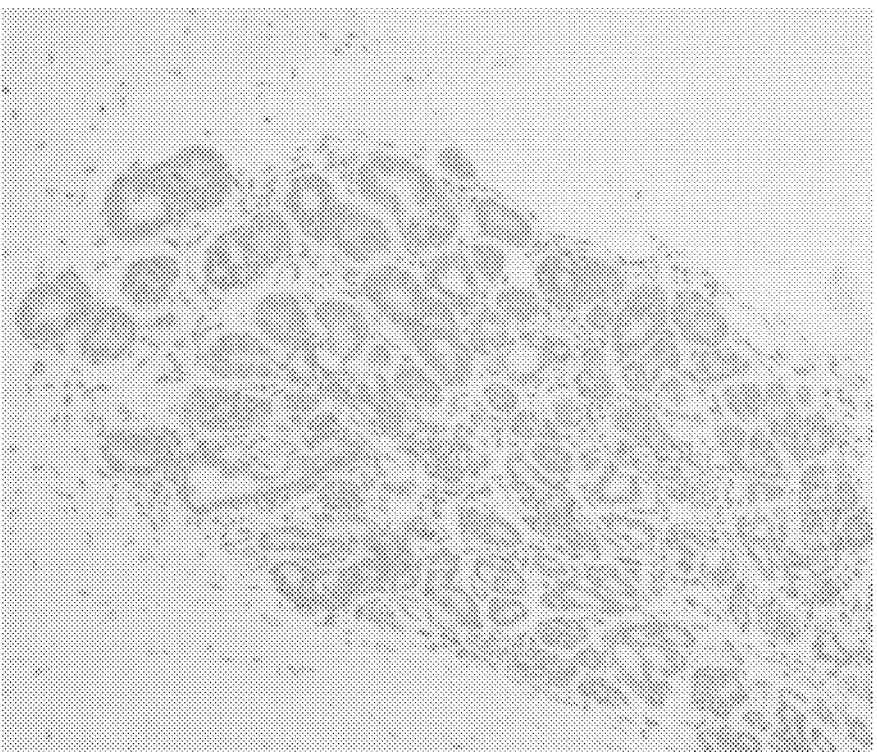
FIG. 25A

| Agent | Biomarker | Platform |
|---|---|---|
| afatinib (assoc. in NSCLC only) | EGFR | NGS Mutation |
| | ERBB2 (Her2) | NGS Mutation |
| afatinib + cetuximab (combination assoc. in NSCLC only) | EGFR T790M | NGS Mutation |
| alectinib, ceritinib | ALK | IHC; NGS Fusion Analysis (RNA) |
| aspirin (assoc. in CRC only) | PIK3CA | NGS Mutation |
| atezolizumab (assoc. in NSCLC only) | PD-L1 | IHC |
| cabozantinib | RET | NGS Fusion Analysis (RNA) |
| capecitabine, fluorouracil, pemetrexed | TS | IHC |
| carboplatin, cisplatin, oxaliplatin | ATM | NGS Mutation |
| | BRCA1[1] | NGS Mutation |
| | BRCA2 | NGS Mutation |
| | ERCC1 | IHC |
| cetuximab, panitumumab[2] (assoc. in CRC only) | BRAF | NGS Mutation |
| | KRAS | NGS Mutation |
| | NRAS | NGS Mutation |
| | PIK3CA | NGS Mutation |
| | PTEN | IHC |
| cetuximab | EGFR | NGS CNV |
| crizotinib | ALK | IHC; NGS Mutation (DNA) & Fusion Analysis (RNA) |
| | cMET | NGS Mutation, CNV (DNA) |
| | ROS1 | NGS Fusion Analysis (RNA) |
| dabrafenib, vemurafenib[2] | BRAF | NGS Mutation |
| dacarbazine, temozolomide | MGMT | IHC |
| | MGMT-Methylation | Pyrosequencing |
| | IDH1 (assoc. in High Grade Glioma only) | NGS |
| docetaxel, paclitaxel, nab-paclitaxel | TUBB3 | IHC |
| doxorubicin, liposomal-doxorubicin, epirubicin | TOP2A | IHC |
| | | CISH |
| enzalutamide, bicalutamide | AR (assoc. in TNBC only) | IHC |
| erlotinib, gefitinib (assoc. in NSCLC only) | EGFR | NGS Mutation |
| | KRAS | NGS Mutation |
| | PIK3CA | NGS Mutation |
| | cMET | NGS CNV (DNA) |
| | PTEN | IHC |

FIG. 26A

| Agent | Biomarker | Platform |
|---|---|---|
| everolimus, temsirolimus | ER (assoc. in Breast only) | IHC |
| | PIK3CA (excluding CRC) | NGS Mutation |
| exemestane + everolimus, fulvestrant, palbociclib combination therapy | ER | IHC |
| | ESR1 | NGS Mutation |
| gemcitabine | RRM1 | IHC |
| hormone therapies³ | AR | IHC |
| | ER | IHC |
| | PR | IHC |
| imatinib | cKIT | NGS Mutation |
| | PDGFRA | NGS Mutation |
| irinotecan | TOPO1 | IHC |
| topotecan (excluding Breast, CRC, NSCLC) | | |
| lapatinib, pertuzumab, T-DM1 | Her2/Neu | NGS CNV (DNA) |
| mitomycin-c | BRCA1¹ | NGS Mutation |
| | BRCA2¹ | |
| nivolumab, pembrolizumab (assoc. in Bladder, Kidney, Melanoma, NSCLC only) | PD-L1 | IHC |
| | MSI (pembrolizumab only) | FA |
| olaparib | ATM (assoc. in Prostate only) | NGS Mutation |
| | BRCA1¹ | |
| | BRCA2¹ | |
| osimertinib (assoc. in NSCLC only) | EGFR T790M | NGS Mutation |
| palbociclib (assoc. in Breast only) | ER | IHC |
| | Her2/Neu | IHC |
| sunitinib (assoc. in GIST only) | cKIT | NGS |
| trametinib² (assoc. in Melanoma only) | BRAF | NGS |
| trastuzumab | ERBB2 (Her2) (assoc. in NSCLC only) | NGS |
| | Her2/Neu | IHC, NGS CNV (DNA) |
| | PTEN (assoc. in Breast only) | IHC |
| | PIK3CA (assoc. in Breast only) | NGS Mutation |
| vandetanib | RET | NGS Mutation (DNA) & Fusion Analysis (RNA) |

FIG. 26B

OLIGONUCLEOTIDE PROBES AND USES THEREOF

CROSS REFERENCE

This application is a continuation of U.S. application Ser. No. 16/084,504, filed Sep. 12, 2018, which is the national stage entry of International Patent Application No. PCT/US2017/023108, filed Mar. 18, 2017, which claims the benefit of U.S. Provisional Patent Application Nos. 62/310,665, filed Mar. 18, 2016; 62/413,361, filed Oct. 26, 2016; 62/420,497, filed Nov. 10, 2016; 62/432,561, filed Dec. 9, 2016; 62/457,691, filed Feb. 10, 2017; and 62/472,953, filed Mar. 17, 2017; all of which applications are incorporated herein by reference in their entirety.

SEQUENCE LISTING SUBMITTED VIA EFS-WEB

The entire content of the following electronic submission of the sequence listing via the USPTO EFS-WEB server, as authorized and set forth in MPEP § 1730 II.B.2(a), is incorporated herein by reference in its entirety for all purposes. The sequence listing is within the electronically filed text file that is identified as follows:
File Name: SequenceListing.txt
Date of Creation: Jun. 10, 2020
Size (bytes): 39,314,000 bytes

BACKGROUND OF THE INVENTION

The invention relates generally to oligonucleotide probes, which are useful for diagnostics of cancer and/or other diseases or disorders and as therapeutics to treat such medical conditions. The invention further relates to materials and methods for the administration of oligonucleotide probes capable of binding to cells of interest.

Oligonucleotide probes, or aptamers, are oligomeric nucleic acid molecules having specific binding affinity to molecules, which may be through interactions other than classic Watson-Crick base pairing. Unless otherwise specified, an "aptamer" as the term is used herein can refer to nucleic acid molecules that can associate with targets, regardless of manner of target recognition. Unless other specified, the terms "aptamer," "oligonucleotide," "polynucleotide," "oligonucleotide probe," or the like may be used interchangeably herein.

Oligonucleotide probes, like peptides generated by phage display or monoclonal antibodies ("mAbs"), are capable of specifically binding to selected targets and modulating the target's activity, e.g., through binding aptamers may block their target's ability to function. Created by an in vitro selection process from pools of random sequence oligonucleotides, aptamers have been generated for numerous proteins including growth factors, transcription factors, enzymes, immunoglobulins, and receptors. A typical aptamer is 10-15 kDa in size (30-45 nucleotides), binds its target with sub-nanomolar affinity, and discriminates against closely related targets (e.g., aptamers can be designed to not bind other proteins from the same gene family). A series of structural studies have shown that aptamers are capable of using the same types of binding interactions (e.g., hydrogen bonding, electrostatic complementarity, hydrophobic contacts, steric exclusion) that drive affinity and specificity in antibody-antigen complexes.

We have previously identified oligonucleotides and libraries of oligonucleotides useful for the detection of microvesicles in bodily fluid samples. Microvesicles can be shed by diseased cells, such as cancer cells, into various bodily fluids such as blood. Thus provide a means of liquid biopsy, including without limitation blood based diagnostics. In some cases, tissue samples are available. The present invention provides methods of enriching oligonucleotide libraries against tissues of interest. Applications of the invention include without limitation theranostics (e.g., predicting a drug response) and diagnostics (e.g., detecting cancer samples). As the methods of the invention provide aptamers that specifically recognize diseased cells, the aptamers themselves can be used in therapeutic applications.

INCORPORATION BY REFERENCE

All publications, patents and patent applications mentioned in this specification are herein incorporated by reference to the same extent as if each individual publication, patent or patent application was specifically and individually indicated to be incorporated by reference.

SUMMARY OF THE INVENTION

Compositions and methods of the invention provide oligonucleotide probes that recognize tissues having phenotypes of interest. In various embodiments, oligonucleotide probes of the invention are used in diagnostic, prognostic or theranostic processes to characterize a phenotype of that sample. The diagnosis may be related to a cancer. In other embodiments, oligonucleotide probes of the invention are chemically modified or composed in a pharmaceutical composition for therapeutic applications.

In an aspect, the invention provides an oligonucleotide comprising a region corresponding to: a) a variable sequence as described in any one of Examples 19-31; b) a variable sequence as described in any one of Tables 20-23, 25, 27, 38-40, or 45; or c) a sequence listed in any one of SEQ ID NO. 1-206506. In some embodiments, the oligonucleotide further comprises a 5' region with sequence 5'-CTAG-CATGACTGCAGTACGT (SEQ ID NO. 4), a 3' region with sequence 5'-CTGTCTCTTATACA-CATCTGACGCTGCCGACGA (SEQ ID NO. 5), or both. The invention further provides an oligonucleotide comprising a nucleic acid sequence or a portion thereof that is at least 50, 55, 60, 65, 70, 75, 80, 85, 90, 95, 96, 97, 98, 99 or 100 percent homologous to such oligonucleotide sequences. In a related aspect, the invention provides a plurality of oligonucleotides comprising at least 1, 2, 3, 4, 5, 6, 7, 8, 9, 10, 11, 12, 13, 14, 15, 16, 17, 18, 19, 20, 25, 30, 40, 45, 50, 55, 60, 65, 70, 75, 80, 85, 90, 95, 100, 125, 150, 175, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, or at least 100000 different oligonucleotide sequences as described above.

In an embodiment, the oligonucleotide or the plurality of oligonucleotides comprise a DNA, RNA, 2'-O-methyl or phosphorothioate backbone, or any combination thereof. In some embodiments, the oligonucleotide or the plurality of oligonucleotides comprises at least one of DNA, RNA, PNA, LNA, UNA, and any combination thereof. The oligonucleotide or at least one member of the plurality of oligonucleotides can have at least one functional modification selected from the group consisting of DNA, RNA, biotinylation, a non-naturally occurring nucleotide, a deletion, an insertion, an addition, and a chemical modification. In some embodiments, the chemical modification comprises at least one of C18, polyethylene glycol (PEG), PEG4, PEG6, PEG8, PEG12 and digoxygenin.

The oligonucleotide or plurality of oligonucleotides of the invention can be labeled. For example, the oligonucleotide or plurality of oligonucleotides can be attached to a nanoparticle, liposome, gold, magnetic label, fluorescent label, light emitting particle, biotin moiety, or radioactive label.

In an aspect, the invention provides a method of enriching an oligonucleotide library using multiple rounds of positive and negative selection. The method of enriching a plurality of oligonucleotides may comprise: a) performing at least one round of positive selection, wherein the positive selection comprises: i) contacting at least one sample with the plurality of oligonucleotides, wherein the at least one sample comprises tissue; and ii) recovering members of the plurality of oligonucleotides that associated with the at least one sample; b) optionally performing at least one round of negative selection, wherein the negative selection comprises: i) contacting at least one additional sample with the plurality of oligonucleotides, wherein at least one additional sample comprises tissue; ii) recovering members of the plurality of oligonucleotides that did not associate with the at least one additional sample; and c) amplifying the members of the plurality of oligonucleotides recovered in at least one or step (a)(ii) and step (b)(ii), thereby enriching the oligonucleotide library. In an embodiments, the recovered members of the plurality of oligonucleotides in step (a)(ii) are used as the input for the next iteration of step (a)(i). In an embodiment, the recovered members of the plurality of oligonucleotides in step (b)(ii) are used as the input for the next iteration of step (a)(i). The unenriched oligonucleotide library may possess great diversity. For example, the unenriched oligonucleotide library may comprise at least 2, 3, 4, 5, 6, 7, 8, 9, 10, 11, 12, 13, 14, 15, 16, 17, 18, 19, 20, 25, 30, 40, 45, 50, 55, 60, 65, 70, 75, 80, 85, 90, 95, 100, 125, 150, 175, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, $10^6$, $10^7$, $10^8$, $10^9$, $10^{10}$, $10^{11}$, $10^{12}$, $10^{13}$, $10^{14}$, $10^{15}$, $10^{16}$, $10^{17}$, or at least $10^{18}$ different oligonucleotide sequences. In an embodiment, the unenriched oligonucleotide library comprises the naïve F-Trin library as described herein.

In some embodiments of the enrichment methods of the invention, the at least one sample and/or at least one additional sample comprise fixed tissue. The fixed tissue may comprise formalin fixed paraffin embedded (FFPE) tissue. In embodiment, the FFPE tissue comprises at least one of a fixed tissue, unstained slide, bone marrow core or clot, biopsy sample, surgical sample, core needle biopsy, malignant fluid, and fine needle aspirate (FNA). The FFPE tissue can be fixed on a substrate. For example, the substrate can be a glass slide or membrane.

In some embodiment, the at least one sample and/or the at least one additional sample are fixed on different substrates. Alternately, the at least one sample and/or the at least one additional sample is fixed on a single substrate. In some embodiments, the at least one sample and/or the at least one additional sample are lysed, scraped from a substrate, or subjected to microdissection. Lysed samples can be arrayed on a substrate. In some embodiments, the substrate comprises a membrane. For example, the membrane can be a nitrocellulose membrane.

In various embodiments of the enrichment methods of the invention, the at least one sample and the at least one additional sample differ in a phenotype of interest. The at least one sample and the at least one additional sample can be from different sections of a same substrate. As a non-limiting example, the samples may comprise cancer tissue and normal adjacent tissue from a fixed tissue sample. In such cases, the at least one sample and the at least one additional sample may be scraped or microdissected from the same substrate to facilitate enrichment.

The oligonucleotide library can be enriched for analysis of any desired phenotype. In embodiments, the phenotype comprises a tissue, anatomical origin, medical condition, disease, disorder, or any combination thereof. For example, the tissue can be muscle, epithelial, connective and nervous tissue, or any combination thereof. For example, the anatomical origin can be the stomach, liver, small intestine, large intestine, rectum, anus, lungs, nose, bronchi, kidneys, urinary bladder, urethra, pituitary gland, pineal gland, adrenal gland, thyroid, pancreas, parathyroid, prostate, heart, blood vessels, lymph node, bone marrow, thymus, spleen, skin, tongue, nose, eyes, ears, teeth, uterus, vagina, testis, penis, ovaries, breast, mammary glands, brain, spinal cord, nerve, bone, ligament, tendon, or any combination thereof.

In various embodiments of the enrichment methods of the invention, the method further comprises determining a target of the enriched members of the oligonucleotide library. Techniques for such determining are provided herein.

In an aspect, the invention provides a method of characterizing a phenotype in a sample comprising: a) contacting the sample with at least one oligonucleotide or plurality of oligonucleotides; and b) identifying a presence or level of a complex formed between the at least one oligonucleotide or plurality of oligonucleotides and the sample, wherein the presence or level is used to characterize the phenotype. In a related aspect, the invention provides a method of visualizing a sample comprising: a) contacting the sample with at least one oligonucleotide or plurality of oligonucleotides; b) removing the at least one oligonucleotide or members of the plurality of oligonucleotides that do not bind the sample; and c) visualizing the at least one oligonucleotide or plurality of oligonucleotides that bound to the sample. The visualization can be used to characterize a phenotype.

The sample to be characterized can be any useful sample, including without limitation a tissue sample, bodily fluid, cell, cell culture, microvesicle, or any combination thereof. In some embodiments, the tissue sample comprises fixed tissue. The fixed tissue can be, e.g., formalin fixed paraffin embedded (FFPE) tissue. In various embodiments, the FFPE sample comprises at least one of a fixed tissue, unstained slide, bone marrow core or clot, biopsy sample, surgical sample, core needle biopsy, malignant fluid, and fine needle aspirate (FNA).

Identifying a presence or level may comprise any useful technique, including without limitation nucleic acid sequencing, amplification, hybridization, gel electrophoresis, chromatography, or visualization. In some embodiments, the identifying by hybridization comprises contacting the sample with at least one labeled probe that is configured to hybridize with at least one oligonucleotide or plurality of oligonucleotides. The at least one labeled probe can be directly or indirectly attached to a label. The label can be, e.g., a fluorescent, radioactive or magnetic label. An indirect label can be, e.g., biotin. In some embodiments, the sequencing comprises next generation sequencing, dye termination sequencing, and/or pyrosequencing of the at least one oligonucleotide or plurality of oligonucleotides. The visualization may be that of a signal linked directly or indirectly to the at least one oligonucleotide or plurality of oligonucleotides. The signal can be any useful signal, e.g., a fluorescent signal or an enzymatic signal. In some embodiments, the enzymatic signal is produced by at least one of a luciferase, firefly luciferase, bacterial luciferase, luciferin, malate dehydrogenase, urease, peroxidase, horseradish peroxidase (HRP), alkaline phosphatase (AP), β-galactosidase, glucoamylase, lysozyme, a saccharide oxidase, glucose oxidase, galactose oxidase, glucose-6-phosphate dehydrogenase, a heterocyclic oxidase, uricase, xanthine oxidase, lactoperoxidase, and microperoxidase. Visualization may comprise use of light microscopy or fluorescent microscopy.

In the methods of the invention directed to characterizing or visualizing a sample, the target of at least one of the at least one oligonucleotide or plurality of oligonucleotides may be known. For example, an oligonucleotide may bind a known protein target. In some embodiments, the target of at least one the at least one oligonucleotide or plurality of oligonucleotides is unknown. For example, the at least one oligonucleotide or plurality of oligonucleotides may themselves provide a biosignature or other useful result that does not necessarily require knowledge of the antigens bound by some or all of the oligonucleotides.

In the methods of characterizing or visualizing a sample, the at least one oligonucleotide or plurality of oligonucleotides can be as provided above. The at least one oligonucleotide or plurality of oligonucleotides may have been determined using the enrichment methods of the invention provided herein.

For example, the at least one oligonucleotide or plurality of oligonucleotides may comprise nucleic acids may have a sequence or a portion thereof that is at least 50, 55, 60, 65, 70, 75, 80, 85, 90, 95, 96, 97, 98, 99 or 100 percent homologous to an oligonucleotide sequence according to at least 1, 2, 3, 4, 5, 6, 7, 8, 9, 10, 12, 15, 20 or all of SEQ ID NOs. 2922-2926, 2929-2947 and 2950-2952. In such cases, the phenotype may be, e.g., lung cancer or prostate cancer.

In another example, the at least one oligonucleotide or plurality of oligonucleotides may comprise nucleic acids having a sequence or a portion thereof that is at least 50, 55, 60, 65, 70, 75, 80, 85, 90, 95, 96, 97, 98, 99 or 100 percent homologous to an oligonucleotide sequence according to at least 1, 2, 3, 4, 5, 6, 7, 8, 9, 10, 12, 15, 20 or all of SEQ ID NOs. 2953-2961 and 2971-2979. In such cases, the phenotype may be, e.g., prostate cancer.

In yet another example, the at least one oligonucleotide or plurality of oligonucleotides may comprise nucleic acids having a sequence or a portion thereof that is at least 50, 55, 60, 65, 70, 75, 80, 85, 90, 95, 96, 97, 98, 99 or 100 percent homologous to an oligonucleotide sequence according to at least 1, 2, 3, 4, 5, 6, 7, 8, 9, 10, 12, 15, 20, 25, 30, 35, 40, 50 or all of SEQ ID NOs. 3039-3061. In such cases, the phenotype may be, e.g., HER2 status (+/−).

In still another example, the at least one oligonucleotide or plurality of oligonucleotides may comprise nucleic acids having a sequence or a portion thereof that is at least 50, 55, 60, 65, 70, 75, 80, 85, 90, 95, 96, 97, 98, 99 or 100 percent homologous to an oligonucleotide sequence according to at least 1, 2, 3, 4, 5, 6, 7, 8, 9, 10, 12, 15, 20, 25, 30, 35, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 150,000 or all of SEQ ID NOs. 3062-103061 and 103062-203061. In such cases, the phenotype may be, e.g., response to anti-HER2 therapy, wherein optionally the anti-HER2 therapy comprises trastuzumab.

In an example, the at least one oligonucleotide or plurality of oligonucleotides may comprise nucleic acids having a sequence or a portion thereof that is at least 50, 55, 60, 65, 70, 75, 80, 85, 90, 95, 96, 97, 98, 99 or 100 percent homologous to an oligonucleotide sequence according to at least 1, 2, 3, 4, 5, 6, 7, 8, 9, 10, 12, 15, 20, 25, 30, 35, 40, 50, 60, 70, 80, 90, 100, 200, 300, 400, 500, 600, 700, 800, 900, 1000, 2000, 3000, 4000 or all of SEQ ID NOs. 203064-203067 and 203076-206478. In such cases, the phenotype may be, e.g., response to at least one of FOLFOX and bevacizumab.

In another example, the at least one oligonucleotide or plurality of oligonucleotides may comprise nucleic acids having a sequence or a portion thereof that is at least 50, 55, 60, 65, 70, 75, 80, 85, 90, 95, 96, 97, 98, 99 or 100 percent homologous to an oligonucleotide sequence according to at least 1, 2, 3, 4, 5, 6, 7, 8, 9, 10, 12, 15 or all of SEQ ID NOs. 206491-206506. In such cases, the phenotype may be, e.g., a tissue identity, including without limitation whether the tissue comprises breast, colon, kidney, lung or pancreatic tissue.

In the methods of the invention, including enriching an oligonucleotide library, characterizing a sample or visualizing a sample, the phenotype can be a biomarker status. In some embodiments, the biomarker is selected from Table 4. In some embodiments, the biomarker status comprises at least one of HER2 positive, HER2 negative, EGFR positive, EGFR negative, TUBB3 positive, or TUBB3 negative. In some embodiments, the biomarker status comprises expression, copy number, mutation, insertion, deletion or other alteration of at least one of ALK, AR, ER, ERCC1, Her2/Neu, MGMT, MLH1, MSH2, MSH6, PD-1, PD-L1, PD-L1 (22c3), PMS2, PR, PTEN, RRM1, TLE3, TOP2A, TOPO1, TrkA, TrkB, TrkC, TS, and TUBB3. In various embodiments, the biomarker status comprises the presence or absence of at least one of EGFR vIII or MET Exon 14 Skipping. In embodiments, the biomarker status comprises expression, copy number, fusion, mutation, insertion, deletion or other alteration of at least one of ALK, BRAF, NTRK1, NTRK2, NTRK3, RET, ROS1, and RSPO3. In embodiments, the biomarker status comprises expression, copy number, fusion, mutation, insertion, deletion or other alteration of at least one of ABL2, ACSL3, ACSL6, AFF1, AFF3, AFF4, AKAP9, AKT2, AKT3, ALDH2, ALK, APC, ARFRP1, ARHGAP26, ARHGEF12, ARID1A, ARID2, ARNT, ASPSCR1, ASXL1, ATF1, ATIC, ATM, ATP1A1, ATR, AURKA, AURKB, AXIN1, AXL, BAP1, BARD1, BCL10, BCL11A, BCL2L11, BCL3, BCL6, BCL7A, BCL9, BCR, BIRC3, BLM, BMPR1A, BRAF, BRCA1, BRCA2, BRIP1, BUB1B, C11orf30 (EMSY), C2orf44, CACNA1D, CALR, CAMTA1, CANT1, CARD11, CARS, CASC5, CASP8, CBFA2T3, CBFB, CBL, CBLB, CCDC6, CCNB11P1, CCND1, CCND2, CCND3, CCNE1, CD274 (PDL1), CD74, CD79A, CDC73, CDH11, CDK4, CDK6, CDK8, CDKN1B, CDKN2A, CDX2, CHEK1, CHEK2, CHIC2, CHN1, CIC, CIITA, CLP1, CLTC, CLTCL1, CNBP, CNTRL, COPB1, CREB1, CREB3L1, CREB3L2, CREBBP, CRKL, CRTC1, CRTC3, CSF1R, CSF3R, CTCF, CTLA4, CTNNA1, CTNNB1, CYLD, CYP2D6, DAXX, DDR2, DDX10, DDX5, DDX6, DEK, DICER1, DOT1L, EBF1, ECT2L, EGFR, ELK4, ELL, EML4, EP300, EPHA3, EPHA5, EPHB1, EPS15, ERBB2 (HER2), ERBB3 (HER3), ERBB4 (HER4), ERC1, ERCC2, ERCC3, ERCC4, ERCC5, ERG, ESR1, ETV1, ETV5, ETV6, EWSR1, EXT1, EXT2, EZH2, EZR, FANCA, FANCC, FANCD2, FANCE, FANCG, FANCL, FAS, FBXO11, FBXW7, FCRL4, FGF10, FGF14, FGF19, FGF23, FGF3, FGF4, FGF6, FGFR1, FGFR1OP, FGFR2, FGFR3, FGFR4, FH, FHIT, FIP1L1, FLCN, FLI1, FLT1, FLT3, FLT4, FNBP1, FOXA1, FOXO1, FOXP1, FUBP1, FUS, GAS7, GATA3, GID4 (C17orf39), GMPS, GNA13, GNAQ, GNAS, GOLGA5, GOPC, GPHN, GPR124, GRIN2A, GSK3B, H3F3A, H3F3B, HERPUD1, HGF, HIP1, HMGA1, HMGA2, HNRNPA2B1, HOOK3, HSP90AA1, HSP90AB1, IDH1, IDH2, IGF1R, IKZF1, IL2, IL21R, IL6ST, IL7R, IRF4, ITK, JAK1, JAK2, JAK3, JAZF1, KDM5A, KDR (VEGFR2), KEAP1, KIAA1549, KIF5B, KIT, KLHL6, KMT2A (MLL), KMT2C (MLL3), KMT2D (MLL2), KRAS, KTN1, LCK, LCP1, LGR5, LHFP, LIFR, LPP, LRIG3, LRP1B, LYL1, MAF, MALT1, MAML2, MAP2K1, MAP2K2, MAP2K4, MAP3K1, MCL1, MDM2, MDM4, MDS2, MEF2B, MEN1, MET (cMET), MITF, MLF1, MLH1 (NGS), MLLT1, MLLT10, MLLT3, MLLT4, MLLT6, MNX1, MRE11A, MSH2 (NGS), MSH6 (NGS), MSI2, MTOR, MYB, MYC, MYCN, MYD88, MYH11, MYH9, NACA, NCKIPSD, NCOA1, NCOA2, NCOA4, NF1, NF2, NFE2L2, NFIB, NFKB2, NFKBIA, NIN, NOTCH2, NPM1, NR4A3, NSD1, NT5C2, NTRK1, NTRK2, NTRK3, NUP214, NUP93, NUP98, NUTM1, PALB2, PAX3, PAX5, PAX7, PBRM1, PBX1, PCM1, PCSK7, PDCD1 (PD1), PDCD1LG2 (PDL2), PDGFB, PDGFRA, PDGFRB, PDK1, PER1, PICALM, PIK3CA, PIK3R1, PIK3R2, PIM1, PML, PMS2 (NGS), POLE, POT1, POU2AF1, PPARG, PRCC, PRDM1, PRDM16, PRKAR1A, PRRX1, PSIP1, PTCH1, PTEN (NGS), PTPN11, PTPRC, RABEP1, RAC1, RAD50, RAD51, RAD51B, RAF1, RALGDS, RANBP17, RAP1GDS1, RARA, RB1, RBM15, REL, RET, RICTOR, RMI2, RNF43, ROS1, RPL22, RPL5, RPN1, RPTOR, RUNX1, RUNX1T1, SBDS, SDC4, SDHAF2, SDHB, SDHC, SDHD, SEPT9, SET, SETBP1, SETD2, SF3B1, SH2B3, SH3GL1, SLC34A2, SMAD2, SMAD4, SMARCB1, SMARCE1, SMO, SNX29, SOX10, SPECC1, SPEN, SRGAP3, SRSF2, SRSF3, SS18, SS18L1, STAT3, STAT4, STAT5B, STIL, STK11, SUFU, SUZ12, SYK, TAF15, TCF12, TCF3, TCF7L2, TET1, TET2, TFEB, TFG, TFRC, TGFBR2, TLX1, TNFAIP3, TNFRSF14, TNFRSF17, TOP1, TP53, TPM3, TPM4, TPR, TRAF7, TRIM26, TRIM27, TRIM33, TRIP11, TRRAP, TSC1, TSC2, TSHR, TTL, U2AF1, USP6, VEGFA, VEGFB, VTI1A, WHSC1, WHSC1L1, WIF1, WISP3, WRN, WT1, WWTR1, XPA, XPC, XPO1, YWHAE, ZMYM2, ZNF217, ZNF331, ZNF384, ZNF521, and ZNF703. The biomarker status may comprise expression, copy number, fusion, mutation, insertion, deletion or other alteration of at least one of ABI1, ABL1, ACKR3, AKT1, AMER1 (FAM123B), AR, ARAF, ATP2B3, ATRX, BCL11B, BCL2, BCL2L2, BCOR, BCORL1, BRD3, BRD4, BTG1, BTK, C15orf65, CBLC, CD79B, CDH1, CDK12, CDKN2B, CDKN2C, CEBPA, CHCHD7, CNOT3, COL1A1, COX6C, CRLF2, DDB2, DDIT3, DNM2, DNMT3A, EIF4A2, ELF4, ELN, ERCC1 (NGS), ETV4, FAM46C, FANCF, FEV, FOXL2, FOXO3, FOXO4, FSTL3, GATA1, GATA2, GNA11, GPC3, HEY1, HIST1H3B, HIST1H4I, HLF, HMGN2P46, HNF1A, HOXA11, HOXA13, HOXA9, HOXC11, HOXC13, HOXD11, HOXD13, HRAS, IKBKE, INHBA, IRS2, JUN, KAT6A (MYST3), KAT6B, KCNJ5, KDM5C, KDM6A, KDSR, KLF4, KLK2, LASP1, LMO1, LMO2, MAFB, MAX, MECOM, MED12, MKL1, MLLT11, MN1, MPL, MSN, MTCP1, MUC1, MUTYH, MYCL (MYCL1), NBN, NDRG1, NKX2-1, NONO, NOTCH1, NRAS, NUMA1, NUTM2B, OLIG2, OMD, P2RY8, PAFAH1B2, PAK3, PATZ1, PAX8, PDE4DIP, PHF6, PHOX2B, PIK3CG, PLAG1, PMS1, POU5F1, PPP2R1A, PRF1, PRKDC, RAD21, RECQL4, RHOH, RNF213, RPL10, SEPT5, SEPT6, SFPQ, SLC45A3, SMARCA4, SOCS1, SOX2, SPOP, SRC, SSX1, STAG2, TAL1, TAL2, TBL1XR1, TCEA1, TCL1A, TERT, TFE3, TFPT, THRAP3, TLX3, TMPRSS2, UBR5, VHL, WAS, ZBTB16, and ZRSR2.

In the methods of the invention, including enriching an oligonucleotide library, characterizing a sample or visualizing a sample, the phenotype can be a phenotype comprises a disease or disorder. The methods can be employed to assist in providing a diagnosis, prognosis and/or theranosis for the disease or disorder. For example, the enriching may be performed using sample such that the enriched library can be used to assist in providing a diagnosis, prognosis and/or theranosis for the disease or disorder. Similarly, the characterizing may comprise assisting in providing a diagnosis, prognosis and/or theranosis for the disease or disorder. The visualization may also comprise assisting in providing a diagnosis, prognosis and/or theranosis for the disease or disorder. In some embodiments, the theranosis comprises predicting a treatment efficacy or lack thereof, classifying a patient as a responder or non-responder to treatment, or monitoring a treatment efficacy. The theranosis can be directed to any appropriate treatment, e.g., the treatment may comprise at least one of chemotherapy, immunotherapy, targeted cancer therapy, a monoclonal antibody, an anti-HER2 antibody, trastuzumab, an anti-VEGF antibody, bevacizumab, and/or platinum/taxane therapy. In some embodiments, the treatment comprises at least one of afatinib, afatinib+cetuximab, alectinib, aspirin, atezolizumab, bicalutamide, cabozantinib, capecitabine, carboplatin, ceritinib, cetuximab, cisplatin, crizotinib, dabrafenib, dacarbazine, doxorubicin, enzalutamide, epirubicin, erlotinib, everolimus, exemestane+everolimus, fluorouracil, fulvestrant, gefitinib, gemcitabine, hormone therapies, irinotecan, lapatinib, liposomal-doxorubicin, matinib, mitomycin-c, nab-paclitaxel, nivolumab, olaparib, osimertinib, oxaliplatin, palbociclib combination therapy, paclitaxel, palbociclib, panitumumab, pembrolizumab, pemetrexed, pertuzumab, sunitinib, T-DM1, temozolomide docetaxel, temsirolimus, topotecan, trametinib, trastuzumab, vandetanib, and vemurafenib. The hormone therapy can be one or more of tamoxifen, toremifene, fulvestrant, letrozole, anastrozole, exemestane, megestrol acetate, leuprolide, goserelin, bicalutamide, flutamide, abiraterone, enzalutamide, triptorelin, abarelix, and degarelix.

In the methods of the invention directed to characterizing a sample, the characterizing may comprise comparing the presence or level to a reference. In some embodiments, the reference comprises a presence or level determined in a sample from an individual without a disease or disorder, or from an individual with a different state of a disease or disorder. The presence or level can be that of a visual level, such as an IHC score, determined by the visualizing. As a non-limiting example, the comparison to the reference of at least one oligonucleotide or plurality of oligonucleotides provided by the invention indicates that the sample comprises a cancer sample or a non-cancer/normal sample.

In some embodiments of the methods of the invention, one or more sample comprises a bodily fluid. The bodily fluid can be any useful bodily fluid, including without limitation peripheral blood, sera, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, female ejaculate, sweat, fecal matter, hair oil, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, blastocyl cavity fluid, or umbilical cord blood.

In the methods of the invention, including characterizing a sample or visualizing a sample, the sample can be from a subject suspected of having or being predisposed to a medical condition, disease, or disorder.

In the methods of the invention, including enriching an oligonucleotide library, characterizing a sample or visualizing a sample, the medical condition, the disease or disorder may be a cancer, a premalignant condition, an inflammatory disease, an immune disease, an autoimmune disease or disorder, a cardiovascular disease or disorder, neurological disease or disorder, infectious disease or pain. In some embodiments, the cancer comprises an acute lymphoblastic leukemia; acute myeloid leukemia; adrenocortical carcinoma; AIDS-related cancers; AIDS-related lymphoma; anal cancer; appendix cancer; astrocytomas; atypical teratoid/rhabdoid tumor; basal cell carcinoma; bladder cancer; brain stem glioma; brain tumor (including brain stem glioma, central nervous system atypical teratoid/rhabdoid tumor, central nervous system embryonal tumors, astrocytomas, craniopharyngioma, ependymoblastoma, ependymoma, medulloblastoma, medulloepithelioma, pineal parenchymal tumors of intermediate differentiation, supratentorial primitive neuroectodermal tumors and pineoblastoma); breast cancer; bronchial tumors; Burkitt lymphoma; cancer of unknown primary site; carcinoid tumor; carcinoma of unknown primary site; central nervous system atypical teratoid/rhabdoid tumor; central nervous system embryonal tumors; cervical cancer; childhood cancers; chordoma; chronic lymphocytic leukemia; chronic myelogenous leukemia; chronic myeloproliferative disorders; colon cancer; colorectal cancer; craniopharyngioma; cutaneous T-cell lymphoma; endocrine pancreas islet cell tumors; endometrial cancer; ependymoblastoma; ependymoma; esophageal cancer; esthesioneuroblastoma; Ewing sarcoma; extracranial germ cell tumor; extragonadal germ cell tumor; extrahepatic bile duct cancer; gallbladder cancer; gastric (stomach) cancer; gastrointestinal carcinoid tumor; gastrointestinal stromal cell tumor; gastrointestinal stromal tumor (GIST); gestational trophoblastic tumor; glioma; hairy cell leukemia; head and neck cancer; heart cancer; Hodgkin lymphoma; hypopharyngeal cancer; intraocular melanoma; islet cell tumors; Kaposi sarcoma; kidney cancer; Langerhans cell histiocytosis; laryngeal cancer; lip cancer; liver cancer; lung cancer; malignant fibrous histiocytoma bone cancer; medulloblastoma; medulloepithelioma; melanoma; Merkel cell carcinoma; Merkel cell skin carcinoma; mesothelioma; metastatic squamous neck cancer with occult primary; mouth cancer; multiple endocrine neoplasia syndromes; multiple myeloma; multiple myeloma/plasma cell neoplasm; mycosis fungoides; myelodysplastic syndromes; myeloproliferative neoplasms; nasal cavity cancer; nasopharyngeal cancer; neuroblastoma; Non-Hodgkin lymphoma; nonmelanoma skin cancer; non-small cell lung cancer; oral cancer; oral cavity cancer; oropharyngeal cancer; osteosarcoma; other brain and spinal cord tumors; ovarian cancer; ovarian epithelial cancer; ovarian germ cell tumor; ovarian low malignant potential tumor; pancreatic cancer; papillomatosis; paranasal sinus cancer; parathyroid cancer; pelvic cancer; penile cancer; pharyngeal cancer; pineal parenchymal tumors of intermediate differentiation; pineoblastoma; pituitary tumor; plasma cell neoplasm/multiple myeloma; pleuropulmonary blastoma; primary central nervous system (CNS) lymphoma; primary hepatocellular liver cancer; prostate cancer; rectal cancer; renal cancer; renal cell (kidney) cancer; renal cell cancer; respiratory tract cancer; retinoblastoma; rhabdomyosarcoma; salivary gland cancer; Sézary syndrome; small cell lung cancer; small intestine cancer; soft tissue sarcoma; squamous cell carcinoma; squamous neck cancer; stomach (gastric) cancer; supratentorial primitive neuroectodermal tumors; T-cell lymphoma; testicular cancer; throat cancer; thymic carcinoma; thymoma; thyroid cancer; transitional cell cancer; transitional cell cancer of the renal pelvis and ureter; trophoblastic tumor; ureter cancer; urethral cancer; uterine cancer; uterine sarcoma; vaginal cancer; vulvar cancer; Waldenström macroglobulinemia; or Wilm's tumor. In some embodiments, the premalignant condition comprises Barrett's Esophagus. In some embodiments, the autoimmune disease comprises inflammatory bowel disease (IBD), Crohn's disease (CD), ulcerative colitis (UC), pelvic inflammation, vasculitis, psoriasis, diabetes, autoimmune hepatitis, multiple sclerosis, myasthenia gravis, Type I diabetes, rheumatoid arthritis, psoriasis, systemic lupus erythematosis (SLE), Hashimoto's Thyroiditis, Grave's disease, Ankylosing Spondylitis Sjogrens Disease, CREST syndrome, Scleroderma, Rheumatic Disease, organ rejection, Primary Sclerosing Cholangitis, or sepsis. In some embodiments, the cardiovascular disease comprises atherosclerosis, congestive heart failure, vulnerable plaque, stroke, ischemia, high blood pressure, stenosis, vessel occlusion or a thrombotic event. In some embodiments, the neurological disease comprises Multiple Sclerosis (MS), Parkinson's Disease (PD), Alzheimer's Disease (AD), schizophrenia, bipolar disorder, depression, autism, Prion Disease, Pick's disease, dementia, Huntington disease (HD), Down's syndrome, cerebrovascular disease, Rasmussen's encephalitis, viral meningitis, neurospsychiatric systemic lupus erythematosus (NPSLE), amyotrophic lateral sclerosis, Creutzfeldt-Jacob disease, Gerstmann-Straussler-Scheinker disease, transmissible spongiform encephalopathy, ischemic reperfusion damage (e.g. stroke), brain trauma, microbial infection, or chronic fatigue syndrome. In some embodiments, the pain comprises fibromyalgia, chronic neuropathic pain, or peripheral neuropathic pain. In some embodiments, the infectious disease comprises a bacterial infection, viral infection, yeast infection, Whipple's Disease, Prion Disease, cirrhosis, methicillin-resistant *Staphylococcus aureus*, HIV, HCV, hepatitis, syphilis, meningitis, malaria, tuberculosis, influenza.

In an aspect, the invention provides a kit comprising at least one reagent for carrying out the methods provided by the invention, including enriching an oligonucleotide library, characterizing a sample or visualizing a sample. In a related aspect, the invention provides use of at least one reagent for carrying out the methods provided by the invention, including enriching an oligonucleotide library, characterizing a sample or visualizing a sample. In some embodiments, the at least one reagent comprises an oligonucleotide or a plurality of oligonucleotides provided herein. Additional useful reagents are also provided herein. See, e.g., the protocols provided in the Examples.

In an aspect, the invention provides a method of imaging at least one cell or tissue, comprising contacting the at least one cell or tissue with at least one oligonucleotide or plurality of oligonucleotides provided herein, and detecting the at least one oligonucleotide or the plurality of oligonucleotides in contact with at least one cell or tissue.

For example, the at least one oligonucleotide or plurality of oligonucleotides may comprise nucleic acids may have a sequence or a portion thereof that is at least 50, 55, 60, 65, 70, 75, 80, 85, 90, 95, 96, 97, 98, 99 or 100 percent homologous to an oligonucleotide sequence according to at least 1, 2, 3, 4, 5, 6, 7, 8, 9, 10, 12, 15, 20 or all of SEQ ID NOs. 2922-2926, 2929-2947 and 2950-2952. In such cases, the imaging may be, e.g., directed to lung or prostate tissue.

In another example, the at least one oligonucleotide or plurality of oligonucleotides may comprise nucleic acids having a sequence or a portion thereof that is at least 50, 55, 60, 65, 70, 75, 80, 85, 90, 95, 96, 97, 98, 99 or 100 percent homologous to an oligonucleotide sequence according to at least 1, 2, 3, 4, 5, 6, 7, 8, 9, 10, 12, 15, 20 or all of SEQ ID NOs. 2953-2961 and 2971-2979. In such cases, the phenotype may be, e.g., prostate cancer.

In yet another example, the at least one oligonucleotide or plurality of oligonucleotides may comprise nucleic acids having a sequence or a portion thereof that is at least 50, 55, 60, 65, 70, 75, 80, 85, 90, 95, 96, 97, 98, 99 or 100 percent homologous to an oligonucleotide sequence according to at least 1, 2, 3, 4, 5, 6, 7, 8, 9, 10, 12, 15, 20, 25, 30, 35, 40, 50 or all of SEQ ID NOs. 3039-3061. In such cases, the imaging may be, e.g., directed to HER2 status of a cell or tissue.

In still another example, the at least one oligonucleotide or plurality of oligonucleotides may comprise nucleic acids having a sequence or a portion thereof that is at least 50, 55, 60, 65, 70, 75, 80, 85, 90, 95, 96, 97, 98, 99 or 100 percent homologous to an oligonucleotide sequence according to at least 1, 2, 3, 4, 5, 6, 7, 8, 9, 10, 12, 15, 20, 25, 30, 35, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 150,000 or all of SEQ ID NOs. 3062-103061 and 103062-203061. In such cases, the imaging may be, e.g., directed to a HER2 status of a cell or tissue.

In an example, the at least one oligonucleotide or plurality of oligonucleotides may comprise nucleic acids having a sequence or a portion thereof that is at least 50, 55, 60, 65, 70, 75, 80, 85, 90, 95, 96, 97, 98, 99 or 100 percent homologous to an oligonucleotide sequence according to at least 1, 2, 3, 4, 5, 6, 7, 8, 9, 10, 12, 15, 20, 25, 30, 35, 40, 50, 60, 70, 80, 90, 100, 200, 300, 400, 500, 600, 700, 800, 900, 1000, 2000, 3000, 4000 or all of SEQ ID NOs. 203064-203067 and 203076-206478. In such cases, the imaging may be, e.g., directed to colorectal cells or tissue.

In another example, the at least one oligonucleotide or plurality of oligonucleotides may comprise nucleic acids having a sequence or a portion thereof that is at least 50, 55, 60, 65, 70, 75, 80, 85, 90, 95, 96, 97, 98, 99 or 100 percent homologous to an oligonucleotide sequence according to at least 1, 2, 3, 4, 5, 6, 7, 8, 9, 10, 12, 15 or all of SEQ ID NOs. 206491-206506. In such cases, the imaging may be, e.g., directed to a tissue, including without limitation breast, colon, kidney, lung or pancreatic tissue.

In the imaging methods provided by the invention, the at least one oligonucleotide or the plurality of oligonucleotides can carry various useful chemical structures or modifications such as described herein.

In the imaging methods provided by the invention, the at least one oligonucleotide or the plurality of oligonucleotides can be administered to a subject prior to the detecting. Such method may allow imaging of at least one cell or tissue in the subject. In some embodiments, the at least one cell or tissue comprises neoplastic, malignant, tumor, hyperplastic, or dysplastic cells. In some embodiments, the at least one cell or tissue comprises at least one of lymphoma, leukemia, renal carcinoma, sarcoma, hemangiopericytoma, melanoma, abdominal cancer, gastric cancer, colon cancer, cervical cancer, prostate cancer, pancreatic cancer, breast cancer, or non-small cell lung cancer cells. In some embodiments, the at least one cell or tissue comprises a medical condition, disease or disorder.

In an aspect, the invention provides a pharmaceutical composition comprising a construct comprising a therapeutically effective amount of the at least one oligonucleotide or the plurality of oligonucleotides as provided herein, or a salt thereof, and a pharmaceutically acceptable carrier, diluent, or both. In some embodiments, the at least one oligonucleotide or the plurality of oligonucleotides associates with at least one protein listed in Table 28 herein.

For example, the at least one oligonucleotide or plurality of oligonucleotides may comprise nucleic acids having a sequence or a portion thereof that is at least 50, 55, 60, 65, 70, 75, 80, 85, 90, 95, 96, 97, 98, 99 or 100 percent homologous to an oligonucleotide sequence according to at least 1, 2, 3, 4, 5, 6, 7, 8, 9, 10, 12, 15, 20 or all of SEQ ID NOs. 2922-2926, 2929-2947 and 2950-2952. Such pharmaceutical composition may be useful for therapy related to a cancer, wherein optionally the cancer comprises lung cancer or prostate cancer.

In another example, the at least one oligonucleotide or plurality of oligonucleotides may comprise nucleic acids having a sequence or a portion thereof that is at least 50, 55, 60, 65, 70, 75, 80, 85, 90, 95, 96, 97, 98, 99 or 100 percent homologous to an oligonucleotide sequence according to at least 1, 2, 3, 4, 5, 6, 7, 8, 9, 10, 12, 15, 20 or all of SEQ ID NOs. 2953-2961 and 2971-2979. Such pharmaceutical composition may be useful for therapy related to a cancer, wherein optionally the cancer comprises prostate cancer.

In still another example, the at least one oligonucleotide or plurality of oligonucleotides may comprise nucleic acids having a sequence or a portion thereof that is at least 50, 55, 60, 65, 70, 75, 80, 85, 90, 95, 96, 97, 98, 99 or 100 percent homologous to an oligonucleotide sequence according to at least 1, 2, 3, 4, 5, 6, 7, 8, 9, 10, 12, 15, 20, 25, 30, 35, 40, 50 or all of SEQ ID NOs. 3039-3061. Such pharmaceutical composition may be useful for therapy related to a cancer, wherein optionally the cancer comprises breast cancer.

In yet another example, the at least one oligonucleotide or plurality of oligonucleotides may comprise nucleic acids having a sequence or a portion thereof that is at least 50, 55, 60, 65, 70, 75, 80, 85, 90, 95, 96, 97, 98, 99 or 100 percent homologous to an oligonucleotide sequence according to at least 1, 2, 3, 4, 5, 6, 7, 8, 9, 10, 12, 15, 20, 25, 30, 35, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 150,000 or all of SEQ ID NOs. 3062-103061 and 103062-203061. Such pharmaceutical composition may be useful for therapy related to a cancer, wherein optionally the cancer comprises breast cancer.

In an example, the at least one oligonucleotide or plurality of oligonucleotides may comprise nucleic acids having a sequence or a portion thereof that is at least 50, 55, 60, 65, 70, 75, 80, 85, 90, 95, 96, 97, 98, 99 or 100 percent homologous to an oligonucleotide sequence according to at least 1, 2, 3, 4, 5, 6, 7, 8, 9, 10, 12, 15, 20, 25, 30, 35, 40, 50, 60, 70, 80, 90, 100, 200, 300, 400, 500, 600, 700, 800, 900, 1000, 2000, 3000, 4000 or all of SEQ ID NOs. 203064-203067 and 203076-206478. Such pharmaceutical composition may be useful for therapy related to a cancer, wherein optionally the cancer comprises colorectal cancer.

In yet another example, the at least one oligonucleotide or plurality of oligonucleotides may comprise nucleic acids having a sequence or a portion thereof that is at least 50, 55, 60, 65, 70, 75, 80, 85, 90, 95, 96, 97, 98, 99 or 100 percent homologous to an oligonucleotide sequence according to at least 1, 2, 3, 4, 5, 6, 7, 8, 9, 10, 12, 15 or all of SEQ ID NOs. 206491-206506. Such pharmaceutical composition may be useful for therapy related to a cancer, wherein optionally the cancer comprises a cancer of the breast, colon, kidney, lung or pancreas.

The at least one oligonucleotide or the plurality of oligonucleotides within the pharmaceutical composition can have any useful desired chemical modification. In an embodiment, the at least one oligonucleotide or the plurality of oligonucleotides is attached to a toxin or chemotherapeutic agent. The at least one oligonucleotide or the plurality of oligonucleotides may be comprised within a multipartite construct. The at least one oligonucleotide or the plurality of oligonucleotides can be attached to a liposome or nanoparticle. In some embodiments, the liposome or nanoparticle comprises a toxin or chemotherapeutic agent.

In a related aspect, the invention provides a method of treating or ameliorating a disease or disorder in a subject in need thereof, comprising administering the pharmaceutical composition of the invention to the subject. In another related aspect, the invention provides a method of inducing cytotoxicity in a subject, comprising administering the pharmaceutical composition of the invention to the subject. Any useful means of administering can be used, including without limitation at least one of intradermal, intramuscular, intraperitoneal, intravenous, subcutaneous, intranasal, epidural, oral, sublingual, intracerebral, intravaginal, transdermal, rectal, by inhalation, topical administration, or any combination thereof.

BRIEF DESCRIPTION OF THE DRAWINGS

FIG. 1A is a schematic of a planar substrate coated with a capture agent, such as an aptamer or antibody, which captures cells or microvesicles expressing the target antigen of the capture agent. The capture agent may bind a protein expressed on the surface of the diseased cell or vesicle. The detection agent, which may also be an aptamer or antibody, carries a detectable label, here a fluorescent signal. The detection agent binds to the captured cell or microvesicle and provides a detectable signal via its fluorescent label. The detection agent can detect an antigen that is generally associated a cell-of-origin or a disease, e.g., a cancer. FIG. 1B is a schematic of a particle bead conjugated with a capture agent, which captures cells or microvesicles expressing the target antigen of the capture agent. The capture agent may bind a protein expressed on the surface of the diseased cell or vesicle. The detection agent, which may also be an aptamer or antibody, carries a detectable label, here a fluorescent signal. The detection agent binds to the captured cell or microvesicle and provides a detectable signal via its fluorescent label. The detection agent can detect an antigen that is generally associated with a cell-of-origin or a disease, e.g., a cancer.

FIG. 2A illustrates a secondary structure of a 32-mer oligonucleotide, Aptamer 4, with sequence 5'-CCCCCCGAAT-CACATGACTTGGGCGGGGGTCG (SEQ ID NO. 1). In the figure, the sequence is shown with 6 thymine nucleotides added to the end, which can act as a spacer to attach a biotin molecule. This particular oligo has a high binding affinity to the target, EpCAM. Additional candidate EpCAM binders are identified by modeling the entire database of sequenced oligos to the secondary structure of this oligo. FIG. 2B illustrates another 32-mer oligo with sequence 5'-ACCG-GATAGCGGTTGGAGGCGTGCTCCACTCG (SEQ ID NO. 2) that has a different secondary structure than the aptamer in FIG. 2A. This aptamer is also shown with a 6-thymine tail.

FIGS. 5A-5G illustrate using an oligonucleotide probe library to differentiate cancer and non-cancer samples.

FIGS. 7A-B illustrate a model generated using a training (FIG. 7A) and test (FIG. 7B) set from a round of cross validation. The AUC for the test set was 0.803. Another exemplary round of cross-validation is shown in FIGS. 7C-D with training (FIG. 7C) and test (FIG. 7D) sets. The AUC for the test set was 0.678.

FIG. 8 illustrates multipart oligonucleotide constructs.

FIG. 10A is a schematic 1000 showing an assay configuration that can be used to detect and/or quantify a target of interest. In the figure, capture aptamer 1002 is attached to substrate 1001. Target of interest 1003 is bound by capture aptamer 1002. Detection aptamer 1004 is also bound to target of interest 1003. Detection aptamer 1004 carries label 1005 which can be detected to identify target captured to substrate 1001 via capture aptamer 1002. FIG. 10B is a schematic 1010 showing use of an aptamer pool to characterize a phenotype. A pool of aptamers to a target of interest is provided 1011. The pool is contacted with a test sample to be characterized 1012. The mixture is washed to remove unbound aptamers. The remaining aptamers are disassociated and collected 1013. The collected aptamers are identified 1014 and the identity of the retained aptamers is used to characterize the phenotype 1015. FIG. 10C is a schematic 1020 showing an implementation of the method in FIG. 10B. A pool of aptamers identified as binding a microvesicle population is provided 1019. The input sample comprises microvesicles that are isolated from a test sample 1020. The pool is contacted with the isolated microvesicles to be characterized 1023. The mixture is washed to remove unbound aptamers and the remaining aptamers are disassociated and collected 1025. The collected aptamers are identified and the identity of the retained aptamers is used to characterize the phenotype 1026. FIG. 10D provides an outline 1030 of such method. An aptamer pool is provided that has been enriched against a tissue of interest 1031. The pool is contacted with a tissue sample 1032. The tissue sample can be in a format such as described herein. As a non-limiting example, the tissue sample can be a fixed tumor sample. The sample may be a FFPE sample fixed to a glass slide or membrane. The sample is washed to remove unbound members of the aptamer pool and the remaining aptamers are visualized 1033. Any appropriate method to visualize the aptamers can be used. In an example, the aptamer pool is biotinylated and the bound aptamer are visualized using streptavidin-horse radish peroxidase (SA-HRP). As described herein, other useful visualization methods are known in the art, including alternate labeling. The visualized sample is scored to determine the amount of staining 1034. For example a pathologist can score the slide as in IHC. The score can be used to characterize the sample 1035 as described herein. For example, a score of +1 or higher may indicate that the sample is a cancer sample, or is a cancer sample expressing a given biomarker.

FIGS. 15A-E show identification of oligonucleotide probes that recognize HER2+ cancer samples.

FIGS. 16A-F show oligonucleotide probes that distinguish trastuzamab responder breast cancer samples.

FIGS. 18A-G show development of oligonucleotide probes that predict the response to a combinational therapy with FOLFOX/bevacizumab in individuals diagnosed with colorectal cancer.

FIGS. 20A-D show oligonucleotide probes that distinguish tubulin 3 (TUBB3) positive and negative pancreatic cancer tissue samples.

FIGS. 21A-B show development of oligonucleotide probes that predict the response to platinum/taxane therapy in individuals diagnosed with ovarian cancer.

FIGS. 22A-B show enrichment and staining of an oligonucleotide probe library against kidney tissue anti-digoxigenin (DIG) antibody detection.

FIGS. 23A-D illustrate oligonucleotide probe library enrichment using lysates from fixed tissue samples.

FIGS. 24A-B illustrate oligonucleotide probe library enrichment using scraped tissue from cancer and non-cancer regions from fixed tissue samples.

FIGS. 25A-B illustrate oligonucleotide probe library enrichment using microdissection of fixed tissue samples.

FIGS. 26A-B illustrate therapeutic agents whose benefit or lack of benefit for treating a cancer may depend on a biomarker status.

DETAILED DESCRIPTION OF THE INVENTION

Figure 1A:
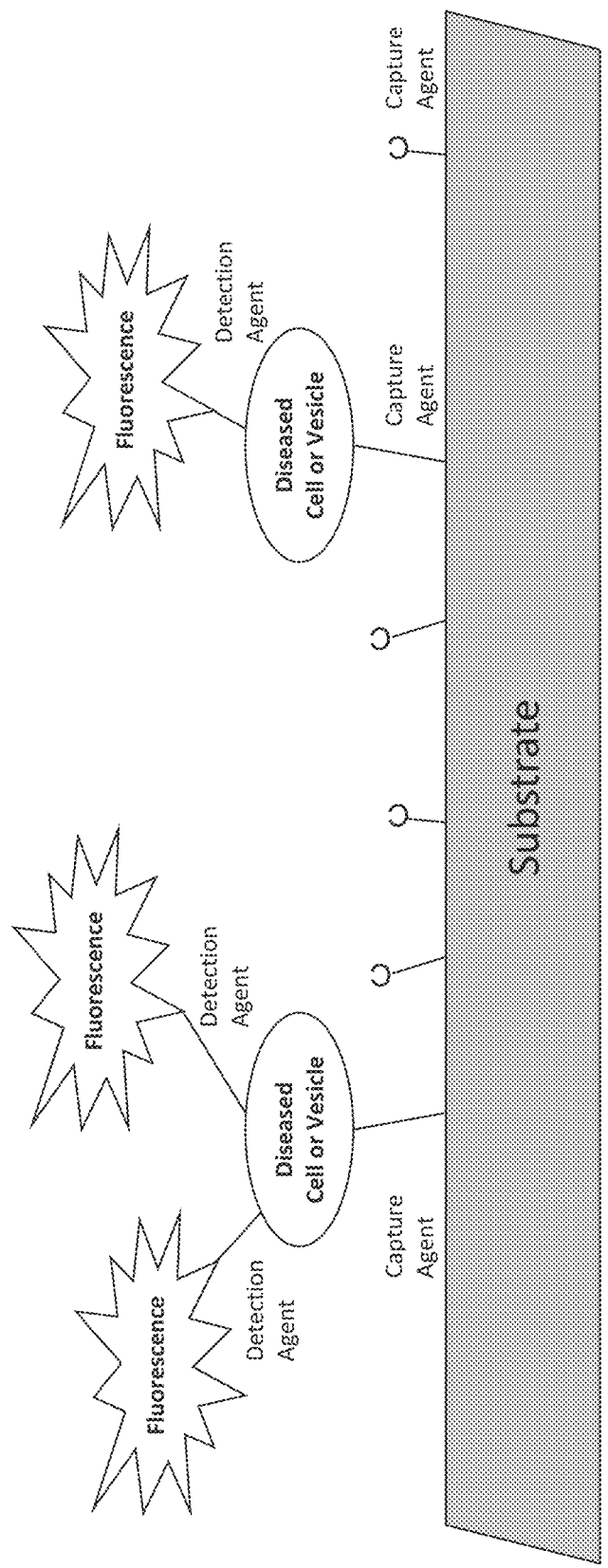
FIGS. 1A-1B illustrate methods of assessing biomarkers such as cellular or microvesicle surface antigens.

The details of one or more embodiments of the invention are set forth in the accompanying description below. Although any methods and materials similar or equivalent to those described herein can be used in the practice or testing of the present invention, the preferred methods and materials are now described. Other features, objects, and advantages of the invention will be apparent from the description. In the specification, the singular forms also include the plural unless the context clearly dictates otherwise. Unless defined otherwise, all technical and scientific terms used herein have the same meaning as commonly understood by one of ordinary skill in the art to which this invention belongs. In the case of conflict, the present Specification will control.

Disclosed herein are compositions and methods that can be used to characterize a phenotype, or assess, a biological sample. The compositions and methods of the invention comprise the use of oligonucleotide probes (aptamers) that bind biological entities of interest, including without limitation tissues, cell, microvesicles, or fragments thereof. The antigens recognized by the oligonucleotide aptamers may comprise proteins or polypeptides or any other useful biological components such as nucleic acids, lipids and/or carbohydrates. In general, the oligonucleotides disclosed are synthetic nucleic acid molecules, including DNA and RNA, and variations thereof. Unless otherwise specified, the oligonucleotide probes can be synthesized in DNA or RNA format or as hybrid molecules as desired. The methods disclosed herein comprise diagnostic, prognostic and theranostic processes and techniques using one or more aptamer of the invention. Alternatively, an oligonucleotide probe of the invention can also be used as a binding agent to capture, isolate, or enrich, a cell, cell fragment, microvesicle or any other fragment or complex that comprises the antigen or functional fragments thereof.

The compositions and methods of the invention also comprise individual oligonucleotides that can be used to assess biological samples. The invention further discloses compositions and methods of oligonucleotide pools that can be used to detect a biosignature in a sample.

Oligonucleotide probes and sequences disclosed in the compositions and methods of the invention may be identified herein in the form of DNA or RNA. Unless otherwise specified, one of skill in the art will appreciate that an oligonucleotide may generally be synthesized as either form of nucleic acid and carry various chemical modifications and remain within the scope of the invention. The term aptamer may be used in the art to refer to a single oligonucleotide that binds specifically to a target of interest through mechanisms other than Watson crick base pairing, similar to binding of a monoclonal antibody to a particular antigen. Within the scope of this disclosure and unless stated explicitly or otherwise implicit in context, the terms aptamer, oligonucleotide and oligonucleotide probe, and variations thereof, may be used interchangeably to refer to an oligonucleotide capable of distinguishing biological entities of interest (e.g., tissues, cells, microvesicles, biomarkers) whether or not the specific entity has been identified or whether the precise mode of binding has been determined.

An oligonucleotide probe or plurality of such probes of the invention can also be used to provide in vitro or in vivo detection or imaging and to provide diagnostic readouts, including for diagnostic, prognostic or theranostic purposes.

Separately, an oligonucleotide probe of the invention can also be used for treatment or as a therapeutic to specifically target a cell, tissue, organ or the like. As the invention provides methods to identify oligonucleotide probes that bind to specific tissues, cells, microvesicles or other biological entities of interest, the oligonucleotide probes of the invention target such entities and are inherently drug candidates, agents that can be used for targeted drug delivery, or both.

Phenotypes

Disclosed herein are products and processes for characterizing a phenotype using the methods and compositions of the invention. The term "phenotype" as used herein can mean any trait or characteristic that can be identified using in part or in whole the compositions and/or methods of the invention. For example, a phenotype can be a diagnostic, prognostic or theranostic determination based on a characterized biomarker profile for a sample obtained from a subject. A phenotype can be any observable characteristic or trait of, such as a disease or condition, a stage of a disease or condition, susceptibility to a disease or condition, prognosis of a disease stage or condition, a physiological state, or response/potential response to therapeutics. A phenotype can result from a subject's genetic makeup as well as the influence of environmental factors and the interactions between the two, as well as from epigenetic modifications to nucleic acid sequences.

A phenotype in a subject can be characterized by obtaining a biological sample from a subject and analyzing the sample using the compositions and/or methods of the invention. For example, characterizing a phenotype for a subject or individual can include detecting a disease or condition (including pre-symptomatic early stage detecting), determining a prognosis, diagnosis, or theranosis of a disease or condition, or determining the stage or progression of a disease or condition. Characterizing a phenotype can include identifying appropriate treatments or treatment efficacy for specific diseases, conditions, disease stages and condition stages, predictions and likelihood analysis of disease progression, particularly disease recurrence, metastatic spread or disease relapse. A phenotype can also be a clinically distinct type or subtype of a condition or disease, such as a cancer or tumor. Phenotype determination can also be a determination of a physiological condition, or an assessment of organ distress or organ rejection, such as post-transplantation. The compositions and methods described herein allow assessment of a subject on an individual basis, which can provide benefits of more efficient and economical decisions in treatment.

In an aspect, the invention relates to the analysis of tissues, microvesicles, and circulating biomarkers to provide a diagnosis, prognosis, and/or theranosis of a disease or condition. Theranostics includes diagnostic testing that provides the ability to affect therapy or treatment of a disease or disease state. Theranostics testing provides a theranosis in a similar manner that diagnostics or prognostic testing provides a diagnosis or prognosis, respectively. As used herein, theranostics encompasses any desired form of therapy related testing, including predictive medicine, personalized medicine, precision medicine, integrated medicine, pharmacodiagnostics and Dx/Rx partnering. Therapy related tests can be used to predict and assess drug response in individual subjects, i.e., to provide personalized medicine. Predicting a drug response can be determining whether a subject is a likely responder or a likely non-responder to a candidate therapeutic agent, e.g., before the subject has been exposed or otherwise treated with the treatment. Assessing a drug response can be monitoring a response to a drug, e.g., monitoring the subject's improvement or lack thereof over a time course after initiating the treatment. Therapy related tests are useful to select a subject for treatment who is particularly likely to benefit from the treatment or to provide an early and objective indication of treatment efficacy in an individual subject. Thus, analysis using the compositions and methods of the invention may indicate that treatment should be altered to select a more promising treatment, thereby avoiding the great expense of delaying beneficial treatment and avoiding the financial and morbidity costs of administering an ineffective drug(s).

In assessing a phenotype, a biosignature can be analyzed in the subject and compared against that of previous subjects that were known to respond or not to a treatment. The biosignature may comprise certain biomarkers or may comprise certain detection agents, such as the oligonucleotide probes as provided herein. If the biosignature in the subject more closely aligns with that of previous subjects that were known to respond to the treatment, the subject can be characterized, or predicted, as a responder to the treatment. Similarly, if the biomarker profile in the subject more closely aligns with that of previous subjects that did not respond to the treatment, the subject can be characterized, or predicted as a non-responder to the treatment. The treatment can be for any appropriate disease, disorder or other condition, including without limitation those disclosed herein.

In some embodiments, the phenotype comprises a medical condition including without limitation a disease or disorder listed in Table 1. For example, the phenotype can comprise detecting the presence of or likelihood of developing a tumor, neoplasm, or cancer, or characterizing the tumor, neoplasm, or cancer (e.g., stage, grade, aggressiveness, likelihood of metastatis or recurrence, etc). Cancers that can be detected or assessed by methods or compositions described herein include, but are not limited to, breast cancer, ovarian cancer, lung cancer, colon cancer, hyperplastic polyp, adenoma, colorectal cancer, high grade dysplasia, low grade dysplasia, prostatic hyperplasia, prostate cancer, melanoma, pancreatic cancer, brain cancer (such as a glioblastoma), hematological malignancy, hepatocellular carcinoma, cervical cancer, endometrial cancer, head and neck cancer, esophageal cancer, gastrointestinal stromal tumor (GIST), renal cell carcinoma (RCC) or gastric cancer. The colorectal cancer can be CRC Dukes B or Dukes C-D. The hematological malignancy can be B-Cell Chronic Lymphocytic Leukemia, B-Cell Lymphoma-DLBCL, B-Cell Lymphoma-DLBCL-germinal center-like, B-Cell Lymphoma-DLBCL-activated B-cell-like, and Burkitt's lymphoma.

The phenotype can be a premalignant condition, such as actinic keratosis, atrophic gastritis, leukoplakia, erythroplasia, Lymphomatoid Granulomatosis, preleukemia, fibrosis, cervical dysplasia, uterine cervical dysplasia, xeroderma pigmentosum, Barrett's Esophagus, colorectal polyp, or other abnormal tissue growth or lesion that is likely to develop into a malignant tumor. Transformative viral infections such as HIV and HPV also present phenotypes that can be assessed according to the invention.

A cancer characterized by the compositions and methods of the invention can comprise, without limitation, a carcinoma, a sarcoma, a lymphoma or leukemia, a germ cell tumor, a blastoma, or other cancers. Carcinomas include without limitation epithelial neoplasms, squamous cell neoplasms squamous cell carcinoma, basal cell neoplasms basal cell carcinoma, transitional cell papillomas and carcinomas, adenomas and adenocarcinomas (glands), adenoma, adenocarcinoma, linitis plastica insulinoma, glucagonoma, gastrinoma, vipoma, cholangiocarcinoma, hepatocellular carcinoma, adenoid cystic carcinoma, carcinoid tumor of appendix, prolactinoma, oncocytoma, hurthle cell adenoma, renal cell carcinoma, grawitz tumor, multiple endocrine adenomas, endometrioid adenoma, adnexal and skin appendage neoplasms, mucoepidermoid neoplasms, cystic, mucinous and serous neoplasms, cystadenoma, pseudomyxoma peritonei, ductal, lobular and medullary neoplasms, acinar cell neoplasms, complex epithelial neoplasms, warthin's tumor, thymoma, specialized gonadal neoplasms, sex cord stromal tumor, thecoma, granulosa cell tumor, arrhenoblastoma, sertoli leydig cell tumor, glomus tumors, paraganglioma, pheochromocytoma, glomus tumor, nevi and melanomas, melanocytic nevus, malignant melanoma, melanoma, nodular melanoma, dysplastic nevus, lentigo maligna melanoma, superficial spreading melanoma, and malignant acral lentiginous melanoma. Sarcoma includes without limitation Askin's tumor, botryodies, chondrosarcoma, Ewing's sarcoma, malignant hemangio endothelioma, malignant schwannoma, osteosarcoma, soft tissue sarcomas including: alveolar soft part sarcoma, angiosarcoma, cystosarcoma phyllodes, dermatofibrosarcoma, desmoid tumor, desmoplastic small round cell tumor, epithelioid sarcoma, extraskeletal chondrosarcoma, extraskeletal osteosarcoma, fibrosarcoma, hemangiopericytoma, hemangiosarcoma, kaposi's sarcoma, leiomyosarcoma, liposarcoma, lymphangiosarcoma, lymphosarcoma, malignant fibrous histiocytoma, neurofibrosarcoma, rhabdomyosarcoma, and synovialsarcoma. Lymphoma and leukemia include without limitation chronic lymphocytic leukemia/small lymphocytic lymphoma, B-cell prolymphocytic leukemia, lymphoplasmacytic lymphoma (such as waldenstrom macroglobulinemia), splenic marginal zone lymphoma, plasma cell myeloma, plasmacytoma, monoclonal immunoglobulin deposition diseases, heavy chain diseases, extranodal marginal zone B cell lymphoma, also called malt lymphoma, nodal marginal zone B cell lymphoma (nmzl), follicular lymphoma, mantle cell lymphoma, diffuse large B cell lymphoma, mediastinal (thymic) large B cell lymphoma, intravascular large B cell lymphoma, primary effusion lymphoma, burkitt lymphoma/leukemia, T cell prolymphocytic leukemia, T cell large granular lymphocytic leukemia, aggressive NK cell leukemia, adult T cell leukemia/lymphoma, extranodal NK/T cell lymphoma, nasal type, enteropathy-type T cell lymphoma, hepatosplenic T cell lymphoma, blastic NK cell lymphoma, mycosis fungoides/sezary syndrome, primary cutaneous CD30-positive T cell lymphoproliferative disorders, primary cutaneous anaplastic large cell lymphoma, lymphomatoid papulosis, angioimmunoblastic T cell lymphoma, peripheral T cell lymphoma, unspecified, anaplastic large cell lymphoma, classical hodgkin lymphomas (nodular sclerosis, mixed cellularity, lymphocyte-rich, lymphocyte depleted or not depleted), and nodular lymphocyte-predominant hodgkin lymphoma. Germ cell tumors include without limitation germinoma, dysgerminoma, seminoma, nongerminomatous germ cell tumor, embryonal carcinoma, endodermal sinus turmor, choriocarcinoma, teratoma, polyembryoma, and gonadoblastoma. Blastoma includes without limitation nephroblastoma, medulloblastoma, and retinoblastoma. Other cancers include without limitation labial carcinoma, larynx carcinoma, hypopharynx carcinoma, tongue carcinoma, salivary gland carcinoma, gastric carcinoma, adenocarcinoma, thyroid cancer (medullary and papillary thyroid carcinoma), renal carcinoma, kidney parenchyma carcinoma, cervix carcinoma, uterine corpus carcinoma, endometrium carcinoma, chorion carcinoma, testis carcinoma, urinary carcinoma, melanoma, brain tumors such as glioblastoma, astrocytoma, meningioma, medulloblastoma and peripheral neuroectodermal tumors, gall bladder carcinoma, bronchial carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma, and plasmocytoma.

In a further embodiment, the cancer under analysis may be a lung cancer including non-small cell lung cancer and small cell lung cancer (including small cell carcinoma (oat cell cancer), mixed small cell/large cell carcinoma, and combined small cell carcinoma), colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemia, lymphoma, myeloma, or a solid tumor.

In embodiments, the cancer comprises an acute lymphoblastic leukemia; acute myeloid leukemia; adrenocortical carcinoma; AIDS-related cancers; AIDS-related lymphoma; anal cancer; appendix cancer; astrocytomas; atypical teratoid/rhabdoid tumor; basal cell carcinoma; bladder cancer; brain stem glioma; brain tumor (including brain stem glioma, central nervous system atypical teratoid/rhabdoid tumor, central nervous system embryonal tumors, astrocytomas, craniopharyngioma, ependymoblastoma, ependymoma, medulloblastoma, medulloepithelioma, pineal parenchymal tumors of intermediate differentiation, supratentorial primitive neuroectodermal tumors and pineoblastoma); breast cancer; bronchial tumors; Burkitt lymphoma; cancer of unknown primary site; carcinoid tumor; carcinoma of unknown primary site; central nervous system atypical teratoid/rhabdoid tumor; central nervous system embryonal tumors; cervical cancer; childhood cancers; chordoma; chronic lymphocytic leukemia; chronic myelogenous leukemia; chronic myeloproliferative disorders; colon cancer; colorectal cancer; craniopharyngioma; cutaneous T-cell lymphoma; endocrine pancreas islet cell tumors; endometrial cancer; ependymoblastoma; ependymoma; esophageal cancer; esthesioneuroblastoma; Ewing sarcoma; extracranial germ cell tumor; extragonadal germ cell tumor; extrahepatic bile duct cancer; gallbladder cancer; gastric (stomach) cancer; gastrointestinal carcinoid tumor; gastrointestinal stromal cell tumor; gastrointestinal stromal tumor (GIST); gestational trophoblastic tumor; glioma; hairy cell leukemia; head and neck cancer; heart cancer; Hodgkin lymphoma; hypopharyngeal cancer; intraocular melanoma; islet cell tumors; Kaposi sarcoma; kidney cancer; Langerhans cell histiocytosis; laryngeal cancer; lip cancer; liver cancer; malignant fibrous histiocytoma bone cancer; medulloblastoma; medulloepithelioma; melanoma; Merkel cell carcinoma; Merkel cell skin carcinoma; mesothelioma; metastatic squamous neck cancer with occult primary; mouth cancer; multiple endocrine neoplasia syndromes; multiple myeloma; multiple myeloma/plasma cell neoplasm; mycosis fungoides; myelodysplastic syndromes; myeloproliferative neoplasms; nasal cavity cancer; nasopharyngeal cancer; neuroblastoma; Non-Hodgkin lymphoma; nonmelanoma skin cancer; non-small cell lung cancer; oral cancer; oral cavity cancer; oropharyngeal cancer; osteosarcoma; other brain and spinal cord tumors; ovarian cancer; ovarian epithelial cancer; ovarian germ cell tumor; ovarian low malignant potential tumor; pancreatic cancer; papillomatosis; paranasal sinus cancer; parathyroid cancer; pelvic cancer; penile cancer; pharyngeal cancer; pineal parenchymal tumors of intermediate differentiation; pineoblastoma; pituitary tumor; plasma cell neoplasm/multiple myeloma; pleuropulmonary blastoma; primary central nervous system (CNS) lymphoma; primary hepatocellular liver cancer; prostate cancer; rectal cancer; renal cancer; renal cell (kidney) cancer; renal cell cancer; respiratory tract cancer; retinoblastoma; rhabdomyosarcoma; salivary gland cancer; Sézary syndrome; small cell lung cancer; small intestine cancer; soft tissue sarcoma; squamous cell carcinoma; squamous neck cancer; stomach (gastric) cancer; supratentorial primitive neuroectodermal tumors; T-cell lymphoma; testicular cancer; throat cancer; thymic carcinoma; thymoma; thyroid cancer; transitional cell cancer; transitional cell cancer of the renal pelvis and ureter; trophoblastic tumor; ureter cancer; urethral cancer; uterine cancer; uterine sarcoma; vaginal cancer; vulvar cancer; Waldenström macroglobulinemia; or Wilm's tumor. The methods of the invention can be used to characterize these and other cancers. Thus, characterizing a phenotype can be providing a diagnosis, prognosis or theranosis of one of the cancers disclosed herein.

In some embodiments, the cancer comprises an acute myeloid leukemia (AML), breast carcinoma, cholangiocarcinoma, colorectal adenocarcinoma, extrahepatic bile duct adenocarcinoma, female genital tract malignancy, gastric adenocarcinoma, gastroesophageal adenocarcinoma, gastrointestinal stromal tumors (GIST), glioblastoma, head and neck squamous carcinoma, leukemia, liver hepatocellular carcinoma, low grade glioma, lung bronchioloalveolar carcinoma (BAC), lung non-small cell lung cancer (NSCLC), lung small cell cancer (SCLC), lymphoma, male genital tract malignancy, malignant solitary fibrous tumor of the pleura (MSFT), melanoma, multiple myeloma, neuroendocrine tumor, nodal diffuse large B-cell lymphoma, non epithelial ovarian cancer (non-EOC), ovarian surface epithelial carcinoma, pancreatic adenocarcinoma, pituitary carcinomas, oligodendroglioma, prostatic adenocarcinoma, retroperitoneal or peritoneal carcinoma, retroperitoneal or peritoneal sarcoma, small intestinal malignancy, soft tissue tumor, thymic carcinoma, thyroid carcinoma, or uveal melanoma. The methods of the invention can be used to characterize these and other cancers. Thus, characterizing a phenotype can be providing a diagnosis, prognosis or theranosis of one of the cancers disclosed herein.

The phenotype can also be an inflammatory disease, immune disease, or autoimmune disease. For example, the disease may be inflammatory bowel disease (IBD), Crohn's disease (CD), ulcerative colitis (UC), pelvic inflammation, vasculitis, psoriasis, diabetes, autoimmune hepatitis, Multiple Sclerosis, Myasthenia Gravis, Type I diabetes, Rheumatoid Arthritis, Psoriasis, Systemic Lupus Erythematosis (SLE), Hashimoto's Thyroiditis, Grave's disease, Ankylosing Spondylitis Sjogrens Disease, CREST syndrome, Scleroderma, Rheumatic Disease, organ rejection, Primary Sclerosing Cholangitis, or sepsis.

The phenotype can also comprise a cardiovascular disease, such as atherosclerosis, congestive heart failure, vulnerable plaque, stroke, or ischemia. The cardiovascular disease or condition can be high blood pressure, stenosis, vessel occlusion or a thrombotic event.

The phenotype can also comprise a neurological disease, such as Multiple Sclerosis (MS), Parkinson's Disease (PD), Alzheimer's Disease (AD), schizophrenia, bipolar disorder, depression, autism, Prion Disease, Pick's disease, dementia, Huntington disease (HD), Down's syndrome, cerebrovascular disease, Rasmussen's encephalitis, viral meningitis, neurospsychiatric systemic lupus erythematosus (NPSLE), amyotrophic lateral sclerosis, Creutzfeldt-Jacob disease, Gerstmann-Straussler-Scheinker disease, transmissible spongiform encephalopathy, ischemic reperfusion damage (e.g. stroke), brain trauma, microbial infection, or chronic fatigue syndrome. The phenotype may also be a condition such as fibromyalgia, chronic neuropathic pain, or peripheral neuropathic pain.

The phenotype may also comprise an infectious disease, such as a bacterial, viral or yeast infection. For example, the disease or condition may be Whipple's Disease, Prion Disease, cirrhosis, methicillin-resistant *Staphylococcus aureus*, HIV, hepatitis, syphilis, meningitis, malaria, tuberculosis, or influenza. Viral proteins, such as HIV or HCV-like particles can be assessed in a vesicle, to characterize a viral condition.

The phenotype can also comprise a perinatal or pregnancy related condition (e.g. preeclampsia or preterm birth), metabolic disease or condition, such as a metabolic disease or condition associated with iron metabolism. For example, hepcidin can be assayed in a vesicle to characterize an iron deficiency. The metabolic disease or condition can also be diabetes, inflammation, or a perinatal condition.

The compositions and methods of the invention can be used to characterize these and other diseases and disorders. Thus, characterizing a phenotype can be providing a diagnosis, prognosis or theranosis of a medical condition, disease or disorder, including without limitation one of the diseases and disorders disclosed herein.

Subject

One or more phenotypes of a subject can be determined by analyzing a biological sample obtained from the subject. A subject or patient can include, but is not limited to, mammals such as bovine, avian, canine, equine, feline, ovine, porcine, or primate animals (including humans and non-human primates). A subject can also include a mammal of importance due to being endangered, such as a Siberian tiger; or economic importance, such as an animal raised on a farm for consumption by humans, or an animal of social importance to humans, such as an animal kept as a pet or in a zoo. Examples of such animals include, but are not limited to, carnivores such as cats and dogs; swine including pigs, hogs and wild boars; ruminants or ungulates such as cattle, oxen, sheep, giraffes, deer, goats, bison, camels or horses. Also included are birds that are endangered or kept in zoos, as well as fowl and more particularly domesticated fowl, e.g., poultry, such as turkeys and chickens, ducks, geese, guinea fowl. Also included are domesticated swine and horses (including race horses). In addition, any animal species connected to commercial activities are also included such as those animals connected to agriculture and aquaculture and other activities in which disease monitoring, diagnosis, and therapy selection are routine practice in husbandry for economic productivity and/or safety of the food chain.

The subject can have a pre-existing disease or condition, including without limitation cancer. Alternatively, the subject may not have any known pre-existing condition. The subject may also be non-responsive to an existing or past treatment, such as a treatment for cancer.

Samples

A sample used and/or assessed via the compositions and methods of the invention includes any relevant biological sample that can be used to characterize a phenotype of interest, including without limitation sections of tissues such as biopsy or tissue removed during surgical or other procedures, bodily fluids, autopsy samples, frozen sections taken for histological purposes, and cell cultures. Such samples include blood and blood fractions or products (e.g., serum, buffy coat, plasma, platelets, red blood cells, and the like), sputum, malignant effusion, cheek cells tissue, cultured cells (e.g., primary cultures, explants, and transformed cells), stool, urine, other biological or bodily fluids (e.g., prostatic fluid, gastric fluid, intestinal fluid, renal fluid, lung fluid, cerebrospinal fluid, and the like), etc. The sample can comprise biological material that is a fresh frozen & formalin fixed paraffin embedded (FFPE) block, formalin-fixed paraffin embedded, or is within an RNA preservative+formalin fixative. More than one sample of more than one type can be used for each patient.

The sample used in the methods described herein can be a formalin fixed paraffin embedded (FFPE) sample. The FFPE sample can be one or more of fixed tissue, unstained slides, bone marrow core or clot, core needle biopsy, malignant fluids and fine needle aspirate (FNA). In an embodiment, the fixed tissue comprises a tumor containing formalin fixed paraffin embedded (FFPE) block from a surgery or biopsy. In another embodiment, the unstained slides comprise unstained, charged, unbaked slides from a paraffin block. In another embodiment, bone marrow core or clot comprises a decalcified core. A formalin fixed core and/or clot can be paraffin-embedded. In still another embodiment, the core needle biopsy comprises 1, 2, 3, 4, 5, 6, 7, 8, 9, 10 or more, e.g., 3-6, paraffin embedded biopsy samples. An 18 gauge needle biopsy can be used. The malignant fluid can comprise a sufficient volume of fresh pleural/ascitic fluid to produce a 5×5×2 mm cell pellet. The fluid can be formalin fixed in a paraffin block. In an embodiment, the core needle biopsy comprises 1, 2, 3, 4, 5, 6, 7, 8, 9, 10 or more, e.g., 4-6, paraffin embedded aspirates.

A sample may be processed according to techniques understood by those in the art. A sample can be without limitation fresh, frozen or fixed cells or tissue. In some embodiments, a sample comprises formalin-fixed paraffin-embedded (FFPE) tissue, fresh tissue or fresh frozen (FF) tissue. A sample can comprise cultured cells, including primary or immortalized cell lines derived from a subject sample. A sample can also refer to an extract from a sample from a subject. For example, a sample can comprise DNA, RNA or protein extracted from a tissue or a bodily fluid. Many techniques and commercial kits are available for such purposes. The fresh sample from the individual can be treated with an agent to preserve RNA prior to further processing, e.g., cell lysis and extraction. Samples can include frozen samples collected for other purposes. Samples can be associated with relevant information such as age, gender, and clinical symptoms present in the subject; source of the sample; and methods of collection and storage of the sample. A sample is typically obtained from a subject, e.g., a human subject.

A biopsy comprises the process of removing a tissue sample for diagnostic or prognostic evaluation, and to the tissue specimen itself. Any biopsy technique known in the art can be applied to the molecular profiling methods of the present invention. The biopsy technique applied can depend on the tissue type to be evaluated (e.g., colon, prostate, kidney, bladder, lymph node, liver, bone marrow, blood cell, lung, breast, etc.), the size and type of the tumor (e.g., solid or suspended, blood or ascites), among other factors. Representative biopsy techniques include, but are not limited to, excisional biopsy, incisional biopsy, needle biopsy, surgical biopsy, and bone marrow biopsy. An "excisional biopsy" refers to the removal of an entire tumor mass with a small margin of normal tissue surrounding it. An "incisional biopsy" refers to the removal of a wedge of tissue that includes a cross-sectional diameter of the tumor. The invention can make use a "core-needle biopsy" of the tumor mass, or a "fine-needle aspiration biopsy" which generally obtains a suspension of cells from within the tumor mass. Biopsy techniques are discussed, for example, in Harrison's Principles of Internal Medicine, Kasper, et al., eds., 16th ed., 2005, Chapter 70, and throughout Part V.

Standard molecular biology techniques known in the art and not specifically described are generally followed as in Sambrook et al., Molecular Cloning: A Laboratory Manual, Cold Spring Harbor Laboratory Press, New York (1989), and as in Ausubel et al., Current Protocols in Molecular Biology, John Wiley and Sons, Baltimore, Md. (1989) and as in Perbal, A Practical Guide to Molecular Cloning, John Wiley & Sons, New York (1988), and as in Watson et al., Recombinant DNA, Scientific American Books, New York and in Birren et al (eds) Genome Analysis: A Laboratory Manual Series, Vols. 1-4 Cold Spring Harbor Laboratory Press, New York (1998) and methodology as set forth in U.S. Pat. Nos. 4,666,828; 4,683,202; 4,801,531; 5,192,659 and 5,272,057 and incorporated herein by reference. Polymerase chain reaction (PCR) can be carried out generally as in PCR Protocols: A Guide to Methods and Applications, Academic Press, San Diego, Calif. (1990).

The biological sample assessed using the compositions and methods of the invention can be any useful bodily or biological fluid, including but not limited to peripheral blood, sera, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen (including prostatic fluid), Cowper's fluid or pre-ejaculatory fluid, female ejaculate, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates or other lavage fluids, cells, cell culture, or a cell culture supernatant. A biological sample may also include the blastocyl cavity, umbilical cord blood, or maternal circulation which may be of fetal or maternal origin. The biological sample may also be a cell culture, tissue sample or biopsy from which microvesicles, circulating tumor cells (CTCs), and other circulating biomarkers may be obtained. For example, cells of interest can be cultured and microvesicles isolated from the culture. In various embodiments, biomarkers or more particularly biosignatures disclosed herein can be assessed directly from such biological samples (e.g., identification of presence or levels of nucleic acid or polypeptide biomarkers or functional fragments thereof) using various methods, such as extraction of nucleic acid molecules from blood, plasma, serum or any of the foregoing biological samples, use of protein or antibody arrays to identify polypeptide (or functional fragment) biomarker(s), as well as other array, sequencing, PCR and proteomic techniques known in the art for identification and assessment of nucleic acid and polypeptide molecules. In addition, one or more components present in such samples can be first isolated or enriched and further processed to assess the presence or levels of selected biomarkers, to assess a given biosignature (e.g., isolated microvesicles prior to profiling for protein and/or nucleic acid biomarkers).

Table 1 presents a non-limiting listing of diseases, conditions, or biological states and corresponding biological samples that may be used for analysis according to the methods of the invention.

TABLE 1

Examples of Biological Samples for Various Diseases, Conditions, or Biological States

| Illustrative Disease, Condition or Biological State | Illustrative Biological Samples |
|---|---|
| Cancers/neoplasms affecting the following tissue types/bodily systems: breast, lung, ovarian, colon, rectal, prostate, pancreatic, brain, bone, connective tissue, glands, skin, lymph, nervous system, endocrine, germ cell, genitourinary, hematologic/blood, bone marrow, muscle, eye, esophageal, fat tissue, thyroid, pituitary, spinal cord, bile duct, heart, gall bladder, bladder, testes, cervical, endometrial, renal, ovarian, digestive/gastrointestinal, stomach, head and neck, liver, leukemia, respiratory/thoracic, cancers of unknown primary (CUP) | Tumor, blood, serum, plasma, cerebrospinal fluid (CSF), urine, sputum, ascites, synovial fluid, semen, nipple aspirates, saliva, bronchoalveolar lavage fluid, tears, oropharyngeal washes, feces, peritoneal fluids, pleural effusion, sweat, tears, aqueous humor, pericardial fluid, lymph, chyme, chyle, bile, stool water, amniotic fluid, breast milk, pancreatic juice, cerumen, Cowper's fluid or pre-ejaculatory fluid, female ejaculate, interstitial fluid, menses, mucus, pus, sebum, vaginal lubrication, vomit |
| Neurodegenerative/neurological disorders: Parkinson's disease, Alzheimer's Disease and multiple sclerosis, Schizophrenia, and bipolar disorder, spasticity disorders, epilepsy | Blood, serum, plasma, CSF, urine |
| Cardiovascular Disease: atherosclerosis, cardiomyopathy, endocarditis, vunerable plaques, infection | Blood, serum, plasma, CSF, urine |
| Stroke: ischemic, intracerebral hemorrhage, subarachnoid hemorrhage, transient ischemic attacks (TIA) | Blood, serum, plasma, CSF, urine |
| Pain disorders: peripheral neuropathic pain and chronic neuropathic pain, and fibromyalgia, | Blood, serum, plasma, CSF, urine |
| Autoimmune disease: systemic and localized diseases, rheumatic disease, Lupus, Sjogren's syndrome | Blood, serum, plasma, CSF, urine, synovial fluid |
| Digestive system abnormalities: Barrett's esophagus, irritable bowel syndrome, ulcerative colitis, Crohn's disease, Diverticulosis and Diverticulitis, Celiac Disease | Blood, serum, plasma, CSF, urine |
| Endocrine disorders: diabetes mellitus, various forms of Thyroiditis, adrenal disorders, pituitary disorders | Blood, serum, plasma, CSF, urine |
| Diseases and disorders of the skin: psoriasis | Blood, serum, plasma, CSF, urine, synovial fluid, tears |
| Urological disorders: benign prostatic hypertrophy (BPH), polycystic kidney disease, interstitial cystitis | Blood, serum, plasma, urine |
| Hepatic disease/injury: Cirrhosis, induced hepatotoxicity (due to exposure to natural or synthetic chemical sources) | Blood, serum, plasma, urine |
| Kidney disease/injury: acute, sub-acute, chronic conditions, Podocyte injury, focal segmental glomerulosclerosis | Blood, serum, plasma, urine |
| Endometriosis | Blood, serum, plasma, urine, vaginal fluids |
| Osteoporosis | Blood, serum, plasma, urine, synovial fluid |
| Pancreatitis | Blood, serum, plasma, urine, pancreatic juice |
| Asthma | Blood, serum, plasma, urine, sputum, bronchiolar lavage fluid |
| Allergies | Blood, serum, plasma, urine, sputum, bronchiolar lavage fluid |
| Prion-related diseases | Blood, serum, plasma, CSF, urine |
| Viral Infections: HIV/AIDS | Blood, serum, plasma, urine |
| Sepsis | Blood, serum, plasma, urine, tears, nasal lavage |
| Organ rejection/transplantation | Blood, serum, plasma, urine, various lavage fluids |
| Differentiating conditions: adenoma versus hyperplastic polyp, irritable bowel syndrome (IBS) versus normal, classifying Dukes stages A, B, C, and/or D of colon cancer, adenoma with low-grade hyperplasia versus high-grade hyperplasia, adenoma versus normal, colorectal cancer versus normal, IBS versus. ulcerative colitis (UC) versus Crohn's disease (CD), | Blood, serum, plasma, urine, sputum, feces, colonic lavage fluid |

TABLE 1-continued

Examples of Biological Samples for Various Diseases, Conditions, or Biological States

| Illustrative Disease, Condition or Biological State | Illustrative Biological Samples |
| --- | --- |
| Pregnancy related physiological states, conditions, or affiliated diseases: genetic risk, adverse pregnancy outcomes | Maternal serum, plasma, amniotic fluid, cord blood |

The methods of the invention can be used to characterize a phenotype using a blood sample or blood derivative. Blood derivatives include plasma and serum. Blood plasma is the liquid component of whole blood, and makes up approximately 55% of the total blood volume. It is composed primarily of water with small amounts of minerals, salts, ions, nutrients, and proteins in solution. In whole blood, red blood cells, leukocytes, and platelets are suspended within the plasma. Blood serum refers to blood plasma without fibrinogen or other clotting factors (i.e., whole blood minus both the cells and the clotting factors).

The biological sample may be obtained through a third party, such as a party not performing the analysis of the sample. For example, the sample may be obtained through a clinician, physician, or other health care manager of a subject from which the sample is derived. Alternatively, the biological sample may obtained by the same party analyzing the sample. In addition, biological samples be assayed, are archived (e.g., frozen) or otherwise stored in under preservative conditions.

In various embodiments, the biological sample comprises a microvesicle or cell membrane fragment that is derived from a cell of origin and available extracellularly in a subject's biological fluid or extracellular milieu. Methods of the invention may include assessing one or more such microvesicles, including assessing populations thereof. A vesicle or microvesicle, as used herein, is a membrane vesicle that is shed from cells. Vesicles or membrane vesicles include without limitation: circulating microvesicles (cMVs), microvesicle, exosome, nanovesicle, dexosome, bleb, blebby, prostasome, microparticle, intralumenal vesicle, membrane fragment, intralumenal endosomal vesicle, endosomal-like vesicle, exocytosis vehicle, endosome vesicle, endosomal vesicle, apoptotic body, multivesicular body, secretory vesicle, phospholipid vesicle, liposomal vesicle, argosome, texasome, secresome, tolerosome, melanosome, oncosome, or exocytosed vehicle. Furthermore, although vesicles may be produced by different cellular processes, the methods of the invention are not limited to or reliant on any one mechanism, insofar as such vesicles are present in a biological sample and are capable of being characterized by the methods disclosed herein. Unless otherwise specified, methods that make use of a species of vesicle can be applied to other types of vesicles. Vesicles comprise spherical structures with a lipid bilayer similar to cell membranes which surrounds an inner compartment which can contain soluble components, sometimes referred to as the payload. In some embodiments, the methods of the invention make use of exosomes, which are small secreted vesicles of about 40-100 nm in diameter. For a review of membrane vesicles, including types and characterizations, see Thery et al., *Nat Rev Immunol.* 2009 August; 9(8):581-93. Some properties of different types of vesicles include those in Table 2:

TABLE 2

Vesical Properties

| Feature | Exosomes | Microvesicles | Ectosomes | Membrane particles | Exosome-like vesicles | Apoptotic vesicles |
| --- | --- | --- | --- | --- | --- | --- |
| Size | 50-100 nm | 100-1,000 nm | 50-200 nm | 50-80 nm | 20-50 nm | 50-500 nm |
| Density in sucrose | 1.13-1.19 g/ml | | | 1.04-1.07 g/ml | 1.1 g/ml | 1.16-1.28 g/ml |
| EM appearance | Cup shape | Irregular shape, electron dense | Bilamellar round structures | Round | Irregular shape | Heterogeneous |
| Sedimentation | 100,000 g | 10,000 g | 160,000-200,000 g | 100,000-200,000 g | 175,000 g | 1,200 g, 10,000 g, 100,000 g |
| Lipid composition | Enriched in cholesterol, sphingomyelin and ceramide; contains lipid rafts; expose PPS | Expose PPS | Enriched in cholesterol and diacylglycerol; expose PPS | | No lipid rafts | |
| Major protein markers | Tetraspanins (e.g., CD63, CD9), Alix, TSG101 | Integrins, selectins and CD40 ligand | CR1 and proteolytic enzymes; no CD63 | CD133; no CD63 | TNFRI | Histones |
| Intracellular origin | Internal compartments (endosomes) | Plasma membrane | Plasma membrane | Plasma membrane | | |

Abbreviations: phosphatidylserine (PPS); electron microscopy (EM)

Vesicles include shed membrane bound particles, or "microparticles," that are derived from either the plasma membrane or an internal membrane. Vesicles can be released into the extracellular environment from cells. Cells releasing vesicles include without limitation cells that originate from, or are derived from, the ectoderm, endoderm, or mesoderm. The cells may have undergone genetic, environmental, and/or any other variations or alterations. For example, the cell can be tumor cells. A vesicle can reflect any changes in the source cell, and thereby reflect changes in the originating cells, e.g., cells having various genetic mutations. In one mechanism, a vesicle is generated intracellularly when a segment of the cell membrane spontaneously invaginates and is ultimately exocytosed (see for example, Keller et al., *Immunol. Lett.* 107 (2): 102-8 (2006)). Vesicles also include cell-derived structures bounded by a lipid bilayer membrane arising from both herniated evagination (blebbing) separation and sealing of portions of the plasma membrane or from the export of any intracellular membrane-bounded vesicular structure containing various membrane-associated proteins of tumor origin, including surface-bound molecules derived from the host circulation that bind selectively to the tumor-derived proteins together with molecules contained in the vesicle lumen, including but not limited to tumor-derived microRNAs or intracellular proteins. Blebs and blebbing are further described in Charras et al., *Nature Reviews Molecular and Cell Biology*, Vol. 9, No. 11, p. 730-736 (2008). A vesicle shed into circulation or bodily fluids from tumor cells may be referred to as a "circulating tumor-derived vesicle." When such vesicle is an exosome, it may be referred to as a circulating-tumor derived exosome (CTE). In some instances, a vesicle can be derived from a specific cell of origin. CTE, as with a cell-of-origin specific vesicle, typically have one or more unique biomarkers that permit isolation of the CTE or cell-of-origin specific vesicle, e.g., from a bodily fluid and sometimes in a specific manner. For example, a cell or tissue specific markers are used to identify the cell of origin. Examples of such cell or tissue specific markers are disclosed herein and can further be accessed in the Tissue-specific Gene Expression and Regulation (TiGER) Database, available at bioinfo.wilmer.jhu.edu/tiger/; Liu et al. (2008) TiGER: a database for tissue-specific gene expression and regulation. BMC Bioinformatics. 9:271; TissueDistributionDBs, available at genome.dkfz-heidelberg.de/menu/tissue_db/index.html.

A vesicle can have a diameter of greater than about 10 nm, 20 nm, or 30 nm. A vesicle can have a diameter of greater than 40 nm, 50 nm, 100 nm, 200 nm, 500 nm, 1000 nm, 1500 nm, 2000 nm or greater than 10,000 nm. A vesicle can have a diameter of about 20-2000 nm, about 20-1500 nm, about 30-1000 nm, about 30-800 nm, about 30-200 nm, or about 30-100 nm. In some embodiments, the vesicle has a diameter of less than 10,000 nm, 2000 nm, 1500 nm, 1000 nm, 800 nm, 500 nm, 200 nm, 100 nm, 50 nm, 40 nm, 30 nm, 20 nm or less than 10 nm. As used herein the term "about" in reference to a numerical value means that variations of 10% above or below the numerical value are within the range ascribed to the specified value. Typical sizes for various types of vesicles are shown in Table 2. Vesicles can be assessed to measure the diameter of a single vesicle or any number of vesicles. For example, the range of diameters of a vesicle population or an average diameter of a vesicle population can be determined. Vesicle diameter can be assessed using methods known in the art, e.g., imaging technologies such as electron microscopy. In an embodiment, a diameter of one or more vesicles is determined using optical particle detection. See, e.g., U.S. Pat. No. 7,751,053, entitled "Optical Detection and Analysis of Particles" and issued Jul. 6, 2010; and U.S. Pat. No. 7,399,600, entitled "Optical Detection and Analysis of Particles" and issued Jul. 15, 2010.

In some embodiments, the methods of the invention comprise assessing vesicles directly such as in a biological sample without prior isolation, purification, or concentration from the biological sample. For example, the amount of vesicles in the sample can by itself provide a biosignature that provides a diagnostic, prognostic or theranostic determination. Alternatively, the vesicle in the sample may be isolated, captured, purified, or concentrated from a sample prior to analysis. As noted, isolation, capture or purification as used herein comprises partial isolation, partial capture or partial purification apart from other components in the sample. Vesicle isolation can be performed using various techniques as described herein, e.g., chromatography, filtration, centrifugation, flow cytometry, affinity capture (e.g., to a planar surface or bead), and/or using microfluidics. FIGS. 10B-C present an overview of a method of the invention for assessing microvesicles using an aptamer pool.

Vesicles such as exosomes can be assessed to provide a phenotypic characterization by comparing vesicle characteristics to a reference. In some embodiments, surface antigens on a vesicle are assessed. The surface antigens can provide an indication of the anatomical origin and/or cellular of the vesicles and other phenotypic information, e.g., tumor status. For example, wherein vesicles found in a patient sample, e.g., a bodily fluid such as blood, serum or plasma, are assessed for surface antigens indicative of colorectal origin and the presence of cancer. The surface antigens may comprise any informative biological entity that can be detected on the vesicle membrane surface, including without limitation surface proteins, lipids, carbohydrates, and other membrane components. For example, positive detection of colon derived vesicles expressing tumor antigens can indicate that the patient has colorectal cancer. As such, methods of the invention can be used to characterize any disease or condition associated with an anatomical or cellular origin, by assessing, for example, disease-specific and cell-specific biomarkers of one or more vesicles obtained from a subject.

In another embodiment, the methods of the invention comprise assessing one or more vesicle payload to provide a phenotypic characterization. The payload with a vesicle comprises any informative biological entity that can be detected as encapsulated within the vesicle, including without limitation proteins and nucleic acids, e.g., genomic or cDNA, mRNA, or functional fragments thereof, as well as microRNAs (miRs). In addition, methods of the invention are directed to detecting vesicle surface antigens (in addition or exclusive to vesicle payload) to provide a phenotypic characterization. For example, vesicles can be characterized by using binding agents (e.g., antibodies or aptamers) that are specific to vesicle surface antigens, and the bound vesicles can be further assessed to identify one or more payload components disclosed therein. As described herein, the levels of vesicles with surface antigens of interest or with payload of interest can be compared to a reference to characterize a phenotype. For example, overexpression in a sample of cancer-related surface antigens or vesicle payload, e.g., a tumor associated mRNA or microRNA, as compared to a reference, can indicate the presence of cancer in the sample. The biomarkers assessed can be present or absent, increased or reduced based on the selection of the desired target sample and comparison of the target sample to the desired reference sample. Non-limiting examples of target samples include: disease; treated/not-treated; different time points, such as a in a longitudinal study; and non-limiting examples of reference sample: non-disease; normal; different time points; and sensitive or resistant to candidate treatment(s).

Diagnostic Methods

The aptamers of the invention can be used in various methods to assess presence or level of biomarkers in a biological sample, e.g., biological entities of interest such as proteins, nucleic acids, or microvesicles. The biological entities can be part of larger entities, such as complexes, cells or tissue, or can be circulating in bodily fluids. The aptamers may be used to assess presence or level of the target molecule/s. Therefore, in various embodiments of the invention directed to diagnostics, prognostics or theranostics, one or more aptamers of the invention are configured in a ligand-target based assay, where one or more aptamer of the invention is contacted with a selected biological sample, where the or more aptamer associates with or binds to its target molecules. Aptamers of the invention are used to identify candidate biosignatures based on the biological samples assessed and biomarkers detected. In some embodiments, aptamer or oligonucleotide probes, or libraries thereof, may themselves provide a biosignature for a particular condition or disease. A biosignature refers to a biomarker profile of a biological sample comprising a presence, level or other characteristic that can be assessed (including without limitation a sequence, mutation, rearrangement, translocation, deletion, epigenetic modification, methylation, post-translational modification, allele, activity, complex partners, stability, half life, and the like) of one or more biomarker of interest. Biosignatures can be used to evaluate diagnostic and/or prognostic criteria such as presence of disease, disease staging, disease monitoring, disease stratification, or surveillance for detection, metastasis or recurrence or progression of disease. For example, methods of the invention using aptamers against microvesicle surface antigen are useful for correlating a biosignature comprising microvesicle antigens to a selected condition or disease. As another example, methods of the invention using aptamers against tissue are useful for correlating a biosignature comprising tissue antigens to a selected condition or disease. A biosignature can also be used clinically in making decisions concerning treatment modalities including therapeutic intervention. A biosignature can further be used clinically to make treatment decisions, including whether to perform surgery or what treatment standards should be used along with surgery (e.g., either pre-surgery or post-surgery). As an illustrative example, a biosignature of circulating biomarkers or biomarkers displayed on fixed tissue may indicate an aggressive form of cancer and may call for a more aggressive surgical procedure and/or more aggressive therapeutic regimen to treat the patient.

Characterizing a phenotype, such as providing a diagnosis, prognosis or theranosis, may comprise comparing a biosignature to a reference. For example, the level of a biomarker in a diseased state may be elevated or reduced as compared to a reference control without the disease, or with a different state of the disease. An oligonucleotide probe library according to the invention may be engineered to detect a certain phenotype and not another phenotype. As a non-limiting example, the oligonucleotide probe library may stain a cancer tissue using an immunoassay but not a non-cancer reference tissue. Alternately, the oligonucleotide probe library may stain a cancer tissue using an immunoassay at a detectable higher level than a non-cancer reference tissue. One of skill will appreciate that one may engineer an oligonucleotide probe library to stain a non-cancer tissue using an immunoassay at a detectable higher level than cancer tissue as well.

A biosignature can be used in any methods disclosed herein, e.g., to assess whether a subject is afflicted with disease, is at risk for developing disease or to assess the stage or progression of the disease. For example, a biosignature can be used to assess whether a subject has prostate cancer, colon cancer, or other cancer as described herein. See, e.g., section labeled "Phenotypes." Furthermore, a biosignature can be used to determine a stage of a disease or condition, such as cancer.

A biosignature/biomarker profile comprising a microvesicle can include assessment of payload within the microvesicle. For example, one or more aptamer of the invention can be used to capture a microvesicle population, thereby providing readout of microvesicle antigens, and then the payload content within the captured microvesicles can be assessed, thereby providing further biomarker readout of the payload content.

A biosignature for characterizing a phenotype may comprise any number of useful criteria. The term "phenotype" as used herein can mean any trait or characteristic that is attributed to a biosignature/biomarker profile. A phenotype can be detected or identified in part or in whole using the compositions and/or methods of the invention. In some embodiments, at least one criterion is used for each biomarker. In some embodiments, at least 1, 2, 3, 4, 5, 6, 7, 8, 9, 10, 15, 20, 30, 40, 50, 60, 70, 80, 90 or at least 100 criteria are used. For example, for the characterizing of a cancer, a number of different criteria can be used when the subject is diagnosed with a cancer: 1) if the amount of a biomarker in a sample from a subject is higher than a reference value; 2) if the amount of a biomarker within specific cell types or specific microvesicles (e.g., microvesicles derived from a specific tissue or organ) is higher than a reference value; or 3) if the amount of a biomarker within a cell, tissue or microvesicle with one or more cancer specific biomarkers is higher than a reference value Similar rules can apply if the amount of the biomarkers is less than or the same as the reference. The method can further include a quality control measure, such that the results are provided for the subject if the samples meet the quality control measure. In some embodiments, if the criteria are met but the quality control is questionable, the subject is reassessed.

A biosignature can be used in therapy related diagnostics to provide tests useful to diagnose a disease or choose the correct treatment regimen, such as provide a theranosis. Theranostics includes diagnostic testing that provides the ability to affect therapy or treatment of a diseased state. Theranostics testing provides a theranosis in a similar manner that diagnostics or prognostic testing provides a diagnosis or prognosis, respectively. As used herein, theranostics encompasses any desired form of therapy related testing, including predictive medicine, personalized medicine, integrated medicine, pharmacodiagnostics and Dx/Rx partnering. Therapy related tests can be used to predict and assess drug response in individual subjects, i.e., to provide personalized medicine. Predicting a drug response can be determining whether a subject is a likely responder or a likely non-responder to a candidate therapeutic agent, e.g., before the subject has been exposed or otherwise treated with the treatment. Assessing a drug response can be monitoring a response to a drug, e.g., monitoring the subject's improvement or lack thereof over a time course after initiating the treatment. Therapy related tests are useful to select a subject for treatment who is particularly likely to benefit from the treatment or to provide an early and objective indication of treatment efficacy in an individual subject. Thus, a biosignature as disclosed herein may indicate that treatment should be altered to select a more promising treatment, thereby avoiding the great expense of delaying beneficial treatment and avoiding the financial and morbidity costs of administering an ineffective drug(s).

The compositions and methods of the invention can be used to identify or detect a biosignature associated with a variety of diseases and disorders, which include, but are not limited to cardiovascular disease, cancer, infectious diseases, sepsis, neurological diseases, central nervous system related diseases, endovascular related diseases, and autoimmune related diseases. Therapy related diagnostics also aid in the prediction of drug toxicity, drug resistance or drug response. Therapy related tests may be developed in any suitable diagnostic testing format, which include, but are not limited to, e.g., immunohistochemical tests, clinical chemistry, immunoassay, cell-based technologies, nucleic acid tests or body imaging methods. Therapy related tests can further include but are not limited to, testing that aids in the determination of therapy, testing that monitors for therapeutic toxicity, or response to therapy testing. Thus, a biosignature can be used to predict or monitor a subject's response to a treatment. A biosignature can be determined at different time points for a subject after initiating, removing, or altering a particular treatment.

In some embodiments, the compositions and methods of the invention provide for a determination or prediction as to whether a subject is responding to a treatment is made based on a change in the amount of one or more components of a biosignature (e.g., biomarkers of interest), an amount of one or more components of a particular biosignature, or the biosignature detected for the components. In another embodiment, a subject's condition is monitored by determining a biosignature at different time points. The progression, regression, or recurrence of a condition is determined. Response to therapy can also be measured over a time course. Thus, the invention provides a method of monitoring a status of a disease or other medical condition in a subject, comprising isolating or detecting a biosignature from a biological sample from the subject, detecting the overall amount of the components of a particular biosignature, or detecting the biosignature of one or more components (such as the presence, absence, or expression level of a biomarker). The biosignatures are used to monitor the status of the disease or condition.

One or more novel biosignatures can also be identified by the methods of the invention. For example, one or more vesicles can be isolated from a subject that responds to a drug treatment or treatment regimen and compared to a reference, such as another subject that does not respond to the drug treatment or treatment regimen. Differences between the biosignatures can be determined and used to identify other subjects as responders or non-responders to a particular drug or treatment regimen.

In some embodiments, a biosignature is used to determine whether a particular disease or condition is resistant to a drug, in which case a physician need not waste valuable time with such drug treatment. To obtain early validation of a drug choice or treatment regimen, a biosignature is determined for a sample obtained from a subject. The biosignature is used to assess whether the particular subject's disease has the biomarker associated with drug resistance. Such a determination enables doctors to devote critical time as well as the patient's financial resources to effective treatments.

Biosignatures can be used in the theranosis of diseases such as cancer, e.g., identifying whether a subject suffering from a disease is a likely responder or non-responder to a particular treatment. The subject methods can be used to theranose cancers including without limitation those listed herein, e.g., in the "Phenotypes" section herein. These include without limitation lung cancer, non-small cell lung cancer small cell lung cancer (including small cell carcinoma (oat cell cancer), mixed small cell/large cell carcinoma, and combined small cell carcinoma), colon cancer, breast cancer, prostate cancer, liver cancer, pancreatic cancer, brain cancer, kidney cancer, ovarian cancer, stomach cancer, melanoma, bone cancer, gastric cancer, breast cancer, glioma, glioblastoma, hepatocellular carcinoma, papillary renal carcinoma, head and neck squamous cell carcinoma, leukemia, lymphoma, myeloma, or other solid tumors.

A biosignature of circulating biomarkers, including markers associated with a component present in a biological sample (e.g., cell, cell-fragment, cell-derived microvesicle), in a sample from a subject suffering from a cancer can be used select a candidate treatment for the subject. The biosignature can be determined according to the methods of the invention presented herein. In some embodiments, the candidate treatment comprises a standard of care for the cancer. The treatment can be a cancer treatment such as radiation, surgery, chemotherapy or a combination thereof. The cancer treatment can be a therapeutic such as anti-cancer agents and chemotherapeutic regimens. Further drug associations and rules that are used in embodiments of the invention are found in PCT/US2007/69286, filed May 18, 2007; PCT/US2009/60630, filed Oct. 14, 2009; PCT/2010/000407, filed Feb. 11, 2010; PCT/US12/41393, filed Jun. 7, 2012; PCT/US2013/073184, filed Dec. 4, 2013; PCT/US2010/54366, filed Oct. 27, 2010; PCT/US11/67527, filed Dec. 28, 2011; PCT/US15/13618, filed Jan. 29, 2015; and PCT/US16/20657, filed Mar. 3, 2016; each of which applications is incorporated herein by reference in its entirety.

Biomarkers

The methods and compositions of the invention can be used in assays to detect the presence or level of one or more biomarker of interest. Given the adaptable nature of the invention, the biomarker can be any useful biomarker including those disclosed herein or in the literature, or to be discovered. In an embodiment, the biomarker comprises a protein or polypeptide. As used herein, "protein," "polypeptide" and "peptide" are used interchangeably unless stated otherwise. The biomarker can be a nucleic acid, including DNA, RNA, and various subspecies of any thereof as disclosed herein or known in the art. The biomarker can comprise a lipid. The biomarker can comprise a carbohydrate. The biomarker can also be a complex, e.g., a complex comprising protein, nucleic acids, lipids and/or carbohydrates. In some embodiments, the biomarker comprises a microvesicle. In an embodiment, the invention provides a method wherein a pool of aptamers is used to assess the presence and/or level of a population of microvesicles of interest without knowing the precise microvesicle antigen targeted by each member of the pool. See, e.g., FIGS. 10B-C. In other cases, biomarkers associated with microvesicles are assessed according to the methods of the invention. See, e.g., FIG. 10A. The oligonucleotide pools of the invention can also used to assess cells and tissue whether or not the target biomarkers of the individual oligonucleotide aptamers are known. The invention further includes determining the targets of such oligonucleotide aptamer pools and members thereof. See Examples 19-31.

A biosignature may comprise one type of biomarker or multiple types of biomarkers. As a non-limiting example, a biosignature can comprise multiple proteins, multiple nucleic acids, multiple lipids, multiple carbohydrates, multiple biomarker complexes, multiple microvesicles, or a combination of any thereof. For example, the biosignature may comprise one or more microvesicle, one or more protein, and one or more microRNA, wherein the one or more protein and/or one or more microRNA is optionally in association with the microvesicle as a surface antigen and/or payload, as appropriate. As another example, the biosignature may be an oligonucleotide pool signature, and the members of the oligonucleotide pool can associate with various biomarker or multiple types of biomarkers.

In some embodiments, microvesicles are detected using vesicle surface antigens. A commonly expressed vesicle surface antigen can be referred to as a "housekeeping protein," or general vesicle biomarker. The biomarker can be CD63, CD9, CD81, CD82, CD37, CD53, Rab-5b, Annexin V or MFG-E8. Tetraspanins, a family of membrane proteins with four transmembrane domains, can be used as general vesicle biomarkers. The tetraspanins include CD151, CD53, CD37, CD82, CD81, CD9 and CD63. There have been over 30 tetraspanins identified in mammals, including the TSPAN1 (TSP-1), TSPAN2 (TSP-2), TSPAN3 (TSP-3), TSPAN4 (TSP-4, NAG-2), TSPAN5 (TSP-5), TSPAN6 (TSP-6), TSPAN7 (CD231, TALLA-1, A15), TSPAN8 (CO-029), TSPAN9 (NET-5), TSPAN10 (Oculospanin), TSPAN11 (CD151-like), TSPAN12 (NET-2), TSPAN13 (NET-6), TSPAN14, TSPAN15 (NET-7), TSPAN16 (TM4-B), TSPAN17, TSPAN18, TSPAN19, TSPAN20 (UP1b, UPK1B), TSPAN21 (UP1a, UPK1A), TSPAN22 (RDS, PRPH2), TSPAN23 (ROM1), TSPAN24 (CD151), TSPAN25 (CD53), TSPAN26 (CD37), TSPAN27 (CD82), TSPAN28 (CD81), TSPAN29 (CD9), TSPAN30 (CD63), TSPAN31 (SAS), TSPAN32 (TSSC6), TSPAN33, and TSPAN34. Other commonly observed vesicle markers include those listed in Table 3. One or more of these proteins can be useful biomarkers for the characterizing a phenotype using the subject methods and compositions.

TABLE 3

Proteins Observed in Microvesicles from Multiple Cell Types

| Class | Protein |
| --- | --- |
| Antigen Presentation | MHC class I, MHC class II, Integrins, Alpha 4 beta 1, Alpha M beta 2, Beta 2 |
| Immunoglobulin family | ICAM1/CD54, P-selection |
| Cell-surface peptidases | Dipeptidylpeptidase IV/CD26, Aminopeptidase n/CD13 |
| Tetraspanins | CD151, CD53, CD37, CD82, CD81, CD9 and CD63 |
| Heat-shock proteins | Hsp70, Hsp84/90 |
| Cytoskeletal proteins | Actin, Actin-binding proteins, Tubulin |
| Membrane transport and fusion | Annexin I, Annexin II, Annexin IV, Annexin V, Annexin VI, RAB7/RAP1B/RADGDI |
| Signal transduction | Gi2alpha/14-3-3, CBL/LCK |
| Abundant membrane proteins | CD63, GAPDH, CD9, CD81, ANXA2, ENO1, SDCBP, MSN, MFGE8, EZR, GK, ANXA1, LAMP2, DPP4, TSG101, HSPA1A, GDI2, CLTC, LAMP1, Cd86, ANPEP, TFRC, SLC3A2, RDX, RAP1B, RAB5C, RAB5B, MYH9, ICAM1, FN1, RAB11B, PIGR, LGALS3, ITGB1, EHD1, CLIC1, ATP1A1, ARF1, RAP1A, P4HB, MUC1, KRT10, HLA-A, FLOT1, CD59, C1orf58, BASP1, TACSTD1, STOM |
| Other Transmembrane Proteins | Cadherins: CDH1, CDH2, CDH12, CDH3, Deomoglein, DSG1, DSG2, DSG3, DSG4, Desmocollin, DSC1, DSC2, DSC3, Protocadherins, PCDH1, PCDH10, PCDH11x, PCDH11y, PCDH12, FAT, FAT2, FAT4, PCDH15, PCDH17, PCDH18, PCDH19; PCDH20; PCDH7, PCDH8, PCDH9, PCDHA1, PCDHA10, PCDHA11, PCDHA12, PCDHA13, PCDHA2, PCDHA3, PCDHA4, PCDHA5, PCDHA6, PCDHA7, PCDHA8, PCDHA9, PCDHAC1, PCDHAC2, PCDHB1, PCDHB10, PCDHB11, PCDHB12, PCDHB13, PCDHB14, PCDHB15, PCDHB16, PCDHB17, PCDHB18, PCDHB2, PCDHB3, PCDHB4, PCDHB5, PCDHB6, PCDHB7, PCDHB8, PCDHB9, PCDHGA1, PCDHGA10, PCDHGA11, PCDHGA12, PCDHGA2; PCDHGA3, PCDHGA4, PCDHGA5, PCDHGA6, PCDHGA7, PCDHGA8, PCDHGA9, PCDHGB1, PCDHGB2, PCDHGB3, PCDHGB4, PCDHGB5, PCDHGB6, PCDHGB7, PCDHGC3, PCDHGC4, PCDHGC5, CDH9 (cadherin 9, type 2 (T1-cadherin)), CDH10 (cadherin 10, type 2 (T2-cadherin)), CDH5 (VE-cadherin (vascular endothelial)), CDH6 (K-cadherin (kidney)), CDH7 (cadherin 7, type 2), CDH8 (cadherin 8, type 2), CDH11 (OB-cadherin (osteoblast)), CDH13 (T-cadherin - H-cadherin (heart)), CDH15 (M-cadherin (myotubule)), CDH16 (KSP-cadherin), CDH17 (LI cadherin (liver-intestine)), CDH18 (cadherin 18, type 2), CDH19 (cadherin 19, type 2), CDH20 (cadherin 20, type 2), CDH23 (cadherin 23, (neurosensory epithelium)), CDH10, CDH11, CDH13, CDH15, CDH16, CDH17, CDH18, CDH19, CDH22, CDH23, CDH24, CDH26, CDH28, CDH4, CDH5, CDH6, CDH7, CDH8, CDH9, CELSR1, CELSR2, CELSR3, CLSTN1, CLSTN2, CLSTN3, DCHS1, DCHS2, LOC389118, PCLKC, RESDA1, RET |

Any of the types of biomarkers described herein can be used and/or assessed via the subject methods and compositions. Exemplary biomarkers include without limitation those in Table 4. The markers can be detected as protein, RNA or DNA as appropriate, which can be circulating freely or in a complex with other biological molecules. As desired, the markers in Table 4 can also be used to detect tumor tissue or for capture and/or detection of vesicles for characterizing phenotypes as disclosed herein. In some cases, multiple capture and/or detectors are used to enhance the characterization. The markers can be detected as vesicle surface antigens and/or vesicle payload. The "Illustrative Class" indicates indications for which the markers are known markers. Those of skill will appreciate that the markers can also be used in alternate settings in certain instances. For example, a marker which can be used to characterize one type of disease may also be used to characterize another disease as appropriate. Consider a non-limiting example of a tumor marker which can be used as a biomarker for tumors from various lineages. The biomarker references in Tables 3 and 4, or through the specification, are those commonly used in the art. Gene aliases and descriptions can be found using a variety of online databases, including GeneCards® (www-.genecards.org), HUGO Gene Nomenclature (www.genenames.org), Entrez Gene (www.ncbi.nlm.nih.gov/entrez/query.fcgi?db=gene), UniProtKB/Swiss-Prot (www.uniprot.org), UniProtKB/TrEMBL (www.uniprot.org), OMIM (www.ncbi.nlm.nih.gov/entrez/query.fcgi?db=OMIM), GeneLoc (genecards.weizmann.ac.il/geneloc/), and Ensembl (www.ensembl.org). Generally, gene symbols and names below correspond to those approved by HUGO, and protein names are those recommended by UniProtKB/Swiss-Prot. Common alternatives are provided as well. Where a protein name indicates a precursor, the mature protein is also implied. Throughout the application, gene and protein symbols may be used interchangeably and the meaning can be derived from context as necessary.

TABLE 4

Illustrative Biomarkers

| Illustrative Class | Biomarkers |
|---|---|
| Drug associated targets and prognostic markers | ABCC1, ABCG2, ACE2, ADA, ADH1C, ADH4, AGT, AR, AREG, ASNS, BCL2, BCRP, BDCA1, beta III tubulin, BIRC5, B-RAF, BRCA1, BRCA2, CA2, caveolin, CD20, CD25, CD33, CD52, CDA, CDKN2A, CDKN1A, CDKN1B, CDK2, CDW52, CES2, CK 14, CK 17, CK 5/6, c-KIT, c-Met, c-Myc, COX-2, Cyclin D1, DCK, DHFR, DNMT1, DNMT3A, DNMT3B, E-Cadherin, ECGF1, EGFR, EML4-ALK fusion, EPHA2, Epiregulin, ER, ERBR2, ERCC1, ERCC3, EREG, ESR1, FLT1, folate receptor, FOLR1, FOLR2, FSHB, FSHPRH1, FSHR, FYN, GART, GNA11, GNAQ, GNRH1, GNRHR1, GSTP1, HCK, HDAC1, hENT-1, Her2/Neu, HGF, HIF1A, HIG1, HSP90, HSP90AA1, HSPCA, IGF-1R, IGFRBP, IGFRBP3, IGFRBP4, IGFRBP5, IL13RA1, IL2RA, KDR, Ki67, KIT, K-RAS, LCK, LTB, Lymphotoxin Beta Receptor, LYN, MET, MGMT, MLH1, MMR, MRP1, MS4A1, MSH2, MSH5, Myc, NFKB1, NFKB2, NFKBIA, NRAS, ODC1, OGFR, p16, p21, p27, p53, p95, PARP-1, PDGFC, PDGFR, PDGFRA, PDGFRB, PGP, PGR, PI3K, POLA, POLA1, PPARG, PPARGC1, PR, PTEN, PTGS2, PTPN12, RAF1, RARA, ROS1, RRM1, RRM2, RRM2B, RXRB, RXRG, SIK2, SPARC, SRC, SSTR1, SSTR2, SSTR3, SSTR4, SSTR5, Survivin, TK1, TLE3, TNF, TOP1, TOP2A, TOP2B, TS, TUBB3, TXN, TXNRD1, TYMS, VDR, VEGF, VEGFA, VEGFC, VHL, YES1, ZAP70 |
| Drug associated targets and prognostic markers | ABL1, STK11, FGFR2, ERBB4, SMARCB1, CDKN2A, CTNNB1, FGFR1, FLT3, NOTCH1, NPM1, SRC, SMAD4, FBXW7, PTEN, TP53, AKT1, ALK, APC, CDH1, C-Met, HRAS, IDH1, JAK2, MPL, PDGFRA, SMO, VHL, ATM, CSF1R, FGFR3, GNAS, ERBB2, HNF1A, JAK3, KDR, MLH1, PTPN11, RB1, RET, c-Kit, EGFR, PIK3CA, NRAS, GNA11, GNAQ, KRAS, BRAF |
| Drug associated targets and prognostic markers | ALK, AR, BRAF, cKIT, cMET, EGFR, ER, ERCC1, GNA11, HER2, IDH1, KRAS, MGMT, MGMT promoter methylation, NRAS, PDGFRA, Pgp, PIK3CA, PR, PTEN, ROS1, RRM1, SPARC, TLE3, TOP2A, TOPO1, TS, TUBB3, VHL |
| Drug associated targets | ABL1, AKT1, ALK, APC, AR, ATM, BRAF, BRAF, BRCA1, BRCA2, CDH1, cKIT, cMET, CSF1R, CTNNB1, EGFR, EGFR (H-score), EGFRvIII, ER, ERBB2 (HER2), ERBB4, ERCC1, FBXW7, FGFR1, FGFR2, FLT3, GNA11, GNAQ, GNAS, HER2, HNF1A, HRAS, IDH1, IDH2, JAK2, JAK3, KDR (VEGFR2), KRAS, MGMT, MGMT Promoter Methylation, microsatellite instability (MSI), MLH1, MPL, MSH2, MSH6, NOTCH1, NPM1, NRAS, PD-1, PDGFRA, PD-L1, Pgp, PIK3CA, PMS2, PR, PTEN, PTPN11, RB1, RET, ROS1, RRM1, SMAD4, SMARCB1, SMO, SPARC, STK11, TLE3, TOP2A, TOPO1, TP53, TS, TUBB3, VHL |
| Drug associated targets | 1p19q co-deletion, ABL1, AKT1, ALK, APC, AR, ARAF, ATM, BAP1, BRAF, BRCA1, BRCA2, CDH1, CHEK1, CHEK2, cKIT, cMET, CSF1R, CTNNB1, DDR2, EGFR, EGFRvIII, ER, ERBB2 (HER2), ERBB3, ERBB4, ERCC1, FBXW7, FGFR1, FGFR2, FLT3, GNA11, GNAQ, GNAS, H3K36me3, HER2, HNF1A, HRAS, IDH1, IDH2, JAK2, JAK3, KDR (VEGFR2), KRAS, MDMT, MGMT, MGMT Methylation, Microsatellite instability, MLH1, MPL, MSH2, MSH6, NF1, NOTCH1, NPM1, NRAS, NY-ESO-1, PD-1, PDGFRA, PD-L1, Pgp, PIK3CA, PMS2, PR, PTEN, PTPN11, RAF1, RB1, RET, ROS1, ROS1, RRM1, SMAD4, SMARCB1, SMO, SPARC, STK11, TLE3, TOP2A, TOPO1, TP53, TRKA, TS, TUBB3, VHL, WT1 |
| Drug associated targets | ABL1, AKT1, ALK, APC, AR, ATM, BRAF, BRAF, BRCA1, BRCA2, CDH1, cKIT, cMET, CSF1R, CTNNB1, EGFR, EGFR (H-score), EGFRvIII, ER, ERBB2 (HER2), ERBB4, ERCC1, FBXW7, FGFR1, FGFR2, FLT3, GNA11, GNAQ, GNAS, HER2, HNF1A, HRAS, IDH1, IDH2, JAK2, JAK3, KDR (VEGFR2), KRAS, MGMT, MGMT Promoter Methylation, microsatellite instability (MSI), MLH1, MPL, MSH2, MSH6, NOTCH1, NPM1, NRAS, PD-1, PDGFRA, PD-L1, Pgp, PIK3CA, PMS2, PR, PTEN, PTPN11, RB1, RET, ROS1, RRM1, SMAD4, SMARCB1, SMO, SPARC, STK11, TLE3, TOP2A, TOPO1, TP53, TS, TUBB3, VHL |

TABLE 4-continued

Illustrative Biomarkers

| Illustrative Class | Biomarkers |
|---|---|
| Drug associated targets | 1p19q, ALK, ALK (2p23), Androgen Receptor, BRCA, cMET, EGFR, EGFR, EGFRvIII, ER, ERCC1, Her2, Her2/Neu, MGMT, MGMT Promoter Methylation, microsatellite instability (MSI), MLH1, MSH2, MSH6, PD-1, PD-L1, PMS2, PR, PTEN, ROS1, RRM1, TLE3, TOP2A, TOP2A, TOPO1, TS, TUBB3 |
| Drug associated targets | TOP2A, Chromosome 17 alteration, PBRM1 (PB1/BAF180), BAP1, SETD2 (ANTI-HISTONE H3), MDM2, Chromosome 12 alteration, ALK, CTLA4, CD3, NY-ESO-1, MAGE-A, TP, EGFR |
| 5-aminosalicyclic acid (5-ASA) efficacy | μ-protocadherin, KLF4, CEBPα |
| Cancer treatment associated markers | AR, AREG (Amphiregulin), BRAF, BRCA1, cKIT, cMET, EGFR, EGFR w/T790M, EML4-ALK, ER, ERBB3, ERBB4, ERCC1, EREG, GNA11, GNAQ, hENT-1, Her2, Her2 Exon 20 insert, IGF1R, Ki67, KRAS, MGMT, MGMT methylation, MSH2, MSI, NRAS, PGP (MDR1), PIK3CA, PR, PTEN, ROS1, ROS1 translocation, RRM1, SPARC, TLE3, TOPO1, TOPO2A, TS, TUBB3, VEGFR2 |
| Cancer treatment associated markers | AR, AREG, BRAF, BRCA1, cKIT, cMET, EGFR, EGFR w/T790M, EML4-ALK, ER, ERBB3, ERBB4, ERCC1, EREG, GNA11, GNAQ, Her2, Her2 Exon 20 insert, IGFR1, Ki67, KRAS, MGMT-Me, MSH2, MSI, NRAS, PGP (MDR-1), PIK3CA, PR, PTEN, ROS1 translocation, RRM1, SPARC, TLE3, TOPO1, TOPO2A, TS, TUBB3, VEGFR2 |
| Colon cancer treatment associated markers | AREG, BRAF, EGFR, EML4-ALK, ERCC1, EREG, KRAS, MSI, NRAS, PIK3CA, PTEN, TS, VEGFR2 |
| Colon cancer treatment associated markers | AREG, BRAF, EGFR, EML4-ALK, ERCC1, EREG, KRAS, MSI, NRAS, PIK3CA, PTEN, TS, VEGFR2 |
| Melanoma treatment associated markers | BRAF, cKIT, ERBB3, ERBB4, ERCC1, GNA11, GNAQ, MGMT, MGMT methylation, NRAS, PIK3CA, TUBB3, VEGFR2 |
| Melanoma treatment associated markers | BRAF, cKIT, ERBB3, ERBB4, ERCC1, GNA11, GNAQ, MGMT-Me, NRAS, PIK3CA, TUBB3, VEGFR2 |
| Ovarian cancer treatment associated markers | BRCA1, cMET, EML4-ALK, ER, ERBB3, ERCC1, hENT-1, HER2, IGF1R, PGP(MDR1), PIK3CA, PR, PTEN, RRM1, TLE3, TOPO1, TOPO2A, TS |
| Ovarian cancer treatment associated markers | BRCA1, cMET, EML4-ALK (translocation), ER, ERBB3, ERCC1, HER2, PIK3CA, PR, PTEN, RRM1, TLE3, TS |
| Breast cancer treatment associated markers | BRAF, BRCA1, EGFR, EGFR T790M, EML4-ALK, ER, ERBB3, ERCC1, HER2, Ki67, PGP (MDR1), PIK3CA, PR, PTEN, ROS1, ROS1 translocation, RRM1, TLE3, TOPO1, TOPO2A, TS |
| Breast cancer treatment associated markers | BRAF, BRCA1, EGFR w/T790M, EML4-ALK, ER, ERBB3, ERCC1, HER2, Ki67, KRAS, PIK3CA, PR, PTEN, ROS1 translocation, RRM1, TLE3, TOPO1, TOPO2A, TS |
| NSCLC cancer treatment associated markers | BRAF, BRCA1, cMET, EGFR, EGFR w/T790M, EML4-ALK, ERCC1, Her2 Exon 20 insert, KRAS, MSH2, PIK3CA, PTEN, ROS1 (trans), RRM1, TLE3, TS, VEGFR2 |
| NSCLC cancer treatment associated markers | BRAF, cMET, EGFR, EGFR w/T790M, EML4-ALK, ERCC1, Her2 Exon 20 insert, KRAS, MSH2, PIK3CA, PTEN, ROS1 translocation, RRM1, TLE3, TS |
| Mutated in cancers | AKT1, ALK, APC, ATM, BRAF, CDH1, CDKN2A, c-Kit, C-Met, CSF1R, CTNNB1, EGFR, ERBB2, ERBB4, FBXW7, FGFR1, FGFR2, FGFR3, FLT3, GNA11, GNAQ, GNAS, HNF1A, HRAS, IDH1, JAK2, JAK3, KDR, KRAS, MLH1, MPL, NOTCH1, NPM1, NRAS, PDGFRA, PIK3CA, PTEN, PTPN11, RB1, RET, SMAD4, SMARCB1, SMO, SRC, STK11, TP53, VHL |
| Mutated in cancers | ALK, BRAF, BRCA1, BRCA2, EGFR, ERRB2, GNA11, GNAQ, IDH1, IDH2, KIT, KRAS, MET, NRAS, PDGFRA, PIK3CA, PTEN, RET, SRC, TP53 |
| Mutated in cancers | AKT1, HRAS, GNAS, MEK1, MEK2, ERK1, ERK2, ERBB3, CDKN2A, PDGFRB, IFG1R, FGFR1, FGFR2, FGFR3, ERBB4, SMO, DDR2, GRB1, PTCH, SHH, PD1, UGT1A1, BIM, ESR1, MLL, AR, CDK4, SMAD4 |
| Mutated in cancers | ABL, APC, ATM, CDH1, CSFR1, CTNNB1, FBXW7, FLT3, HNF1A, JAK2, JAK3, KDR, MLH1, MPL, NOTCH1, NPM1, PTPN11, RB1, SMARCB1, STK11, VHL |

TABLE 4-continued

Illustrative Biomarkers

| Illustrative Class | Biomarkers |
|---|---|
| Mutated in cancers | ABL1, AKT1, AKT2, AKT3, ALK, APC, AR, ARAF, ARFRP1, ARID1A, ARID2, ASXL1, ATM, ATR, ATRX, AURKA, AURKB, AXL, BAP1, BARD1, BCL2, BCL2L2, BCL6, BCOR, BCORL1, BLM, BRAF, BRCA1, BRCA2, BRIP1, BTK, CARD11, CBFB, CBL, CCND1, CCND2, CCND3, CCNE1, CD79A, CD79B, CDC73, CDH1, CDK12, CDK4, CDK6, CDK8, CDKN1B, CDKN2A, CDKN2B, CDKN2C, CEBPA, CHEK1, CHEK2, CIC, CREBBP, CRKL, CRLF2, CSF1R, CTCF, CTNNA1, CTNNB1, DAXX, DDR2, DNMT3A, DOT1L, EGFR, EMSY (C11orf30), EP300, EPHA3, EPHA5, EPHB1, ERBB2, ERBB3, ERBB4, ERG, ESR1, EZH2, FAM123B (WTX), FAM46C, FANCA, FANCC, FANCD2, FANCE, FANCF, FANCG, FANCL, FBXW7, FGF10, FGF14, FGF19, FGF23, FGF3, FGF4, FGF6, FGFR1, FGFR2, FGFR3, FGFR4, FLT1, FLT3, FLT4, FOXL2, GATA1, GATA2, GATA3, GID4 (C17orf39), GNA11, GNA13, GNAQ, GNAS, GPR124, GRIN2A, GSK3B, HGF, HRAS, IDH1, IDH2, IGF1R, IKBKE, IKZF1, IL7R, INHBA, IRF4, IRS2, JAK1, JAK2, JAK3, JUN, KAT6A (MYST3), KDM5A, KDM5C, KDM6A, KDR, KEAP1, KIT, KLHL6, KRAS, LRP1B, MAP2K1, MAP2K2, MAP2K4, MAP3K1, MCL1, MDM2, MDM4, MED12, MEF2B, MEN1, MET, MITF, MLH1, MLL, MLL2, MPL, MRE11A, MSH2, MSH6, MTOR, MUTYH, MYC, MYCL1, MYCN, MYD88, NF1, NF2, NFE2L2, NFKBIA, NKX2-1, NOTCH1, NOTCH2, NPM1, NRAS, NTRK1, NTRK2, NTRK3, NUP93, PAK3, PALB2, PAX5, PBRM1, PDGFRA, PDGFRB, PDK1, PIK3CA, PIK3CG, PIK3R1, PIK3R2, PPP2R1A, PRDM1, PRKAR1A, PRKDC, PTCH1, PTEN, PTPN11, RAD50, RAD51, RAF1, RARA, RB1, RET, RICTOR, RNF43, RPTOR, RUNX1, SETD2, SF3B1, SMAD2, SMAD4, SMARCA4, SMARCB1, SMO, SOCS1, SOX10, SOX2, SPEN, SPOP, SRC, STAG2, STAT4, STK11, SUFU, TET2, TGFBR2, TNFAIP3, TNFRSF14, TOP1, TP53, TSC1, TSC2, TSHR, VHL, WISP3, WT1, XPO1, ZNF217, ZNF703 |
| Gene rearrangement in cancer | ALK, BCR, BCL2, BRAF, EGFR, ETV1, ETV4, ETV5, ETV6, EWSR1, MLL, MYC, NTRK1, PDGFRA, RAF1, RARA, RET, ROS1, TMPRSS2 |
| Cancer Related | ABL1, ACE2, ADA, ADH1C, ADH4, AGT, AKT1, AKT2, AKT3, ALK, APC, AR, ARAF, AREG, ARFRP1, ARID1A, ARID2, ASNS, ASXL1, ATM, ATR, ATRX, AURKA, AURKB, AXL, BAP1, BARD1, BCL2, BCL2L2, BCL6, BCOR, BCORL1, BCR, BIRC5 (survivin), BLM, BRAF, BRCA1, BRCA2, BRIP1, BTK, CA2, CARD11, CAV, CBFB, CBL, CCND1, CCND2, CCND3, CCNE1, CD33, CD52 (CDW52), CD79A, CD79B, CDC73, CDH1, CDK12, CDK2, CDK4, CDK6, CDK8, CDKN1B, CDKN2A, CDKN2B, CDKN2C, CEBPA, CES2, CHEK1, CHEK2, CIC, CREBBP, CRKL, CRLF2, CSF1R, CTCF, CTNNA1, CTNNB1, DAXX, DCK, DDR2, DHFR, DNMT1, DNMT3A, DNMT3B, DOT1L, EGFR, EMSY (C11orf30), EP300, EPHA2, EPHA3, EPHA5, EPHB1, ERBB2, ERBB3, ERBB4, ERBR2 (typo?), ERCC3, EREG, ERG, ESR1, ETV1, ETV4, ETV5, ETV6, EWSR1, EZH2, FAM123B (WTX), FAM46C, FANCA, FANCC, FANCD2, FANCE, FANCF, FANCG, FANCL, FBXW7, FGF10, FGF14, FGF19, FGF23, FGF3, FGF4, FGF6, FGFR1, FGFR2, FGFR3, FGFR4, FLT1, FLT3, FLT4, FOLR1, FOLR2, FOXL2, FSHB, FSHPRH1, FSHR, GART, GATA1, GATA2, GATA3, GID4 (C17orf39), GNA11, GNA13, GNAQ, GNAS, GNRH1, GNRHR1, GPR124, GRIN2A, GSK3B, GSTP1, HDAC1, HGF, HIG1, HNF1A, HRAS, HSPCA (HSP90), IDH1, IDH2, IGF1R, IKBKE, IKZF1, IL13RA1, IL2, IL2RA (CD25), IL7R, INHBA, IRF4, IRS2, JAK1, JAK2, JAK3, JUN, KAT6A (MYST3), KDM5A, KDM5C, KDM6A, KDR (VEGFR2), KEAP1, KIT, KLHL6, KRAS, LCK, LRP1B, LTB, LTBR, MAP2K1, MAP2K2, MAP2K4, MAP3K1, MAPK, MCL1, MDM2, MDM4, MED12, MEF2B, MEN1, MET, MGMT, MITF, MLH1, MLL, MLL2, MPL, MRE11A, MS4A1 (CD20), MSH2, MSH6, MTAP, MTOR, MUTYH, MYC, MYCL1, MYCN, MYD88, NF1, NF2, NFE2L2, NFKB1, NFKB2, NFKBIA, NGF, NKX2-1, NOTCH1, NOTCH2, NPM1, NRAS, NTRK1, NTRK2, NTRK3, NUP93, ODC1, OGFR, PAK3, PALB2, PAX5, PBRM1, PDGFC, PDGFRA, PDGFRB, PDK1, PGP, PGR (PR), PIK3CA, PIK3CG, PIK3R1, PIK3R2, POLA, PPARG, PPARGC1, PPP2R1A, PRDM1, PRKAR1A, PRKDC, PTCH1, PTEN, PTPN11, RAD50, RAD51, RAF1, RARA, RB1, RET, RICTOR, RNF43, ROS1, RPTOR, RRM1, RRM2, RRM2B, RUNX1, RXR, RXRB, RXRG, SETD2, SF3B1, SMAD2, SMAD4, SMARCA4, SMARCB1, SMO, SOCS1, SOX10, SOX2, SPARC, SPEN, SPOP, SRC, SST, SSTR1, SSTR2, SSTR3, SSTR4, SSTR5, STAG2, STAT4, STK11, SUFU, TET2, TGFBR2, TK1, TLE3, TMPRSS2, TNF, TNFAIP3, TNFRSF14, TOP1, TOP2, TOP2A, TOP2B, TP53, TS, TSC1, TSC2, TSHR, TUBB3, TXN, TYMP, VDR, VEGF (VEGFA), VEGFC, VHL, WISP3, WT1, XDH, XPO1, YES1, ZAP70, ZNF217, ZNF703 |
| Cancer Related | 5T4, ABI1, ABL1, ABL2, ACKR3, ACSL3, ACSL6, ACVR1B, ACVR2A, AFF1, AFF3, AFF4, AKAP9, AKT1, AKT2, AKT3, ALDH2, ALK, AMER1, ANG1/ANGPT1/TM7SF2, ANG2/ANGPT2/VPS51, APC, AR, ARAF, ARFRP1, ARHGAP26, ARHGEF12, ARID1A, ARID1B, ARID2, ARNT, ASPSCR1, ASXL1, ATF1, ATIC, ATM, ATP1A1, ATP2B3, ATR, ATRX, AURKA, AURKB, AXIN1, AXL, BAP1, BARD1, BBC3, BCL10, BCL11A, BCL11B, BCL2, BCL2L1, BCL2L11, BCL2L2, BCL3, BCL6, BCL7A, BCL9, BCOR, BCORL1, BCR, BIRC3, BLM, BMPR1A, BRAF, BRCA1, BRCA2, BRD3, BRD4, BRIP1, BTG1, BTK, BUB1B, c-KIT, C11orf30, c15orf21, C15orf65, C2orf44, CA6, CACNA1D, CALR, CAMTA1, CANT1, CARD11, CARS, CASC5, CASP8, CBFA2T3, CBFB, |

TABLE 4-continued

Illustrative Biomarkers

| Illustrative Class | Biomarkers |
|---|---|
| | CBL, CBLB, CBLC, CCDC6, CCNB1IP1, CCND1, CCND2, CCND3, CCNE1, CD110, CD123, CD137, CD19, CD20, CD274, CD27L, CD38, CD4, CD74, CD79A, CD79B, CDC73, CDH1, CDH11, CDK12, CDK4, CDK6, CDK7, CDK8, CDK9, CDKN1A, CDKN1B, CDKN2A, CDKN2B, CDKN2C, CDX2, CEBPA, CHCHD7, CHD2, CHD4, CHEK1, CHEK2, CHIC2, Chk1, CHN1, CIC, CIITA, CLP1, CLTC, CLTCL1, CNBP, CNOT3, CNTRL, COL1A1, COPB1, CoREST, COX6C, CRAF, CREB1, CREB3L1, CREB3L2, CREBBP, CRKL, CRLF2, CRTC1, CRTC3, CSF1R, CSF3R, CTCF, CTLA4, CTNNA1, CTNNB1, CUL3, CXCR4, CYLD, CYP17A1, CYP2D6, DAXX, DDB2, DDIT3, DDR1, DDR2, DDX10, DDX5, DDX6, DEK, DICER1, DLL-4, DNAPK, DNM2, DNMT3A, DOT1L, EBF1, ECT2L, EGFR, EIF4A2, ELF4, ELK4, ELL, ELN, EML4, EP300, EPHA3, EPHA5, EPHA7, EPHA8, EPHB1, EPHB2, EPS15, ERBB2, ERBB3, ERBB4, ERC1, ERCC1, ERCC2, ERCC3, ERCC4, ERCC5, ERG, ERRFI1, ESR1, ETBR, ETV1, ETV4, ETV5, ETV6, EWSR1, EXT1, EXT2, EZH2, EZR, FAK, FAM46C, FANCA, FANCC, FANCD2, FANCE, FANCF, FANCG, FANCL, FAS, FAT1, FBXO11, FBXW7, FCRL4, FEV, FGF10, FGF14, FGF19, FGF2, FGF23, FGF3, FGF4, FGF6, FGFR1, FGFR1OP, FGFR2, FGFR3, FGFR4, FH, FHIT, FIP1L1, FKBP12, FLCN, FLI1, FLT1, FLT3, FLT4, FNBP1, FOXA1, FOXL2, FOXO1, FOXO3, FOXO4, FOXP1, FRS2, FSTL3, FUBP1, FUS, GABRA6, GAS7, GATA1, GATA2, GATA3, GATA4, GATA6, GID4, GITR, GLI1, GMPS, GNA11, GNA13, GNAQ, GNAS, GNRH1, GOLGA5, GOPC, GPC3, GPHN, GPR124, GRIN2A, GRM3, GSK3B, GUCY2C, H3F3A, H3F3B, HCK, HERPUD1, HEY1, HGF, HIP1, HIST1H3B, HIST1H4I, HLF, HMGA1, HMGA2, HMT, HNF1A, HNRNPA2B1, HOOK3, HOXA11, HOXA13, HOXA9, HOXC11, HOXC13, HOXD11, HOXD13, HRAS, HSD3B1, HSP90AA1, HSP90AB1, IAP, IDH1, IDH2, IGF1R, IGF2, IKBKE, IKZF1, IL2, IL21R, IL6, IL6ST, IL7R, INHBA, INPP4B, IRF2, IRF4, IRS2, ITGAV, ITGB1, ITK, JAK1, JAK2, JAK3, JAZF1, JUN, KAT6A, KAT6B, KCNJ5, KDM5A, KDM5C, KDM6A, KDR, KDSR, KEAP1, KEL, KIAA1549, KIF5B, KIR3DL1, KLF4, KLHL6, KLK2, KMT2A, KMT2C, KMT2D, KRAS, KTN1, LASP1, LCK, LCP1, LGALS3, LGR5, LHFP, LIFR, LMO1, LMO2, LOXL2, LPP, LRIG3, LRP1B, LSD1, LYL1, LYN, LZTR1, MAF, MAFB, MAGI2, MALT1, MAML2, MAP2K1, MAP2K2, MAP2K4, MAP3K1, MAPK1, MAPK11, MAX, MCL1, MDM2, MDM4, MDS2, MECOM, MED12, MEF2B, MEK1, MEK2, MEN1, MET, MITF, MKL1, MLF1, MLH1, MLLT1, MLLT10, MLLT11, MLLT3, MLLT4, MLLT6, MMP9, MN1, MNX1, MPL, MPS1, MRE11A, MS4A1, MSH2, MSH6, MSI2, MSN, MST1R, MTCP1, MTOR, MUC1, MUC16, MUTYH, MYB, MYC, MYCL, MYCN, MYD88, MYH11, MYH9, NACA, NAE1, NBN, NCKIPSD, NCOA1, NCOA2, NCOA4, NDRG1, NF1, NF2, NFE2L2, NFIB, NFKB2, NFKBIA, NIN, NKX2-1, NONO, NOTCH1, NOTCH2, NOTCH3, NPM1, NR4A3, NRAS, NSD1, NT5C2, NTRK1, NTRK2, NTRK3, NUMA1, NUP214, NUP93, NUP98, NUTM1, NUTM2B, OLIG2, OMD, P2RY8, PAFAH1B2, PAK3, PALB2, PARK2, PARP1, PATZ1, PAX3, PAX5, PAX7, PAX8, PBRM1, PBX1, PCM1, PCSK7, PDCD1, PDCD1LG2, PDE4DIP, PDGFB, PDGFRA, PDGFRB, PDK1, PER1, PHF6, PHOX2B, PICALM, PIK3C2B, PIK3CA, PIK3CB, PIK3CD, PIK3CG, PIK3R1, PIK3R2, PIM1, PKC, PLAG1, PLCG2, PML, PMS1, PMS2, POLD1, POLE, POT1, POU2AF1, POU5F1, PPARG, PPP2R1A, PRCC, PRDM1, PRDM16, PREX2, PRF1, PRKAR1A, PRKCI, PRKDC, PRLR, PRRX1, PRSS8, PSIP1, PTCH1, PTEN, PTK2, PTPN11, PTPRC, PTPRD, QKI, RABEP1, RAC1, RAD21, RAD50, RAD51, RAD51B, RAF1, RALGDS, RANBP17, RANBP2, RANKL, RAP1GDS1, RARA, RB1, RBM10, RBM15, RECQL4, REL, RET, RHOH, RICTOR, RMI2, RNF213, RNF43, ROS1, RPL10, RPL20, RPL5, RPN1, RPS6KB1, RPTOR, RUNX1, RUNx1T1, SBDS, SDC4, SDHA, SDHAF2, SDHB, SDHC, SDHD, SEPT5, SEPT6, SEPT9, SET, SETBP1, SETD2, SF3B1, SFPQ, SH2B3, SH3GL1, SLAMF7, SLC34A2, SLC45A3, SLIT2, SMAD2, SMAD3, SMAD4, SMARCA4, SMARCB1, SMARCE1, SMO, SNCAIP, SNX29, SOCS1, SOX10, SOX2, SOX9, SPECC1, SPEN, SPOP, SPTA1, SRC, SRGAP3, SRSF2, SRSF3, SS18, SS18L1, SSX1, SSX2, SSX4, STAG2, STAT3, STAT4, STAT5B, STEAP1, STIL, STK11, SUFU, SUZ12, SYK, TAF1, TAF15, TAL1, TAL2, TBL1XR1, TBX3, TCEA1, TCF12, TCF3, TCF7L2, TCL1A, TERC, TERT, TET1, TET2, TFE3, TFEB, TFG, TFPT, TFRC, TGFB1, TGFBR2, THRAP3, TIE2, TLX1, TLX3, TMPRSS2, TNFAIP3, TNFRSF14, TNFRSF17, TOP1, TOP2A, TP53, TPM3, TPM4, TPR, TRAF7, TRIM26, TRIM27, TRIM33, TRIP11, TRRAP, TSC1, TSC2, TSHR, TTL, U2AF1, UBA1, UBR5, USP6, VEGFA, VEGFB, VEGFR, VHL, VTI1A, WAS, WEE1, WHSC1, WHSC1L1, WIF1, WISP3, WNT11, WNT2B, WNT3, WNT3A, WNT4, WNT5A, WNT6, WNT7B, WRN, WT1, WWTR1, XPA, XPC, XPO1, YWHAE, ZAK, ZBTB16, ZBTB2, ZMYM2, ZNF217, ZNF331, ZNF384, ZNF521, ZNF703, ZRSR2 |
| Cancer Related | ABL2, ACSL3, ACSL6, AFF1, AFF3, AFF4, AKAP9, AKT3, ALDH2, APC, ARFRP1, ARHGAP26, ARHGEF12, ARID2, ARNT, ASPSCR1, ASXL1, ATF1, ATIC, ATM, ATP1A1, ATR, AURKA, AXIN1, AXL, BAP1, BARD1, BCL10, BCL11A, BCL2L11, BCL3, BCL6, BCL7A, BCL9, BCR, BIRC3, BLM, BMPR1A, BRAF, BRCA1, BRCA2, BRIP1, BUB1B, C11orf30, C2orf44, CACNA1D, CALR, CAMTA1, CANT1, CARD11, CARS, CASC5, CASP8, CBFA2T3, CBFB, CBL, CBLB, CCDC6, CCNB1IP1, CCND2, CD274, CD74, CD79A, CDC73, CDH11, CDKN1B, CDX2, CHEK1, CHEK2, CHIC2, CHN1, CIC, CIITA, CLP1, CLTC, |

TABLE 4-continued

Illustrative Biomarkers

| Illustrative Class | Biomarkers |
|---|---|
| | CLTCL1, CNBP, CNTRL, COPB1, CREB1, CREB3L1, CREB3L2, CRTC1, CRTC3, CSF1R, CSF3R, CTCF, CTLA4, CTNNA1, CTNNB1, CYLD, CYP2D6, DAXX, DDR2, DDX10, DDX5, DDX6, DEK, DICER1, DOT1L, EBF1, ECT2L, ELK4, ELL, EML4, EPHA3, EPHA5, EPHB1, EPS15, ERBB3, ERBB4, ERC1, ERCC2, ERCC3, ERCC4, ERCC5, ERG, ESR1, ETV1, ETV5, ETV6, EWSR1, EXT1, EXT2, EZR, FANCA, FANCC, FANCD2, FANCE, FANCG, FANCL, FAS, FBXO11, FBXW7, FCRL4, FGF14, FGF19, FGF23, FGF6, FGFR1OP, FGFR4, FH, FHIT, FIP1L1, FLCN, FLI1, FLT1, FLT3, FLT4, FNBP1, FOXA1, FOXO1, FOXP1, FUBP1, FUS, GAS7, GID4, GMPS, GNA13, GNAQ, GNAS, GOLGA5, GOPC, GPHN, GPR124, GRIN2A, GSK3B, H3F3A, H3F3B, HERPUD1, HGF, HIP1, HMGA1, HMGA2, HNRNPA2B1, HOOK3, HSP90AA1, HSP90AB1, IDH1, IDH2, IGF1R, IKZF1, IL2, IL21R, IL6ST, IL7R, IRF4, ITK, JAK1, JAK2, JAK3, JAZF1, KDM5A, KEAP1, KIAA1549, KIF5B, KIT, KLHL6, KMT2A, KMT2C, KMT2D, KRAS, KTN1, LCK, LCP1, LGR5, LHFP, LIFR, LPP, LRIG3, LRP1B, LYL1, MAF, MALT1, MAML2, MAP2K2, MAP2K4, MAP3K1, MDM4, MDS2, MEF2B, MEN1, MITF, MLF1, MLH1, MLLT1, MLLT10, MLLT3, MLLT4, MLLT6, MNX1, MRE11A, MSH2, MSH6, MSI2, MTOR, MYB, MYCN, MYD88, MYH11, MYH9, NACA, NCKIPSD, NCOA1, NCOA2, NCOA4, NF1, NFE2L2, NFIB, NFKB2, NIN, NOTCH2, NPM1, NR4A3, NSD1, NT5C2, NTRK2, NTRK3, NUP214, NUP93, NUP98, NUTM1, PALB2, PAX3, PAX5, PAX7, PBRM1, PBX1, PCM1, PCSK7, PDCD1, PDCD1LG2, PDGFB, PDGFRA, PDGFRB, PDK1, PER1, PICALM, PIK3CA, PIK3R1, PIK3R2, PIM1, PML, PMS2, POLE, POT1, POU2AF1, PPARG, PRCC, PRDM1, PRDM16, PRKAR1A, PRRX1, PSIP1, PTCH1, PTEN, PTPN11, PTPRC, RABEP1, RAC1, RAD50, RAD51, RAD51B, RAF1, RALGDS, RANBP17, RAP1GDS1, RARA, RBM15, REL, RET, RMI2, RNF43, RPL20, RPL5, RPN1, RPTOR, RUNX1, RUNX1T1, SBDS, SDC4, SDHAF2, SDHB, SDHC, SDHD, 8-Sep, SET, SETBP1, SETD2, SF3B1, SH2B3, SH3GL1, SLC34A2, SMAD2, SMAD4, SMARCB1, SMARCE1, SMO, SNX29, SOX10, SPECC1, SPEN, SRGAP3, SRSF2, SRSF3, SS18, SS18L1, STAT3, STAT4, STAT5B, STIL, STK11, SUFU, SUZ12, SYK, TAF15, TCF12, TCF3, TCF7L2, TET1, TET2, TFEB, TFG, TFRC, TGFBR2, TLX1, TNFAIP3, TNFRSF14, TNFRSF17, TP53, TPM3, TPM4, TPR, TRAF7, TRIM26, TRIM27, TRIM33, TRIP11, TRRAP, TSC1, TSC2, TSHR, TTL, U2AF1, USP6, VEGFA, VEGFB, VTI1A, WHSC1, WHSC1L1, WIF1, WISP3, WRN, WWTR1, XPA, XPC, XPO1, YWHAE, ZMYM2, ZNF217, ZNF331, ZNF384, ZNF521, ZNF703 |
| Gene fusions and mutations in cancer | AKT3, ALK, ARHGAP26, AXL, BRAF, BRD3/4, EGFR, ERG, ESR1, ETV1/4/5/6, EWSR1, FGFR1, FGFR2, FGFR3, FGR, INSR, MAML2, MAST1/2, MET, MSMB, MUSK, MYB, NOTCH1/2, NRG1, NTRK1/2/3, NUMBL, NUTM1, PDGFRA/B, PIK3CA, PKN1, PPARG, PRKCA/B, RAF1, RELA, RET, ROS1, RSPO2/3, TERT, TFE3, TFEB, THADA, TMPRSS2 |
| Gene fusions and mutations in cancer | ABL1 fusion to (ETV6, NUP214, RCSD1, RANBP2, SNX2, or ZMIZ1); ABL2 fusion to (PAG1 or RCSD1); CSF1R fusion to (SSBP2); PDGFRB fusion to (EBF1, SSBP2, TNIP1 or ZEB2); CRLF2 fusion to (P2RY8); JAK2 fusion to (ATF7IP, BCR, ETV6, PAX5, PPFIBP1, SSBP2, STRN3, TERF2, or TPR); EPOR fusion to (IGH or IGK); IL2RB fusion to (MYH9); NTRK3 fusion to (ETV6); PTK2B fusion to (KDM6A or STAG2); TSLP fusion to (IQGAP2); TYK2 fusion to (MYB) |
| Cytohesions | cytohesin-1 (CYTH1), cytohesin-2 (CYTH2; ARNO), cytohesin-3 (CYTH3; Grp1; ARNO3), cytohesin-4 (CYTH4) |
| Cancer/Angio | Erb 2, Erb 3, Erb 4, UNC93a, B7H3, MUC1, MUC2, MUC16, MUC17, 5T4, RAGE, VEGF A, VEGFR2, FLT1, DLL4, Epcam |
| Tissue (Breast) | BIG H3, GCDFP-15, PR(B), GPR 30, CYFRA 21, BRCA 1, BRCA 2, ESR 1, ESR2 |
| Tissue (Prostate) | PSMA, PCSA, PSCA, PSA, TMPRSS2 |
| Inflammation/ Immune | MFG-E8, IFNAR, CD40, CD80, MICB, HLA-DRb, IL-17-Ra |

Examples of additional biomarkers that can be incorporated into the methods and compositions of the invention include without limitation those disclosed in International Patent Application Nos. PCT/US2009/62880, filed Oct. 30, 2009; PCT/US2009/006095, filed Nov. 12, 2009; PCT/US2011/26750, filed Mar. 1, 2011; PCT/US2011/031479, filed Apr. 6, 2011; PCT/US11/48327, filed Aug. 18, 2011; PCT/US2008/71235, filed Jul. 25, 2008; PCT/US10/58461, filed Nov. 30, 2010; PCT/US2011/21160, filed Jan. 13, 2011; PCT/US2013/030302, filed Mar. 11, 2013; PCT/US12/25741, filed Feb. 17, 2012; PCT/2008/76109, filed Sep. 12, 2008; PCT/US12/42519, filed Jun. 14, 2012; PCT/US12/50030, filed Aug. 8, 2012; PCT/US12/49615, filed Aug. 3, 2012; PCT/US12/41387, filed Jun. 7, 2012; PCT/US2013/072019, filed Nov. 26, 2013; PCT/US2014/039858, filed May 28, 2013; PCT/IB2013/003092, filed Oct. 23, 2013; PCT/US13/76611, filed Dec. 19, 2013; PCT/US14/53306, filed Aug. 28, 2014; and PCT/US15/62184, filed Nov. 23, 2015; PCT/US16/40157, filed Jun. 29, 2016; PCT/US16/44595, filed Jul. 28, 2016; and PCT/US16/21632, filed Mar. 9, 2016; each of which applications is incorporated herein by reference in its entirety.

In various embodiments of the invention, the biomarkers or biosignature used to detect or assess any of the conditions or diseases disclosed herein can comprise one or more biomarkers in one of several different categories of markers, wherein the categories include without limitation one or more of: 1) disease specific biomarkers; 2) cell- or tissue-specific biomarkers; 3) vesicle-specific markers (e.g., general vesicle biomarkers); 4) angiogenesis-specific biomarkers; and 5) immunomodulatory biomarkers. Examples of all such markers are disclosed herein and known to a person having ordinary skill in the art. Furthermore, a biomarker known in the art that is characterized to have a role in a particular disease or condition can be adapted for use as a target in compositions and methods of the invention. In further embodiments, such biomarkers of interest may be cellular or vesicular surface markers, or a combination of surface markers and soluble or payload markers (e.g., molecules enclosed by a microvesicle). The biomarkers assessed can be from a combination of sources. For example, a disease or disorder may be detected or characterized by assessing a combination of proteins, nucleic acids, vesicles, circulating biomarkers, biomarkers from a tissue sample, and the like. In addition, as noted herein, the biological sample assessed can be any biological fluid, or can comprise individual components present within such biological fluid (e.g., vesicles, nucleic acids, proteins, or complexes thereof).

Biomarker Detection

The compositions and methods of the invention can be used to assess any useful biomarkers in a biological sample for characterizing a phenotype associated with the sample. Such biomarkers include all sorts of biological entities such as proteins, nucleic acids, lipids, carbohydrates, complexes of any thereof, and microvesicles.

The aptamers of the invention can be used to provide a biosignature in tissue or bodily fluids, e.g., by assessing various biomarkers therein. See, e.g., FIGS. 10B-C. The aptamers of the invention can also be used to assess levels or presence of their specific target molecule. See, e.g., FIG. 10A. In addition, aptamers of the invention are used to capture or isolated a component present in a biological sample that has the aptamer's target molecule present. For example, if a given surface antigen is present on a cell, cell fragment or cell-derived extracellular vesicle, a binding agent to the biomarker, including without limitation an aptamer provided by the invention, may be used to capture or isolate the cell, cell fragment or cell-derived extracellular vesicles. See, e.g., FIGS. 1A-B, 10A. Such captured or isolated entities may be further characterized to assess additional surface antigens or internal "payload" molecules, e.g., nucleic acid molecules, lipids, sugars, polypeptides or functional fragments thereof, or anything else present in the cellular milieu that may be used as a biomarker. Therefore, aptamers of the invention are used not only to assess one or more surface antigen of interest but are also used to separate a component present in a biological sample, where the components themselves can be comprised within the biosignature.

The methods of the invention can comprise multiplex analysis of at least 2, 3, 4, 5, 6, 7, 8, 9, 10, 11, 12, 13, 14, 15, 16, 17, 18, 19, 20, 25, 50, 75, 100, 200, 300, 400, 500, 600, 700, 800, 900, 1000, or more different biomarkers. For example, an oligonucleotide pool may contain any number of individual aptamers that can target different biomarkers. As another example, an assay can be performed with a plurality of particles that are differentially labeled. There can be at least 2, 3, 4, 5, 6, 7, 8, 9, 10, 11, 12, 13, 14, 15, 16, 17, 18, 19, 20, 25, 50, 75 or 100 differentially labeled particles. The particles may be externally labeled, such as with a tag, or they may be intrinsically labeled. Each differentially labeled particle can be coupled to a capture agent, such as a antibody or aptamer, and can be used to capture its target. The multiple capture agents can be selected to characterize a phenotype of interest, including capture agents against general vesicle biomarkers, cell-of-origin specific biomarkers, and disease biomarkers. One or more captured biomarkers can be detected by a plurality of binding agents. The binding agent can be directly labeled to facilitate detection. Alternatively, the binding agent is labeled by a secondary agent. For example, the binding agent may be an antibody or aptamer for a biomarker, wherein the binding agent is linked to biotin. A secondary agent comprises streptavidin linked to a reporter and can be added to detect the biomarker. In some embodiments, the captured vesicle is assayed for at least 2, 3, 4, 5, 6, 7, 8, 9, 10, 11, 12, 13, 14, 15, 16, 17, 18, 19, 20, 25, 50, 75 or 100 different biomarkers. For example, multiple detectors, i.e., detection of multiple biomarkers of a captured vesicle or population of vesicles, can increase the signal obtained, permitted increased sensitivity, specificity, or both, and the use of smaller amounts of samples. Detection can be with more than one biomarker, including without limitation more than one vesicle marker such as in any of Tables 3-4, and Tables 10-17.

An immunoassay based method (e.g., sandwich assay) can be used to detect a biomarker of interest. An example includes ELISA. A binding agent can be bound to a well. For example, a binding agent such as an aptamer or antibody to biomarker of interest can be attached to a well. A captured biomarker can be detected based on the methods described herein. FIG. 1A shows an illustrative schematic for a sandwich-type of immunoassay. The capture agent can be against a cellular or vesicular antigen of. In the figure, the captured entities are detected using fluorescently labeled binding agent (detection agent) against antigens of interest. Multiple capture binding agents can be used, e.g., in distinguishable addresses on an array or different wells of an immunoassay plate. The detection binding agents can be against the same antigen as the capture binding agent, or can be directed against other markers. The capture binding agent can be any useful binding agent, e.g., tethered aptamers, antibodies or lectins, and/or the detector antibodies can be similarly substituted, e.g., with detectable (e.g., labeled) aptamers, antibodies, lectins or other binding proteins or entities.

In an embodiment, one or more capture agents to a general vesicle biomarker, a cell-of-origin marker, and/or a disease marker are used along with detection agents against general vesicle biomarker, such as tetraspanin molecules including without limitation one or more of CD9, CD63 and CD81, or other markers in Table 3 herein. Examples of microvesicle surface antigens are disclosed herein, e.g. in Tables 3-4 and 10-17. Further biomarkers and detection techniques are disclosed in International Patent Application Nos. PCT/US2009/62880, filed Oct. 30, 2009; PCT/US2009/006095, filed Nov. 12, 2009; PCT/US2011/26750, filed Mar. 1, 2011; PCT/US2011/031479, filed Apr. 6, 2011; PCT/US11/48327, filed Aug. 18, 2011; PCT/US2008/71235, filed Jul. 25, 2008; PCT/US10/58461, filed Nov. 30, 2010; PCT/US2011/21160, filed Jan. 13, 2011; PCT/US2013/030302, filed Mar. 11, 2013; PCT/US12/25741, filed Feb. 17, 2012; PCT/2008/76109, filed Sep. 12, 2008; PCT/US12/42519, filed Jun. 14, 2012; PCT/US12/50030, filed Aug. 8, 2012; PCT/US12/49615, filed Aug. 3, 2012; PCT/US12/41387, filed Jun. 7, 2012; PCT/US2013/072019, filed Nov. 26, 2013; PCT/US2014/039858, filed May 28, 2013; PCT/IB2013/003092, filed Oct. 23, 2013; PCT/US13/76611, filed Dec. 19, 2013; PCT/US14/53306, filed Aug. 28, 2014; PCT/US15/62184, filed Nov. 23, 2015; PCT/US16/40157, filed Jun. 29, 2016; PCT/US16/44595, filed Jul. 28, 2016; and PCT/US16/21632, filed Mar. 9, 2016; each of which applications is incorporated herein by reference in its entirety.

Techniques of detecting biomarkers or capturing sample components using an aptamer of the invention include the use of a planar substrate such as an array (e.g., biochip or microarray), with molecules immobilized to the substrate as capture agents that facilitate the detection of a particular biosignature. The array can be provided as part of a kit for assaying one or more biomarkers. Aptamers of the invention can be included in an array for detection and diagnosis of diseases including presymptomatic diseases. In some embodiments, an array comprises a custom array comprising biomolecules selected to specifically identify biomarkers of interest. Customized arrays can be modified to detect biomarkers that increase statistical performance, e.g., additional biomolecules that identifies a biosignature which lead to improved cross-validated error rates in multivariate prediction models (e.g., logistic regression, discriminant analysis, or regression tree models). In some embodiments, customized array(s) are constructed to study the biology of a disease, condition or syndrome and profile biosignatures in defined physiological states. Markers for inclusion on the customized array be chosen based upon statistical criteria, e.g., having a desired level of statistical significance in differentiating between phenotypes or physiological states. In some embodiments, standard significance of p-value=0.05 is chosen to exclude or include biomolecules on the microarray. The p-values can be corrected for multiple comparisons. As an illustrative example, nucleic acids extracted from samples from a subject with or without a disease can be hybridized to a high density microarray that binds to thousands of gene sequences. Nucleic acids whose levels are significantly different between the samples with or without the disease can be selected as biomarkers to distinguish samples as having the disease or not. A customized array can be constructed to detect the selected biomarkers. In some embodiments, customized arrays comprise low density microarrays, which refer to arrays with lower number of addressable binding agents, e.g., tens or hundreds instead of thousands. Low density arrays can be formed on a substrate. In some embodiments, customizable low density arrays use PCR amplification in plate wells, e.g., TaqMan® Gene Expression Assays (Applied Biosystems by Life Technologies Corporation, Carlsbad, Calif.).

An aptamer of the invention or other useful binding agent may be linked directly or indirectly to a solid surface or substrate. A solid surface or substrate can be any physically separable solid to which a binding agent can be directly or indirectly attached including, but not limited to, surfaces provided by microarrays and wells, particles such as beads, columns, optical fibers, wipes, glass and modified or functionalized glass, quartz, mica, diazotized membranes (paper or nylon), polyformaldehyde, cellulose, cellulose acetate, paper, ceramics, metals, metalloids, semiconductive materials, quantum dots, coated beads or particles, other chromatographic materials, magnetic particles; plastics (including acrylics, polystyrene, copolymers of styrene or other materials, polypropylene, polyethylene, polybutylene, polyurethanes, Teflon material, etc.), polysaccharides, nylon or nitrocellulose, resins, silica or silica-based materials including silicon and modified silicon, carbon, metals, inorganic glasses, plastics, ceramics, conducting polymers (including polymers such as polypyrrole and polyindole); micro or nanostructured surfaces such as nucleic acid tiling arrays, nanotube, nanowire, or nanoparticulate decorated surfaces; or porous surfaces or gels such as methacrylates, acrylamides, sugar polymers, cellulose, silicates, or other fibrous or stranded polymers. In addition, as is known in the art, the substrate may be coated using passive or chemically-derivatized coatings with any number of materials, including polymers, such as dextrans, acrylamides, gelatins or agarose. Such coatings can facilitate the use of the array with a biological sample.

An aptamer or other useful binding agent can be conjugated to a detectable entity or label. Appropriate labels include without limitation a magnetic label, a fluorescent moiety, an enzyme, a chemiluminescent probe, a metal particle, a non-metal colloidal particle, a polymeric dye particle, a pigment molecule, a pigment particle, an electrochemically active species, semiconductor nanocrystal or other nanoparticles including quantum dots or gold particles, fluorophores, quantum dots, or radioactive labels. Protein labels include green fluorescent protein (GFP) and variants thereof (e.g., cyan fluorescent protein and yellow fluorescent protein); and luminescent proteins such as luciferase, as described below. Radioactive labels include without limitation radioisotopes (radionuclides), such as $^3$H, $^{11}$C, $^{14}$C, $^{18}$F, $^{32}$P, $^{35}$S, $^{64}$Cu, $^{68}$Ga, $^{86}$Y, $^{99}$Tc, $^{111}$In, $^{123}$I, $^{124}$I, $^{125}$I, $^{131}$I, $^{133}$Xe, $^{177}$Lu, $^{211}$At, or $^{213}$Bi. Fluorescent labels include without limitation a rare earth chelate (e.g., europium chelate), rhodamine; fluorescein types including without limitation FITC, 5-carboxyfluorescein, 6-carboxy fluorescein; a rhodamine type including without limitation TAMRA; dansyl; Lissamine; cyanines; phycoerythrins; Texas Red; Cy3, Cy5, dapoxyl, NBD, Cascade Yellow, dansyl, PyMPO, pyrene, 7-diethylaminocoumarin-3-carboxylic acid and other coumarin derivatives, Marina Blue™, Pacific Blue™, Cascade Blue™, 2-anthracenesulfonyl, PyMPO, 3,4,9,10-perylene-tetracarboxylic acid, 2,7-difluorofluorescein (Oregon Green™ 488-X), 5-carboxyfluorescein, Texas Red™-X, Alexa Fluor 430, 5-carboxytetramethylrhodamine (5-TAMRA), 6-carboxytetramethylrhodamine (6-TAMRA), BODIPY FL, bimane, and Alexa Fluor 350, 405, 488, 500, 514, 532, 546, 555, 568, 594, 610, 633, 647, 660, 680, 700, and 750, and derivatives thereof, among many others. See, e.g., "The Handbook—A Guide to Fluorescent Probes and Labeling Technologies," Tenth Edition, available on the internet at probes (dot) invitrogen (dot) com/handbook. The fluorescent label can be one or more of FAM, dRHO, 5-FAM, 6FAM, dR6G, JOE, HEX, VIC, TET, dTAMRA, TAMRA, NED, dROX, PET, BHQ, Gold540 and LIZ.

Using conventional techniques, an aptamer can be directly or indirectly labeled. In a non-limiting example, the label is attached to the aptamer through biotin-streptavidin/avidin chemistry. For example, synthesize a biotinylated aptamer, which is then capable of binding a streptavidin molecule that is itself conjugated to a detectable label; non-limiting example is streptavidin, phycoerythrin conjugated (SAPE)). Methods for chemical coupling using multiple step procedures include biotinylation, coupling of trinitrophenol (TNP) or digoxigenin using for example succinimide esters of these compounds. Biotinylation can be accomplished by, for example, the use of D-biotinyl-N-hydroxysuccinimide Succinimide groups react effectively with amino groups at pH values above 7, and preferentially between about pH 8.0 and about pH 8.5. The labeling may comprise a secondary labeling system. As a non-limiting example, the aptamer can be conjugated to biotin or digoxigenin. Target bound aptamer can be detected using streptavidin/avidin or anti-digoxigenin antibodies, respectively.

Various enzyme-substrate labels may also be used in conjunction with a composition or method of the invention. Such enzyme-substrate labels are available commercially (e.g., U.S. Pat. No. 4,275,149). The enzyme generally catalyzes a chemical alteration of a chromogenic substrate that can be measured using various techniques. For example, the enzyme may catalyze a color change in a substrate, which can be measured spectrophotometrically. Alternatively, the enzyme may alter the fluorescence or chemiluminescence of the substrate. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRP), alkaline phosphatase (AP), β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Examples of enzyme-substrate combinations include, but are not limited to, horseradish peroxidase (HRP) with hydrogen peroxidase as a substrate, wherein the hydrogen peroxidase oxidizes a dye precursor (e.g., orthophenylene diamine (OPD) or 3,3',5,5'-tetramethylbenzidine hydrochloride (TMB)); alkaline phosphatase (AP) with para-nitrophenyl phosphate as chromogenic substrate; and β-D-galactosidase (β-D-Gal) with a chromogenic substrate (e.g., p-nitrophenyl-β-D-galactosidase) or fluorogenic substrate 4-methylumbelliferyl-β-D-galactosidase.

Aptamer(s) can be linked to a substrate such as a planar substrate. A planar array generally contains addressable locations (e.g., pads, addresses, or micro-locations) of biomolecules in an array format. The size of the array will depend on the composition and end use of the array. Arrays can be made containing from 2 different molecules to many thousands. Generally, the array comprises from two to as many as 100,000 or more molecules, depending on the end use of the array and the method of manufacture. A microarray for use with the invention comprises at least one biomolecule that identifies or captures a biomarker present in a biosignature of interest, e.g., a cell, microRNA or other biomolecule or vesicle that makes up the biosignature. In some arrays, multiple substrates are used, either of different or identical compositions. Accordingly, planar arrays may comprise a plurality of smaller substrates.

The present invention can make use of many types of arrays for detecting a biomarker, e.g., a biomarker associated with a biosignature of interest. Useful arrays or microarrays include without limitation DNA microarrays, such as cDNA microarrays, oligonucleotide microarrays and SNP microarrays, microRNA arrays, protein microarrays, antibody microarrays, tissue microarrays, cellular microarrays (also called transfection microarrays), chemical compound microarrays, and carbohydrate arrays (glycoarrays). These arrays are described in more detail above. In some embodiments, microarrays comprise biochips that provide high-density immobilized arrays of recognition molecules (e.g., aptamers or antibodies), where biomarker binding is monitored indirectly (e.g., via fluorescence).

An array or microarray that can be used to detect a biosignature comprising one or more aptamers of the invention can be made according to the methods described in U.S. Pat. Nos. 6,329,209; 6,365,418; 6,406,921; 6,475,808; and 6,475,809, and U.S. patent application Ser. No. 10/884,269, each of which is herein incorporated by reference in its entirety. Custom arrays to detect specific can be made using the methods described in these patents. Commercially available microarrays can also be used to carry out the methods of the invention, including without limitation those from Affymetrix (Santa Clara, Calif.), Illumina (San Diego, Calif.), Agilent (Santa Clara, Calif.), Exiqon (Denmark), or Invitrogen (Carlsbad, Calif.). Custom and/or commercial arrays include arrays for detection proteins, nucleic acids, and other biological molecules and entities (e.g., cells, vesicles, virii) as described herein.

In some embodiments, multiple capture molecules are disposed on an array, e.g., proteins, peptides or additional nucleic acid molecules. In certain embodiments, the proteins are immobilized using methods and materials that minimize the denaturing of the proteins, that minimize alterations in the activity of the proteins, or that minimize interactions between the protein and the surface on which they are immobilized. The capture molecules can comprise one or more aptamer of the invention. In one embodiment, an array is constructed for the hybridization of a pool of aptamers. The array can then be used to identify pool members that bind a sample, thereby facilitating characterization of a phenotype. See FIGS. 10B-10C and related disclosure for further details.

Array surfaces useful may be of any desired shape, form, or size. Non-limiting examples of surfaces include chips, continuous surfaces, curved surfaces, flexible surfaces, films, plates, sheets, or tubes. Surfaces can have areas ranging from approximately a square micron to approximately 500 $cm^2$. The area, length, and width of surfaces may be varied according to the requirements of the assay to be performed. Considerations may include, for example, ease of handling, limitations of the material(s) of which the surface is formed, requirements of detection systems, requirements of deposition systems (e.g., arrayers), or the like.

In certain embodiments, it is desirable to employ a physical means for separating groups or arrays of binding islands or immobilized biomolecules: such physical separation facilitates exposure of different groups or arrays to different solutions of interest. Therefore, in certain embodiments, arrays are situated within microwell plates having any number of wells. In such embodiments, the bottoms of the wells may serve as surfaces for the formation of arrays, or arrays may be formed on other surfaces and then placed into wells. In certain embodiments, such as where a surface without wells is used, binding islands may be formed or molecules may be immobilized on a surface and a gasket having holes spatially arranged so that they correspond to the islands or biomolecules may be placed on the surface. Such a gasket is preferably liquid tight. A gasket may be placed on a surface at any time during the process of making the array and may be removed if separation of groups or arrays is no longer desired.

In some embodiments, the immobilized molecules can bind to one or more biomarkers present in a biological sample contacting the immobilized molecules. Contacting the sample typically comprises overlaying the sample upon the array.

Modifications or binding of molecules in solution or immobilized on an array can be detected using detection techniques known in the art. Examples of such techniques include immunological techniques such as competitive binding assays and sandwich assays; fluorescence detection using instruments such as confocal scanners, confocal microscopes, or CCD-based systems and techniques such as fluorescence, fluorescence polarization (FP), fluorescence resonant energy transfer (FRET), total internal reflection fluorescence (TIRF), fluorescence correlation spectroscopy (FCS); colorimetric/spectrometric techniques; surface plasmon resonance, by which changes in mass of materials adsorbed at surfaces are measured; techniques using radioisotopes, including conventional radioisotope binding and scintillation proximity assays (SPA); mass spectroscopy, such as matrix-assisted laser desorption/ionization mass spectroscopy (MALDI) and MALDI-time of flight (TOF) mass spectroscopy; ellipsometry, which is an optical method of measuring thickness of protein films; quartz crystal microbalance (QCM), a very sensitive method for measuring mass of materials adsorbing to surfaces; scanning probe microscopies, such as atomic force microscopy (AFM), scanning force microscopy (SFM) or scanning electron microscopy (SEM); and techniques such as electrochemical, impedance, acoustic, microwave, and IR/Raman detection. See, e.g., Mere L, et al., "*Miniaturized FRET assays and microfluidics: key components for ultra-high-throughput screening,*" *Drug Discovery Today* 4(8):363-369 (1999), and references cited therein; Lakowicz J R, *Principles of Fluorescence Spectroscopy*, 2nd Edition, Plenum Press (1999), or Jain K K: *Integrative Omics, Pharmacoproteomics, and Human Body Fluids. In: Thongboonkerd V, ed., ed. Proteomics of Human Body Fluids: Principles, Methods and Applications.* Volume 1: Totowa, N.J.: Humana Press, 2007, each of which is herein incorporated by reference in its entirety.

Microarray technology can be combined with mass spectroscopy (MS) analysis and other tools. Electrospray interface to a mass spectrometer can be integrated with a capillary in a microfluidics device. For example, one commercially available system contains eTag reporters that are fluorescent labels with unique and well-defined electrophoretic mobilities; each label is coupled to biological or chemical probes via cleavable linkages. The distinct mobility address of each eTag reporter allows mixtures of these tags to be rapidly deconvoluted and quantitated by capillary electrophoresis. This system allows concurrent gene expression, protein expression, and protein function analyses from the same sample Jain K K: *Integrative Omics, Pharmacoproteomics, and Human Body Fluids. In: Thongboonkerd V, ed., ed. Proteomics of Human Body Fluids: Principles, Methods and Applications.* Volume 1: Totowa, N.J.: Humana Press, 2007, which is herein incorporated by reference in its entirety.

A biochip can include components for a microfluidic or nanofluidic assay. A microfluidic device can be used for isolating or analyzing biomarkers, such as determining a biosignature. Microfluidic systems allow for the miniaturization and compartmentalization of one or more processes for detecting a biosignature, and other processes. The microfluidic devices can use one or more detection reagents in at least one aspect of the system, and such a detection reagent can be used to detect one or more biomarkers. Various probes, antibodies, proteins, or other binding agents can be used to detect a biomarker within the microfluidic system. The detection agents, e.g., oligonucleotide probes of the invention, may be immobilized in different compartments of the microfluidic device or be entered into a hybridization or detection reaction through various channels of the device.

Nanofabrication techniques are opening up the possibilities for biosensing applications that rely on fabrication of high-density, precision arrays, e.g., nucleotide-based chips and protein arrays otherwise known as heterogeneous nanoarrays. Nanofluidics allows a further reduction in the quantity of fluid analyte in a microchip to nanoliter levels, and the chips used here are referred to as nanochips. See, e.g., Unger M et al., *Biotechniques* 1999; 27(5):1008-14, Kartalov E P et al., *Biotechniques* 2006; 40(1):85-90, each of which are herein incorporated by reference in their entireties. Commercially available nanochips currently provide simple one step assays such as total cholesterol, total protein or glucose assays that can be run by combining sample and reagents, mixing and monitoring of the reaction. Gel-free analytical approaches based on liquid chromatography (LC) and nanoLC separations (Cutillas et al. *Proteomics,* 2005; 5: 101-112 and Cutillas et al., *Mol Cell Proteomics* 2005; 4: 1038-1051, each of which is herein incorporated by reference in its entirety) can be used in combination with the nanochips.

An array suitable for identifying a disease, condition, syndrome or physiological status can be included in a kit. A kit can include, an aptamer of the invention, including as non-limiting examples, one or more reagents useful for preparing molecules for immobilization onto binding islands or areas of an array, reagents useful for detecting binding of biomarkers to immobilized molecules, e.g., aptamers, and instructions for use.

Further provided herein is a rapid detection device that facilitates the detection of a particular biosignature in a biological sample. The device can integrate biological sample preparation with polymerase chain reaction (PCR) on a chip. The device can facilitate the detection of a particular biosignature of a vesicle in a biological sample, and an example is provided as described in Pipper et al., *Angewandte Chemie,* 47(21), p. 3900-3904 (2008), which is herein incorporated by reference in its entirety. A biosignature can be incorporated using micro-/nano-electrochemical system (MEMS/NEMS) sensors and oral fluid for diagnostic applications as described in Li et al., *Adv Dent Res* 18(1): 3-5 (2005), which is herein incorporated by reference in its entirety.

As an alternative to planar arrays, assays using particles, such as bead based assays are also capable of use with an aptamer of the invention. Aptamers are easily conjugated with commercially available beads. See, e.g., Srinivas et al. Anal. Chem. 2011 Oct. 21, *Aptamer functionalized Microgel Particles for Protein Detection*; See also, review article on aptamers as therapeutic and diagnostic agents, Brody and Gold, Rev. Mol. Biotech. 2000, 74:5-13.

Figure 1B:
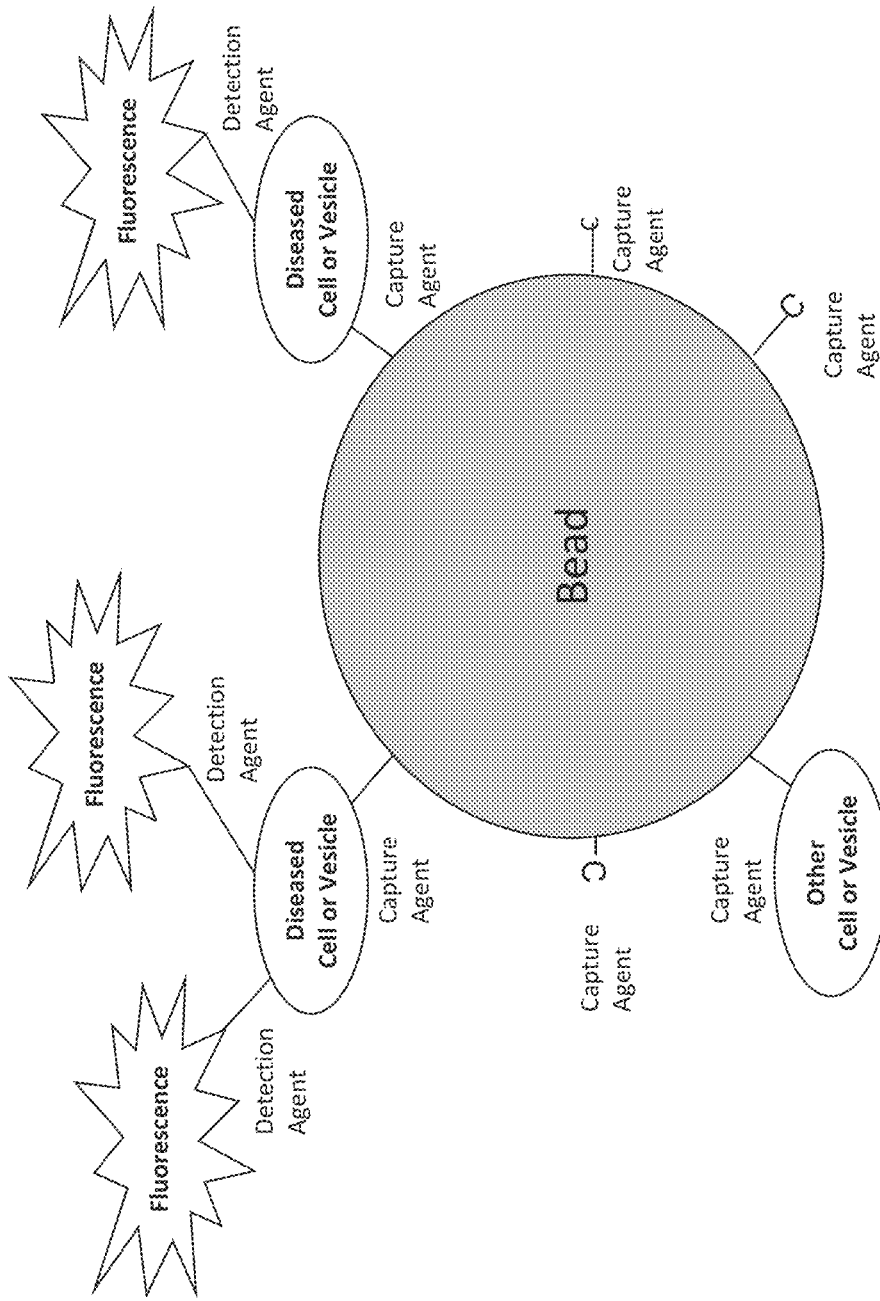

Multiparametric assays or other high throughput detection assays using bead coatings with cognate ligands and reporter molecules with specific activities consistent with high sensitivity automation can be used. In a bead based assay system, a binding agent such as an antibody or aptamer can be immobilized on an addressable microsphere. Each binding agent for each individual binding assay can be coupled to a distinct type of microsphere (i.e., microbead) and the assay reaction takes place on the surface of the microsphere, such as depicted in FIG. 1B. In a non-limiting example, a binding agent for a cell or microvesicle can be a capture antibody or aptamer coupled to a bead. Dyed microspheres with discrete fluorescence intensities are loaded separately with their appropriate binding agent or capture probes. The different bead sets carrying different binding agents can be pooled as desired to generate custom bead arrays. Bead arrays are then incubated with the sample in a single reaction vessel to perform the assay.

Bead-based assays can be used with one or more aptamers of the invention. A bead substrate can provide a platform for attaching one or more binding agents, including aptamer(s). For multiplexing, multiple different bead sets (e.g., Illumina, Luminex) can have different binding agents (specific to different target molecules). For example, a bead can be conjugated to an aptamer of the invention used to detect the presence (quantitatively or qualitatively) of an antigen of interest, or it can also be used to isolate a component present in a selected biological sample (e.g., cell, cell-fragment or vesicle comprising the target molecule to which the aptamer is configured to bind or associate). Any molecule of organic origin can be successfully conjugated to a polystyrene bead through use of commercially available kits.

One or more aptamers of the invention can be used with any bead based substrate, including but not limited to magnetic capture method, fluorescence activated cell sorting (FACS) or laser cytometry. Magnetic capture methods can include, but are not limited to, the use of magnetically activated cell sorter (MACS) microbeads or magnetic columns Examples of bead or particle based methods that can be modified to use an aptamer of the invention include methods and bead systems described in U.S. Pat. Nos. 4,551,435, 4,795,698, 4,925,788, 5,108,933, 5,186,827, 5,200,084 or 5,158,871; 7,399,632; 8,124,015; 8,008,019; 7,955,802; 7,445,844; 7,274,316; 6,773,812; 6,623,526; 6,599,331; 6,057,107; 5,736,330; International Patent Publication No. WO/2012/174282; WO/1993/022684.

Isolation or detection of circulating biomarkers, e.g., protein antigens, from a biological sample, or of the biomarker-comprising cells, cell fragments or vesicles may also be achieved using an aptamer of the invention in a cytometry process. As a non-limiting example, aptamers of the invention can be used in an assay comprising using a particle such as a bead or microsphere. The invention provides aptamers as binding agents, which may be conjugated to the particle. Flow cytometry can be used for sorting microscopic particles suspended in a stream of fluid. As particles pass through they can be selectively charged and on their exit can be deflected into separate paths of flow. It is therefore possible to separate populations from an original mix, such as a biological sample, with a high degree of accuracy and speed. Flow cytometry allows simultaneous multiparametric analysis of the physical and/or chemical characteristics of single cells flowing through an optical/electronic detection apparatus. A beam of light, usually laser light, of a single frequency (color) is directed onto a hydrodynamically focused stream of fluid. A number of detectors are aimed at the point where the stream passes through the light beam; one in line with the light beam (Forward Scatter or FSC) and several perpendicular to it (Side Scatter or SSC) and one or more fluorescent detectors.

Each suspended particle passing through the beam scatters the light in some way, and fluorescent chemicals in the particle may be excited into emitting light at a lower frequency than the light source. This combination of scattered and fluorescent light is picked up by the detectors, and by analyzing fluctuations in brightness at each detector (one for each fluorescent emission peak), it is possible to deduce various facts about the physical and chemical structure of each individual particle. FSC correlates with the cell size and SSC depends on the inner complexity of the particle, such as shape of the nucleus, the amount and type of cytoplasmic granules or the membrane roughness. Some flow cytometers have eliminated the need for fluorescence and use only light scatter for measurement.

Flow cytometers can analyze several thousand particles every second in "real time" and can actively separate out and isolate particles having specified properties. They offer high-throughput automated quantification, and separation, of the set parameters for a high number of single cells during each analysis session. Flow cytometers can have multiple lasers and fluorescence detectors, allowing multiple labels to be used to more precisely specify a target population by their phenotype. Thus, a flow cytometer, such as a multicolor flow cytometer, can be used to detect targets of interest using multiple fluorescent labels or colors. In some embodiments, the flow cytometer can also sort or isolate different targets of interest, such as by size or by different markers.

The flow cytometer may have one or more lasers, such as 1, 2, 3, 4, 5, 6, 7, 8, 9, 10 or more lasers. In some embodiments, the flow cytometer can detect more than one color or fluorescent label, such as at least 2, 3, 4, 5, 6, 7, 8, 9, 10, 11, 12, 13, 14, 15, 16, 17, 18, 19, or 20 different colors or fluorescent labels. For example, the flow cytometer can have at least 2, 3, 4, 5, 6, 7, 8, 9, 10, 11, 12, 13, 14, 15, 16, 17, 18, 19, or 20 fluorescence detectors.

Examples of commercially available flow cytometers include, but are not limited to the MoFlo™ XDP Cell Sorter (Beckman Coulter, Brea, Calif.), MoFlo™ Legacy Cell Sorter (Beckman Coulter, Brea, Calif.), BD FACSAria™ Cell Sorter (BD Biosciences, San Jose, Calif.), BD™ LSRII (BD Biosciences, San Jose, Calif.), and BD FACSCalibur™ (BD Biosciences, San Jose, Calif.). Use of multicolor or multi-fluor cytometers can be used in multiplex analysis. In some embodiments, the flow cytometer can sort, and thereby collect or sort more than one population of cells, microvesicles, or particles, based one or more characteristics. For example, two populations differ in size, such that the populations have a similar size range can be differentially detected or sorted. In another embodiment, two different populations are differentially labeled.

The data resulting from flow-cytometers can be plotted in 1 dimension to produce histograms or seen in 2 dimensions as dot plots or in 3 dimensions with newer software. The regions on these plots can be sequentially separated by a series of subset extractions which are termed gates. Specific gating protocols exist for diagnostic and clinical purposes especially in relation to hematology. The plots are often made on logarithmic scales. Because different fluorescent dye's emission spectra overlap, signals at the detectors have to be compensated electronically as well as computationally. Fluorophores for labeling biomarkers may include those described in Ormerod, *Flow Cytometry* 2nd ed., Springer-Verlag, New York (1999), and in Nida et al., *Gynecologic Oncology* 2005; 4 889-894 which is incorporated herein by reference. In a multiplexed assay, including but not limited to a flow cytometry assay, one or more different target molecules can be assessed using an aptamer of the invention.

One or more aptamer of the invention can be disposed on any useful planar or bead substrate. In one aspect of the invention one or more aptamer of the invention is disposed on a microfluidic device, thereby facilitating assessing, characterizing or isolating a component of a biological sample comprising a polypeptide antigen of interest or a functional fragment thereof. For example, the circulating antigen or a cell, cell fragment or cell-derived microvesicles comprising the antigen can be assessed using one or more aptamers of the invention (alternatively along with additional binding agents). Microfluidic devices, which may also be referred to as "lab-on-a-chip" systems, biomedical micro-electro-mechanical systems (bioMEMs), or multicomponent integrated systems, can be used for isolating and analyzing such entities. Such systems miniaturize and compartmentalize processes that allow for detection of biosignatures and other processes.

A microfluidic device can also be used for isolation of a cell, cell fragment or cell-derived microvesicles through size differential or affinity selection. For example, a microfluidic device can use one more channels for isolating entities from a biological sample based on size or by using one or more binding agents. A biological sample can be introduced into one or more microfluidic channels, which selectively allows the passage of the entity. The selection can be based on a property such as the size, shape, deformability, or biosignature.

In one embodiment, a heterogeneous population of cells, cell fragments, microvesicles or other biomarkers (e.g., protein complexes) is introduced into a microfluidic device, and one or more different homogeneous populations of such entities can be obtained. For example, different channels can have different size selections or binding agents to select for different populations of such entities. Thus, a microfluidic device can isolate a plurality of entities wherein at least a subset of the plurality comprises a different biosignature from another subset of the plurality. For example, the microfluidic device can isolate at least 2, 3, 4, 5, 6, 7, 8, 9, 10, 15, 20, 25, 30, 40, 50, 60, 70, 80, 90, or 100 different subsets, wherein each subset comprises a different biosignature.

In some embodiments, the microfluidic device can comprise one or more channels that permit further enrichment or selection of targets of interest. A population that has been enriched after passage through a first channel can be introduced into a second channel, which allows the passage of the desired population to be further enriched, such as through one or more binding agents present in the second channel.

Array-based assays and bead-based assays can be used with a microfluidic device. For example, the binding agent, such as an oligonucleotide probe, can be coupled to beads and the binding reaction between the beads and targets of the binding agent can be performed in a microfluidic device. Multiplexing can also be performed using a microfluidic device. Different compartments can comprise different binding agents for different target populations. In one embodiment, each population has a different biosignature. The hybridization reaction between the microsphere and target can be performed in a microfluidic device and the reaction mixture can be delivered to a detection device. The detection device, such as a dual or multiple laser detection system can be part of the microfluidic system and can use a laser to identify each bead or microsphere by its color-coding, and another laser can detect the hybridization signal associated with each bead.

Any appropriate microfluidic device can be used in the methods of the invention. Examples of microfluidic devices that may be used include but are not limited to those described in U.S. Pat. Nos. 7,591,936, 7,581,429, 7,579,136, 7,575,722, 7,568,399, 7,552,741, 7,544,506, 7,541,578, 7,518,726, 7,488,596, 7,485,214, 7,467,928, 7,452,713, 7,452,509, 7,449,096, 7,431,887, 7,422,725, 7,422,669, 7,419,822, 7,419,639, 7,413,709, 7,411,184, 7,402,229, 7,390,463, 7,381,471, 7,357,864, 7,351,592, 7,351,380, 7,338,637, 7,329,391, 7,323,140, 7,261,824, 7,258,837, 7,253,003, 7,238,324, 7,238,255, 7,233,865, 7,229,538, 7,201,881, 7,195,986, 7,189,581, 7,189,580, 7,189,368, 7,141,978, 7,138,062, 7,135,147, 7,125,711, 7,118,910, 7,118,661, 7,640,947, 7,666,361, 7,704,735; and International Patent Publication WO 2010/072410; each of which patents or applications are incorporated herein by reference in their entirety. Another example for use with methods disclosed herein is described in Chen et al., "Microfludic isolation and transcriptome analysis of serum vesicles," *Lab on a Chip*, Dec. 8, 2009 DOI: 10.1039/b916199f.

Other microfluidic devices for use with the invention include devices comprising elastomeric layers, valves and pumps, including without limitation those disclosed in U.S. Pat. Nos. 5,376,252, 6,408,878, 6,645,432, 6,719,868, 6,793,753, 6,899,137, 6,929,030, 7,040,338, 7,118,910, 7,144,616, 7,216,671, 7,250,128, 7,494,555, 7,501,245, 7,601,270, 7,691,333, 7,754,010, 7,837,946; U.S. Patent Application Nos. 2003/0061687, 2005/0084421, 2005/0112882, 2005/0129581, 2005/0145496, 2005/0201901, 2005/0214173, 2005/0252773, 2006/0006067; and EP Patent Nos. 0527905 and 1065378; each of which application is herein incorporated by reference.

The microfluidic device can have one or more binding agents attached to a surface in a channel, or present in a channel. For example, the microchannel can have one or more capture agents, such as an oligonucleotide probe of the invention. The surface of the channel can also be contacted with a blocking aptamer if desired. In one embodiment, a microchannel surface is treated with avidin/streptavidin and a capture agent, such as an antibody or aptamer, that is biotinylated can be injected into the channel to bind the avidin. In other embodiments, the capture agents are present in chambers or other components of a microfluidic device. The capture agents can also be attached to beads that can be manipulated to move through the microfluidic channels. In one embodiment, the capture agents are attached to magnetic beads. The beads can be manipulated using magnets.

A biological sample can be flowed into the microfluidic device, or a microchannel, at rates such as at least about 1, 2, 3, 4, 5, 6, 7, 8, 9, 10, 11, 12, 13, 14, 15, 16, 17, 18, 19, 20, 25, 30, 35, 40, 45, or 50 µl per minute, such as between about 1-50, 5-40, 5-30, 3-20 or 5-15 µl per minute. One or more targets of interest can be captured and directly detected in the microfluidic device. Alternatively, the captured target may be released and exit the microfluidic device prior to analysis. In another embodiment, one or more captured cells or microvesicles are lysed in the microchannel and the lysate can be analyzed. Lysis buffer can be flowed through the channel. The lysate can be collected and analyzed, such as performing RT-PCR, PCR, mass spectrometry, Western blotting, or other assays, to detect one or more biomarkers of the captured cells or microvesicles.

Microvesicles and related biomarkers can be analyzed using the oligonucleotide probes of the invention. Microvesicle isolation can be performed using various techniques as, including without limitation size exclusion chromatography, density gradient centrifugation, differential centrifugation, nanomembrane ultrafiltration, immunoabsorbent capture, affinity purification, affinity capture, immunoassay, immunoprecipitation, microfluidic separation, flow cytometry, polymeric isolation (e.g., using polyethylene glycol (PEG)) or combinations thereof. Methods and techniques for microvesicle and vesicular payload isolation and analysis are disclosed in International Patent Application Nos. PCT/US2009/62880, filed Oct. 30, 2009; PCT/US2009/006095, filed Nov. 12, 2009; PCT/US2011/26750, filed Mar. 1, 2011; PCT/US2011/031479, filed Apr. 6, 2011; PCT/US11/48327, filed Aug. 18, 2011; PCT/US2008/71235, filed Jul. 25, 2008; PCT/US10/58461, filed Nov. 30, 2010; PCT/US2011/21160, filed Jan. 13, 2011; PCT/US2013/030302, filed Mar. 11, 2013; PCT/US12/25741, filed Feb. 17, 2012; PCT/2008/76109, filed Sep. 12, 2008; PCT/US12/42519, filed Jun. 14, 2012; PCT/US12/50030, filed Aug. 8, 2012; PCT/US12/49615, filed Aug. 3, 2012; PCT/US12/41387, filed Jun. 7, 2012; PCT/US2013/072019, filed Nov. 26, 2013; PCT/US2014/039858, filed May 28, 2013; PCT/IB2013/003092, filed Oct. 23, 2013; PCT/US13/76611, filed Dec. 19, 2013; PCT/US14/53306, filed Aug. 28, 2014; and PCT/US15/62184, filed Nov. 23, 2015; PCT/US16/40157, filed Jun. 29, 2016; PCT/US16/44595, filed Jul. 28, 2016; and PCT/US16/21632, filed Mar. 9, 2016; each of which applications is incorporated herein by reference in its entirety.

The compositions and methods of the invention can be used in and with various immune assay formats Immunoaffinity assays can be based on antibodies and aptamers selectively immunoreactive with proteins or other biomarkers of interest. These techniques include without limitation immunoprecipitation, Western blot analysis, molecular binding assays, enzyme-linked immunosorbent assay (ELISA), enzyme-linked immunofiltration assay (ELIFA), fluorescence activated cell sorting (FACS), immunohistochemistry (IHC) and the like. For example, an optional method of detecting the expression of a biomarker in a sample comprises contacting the sample with an antibody or aptamer against the biomarker, or an immunoreactive fragment thereof, or a recombinant protein containing an antigen binding region against the biomarker; and then detecting the binding of the biomarker in the sample. Various methods for producing antibodies and aptamers are known in the art. Such binding agents can be used to immunoprecipitate specific proteins from solution samples or to immunoblot proteins separated by, e.g., polyacrylamide gels Immunocytochemical methods can also be used in detecting specific protein polymorphisms in tissues or cells. Other well-known immunoassay techniques can also be used including, e.g., ELISA, radioimmunoassay (RIA), immunoradiometric assays (IRMA) and immunoenzymatic assays (IEMA), including sandwich assays. See, e.g., U.S. Pat. Nos. 4,376,110 and 4,486,530, both of which are incorporated herein by reference.

In alternative methods, a sample may be contacted with an antibody or aptamer specific for a biomarker under conditions sufficient for a complex to form, and then detecting such complex. The presence of the biomarker may be detected in a number of ways, such as by Western blotting and ELISA procedures for assaying a wide variety of tissues and samples, including bodily fluids such as plasma or serum. A wide range of immunoassay techniques using such an assay format are available, see, e.g., U.S. Pat. Nos. 4,016,043, 4,424,279 and 4,018,653. These include both single-site and two-site or "sandwich" assays of the non-competitive types, as well as in the traditional competitive binding assays. These assays also include direct binding of a labelled antibody or aptamer to a target biomarker.

There are a number of variations of the sandwich assay technique which can be encompassed within the present invention. In a typical forward assay, an unlabeled binding agent, e.g., an antibody or aptamer, is immobilized on a solid substrate, and the sample to be tested brought into contact with the bound molecule. After a suitable period of time sufficient to allow formation of an complex, a second binding agent specific to the antigen, labelled with a reporter molecule capable of producing a detectable signal is then added and incubated, allowing time sufficient for the formation of another complex comprising the labelled binding agent. Any unreacted material is washed away, and the presence of the antigen is determined by observation of a signal produced by the reporter molecule. The results may either be qualitative, by simple observation of the visible signal, or may be quantitated by comparing with a control sample containing known amounts of biomarker.

Variations on the above assay include a simultaneous assay, in which both sample and labelled binding agent are added simultaneously to the tethered binding agent. In a typical forward sandwich assay, a first binding agent, e.g., an antibody or aptamer, having specificity for a tissue/cell/biomarker or such target of interest is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes generally consist of cross-linking, covalently binding or physically adsorbing, the polymer-antibody complex to the support, which is then washed in preparation for the test sample. An aliquot of the sample to be tested is then added to the solid phase complex and incubated for a period of time sufficient (e.g., 2-40 minutes or overnight) and under suitable conditions (e.g., from room temperature to 40° C. such as between 25° C. and 32° C. inclusive) to allow binding of the target to the support. Following the incubation period, the support is washed and incubated with a second binding agent specific for a portion of the biomarker. The second binding agent is linked to a reporter molecule which is used to indicate the binding of the second binding agent to the molecular marker.

An alternative method involves immobilizing the target biomarkers in the sample and then exposing the immobilized target to specific binding agents, e.g., antibodies or aptamers, which may or may not be labelled with a reporter molecule. Depending on the amount of target and the strength of the reporter molecule signal, a bound target may be detectable by direct labelling with the binding agent. Alternatively, a second labelled binding agent, specific to the first binding agent, is exposed to the first target complex to form a tertiary complex. The complex is detected by the signal emitted by the reporter molecule. A "reporter molecule" includes molecule which, by its chemical nature, provides an analytically identifiable signal which allows the detection of antigen-bound complexes. Some commonly used reporter molecules in this type of assay include enzymes, fluorophores or radionuclide containing molecules (i.e. radioisotopes) and chemiluminescent molecules. Examples of such detectable labels are disclosed herein.

In the case of an enzyme immunoassay, an enzyme is conjugated to the secondary binding agent. Commonly used enzymes include horseradish peroxidase, glucose oxidase, β-galactosidase and alkaline phosphatase, amongst others. The substrates to be used with the specific enzymes are generally chosen for the production, upon hydrolysis by the corresponding enzyme, of a detectable color change. Examples of suitable enzymes include alkaline phosphatase and peroxidase. It is also possible to employ fluorogenic substrates, which yield a fluorescent product rather than the chromogenic substrates noted above. In all cases, the enzyme-labelled binding agent is added to the first bound molecular marker complex, allowed to bind, and then the excess reagent is washed away. A solution containing the appropriate substrate is then added to the tertiary complex comprising primary binding agent, antigen, and secondary binding agent. The substrate will react with the enzyme linked to the secondary binding agent, giving a qualitative visual signal, which may be further quantitated, usually spectrophotometrically, to give an indication of the amount of antigen which was present in the sample. Alternately, fluorescent compounds, such as fluorescein and rhodamine, may be chemically coupled to secondary binding agent without altering their binding capacity. When activated by illumination with light of a particular wavelength, the fluorochrome-labelled secondary binding agent adsorbs the light energy, inducing a state to excitability in the molecule, followed by emission of the light at a characteristic color visually detectable with a light microscope. As in the EIA, the fluorescent labelled secondary binding agent is allowed to bind to antigen complex. After washing off the unbound reagent, the remaining tertiary complex is then exposed to the light of the appropriate wavelength. The fluorescence observed indicates the presence of the molecular marker of interest. Immunofluorescence and EIA techniques are both very well established in the art. However, other reporter molecules, such as radioisotope, chemiluminescent or bioluminescent molecules, may also be employed.

Immunohistochemistry (IHC) is a process of localizing antigens (e.g., proteins) in cells of a tissue using binding agents (e.g., antibodies or aptamers) specifically to antigens in the tissues. The antigen-binding binding agent can be conjugated or fused to a tag that allows its detection, e.g., via visualization. In some embodiments, the tag is an enzyme that can catalyze a color-producing reaction, such as alkaline phosphatase or horseradish peroxidase. The enzyme can be fused to the binding agent or non-covalently bound, e.g., using a biotin-avadin/streptavidin system. Alternatively, the binding agent can be tagged with a fluorophore, such as fluorescein, rhodamine, DyLight Fluor or Alexa Fluor. The binding agent can be directly tagged or it can itself be recognized by a secondary detection binding agent (antibody or antigen) that carries the tag. Using IHC, one or more proteins may be detected. The expression of a gene product can be related to its staining intensity compared to control levels. In some embodiments, the gene product is considered differentially expressed if its staining varies at least 1.2, 1.3, 1.4, 1.5, 1.6, 1.7, 1.8, 1.9, 2.0, 2.2, 2.5, 2.7, 3.0, 4, 5, 6, 7, 8, 9 or 10-fold in the sample versus the control.

IHC comprises the application of such immunoassay formats to histochemical techniques. In an illustrative example, a tissue section is mounted on a slide and is incubated with a binding agent. The binding agents are typically polyclonal or monoclonal antibodies, and can be aptamers such as oligonucleotide probes of the invention, specific to the antigen. The primary reaction comprises contacting the tissue section with this primary binding agent, forming primary complexes. The antigen-antibody signal is then amplified using a second binding agent conjugated to a complex of that can provide a visible signal, such as enzymes including without limitation peroxidase antiperoxidase (PAP), avidin-biotin-peroxidase (ABC) or avidin-biotin alkaline phosphatase. In the presence of substrate and chromogen, the enzyme forms a colored deposit at the sites of primary complexes Immunofluorescence is an alternate approach to visualize antigens. In this technique, the primary signal is amplified using a second binding agent conjugated to a fluorochrome. On UV light absorption, the fluorochrome emits its own light at a longer wavelength (fluorescence), thus allowing localization of the primary complexes.

The invention provides methods of performing an IHC assay using an oligonucleotide probe library. This may be referred to as a polyligand histochemistry assay (PHC). As an example of this approach, a tissue section is contacted with an enriched oligonucleotide probe library. Members of the library can be labeled, e.g., with a biotin molecule, digoxigenin, or other label as appropriate. The bound library members are visualized using a secondary labeling system, e.g., streptavidin-horse radish peroxidase (SA-HRP) or anti-digoxigenin horse radish peroxidase. The resulting slides can be read and scored as in typical antibody based IHC methods. See Examples 19-31 herein.

Oligonucleotide Probes/Aptamers

Aptamers have a number of desirable characteristics for use as therapeutics and diagnostics including high specificity and affinity, biological efficacy, and excellent pharmacokinetic properties. In addition, they offer certain advantages over antibodies and other protein biologics. For example, aptamers are produced by an entirely in vitro process, allowing for the rapid synthesis. In vitro selection allows the specificity and affinity of the aptamer to be tightly controlled. In addition, aptamers as a class have demonstrated little or no toxicity or immunogenicity. Whereas the efficacy of many monoclonal antibodies can be severely limited by immune response to antibodies themselves, it is difficult to elicit antibodies to aptamers most likely because aptamers cannot be presented by T-cells via the MHC and the immune response is generally trained not to recognize nucleic acid fragments. Whereas most currently approved antibody therapeutics are administered by intravenous infusion (typically over 2-4 hours), aptamers can be administered by subcutaneous injection. This difference is primarily due to the comparatively low solubility and thus large volumes necessary for most therapeutic mAbs. With good solubility (>150 mg/mL) and comparatively low molecular weight (aptamer: 10-50 kDa; antibody: 150 kDa), a weekly dose of aptamer may be delivered by injection in a volume of less than 0.5 mL. In addition, the small size of aptamers allows them to penetrate into areas of conformational constrictions that do not allow for antibodies or antibody fragments to penetrate, presenting yet another advantage of aptamer-based therapeutics or prophylaxis.

Aptamers are chemically synthesized and are readily scaled as needed to meet production demand for diagnostic or therapeutic applications. In addition, aptamers are chemically robust. They can be adapted to regain activity following exposure to factors such as heat and denaturants and can be stored for extended periods (>1 yr) at room temperature as lyophilized powders.

SELEX

The classical method for generating an aptamer is with the process entitled "Systematic Evolution of Ligands by Exponential Enrichment" ("SELEX") generally described in, e.g., U.S. patent application Ser. No. 07/536,428, filed Jun. 11, 1990, now abandoned, U.S. Pat. No. 5,475,096 entitled "Nucleic Acid Ligands", and U.S. Pat. No. 5,270,163 (see also WO 91/19813) entitled "Nucleic Acid Ligands." Each SELEX-identified nucleic acid ligand, i.e., each aptamer (or oligonucleotide probe), is a specific ligand of a given target compound or molecule. The SELEX process is based on the insight that nucleic acids have sufficient capacity for forming a variety of two- and three-dimensional structures and sufficient chemical versatility available within their monomers to act as ligands (i.e., form specific binding pairs) with any variety of chemical compounds, whether monomeric or polymeric. Molecules of any size or composition can serve as targets.

SELEX relies as a starting point upon a large library or pool of single stranded oligonucleotides comprising randomized sequences. The oligonucleotides can be modified or unmodified DNA, RNA, or DNA/RNA hybrids. In some examples, the pool comprises 100% random or partially random oligonucleotides. In other examples, the pool comprises random or partially random oligonucleotides containing at least one fixed and/or conserved sequence incorporated within randomized sequence. In other examples, the pool comprises random or partially random oligonucleotides containing at least one fixed and/or conserved sequence at its 5' and/or 3' end which may comprise a sequence shared by all the molecules of the oligonucleotide pool. Fixed sequences are sequences such as hybridization sites for PCR primers, promoter sequences for RNA polymerases (e.g., T3, T4, T7, and SP6), restriction sites, or homopolymeric sequences, such as poly A or poly T tracts, catalytic cores, sites for selective binding to affinity columns, and other sequences to facilitate cloning and/or sequencing of an oligonucleotide of interest. Conserved sequences are sequences, other than the previously described fixed sequences, shared by a number of aptamers that bind to the same target.

The oligonucleotides of the pool preferably include a randomized sequence portion as well as fixed sequences necessary for efficient amplification. Typically the oligonucleotides of the starting pool contain fixed 5' and 3' terminal sequences which flank an internal region of 30-50 random nucleotides. The randomized nucleotides can be produced in a number of ways including chemical synthesis and size selection from randomly cleaved cellular nucleic acids. Sequence variation in test nucleic acids can also be introduced or increased by mutagenesis before or during the selection/amplification iterations.

The random sequence portion of the oligonucleotide can be of any appropriate length and can comprise ribonucleotides and/or deoxyribonucleotides and can include modified or non-natural nucleotides or nucleotide analogs. See, e.g. U.S. Pat. Nos. 5,958,691; 5,660,985; 5,958,691; 5,698,687; 5,817,635; 5,672,695, and PCT Publication WO 92/07065. Random oligonucleotides can be synthesized from phosphodiester-linked nucleotides using solid phase oligonucleotide synthesis techniques well known in the art. See, e.g., Froehler et al., Nucl. Acid Res. 14:5399-5467 (1986) and Froehler et al., Tet. Lett. 27:5575-5578 (1986). Random oligonucleotides can also be synthesized using solution phase methods such as triester synthesis methods. See, e.g., Sood et al., Nucl. Acid Res. 4:2557 (1977) and Hirose et al., Tet. Lett., 28:2449 (1978). Typical syntheses carried out on automated DNA synthesis equipment yield $10^{14}$-$10^{16}$ individual molecules, a number sufficient for most SELEX experiments. Sufficiently large regions of random sequence in the sequence design increases the likelihood that each synthesized molecule is likely to represent a unique sequence.

The starting library of oligonucleotides may be generated by automated chemical synthesis on a DNA synthesizer. To synthesize randomized sequences, mixtures of all four nucleotides are added at each nucleotide addition step during the synthesis process, allowing for random incorporation of nucleotides. As stated above, in one embodiment, random oligonucleotides comprise entirely random sequences; however, in other embodiments, random oligonucleotides can comprise stretches of nonrandom or partially random sequences. Partially random sequences can be created by adding the four nucleotides in different molar ratios at each addition step.

The starting library of oligonucleotides may be for example, RNA, DNA, or RNA/DNA hybrid. A starting RNA library can be generated by transcribing a DNA library in vitro using T7 RNA polymerase or modified T7 RNA polymerases and purified. The library is then mixed with the target under conditions favorable for binding and subjected to step-wise iterations of binding, partitioning and amplification, using the same general selection scheme, to achieve virtually any desired criterion of binding affinity and selectivity. More specifically, starting with a mixture containing the starting pool of nucleic acids, the SELEX method includes steps of: (a) contacting the mixture with the target under conditions favorable for binding; (b) partitioning unbound nucleic acids from those nucleic acids which have bound specifically to target molecules; (c) dissociating the nucleic acid-target complexes; (d) amplifying the nucleic acids dissociated from the nucleic acid-target complexes to yield a ligand-enriched mixture of nucleic acids; and (e) reiterating the steps of binding, partitioning, dissociating and amplifying through as many cycles as desired to yield highly specific, high affinity nucleic acid ligands to the target molecule. In those instances where RNA aptamers are being selected, the SELEX method further comprises the steps of: (i) reverse transcribing the nucleic acids dissociated from the nucleic acid-target complexes before amplification in step (d); and (ii) transcribing the amplified nucleic acids from step (d) before restarting the process.

Within a nucleic acid mixture containing a large number of possible sequences and structures, there is a wide range of binding affinities for a given target. A nucleic acid mixture comprising, for example, a 20 nucleotide randomized segment can have $4^{20}$ candidate possibilities. Those which have the higher affinity constants for the target are most likely to bind to the target. After partitioning, dissociation and amplification, a second nucleic acid mixture is generated, enriched for the higher binding affinity candidates. Additional rounds of selection progressively favor better ligands until the resulting nucleic acid mixture is predominantly composed of only one or a few sequences. These can then be cloned, sequenced and individually tested for binding affinity as pure ligands or aptamers.

Cycles of selection and amplification are repeated until a desired goal is achieved. In the most general case, selection/amplification is continued until no significant improvement in binding strength is achieved on repetition of the cycle. The method is typically used to sample approximately $10^{14}$ different nucleic acid species but may be used to sample as many as about $10^{18}$ different nucleic acid species. Generally, nucleic acid aptamer molecules are selected in a 5 to 20 cycle procedure. In one embodiment, heterogeneity is introduced only in the initial selection stages and does not occur throughout the replicating process.

In one embodiment of SELEX, the selection process is so efficient at isolating those nucleic acid ligands that bind most strongly to the selected target, that only one cycle of selection and amplification is required. Such an efficient selection may occur, for example, in a chromatographic-type process wherein the ability of nucleic acids to associate with targets bound on a column operates in such a manner that the column is sufficiently able to allow separation and isolation of the highest affinity nucleic acid ligands.

In many cases, it is not necessarily desirable to perform the iterative steps of SELEX until a single nucleic acid ligand is identified. The target-specific nucleic acid ligand solution may include a family of nucleic acid structures or motifs that have a number of conserved sequences and a number of sequences which can be substituted or added without significantly affecting the affinity of the nucleic acid ligands to the target. By terminating the SELEX process prior to completion, it is possible to determine the sequence of a number of members of the nucleic acid ligand solution family. The invention provides for the identification of aptamer pools and uses thereof that jointly can be used to characterize a test sample. For example, the aptamer pools can be identified through rounds of positive and negative selection to identify cells, tissue or microvesicles indicative of a disease or condition. The invention further provides use of such aptamer pools to stain, detect and/or quantify such cells, tissue or microvesicles in a sample, thereby allowing a diagnosis, prognosis or theranosis to be provided.

A variety of nucleic acid primary, secondary and tertiary structures are known to exist. The structures or motifs that have been shown most commonly to be involved in non-Watson-Crick type interactions are referred to as hairpin loops, symmetric and asymmetric bulges, pseudoknots and myriad combinations of the same. Such motifs can typically be formed in a nucleic acid sequence of no more than 30 nucleotides. For this reason, it is often preferred that SELEX procedures with contiguous randomized segments be initiated with nucleic acid sequences containing a randomized segment of between about 20 to about 50 nucleotides and in some embodiments, about 30 to about 40 nucleotides. In one example, the 5'-fixed:random:3'-fixed sequence comprises a random sequence of about 30 to about 50 nucleotides. The random region may be referred to as the variable region herein.

The core SELEX method has been modified to achieve a number of specific objectives. For example, U.S. Pat. No. 5,707,796 describes the use of SELEX in conjunction with gel electrophoresis to select nucleic acid molecules with specific structural characteristics, such as bent DNA. U.S. Pat. No. 5,763,177 describes SELEX based methods for selecting nucleic acid ligands containing photoreactive groups capable of binding and/or photocrosslinking to and/or photoinactivating a target molecule. U.S. Pat. Nos. 5,567,588 and 5,861,254 describe SELEX based methods which achieve highly efficient partitioning between oligonucleotides having high and low affinity for a target molecule. U.S. Pat. No. 5,496,938 describes methods for obtaining improved nucleic acid ligands after the SELEX process has been performed. U.S. Pat. No. 5,705,337 describes methods for covalently linking a ligand to its target.

SELEX can also be used to obtain nucleic acid ligands that bind to more than one site on the target molecule, and to obtain nucleic acid ligands that include non-nucleic acid species that bind to specific sites on the target. SELEX provides means for isolating and identifying nucleic acid ligands which bind to any envisionable target, including large and small biomolecules such as nucleic acid-binding proteins and proteins not known to bind nucleic acids as part of their biological function as well as lipids, cofactors and other small molecules. For example, U.S. Pat. No. 5,580,737 discloses nucleic acid sequences identified through SELEX which are capable of binding with high affinity to caffeine and the closely related analog, theophylline.

Counter-SELEX is a method for improving the specificity of nucleic acid ligands to a target molecule by eliminating nucleic acid ligand sequences with cross-reactivity to one or more non-target molecules. Counter-SELEX is comprised of the steps of: (a) preparing a candidate mixture of nucleic acids; (b) contacting the candidate mixture with the target, wherein nucleic acids having an increased affinity to the target relative to the candidate mixture may be partitioned from the remainder of the candidate mixture; (c) partitioning the increased affinity nucleic acids from the remainder of the candidate mixture; (d) dissociating the increased affinity nucleic acids from the target; e) contacting the increased affinity nucleic acids with one or more non-target molecules such that nucleic acid ligands with specific affinity for the non-target molecule(s) are removed; and (f) amplifying the nucleic acids with specific affinity only to the target molecule to yield a mixture of nucleic acids enriched for nucleic acid sequences with a relatively higher affinity and specificity for binding to the target molecule. As described above for SELEX, cycles of selection and amplification are repeated until a desired goal is achieved.

A potential problem encountered in the use of nucleic acids as therapeutics and vaccines is that oligonucleotides in their phosphodiester form may be quickly degraded in body fluids by intracellular and extracellular enzymes such as endonucleases and exonucleases before the desired effect is manifest. The SELEX method thus encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX identified nucleic acid ligands containing modified nucleotides are described, e.g., in U.S. Pat. No. 5,660,985, which describes oligonucleotides containing nucleotide derivatives chemically modified at the 2' position of ribose, 5' position of pyrimidines, and 8' position of purines, U.S. Pat. No. 5,756,703 which describes oligonucleotides containing various 2'-modified pyrimidines, and U.S. Pat. No. 5,580,737 which describes highly specific nucleic acid ligands containing one or more nucleotides modified with 2'-amino (2'-$NH_2$), 2'-fluoro (2'-F), and/or 2'-O-methyl (2'-OMe) substituents.

Modifications of the nucleic acid ligands contemplated in this invention include, but are not limited to, those which provide other chemical groups that incorporate additional charge, polarizability, hydrophobicity, hydrogen bonding, electrostatic interaction, and fluxionality to the nucleic acid ligand bases or to the nucleic acid ligand as a whole. Modifications to generate oligonucleotide populations which are resistant to nucleases can also include one or more substitute internucleotide linkages, altered sugars, altered bases, or combinations thereof. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, phosphorothioate or allyl phosphate modifications, methylations, and unusual base-pairing combinations such as the isobases isocytidine and isoguanosine. Modifications can also include 3' and 5' modifications such as capping.

In one embodiment, oligonucleotides are provided in which the P(O)O group is replaced by P(O)S ("thioate"), P(S)S ("dithioate"), P(O)$NR_2$ ("amidate"), P(O)R, P(O)OR', CO or $CH_2$ ("formacetal") or 3'-amine (—NH—$CH_2$—$CH_2$—), wherein each R or R' is independently H or substituted or unsubstituted alkyl. Linkage groups can be attached to adjacent nucleotides through an —O—, —N—, or —S— linkage. Not all linkages in the oligonucleotide are required to be identical. As used herein, the term phosphorothioate encompasses one or more non-bridging oxygen atoms in a phosphodiester bond replaced by one or more sulfur atoms.

In further embodiments, the oligonucleotides comprise modified sugar groups, for example, one or more of the hydroxyl groups is replaced with halogen, aliphatic groups, or functionalized as ethers or amines. In one embodiment, the 2'-position of the furanose residue is substituted by any of an O-methyl, O-alkyl, O-allyl, S-alkyl, S-allyl, or halo group. Methods of synthesis of 2'-modified sugars are described, e.g., in Sproat, et al., Nucl. Acid Res. 19:733-738 (1991); Cotten, et al., Nucl. Acid Res. 19:2629-2635 (1991); and Hobbs, et al., Biochemistry 12:5138-5145 (1973). Other modifications are known to one of ordinary skill in the art. Such modifications may be pre-SELEX process modifications or post-SELEX process modifications (modification of previously identified unmodified ligands) or may be made by incorporation into the SELEX process.

Pre-SELEX process modifications or those made by incorporation into the SELEX process yield nucleic acid ligands with both specificity for their SELEX target and improved stability, e.g., in vivo stability. Post-SELEX process modifications made to nucleic acid ligands may result in improved stability, e.g., in vivo stability without adversely affecting the binding capacity of the nucleic acid ligand.

The SELEX method encompasses combining selected oligonucleotides with other selected oligonucleotides and non-oligonucleotide functional units as described in U.S. Pat. Nos. 5,637,459 and 5,683,867. The SELEX method further encompasses combining selected nucleic acid ligands with lipophilic or non-immunogenic high molecular weight compounds in a diagnostic or therapeutic complex, as described, e.g., in U.S. Pat. Nos. 6,011,020, 6,051,698, and PCT Publication No. WO 98/18480. These patents and applications teach the combination of a broad array of shapes and other properties, with the efficient amplification and replication properties of oligonucleotides, and with the desirable properties of other molecules.

The identification of nucleic acid ligands to small, flexible peptides via the SELEX method has also been explored. U.S. Pat. No. 5,648,214 identified high affinity RNA nucleic acid ligands to an 11 amino acid.

Aptamers/oligonucleotide probes with desired specificity and binding affinity to the target(s) of interest to the present invention can be selected by the SELEX N process as described herein. As part of the SELEX process, the sequences selected to bind to the target are then optionally minimized to determine the minimal sequence having the desired binding affinity. The selected sequences and/or the minimized sequences are optionally optimized by performing random or directed mutagenesis of the sequence to increase binding affinity or alternatively to determine which positions in the sequence are essential for binding activity. Additionally, selections can be performed with sequences incorporating modified nucleotides to stabilize the aptamer molecules against degradation in vivo.

For an aptamer to be suitable for use as a therapeutic, it is preferably inexpensive to synthesize, and safe and stable in vivo. Wild-type RNA and DNA aptamers are typically not stable is vivo because of their susceptibility to degradation by nucleases. Resistance to nuclease degradation can be greatly increased by the incorporation of modifying groups at the 2'-position.

Fluoro and amino groups have been successfully incorporated into oligonucleotide pools from which aptamers have been subsequently selected. However, these modifications greatly increase the cost of synthesis of the resultant aptamer, and may introduce safety concerns in some cases because of the possibility that the modified nucleotides could be recycled into host DNA by degradation of the modified oligonucleotides and subsequent use of the nucleotides as substrates for DNA synthesis.

Aptamers that contain 2'-O-methyl ("2'-OMe") nucleotides, as provided herein, may overcome one or more potential drawbacks. Oligonucleotides containing 2'-OMe nucleotides are nuclease-resistant and inexpensive to synthesize. Although 2'-OMe nucleotides are ubiquitous in biological systems, natural polymerases do not accept 2'-OMe NTPs as substrates under physiological conditions, thus there are no safety concerns over the recycling of 2'-OMe nucleotides into host DNA. The SELEX method used to generate 2'-modified aptamers is described, e.g., in U.S. Provisional Patent Application Ser. No. 60/430,761, filed Dec. 3, 2002, U.S. Provisional Patent Application Ser. No. 60/487,474, filed Jul. 15, 2003, U.S. Provisional Patent Application Ser. No. 60/517,039, filed Nov. 4, 2003, U.S. patent application Ser. No. 10/729,581, filed Dec. 3, 2003, and U.S. patent application Ser. No. 10/873,856, filed Jun. 21, 2004, entitled "Method for in vitro Selection of 2'-O-methyl substituted Nucleic Acids," each of which is herein incorporated by reference in its entirety.

Therapeutics

As used herein "therapeutically effective amount" refers to an amount of a composition that relieves (to some extent, as judged by a skilled medical practitioner) one or more symptoms of a medical condition such as a disease or disorder in a subject. Additionally, by "therapeutically effective amount" of a composition is meant an amount that returns to normal, either partially or completely, physiological or biochemical parameters associated with or causative of a disease or condition. A clinician skilled in the art can determine the therapeutically effective amount of a composition in order to treat or prevent a particular disease condition, or disorder when it is administered, such as intravenously, subcutaneously, intraperitoneally, orally, or through inhalation. The precise amount of the composition required to be therapeutically effective will depend upon numerous factors, e.g., such as the specific activity of the active agent, the delivery device employed, physical characteristics of the agent, purpose for the administration, in addition to many patient specific considerations. But a determination of a therapeutically effective amount is within the skill of an ordinarily skilled clinician upon the appreciation of the disclosure set forth herein.

The terms "treating," "treatment," "therapy," and "therapeutic treatment" as used herein refer to curative therapy, prophylactic therapy, or preventative therapy. An example of "preventative therapy" is the prevention or lessening the chance of a targeted disease (e.g., cancer or other proliferative disease) or related condition thereto. Those in need of treatment include those already with the disease or condition as well as those prone to have the disease or condition to be prevented. The terms "treating," "treatment," "therapy," and "therapeutic treatment" as used herein also describe the management and care of a mammal for the purpose of combating a disease, or related condition, and includes the administration of a composition to alleviate the symptoms, side effects, or other complications of the disease, condition. Therapeutic treatment for cancer includes, but is not limited to, surgery, chemotherapy, radiation therapy, gene therapy, and immunotherapy.

As used herein, the term "agent" or "drug" or "therapeutic agent" refers to a chemical compound, a mixture of chemical compounds, a biological macromolecule, or an extract made from biological materials such as bacteria, plants, fungi, or animal (particularly mammalian) cells or tissues that are suspected of having therapeutic properties. The agent or drug can be purified, substantially purified or partially purified. An "agent" according to the present invention, also includes a radiation therapy agent or a "chemotherapuetic agent."

As used herein, the term "diagnostic agent" refers to any chemical used in the imaging of diseased tissue, such as, e.g., a tumor.

As used herein, the term "chemotherapuetic agent" refers to an agent with activity against cancer, neoplastic, and/or proliferative diseases, or that has ability to kill cancerous cells directly.

As used herein, "pharmaceutical formulations" include formulations for human and veterinary use with no significant adverse toxicological effect. "Pharmaceutically acceptable formulation" as used herein refers to a composition or formulation that allows for the effective distribution of the nucleic acid molecules of the instant invention in the physical location most suitable for their desired activity.

As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated.

Aptamer-Toxin Conjugates as a Cancer Therapeutic

Previous work has developed the concept of antibody-toxin conjugates ("immunoconjugates") as potential therapies for a range of indications, mostly directed at the treatment of cancer with a primary focus on hematological tumors. A variety of different payloads for targeted delivery have been tested in pre-clinical and clinical studies, including protein toxins, high potency small molecule cytotoxics, radioisotopes, and liposome-encapsulated drugs. While these efforts have successfully yielded several FDA-approved therapies for hematological tumors, immunoconjugates as a class (especially for solid tumors) face challenges that have been attributable to multiple different properties of antibodies, including tendencies to develop neutralizing antibody responses to non-humanized antibodies, limited penetration in solid tumors, loss of target binding affinity as a result of toxin conjugation, and imbalances between antibody half-life and toxin conjugate half-life that limit the overall therapeutic index (reviewed by Reff and Heard, Critical Reviews in Oncology/Hematology, 40 (2001):25-35).

Aptamers are functionally similar to antibodies in target recognition, although their absorption, distribution, metabolism, and excretion ("ADME") properties are intrinsically different and they generally lack many of the immune effector functions generally associated with antibodies (e.g., antibody-dependent cellular cytotoxicity, complement-dependent cytotoxicity). In comparing many of the properties of aptamers and antibodies previously described, several factors suggest that toxin-delivery via aptamers offers several concrete advantages over delivery with antibodies, ultimately affording them better potential as therapeutics. Several examples of the advantages of toxin-delivery via aptamers over antibodies are as follows:

1) Aptamer-toxin conjugates are entirely chemically synthesized. Chemical synthesis provides more control over the nature of the conjugate. For example, the stoichiometry (ratio of toxins per aptamer) and site of attachment can be precisely defined. Different linker chemistries can be readily tested. The reversibility of aptamer folding means that loss of activity during conjugation is unlikely and provides more flexibility in adjusting conjugation conditions to maximize yields.

2) Smaller size allows better tumor penetration. Poor penetration of antibodies into solid tumors is often cited as a factor limiting the efficacy of conjugate approaches. See Colcher, D., Goel, A., Pavlinkova, G., Beresford, G., Booth, B., Batra, S. K. (1999) "Effects of genetic engineering on the pharmacokinetics of antibodies," Q. J. Nucl. Med., 43: 132-139. Studies comparing the properties of unPEGylated anti-tenascin C aptamers with corresponding antibodies demonstrate efficient uptake into tumors (as defined by the tumor:blood ratio) and evidence that aptamer localized to the tumor is unexpectedly long-lived ($t_{1/2}$>12 hours) (Hicke, B. J., Stephens, A. W., "Escort aptamers: a delivery service for diagnosis and therapy", J. Clin. Invest., 106:923-928 (2000)).

3) Tunable PK. Aptamer half-life/metabolism can be more easily tuned to match properties of payload, optimizing the ability to deliver toxin to the tumor while minimizing systemic exposure. Appropriate modifications to the aptamer backbone and addition of high molecular weight PEGs should make it possible to match the half-life of the aptamer to the intrinsic half-life of the conjugated toxin/linker, minimizing systemic exposure to non-functional toxin-bearing metabolites (expected if $t_{1/2}$(aptamer)<<$t_{1/2}$(toxin)) and reducing the likelihood that persisting unconjugated aptamer will functionally block uptake of conjugated aptamer (expected if $t_{1/2}$(aptamer)>>$t_{1/2}$ (toxin)).

4) Relatively low material requirements. It is likely that dosing levels will be limited by toxicity intrinsic to the cytotoxic payload. As such, a single course of treatment will likely entail relatively small (<100 mg) quantities of aptamer, reducing the likelihood that the cost of oligonucleotide synthesis will be a barrier for aptamer-based therapies.

5) Parenteral administration is preferred for this indication. There will be no special need to develop alternative formulations to drive patient/physician acceptance.

The invention provides a pharmaceutical composition comprising a therapeutically effective amount of an aptamer provided by the invention or a salt thereof, and a pharmaceutically acceptable carrier or diluent. The invention also provides a pharmaceutical composition comprising a therapeutically effective amount of the aptamer or a salt thereof, and a pharmaceutically acceptable carrier or diluent. Relatedly, the invention provides a method of treating or ameliorating a disease or disorder, comprising administering the pharmaceutical composition to a subject in need thereof. Administering a therapeutically effective amount of the composition to the subject may result in: (a) an enhancement of the delivery of the active agent to a disease site relative to delivery of the active agent alone; or (b) an enhancement of microvesicles clearance resulting in a decrease of at least 10%, 20%, 30%, 40%, 50%, 60%, 70%, 80%, or 90% in a blood level of microvesicles targeted by the aptamer; or (c) an decrease in biological activity of microvesicles targeted by the aptamer of at least 10%, 20%, 30%, 40%, 50%, 60%, 70%, 80%, or 90%. In an embodiment, the biological activity of microvesicles comprises immune suppression or transfer of genetic information. The disease or disorder can include without limitation those disclosed herein. For example, the disease or disorder may comprise a neoplastic, proliferative, or inflammatory, metabolic, cardiovascular, or neurological disease or disorder. See, e.g., section "Phenotypes."

Anti-Target and Multivalent Oligonucleotides

As described herein, the target of oligonucleotide probes can be identified. For example, when the target comprises a protein or protein complex (e.g., a nucleoprotein or lipoprotein), identifying the target may comprise use of mass spectrometry (MS), peptide mass fingerprinting (PMF; protein fingerprinting), sequencing, N-terminal amino acid analysis, C-terminal amino acid analysis, Edman degradation, chromatography, electrophoresis, two-dimensional gel electrophoresis (2D gel), antibody array, or immunoassay. Such approaches can be applied to identify a number of targets recognized by an oligonucleotide probe library. For example, an oligonucleotide probe library can be incubated with a sample of interest, bound members of the library captured, and the targets bound to the captured members identified. See Example 9 herein for an example of such target identification using mass spectrometry.

The oligonucleotide aptamers to the various targets can be used for multiple purposes. In some embodiments, the aptamers are used as therapeutic agents Immunotherapeutic approaches using antibodies that recognize foreign/misfolded antigens (e.g., anti-CD20, anti-CD30, anti-CD33, anti-CD52, anti-EGFR, anti-nucleolin, anti-nucleophosmin, etc.) can selectively kill target cells via linked therapeutic agents or by stimulating the immune system through activation of cell-mediated cytotoxicity. Aptamers or oligonucleotides are an attractive immunotherapeutic alternative for various reasons such as low cost, small size, ease and speed of synthesis, stability and low immunogenicity. In an embodiment, immunotherapeutic agents are conjugated to disease specific target oligonucleotide or antibody (Ab) for targeted cell killing via recruitment of complement proteins and the downstream membrane attack complex. See, e.g., Zhou and Rossi, Cell-type-specific, Aptamer-functionalized Agents for Targeted Disease Therapy, Mol Ther Nucleic Acids. 2014 Jun. 17; 3:e169. doi: 10.1038/mtna.2014.21; Pei et al., Clinical applications of nucleic acid aptamers in cancer, Mol Clin Oncol. 2014 May; 2(3):341-348. Epub 2014 Feb. 10. This approach can be applied to target diseased host cells such as cancer cells, gram negative bacteria, viral and/or parasitic infections, and the like.

In some embodiments, the invention provides a multipartite construct comprising a binding agent specific to a biological target with another binding agent specific to immunomodulatory entity. Examples of such constructs are shown in FIG. 8. In Design 1 in the figure, the horizontal line indicates an oligonucleotide construct, which construct comprises a 5' primer 801 (Primer 1), a variable region 802 that can be an aptamer to a target of interest, a 3' primer 803 (Primer 2), and an immunomodulatory domain region ("IMD") 804. The complete Design 1 construct can be used to bring a target of interest in proximity with an immunomodulatory agent. The primers can be designed for any desired purpose, e.g., amplification, capture, modification, direct or indirect labeling, and the like. In some embodiments, the target of the variable region is a disease marker and thus the construct is targeted to a diseased tissue, cell or microvesicle. The immunomodulatory domain region can act as an immune stimulator or suppressor. Any appropriate immune stimulator or suppressor can be used, e.g., a small molecule, antibody or an aptamer. Thus, the construct can modulate the immune response at a target of interest, e.g., at a cell or microvesicle carrying the target. The basic construct can be modified as desired. For example, Design 2 in FIG. 8 shows the construct carrying a linker 805 between Primer 2 803 and the IMD 804. Such linkers are explained further below and can be inserted between any components of the construct as desired. Linkers can provide a desired space between the regions of the construct and can be manipulated to influence other properties such as stability. Design 3 in FIG. 8 shows another example wherein the IMD 804 is an oligonucleotide and the variable region 802 and IMD 804 lie between the primers 801 and 803. One of skill will appreciate that one or more linker, such as 805 of Design 2, can also be inserted into Design 3, e.g., between the variable region 802 and IMD 804. One of skill will further appreciate that the ordering of the oligonucleotide segments from 5' to 3' can be modified, e.g., reversed.

As noted, the multipartite constructs may be synthesized and/or modified as desired. In some embodiments of the invention, the multipartite oligonucleotide construct is synthesized directly with or without a linker in between the oligonucleotide segments. See, e.g., FIG. 8 Design 3, which can be generated directly via amplification by Primer 1 801 and Primer 2 803. One or more linker can act as a spacer to create a desired spacing between the target of the variable region segment 802 and the target of the IMD segment 804. The spacing can be determined via computer modeling or via experimentation due to steric hindrance or other considerations.

The multipartite constructs can be generated against any appropriate target. The targets can include without limitation tumors or diseased tissues, cells, cancer cells, circulating tumor cells (CTCs), immune cells (e.g., B-cells, T-cells, macrophages, dendritic cells), microvesicles, bacteria, viruses or other parasites. The target can be large biological complexes, e.g., protein complexes, ribonucleoprotein complexes, lipid complexes, or a combination thereof. It will be understood that the specific target of the multipartite constructs can be a certain member of the foregoing macromolecular targets. For example, consider that the desired target of the multipartite construct is a cell or microvesicle. In such case, the multipartite construct can be directed to a specific biomarker, e.g., a surface antigen, of the cell or microvesicle. As a non-limiting example, the target of interest can be B-cells and the specific target of the variable region of the multipartite construct can be CD20. CD20 is a cellular marker of B-cells targeted by the monoclonal antibodies (mAb) rituximab, obinutuzumab, ofatumumab, ibritumomab tiuxetan, and tositumomab, which are used as agents in the treatment of B-cell lymphomas and leukemias. As another non-limiting example, the target of interest can be cancer cells and the specific target of the variable region of the multipartite construct can be c-MET. MET is a membrane receptor that is essential for embryonic development and wound healing. Abnormal MET activation in cancer correlates with poor prognosis, where aberrantly active MET triggers tumor growth, formation of new blood vessels (angiogenesis), and cancer spread to other organs (metastasis). MET has been observed to be deregulated in many types of human malignancies, including cancers of kidney, liver, stomach, breast, and brain. Other biomarkers can be used as the specific target as desired. For example, the biomarker can be selected from any of Tables 3-4, or 10-17 herein, or Table 4 of International Patent Application PCT/US2016/040157, filed Jun. 29, 2016.

As noted above, the IDM domain can be constructed to illicit a complement mediated immune response that can induce apoptosis. Such IDM can include but are not limited to C1q, C1r, C1s, C1, C3a, C3b, C3d, C5a, C2, C4, and cytokines. The IDM region may comprise an oligonucleotide sequence including without limitation Toll-Like Receptor (TLR) agonists like CpG sequences which are immunostimulatory and/or polyG sequences which can be anti-proliferative or pro-apoptotic. The moiety can be vaccine like moiety or antigen that stimulates an immune response. In an embodiment, the immune stimulating moiety comprises a superantigen. In some embodiments, the superantigen can be selected from the group consisting of staphylococcal enterotoxins (SEs), a *Streptococcus pyogenes* exotoxin (SPE), a *Staphylococcus aureus* toxic shock-syndrome toxin (TSST-1), a streptococcal mitogenic exotoxin (SME), a streptococcal superantigen (SSA), a hepatitis surface antigen, or a combination thereof. Other bacterial antigens that can be used with the invention comprise bacterial antigens such as Freund's complete adjuvant, Freund's incomplete adjuvant, monophosphoryl-lipid A/trehalose dicorynomycolate (Ribi's adjuvant), BCG (Calmette-Guerin Bacillus; *Mycobacterium bovis*), and *Corynebacterium parvum*. The immune stimulating moiety can also be a non-specific immunostimulant, such as an adjuvant or other non-specific immunostimulator. Useful adjuvants comprise without limitation aluminium salts, alum, aluminium phosphate, aluminium hydroxide, squalene, oils, MF59, and AS03 ("Adjuvant System 03"). The adjuvant can be selected from the group consisting of Cationic liposome-DNA complex JVRS-100, aluminum hydroxide vaccine adjuvant, aluminum phosphate vaccine adjuvant, aluminum potassium sulfate adjuvant, Alhydrogel, ISCOM(s)™, Freund's Complete Adjuvant, Freund's Incomplete Adjuvant, CpG DNA Vaccine Adjuvant, Cholera toxin, Cholera toxin B subunit, Liposomes, Saponin Vaccine Adjuvant, DDA Adjuvant, Squalene-based Adjuvants, Etx B subunit Adjuvant, IL-12 Vaccine Adjuvant, LTK63 Vaccine Mutant Adjuvant, TiterMax Gold Adjuvant, Ribi Vaccine Adjuvant, Montanide ISA 720 Adjuvant, *Corynebacterium*-derived P40 Vaccine Adjuvant, MPL™ Adjuvant, AS04, AS02, Lipopolysaccharide Vaccine Adjuvant, Muramyl Dipeptide Adjuvant, CRL1005, Killed *Corynebacterium parvum* Vaccine Adjuvant, Montanide ISA 51, *Bordetella pertussis* component Vaccine Adjuvant, Cationic Liposomal Vaccine Adjuvant, Adamantylamide Dipeptide Vaccine Adjuvant, Arlacel A, VSA-3 Adjuvant, Aluminum vaccine adjuvant, Polygen Vaccine Adjuvant, Adjumer™, Algal Glucan, Bay R1005, Theramide®, Stearyl Tyrosine, Specol, Algammulin, Avridine®, Calcium Phosphate Gel, CTA1-DD gene fusion protein, DOC/Alum Complex, Gamma Inulin, Gerbu Adjuvant, GM-CSF, GMDP, Recombinant hIFN-gamma/Interferon-g, Interleukin-1β, Interleukin-2, Interleukin-7, Sclavo peptide, Rehydragel LV, Rehydragel HPA, Loxoribine, MF59, MTP-PE Liposomes, Murametide, Murapalmitine, D-Murapalmitine, NAGO, Non-Ionic Surfactant Vesicles, PMMA, Protein Cochleates, QS-21, SPT (Antigen Formulation), nanoemulsion vaccine adjuvant, AS03, Quil-A vaccine adjuvant, RC529 vaccine adjuvant, LTR192G Vaccine Adjuvant, *E. coli* heat-labile toxin, LT, amorphous aluminum hydroxyphosphate sulfate adjuvant, Calcium phosphate vaccine adjuvant, Montanide Incomplete Seppic Adjuvant, Imiquimod, Resiquimod, AF03, Flagellin, Poly(I:C), ISCOMATRIX®, Abisco-100 vaccine adjuvant, Albumin-heparin microparticles vaccine adjuvant, AS-2 vaccine adjuvant, B7-2 vaccine adjuvant, DHEA vaccine adjuvant, Immunoliposomes Containing Antibodies to Costimulatory Molecules, SAF-1, Sendai Proteoliposomes, Sendai-containing Lipid Matrices, Threonyl muramyl dipeptide (TMDP), Ty Particles vaccine adjuvant, Bupivacaine vaccine adjuvant, DL-PGL (Polyester poly (DL-lactide-co-glycolide)) vaccine adjuvant, IL-15 vaccine adjuvant, LTK72 vaccine adjuvant, MPL-SE vaccine adjuvant, non-toxic mutant E112K of Cholera Toxin mCT-E112K, and Matrix-S. Additional adjuvants that can be used with the multipartite constructs of the invention can be identified using the Vaxjo database. See Sayers S, Ulysse G, Xiang Z, and He Y. Vaxjo: a web-based vaccine adjuvant database and its application for analysis of vaccine adjuvants and their uses in vaccine development. Journal of Biomedicine and Biotechnology. 2012; 2012: 831486. Epub 2012 Mar. 13. PMID: 22505817; www.violinet.org/vaxjo/. Other useful non-specific immunostimulators comprise histamine, interferon, transfer factor, tuftsin, interleukin-1, female sex hormones, prolactin, growth hormone vitamin D, deoxycholic acid (DCA), tetrachlorodecaoxide (TCDO), and imiquimod or resiquimod, which are drugs that activate immune cells through the toll-like receptor 7. A multipartite construct can be created that comprises more than one immunomodulating moiety, e.g., using segments that span CpG sequences which are immunostimulatory with complement directed segments that can stimulate apoptosis.

Modifications

Modifications to the one or more oligonucleotide of the invention can be made to alter desired characteristics, including without limitation in vivo stability, specificity, affinity, avidity or nuclease susceptibility. Alterations to the half life may improve stability in vivo or may reduce stability to limit in vivo toxicity. Such alterations can include mutations, truncations or extensions. The 5' and/or 3' ends of the multipartite oligonucleotide constructs can be protected or deprotected to modulate stability as well. Modifications to improve in vivo stability, specificity, affinity, avidity or nuclease susceptibility or alter the half life to influence in vivo toxicity may be at the 5' or 3' end and include but are not limited to the following: locked nucleic acid (LNA) incorporation, unlocked nucleic acid (UNA) incorporation, phosphorothioate backbone instead of phosphodiester backbone, amino modifiers (i.e. C6-dT), dye conjugates (Cy dues, Fluorophores, etc), Biotinylation, PEG linkers, Click chemistry linkers, dideoxynucleotide end blockers, inverted end bases, cholesterol TEG or other lipid based labels.

Linkage options for segments of the oligonucleotide of the invention can be on the 5' or 3' end of an oligonucleotide or to a primary amine, sulfhydryl or carboxyl group of an antibody and include but are not limited to the following: Biotin-target oligonucleotide/Ab, streptavidin-complement oligonucleotide or vice versa, amino modified-target Ab/oligonucleotide, thiol/carboxy-complement oligonucleotide or vice versa, Click chemistry-target Ab/oligonucleotide, corresponding Click chemistry partner-complement oligonucleotide or vice versa. The linkages may be covalent or non-covalent and may include but are not limited to monovalent, multivalent (i.e. bi, tri or tetra-valent) assembly, to a DNA scaffold (i.e. DNA origami structure), drug/chemotherapeutic agent, nanoparticle, microparticle or a micelle or liposome.

A linker region can comprise a spacer with homo- or multifunctional reactive groups that can vary in length and type. These include but are not limited to the following: spacer C18, PEG4, PEG6, PEG8, and PEG12.

The multipartite oligonucleotide of the invention can further comprise additional elements to add desired biological effects. For example, the oligonucleotide of the invention may comprise a membrane disruptive moiety. The oligonucleotide of the invention may also be conjugated to one or more chemical moiety that provides such effects. For example, the oligonucleotide of the invention may be conjugated to a detergent-like moiety to disrupt the membrane of a target cell or microvesicle. Useful ionic detergents include sodium dodecyl sulfate (SDS, sodium lauryl sulfate (SLS)), sodium laureth sulfate (SLS, sodium lauryl ether sulfate (SLES)), ammonium lauryl sulfate (ALS), cetrimonium bromide, cetrimonium chloride, cetrimonium stearate, and the like. Useful non-ionic (zwitterionic) detergents include polyoxyethylene glycols, polysorbate 20 (also known as Tween 20), other polysorbates (e.g., 40, 60, 65, 80, etc), Triton-X (e.g., X100, X114), 3-[(3-cholamidopropyl) dimethylammonio]-1-propanesulfonate (CHAPS), CHAPSO, deoxycholic acid, sodium deoxycholate, NP-40, glycosides, octyl-thio-glucosides, maltosides, and the like. One of skill will appreciate that functional fragments, such as membrane disruptive moieties, can be covalently or non-covalently attached to the oligonucleotide of the invention.

Oligonucleotide segments, including those of a multipartite construct, can include any desirable base modification known in the art. In certain embodiments, oligonucleotide segments are 10 to 50 nucleotides in length. One having ordinary skill in the art will appreciate that this embodies oligonucleotides of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range derivable there within.

In certain embodiments, a multipartite construct comprises a chimeric oligonucleotide that contains two or more chemically distinct regions, each made up of at least one nucleotide. Such chimeras can be referred to using terms such as multipartite, multivalent, or the like. The oligonucleotides portions may contain at least one region of modified nucleotides that confers one or more beneficial properties, e.g., increased nuclease resistance, bioavailability, increased binding affinity for the target. Chimeric nucleic acids of the invention may be formed as composite structures of two or more oligonucleotides, two or more types of oligonucleotides (e.g., both DNA and RNA segments), modified oligonucleotides, oligonucleosides and/or oligonucleotide mimetics. Such compounds have also been referred to in the art as hybrids. Representative United States patents that teach the preparation of such hybrid structures comprise, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference in its entirety.

In certain embodiments, an oligonucleotide of the invention comprises at least one nucleotide modified at the 2' position of the sugar, including without limitation a 2'-0-alkyl, 2'-0-alkyl-0-alkyl or 2'-fluoro-modified nucleotide. In other embodiments, RNA modifications include 2'-fluoro, 2'-amino and 2' O-methyl modifications on the ribose of pyrimidines, a basic residue or an inverted base at the 3' end of the RNA. Such modifications are routinely incorporated into oligonucleotides and these oligonucleotides have been shown to have higher target binding affinity in some cases than 2'-deoxyoligonucleotides against a given target.

A number of nucleotide and nucleoside modifications have been shown to make an oligonucleotide more resistant to nuclease digestion, thereby prolonging in vivo half-life. Specific examples of modified oligonucleotides include those comprising backbones comprising, for example, phosphorothioates, phosphotriesters, methyl phosphonates, short chain alkyl or cycloalkyl intersugar linkages or short chain heteroatomic or heterocyclic intersugar linkages. The constructs of the invention can comprise oligonucleotides with phosphorothioate backbones and/or heteroatom backbones, e.g., CH2-NH-0-CH2, CH, ~N(CH3)~0~CH2 (known as a methylene(methylimino) or MMI backbone], CH2-O—N (CH3)-CH2, CH2-N (CH3)-N (CH3)-CH2 and O—N (CH3)-CH2-CH2 backbones, wherein the native phosphodiester backbone is represented as O—P—O—CH); amide backbones (De Mesmaeker et ah, 1995); morpholino backbone structures (Summerton and Weller, U.S. Pat. No. 5,034,506); peptide nucleic acid (PNA) backbone (wherein the phosphodiester backbone of the oligonucleotide is replaced with a polyamide backbone, the nucleotides being bound directly or indirectly to the aza nitrogen atoms of the polyamide backbone (Nielsen, et al., 1991), each of which is herein incorporated by reference in its entirety. Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3*-5* to 5*-3* or 2*-5* to 5*-2*; see U.S. Pat. Nos. 3,687,808; 4,469,863; 4,476,301; 5,023,243; 5, 177,196; 5,188,897; 5,264,423; 5,276,019; 5,278,302; 5,286,717; 5,321, 131; 5,399,676; 5,405,939; 5,453,496; 5,455, 233; 5,466,677; 5,476,925; 5,519,126; 5,536,821; 5,541,306; 5,550,111; 5,563, 253; 5,571,799; 5,587,361; and 5,625,050, each of which is herein incorporated by reference in its entirety. Morpholino-based oligomeric compounds are known in the art described in Braasch & Corey, Biochemistry vol. 41, no. 14, 2002, pages 4503-4510; Genesis vol. 30, 2001, page 3; Heasman, J. Dev. Biol. vol. 243, 2002, pages 209-214; Nasevicius et al. Nat. Genet. vol. 26, 2000, pages 216-220; Lacerra et al. Proc. Natl. Acad. Sci. vol. 97, 2000, pages 9591-9596 and U.S. Pat. No. 5,034,506, issued Jul. 23, 1991, each of which is herein incorporated by reference in its entirety. Cyclohexenyl nucleic acid oligonucleotide mimetics are described in Wang et al., J. Am. Chem. Soc. Vol. 122, 2000, pages 8595-8602, the contents of which is incorporated herein in its entirety. An oligonucleotide of the invention can comprise at least such modification as desired.

Modified oligonucleotide backbones that do not include a phosphorus atom therein have backbones that can be formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts; see U.S. Pat. Nos. 5,034,506; 5,166,315; 5,185,444; 5,214,134; 5,216, 141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference in its entirety. An oligonucleotide of the invention can comprise at least such modification as desired.

In certain embodiments, an oligonucleotide of the invention comprises one or more substituted sugar moieties, e.g., one of the following at the 2' position: OH, SH, $SCH_3$, F, OCN, $OCH_3$ $OCH_3$, $OCH_3$ $O(CH_2)n$ $CH_3$, $O(CH_2)n$ $NH_2$ or $O(CH_2)n$ $CH_3$ where n is from 1 to about 10; Ci to CIO lower alkyl, alkoxyalkoxy, substituted lower alkyl, alkaryl or aralkyl; CI; Br; CN; $CF_3$; $OCF_3$; O-, S-, or N-alkyl; O-, S-, or N-alkenyl; $SOCH_3$; $SO_2$ $CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacokinetic/pharmacodynamic properties of an oligonucleotide and other substituents having similar properties. A preferred modification includes 2'-methoxyethoxy [2'-0-CH2CH2OCH3, also known as 2'-0-(2-methoxyethyl)]. Other preferred modifications include 2*-methoxy (2*-0-CH3), 2*-propoxy (2*-OCH2 CH2CH3) and 2*-fluoro (2*-F) Similar modifications may also be made at other positions on the oligonucleotide, e.g., the 3' position of the sugar on the 3' terminal nucleotide and the 5' position of 5' terminal nucleotide. Oligonucleotides may also have sugar mimetics such as cyclobutyls in place of the pentofuranosyl group.

In certain embodiments, an oligonucleotide of the invention comprises one or more base modifications and/or substitutions. As used herein, "unmodified" or "natural" bases include adenine (A), guanine (G), thymine (T), cytosine (C) and uracil (U). Modified bases include, without limitation, bases found only infrequently or transiently in natural nucleic acids, e.g., hypoxanthine, 6-methyladenine, 5-Me pyrimidines, particularly 5-methylcytosine (also referred to as 5-methyl-2' deoxy cytosine and often referred to in the art as 5-Me-C), 5-hydroxymethylcytosine (HMC), glycosyl HMC and gentobiosyl HMC, as well as synthetic bases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine and 2,6-diaminopurine (Kornberg, 1980; Gebeyehu, et ah, 1987). A "universal" base known in the art, e.g., inosine, can also be included. 5-Me-C substitutions can also be included. These have been shown to increase nucleic acid duplex stability by 0.6-1.20C. See, e.g., Sanghvi et al., 'Antisense Research & Applications', 1993, CRC PRESS pages 276-278. Further suitable modified bases are described in U.S. Pat. Nos. 3,687,808, as well as 4,845,205; 5,130,302; 5,134,066; 5,175, 273; 5, 367,066; 5,432,272; 5,457,187; 5,459,255; 5,484,908; 5,502,177; 5,525,711; 5,552,540; 5,587,469; 5,596,091; 5,614,617; 5,750,692, and 5,681,941, each of which is herein incorporated by reference.

It is not necessary for all positions in a given oligonucleotide to be uniformly modified, and in fact more than one of the aforementioned modifications may be incorporated in a single oligonucleotide or even at within a single nucleoside within an oligonucleotide.

In certain embodiments, both a sugar and an internucleoside linkage, i.e., the backbone, of one or more nucleotide units within an oligonucleotide of the invention are replaced with novel groups. The base can be maintained for hybridization with an appropriate nucleic acid target compound. One such oligomeric compound, an oligonucleotide mimetic that has been shown to retain hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone. Representative patents that teach the preparation of PNA compounds comprise, but are not limited to, U.S. Pat. Nos. 5,539,082; 5,714,331; and 5,719,262, each of which is herein incorporated by reference. Further teaching of PNA compounds can be found in Nielsen et al. Science vol. 254, 1991, page 1497, which is herein incorporated by reference.

In certain embodiments, the oligonucleotide of the invention is linked (covalently or non-covalently) to one or more moieties or conjugates that enhance activity, cellular distribution, or localization. Such moieties include, without limitation, lipid moieties such as a cholesterol moiety (Letsinger et al. Proc. Natl. Acad. Sci. Usa. vol. 86, 1989, pages 6553-6556), cholic acid (Manoharan et al. Bioorg. Med. Chem. Let. vol. 4, 1994, pages 1053-1060), a thioether, e.g., hexyl-S-tritylthiol (Manoharan et al. Ann. N. Y. Acad. Sci. Vol. 660, 1992, pages 306-309; Manoharan et al. Bioorg. Med. Chem. Let. vol. 3, 1993, pages 2765-2770), a thiocholesterol (Oberhauser et al. Nucl. Acids Res. vol. 20, 1992, pages 533-538), an aliphatic chain, e.g., dodecandiol or undecyl residues (Kabanov et al. Febs Lett. vol. 259, 1990, pages 327-330; Svinarchuk et al. Biochimie vol. 75, 1993, pages 49-54), a phospholipid, e.g., di-hexadecyl-rac-glycerol or triethylammonium 1,2-di-O-hexadecyl-rac-glycero-3-H-phosphonate (Manoharan et al. Tetrahedron Lett. vol. 36, 1995, pages 3651-3654; Shea et al. Nucl. Acids Res. vol. 18, 1990, pages 3777-3783), a polyamine or a polyethylene glycol chain (Mancharan et al. Nucleosides & Nucleotides vol. 14, 1995, pages 969-973), or adamantane acetic acid (Manoharan et al. Tetrahedron Lett. vol. 36, 1995, pages 3651-3654), a palmityl moiety (Mishra et al. Biochim. Biophys. Acta vol. 1264, 1995, pages 229-237), or an octadecylamine or hexylamino-carbonyl-t oxycholesterol moiety (Crooke et al. J. Pharmacol. Exp. Ther. vol. 277, 1996, pages 923-937), each of which is herein incorporated by reference in its entirety. See also U.S. Pat. Nos. 4,828, 979; 4,948,882; 5,218,105; 5,525,465; 5,541,313; 5,545, 730; 5,552,538; 5,578,717; 5,580,731; 5,580,731; 5,591, 584; 5,109,124; 5,118,802; 5,138,045; 5,414,077; 5,486, 603; 5,512,439; 5,578,718; 5,608,046; 4,587,044; 4,605, 735; 4,667,025; 4,762,779; 4,789,737; 4,824,941; 4,835, 263; 4,876,335; 4,904,582; 4,958,013; 5,082,830; 5,112, 963; 5,214,136; 5,082,830; 5,112,963; 5,214,136; 5,245, 022; 5,254,469; 5,258,506; 5,262,536; 5,272,250; 5,292, 873; 5,317,098; 5,371,241, 5,391,723; 5,416,203, 5,451, 463; 5,510,475; 5,512,667; 5,514,785; 5,565,552; 5,567, 810; 5,574,142; 5,585,481; 5,587,371; 5,595,726; 5,597, 696; 5,599,923; 5,599,928 and 5,688,941, each of which is herein incorporated by reference in its entirety.

The oligonucleotide of the invention can be modified to incorporate a wide variety of modified nucleotides as desired. For example, the construct may be synthesized entirely of modified nucleotides or with a subset of modified nucleotides. The modifications can be the same or different. Some or all nucleotides may be modified, and those that are modified may contain the same modification. For example, all nucleotides containing the same base may have one type of modification, while nucleotides containing other bases may have different types of modification. All purine nucleotides may have one type of modification (or are unmodified), while all pyrimidine nucleotides have another, different type of modification (or are unmodified). Thus, the construct may comprise any combination of desired modifications, including for example, ribonucleotides (2'-OH), deoxyribonucleotides (2'-deoxy), 2'-amino nucleotides (2'-NH2), 2'-fluoro nucleotides (2'-F) and 2'-0-methyl (2'-OMe) nucleotides.

In some embodiments, the oligonucleotide of the invention is synthesized using a transcription mixture containing modified nucleotides in order to generate a modified construct. For example, a transcription mixture may contain only 2'-OMe A, G, C and U and/or T triphosphates (2'-OMe ATP, 2'-OMe UTP and/or 2*-OMe TTP, 2*-OMe CTP and 2*-OMe GTP), referred to as an MNA or mRmY mixture. Oligonucleotides generated therefrom are referred to as MNA oligonucleotides or mRmY oligonucleotides and contain only 2'-0-methyl nucleotides. A transcription mixture containing all 2'-OH nucleotides is referred to as an "rN" mixture, and oligonucleotides generated therefrom are referred to as "rN", "rRrY" or RNA oligonucleotides. A transcription mixture containing all deoxy nucleotides is referred to as a "dN" mixture, and oligonucleotides generated therefrom are referred to as "dN", "dRdY" or DNA oligonucleotides. Alternatively, a subset of nucleotides (e.g., C, U and/or T) may comprise a first modified nucleotides (e.g, 2'-OMe) nucleotides and the remainder (e.g., A and G) comprise a second modified nucleotide (e.g., 2'-OH or 2'-F). For example, a transcription mixture containing 2'-F U and 2'-OMe A, G and C is referred to as a "fUmV" mixture, and oligonucleotides generated therefrom are referred to as "fUmV" oligonucleotides. A transcription mixture containing 2'-F A and G, and 2'-OMe C and U and/or T is referred to as an "fRmY" mixture, and oligonucleotides generated therefrom are referred to as "fRmY" oligonucleotides. A transcription mixture containing 2'-F A and 2'-OMe C, G and U and/or T is referred to as "fAmB" mixture, and oligonucleotides generated therefrom are referred to as "fAmB" oligonucleotides.

One of skill in the art can improve pre-identified aptamer segments (e.g., variable regions or immunomodulatory regions that comprise an aptamer to a biomarker target or other entity) using various process modifications. Examples of such process modifications include, but are not limited to, truncation, deletion, substitution, or modification of a sugar or base or internucleotide linkage, capping, and PEGylation. In addition, the sequence requirements of an aptamer may be explored through doped reselections or aptamer medicinal chemistry. Doped reselections are carried out using a synthetic, degenerate pool that has been designed based on the aptamer of interest. The level of degeneracy usually varies from about 70-85% from the aptamer of interest. In general, sequences with neutral mutations are identified through the doped reselection process. Aptamer medicinal chemistry is an aptamer improvement technique in which sets of variant aptamers are chemically synthesized. These variants are then compared to each other and to the parent aptamer. Aptamer medicinal chemistry is used to explore the local, rather than global, introduction of substituents. For example, the following modifications may be introduced: modifications at a sugar, base, and/or internucleotide linkage, such as 2'-deoxy, 2'-ribo, or 2'-0-methyl purines or pyrimidines, phosphorothioate linkages may be introduced between nucleotides, a cap may be introduced at the 5' or 3' end of the aptamer (such as 3' inverted dT cap) to block degradation by exonucleases, or a polyethylene glycol (PEG) element may be added to the aptamer to increase the half-life of the aptamer in the subject.

Additional compositions comprising an oligonucleotide of the invention and uses thereof are further described below. As the invention provides methods to identify oligonucleotide probes that bind to specific tissues, cells, microvesicles or other biological entities of interest, the oligonucleotide probes of the invention target such entities and are inherently drug candidates, agents that can be used for targeted drug delivery, or both.

Pharmaceutical Compositions

In an aspect, the invention provides pharmaceutical compositions comprising one or more oligonucleotide of the invention, e.g., as a standalone drug, as a drug delivery agent, as a multipartite construct as described above, or any combination thereof. The invention further provides methods of administering such compositions.

The term "condition," as used herein means an interruption, cessation, or disorder of a bodily function, system, or organ. Representative conditions include, but are not limited to, diseases such as cancer, inflammation, diabetes, and organ failure.

The phrase "treating," "treatment of," and the like include the amelioration or cessation of a specified condition.

The phrase "preventing," "prevention of," and the like include the avoidance of the onset of a condition.

The term "salt," as used herein, means two compounds that are not covalently bound but are chemically bound by ionic interactions.

The term "pharmaceutically acceptable," as used herein, when referring to a component of a pharmaceutical composition means that the component, when administered to an animal, does not have undue adverse effects such as excessive toxicity, irritation, or allergic response commensurate with a reasonable benefit/risk ratio. Accordingly, the term "pharmaceutically acceptable organic solvent," as used herein, means an organic solvent that when administered to an animal does not have undue adverse effects such as excessive toxicity, irritation, or allergic response commensurate with a reasonable benefit/risk ratio. Preferably, the pharmaceutically acceptable organic solvent is a solvent that is generally recognized as safe ("GRAS") by the United States Food and Drug Administration ("FDA"). Similarly, the term "pharmaceutically acceptable organic base," as used herein, means an organic base that when administered to an animal does not have undue adverse effects such as excessive toxicity, irritation, or allergic response commensurate with a reasonable benefit/risk ratio.

The phrase "injectable" or "injectable composition," as used herein, means a composition that can be drawn into a syringe and injected subcutaneously, intraperitoneally, or intramuscularly into an animal without causing adverse effects due to the presence of solid material in the composition. Solid materials include, but are not limited to, crystals, gummy masses, and gels. Typically, a formulation or composition is considered to be injectable when no more than about 15%, preferably no more than about 10%, more preferably no more than about 5%, even more preferably no more than about 2%, and most preferably no more than about 1% of the formulation is retained on a 0.22 µm filter when the formulation is filtered through the filter at 98° F. There are, however, some compositions of the invention, which are gels, that can be easily dispensed from a syringe but will be retained on a 0.22 µm filter. In one embodiment, the term "injectable," as used herein, includes these gel compositions. In one embodiment, the term "injectable," as used herein, further includes compositions that when warmed to a temperature of up to about 40° C. and then filtered through a 0.22 µm filter, no more than about 15%, preferably no more than about 10%, more preferably no more than about 5%, even more preferably no more than about 2%, and most preferably no more than about 1% of the formulation is retained on the filter. In one embodiment, an example of an injectable pharmaceutical composition is a solution of a pharmaceutically active compound (for example, one or more oligonucleotide of the invention, e.g., a multipartite construct, an anti-C1Q oligonucleotide, a 10.36 oligonucleotide, as described above, or any combination thereof) in a pharmaceutically acceptable solvent. One of skill will appreciate that injectable solutions have inherent properties, e.g., sterility, pharmaceutically acceptable excipients and free of harmful measures of pyrogens or similar contaminants.

The term "solution," as used herein, means a uniformly dispersed mixture at the molecular or ionic level of one or more substances (solute), in one or more other substances (solvent), typically a liquid.

The term "suspension," as used herein, means solid particles that are evenly dispersed in a solvent, which can be aqueous or non-aqueous.

The term "animal," as used herein, includes, but is not limited to, humans, canines, felines, equines, bovines, ovines, porcines, amphibians, reptiles, and avians. Representative animals include, but are not limited to a cow, a horse, a sheep, a pig, an ungulate, a chimpanzee, a monkey, a baboon, a chicken, a turkey, a mouse, a rabbit, a rat, a guinea pig, a dog, a cat, and a human. In one embodiment, the animal is a mammal. In one embodiment, the animal is a human. In one embodiment, the animal is a non-human. In one embodiment, the animal is a canine, a feline, an equine, a bovine, an ovine, or a porcine.

The phrase "drug depot," as used herein means a precipitate, which includes one or more oligonucleotide of the invention, e.g., a multipartite construct, an anti-C1Q oligonucleotide, a 10.36 oligonucleotide, as described above, or any combination thereof, formed within the body of a treated animal that releases the oligonucleotide over time to provide a pharmaceutically effective amount of the oligonucleotide.

The phrase "substantially free of," as used herein, means less than about 2 percent by weight. For example, the phrase "a pharmaceutical composition substantially free of water" means that the amount of water in the pharmaceutical composition is less than about 2 percent by weight of the pharmaceutical composition.

The term "effective amount," as used herein, means an amount sufficient to treat or prevent a condition in an animal.

The nucleotides that make up the oligonucleotide of the invention can be modified to, for example, improve their stability, i.e., improve their in vivo half-life, and/or to reduce their rate of excretion when administered to an animal. The term "modified" encompasses nucleotides with a covalently modified base and/or sugar. For example, modified nucleotides include nucleotides having sugars which are covalently attached to low molecular weight organic groups other than a hydroxyl group at the 3' position and other than a phosphate group at the 5' position. Modified nucleotides may also include 2' substituted sugars such as 2'-O-methyl-; 2'-O-alkyl; 2'-O-allyl; 2'-S-alkyl; 2'-S-allyl; 2'-fluoro-; 2'-halo or 2'-azido-ribose; carbocyclic sugar analogues; α-anomeric sugars; and epimeric sugars such as arabinose, xyloses or lyxoses, pyranose sugars, furanose sugars, and sedoheptulose.

Modified nucleotides are known in the art and include, but are not limited to, alkylated purines and/or pyrimidines; acylated purines and/or pyrimidines; or other heterocycles. These classes of pyrimidines and purines are known in the art and include, pseudoisocytosine; N4,N4-ethanocytosine; 8-hydroxy-N6-methyladenine; 4-acetylcytosine, 5-(carboxyhydroxylmethyl) uracil; 5-fluorouracil; 5-bromouracil; 5-carboxymethylaminomethyl-2-thiouracil; 5-carboxymethylaminomethyl uracil; dihydrouracil; inosine; N6-isopentyladenine; 1-methyladenine; 1-methylpseudouracil; 1-methylguanine; 2,2-dimethylguanine; 2-methyladenine; 2-methylguanine; 3-methylcytosine; 5-methylcytosine; N6-methyladenine; 7-methylguanine; 5-methylaminomethyl uracil; 5-methoxy amino methyl-2-thiouracil; β-D-mannosylqueosine; 5-methoxycarbonylmethyluracil; 5-methoxyuracil; 2 methylthio-N6-isopentenyladenine; uracil-5-oxyacetic acid methyl ester; pseudouracil; 2-thiocytosine; 5-methyl-2 thiouracil, 2-thiouracil; 4-thiouracil; 5-methyluracil; N-uracil-5-oxyacetic acid methylester; uracil 5-oxyacetic acid; queosine; 2-thiocytosine; 5-propyluracil; 5-propylcytosine; 5-ethyluracil; 5-ethylcytosine; 5-butyluracil; 5-phenyluracil; 5-pentylcytosine; and 2,6,-diaminopurine; methylpseudouracil; 1-methylguanine; and 1-methylcytosine.

An oligonucleotide of the invention can also be modified by replacing one or more phosphodiester linkages with alternative linking groups. Alternative linking groups include, but are not limited to embodiments wherein P(O)O is replaced by P(O)S, P(S)S, P(O)NR2, P(O)R, P(O)OR', CO, or CH2, wherein each R or R' is independently H or a substituted or unsubstituted C1-C20 alkyl. A preferred set of R substitutions for the P(O)NR2 group are hydrogen and methoxyethyl Linking groups are typically attached to each adjacent nucleotide through an —O— bond, but may be modified to include —N— or —S— bonds. Not all linkages in an oligomer need to be identical.

The oligonucleotide of the invention can also be modified by conjugation to a polymer, for example, to reduce the rate of excretion when administered to an animal. For example, the oligonucleotide can be "PEGylated," i.e., conjugated to polyethylene glycol ("PEG"). In one embodiment, the PEG has an average molecular weight ranging from about 20 kD to 80 kD. Methods to conjugate an oligonucleotide with a polymer, such PEG, are known to those skilled in the art (See, e.g., Greg T. Hermanson, Bioconjugate Techniques, Academic Press, 1966).

The oligonucleotide of the invention, e.g., a multipartite construct, an anti-C1Q oligonucleotide, a 10.36 oligonucleotide, as described above, or any combination thereof, can be used in the pharmaceutical compositions disclosed herein or known in the art.

In one embodiment, the pharmaceutical composition further comprises a solvent.

In one embodiment, the solvent comprises water.

In one embodiment, the solvent comprises a pharmaceutically acceptable organic solvent. Any useful and pharmaceutically acceptable organic solvents can be used in the compositions of the invention.

In one embodiment, the pharmaceutical composition is a solution of the salt in the pharmaceutically acceptable organic solvent.

In one embodiment, the pharmaceutical composition comprises a pharmaceutically acceptable organic solvent and further comprises a phospholipid, a sphingomyelin, or phosphatidyl choline. Without wishing to be bound by theory, it is believed that the phospholipid, sphingomyelin, or phosphatidyl choline facilitates formation of a precipitate when the pharmaceutical composition is injected into water and can also facilitate controlled release of the oligonucleotide from the resulting precipitate. Typically, the phospholipid, sphingomyelin, or phosphatidyl choline is present in an amount ranging from greater than 0 to 10 percent by weight of the pharmaceutical composition. In one embodiment, the phospholipid, sphingomyelin, or phosphatidyl choline is present in an amount ranging from about 0.1 to 10 percent by weight of the pharmaceutical composition. In one embodiment, the phospholipid, sphingomyelin, or phosphatidyl choline is present in an amount ranging from about 1 to 7.5 percent by weight of the pharmaceutical composition. In one embodiment, the phospholipid, sphingomyelin, or phosphatidyl choline is present in an amount ranging from about 1.5 to 5 percent by weight of the pharmaceutical composition. In one embodiment, the phospholipid, sphingomyelin, or phosphatidyl choline is present in an amount ranging from about 2 to 4 percent by weight of the pharmaceutical composition.

The pharmaceutical compositions can optionally comprise one or more additional excipients or additives to provide a dosage form suitable for administration to an animal. When administered to an animal, the oligonucleotide containing pharmaceutical compositions are typically administered as a component of a composition that comprises a pharmaceutically acceptable carrier or excipient so as to provide the form for proper administration to the animal. Suitable pharmaceutical excipients are described in Remington's Pharmaceutical Sciences 1447-1676 (Alfonso R. Gennaro ed., 19th ed. 1995), incorporated herein by reference. The pharmaceutical compositions can take the form of solutions, suspensions, emulsion, tablets, pills, pellets, capsules, capsules containing liquids, powders, suppositories, emulsions, aerosols, sprays, suspensions, or any other form suitable for use.

In one embodiment, the pharmaceutical compositions are formulated for intravenous or parenteral administration. Typically, compositions for intravenous or parenteral administration comprise a suitable sterile solvent, which may be an isotonic aqueous buffer or pharmaceutically acceptable organic solvent. Where necessary, the compositions can also include a solubilizing agent. Compositions for intravenous administration can optionally include a local anesthetic such as lidocaine to lessen pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where oligonucleotide-containing pharmaceutical compositions are to be administered by infusion, they can be dispensed, for example, with an infusion bottle containing, for example, sterile pharmaceutical grade water or saline. Where the pharmaceutical compositions are administered by injection, an ampoule of sterile water for injection, saline, or other solvent such as a pharmaceutically acceptable organic solvent can be provided so that the ingredients can be mixed prior to administration.

In another embodiment, the pharmaceutical compositions are formulated in accordance with routine procedures as a composition adapted for oral administration. Compositions for oral delivery can be in the form of tablets, lozenges, aqueous or oily suspensions, granules, powders, emulsions, capsules, syrups, or elixirs, for example. Oral compositions can include standard excipients such as mannitol, lactose, starch, magnesium stearate, sodium saccharin, cellulose, and magnesium carbonate. Typically, the excipients are of pharmaceutical grade. Orally administered compositions can also contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, when in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compositions. A time-delay material such as glycerol monostearate or glycerol stearate can also be used.

The pharmaceutical compositions further comprising a solvent can optionally comprise a suitable amount of a pharmaceutically acceptable preservative, if desired, so as to provide additional protection against microbial growth. Examples of preservatives useful in the pharmaceutical compositions of the invention include, but are not limited to, potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chlorides (e.g., benzethonium chloride).

In one embodiment, the pharmaceutical compositions of the invention optionally contain a suitable amount of a pharmaceutically acceptable polymer. The polymer can increase the viscosity of the pharmaceutical composition. Suitable polymers for use in the compositions and methods of the invention include, but are not limited to, hydroxypropylcellulose, hydoxypropylmethylcellulose (HPMC), chitosan, polyacrylic acid, and polymethacrylic acid.

Typically, the polymer is present in an amount ranging from greater than 0 to 10 percent by weight of the pharmaceutical composition. In one embodiment, the polymer is present in an amount ranging from about 0.1 to 10 percent by weight of the pharmaceutical composition. In one embodiment, the polymer is present in an amount ranging from about 1 to 7.5 percent by weight of the pharmaceutical composition. In one embodiment, the polymer is present in an amount ranging from about 1.5 to 5 percent by weight of the pharmaceutical composition. In one embodiment, the polymer is present in an amount ranging from about 2 to 4 percent by weight of the pharmaceutical composition. In one embodiment, the pharmaceutical compositions of the invention are substantially free of polymers.

In one embodiment, any additional components added to the pharmaceutical compositions of the invention are designated as GRAS by the FDA for use or consumption by animals. In one embodiment, any additional components added to the pharmaceutical compositions of the invention are designated as GRAS by the FDA for use or consumption by humans.

The components of the pharmaceutical composition (the solvents and any other optional components) are preferably biocompatible and non-toxic and, over time, are simply absorbed and/or metabolized by the body.

As described above, the pharmaceutical compositions of the invention can further comprise a solvent.

In one embodiment, the solvent comprises water.

In one embodiment, the solvent comprises a pharmaceutically acceptable organic solvent.

In an embodiment, the oligonucleotide of the invention, e.g., a multipartite construct, an anti-C1Q oligonucleotide, a 10.36 oligonucleotide, as described above, or any combination thereof, are available as the salt of a metal cation, for example, as the potassium or sodium salt. These salts, however, may have low solubility in aqueous solvents and/or organic solvents, typically, less than about 25 mg/mL. The pharmaceutical compositions of the invention comprising (i) an amino acid ester or amino acid amide and (ii) a protonated oligonucleotide, however, may be significantly more soluble in aqueous solvents and/or organic solvents. Without wishing to be bound by theory, it is believed that the amino acid ester or amino acid amide and the protonated oligonucleotide form a salt, such as illustrated above, and the salt is soluble in aqueous and/or organic solvents.

Similarly, without wishing to be bound by theory, it is believed that the pharmaceutical compositions comprising (i) an oligonucleotide of the invention; (ii) a divalent metal cation; and (iii) optionally a carboxylate, a phospholipid, a phosphatidyl choline, or a sphingomyelin form a salt, such as illustrated above, and the salt is soluble in aqueous and/or organic solvents.

In one embodiment, the concentration of the oligonucleotide of the invention in the solvent is greater than about 2 percent by weight of the pharmaceutical composition. In one embodiment, the concentration of the oligonucleotide of the invention in the solvent is greater than about 5 percent by weight of the pharmaceutical composition. In one embodiment, the concentration of the oligonucleotide in the solvent is greater than about 7.5 percent by weight of the pharmaceutical composition. In one embodiment, the concentration of the oligonucleotide in the solvent is greater than about 10 percent by weight of the pharmaceutical composition. In one embodiment, the concentration of the oligonucleotide in the solvent is greater than about 12 percent by weight of the pharmaceutical composition. In one embodiment, the concentration of the oligonucleotide in the solvent is greater than about 15 percent by weight of the pharmaceutical composition. In one embodiment, the concentration of the oligonucleotide in the solvent is ranges from about 2 percent to 5 percent by weight of the pharmaceutical composition. In one embodiment, the concentration of the oligonucleotide in the solvent is ranges from about 2 percent to 7.5 percent by weight of the pharmaceutical composition. In one embodiment, the concentration of the oligonucleotide in the solvent ranges from about 2 percent to 10 percent by weight of the pharmaceutical composition. In one embodiment, the concentration of the oligonucleotide in the solvent is ranges from about 2 percent to 12 percent by weight of the pharmaceutical composition. In one embodiment, the concentration of the oligonucleotide in the solvent is ranges from about 2 percent to 15 percent by weight of the pharmaceutical composition. In one embodiment, the concentration of the oligonucleotide in the solvent is ranges from about 2 percent to 20 percent by weight of the pharmaceutical composition.

Any pharmaceutically acceptable organic solvent can be used in the pharmaceutical compositions of the invention. Representative, pharmaceutically acceptable organic solvents include, but are not limited to, pyrrolidone, N-methyl-2-pyrrolidone, polyethylene glycol, propylene glycol (i.e., 1,3-propylene glycol), glycerol formal, isosorbid dimethyl ether, ethanol, dimethyl sulfoxide, tetraglycol, tetrahydrofurfuryl alcohol, triacetin, propylene carbonate, dimethyl acetamide, dimethyl formamide, dimethyl sulfoxide, and combinations thereof.

In one embodiment, the pharmaceutically acceptable organic solvent is a water soluble solvent. A representative pharmaceutically acceptable water soluble organic solvents is triacetin.

In one embodiment, the pharmaceutically acceptable organic solvent is a water miscible solvent. Representative pharmaceutically acceptable water miscible organic solvents include, but are not limited to, glycerol formal, polyethylene glycol, and propylene glycol.

In one embodiment, the pharmaceutically acceptable organic solvent comprises pyrrolidone. In one embodiment, the pharmaceutically acceptable organic solvent is pyrrolidone substantially free of another organic solvent.

In one embodiment, the pharmaceutically acceptable organic solvent comprises N-methyl-2-pyrrolidone. In one embodiment, the pharmaceutically acceptable organic solvent is N-methyl-2-pyrrolidone substantially free of another organic solvent.

In one embodiment, the pharmaceutically acceptable organic solvent comprises polyethylene glycol. In one embodiment, the pharmaceutically acceptable organic solvent is polyethylene glycol substantially free of another organic solvent.

In one embodiment, the pharmaceutically acceptable organic solvent comprises propylene glycol. In one embodiment, the pharmaceutically acceptable organic solvent is propylene glycol substantially free of another organic solvent.

In one embodiment, the pharmaceutically acceptable organic solvent comprises glycerol formal. In one embodiment, the pharmaceutically acceptable organic solvent is glycerol formal substantially free of another organic solvent.

In one embodiment, the pharmaceutically acceptable organic solvent comprises isosorbid dimethyl ether. In one embodiment, the pharmaceutically acceptable organic solvent is isosorbid dimethyl ether substantially free of another organic solvent.

In one embodiment, the pharmaceutically acceptable organic solvent comprises ethanol. In one embodiment, the pharmaceutically acceptable organic solvent is ethanol substantially free of another organic solvent.

In one embodiment, the pharmaceutically acceptable organic solvent comprises dimethyl sulfoxide. In one embodiment, the pharmaceutically acceptable organic solvent is dimethyl sulfoxide substantially free of another organic solvent.

In one embodiment, the pharmaceutically acceptable organic solvent comprises tetraglycol. In one embodiment, the pharmaceutically acceptable organic solvent is tetraglycol substantially free of another organic solvent.

In one embodiment, the pharmaceutically acceptable organic solvent comprises tetrahydrofurfuryl alcohol. In one embodiment, the pharmaceutically acceptable organic solvent is tetrahydrofurfuryl alcohol substantially free of another organic solvent.

In one embodiment, the pharmaceutically acceptable organic solvent comprises triacetin. In one embodiment, the pharmaceutically acceptable organic solvent is triacetin substantially free of another organic solvent.

In one embodiment, the pharmaceutically acceptable organic solvent comprises propylene carbonate. In one embodiment, the pharmaceutically acceptable organic solvent is propylene carbonate substantially free of another organic solvent.

In one embodiment, the pharmaceutically acceptable organic solvent comprises dimethyl acetamide. In one embodiment, the pharmaceutically acceptable organic solvent is dimethyl acetamide substantially free of another organic solvent.

In one embodiment, the pharmaceutically acceptable organic solvent comprises dimethyl formamide. In one embodiment, the pharmaceutically acceptable organic solvent is dimethyl formamide substantially free of another organic solvent.

In one embodiment, the pharmaceutically acceptable organic solvent comprises at least two pharmaceutically acceptable organic solvents.

In one embodiment, the pharmaceutically acceptable organic solvent comprises N-methyl-2-pyrrolidone and glycerol formal. In one embodiment, the pharmaceutically acceptable organic solvent is N-methyl-2-pyrrolidone and glycerol formal. In one embodiment, the ratio of N-methyl-2-pyrrolidone to glycerol formal ranges from about 90:10 to 10:90.

In one embodiment, the pharmaceutically acceptable organic solvent comprises propylene glycol and glycerol formal. In one embodiment, the pharmaceutically acceptable organic solvent is propylene glycol and glycerol formal. In one embodiment, the ratio of propylene glycol to glycerol formal ranges from about 90:10 to 10:90.

In one embodiment, the pharmaceutically acceptable organic solvent is a solvent that is recognized as GRAS by the FDA for administration or consumption by animals. In one embodiment, the pharmaceutically acceptable organic solvent is a solvent that is recognized as GRAS by the FDA for administration or consumption by humans.

In one embodiment, the pharmaceutically acceptable organic solvent is substantially free of water. In one embodiment, the pharmaceutically acceptable organic solvent contains less than about 1 percent by weight of water. In one embodiment, the pharmaceutically acceptable organic solvent contains less about 0.5 percent by weight of water. In one embodiment, the pharmaceutically acceptable organic solvent contains less about 0.2 percent by weight of water. Pharmaceutically acceptable organic solvents that are substantially free of water are advantageous since they are not conducive to bacterial growth. Accordingly, it is typically not necessary to include a preservative in pharmaceutical compositions that are substantially free of water. Another advantage of pharmaceutical compositions that use a pharmaceutically acceptable organic solvent, preferably substantially free of water, as the solvent is that hydrolysis of the oligonucleotide is minimized. Typically, the more water present in the solvent the more readily the oligonucleotide can be hydrolyzed. Accordingly, oligonucleotide containing pharmaceutical compositions that use a pharmaceutically acceptable organic solvent as the solvent can be more stable than oligonucleotide containing pharmaceutical compositions that use water as the solvent.

In one embodiment, comprising a pharmaceutically acceptable organic solvent, the pharmaceutical composition is injectable.

In one embodiment, the injectable pharmaceutical compositions are of sufficiently low viscosity that they can be easily drawn into a 20 gauge and needle and then easily expelled from the 20 gauge needle. Typically, the viscosity of the injectable pharmaceutical compositions are less than about 1,200 cps. In one embodiment, the viscosity of the injectable pharmaceutical compositions are less than about 1,000 cps. In one embodiment, the viscosity of the injectable pharmaceutical compositions are less than about 800 cps. In one embodiment, the viscosity of the injectable pharmaceutical compositions are less than about 500 cps. Injectable pharmaceutical compositions having a viscosity greater than about 1,200 cps and even greater than about 2,000 cps (for example gels) are also within the scope of the invention provided that the compositions can be expelled through an 18 to 24 gauge needle.

In one embodiment, comprising a pharmaceutically acceptable organic solvent, the pharmaceutical composition is injectable and does not form a precipitate when injected into water.

In one embodiment, comprising a pharmaceutically acceptable organic solvent, the pharmaceutical composition is injectable and forms a precipitate when injected into water. Without wishing to be bound by theory, it is believed, for pharmaceutical compositions that comprise a protonated oligonucleotide and an amino acid ester or amide, that the a-amino group of the amino acid ester or amino acid amide is protonated by the oligonucleotide to form a salt, such as illustrated above, which is soluble in the pharmaceutically acceptable organic solvent but insoluble in water. Similarly, when the pharmaceutical composition comprises (i) an oligonucleotide; (ii) a divalent metal cation; and (iii) optionally a carboxylate, a phospholipid, a phosphatidyl choline, or a sphingomyelin, it is believed that the components of the composition form a salt, such as illustrated above, which is soluble in the pharmaceutically acceptable organic solvent but insoluble in water. Accordingly, when the pharmaceutical compositions are injected into an animal, at least a portion of the pharmaceutical composition precipitates at the injection site to provide a drug depot. Without wishing to be bound by theory, it is believed that when the pharmaceutically compositions are injected into an animal, the pharmaceutically acceptable organic solvent diffuses away from the injection site and aqueous bodily fluids diffuse towards the injection site, resulting in an increase in concentration of water at the injection site, that causes at least a portion of the composition to precipitate and form a drug depot. The precipitate can take the form of a solid, a crystal, a gummy mass, or a gel. The precipitate, however, provides a depot of the oligonucleotide at the injection site that releases the oligonucleotide over time. The components of the pharmaceutical composition, i.e., the amino acid ester or amino acid amide, the pharmaceutically acceptable organic solvent, and any other components are biocompatible and non-toxic and, over time, are simply absorbed and/or metabolized by the body.

In one embodiment, comprising a pharmaceutically acceptable organic solvent, the pharmaceutical composition is injectable and forms liposomal or micellar structures when injected into water (typically about 500 μL are injected into about 4 mL of water). The formation of liposomal or micellar structures are most often formed when the pharmaceutical composition includes a phospholipid. Without wishing to be bound by theory, it is believed that the oligonucleotide in the form of a salt, which can be a salt formed with an amino acid ester or amide or can be a salt with a divalent metal cation and optionally a carboxylate, a phospholipid, a phosphatidyl choline, or a sphingomyelin, that is trapped within the liposomal or micellar structure. Without wishing to be bound by theory, it is believed that when these pharmaceutically compositions are injected into an animal, the liposomal or micellar structures release the oligonucleotide over time.

In one embodiment, the pharmaceutical composition further comprising a pharmaceutically acceptable organic solvent is a suspension of solid particles in the pharmaceutically acceptable organic solvent. Without wishing to be bound by theory, it is believed that the solid particles comprise a salt formed between the amino acid ester or amino acid amide and the protonated oligonucleotide wherein the acidic phosphate groups of the oligonucleotide protonates the amino group of the amino acid ester or amino acid amide, such as illustrated above, or comprises a salt formed between the oligonucleotide; divalent metal cation; and optional carboxylate, phospholipid, phosphatidyl choline, or sphingomyelin, as illustrated above. Pharmaceutical compositions that are suspensions can also form drug depots when injected into an animal.

By varying the lipophilicity and/or molecular weight of the amino acid ester or amino acid amide it is possible to vary the properties of pharmaceutical compositions that include these components and further comprise an organic solvent. The lipophilicity and/or molecular weight of the amino acid ester or amino acid amide can be varied by varying the amino acid and/or the alcohol (or amine) used to form the amino acid ester (or amino acid amide). For example, the lipophilicity and/or molecular weight of the amino acid ester can be varied by varying the R1 hydrocarbon group of the amino acid ester. Typically, increasing the molecular weight of R1 increase the lipophilicity of the amino acid ester. Similarly, the lipophilicity and/or molecular weight of the amino acid amide can be varied by varying the R3 or R4 groups of the amino acid amide.

For example, by varying the lipophilicity and/or molecular weight of the amino acid ester or amino acid amide it is possible to vary the solubility of the oligonucleotide of the invention in water, to vary the solubility of the oligonucleotide in the organic solvent, vary the viscosity of the pharmaceutical composition comprising a solvent, and vary the ease at which the pharmaceutical composition can be drawn into a 20 gauge needle and then expelled from the 20 gauge needle.

Furthermore, by varying the lipophilicity and/or molecular weight of the amino acid ester or amino acid amide (i.e., by varying R1 of the amino acid ester or R3 and R4 of the amino acid amide) it is possible to control whether the pharmaceutical composition that further comprises an organic solvent will form a precipitate when injected into water. Although different oligonucleotides exhibit different solubility and behavior, generally the higher the molecular weight of the amino acid ester or amino acid amide, the more likely it is that the salt of the protonated oligonucleotide and the amino acid ester of the amide will form a precipitate when injected into water. Typically, when R1 of the amino acid ester is a hydrocarbon of about C16 or higher the pharmaceutical composition will form a precipitate when injected into water and when R1 of the amino acid ester is a hydrocarbon of about C12 or less the pharmaceutical composition will not form a precipitate when injected into water. Indeed, with amino acid esters wherein R1 is a hydrocarbon of about C12 or less, the salt of the protonated oligonucleotide and the amino acid ester is, in many cases, soluble in water. Similarly, with amino acid amides, if the combined number of carbons in R3 and R4 is 16 or more the pharmaceutical composition will typically form a precipitate when injected into water and if the combined number of carbons in R3 and R4 is 12 or less the pharmaceutical composition will not form a precipitate when injected into water. Whether or not a pharmaceutical composition that further comprises a pharmaceutically acceptable organic solvent will form a precipitate when injected into water can readily be determined by injecting about 0.05 mL of the pharmaceutical composition into about 4 mL of water at about 98° F. and determining how much material is retained on a 0.22 μm filter after the composition is mixed with water and filtered. Typically, a formulation or composition is considered to be injectable when no more than 10% of the formulation is retained on the filter. In one embodiment, no more than 5% of the formulation is retained on the filter. In one embodiment, no more than 2% of the formulation is retained on the filter. In one embodiment, no more than 1% of the formulation is retained on the filter.

Similarly, in pharmaceutical compositions that comprise a protonated oligonucleotide and a diester or diamide of aspartic or glutamic acid, it is possible to vary the properties of pharmaceutical compositions by varying the amount and/or lipophilicity and/or molecular weight of the diester or diamide of aspartic or glutamic acid. Similarly, in pharmaceutical compositions that comprise an oligonucleotide; a divalent metal cation; and a carboxylate, a phospholipid, a phosphatidyl choline, or a sphingomyelin, it is possible to vary the properties of pharmaceutical compositions by varying the amount and/or lipophilicity and/or molecular weight of the carboxylate, phospholipid, phosphatidyl choline, or sphingomyelin.

Further, when the pharmaceutical compositions that further comprises an organic solvent form a depot when administered to an animal, it is also possible to vary the rate at which the oligonucleotide is released from the drug depot by varying the lipophilicity and/or molecular weight of the amino acid ester or amino acid amide. Generally, the more lipophilic the amino acid ester or amino acid amide, the more slowly the oligonucleotide is released from the depot. Similarly, when the pharmaceutical compositions that further comprises an organic solvent and also further comprise a carboxylate, phospholipid, phosphatidyl choline, sphingomyelin, or a diester or diamide of aspartic or glutamic acid and form a depot when administered to an animal, it is possible to vary the rate at which the oligonucleotide is released from the drug depot by varying the amount and/or lipophilicity and/or molecular weight of the carboxylate, phospholipid, phosphatidyl choline, sphingomyelin, or the diester or diamide of aspartic or glutamic acid.

Release rates from a precipitate can be measured injecting about 50 μL of the pharmaceutical composition into about 4 mL of deionized water in a centrifuge tube. The time that the pharmaceutical composition is injected into the water is recorded as T=0. After a specified amount of time, T, the sample is cooled to about −9° C. and spun on a centrifuge at about 13,000 rpm for about 20 min. The resulting supernatant is then analyzed by HPLC to determine the amount of oligonucleotide present in the aqueous solution. The amount of oligonucleotide in the pellet resulting from the centrifugation can also be determined by collecting the pellet, dissolving the pellet in about 10 μL of methanol, and analyzing the methanol solution by HPLC to determine the amount of oligonucleotide in the precipitate. The amount of oligonucleotide in the aqueous solution and the amount of oligonucleotide in the precipitate are determined by comparing the peak area for the HPLC peak corresponding to the oligonucleotide against a standard curve of oligonucleotide peak area against concentration of oligonucleotide. Suitable HPLC conditions can be readily determined by one of ordinary skill in the art.

Methods of Treatment

The pharmaceutical compositions of the invention are useful in human medicine and veterinary medicine. Accordingly, the invention further relates to a method of treating or preventing a condition in an animal comprising administering to the animal an effective amount of the pharmaceutical composition of the invention.

In one embodiment, the invention relates to methods of treating a condition in an animal comprising administering to an animal in need thereof an effective amount of a pharmaceutical composition of the invention.

In one embodiment, the invention relates to methods of preventing a condition in an animal comprising administering to an animal in need thereof an effective amount of a pharmaceutical composition of the invention.

Methods of administration include, but are not limited to, intradermal, intramuscular, intraperitoneal, intravenous, subcutaneous, intranasal, epidural, oral, sublingual, intracerebral, intravaginal, transdermal, rectal, by inhalation, or topical. The mode of administration is left to the discretion of the practitioner. In some embodiments, administration will result in the release of the oligonucleotide of the invention, e.g., an aptamer, an drug targeting aptamer, a multipartite construct, or any combination thereof, into the bloodstream.

In one embodiment, the method of treating or preventing a condition in an animal comprises administering to the animal in need thereof an effective amount of an oligonucleotide by parenterally administering the pharmaceutical composition of the invention. In one embodiment, the pharmaceutical compositions are administered by infusion or bolus injection. In one embodiment, the pharmaceutical composition is administered subcutaneously.

In one embodiment, the method of treating or preventing a condition in an animal comprises administering to the animal in need thereof an effective amount of an oligonucleotide by orally administering the pharmaceutical composition of the invention. In one embodiment, the composition is in the form of a capsule or tablet.

The pharmaceutical compositions can also be administered by any other convenient route, for example, topically, by absorption through epithelial or mucocutaneous linings (e.g., oral, rectal, and intestinal mucosa, etc.).

The pharmaceutical compositions can be administered systemically or locally.

The pharmaceutical compositions can be administered together with another biologically active agent.

In one embodiment, the animal is a mammal.

In one embodiment the animal is a human.

In one embodiment, the animal is a non-human animal.

In one embodiment, the animal is a canine, a feline, an equine, a bovine, an ovine, or a porcine.

The effective amount administered to the animal depends on a variety of factors including, but not limited to the type of animal being treated, the condition being treated, the severity of the condition, and the specific multipartite construct being administered. A treating physician can determine an effective amount of the pharmaceutical composition to treat a condition in an animal.

In one embodiment, the multipartite construct can inhibit angiogenesis. In one embodiment, the multipartite construct can inhibit angiogenesis and the disease being treated is cancer. In one embodiment, the aptamer can inhibit angiogenesis and the disease being treated is a solid tumor.

The multipartite construct can be a multipartite construct that inhibits a neoplastic growth or a cancer. In embodiments, the cancer comprises an acute lymphoblastic leukemia; acute myeloid leukemia; adrenocortical carcinoma; AIDS-related cancers; AIDS-related lymphoma; anal cancer; appendix cancer; astrocytomas; atypical teratoid/rhabdoid tumor; basal cell carcinoma; bladder cancer; brain stem glioma; brain tumor (including brain stem glioma, central nervous system atypical teratoid/rhabdoid tumor, central nervous system embryonal tumors, astrocytomas, craniopharyngioma, ependymoblastoma, ependymoma, medulloblastoma, medulloepithelioma, pineal parenchymal tumors of intermediate differentiation, supratentorial primitive neuroectodermal tumors and pineoblastoma); breast cancer; bronchial tumors; Burkitt lymphoma; cancer of unknown primary site; carcinoid tumor; carcinoma of unknown primary site; central nervous system atypical teratoid/rhabdoid tumor; central nervous system embryonal tumors; cervical cancer; childhood cancers; chordoma; chronic lymphocytic leukemia; chronic myelogenous leukemia; chronic myeloproliferative disorders; colon cancer; colorectal cancer; craniopharyngioma; cutaneous T-cell lymphoma; endocrine pancreas islet cell tumors; endometrial cancer; ependymoblastoma; ependymoma; esophageal cancer; esthesioneuroblastoma; Ewing sarcoma; extracranial germ cell tumor; extragonadal germ cell tumor; extrahepatic bile duct cancer; gallbladder cancer; gastric (stomach) cancer; gastrointestinal carcinoid tumor; gastrointestinal stromal cell tumor; gastrointestinal stromal tumor (GIST); gestational trophoblastic tumor; glioma; hairy cell leukemia; head and neck cancer; heart cancer; Hodgkin lymphoma; hypopharyngeal cancer; intraocular melanoma; islet cell tumors; Kaposi sarcoma; kidney cancer; Langerhans cell histiocytosis; laryngeal cancer; lip cancer; liver cancer; malignant fibrous histiocytoma bone cancer; medulloblastoma; medulloepithelioma; melanoma; Merkel cell carcinoma; Merkel cell skin carcinoma; mesothelioma; metastatic squamous neck cancer with occult primary; mouth cancer; multiple endocrine neoplasia syndromes; multiple myeloma; multiple myeloma/plasma cell neoplasm; mycosis fungoides; myelodysplastic syndromes; myeloproliferative neoplasms; nasal cavity cancer; nasopharyngeal cancer; neuroblastoma; Non-Hodgkin lymphoma; nonmelanoma skin cancer; non-small cell lung cancer; oral cancer; oral cavity cancer; oropharyngeal cancer; osteosarcoma; other brain and spinal cord tumors; ovarian cancer; ovarian epithelial cancer; ovarian germ cell tumor; ovarian low malignant potential tumor; pancreatic cancer; papillomatosis; paranasal sinus cancer; parathyroid cancer; pelvic cancer; penile cancer; pharyngeal cancer; pineal parenchymal tumors of intermediate differentiation; pineoblastoma; pituitary tumor; plasma cell neoplasm/multiple myeloma; pleuropulmonary blastoma; primary central nervous system (CNS) lymphoma; primary hepatocellular liver cancer; prostate cancer; rectal cancer; renal cancer; renal cell (kidney) cancer; renal cell cancer; respiratory tract cancer; retinoblastoma; rhabdomyosarcoma; salivary gland cancer; Sézary syndrome; small cell lung cancer; small intestine cancer; soft tissue sarcoma; squamous cell carcinoma; squamous neck cancer; stomach (gastric) cancer; supratentorial primitive neuroectodermal tumors; T-cell lymphoma; testicular cancer; throat cancer; thymic carcinoma; thymoma; thyroid cancer; transitional cell cancer; transitional cell cancer of the renal pelvis and ureter; trophoblastic tumor; ureter cancer; urethral cancer; uterine cancer; uterine sarcoma; vaginal cancer; vulvar cancer; Waldenström macroglobulinemia; or Wilm's tumor. The compositions and methods of the invention can be used to treat these and other cancers.

Oligonucleotide Probe Methods

Nucleic acid sequences fold into secondary and tertiary motifs particular to their nucleotide sequence. These motifs position the positive and negative charges on the nucleic acid sequences in locations that enable the sequences to bind to specific locations on target molecules, including without limitation proteins and other amino acid sequences. These binding sequences are known in the field as aptamers. Due to the trillions of possible unique nucleotide sequences in even a relatively short stretch of nucleotides (e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides), a large variety of motifs can be generated, resulting in aptamers for almost any desired protein or other target.

As described above, aptamers can be created by randomly generating oligonucleotides of a specific length, typically 20-80 base pairs long, e.g., 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 or 80 base pairs. These random oligonucleotides are then incubated with the target of interest (e.g., tissue, cell, microvesicle, protein, etc). After several wash steps, the oligonucleotides that bind to the target are collected and amplified. The amplified aptamers are iteratively added to the target and the process is repeated, often 15-20 times. A common version of this process known to those of skill in the art as the SELEX method.

The end result comprises one or more oligonucleotide probes/aptamers with high affinity to the target. The invention provides further processing of such resulting aptamers that can be use to provide desirable characteristics: 1) competitive binding assays to identify aptamers to a desired epitope; 2) motif analysis to identify high affinity binding aptamers in silico; and 3) aptamer selection assays to identify aptamers that can be used to detect a particular disease. The methods are described in more detail below and further in the Examples.

The invention further contemplates aptamer sequences that are highly homologous to the sequences that are discovered by the methods of the invention. "High homology" typically refers to a homology of 40% or higher, preferably 60% or higher, 70% or higher, more preferably 80% or higher, even more preferably 85%, 90%, 91%, 92%, 93%, 94%, 95%, 96%, 97%, 98%, 99% or higher between a polynucleotide sequence and a reference sequence. In an embodiment, the reference sequence comprises the sequence of one or more aptamer provided herein. Percent homologies (also referred to as percent identity) are typically carried out between two optimally aligned sequences. Methods of alignment of sequences for comparison are well-known in the art. Optimal alignment of sequences and comparison can be conducted, e.g., using the algorithm in "Wilbur and Lipman, Proc Natl Acad Sci USA 80: 726-30 (1983)". Homology calculations can also be performed using BLAST, which can be found on the NCBI server at: www.ncbi.nlm.nih.gov/BLAST/ (Altschul S F, et al, Nucleic Acids Res. 1997; 25(17):3389-402; Altschul S F, et al, J Mol. Biol. 1990; 215(3):403-10). In the case of an isolated polynucleotide which is longer than or equivalent in length to the reference sequence, e.g., a sequence identified by the methods herein, the comparison is made with the full length of the reference sequence. Where the isolated polynucleotide is shorter than the reference sequence, e.g., shorter than a sequence identified by the methods herein, the comparison is made to a segment of the reference sequence of the same length (excluding any loop required by the homology calculation).

The invention further contemplates aptamer sequences that are functional fragments of the sequences that are discovered by the methods of the invention. In the context of an aptamer sequence, a "functional fragment" of the aptamer sequence may comprise a subsequence that binds to the same target as the full length sequence. In some instances, a candidate aptamer sequence is from a member of a library that contains a 5' leader sequences and/or a 3' tail sequence. Such leader sequences or tail sequences may serve to facilitate primer binding for amplification or capture, etc. In these embodiments, the functional fragment of the full length sequence may comprise the subsequence of the candidate aptamer sequence absent the leader and/or tail sequences.

Competitive Antibody Addition

Known aptamer production methods may involve eluting all bound aptamers from the target sequence. In some cases, this may not easily identify the desired aptamer sequence. For example, when trying to replace an antibody in an assay, it may be desirable to only collect aptamers that bind to the specific epitope of the antibody being replaced. The invention provides a method comprising addition of an antibody that is to be replaced to the aptamer/target reaction in order to allow for the selective collection of aptamers which bind to the antibody epitope. In an embodiment, the method comprises incubating a reaction mixture comprising randomly generated oligonucleotides with a target of interest, removing unbound aptamers from the reaction mixture that do not bind the target, adding an antibody to the reaction mixture that binds to that epitope of interest, and collecting the aptamers that are displaced by the antibody. The target can be a biological entity such as disclosed herein, e.g., a protein.

Motif Analysis

Figure 2B:
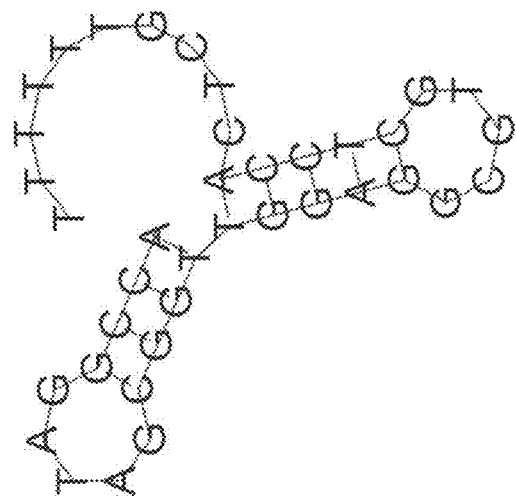
FIGS. 2A-B illustrates a non-limiting example of an aptamer nucleotide sequence and its secondary structure.
Figure 2A:
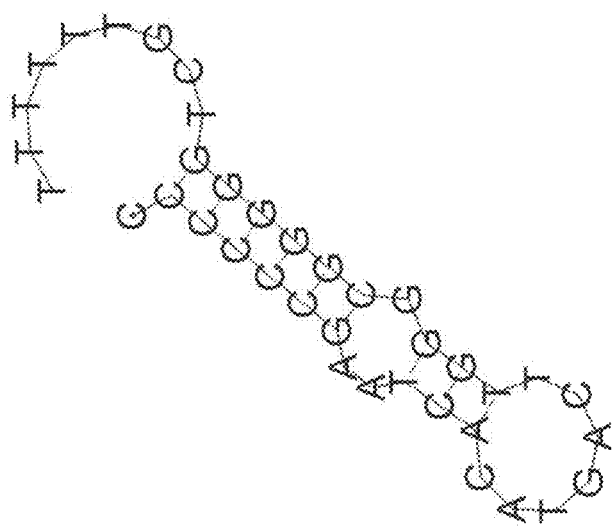

In aptamer experiments, multiple aptamer sequences can be identified that bind to a given target. These aptamers will have various binding affinities. It can be time consuming and laborious to generate quantities of these many aptamers sufficient to assess the affinities of each. To identify large numbers of aptamers with the highest affinities without physically screening large subsets, the invention provides a method comprising the analysis of the two dimensional structure of one or more high affinity aptamers to the target of interest. In an embodiment, the method comprises screening the database for aptamers that have similar two-dimensional structures, or motifs, but not necessarily similar primary sequences. In an embodiment, the method comprises identifying a high affinity aptamer using traditional methods such as disclosed herein or known in the art (e.g. surface plasmon resonance binding assay), approximating the two-dimensional structure of the high affinity aptamer, and identifying aptamers from a pool of sequences that are predicted to have a similar two-dimensional structure to the high affinity aptamer. The method thereby provides a pool of candidates that also bind the target of interest. The two-dimensional structure of an oligo can be predicting using methods known in the art, e.g., via free energy ($\Delta G$) calculations performed using a commercially available software program such as Vienna or mFold, for example as described in Mathews, D., Sabina, J., Zucker, M. & Turner, H. Expanded sequence dependence of thermodynamic parameters provides robust prediction of RNA secondary structure. J. Mol. Biol. 288, 911-940 (1999); Hofacker et al., Monatshefte f. Chemie 125: 167-188 (1994); and Hofacker, I. L. Vienna RNA secondary structure server. Nucleic Acids Res. 31, 3429-3431 (2003), the contents of which are incorporated herein by reference in their entirety. See FIGS. 2A-2B. The pool of sequences can be sequenced from a pool of randomly generated aptamer candidates using a high-throughput sequencing platform, such as the Ion Torrent platform from Thermo Fisher Scientific (Waltham, Mass.) or HiSeq/NextSeq/MiSeq platform from Illumina, Inc (San Diego, Calif.). Identifying aptamers from a pool of sequences that are predicted to have a similar two-dimensional structure to the high affinity aptamer may comprise loading the resulting sequences into the software program of choice to identify members of the pool of sequences with similar two-dimensional structures as the high affinity aptamer. The affinities of the pool of sequences can then be determined in situ, e.g., surface plasmon resonance binding assay or the like.

Aptamer Subtraction Methods

In order to develop an assay to detect a disease, for example, cancer, one typically screens a large population of known biomarkers from normal and diseased patients in order to identify markers that correlate with disease. This process works where discriminating markers are already described. In order to address this problem, the invention provides a method comprising subtracting out non-discriminating aptamers from a large pool of aptamers by incubating them initially with non-target tissue, microvesicles, cells, or other targets of interest. The non-target entities can be from a normal/healthy/non-diseased sample. The aptamers that did not bind to the normal non-target entities are then incubated with diseased entities. The aptamers that bind to the diseased entities but that did not bind the normal entities are then possible candidates for an assay to detect the disease. This process is independent of knowing the existence of a particular marker in the diseased sample.

Subtraction methods can be used to identify aptamers that preferentially recognize a desired population of targets. In an embodiment, the subtraction method is used to identify aptamers that preferentially recognize target from a diseased target population over a control (e.g., normal or non-diseased) population. The diseased target population may be a tissue or a population of cells or microvesicles from a diseased individual or individuals, whereas the control population comprises corresponding tissue, cells or microvesicles from a non-diseased individual or individuals. The disease can be a cancer or other disease disclosed herein or known in the art. Accordingly, the method provides aptamers that preferentially identify disease targets versus control targets.

Circulating microvesicles can be isolated from control samples, e.g., plasma from "normal" individuals that are absent a disease of interest, such as an absence of cancer. Vesicles in the sample are isolated using a method disclosed herein or as known in the art. For example, vesicles can be isolated from the plasma by one of the following methods: filtration, ultrafiltration, nanomembrane ultrafiltration, the ExoQuick reagent (System Biosciences, Inc., Mountain View, Calif.), centrifugation, ultracentrifugation, using a molecular crowding reagent (e.g., TEXIS from Life Technologies), polymer precipitation (e.g., polyethylene glycol (PEG)), affinity isolation, affinity selection, immunoprecipitation, chromatography, size exclusion, or a combination of any of these methods. The microvesicles isolated in each case will be a mixture of vesicle types and will be various sizes although ultracentrifugation methods may have more tendencies to produce exosomal-sized vesicles. Randomly generated oligonucleotide libraries (e.g., produced as described in the Examples herein) are incubated with the isolated normal vesicles. The aptamers that do not bind to these vesicles are isolated, e.g., by precipitating the vesicles (e.g, with PEG) and collecting the supernatant containing the non-binding aptamers. These non-binding aptamers are then contacted with vesicles isolated from diseased patients (e.g., using the same methods as described above) to allow the aptamers to recognize the disease vesicles. Next, aptamers that are bound to the diseased vesicles are collected. In an embodiment, the vesicles are isolated then lysed using a chaotropic agent (e.g., SDS or a similar detergent), and the aptamers are then captured by running the lysis mixture over an affinity column. The affinity column may comprise streptavidin beads in the case of biotin conjugated aptamer pools. The isolated aptamers are the amplified. The process can then then repeated, e.g., 1, 2, 3, 4, 5, 6, 7, 8, 9, 10, 11, 12, 13, 14, 15, 16, 17, 18, 19 or 20 or more times to achieve aptamers having a desired selectivity for the target.

In one aspect of the invention, an aptamer profile is identified that can be used to characterize a biological sample of interest. In an embodiment, a pool of randomly generated oligonucleotides, e.g., at least 10, $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, $10^{19}$ or at least $10^{20}$ oligonucleotides, is contacted with a biological component or target of interest from a control population. The oligonucleotides that do not bind the biological component or target of interest from the control population are isolated and then contacted with a biological component or target of interest from a test population. The oligonucleotides that bind the biological component or target of interest from the test population are retained. The retained oligonucleotides can be used to repeat the process by contacting the retained oligonucleotides with the biological component or target of interest from the control population, isolating the retained oligonucleotides that do not bind the biological component or target of interest from the control population, and again contacting these isolated oligonucleotides with the biological component or target of interest from the test population and isolating the binding oligonucleotides. The "component" or "target" can be anything that is present in sample to which the oligonucleotides are capable of binding (e.g., tissue, cells, microvesicles, polypeptides, peptide, nucleic acid molecules, carbohydrates, lipids, etc.). The process can be repeated any number of desired iterations, e.g., 1, 2, 3, 4, 5, 6, 7, 8, 9, 10, 11, 12, 13, 14, 15, 16, 17, 18, 19 or 20 or more times. The resulting oligonucleotides comprise aptamers that can differentially detect the test population versus the control. These aptamers provide an aptamer profile, which comprises a biosignature that is determined using one or more aptamer, e.g., a biosignature comprising a presence or level of the component or target which is detected using the one or more aptamer.

Figure 3:
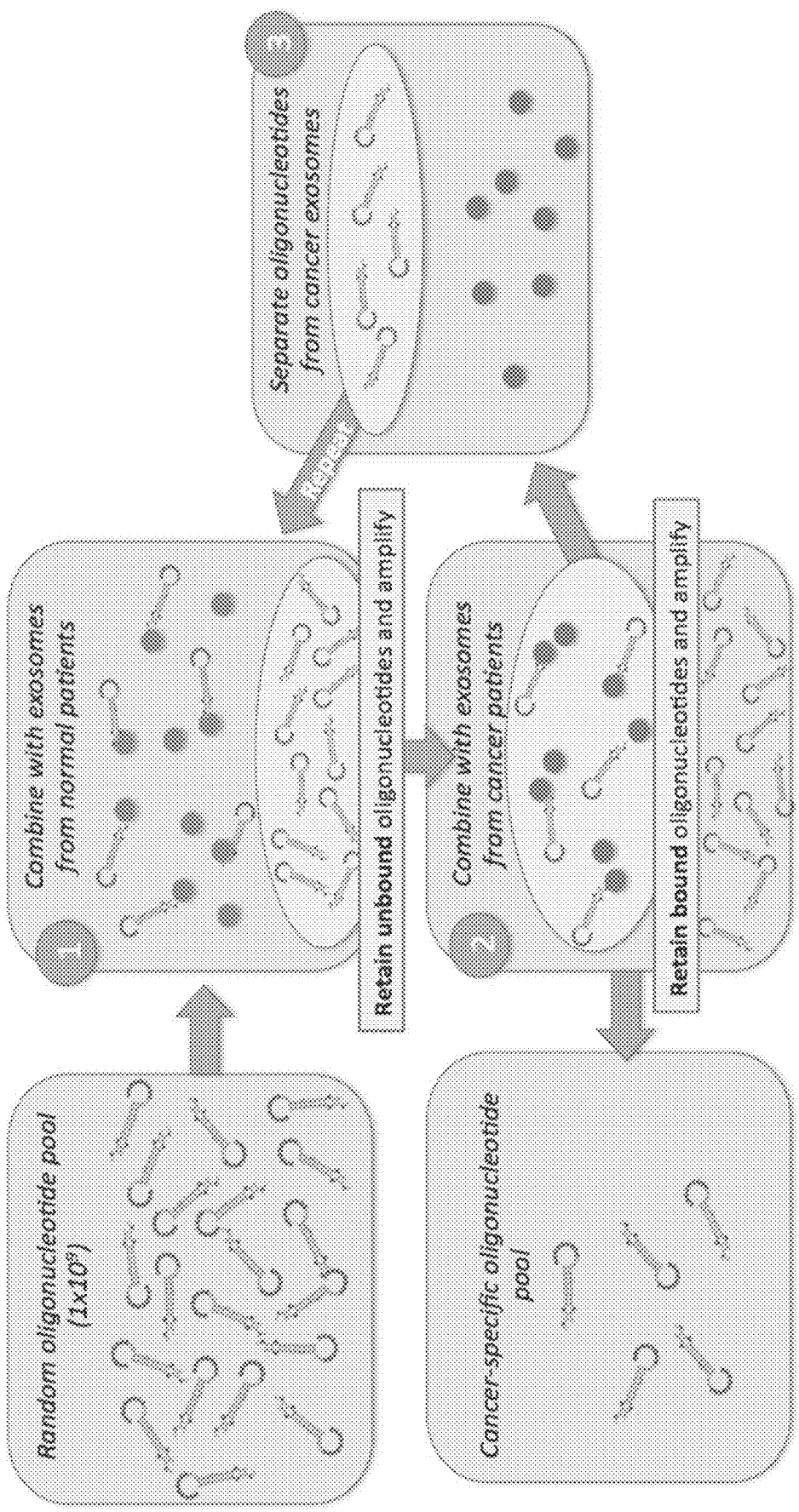
FIG. 3 illustrates a process for producing a target-specific set of aptamers using a cell subtraction method, wherein the target is a biomarker associated with a specific disease. In Step 1, a random pool of oligonucleotides are contacted with a biological sample from a normal patient. In Step 2, the oligos that did not bind in Step 1 are added to a biological sample isolated from diseased patients. The bound oligos from this step are then eluted, captured via their biotin linkage and then combined again with normal biological sample. The unbound oligos are then added again to disease-derived biological sample and isolated. This process can be repeated iteratively. The final eluted aptamers are tested against patient samples to measure the sensitivity and specificity of the set. Biological samples can include blood, including plasma or serum, or other components of the circulatory system, such as microvesicles.

An exemplary process is illustrated in FIG. 3, which demonstrates the method to identify aptamer that preferentially recognize cancer exosomes using exosomes from normal (non-cancer) individuals as a control. In the figure, exosomes are exemplified but one of skill will appreciate that other microvesicles can be used in the same manner. The resulting aptamers can provide a profile that can differentially detect the cancer exosomes from the normal exosomes. One of skill will appreciate that the same steps can be used to derive an aptamer profile to characterize any disease or condition of interest. The process can also be applied with tissue, cells, or other targets of interest.

In an embodiment, the invention provides an isolated polynucleotide that encodes a polypeptide, or a fragment thereof, identified by the methods above. The invention further provides an isolated polynucleotide having a nucleotide sequence that is at least 60% identical to the nucleotide sequence identified by the methods above. More preferably, the isolated nucleic acid molecule is at least 65%, 70%, 75%, 80%, 85%, 90%, 91%, 92%, 93%, 94%, 95%, 96%, 97%, 98%, 99% or more, identical to the nucleotide sequence identified by the methods above. In the case of an isolated polynucleotide which is longer than or equivalent in length to the reference sequence, e.g., a sequence identified by the methods above, the comparison is made with the full length of the reference sequence. Where the isolated polynucleotide is shorter than the reference sequence, e.g., shorter than a sequence identified by the methods above, the comparison is made to a segment of the reference sequence of the same length (excluding any loop required by the homology calculation).

In a related aspect, the invention provides a method of characterizing a biological phenotype using an aptamer profile. The aptamer profile can be determined using the method above. The aptamer profile can be determined for a test sample and compared to a control aptamer profile. The phenotype may be a disease or disorder such as a cancer. Characterizing the phenotype can include without limitation providing a diagnosis, prognosis, or theranosis. Thus, the aptamer profile can provide a diagnostic, prognostic and/or theranostic readout for the subject from whom the test sample is obtained.

In another embodiment, an aptamer profile is determined for a test sample by contacting a pool of aptamer molecules to the test sample, contacting the same pool of aptamers to a control sample, and identifying one or more aptamer molecules that differentially bind a component or target in the test sample but not in the control sample (or vice versa). A "component" or "target" as used in the context of the biological test sample or control sample can be anything that is present in sample to which the aptamers are capable of binding (e.g., tissue, cells, microvesicles, polypeptides, peptide, nucleic acid molecules, carbohydrates, lipids, etc.). For example, if a sample is a plasma or serum sample, the aptamer molecules may bind a polypeptide biomarker that is solely expressed or differentially expressed (over- or under-expressed) in a disease state as compared to a non-diseased subject. Comparison of the aptamer profile in the test sample as compared to the control sample may be based on qualitative and quantitative measure of aptamer binding (e.g., binding versus no binding, or level of binding in test sample versus different level of binding in the reference control sample).

In an aspect, the invention provides a method of identifying a target-specific aptamer profile, comprising contacting a biological test sample with a pool of aptamer molecules, contacting the pool to a control biological sample, identifying one or more aptamers that bind to a component in said test sample but not to the control sample, thereby identifying an aptamer profile for said biological test sample. In an embodiment, a pool of aptamers is selected against a disease sample and compared to a reference sample, the aptamers in a subset that bind to a component(s) in the disease sample but not in the reference sample can be sequenced using conventional sequencing techniques to identify the subset that bind, thereby identifying an aptamer profile for the particular disease sample. In this way, the aptamer profile provides an individualized platform for detecting disease in other samples that are screened. Furthermore, by selecting an appropriate reference or control sample, the aptamer profile can provide a diagnostic, prognostic and/or theranostic readout for the subject from whom the test sample is obtained.

In a related aspect, the invention provides a method of selecting a pool of aptamers, comprising: (a) contacting a biological control sample with a pool of oligonucleotides; (b) isolating a first subset of the pool of oligonucleotides that do not bind the biological control sample; (c) contacting the biological test sample with the first subset of the pool of oligonucleotides; and (d) isolating a second subset of the pool of oligonucleotides that bind the biological test sample, thereby selecting the pool of aptamers. The pool of oligonucleotides may comprise any number of desired sequences, e.g., at least $10$, $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, $10^{19}$ or at least $10^{20}$ oligonucleotides may be present in the starting pool. Steps (a)-(d) may be repeated to further hone the pool of aptamers. In an embodiment, these steps are repeated at least 1, 2, 3, 4, 5, 6, 7, 8, 9, 10, 11, 12, 13, 14, 15, 16, 17, 18, 19 or at least 20 times.

As described herein, the biological test sample and biological control sample may comprise tissues, cells, microvesicles, or biomarkers of interest. In an embodiment, the biological test sample and optionally biological control sample comprise a bodily fluid. The bodily fluid may comprise without limitation peripheral blood, sera, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, Cowper's fluid, pre-ejaculatory fluid, female ejaculate, sweat, fecal matter, hair, tears, cyst fluid, pleural fluid, peritoneal fluid, malignant fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates or other lavage fluids. The biological test sample and optionally biological control may also comprise a tumor sample, e.g., cells from a tumor or tumor tissue. In other embodiments, the biological test sample and optionally biological control sample comprise a cell culture medium. In embodiments, the biological test sample comprises a diseased sample and the biological control sample comprises a non-diseased sample. Accordingly, the pool of aptamers may be used to provide a diagnostic, prognostic and/or theranostic readout for the disease.

As noted, the invention can be used to assess microvesicles. Microvesicles are powerful biomarkers because the vesicles provide one biological entity that comprises multiple pieces of information. For example as described, a vesicle can have multiple surface antigens, each of which provides complementary information. Consider a cancer marker and a tissue specific marker. If both markers are individually present in a sample, e.g., both are circulating proteins or nucleic acids, it may not be ascertainable whether the cancer marker and the tissue specific marker are derived from the same anatomical locale. However, if both the cancer marker and the tissue specific marker are surface antigens on a single microvesicle, the vesicle itself links the two markers and provides an indication of a disease (via the cancer marker) and origin of the disease (via the tissue specific marker). Furthermore, the vesicle can have any number of surface antigens and also payload that can be assessed. Accordingly, the invention provides a method for identifying binding agents comprising contacting a plurality of extracellular microvesicles with a randomly generated library of binding agents, identifying a subset of the library of binding agents that have an affinity to one or more components of the extracellular microvesicles. The binding agents may comprise aptamers, antibodies, and/or any other useful type of binding agent disclosed herein or known in the art.

In a related aspect, the invention provides a method for identifying a plurality of target ligands comprising, (a) contacting a reference microvesicle population with a plurality of ligands that are capable of binding one or more microvesicle surface markers, (b) isolating a plurality of reference ligands, wherein the plurality of reference ligands comprise a subset of the plurality of ligands that do not have an affinity for the reference microvesicle population; (c) contacting one or more test microvesicle with the plurality of reference ligands; and (d) identifying a subset of ligands from the plurality of reference ligands that form complexes with a surface marker on the one or more test microvesicle, thereby identifying the plurality of target ligands. The term "ligand" can refer a molecule, or a molecular group, that binds to another chemical entity to form a larger complex. Accordingly, a binding agent comprises a ligand. The plurality of ligands may comprise aptamers, antibodies and/or other useful binding agents described herein or known in the art. The process can also be applied to tissue samples. See, e.g., Examples 19-31 herein.

The invention further provides kits comprising one or more reagent to carry out the methods above. In an embodiment, the one or more reagent comprises a library of potential binding agents that comprises one or more of an aptamer, antibody, and other useful binding agents described herein or known in the art.

Negative and Positive Aptamer Selection

Aptamers can be used in various biological assays, including numerous types of assays which rely on a binding agent. For example, aptamers can be used instead of or along side antibodies in various immunoassay formats, such as sandwich assays, flow cytometry and IHC. The invention provides an aptamer screening method that identifies aptamers that do not bind to any surfaces (substrates, tubes, filters, beads, other antigens, etc.) throughout the assay steps and bind specifically to an antigen of interest. The assay relies on negative selection to remove aptamers that bind non-target antigen components of the final assay. The negative selection is followed by positive selection to identify aptamers that bind the desired antigen.

In an aspect, the invention provides a method of identifying an aptamer specific to a target of interest, comprising (a) contacting a pool of candidate aptamers with one or more assay components, wherein the assay components do not comprise the target of interest; (b) recovering the members of the pool of candidate aptamers that do not bind to the one or more assay components in (a); (c) contacting the members of the pool of candidate aptamers recovered in (b) with the target of interest in the presence of one or more confounding target; and (d) recovering a candidate aptamer that binds to the target of interest in step (c), thereby identifying the aptamer specific to the target of interest. In the method, steps (a) and (b) provide negative selection to remove aptamers that bind non-target entities. Conversely, steps (c) and (d) provide positive selection by identifying aptamers that bind the target of interest but not other confounding targets, e.g., other antigens that may be present in a biological sample which comprises the target of interest. The pool of candidate aptamers may comprise at least 10, $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, $10^{19}$ or at least $10^{20}$ nucleic acid sequences.

In some embodiments, steps (a)-(b) are optional. In other embodiments, steps (a)-(b) are repeated at least 1, 2, 3, 4, 5, 6, 7, 8, 9, 10, 11, 12, 13, 14, 15, 16, 17, 18, 19 or at least 20 times before positive selection in step (c) is performed. The positive selection can also be performed in multiple rounds. Steps (c)-(d) can be repeated at least 1, 2, 3, 4, 5, 6, 7, 8, 9, 10, 11, 12, 13, 14, 15, 16, 17, 18, 19 or at least 20 times before identifying the aptamer specific to the target of interest. Multiple rounds may provide improved stringency of selection.

In some embodiments, the one or more assay components contacted with the aptamer pool during negative selection comprise one or more of a substrate, a bead, a planar array, a column, a tube, a well, or a filter. One of skill will appreciate that the assay components can include any substance that may be part of a desired biological assay.

The target of interest can be any appropriate entity that can be detected when recognized by an aptamer. In an embodiment, the target of interest comprises a protein or polypeptide. As used herein, "protein," "polypeptide" and "peptide" are used interchangeably unless stated otherwise. The target of interest can be a nucleic acid, including DNA, RNA, and various subspecies of any thereof as disclosed herein or known in the art. The target of interest can comprise a lipid. The target of interest can comprise a carbohydrate. The target of interest can also be a complex, e.g., a complex comprising protein, nucleic acids, lipids and/or carbohydrates. In some embodiments, the target of interest comprises a tissue, cell, or microvesicle. In such cases, the aptamer may be a binding agent to a surface antigen or disease antigen.

The surface antigen can be a biomarker of a disease or disorder. In such cases, the aptamer may be used to provide a diagnosis, prognosis or theranosis of the disease or disorder. For example, the one or more protein may comprise one or more of PSMA, PCSA, B7H3, EpCam, ADAM-10, BCNP, EGFR, IL1B, KLK2, MMP7, p53, PBP, SERPINB3, SPDEF, SSX2, and SSX4. These markers can be used detect a prostate cancer. Additional surface antigens and disease antigens are provided in Tables 3-4 herein.

The one or more confounding target can be an antigen other than the target of interest. For example, a confounding target can be another entity that may be present in a sample to be assayed. As a non-limiting example, consider that the sample to be assessed is a tissue or blood sample from an individual. The target of interest may be a protein, e.g., a surface antigen, which is present in the sample. In this case, a confounding target could be selected from any other antigen that is likely to be present in the sample. Accordingly, the positive selection should provide candidate aptamers that recognize the target of interest but have minimal, if any, interactions with the confounding targets. In some embodiments, the target of interest and the one or more confounding target comprise the same type of biological entity, e.g., all protein, all nucleic acid, all carbohydrate, or all lipids. As a non-limiting example, the target of interest can be a protein selected from the group consisting of SSX4, SSX2, PBP, KLK2, SPDEF, and EpCAM, and the one or more confounding target comprises the other members of this group. In other embodiments, the target of interest and the one or more confounding target comprise different types of biological entities, e.g., any combination of protein, nucleic acid, carbohydrate, and lipids. The one or more confounding targets may also comprise different types of biological entities, e.g., any combination of protein, nucleic acid, carbohydrate, and lipids.

In an embodiment, the invention provides an isolated polynucleotide, or a fragment thereof, identified by the methods above. The invention further provides an isolated polynucleotide having a nucleotide sequence that is at least 60% identical to the nucleotide sequence identified by the methods above. The isolated polynucleotide is also referred to as an aptamer or oligonucleotide probe. More preferably, the isolated nucleic acid molecule is at least 65%, 70%, 75%, 80%, 85%, 90%, 91%, 92%, 93%, 94%, 95%, 96%, 97%, 98%, 99% or more, identical to the nucleotide sequence identified by the methods above. In the case of an isolated polynucleotide which is longer than or equivalent in length to the reference sequence, e.g., a sequence identified by the methods above, the comparison is made with the full length of the reference sequence. Where the isolated polynucleotide is shorter than the reference sequence, e.g., shorter than a sequence identified by the methods above, the comparison is made to a segment of the reference sequence of the same length (excluding any loop required by the homology calculation).

In a related aspect, the invention provides a method of selecting a group of aptamers, comprising: (a) contacting a pool of aptamers to a population of microvesicles from a first sample; (b) enriching a subpool of aptamers that show affinity to the population of microvesicles from the first sample; (c) contacting the subpool to a second population of microvesicles from a second sample; and (d) depleting a second subpool of aptamers that show affinity to the second population of microvesicles from the second sample, thereby selecting the group of aptamers that have preferential affinity for the population of microvesicles from the first sample. The first sample and/or second sample may comprise a biological fluid such as disclosed herein. For example, the biological fluid may include without limitation blood, a blood derivative, plasma, serum or urine. The first sample and/or second sample may also be derived from a cell culture.

In another related aspect, the invention provides a method of selecting a group of aptamers, comprising: (a) contacting a pool of aptamers to a tissue from a first sample; (b) enriching a subpool of aptamers that show affinity to the tissue from the first sample; (c) contacting the subpool to a second tissue from a second sample; and (d) depleting a second subpool of aptamers that show affinity to the second tissue from the second sample, thereby selecting the group of aptamers that have preferential affinity for the tissue from the first sample as compared to the second sample. The first sample and/or second sample may comprise a fixed tissue such as disclosed herein. For example, the fixed tissue may include FFPE tissue. The first sample and/or second sample may comprise a tumor sample.

In an embodiment, the first sample comprises a cancer sample and the second sample comprises a control sample, such as a non-cancer sample. The first sample and/or and the second sample may each comprise a pooled sample. For example, the first sample and/or second sample can comprise bodily fluid from 2, 3, 4, 5, 6, 7, 8, 9, 10, 11, 12, 13, 14, 15, 16, 17, 18, 19, 20, 25, 30, 40, 50, 60, 70, 80, 90, 100 or more than 100 individuals. In such cases, the members of a pool may be chosen to represent a desired phenotype. In a non-limiting example, the members of the first sample pool may be from patients with a cancer and the members of the second sample pool may be from non-cancer controls. With tissue samples, the first sample may comprise tissues from different individuals, e.g., from 2, 3, 4, 5, 6, 7, 8, 9, 10, 11, 12, 13, 14, 15, 16, 17, 18, 19, 20, 25, 30, 40, 50, 60, 70, 80, 90, 100 or more than 100 individuals. As a non-limiting example, the first sample may comprise a fixed tissue from each individual.

Steps (a)-(d) can be repeated a desired number of times in order to further enrich the pool in aptamers that have preferential affinity for the target from the first sample. For example, steps (a)-(d) can be repeated 1, 2, 3, 4, 5, 6, 7, 8, 9, 10, 11, 12, 13, 14, 15, 16, 17, 18, 19, 20 or more than 20 times. The output from step (d) can be used as the input to repeated step (a). In embodiment, the first sample and/or second sample are replaced with a different sample before repeating steps (a)-(d). In a non-limiting example, members of a first sample pool may be from patients with a cancer and members of a second sample pool may be from non-cancer controls. During subsequent repetitions of steps (a)-(d), the first sample pool may comprise samples from different cancer patients than in the prior round/s. Similarly, the second sample pool may comprise samples from different controls than in the prior round/s.

In still another related aspect, the invention provides a method of enriching a plurality of oligonucleotides, comprising: (a) contacting a first sample with the plurality of oligonucleotides; (b) fractionating the first sample contacted in step (a) and recovering members of the plurality of oligonucleotides that fractionated with the first sample; (c) contacting the recovering members of the plurality of oligonucleotides from step (b) with a second sample; (d) fractionating the second sample contacted in step (c) and recovering members of the plurality of oligonucleotides that did not fractionate with the second sample; (e) contacting the recovering members of the plurality of oligonucleotides from step (d) with a third sample; and (f) fractionating the third sample contacted in step (a) and recovering members of the plurality of oligonucleotides that fractionated with the third sample; thereby enriching the plurality of oligonucleotides. The samples can be of any appropriate form as described herein, e.g., tissue, cells, microvesicles, etc. The first and third samples may have a first phenotype while the second sample has a second phenotype. Thus, positive selection occurs for the samples associated with the first phenotype and negative selection occurs for the samples associated with the second phenotype. In one non-limiting example of such selection schemes, the first phenotype comprises biopsy-positive breast cancer and the second phenotype comprises non-breast cancer (biopsy-negative or healthy).

In some embodiments, the first phenotype comprises a medical condition, disease or disorder and the second phenotype comprises a healthy state or a different state of the medical condition, disease or disorder. The first phenotype can be a healthy state and the second phenotype comprises a medical condition, disease or disorder. The medical condition, disease or disorder can be any detectable medical condition, disease or disorder, including without limitation a cancer, a premalignant condition, an inflammatory disease, an immune disease, an autoimmune disease or disorder, a cardiovascular disease or disorder, neurological disease or disorder, infectious disease or pain. Various types of such conditions are disclosed herein. See, e.g., Section "Phenotypes" herein.

Any useful method to isolate microvesicles in whole or in part can be used to fractionate the samples as appropriate. Several useful techniques are described herein. In an embodiment, the fractionating comprises ultracentrifugation in step (b) and polymer precipitation in steps (d) and (f). In other embodiments, polymer precipitation is used in all steps. The polymer can be polyethylene glycol (PEG). Any appropriate form of PEG may be used. For example, the PEG may be PEG 8000. The PEG may be used at any appropriate concentration. For example, the PEG can be used at a concentration of 1%, 2%, 3%, 4%, 5%, 6%, 7%, 8%, 9%, 10%, 11%, 12%, 13%, 14% or 15% to isolate the microvesicles. In some embodiments, the PEG is used at a concentration of 6%.

When the sample comprises an FFPE tissue sample, the sample can be subjected to epitope retrieval, also known as antigen retrieval, prior to the enrichment process. Although tissue fixation is useful for the preservation of tissue morphology, this process can also have a negative impact on immuno detection methods. For example, fixation can alter protein biochemistry such that the epitope of interest is masked and can no longer bind to the primary antibody. Masking of the epitope can be caused by cross-linking of amino acids within the epitope, cross-linking unrelated peptides at or near an epitope, altering the conformation of an epitope, or altering the electrostatic charge of the antigen. Epitope retrieval refers to any technique in which the masking of an epitope is reversed and epitope-recognition is restored. Techniques for epitope retrieval are known in the art. For example, enzymes including Proteinase K, Trypsin, and Pepsin have been used successfully to restore epitope binding. Without being bound by theory, the mechanism of action may be the cleavage of peptides that may be masking the epitope. Heating the sample may also reverse some cross-links and allows for restoration of secondary or tertiary structure of the epitope. Change in pH or cation concentration may also influence epitope availability.

The contacting can be performed in the presence of a competitor, which may reduce non-specific binding events. Any useful competitor can be used. In an embodiment, the competitor comprises at least one of salmon sperm DNA, tRNA, dextran sulfate and carboxymethyl dextran. As desired, different competitors or competitor concentrations can be used at different contacting steps.

The method can be repeated to achieve a desired enrichment. In an embodiment, steps (a)-(f) are repeated at least once. These steps can be repeated 1, 2, 3, 4, 5, 6, 7, 8, 9, 10, 11, 12, 13, 14, 15, 16, 17, 18, 19, 20, or more than 20 times as desired. At the same time, each of the contacting steps can be repeated as desired. In some embodiments, the method further comprises: (i) repeating steps (a)-(b) at least once prior to step (c), wherein the recovered members of the plurality of oligonucleotides that fractionated with the first sample in step (b) are used as the input plurality of oligonucleotides for the repetition of step (a); (ii) repeating steps (c)-(d) at least once prior to step (e), wherein the recovered members of the plurality of oligonucleotides that did not fractionate with the second sample in step (d) are used as the input plurality of oligonucleotides for the repetition of step (c); and/or (iii) repeating steps (e)-(f) at least once, wherein the recovered members of the plurality of oligonucleotides that fractionated with the third sample in step (f) are used as the input plurality of oligonucleotides for the repetition of step (e). Repetitions (i)-(iii) can be repeated any desired number of times, e.g., (i)-(iii) can be repeated 1, 2, 3, 4, 5, 6, 7, 8, 9, 10, 11, 12, 13, 14, 15, 16, 17, 18, 19, 20 or more than 20 times. In an embodiment, (i)-(iii) each comprise three repetitions.

The method may further comprise identifying the members of the selected group of aptamers or oligonucleotides, e.g., by DNA sequencing. The sequencing may be performed by Next Generation sequencing as desired and after or before any desired step in the method.

The method may also comprise identifying the targets of the selected group of aptamers/oligonucleotides. Useful methods to identify such targets are disclosed herein. In a non-limiting example, an enriched oligonucleotide library is contacted with an appropriate sample (e.g., the first or third sample), the library is cross-linked to the sample, and the library is recovered. Proteins cross-linked with the recovered library are identified, e.g., by mass spectrometry.

Oligonucleotide Probe Target Identification

The methods and kits above can be used to identify binding agents that differentiate between two target populations. The invention further provides methods of identifying the targets of such binding agents. For example, the methods may further comprise identifying a surface marker of a cell or microvesicle that is recognized by the binding agent.

In an embodiment, the invention provides a method of identifying a target of a binding agent comprising: (a) contacting the binding agent with the target to bind the target with the binding agent, wherein the target comprises a surface antigen of a cell or microvesicle; (b) disrupting the cell or microvesicle under conditions which do not disrupt the binding of the target with the binding agent; (c) isolating the complex between the target and the binding agent; and (d) identifying the target bound by the binding agent. The binding agent can be a binding agent identified by the methods above, e.g., an oligonucleotide probe, ligand, antibody, or other useful binding agent that can differentiate between two target populations, e.g., by differentiating between biomarkers thereof.

Figure 4:
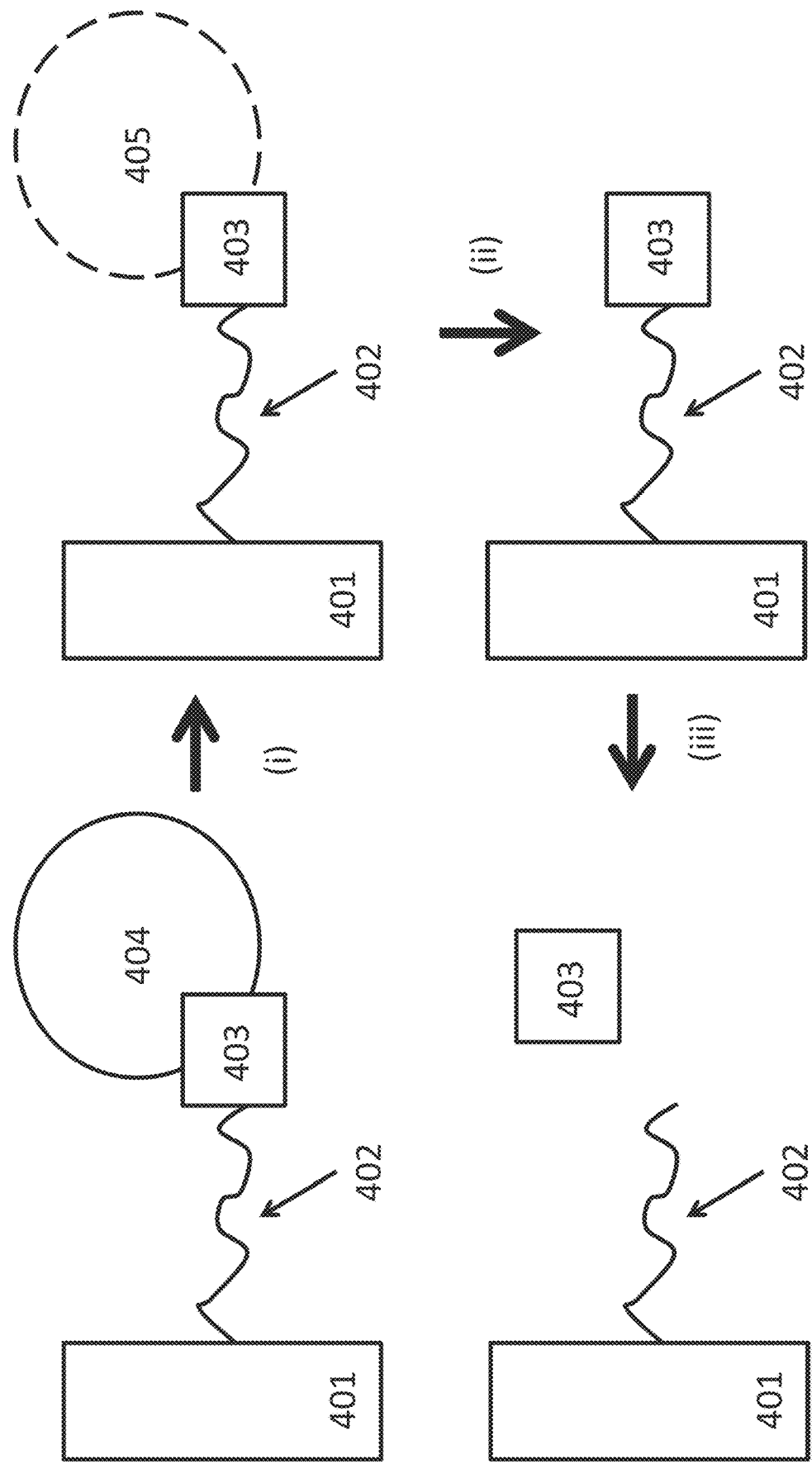
FIG. 4 comprises a schematic for identifying a target of a selected aptamer, such as an aptamer selected by the process of the invention. The figure shows a binding agent 402, here an aptamer for purposes of illustration, tethered to a substrate 401. The binding agent 402 can be covalently attached to substrate 401. The binding agent 402 may also be non-covalently attached. For example, binding agent 402 can comprise a label which can be attracted to the substrate, such as a biotin group which can form a complex with an avidin/streptavidin molecule that is covalently attached to the substrate. The binding agent 402 binds to a surface antigen 403 of microvesicle 404. In the step signified by arrow (i), the microvesicle is disrupted while leaving the complex between the binding agent 402 and surface antigen 403 intact. Disrupted microvesicle 405 is removed, e.g., via washing or buffer exchange, in the step signified by arrow (ii). In the step signified by arrow (iii), the surface antigen 403 is released from the binding agent 402. The surface antigen 403 can be analyzed to determine its identity.

An illustrative schematic for carrying on the method is shown in FIG. 4. The figure shows a binding agent 402, here an oligonucleotide probe or aptamer for purposes of illustration, tethered to a substrate 401. The binding agent 402 can be covalently attached to substrate 401. The binding agent 402 may also be non-covalently attached. For example, binding agent 402 can comprise a label which can be attracted to the substrate, such as a biotin group which can form a complex with an avidin/streptavidin molecule that is covalently attached to the substrate. This can allow a complex to be formed between the aptamer and the microvesicle while in solution, followed by capture of the aptamer using the biotin label. The binding agent 402 binds to a surface antigen 403 of cell or microvesicle 404. In the step signified by arrow (i), the cell or microvesicle 405 is disrupted while leaving the complex between the binding agent 402 and surface antigen 403 intact. Disrupted cell or microvesicle 405 is removed, e.g., via washing or buffer exchange, in the step signified by arrow (ii). In the step signified by arrow (iii), the surface antigen 403 is released from the binding agent 402. The surface antigen 403 can be analyzed to determine its identity using methods disclosed herein and/or known in the art. The target of the method can be any useful biological entity associated with a cell or microvesicle. For example, the target may comprise a protein, nucleic acid, lipid or carbohydrate, or other biological entity disclosed herein or known in the art.

In some embodiments of the method, the target is cross-linked to the binding agent prior disrupting the cell or microvesicle. Without being bound by theory, this step may assist in maintaining the complex between the binding agent and the target during the disruption process. Any useful method of crosslinking disclosed herein or known in the art can be used. In embodiments, the cross-linking comprises photocrosslinking, an imidoester crosslinker, dimethyl suberimidate, an N-Hydroxysuccinimide-ester crosslinker, bissulfosuccinimidyl suberate (BS3), an aldehyde, acrolein, crotonaldehyde, formaldehyde, a carbodiimide crosslinker, N,N'-dicyclohexylcarbodiimide (DDC), N,N'-diisopropylcarbodiimide (DIC), 1-Ethyl-3-[3-dimethylaminopropyl] carbodiimide hydrochloride (EDC or EDAC), Succinimidyl-4-(N-maleimidomethyl)cyclohexane-1-carboxylate (SMCC), a Sulfosuccinimidyl-4-(N-maleimidomethyl)cyclohexane-1-carboxylate (Sulfo-SMCC), a Sulfo-N-hydroxy succinimidyl-2-(6-[biotinamido]-2-(p-azido benzamido)-hexanoamido) ethyl-1,3'-dithioproprionate (Sulfo-SBED), 2-[N2-(4-Azido-2,3,5,6-tetrafluorobenzoyl)-N6-(6-biotin-amidocaproyl)-L-lysinyl]ethyl methanethiosulfonate (Mts-Atf-Biotin; available from Thermo Fisher Scientific Inc, Rockford Ill.), 2-{N2-[N6-(4-Azido-2,3,5,6-tetrafluorobenzoyl-6-amino-caproyl)-N6-(6-biotinamidocaproyl)-L-lysinylamido]}ethyl methanethiosultonate (Mts-Atf-LC-Biotin; available from Thermo Fisher Scientific Inc), a photoreactive amino acid (e.g., L-Photo-Leucine and L-Photo-Methionine, see, e.g., Suchanek, M., et al. (2005). Photo-leucine and photo-methionine allow identification of protein-protein interactions. Nat. Methods 2:261-267), an N-Hydroxysuccinimide (NHS) crosslinker, an NHS-Azide reagent (e.g., NHS-Azide, NHS-PEG4-Azide, NHS-PEG12-Azide; each available from Thermo Fisher Scientific, Inc.), an NHS-Phosphine reagent (e.g., NHS-Phosphine, Sulfo-NHS-Phosphine; each available from Thermo Fisher Scientific, Inc.), or any combination or modification thereof.

A variety of methods can be used to disrupt the cell or microvesicle. For example, the cellular or vesicular membrane can be disrupted using mechanical forces, chemical agents, or a combination thereof. In embodiments, disrupting the cell or microvesicle comprises use of one or more of a detergent, a surfactant, a solvent, an enzyme, or any useful combination thereof. The enzyme may comprise one or more of lysozyme, lysostaphin, zymolase, cellulase, mutanoly sin, a glycanase, a protease, and mannase. The detergent or surfactant may comprise one or more of a octylthioglucoside (OTG), octyl beta-glucoside (OG), a nonionic detergent, Triton X, Tween 20, a fatty alcohol, a cetyl alcohol, a stearyl alcohol, cetostearyl alcohol, an oleyl alcohol, a polyoxyethylene glycol alkyl ether (Brij), octaethylene glycol monododecyl ether, pentaethylene glycol monododecyl ether, a polyoxypropylene glycol alkyl ether, a glucoside alkyl ether, decyl glucoside, lauryl glucoside, octyl glucoside, a polyoxyethylene glycol octylphenol ethers, a polyoxyethylene glycol alkylphenol ether, nonoxynol-9, a glycerol alkyl ester, glyceryl laurate, a polyoxyethylene glycol sorbitan alkyl esters, polysorbate, a sorbitan alkyl ester, cocamide MEA, cocamide DEA, dodecyldimethylamine oxide, a block copolymers of polyethylene glycol and polypropylene glycol, poloxamers, polyethoxylated tallow amine (POEA), a zwitterionic detergent, 3-[(3-cholamidopropyl)dimethylammonio]-1-propanesulfonate (CHAPS), a linear alkylbenzene sulfonate (LAS), a alkyl phenol ethoxylate (APE), cocamidopropyl hydroxysultaine, a betaine, cocamidopropyl betaine, lecithin, an ionic detergent, sodium dodecyl sulfate (SDS), cetrimonium bromide (CTAB), cetyl trimethylammonium chloride (CTAC), octenidine dihydrochloride, cetylpyridinium chloride (CPC), benzalkonium chloride (BAC), benzethonium chloride (BZT), 5-Bromo-5-nitro-1,3-dioxane, dimethyldioctadecylammonium chloride, dioctadecyldimethylammonium bromide (DODAB), sodium deoxycholate, nonyl phenoxypolyethoxylethanol (Tergitol-type NP-40; NP-40), ammonium lauryl sulfate, sodium laureth sulfate (sodium lauryl ether sulfate (SLES)), sodium myreth sulfate, an alkyl carboxylate, sodium stearate, sodium lauroyl sarcosinate, a carboxylate-based fluorosurfactant, perfluorononanoate, perfluorooctanoate (PFOA or PFO), and a biosurfactant. Mechanical methods of disruption that can be used comprise without limitation mechanical shear, bead milling, homogenation, microfluidization, sonication, French Press, impingement, a colloid mill, decompression, osmotic shock, thermolysis, freeze-thaw, desiccation, or any combination thereof.

As shown in FIG. 4, the binding agent may be tethered to a substrate. The binding agent can be tethered before or after the complex between the binding agent and target is formed. The substrate can be any useful substrate such as disclosed herein or known in the art. In an embodiment, the substrate comprises a microsphere. In another embodiment, the substrate comprises a planar substrate. In another embodiment, the substrate comprises column material. The binding agent can also be labeled. Isolating the complex between the target and the binding agent may comprise capturing the binding agent via the label. As a non-limiting example, the label can be a biotin label. In such cases, the binding agent can be attached to the substrate via a biotin-avidin/streptavidin binding event.

Methods of identifying the target after release from the binding agent will depend on the type of target of interest. For example, when the target comprises a protein, identifying the target may comprise use of mass spectrometry (MS), peptide mass fingerprinting (PMF; protein fingerprinting), sequencing, N-terminal amino acid analysis, C-terminal amino acid analysis, Edman degradation, chromatography, electrophoresis, two-dimensional gel electrophoresis (2D gel), antibody array, and immunoassay. Nucleic acids can be identified by amplification, hybridization or sequencing.

One of skill will appreciate that the method can be used to identify any appropriate target, including those not associated with a membrane. For example, with respect to the FIG. 4, all steps except for the step signified by arrow (i) (i.e., disrupting the cell or microvesicle 405), could be performed for a tissue lysate or a circulating target such as a protein, nucleic acid, lipid, carbohydrate, or combination thereof. The target can be any useful target, including without limitation a tissue, a cell, an organelle, a protein complex, a lipoprotein, a carbohydrate, a microvesicle, a virus, a membrane fragment, a small molecule, a heavy metal, a toxin, a drug, a nucleic acid, mRNA, microRNA, a protein-nucleic acid complex, and various combinations, fragments and/or complexes of any of these.

In an aspect, the invention provides a method of identifying at least one protein associated with at least one cell or microvesicle in a biological sample, comprising: a) contacting the at least one cell or microvesicle with an oligonucleotide probe library, b) isolating at least one protein bound by at least one member of the oligonucleotide probe library in step a); and c) identifying the at least one protein isolated in step b). The isolating can be performed using any useful method such as disclosed herein, e.g., by immunoprecipitation or capture to a substrate. Similarly, the identifying can be performed using any useful method such as disclosed herein, including without limitation use of mass spectrometry, 2-D gel electrophoresis or an antibody array. Examples of such methodology are presented herein in Examples 9-11.

The targets identified by the methods of the invention can be detected, e.g., using the oligonucleotide probes of the invention, for various purposes as desired. For example, an identified surface antigen can be used to detect a cell or microvesicle displaying such antigen. In an aspect, the invention provides a method of detecting at least one cell or microvesicle in a biological sample comprising contacting the biological sample with at least one binding agent to at least one surface antigen and detecting the at least one cell or microvesicle recognized by the binding agent to the at least one protein. In an embodiment, the at least one surface antigen is selected from Tables 3-4 herein. The at least one surface antigen can be selected those disclosed in International Patent Application Nos. PCT/US2009/62880, filed Oct. 30, 2009; PCT/US2009/006095, filed Nov. 12, 2009; PCT/US2011/26750, filed Mar. 1, 2011; PCT/US2011/031479, filed Apr. 6, 2011; PCT/US11/48327, filed Aug. 18, 2011; PCT/US2008/71235, filed Jul. 25, 2008; PCT/US10/58461, filed Nov. 30, 2010; PCT/US2011/21160, filed Jan. 13, 2011; PCT/US2013/030302, filed Mar. 11, 2013; PCT/US12/25741, filed Feb. 17, 2012; PCT/2008/76109, filed Sep. 12, 2008; PCT/US12/42519, filed Jun. 14, 2012; PCT/US12/50030, filed Aug. 8, 2012; PCT/US12/49615, filed Aug. 3, 2012; PCT/US12/41387, filed Jun. 7, 2012; PCT/US2013/072019, filed Nov. 26, 2013; PCT/US2014/039858, filed May 28, 2013; PCT/IB2013/003092, filed Oct. 23, 2013; PCT/US13/76611, filed Dec. 19, 2013; PCT/US14/53306, filed Aug. 28, 2014; and PCT/US15/62184, filed Nov. 23, 2015; PCT/US16/40157, filed Jun. 29, 2016; PCT/US16/44595, filed Jul. 28, 2016; and PCT/US16/21632, filed Mar. 9, 2016; each of which applications is incorporated herein by reference in its entirety. The at least one surface antigen can be a protein in any of Tables 10-17 herein. See Example 9. The at least one binding agent may comprise any useful binding agent, including without limitation a nucleic acid, DNA molecule, RNA molecule, antibody, antibody fragment, aptamer, peptoid, zDNA, peptide nucleic acid (PNA), locked nucleic acid (LNA), lectin, peptide, dendrimer, membrane protein labeling agent, chemical compound, or a combination thereof. In some embodiments, the at least one binding agent comprises at least one oligonucleotide, such as an oligonucleotide probe as provided herein. The cell can be part of a tissue.

The at least one binding agent can be used to capture and/or detect the at least one cell or microvesicle, which can be a circulating cell or microvesicle, including without limitation a microvesicle shed into bodily fluids. Methods of detecting soluble biomarkers and circulating cells or microvesicles using binding agents are provided herein. See, e.g., FIGS. 2A-B, which figures describe sandwich assay formats. In some embodiments, the at least one binding agent used to capture the at least one cell or microvesicle is bound to a substrate. Any useful substrate can be used, including without limitation a planar array, a column matrix, or a microbead. See, e.g., FIGS. 2A-B. In some embodiments, the at least one binding agent used to detect the at least one cell or microvesicle is labeled. Various useful labels are provided herein or known in the art, including without limitation a magnetic label, a fluorescent moiety, an enzyme, a chemiluminescent probe, a metal particle, a non-metal colloidal particle, a polymeric dye particle, a pigment molecule, a pigment particle, an electrochemically active species, a semiconductor nanocrystal, a nanoparticle, a quantum dot, a gold particle, a fluorophore, or a radioactive label.

In an embodiment, the detecting is used to characterize a phenotype. The phenotype can be any appropriate phenotype of interest. In some embodiments, the phenotype is a disease or disorder. The characterizing may comprise providing diagnostic, prognostic and/or theranostic information for the disease or disorder. The characterizing may be performed by comparing a presence or level of the at least one cell or microvesicle to a reference. The reference can be selected per the characterizing to be performed. For example, when the phenotype comprises a disease or disorder, the reference may comprise a presence or level of the at least one microvesicle in a sample from an individual or group of individuals without the disease or disorder. The comparing can be determining whether the presence or level of the cell or microvesicle differs from that of the reference. In some embodiments, the detected cell or microvesicle is found at higher levels in a healthy sample as compared to a diseased sample. In another embodiment, the detected cell or microvesicle is found at higher levels in a diseased sample as compared to a healthy sample. When multiplex assays are performed, e.g., using a plurality of binding agents to different biomarkers, some antigens may be observed at a higher level in the biological samples as compared to the reference whereas other antigens may be observed at a lower level in the biological samples as compared to the reference.

The method can be used to detect the at least one cell or microvesicle in any appropriate biological sample. For example, the biological sample may comprise a bodily fluid, tissue sample or cell culture. The bodily fluid or tissue sample can be from a subject having or suspected of having a medical condition, a disease or a disorder. Thus, the method can be used to provide a diagnostic, prognostic, or theranostic read out for the subject. Any appropriate bodily fluid can be used, including without limitation peripheral blood, sera, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, female ejaculate, sweat, fecal matter, hair oil, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, blastocyl cavity fluid, or umbilical cord blood.

The method of the invention can be used to detect or characterize any appropriate disease or disorder of interest, including without limitation Breast Cancer, Alzheimer's disease, bronchial asthma, Transitional cell carcinoma of the bladder, Giant cellular osteoblastoclastoma, Brain Tumor, Colorectal adenocarcinoma, Chronic obstructive pulmonary disease (COPD), Squamous cell carcinoma of the cervix, acute myocardial infarction (AMI)/acute heart failure, Chron's Disease, diabetes mellitus type II, Esophageal carcinoma, Squamous cell carcinoma of the larynx, Acute and chronic leukemia of the bone marrow, Lung carcinoma, Malignant lymphoma, Multiple Sclerosis, Ovarian carcinoma, Parkinson disease, Prostate adenocarcinoma, psoriasis, Rheumatoid Arthritis, Renal cell carcinoma, Squamous cell carcinoma of skin, Adenocarcinoma of the stomach, carcinoma of the thyroid gland, Testicular cancer, ulcerative colitis, or Uterine adenocarcinoma.

In some embodiments, the disease or disorder comprises a cancer, a premalignant condition, an inflammatory disease, an immune disease, an autoimmune disease or disorder, a cardiovascular disease or disorder, neurological disease or disorder, infectious disease or pain. The cancer can include without limitation one of acute lymphoblastic leukemia; acute myeloid leukemia; adrenocortical carcinoma; AIDS-related cancers; AIDS-related lymphoma; anal cancer; appendix cancer; astrocytomas; atypical teratoid/rhabdoid tumor; basal cell carcinoma; bladder cancer; brain stem glioma; brain tumor (including brain stem glioma, central nervous system atypical teratoid/rhabdoid tumor, central nervous system embryonal tumors, astrocytomas, craniopharyngioma, ependymoblastoma, ependymoma, medulloblastoma, medulloepithelioma, pineal parenchymal tumors of intermediate differentiation, supratentorial primitive neuroectodermal tumors and pineoblastoma); breast cancer; bronchial tumors; Burkitt lymphoma; cancer of unknown primary site; carcinoid tumor; carcinoma of unknown primary site; central nervous system atypical teratoid/rhabdoid tumor; central nervous system embryonal tumors; cervical cancer; childhood cancers; chordoma; chronic lymphocytic leukemia; chronic myelogenous leukemia; chronic myeloproliferative disorders; colon cancer; colorectal cancer; craniopharyngioma; cutaneous T-cell lymphoma; endocrine pancreas islet cell tumors; endometrial cancer; ependymoblastoma; ependymoma; esophageal cancer; esthesioneuroblastoma; Ewing sarcoma; extracranial germ cell tumor; extragonadal germ cell tumor; extrahepatic bile duct cancer; gallbladder cancer; gastric (stomach) cancer; gastrointestinal carcinoid tumor; gastrointestinal stromal cell tumor; gastrointestinal stromal tumor (GIST); gestational trophoblastic tumor; glioma; hairy cell leukemia; head and neck cancer; heart cancer; Hodgkin lymphoma; hypopharyngeal cancer; intraocular melanoma; islet cell tumors; Kaposi sarcoma; kidney cancer; Langerhans cell histiocytosis; laryngeal cancer; lip cancer; liver cancer; lung cancer; malignant fibrous histiocytoma bone cancer; medulloblastoma; medulloepithelioma; melanoma; Merkel cell carcinoma; Merkel cell skin carcinoma; mesothelioma; metastatic squamous neck cancer with occult primary; mouth cancer; multiple endocrine neoplasia syndromes; multiple myeloma; multiple myeloma/plasma cell neoplasm; mycosis fungoides; myelodysplastic syndromes; myeloproliferative neoplasms; nasal cavity cancer; nasopharyngeal cancer; neuroblastoma; Non-Hodgkin lymphoma; nonmelanoma skin cancer; non-small cell lung cancer; oral cancer; oral cavity cancer; oropharyngeal cancer; osteosarcoma; other brain and spinal cord tumors; ovarian cancer; ovarian epithelial cancer; ovarian germ cell tumor; ovarian low malignant potential tumor; pancreatic cancer; papillomatosis; paranasal sinus cancer; parathyroid cancer; pelvic cancer; penile cancer; pharyngeal cancer; pineal parenchymal tumors of intermediate differentiation; pineoblastoma; pituitary tumor; plasma cell neoplasm/multiple myeloma; pleuropulmonary blastoma; primary central nervous system (CNS) lymphoma; primary hepatocellular liver cancer; prostate cancer; rectal cancer; renal cancer; renal cell (kidney) cancer; renal cell cancer; respiratory tract cancer; retinoblastoma; rhabdomyosarcoma; salivary gland cancer; Sézary syndrome; small cell lung cancer; small intestine cancer; soft tissue sarcoma; squamous cell carcinoma; squamous neck cancer; stomach (gastric) cancer; supratentorial primitive neuroectodermal tumors; T-cell lymphoma; testicular cancer; throat cancer; thymic carcinoma; thymoma; thyroid cancer; transitional cell cancer; transitional cell cancer of the renal pelvis and ureter; trophoblastic tumor; ureter cancer; urethral cancer; uterine cancer; uterine sarcoma; vaginal cancer; vulvar cancer; Waldenström macroglobulinemia; or Wilm's tumor. The premalignant condition can include without limitation Barrett's Esophagus. The autoimmune disease can include without limitation one of inflammatory bowel disease (IBD), Crohn's disease (CD), ulcerative colitis (UC), pelvic inflammation, vasculitis, psoriasis, diabetes, autoimmune hepatitis, multiple sclerosis, myasthenia gravis, Type I diabetes, rheumatoid arthritis, psoriasis, systemic lupus erythematosis (SLE), Hashimoto's Thyroiditis, Grave's disease, Ankylosing Spondylitis Sjogrens Disease, CREST syndrome, Scleroderma, Rheumatic Disease, organ rejection, Primary Sclerosing Cholangitis, or sepsis. The cardiovascular disease can include without limitation one of atherosclerosis, congestive heart failure, vulnerable plaque, stroke, ischemia, high blood pressure, stenosis, vessel occlusion or a thrombotic event. The neurological disease can include without limitation one of Multiple Sclerosis (MS), Parkinson's Disease (PD), Alzheimer's Disease (AD), schizophrenia, bipolar disorder, depression, autism, Prion Disease, Pick's disease, dementia, Huntington disease (HD), Down's syndrome, cerebrovascular disease, Rasmussen's encephalitis, viral meningitis, neurospsychiatric systemic lupus erythematosus (NPSLE), amyotrophic lateral sclerosis, Creutzfeldt-Jacob disease, Gerstmann-Straussler-Scheinker disease, transmissible spongiform encephalopathy, ischemic reperfusion damage (e.g. stroke), brain trauma, microbial infection, or chronic fatigue syndrome. The pain can include without limitation one of fibromyalgia, chronic neuropathic pain, or peripheral neuropathic pain. The infectious disease can include without limitation one of a bacterial infection, viral infection, yeast infection, Whipple's Disease, Prion Disease, cirrhosis, methicillin-resistant *Staphylococcus aureus*, HIV, HCV, hepatitis, syphilis, meningitis, malaria, tuberculosis, or influenza. One of skill will appreciate that oligonucleotide probes or plurality of oligonucleotides or methods of the invention can be used to assess any number of these or other related diseases and disorders.

In a related aspect, the invention provides a kit comprising a reagent for carrying out the methods herein. In still another related aspect, the invention provides for use of a reagent for carrying out the methods. The reagent may comprise at least one binding agent to the at least one protein. The binding agent may be an oligonucleotide probe as provided herein.

Sample Characterization

The oligonucleotide probe/aptamers of the invention can be used to characterize a biological sample. For example, an oligonucleotide probe or oligonucleotide probe library can be used to provide a biosignature for the sample. The biosignature can indicate a characteristic of the sample, such as a diagnosis, prognosis or theranosis of a disease or disorder associated with the sample. In some embodiments, the biosignature comprises a presence or level of one or more biomarker present in the sample. In some embodiments, biosignature comprises a presence or level of the oligonucleotide probe or members of the oligonucleotide probe library that associated with the sample (e.g., by forming a complex with the sample).

In an aspect, the invention provides an aptamer comprising a nucleic acid sequence that is at least about 50, 55, 60, 65, 70, 75, 80, 85, 90, 95, 96, 97, 98, 99 or 100 percent homologous to any one of SEQ ID NOs. 1-206506; or a functional variation or fragment of any preceding sequence. A functional variation or fragment includes a sequence comprising modifications that is still capable of binding a target molecule, wherein the modifications comprise without limitation at least one of a deletion, insertion, point mutation, truncation or chemical modification. In a related aspect, the invention provides a method of characterizing a disease or disorder, comprising: (a) contacting a biological test sample with one or more aptamer of the invention, e.g., any of those in this paragraph or modifications thereof; (b) detecting a presence or level of a complex between the one or more aptamer and the target bound by the one or more aptamer in the biological test sample formed in step (a); (c) contacting a biological control sample with the one or more aptamer; (d) detecting a presence or level of a complex between the one or more aptamer and the target bound by the one or more aptamer in the biological control sample formed in step (c); and (e) comparing the presence or level detected in steps (b) and (d), thereby characterizing the disease or disorder.

The biological test sample and biological control sample can each comprise a tissue sample, a cell culture, or a biological fluid. In some embodiments, the biological test sample and biological control sample comprise the same sample type, e.g., both the test and control samples are tissue samples or both are fluid samples. In other embodiments, different sample types may be used for the test and control samples. For example, the control sample may comprise an engineered or otherwise artificial sample. In some embodiments, the tissue samples comprise fixed samples.

The biological fluid may comprise a bodily fluid. The bodily fluid may include without limitation one or more of peripheral blood, sera, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, female ejaculate, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, blastocyl cavity fluid, or umbilical cord blood. In some embodiments, the bodily fluid comprises blood, serum or plasma.

The biological fluid may comprise microvesicles. For example, the biological fluid can be a tissue, cell culture, or bodily fluid which comprises microvesicles released from cells in the sample. The microvesicles can be circulating microvesicles. The biological fluid may comprise cells. For example, the biological fluid can be a tissue, cell culture, or bodily fluid which comprises cells circulating in the sample.

The one or more aptamer can bind a target biomarker, e.g., a biomarker useful in characterizing the sample. The biomarker may comprise a polypeptide or fragment thereof, or other useful biomarker described herein or known in the art (lipid, carbohydrate, complex, nucleic acid, etc). In embodiments, the polypeptide or fragment thereof is soluble or membrane bound. Membrane bound polypeptides may comprise a cellular surface antigen or a microvesicle surface antigen. The biomarker can be a biomarker selected from Table 3 or Table 4. The biomarker can be selected from one of International Patent Application Nos. PCT/US2009/62880, filed Oct. 30, 2009; PCT/US2009/006095, filed Nov. 12, 2009; PCT/US2011/26750, filed Mar. 1, 2011; PCT/US2011/031479, filed Apr. 6, 2011; PCT/US11/48327, filed Aug. 18, 2011; PCT/US2008/71235, filed Jul. 25, 2008;

PCT/US10/58461, filed Nov. 30, 2010; PCT/US2011/21160, filed Jan. 13, 2011; PCT/US2013/030302, filed Mar. 11, 2013; PCT/US12/25741, filed Feb. 17, 2012; PCT/2008/76109, filed Sep. 12, 2008; PCT/US12/42519, filed Jun. 14, 2012; PCT/US12/50030, filed Aug. 8, 2012; PCT/US12/49615, filed Aug. 3, 2012; PCT/US12/41387, filed Jun. 7, 2012; PCT/US2013/072019, filed Nov. 26, 2013; PCT/US2014/039858, filed May 28, 2013; PCT/IB2013/003092, filed Oct. 23, 2013; PCT/US13/76611, filed Dec. 19, 2013; PCT/US14/53306, filed Aug. 28, 2014; and PCT/US15/62184, filed Nov. 23, 2015; PCT/US16/40157, filed Jun. 29, 2016; PCT/US16/44595, filed Jul. 28, 2016; and PCT/US16/21632, filed Mar. 9, 2016; each of which applications is incorporated herein by reference in its entirety.

The characterizing can comprises a diagnosis, prognosis or theranosis of the disease or disorder. Various diseases and disorders can be characterized using the compositions and methods of the invention, including without limitation a cancer, a premalignant condition, an inflammatory disease, an immune disease, an autoimmune disease or disorder, a cardiovascular disease or disorder, a neurological disease or disorder, an infectious disease, and/or pain. See, e.g., section herein "Phenotypes" for further details. In embodiments, the disease or disorder comprises a proliferative or neoplastic disease or disorder. For example, the disease or disorder can be a cancer. In some embodiments, the cancer comprises a breast cancer, ovarian cancer, prostate cancer, lung cancer, colorectal cancer, melanoma, pancreatic cancer, kidney cancer, or brain cancer.

Figure 10A:
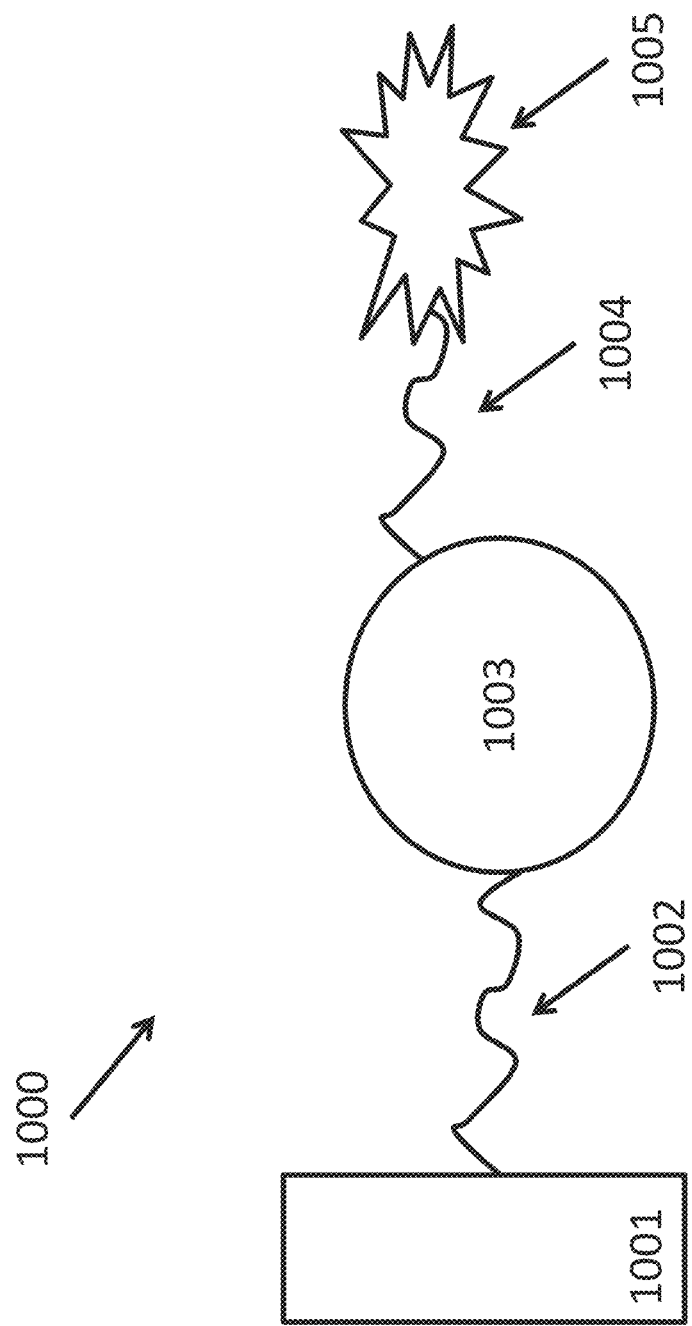
FIGS. 10A-D illustrate use of aptamers in methods of characterizing a phenotype.
Figure 10B:
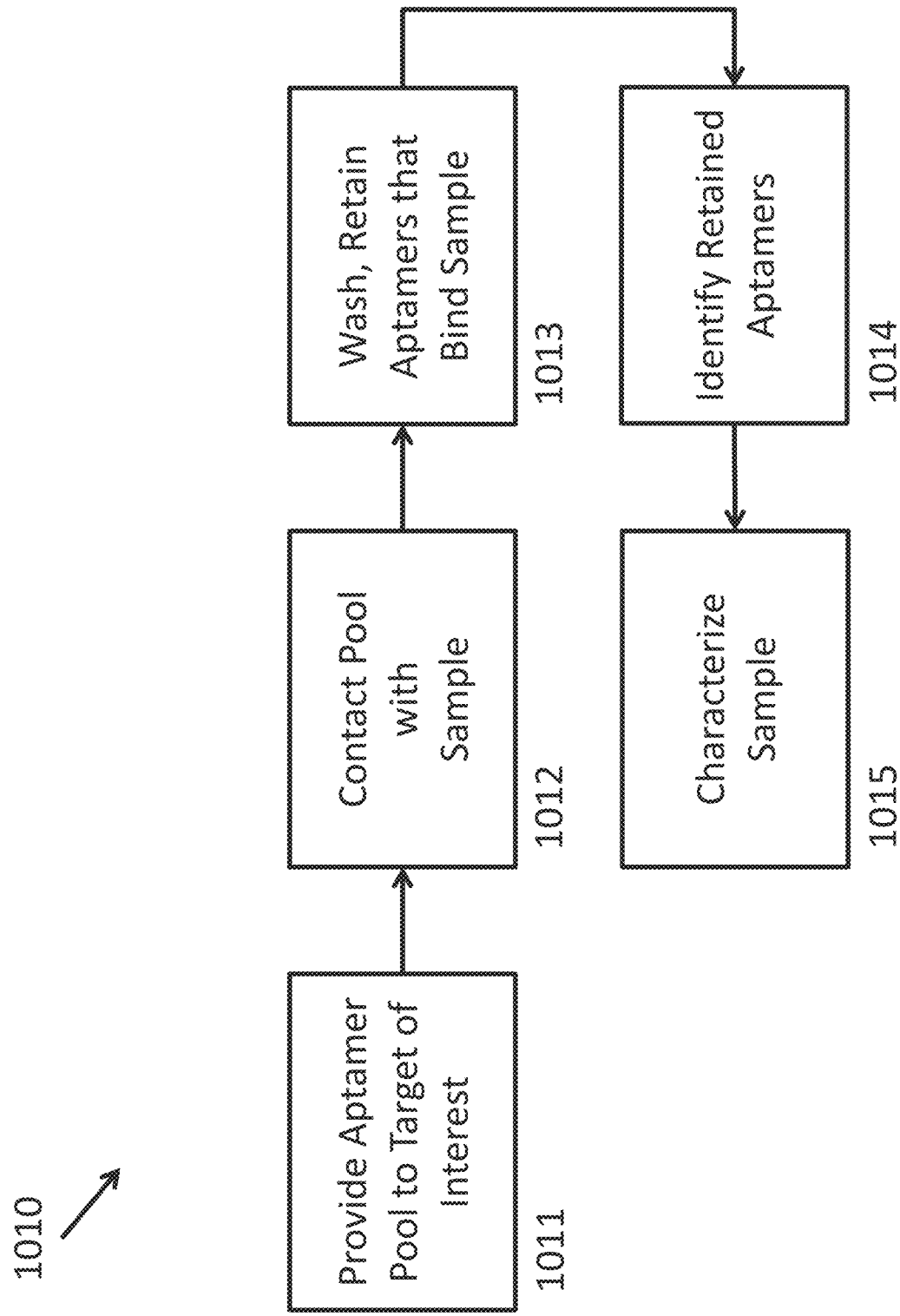
Figure 10C:
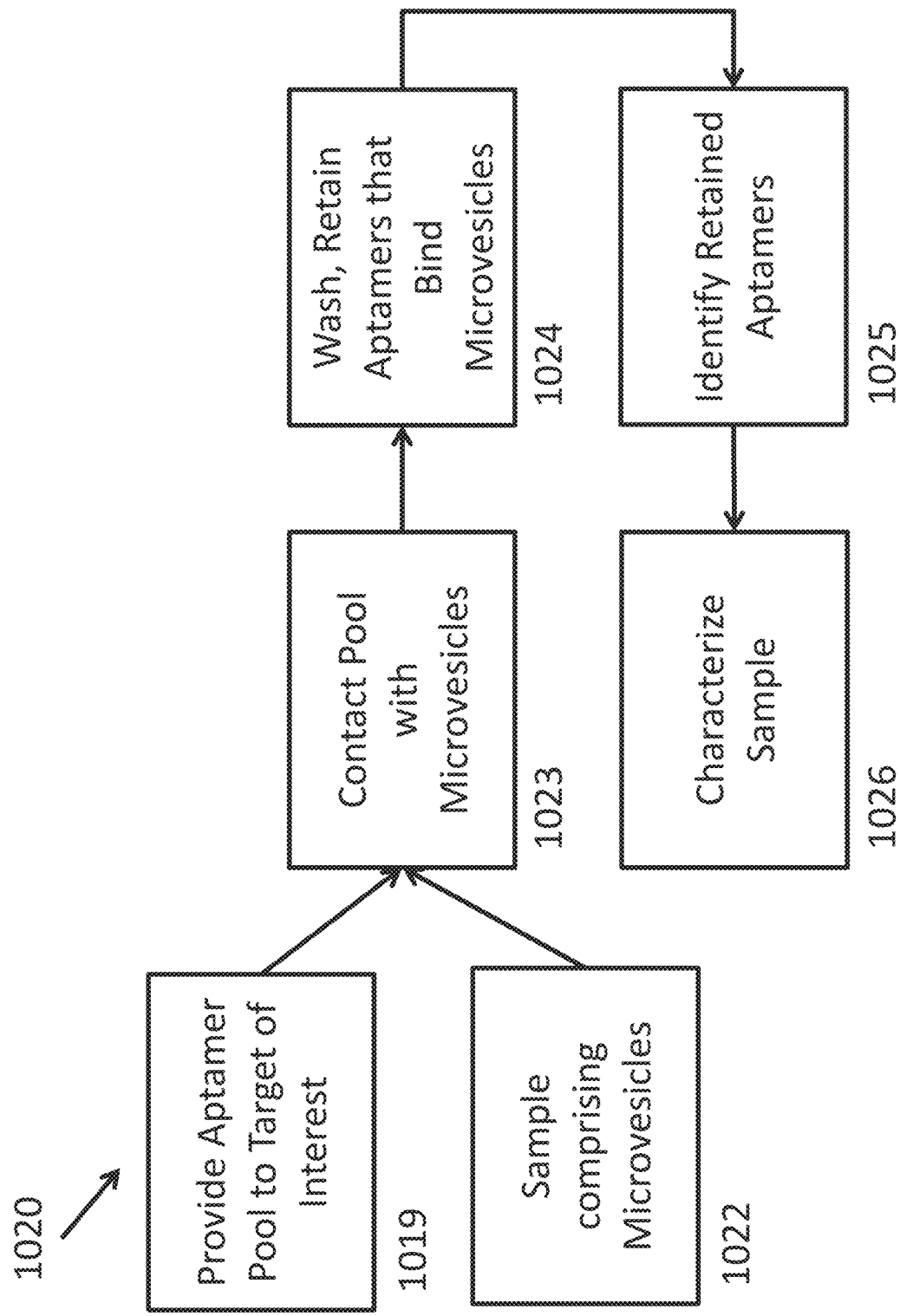

FIG. 10A is a schematic 1000 showing an assay configuration that can be used to detect and/or quantify a target of interest using one or more oligonucleotide probe of the invention. Capture aptamer 1002 is attached to substrate 1001. The substrate can be a planar substrate, well, microbead, or other useful substrate as disclosed herein or known in the art. Target of interest 1003 is bound by capture aptamer 1002. The target of interest can be any appropriate entity that can be detected when recognized by an aptamer or other binding agent. The target of interest may comprise a protein or polypeptide, a nucleic acid, including DNA, RNA, and various subspecies thereof, a lipid, a carbohydrate, a complex, e.g., a complex comprising protein, nucleic acids, lipids and/or carbohydrates. In some embodiments, the target of interest comprises a tissue, cell or microvesicle. The target of interest can be a cellular surface antigen or microvesicle surface antigen. The target of interest may be a biomarker, e.g., as disclosed herein. The target of interest can be isolated from a sample using various techniques as described herein, e.g., chromatography, filtration, centrifugation, flow cytometry, affinity capture (e.g., to a planar surface, column or bead), and/or using microfluidics. Detection aptamer 1004 is also bound to target of interest 1003. Detection aptamer 1004 carries label 1005 which can be detected to identify target captured to substrate 1001 via capture aptamer 1002. The label can be a fluorescent, radiolabel, enzyme, or other detectable label as disclosed herein. Either capture aptamer 1002 or detection aptamer 1004 can be substituted with another binding agent, e.g., an antibody. For example, the target may be captured with an antibody and detected with an aptamer, or vice versa. When the target of interest comprises a complex, the capture and detection agents (aptamer, antibody, etc) can recognize the same or different targets. For example, when the target is a cell or microvesicle, the capture agent may recognize one surface antigen while the detection agent recognizes microvesicle surface antigen. Alternately, the capture and detection agents can recognize the same surface antigen.

The aptamers of the invention may be identified and/or used for various purposes in the form of DNA or RNA. Unless otherwise specified, one of skill in the art will appreciate that an aptamer may generally be synthesized in various forms of nucleic acid. The aptamers may also carry various chemical modifications and remain within the scope of the invention.

In some embodiments, an aptamer of the invention is modified to comprise at least one chemical modification. The modification may include without limitation a chemical substitution at a sugar position; a chemical substitution at a phosphate position; and a chemical substitution at a base position of the nucleic acid. In some embodiments, the modification is selected from the group consisting of: biotinylation, incorporation of a fluorescent label, incorporation of a modified nucleotide, a 2'-modified pyrimidine, 3' capping, conjugation to an amine linker, conjugation to a high molecular weight, non-immunogenic compound, conjugation to a lipophilic compound, conjugation to a drug, conjugation to a cytotoxic moiety, and labeling with a radioisotope, or other modification as disclosed herein. The position of the modification can be varied as desired. For example, the biotinylation, fluorescent label, or cytotoxic moiety can be conjugated to the 5' end of the aptamer. The biotinylation, fluorescent label, or cytotoxic moiety can also be conjugated to the 3' end of the aptamer.

In some embodiments, the cytotoxic moiety is encapsulated in a nanoparticle. The nanoparticle can be selected from the group consisting of: liposomes, dendrimers, and comb polymers. In other embodiments, the cytotoxic moiety comprises a small molecule cytotoxic moiety. The small molecule cytotoxic moiety can include without limitation vinblastine hydrazide, calicheamicin, vinca alkaloid, a cryptophycin, a tubulysin, dolastatin-10, dolastatin-15, auristatin E, rhizoxin, epothilone B, epithilone D, taxoids, maytansinoids and any variants and derivatives thereof. In still other embodiments, the cytotoxic moiety comprises a protein toxin. For example, the protein toxin can be selected from the group consisting of diphtheria toxin, ricin, abrin, gelonin, and *Pseudomonas* exotoxin A. Non-immunogenic, high molecular weight compounds for use with the invention include polyalkylene glycols, e.g., polyethylene glycol. Appropriate radioisotopes include yttrium-90, indium-111, iodine-131, lutetium-177, copper-67, rhenium-186, rhenium-188, bismuth-212, bismuth-213, astatine-211, and actinium-225. The aptamer may be labeled with a gamma-emitting radioisotope.

In some embodiments of the invention, an active agent is conjugated to the aptamer. For example, the active agent may be a therapeutic agent or a diagnostic agent. The therapeutic agent may be selected from the group consisting of tyrosine kinase inhibitors, kinase inhibitors, biologically active agents, biological molecules, radionuclides, adriamycin, ansamycin antibiotics, asparaginase, bleomycin, busulphan, cisplatin, carboplatin, carmustine, capecotabine, chlorambucil, cytarabine, cyclophosphamide, camptothecin, dacarbazine, dactinomycin, daunorubicin, dexrazoxane, docetaxel, doxorubicin, etoposide, epothilones, floxuridine, fludarabine, fluorouracil, gemcitabine, hydroxyurea, idarubicin, ifosfamide, irinotecan, lomustine, mechlorethamine, mercaptopurine, melphalan, methotrexate, rapamycin (sirolimus), mitomycin, mitotane, mitoxantrone, nitrosurea, paclitaxel, pamidronate, pentostatin, plicamycin, procarbazine, rituximab, streptozocin, teniposide, thioguanine, thiotepa, taxanes, vinblastine, vincristine, vinorelbine, taxol, combretastatins, discodermolides, transplatinum, anti-vascular endothelial growth factor compounds ("anti-VEGFs"), anti-epidermal growth factor receptor compounds ("anti-EGFRs"), 5-fluorouracil and derivatives, radionuclides, polypeptide toxins, apoptosis inducers, therapy sensitizers, enzyme or active fragment thereof, and combinations thereof.

Oligonucleotide Pools to Characterize a Sample

Figure 11A:
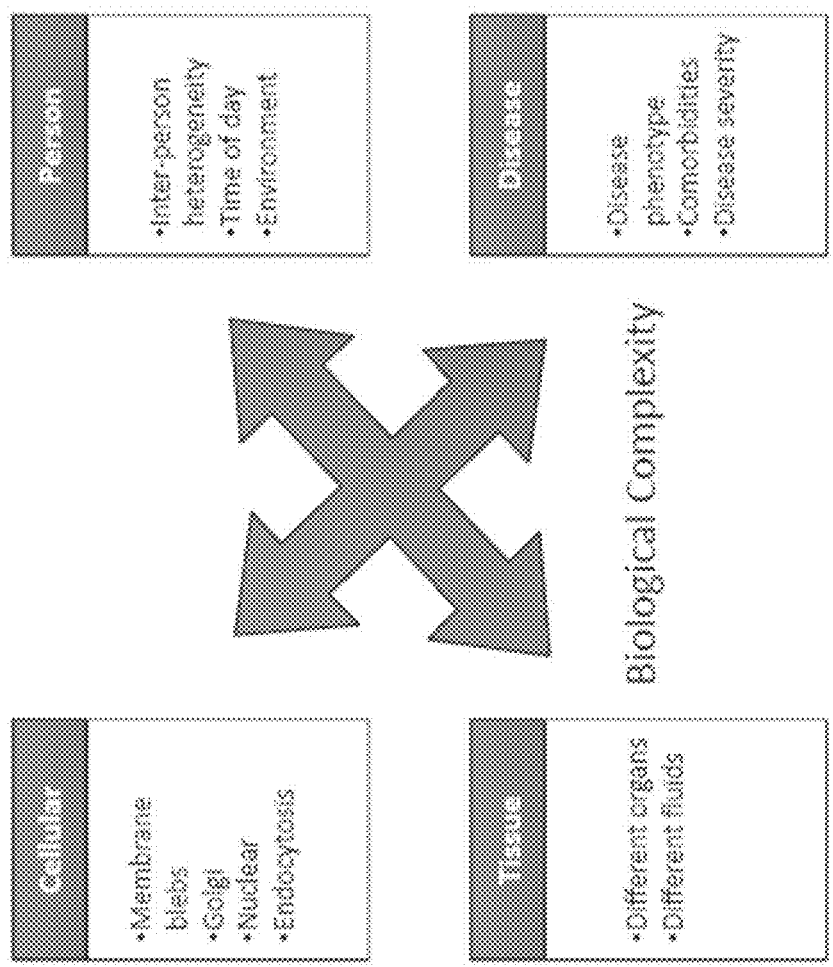
FIGS. 11A-I illustrate development and use of an oligonucleotide probe library to distinguish biological sample types.
Figure 11B:
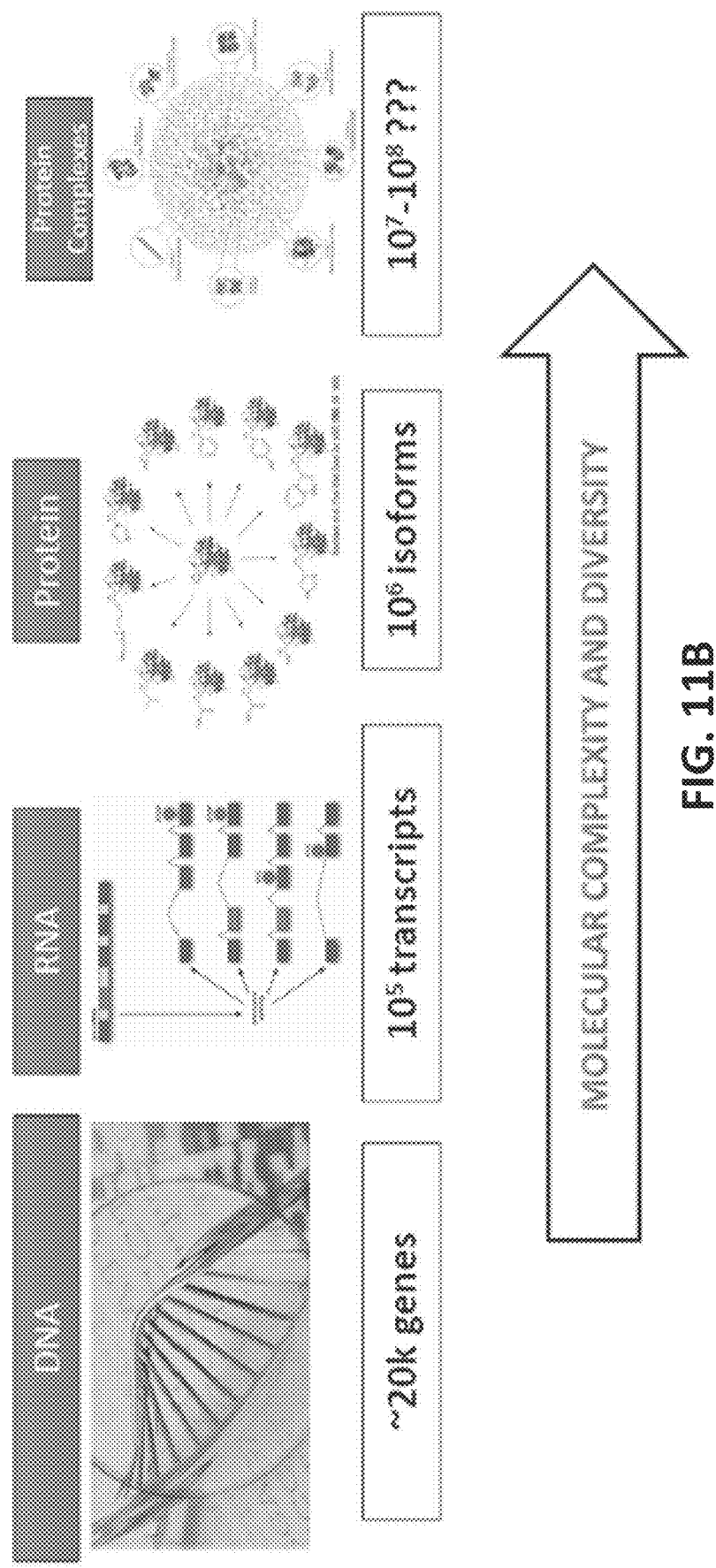

The complexity and heterogeneity present in biology challenges the understanding of biological systems and disease. Diversity exists at various levels, e.g., within and between cells, tissues, individuals and disease states. See, e.g., FIG. 11A. FIG. 11B overviews various biological entities that can be assessed to characterize such samples. As shown in FIG. 11B, as one moves from assessing DNA, to RNA, to protein, and finally to protein complexes, the amount of diversity and complexity increases dramatically. The oligonucleotide probe library method of the invention can be used characterize complex biological sources, e.g., tissue samples, cells, circulating tumor cells, microvesicles, and complexes such as protein and proteolipid complexes.

Figure 11C:
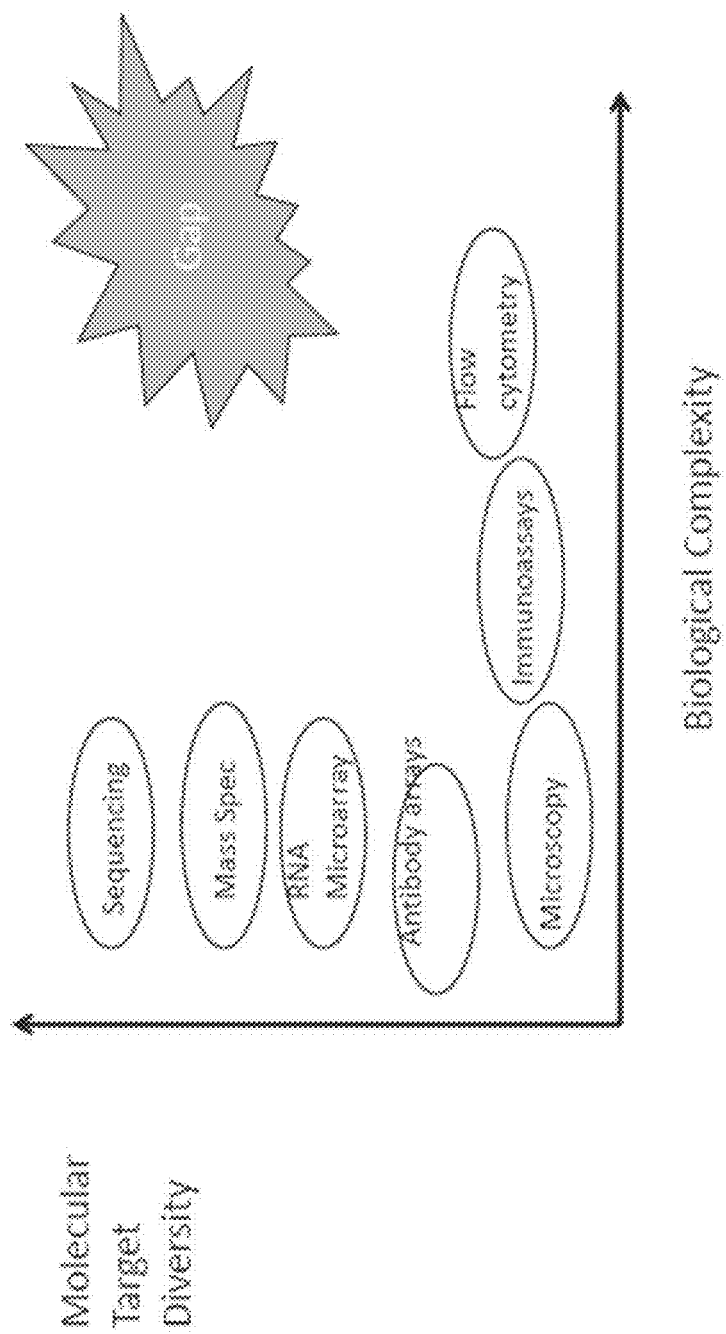

Current methods to characterize biological samples may not adequately address such complexity and diversity. As shown in FIG. 11C, such current methods often have a trade off between measuring diversity and complexity. As an example, consider high throughput sequencing technology. Next generation approaches may query many 1000s of molecular targets in a single assay. However, such approaches only probe individual DNA and/or RNA molecules, and thus miss out on the great diversity of proteins and biological complexes. On the other hand, flow cytometry can probe biological complexes, but are limited to a small number of pre-defined ligands. For example, a single assay can probe a handful of differentially labeled antibodies to pre-defined targets.

The oligonucleotide probe libraries of the invention address the above challenges. The size of the starting library can be adjusted to measure as many different entities as there are library members. For example, the initial untrained oligonucleotide library has the potential to measure $10^{12}$ or more biological features. A larger and/or different library can be constructed as desired. The technology is adapted to find differences between samples without assumptions about what "should be different." For example, the probe library may distinguish based on individual proteins, protein modifications, protein complexes, lipids, nucleic acids, different folds or conformations, or whatever is there that distinguishes a sample of interest. Thus, the method provides an unbiased approach to identify differences in biological samples that can be used to identify different populations of interest.

In the context herein, the use of the oligonucleotide library probe to assess a sample may be referred to as Adaptive Dynamic Artificial Poly-ligand Targeting, or ADAPT™ (alternately referred to as Topological Oligonucleotide Profiling: TOP™). Although as noted the terms aptamer and oligonucleotides are typically used interchangeable herein, some differences between "classic" individual aptamers and ADAPT probes are as follows. Individual aptamers may comprise individual oligonucleotides selected to bind to a known specific target in an antibody-like "key-in-lock" binding mode. They may be evaluated individually based on specificity and binding affinity to the intended target. However, ADAPT probes may comprise a library of oligonucleotides intended to produce multi-probe signatures. The ADAPT probes comprise numerous potential binding modalities (electrostatic, hydrophobic, Watson-Crick, multi-oligo complexes, etc.). The ADAPT probe signatures have the potential to identify heterogeneous patient subpopulations. For example, a single ADAPT library can be assembled to differentiate multiple biological states. Unlike classic single aptamers, the binding targets may or may not be isolated or identified. It will be understood that screening methods that identify individual aptamers, e.g., SELEX, can also be used to enrich a naïve library of oligonucleotides to identify a ADAPT probe library.

Figure 11D:
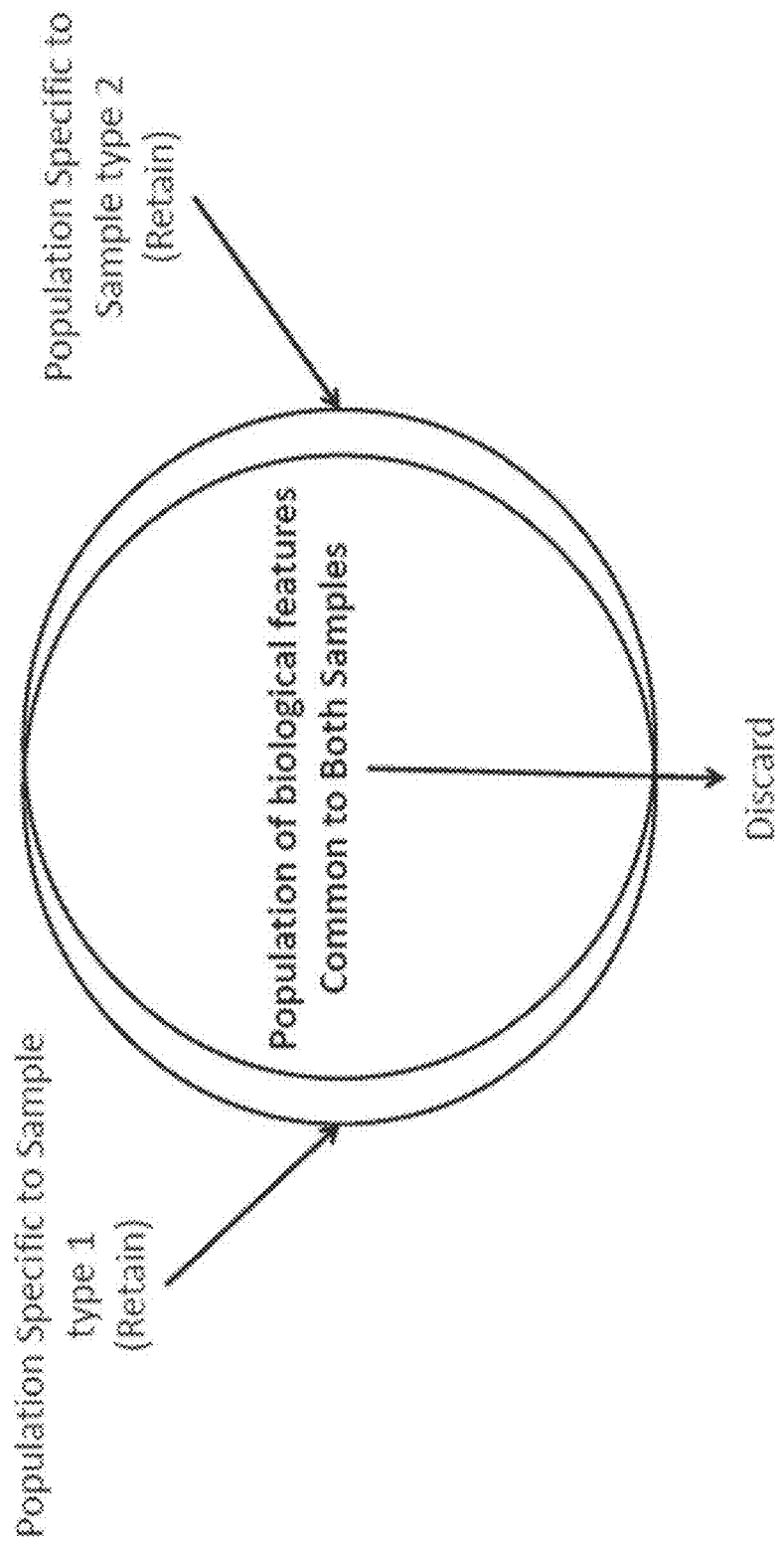

The general method of the invention is outlined in FIG. 11D. One input to the method comprises a randomized oligonucleotide library with the potential to measure $10^{12}$ or more biological features. As outlined in the figure, the method identifies a desired number (e.g., $\sim 10^{5}$-$10^{6}$) that are different between two input sample types. The randomized oligonucleotide library is contacted with a first and a second sample type, and oligonucleotides that bind to each sample are identified. The bound oligonucleotide populations are compared and oligonucleotides that specifically bind to one or the other biological input sample are retained for the oligonucleotide probe library, whereas oligonucleotides that bind both biological input samples are discarded. This trained oligonucleotide probe library can then be contacted with a new test sample and the identities of oligonucleotides that bind the test sample are determined. The test sample is characterized based on the profile of oligonucleotides that bound. See, e.g., FIG. 11H.

Figure 11E:
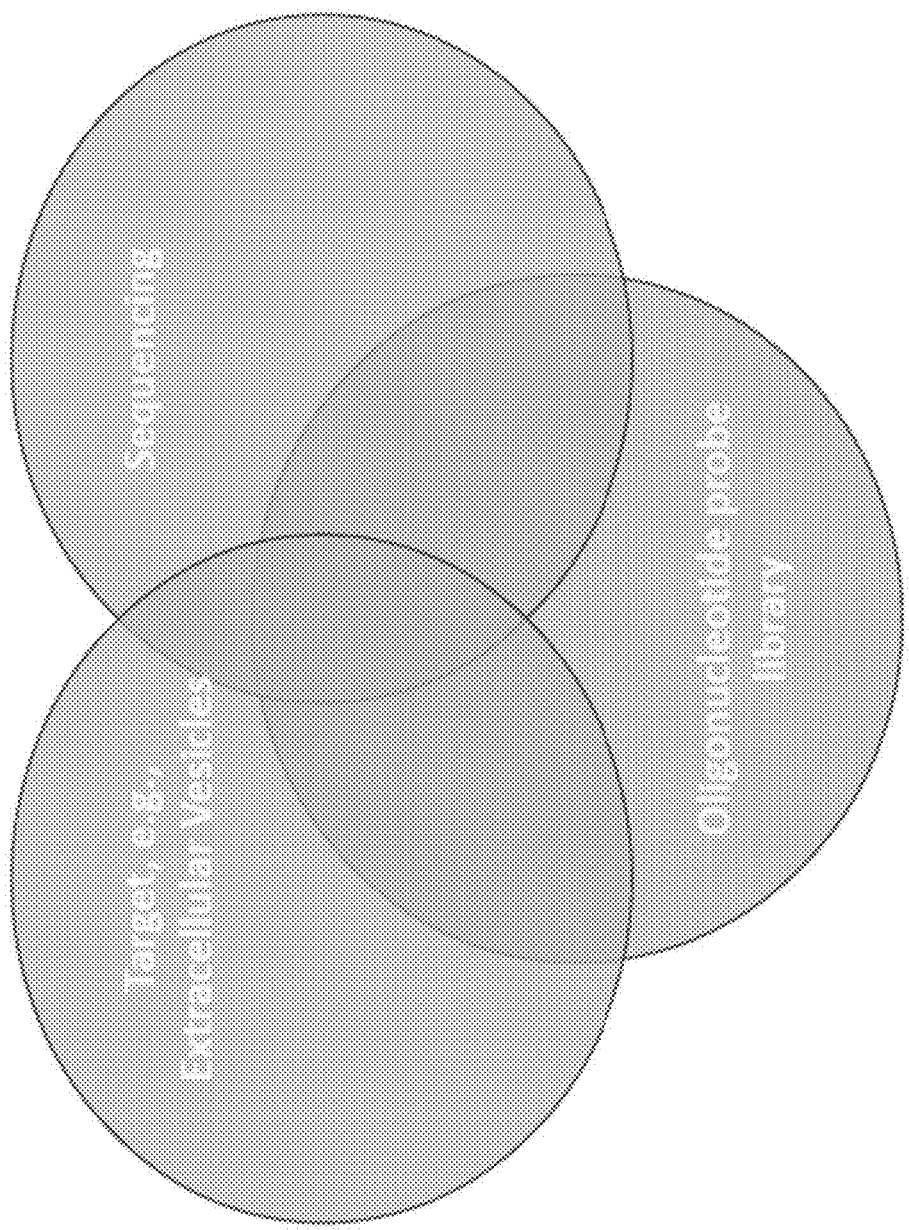

Extracellular vesicles provide an attractive vehicle to profile the biological complexity and diversity driven by many inter-related sources. There can be a great deal of heterogeneity between patient-to-patient microvesicle populations, or even in microvesicle populations from a single patient under different conditions (e.g., stress, diet, exercise, rest, disease, etc). Diversity of molecular phenotypes within microvesicle populations in various disease states, even after microvesicle isolation and sorting by vesicle biomarkers, can present challenges identifying surface binding ligands. This situation is further complicated by vesicle surface-membrane protein complexes. The oligonucleotide probe library can be used to address such challenges and allow for characterization of biological phenotypes. The approach combines the power of diverse oligonucleotide libraries and high throughput (next-generation) sequencing technologies to probe the complexity of extracellular microvesicles. See FIG. 11E.

Figure 11F:
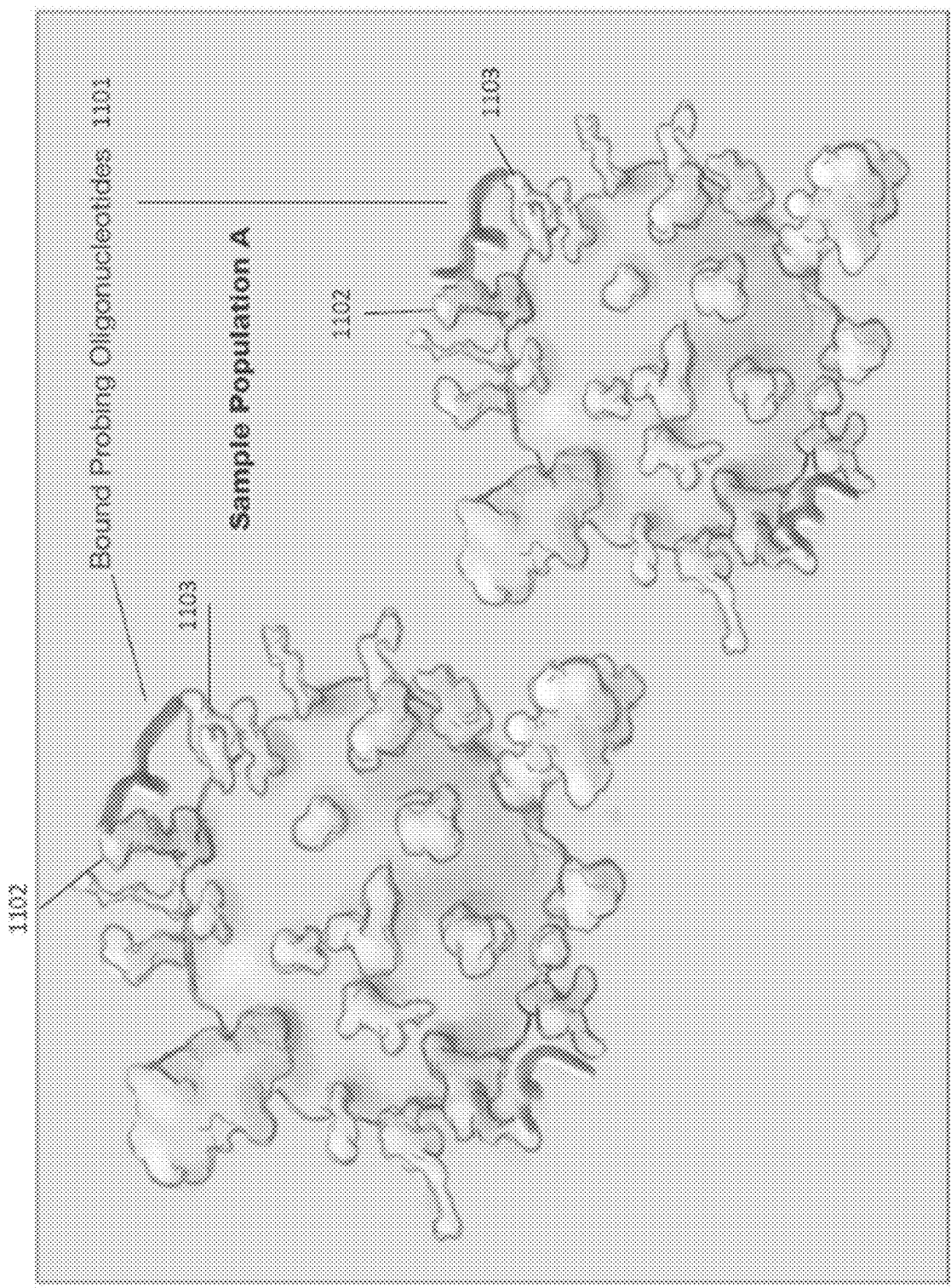
Figure 11G:
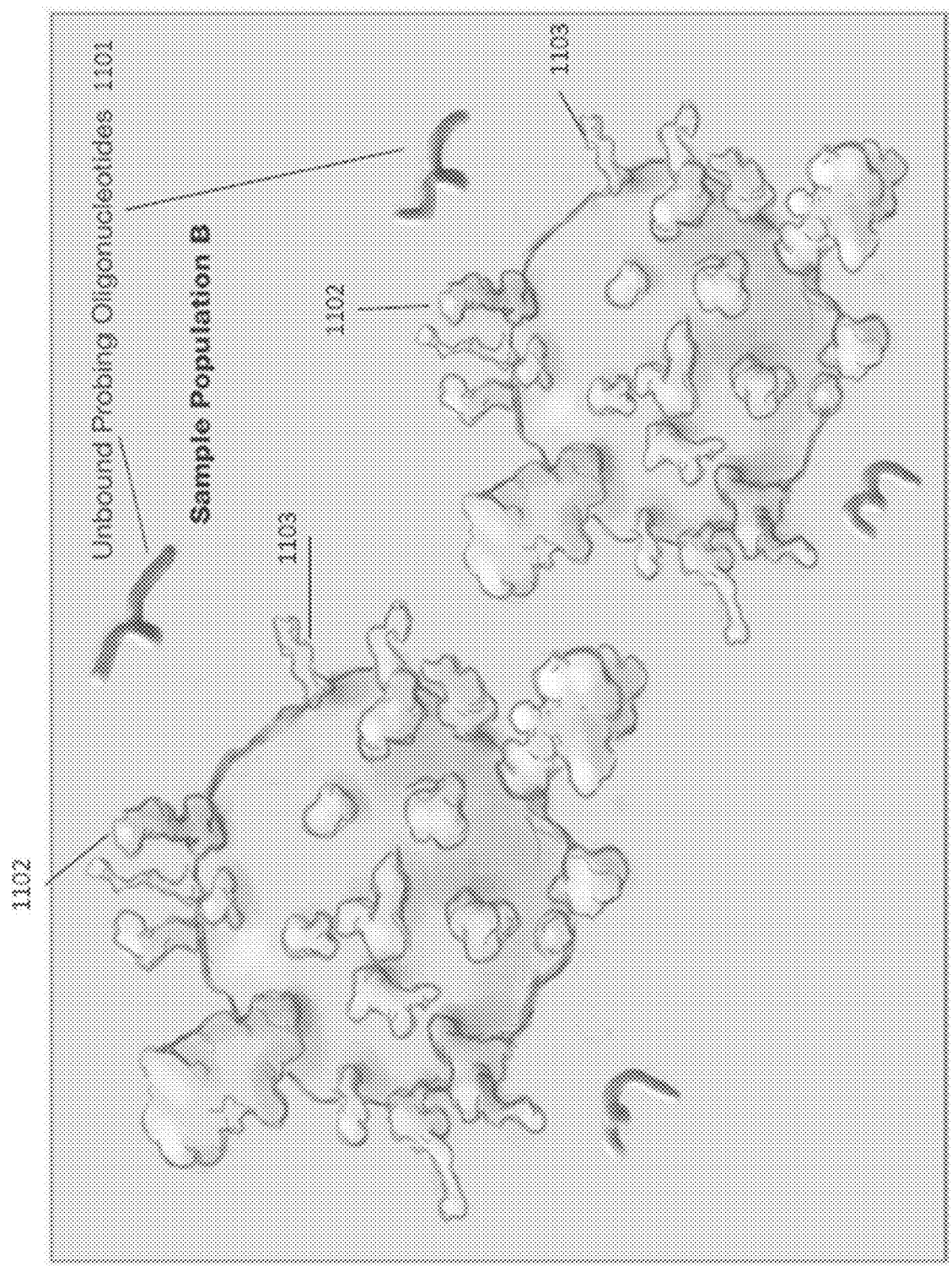

ADAPT™ profiling may provide quantitative measurements of dynamic events in addition to detection of presence/absence of various biomarkers in a sample. For example, the binding probes may detect protein complexes or other post-translation modifications, allowing for differentiation of samples with the same proteins but in different biological configurations. Such configurations are illustrated in FIGS. 11F-G. In FIG. 11F, microvesicles with various surface markers are shown from an example microvesicle sample population: Sample Population A. The indicated Bound Probing Oligonucleotides 1101 are contacted to two surface markers 1102 and 1103 in a given special relationship. Here, probes unique to these functional complexes and spatial relationships may be retained. In contrast, in microvesicle Sample Population B shown in FIG. 11F, the two surface markers 1102 and 1103 are found in disparate spacial relationship. Here, probes 1101 are not bound due to absence of the spatial relationship of the interacting components 1102 and 1103.

Figure 11H:
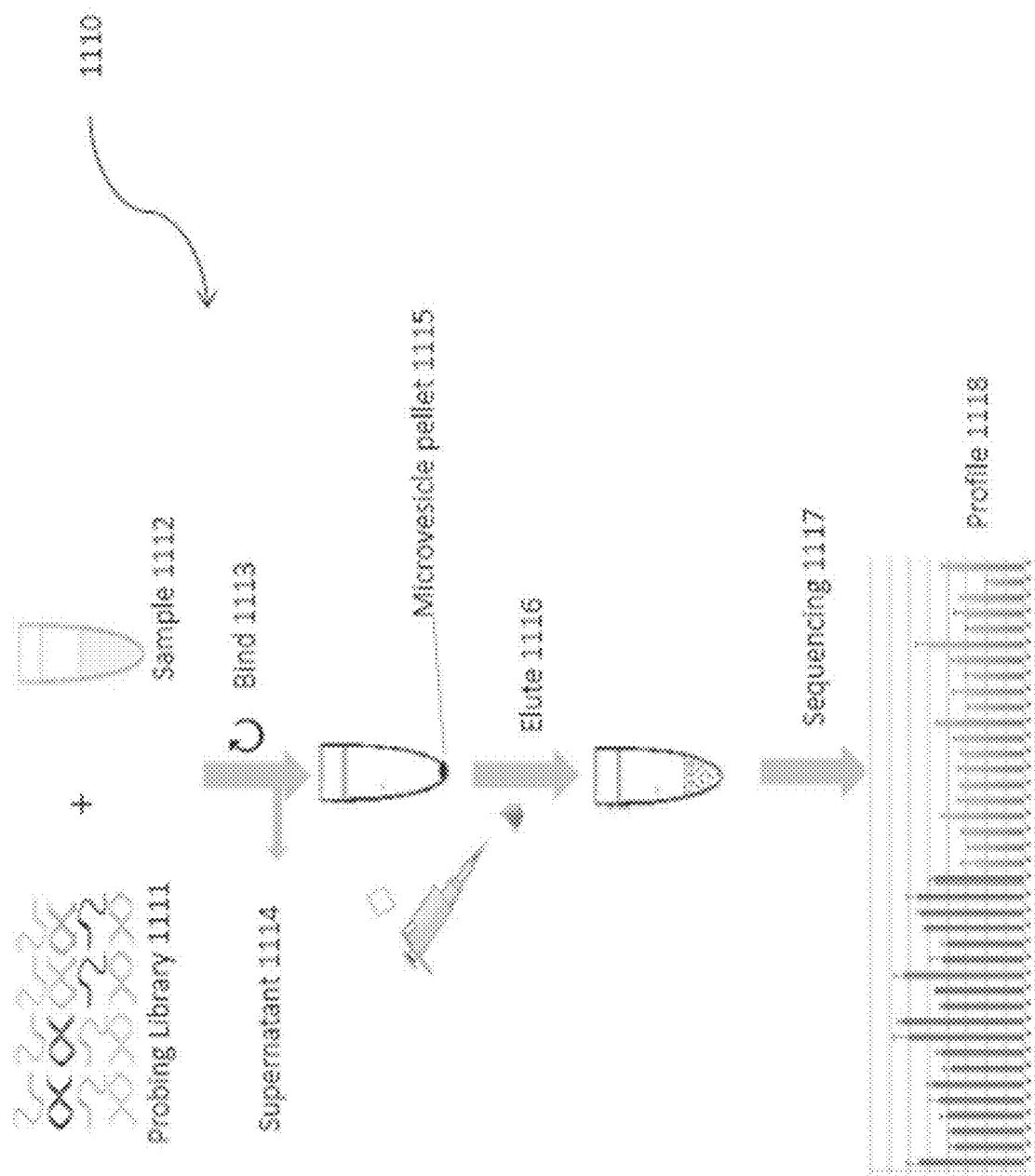
Figure 11I:
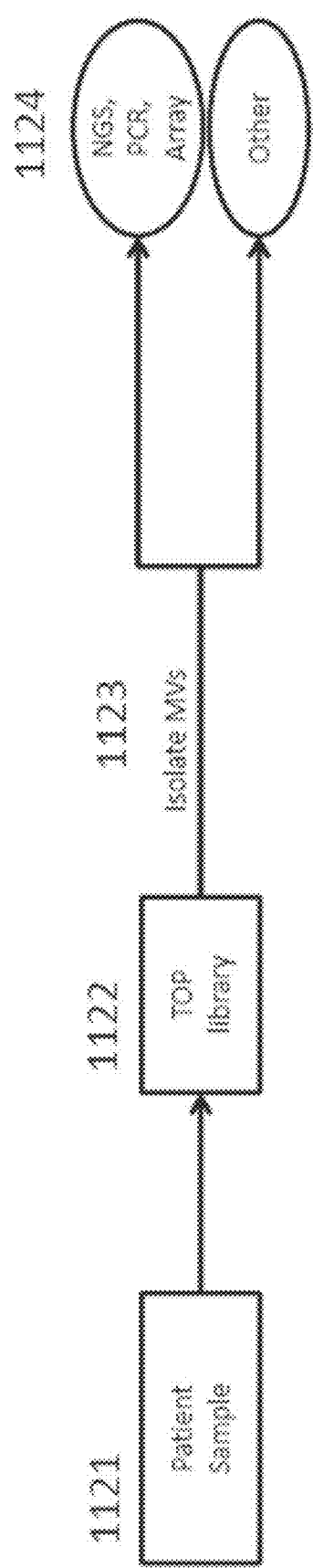

An illustrative approach 1110 for using ADAPT profiling to assess a sample is shown in FIG. 11H. The probing library 1111 is mixed with sample 1112. The sample can be as described herein, e.g., a bodily fluid from a subject having or suspected of having a disease. The probes are allowed to bind the sample 1120 and the microvesicles are pelleted 1115. The supernatant 1114 comprising unbound oligonucleotides is discarded. Oligonucleotide probes bound to the pellet 1115 are eluted 1116 and sequenced 1117. The profile 1118 generated by the bound oligonucleotide probes as determined by the sequencing 1117 is used to characterize the sample 1112. For example, the profile 1118 can be compared to a reference, e.g., to determine if the profile is similar or different from a reference profile indicative of a disease or healthy state, or other phenotypic characterization of interest. The comparison may indicate the presence of a disease, provide a diagnosis, prognosis or theranosis, or otherwise characterize a phenotype associated with the sample 1112. FIG. 11I illustrates another schematic for using ADAPT profiling to characterize a phenotype. A patient sample such as a bodily fluid disclosed herein is collected 1121. The sample is contacted with the ADAPT library pool 1122. Microvesicles (MVs) are isolated from the contacted sample 1123, e.g., using ultracentrifugation, filtration, polymer precipitation or other appropriate technique or combination of techniques disclosed herein. Oligonucleotides that bound the isolated microvesicles are collected and identity is determined 1124. The identity of the bound oligonucleotides can be determined by any useful technique such as sequencing, high throughput sequencing (e.g., NGS), amplification including without limitation qPCR, or hybridization such as to a planar or particle based array. The identity of the bound oligonucleotides is used to characterize the sample, e.g., as containing disease related microvesicles.

The approaches outlined in FIG. 11 can be adapted to any desired sample type, e.g., tissues, cells, microvesicles, circulating biomarkers, and constituents of any of these.

In an aspect, the invention provides a method of characterizing a sample by contacting the sample with a pool of different oligonucleotides (which can be referred to as an aptamer pool or oligonucleotide probe library), and determining the frequency at which various oligonucleotides in the pool bind the sample. For example, a pool of oligonucleotides is identified that preferentially bind to tissues, cells or microvesicles from cancer patients as compared to non-cancer patients. A test sample, e.g., from a patient suspected of having the cancer, is collected and contacted with the pool of oligonucleotides. Oligonucleotides that bind the test sample are eluted from the test sample, collected and identified, and the composition of the bound oligonucleotides is compared to those known to bind cancer samples. Various sequencing, amplification and hybridization techniques can be used to identify the eluted oligonucleotides. For example, when a large pool of oligonucleotides is used, oligonucleotide identification can be performed by high throughput methods such as next generation sequencing or via hybridization. If the test sample is bound by the oligonucleotide pool in a similar manner (e.g., as determined by bioinformatics classification methods) to the sample from cancer patients, then the test sample is indicative of cancer as well. Using this method, a pool of oligonucleotides that bind one or more antigen can be used to characterize the sample without necessarily knowing the precise target of each member of the pool of oligonucleotides. Thus, the pool of oligonucleotides provide a biosignature. Examples 5-7 and 9-31 and others herein illustrate embodiments of the invention.

In an aspect, the invention provides a method for characterizing a condition for a test sample comprising: contacting a sample with a plurality of oligonucleotide capable of binding one or more target(s) present in the sample, identifying a set of oligonucleotides that form a complex with the sample wherein the set is predetermined to characterize a condition for the sample, thereby characterizing a condition for a sample. The sample can be any useful sample such as disclosed herein, e.g., a tissue, cell, microvesicle, or biomarker sample, or any useful combination thereof.

In an related aspect, the invention provides a method for identifying a set of oligonucleotides associated with a test sample, comprising: (a) contacting a sample with a plurality of oligonucleotides, isolating a set of oligonucleotides that form a complex with the sample, (b) determining sequence and/or copy number for each of the oligonucleotides, thereby identifying a set of oligonucleotides associated with the test sample. The sample can be any useful sample such as disclosed herein, e.g., a tissue, cell, microvesicle, or biomarker sample, or any useful combination thereof.

In still another related aspect, the invention provides a method of diagnosing a sample as cancerous or predisposed to be cancerous, comprising contacting the sample with a plurality of oligonucleotides that are predetermined to preferentially form a complex with a cancer sample as compared to a non-cancer sample. The sample can be any useful sample such as disclosed herein, e.g., a tissue, cell, microvesicle, or biomarker sample, or any useful combination thereof.

The oligonucleotides can be identified by sequencing, e.g., by dye termination (Sanger) sequencing or high throughput methods. High throughput methods can comprise techniques to rapidly sequence a large number of nucleic acids, including next generation techniques such as Massively parallel signature sequencing (MPSS; Polony sequencing; 454 pyrosequencing; Illumina (Solexa; MiSeq/HiSeq/NextSeq/etc) sequencing; SOLiD sequencing; Ion Torrent semiconductor sequencing; DNA nanoball sequencing; Heliscope single molecule sequencing; Single molecule real time (SMRT) sequencing, or other methods such as Nanopore DNA sequencing; Tunnelling currents DNA sequencing; Sequencing by hybridization; Sequencing with mass spectrometry; Microfluidic Sanger sequencing; Microscopy-based techniques; RNAP sequencing; In vitro virus high-throughput sequencing. The oligonucleotides may also be identified by hybridization techniques. For example, a microarray having addressable locals to hybridize and thereby detect the various members of the pool can be used. Alternately, detection can be based on one or more differentially labelled oligonucleotides that hybridize with various members of the oligonucleotide pool. The detectable signal of the label can be associated with a nucleic acid molecule that hybridizes with a stretch of nucleic acids present in various oligonucleotides. The stretch can be the same or different as to one or more oligonucleotides in a library. The detectable signal can comprise fluorescence agents, including color-coded barcodes which are known, such as in U.S. Patent Application Pub. No. 20140371088, 2013017837, and 20120258870. Other detectable labels (metals, radioisotopes, etc) can be used as desired.

The plurality or pool of oligonucleotides can comprise any desired number of oligonucleotides to allow characterization of the sample. In various embodiments, the pool comprises at least 2, 3, 4, 5, 6, 7, 8, 9, 10, 11, 12, 13, 14, 15, 16, 17, 18, 19, 20, 25, 30, 40, 50, 60, 70, 80, 90, 100, 150, 200, 250, 300, 350, 400, 450, 500, 600, 700, 800, 900, 1000, 2000, 3000, 4000, 5000, 6000, 7000, 8000, 9000, or at least 10000 different oligonucleotide members.

The plurality of oligonucleotides can be pre-selected through one or more steps of positive or negative selection, wherein positive selection comprises selection of oligonucleotides against a sample having substantially similar characteristics compared to the test sample, and wherein negative selection comprises selection of oligonucleotides against a sample having substantially different characteristics compared to the test sample. Substantially similar characteristics mean that the samples used for positive selection are representative of the test sample in one or more characteristic of interest. For example, the samples used for positive selection can be from cancer patients or cell lines and the test sample can be a sample from a patient having or suspected to have a cancer. Substantially different characteristics mean that the samples used for negative selection differ from the test sample in one or more phenotype/characteristic of interest. For example, the samples used for negative selection can be from individuals or cell lines that do not have cancer (e.g., "normal," "healthy" or otherwise "control" samples) and the test sample can be a sample from a patient having or suspected to have a cancer. The cancer can be a breast cancer, ovarian cancer, prostate cancer, lung cancer, colorectal cancer, melanoma, brain cancer, pancreatic cancer, kidney cancer, or other cancer such as disclosed herein.

By selecting samples representative of the desired phenotypes to detect and/or distinguish, the characterizing can comprise a diagnosis, prognosis or theranosis for any number of diseases or disorders. Various diseases and disorders can be characterized using the compositions and methods of the invention, including without limitation a cancer, a pre-malignant condition, an inflammatory disease, an immune disease, an autoimmune disease or disorder, a cardiovascular disease or disorder, a neurological disease or disorder, an infectious disease, and/or pain. See, e.g., section herein "Phenotypes" for further details. In embodiments, the disease or disorder comprises a proliferative or neoplastic disease or disorder. For example, the disease or disorder can be a cancer.

FIG. 10B is a schematic 1010 showing use of an oligonucleotide pool to characterize a phenotype of a sample, such as those listed above. A pool of oligonucleotides to a target of interest is provided 1011. For example, the pool of oligonucleotides can be enriched to target a tissue, cell, microvesicle biomarker, or any combination thereof. The members of the pool may bind different targets (e.g., different proteins) or different epitopes of the same target (e.g., different epitopes of a single protein). The pool is contacted with a test sample to be characterized 1012. For example, the test sample may be a biological sample from an individual having or suspected of having a given disease or disorder. The mixture is washed to remove unbound oligonucleotides. The remaining oligonucleotides are eluted or otherwise disassociated from the sample and collected 1013. The collected oligonucleotides are identified, e.g., by sequencing or hybridization 1014. The presence and/or copy number of the identified is used to characterize the phenotype 1015.

FIG. 10C is a schematic 1020 showing an implementation of the method in FIG. 10B. A pool of oligonucleotides identified as binding a microvesicle population is provided 1019. The input sample comprises a test sample comprising microvesicles 1022. For example, the test sample may be a biological sample from an individual having or suspected of having a given disease or disorder. The pool is contacted with the isolated microvesicles to be characterized 1023. The microvesicle population can be isolated before or after the contacting 1023 from the sample using various techniques as described herein, e.g., chromatography, filtration, ultrafiltration, centrifugation, ultracentrifugation, flow cytometry, affinity capture (e.g., to a planar surface, column or bead), polymer precipitation, and/or using microfluidics. The mixture is washed to remove unbound oligonucleotides and the remaining oligonucleotides are eluted or otherwise disassociated from the sample and collected 1024. The collected oligonucleotides are identified 1025 and the presence and/or copy number of the retained oligonucleotides is used to characterize the phenotype 1026 as above.

As noted, in embodiment of FIG. 10C, the pool of oligonucleotides 1019 is directly contacted with a biological sample that comprises or is expected to comprise microvesicles. Microvesicles are thereafter isolated from the sample and the mixture is washed to remove unbound oligonucleotides and the remaining oligonucleotides are disassociated and collected 1024. The following steps are performed as above. As an example of this alternate configuration, a biological sample, e.g., a blood, serum or plasma sample, is directly contacted with the pool of oligonucleotides. Microvesicles are then isolated by various techniques disclosed herein, including without limitation ultracentrifugation, ultrafiltration, flow cytometry, affinity isolation, polymer precipitation, chromatography, various combinations thereof, or the like. Remaining oligonucleotides are then identified, e.g., by sequencing, hybridization or amplification.

Figure 10D:
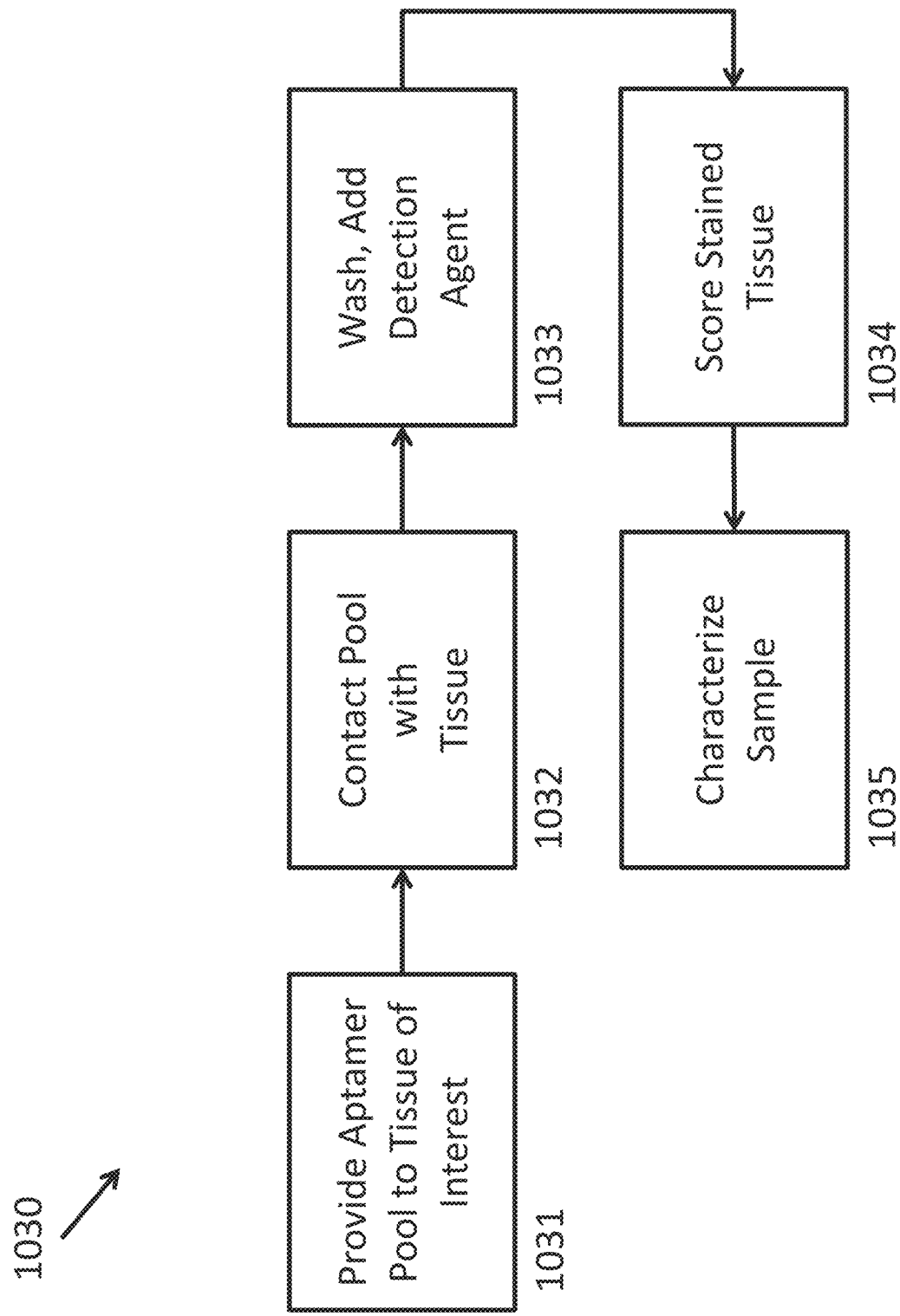

In other embodiments, an enriched library of oligonucleotide probes is used to assess a tissue sample. In some embodiments, the pool is used to stain the sample in a manner similar to IHC. Such method may be referred to herein as PHC, or polyligand histochemistry. FIG. 10D provides an outline 1030 of such method. An aptamer pool is provided that has been enriched against a tissue of interest 1031. The pool is contacted with a tissue sample 1032. The tissue sample can be in a format such as described herein. As a non-limiting example, the tissue sample can be a fixed tumor sample. The sample may be a FFPE sample fixed to a glass slide or membrane. The sample is washed to remove unbound members of the aptamer pool and the remaining aptamers are visualized 1033. Any appropriate method to visualize the aptamers can be used. In an example, the aptamer pool is biotinylated and the bound aptamer are visualized using streptavidin-horse radish peroxidase (SA-HRP). As described herein, other useful visualization methods are known in the art, including alternate labeling. The visualized sample is scored to determine the amount of staining 1034. For example a pathologist can score the slide as in IHC. The score can be used to characterize the sample 1035 as described herein. For example, a score of +1 or higher may indicate that the sample is a cancer sample, or is a cancer sample expressing a given biomarker. See Examples 19-31 herein.

In a related aspect, the invention provides a composition of matter comprising a plurality of oligonucleotides that can be used to carry out the methods comprising use of an oligonucleotide pool to characterize a phenotype. The plurality of oligonucleotides can comprise any of those described herein.

In an aspect, the invention provides a method for identifying oligonucleotides specific for a test sample. The method comprises: (a) enriching a plurality of oligonucleotides for a sample to provide a set of oligonucleotides predetermined to form a complex with a target sample; (b) contacting the plurality in (a) with a test sample to allow formation of complexes of oligonucleotides with test sample; (c) recovering oligonucleotides that formed complexes in (b) to provide a recovered subset of oligonucleotides; and (d) profiling the recovered subset of oligonucleotides by high-throughput sequencing, amplification or hybridization, thereby identifying oligonucleotides specific for a test sample. The test sample may comprise tissue, cells, microvesicles, biomarkers, or other biological entities of interest. The oligonucleotides may comprise RNA, DNA or both. In some embodiment, the method further comprises performing informatics analysis to identify a subset of oligonucleotides comprising sequence identity of at least 50%, 55%, 60%, 65%, 70%, 75%, 80%, 85%, 90%, 91%, 92%, 93%, 94%, 95%, 96%, 97%, 98%, or at least 99% to the oligonucleotides predetermined to form a complex with the target sample.

One of skill will appreciate that the method can be used to identify any appropriate target. The target can be any useful target, including without limitation a cell, an organelle, a protein complex, a lipoprotein, a carbohydrate, a microvesicle, a virus, a membrane fragment, a small molecule, a heavy metal, a toxin, a drug, a nucleic acid (including without limitation microRNA (miR) and messenger RNA (mRNA)), a protein-nucleic acid complex, and various combinations, fragments and/or complexes of any of these. The target can, e.g., comprise a mixture of such biological entities.

In an aspect, the invention also provides a method comprising contacting an oligonucleotide or plurality of oligonucleotides with a sample and detecting the presence or level of binding of the oligonucleotide or plurality of oligonucleotides to a target in the sample, wherein the oligonucleotide or plurality of oligonucleotides can be those provided by the invention above. The sample may comprise a biological sample, an organic sample, an inorganic sample, a tissue, a cell culture, a bodily fluid, blood, serum, a cell, a microvesicle, a protein complex, a lipid complex, a carbohydrate, or any combination, fraction or variation thereof. The target may comprise a cell, an organelle, a protein complex, a lipoprotein, a carbohydrate, a microvesicle, a membrane fragment, a small molecule, a heavy metal, a toxin, or a drug.

In another aspect, the invention provides a method comprising: a) contacting a sample with an oligonucleotide probe library comprising at least $10^6$, $10^7$, $10^8$, $10^9$, $10^{10}$, $10^{11}$, $10^{12}$, $10^{13}$, $10^{14}$, $10^{15}$, $10^{16}$, $10^{17}$, or at least $10^{18}$ different oligonucleotide sequences oligonucleotides to form a mixture in solution, wherein the oligonucleotides are capable of binding a plurality of entities in the sample to form complexes, wherein optionally the oligonucleotide probe library comprises an oligonucleotide or plurality of oligonucleotides as provided by the invention above; b) partitioning the complexes formed in step (a) from the mixture; and c) recovering oligonucleotides present in the complexes partitioned in step (b) to identify an oligonucleotide profile for the sample.

In still another aspect, the invention provides a method for generating an enriched oligonucleotide probe library comprising: a) contacting a first oligonucleotide library with a biological test sample and a biological control sample, wherein complexes are formed between biological entities present in the biological samples and a plurality of oligonucleotides present in the first oligonucleotide library; b) partitioning the complexes formed in step (a) and isolating the oligonucleotides in the complexes to produce a subset of oligonucleotides for each of the biological test sample and biological control sample; c) contacting the subsets of oligonucleotides in (b) with the biological test sample and biological control sample wherein complexes are formed between biological entities present in the biological samples and a second plurality of oligonucleotides present in the subsets of oligonucleotides to generate a second subset group of oligonucleotides; and d) optionally repeating steps b)-c), one, two, three or more times to produce a respective third, fourth, fifth or more subset group of oligonucleotides, thereby producing the enriched oligonucleotide probe library. In a related aspect, the invention provides a plurality of oligonucleotides comprising at least 2, 3, 4, 5, 6, 7, 8, 9, 10, 11, 12, 13, 14, 15, 16, 17, 18, 19, 20, 25, 30, 40, 45, 50, 55, 60, 65, 70, 75, 80, 85, 90, 95, 100, 125, 150, 175, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, or 500000 different oligonucleotide sequences, wherein the plurality results from the method in this paragraph, wherein the library is capable of distinguishing a first phenotype from a second phenotype. In some embodiments, the first phenotype comprises a disease or disorder and the second phenotype comprises a healthy state; or wherein the first phenotype comprises a disease or disorder and the second phenotype comprises a different disease or disorder; or wherein the first phenotype comprises a stage or progression of a disease or disorder and the second phenotype comprises a different stage or progression of the same disease or disorder; or wherein the first phenotype comprises a positive response to a therapy and the second phenotype comprises a negative response to the same therapy.

In yet another aspect, the invention provides a method of characterizing a disease or disorder, comprising: a) contacting a biological test sample with the oligonucleotide or plurality of oligonucleotides provided by the invention; b) detecting a presence or level of complexes formed in step (a) between the oligonucleotide or plurality of oligonucleotides provided by the invention and a target in the biological test sample; and c) comparing the presence or level detected in step (b) to a reference level from a biological control sample, thereby characterizing the disease or disorder. The step of detecting may comprise performing sequencing of all or some of the oligonucleotides in the complexes, amplification of all or some of the oligonucleotides in the complexes, and/or hybridization of all or some of the oligonucleotides in the complexes to an array. The sequencing may be high-throughput or next generation sequencing. In some embodiments, the step of detecting comprises visualizing the oligonucleotide or plurality of oligonucleotides in association with the biological test sample. For example, polyligand histochemistry (PHC) as provided by the invention may be used.

In the methods of the invention, the biological test sample and biological control sample may each comprise a tissue sample, a cell culture, or a biological fluid. In some embodiments, the biological fluid comprises a bodily fluid. Useful bodily fluids within the method of the invention comprise peripheral blood, sera, plasma, ascites, urine, cerebrospinal fluid (CSF), sputum, saliva, bone marrow, synovial fluid, aqueous humor, amniotic fluid, cerumen, breast milk, bronchoalveolar lavage fluid, semen, prostatic fluid, cowper's fluid or pre-ejaculatory fluid, female ejaculate, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, blastocyl cavity fluid, or umbilical cord blood. In some preferred embodiments, the bodily fluid comprises blood, serum or plasma. The biological fluid may comprise microvesicles. In such case, the complexes may be formed between the oligonucleotide or plurality of oligonucleotides and at least one of the microvesicles.

The biological test sample and biological control sample may further comprise isolated microvesicles, wherein optionally the microvesicles are isolated using at least one of chromatography, filtration, ultrafiltration, centrifugation, ultracentrifugation, flow cytometry, affinity capture (e.g., to a planar surface, column or bead), polymer precipitation, and using microfluidics. The vesicles can also be isolated after contact with the oligonucleotide or plurality of oligonucleotides.

The biological test sample and biological control sample may comprise tissue. The tissue can be formalin fixed paraffin embedded (FFPE) tissue. In some embodiments, the FFPE tissue comprises at least one of a fixed tissue, unstained slide, bone marrow core or clot, biopsy sample, surgical sample, core needle biopsy, malignant fluid, and fine needle aspirate (FNA). The FFPE tissue can be fixed on a substrate, e.g., a glass slide or membrane.

In various embodiments of the methods of the invention, the oligonucleotide or plurality of oligonucleotides binds a polypeptide or fragment thereof. The polypeptide or fragment thereof can be soluble or membrane bound, wherein optionally the membrane comprises a cellular or microvesicle membrane. The membrane could also be from a fragment of a cell, organelle or microvesicle. In some embodiments, the polypeptide or fragment thereof comprises a biomarker in Table 3, Table 4 or any one of Tables 10-17. For example, the polypeptide or fragment thereof could be a general vesicle marker such as in Table 3 or a tissue-related or disease-related marker such as in Table 4, or a vesicle associated biomarker provided in any one of Tables 10-17. The oligonucleotide or plurality of oligonucleotides may bind a microvesicle surface antigen in the biological sample. For example, the oligonucleotide or plurality of oligonucleotides can be enriched from a naïve library against microvesicles.

As noted above, the microvesicles may be isolated in whole or in part using polymer precipitation. In an embodiment, the polymer comprises polyethylene glycol (PEG). Any appropriate form of PEG may be used. For example, the PEG may be PEG 8000. The PEG may be used at any appropriate concentration. For example, the PEG can be used at a concentration of 1%, 2%, 3%, 4%, 5%, 6%, 7%, 8%, 9%, 10%, 11%, 12%, 13%, 14% or 15% to isolate the microvesicles. In some embodiments, the PEG is used at a concentration of 6%.

The disease or disorder detected by the oligonucleotide, plurality of oligonucleotides, or methods provided here may comprise any appropriate disease or disorder of interest, including without limitation Breast Cancer, Alzheimer's disease, bronchial asthma, Transitional cell carcinoma of the bladder, Giant cellular osteoblastoclastoma, Brain Tumor, Colorectal adenocarcinoma, Chronic obstructive pulmonary disease (COPD), Squamous cell carcinoma of the cervix, acute myocardial infarction (AMI)/acute heart failure, Chron's Disease, diabetes mellitus type II, Esophageal carcinoma, Squamous cell carcinoma of the larynx, Acute and chronic leukemia of the bone marrow, Lung carcinoma, Malignant lymphoma, Multiple Sclerosis, Ovarian carcinoma, Parkinson disease, Prostate adenocarcinoma, psoriasis, Rheumatoid Arthritis, Renal cell carcinoma, Squamous cell carcinoma of skin, Adenocarcinoma of the stomach, carcinoma of the thyroid gland, Testicular cancer, ulcerative colitis, or Uterine adenocarcinoma.

In some embodiments, the disease or disorder comprises a cancer, a premalignant condition, an inflammatory disease, an immune disease, an autoimmune disease or disorder, a cardiovascular disease or disorder, neurological disease or disorder, infectious disease or pain. The cancer can include without limitation one of acute lymphoblastic leukemia; acute myeloid leukemia; adrenocortical carcinoma; AIDS-related cancers; AIDS-related lymphoma; anal cancer; appendix cancer; astrocytomas; atypical teratoid/rhabdoid tumor; basal cell carcinoma; bladder cancer; brain stem glioma; brain tumor (including brain stem glioma, central nervous system atypical teratoid/rhabdoid tumor, central nervous system embryonal tumors, astrocytomas, craniopharyngioma, ependymoblastoma, ependymoma, medulloblastoma, medulloepithelioma, pineal parenchymal tumors of intermediate differentiation, supratentorial primitive neuroectodermal tumors and pineoblastoma); breast cancer; bronchial tumors; Burkitt lymphoma; cancer of unknown primary site; carcinoid tumor; carcinoma of unknown primary site; central nervous system atypical teratoid/rhabdoid tumor; central nervous system embryonal tumors; cervical cancer; childhood cancers; chordoma; chronic lymphocytic leukemia; chronic myelogenous leukemia; chronic myeloproliferative disorders; colon cancer; colorectal cancer; craniopharyngioma; cutaneous T-cell lymphoma; endocrine pancreas islet cell tumors; endometrial cancer; ependymoblastoma; ependymoma; esophageal cancer; esthesioneuroblastoma; Ewing sarcoma; extracranial germ cell tumor; extragonadal germ cell tumor; extrahepatic bile duct cancer; gallbladder cancer; gastric (stomach) cancer; gastrointestinal carcinoid tumor; gastrointestinal stromal cell tumor; gastrointestinal stromal tumor (GIST); gestational trophoblastic tumor; glioma; hairy cell leukemia; head and neck cancer; heart cancer; Hodgkin lymphoma; hypopharyngeal cancer; intraocular melanoma; islet cell tumors; Kaposi sarcoma; kidney cancer; Langerhans cell histiocytosis; laryngeal cancer; lip cancer; liver cancer; lung cancer; malignant fibrous histiocytoma bone cancer; medulloblastoma; medulloepithelioma; melanoma; Merkel cell carcinoma; Merkel cell skin carcinoma; mesothelioma; metastatic squamous neck cancer with occult primary; mouth cancer; multiple endocrine neoplasia syndromes; multiple myeloma; multiple myeloma/plasma cell neoplasm; mycosis fungoides; myelodysplastic syndromes; myeloproliferative neoplasms; nasal cavity cancer; nasopharyngeal cancer; neuroblastoma; Non-Hodgkin lymphoma; nonmelanoma skin cancer; non-small cell lung cancer; oral cancer; oral cavity cancer; oropharyngeal cancer; osteosarcoma; other brain and spinal cord tumors; ovarian cancer; ovarian epithelial cancer; ovarian germ cell tumor; ovarian low malignant potential tumor; pancreatic cancer; papillomatosis; paranasal sinus cancer; parathyroid cancer; pelvic cancer; penile cancer; pharyngeal cancer; pineal parenchymal tumors of intermediate differentiation; pineoblastoma; pituitary tumor; plasma cell neoplasm/multiple myeloma; pleuropulmonary blastoma; primary central nervous system (CNS) lymphoma; primary hepatocellular liver cancer; prostate cancer; rectal cancer; renal cancer; renal cell (kidney) cancer; renal cell cancer; respiratory tract cancer; retinoblastoma; rhabdomyosarcoma; salivary gland cancer; Sézary syndrome; small cell lung cancer; small intestine cancer; soft tissue sarcoma; squamous cell carcinoma; squamous neck cancer; stomach (gastric) cancer; supratentorial primitive neuroectodermal tumors; T-cell lymphoma; testicular cancer; throat cancer; thymic carcinoma; thymoma; thyroid cancer; transitional cell cancer; transitional cell cancer of the renal pelvis and ureter; trophoblastic tumor; ureter cancer; urethral cancer; uterine cancer; uterine sarcoma; vaginal cancer; vulvar cancer; Waldenström macroglobulinemia; or Wilm's tumor. The premalignant condition can include without limitation Barrett's Esophagus. The autoimmune disease can include without limitation one of inflammatory bowel disease (IBD), Crohn's disease (CD), ulcerative colitis (UC), pelvic inflammation, vasculitis, psoriasis, diabetes, autoimmune hepatitis, multiple sclerosis, myasthenia gravis, Type I diabetes, rheumatoid arthritis, psoriasis, systemic lupus erythematosis (SLE), Hashimoto's Thyroiditis, Grave's disease, Ankylosing Spondylitis Sjogrens Disease, CREST syndrome, Scleroderma, Rheumatic Disease, organ rejection, Primary Sclerosing Cholangitis, or sepsis. The cardiovascular disease can include without limitation one of atherosclerosis, congestive heart failure, vulnerable plaque, stroke, ischemia, high blood pressure, stenosis, vessel occlusion or a thrombotic event. The neurological disease can include without limitation one of Multiple Sclerosis (MS), Parkinson's Disease (PD), Alzheimer's Disease (AD), schizophrenia, bipolar disorder, depression, autism, Prion Disease, Pick's disease, dementia, Huntington disease (HD), Down's syndrome, cerebrovascular disease, Rasmussen's encephalitis, viral meningitis, neurospsychiatric systemic lupus erythematosus (NPSLE), amyotrophic lateral sclerosis, Creutzfeldt-Jacob disease, Gerstmann-Straussler-Scheinker disease, transmissible spongiform encephalopathy, ischemic reperfusion damage (e.g. stroke), brain trauma, microbial infection, or chronic fatigue syndrome. The pain can include without limitation one of fibromyalgia, chronic neuropathic pain, or peripheral neuropathic pain. The infectious disease can include without limitation one of a bacterial infection, viral infection, yeast infection, Whipple's Disease, Prion Disease, cirrhosis, methicillin-resistant *Staphylococcus aureus*, HIV, HCV, hepatitis, syphilis, meningitis, malaria, tuberculosis, or influenza. One of skill will appreciate that the oligonucleotide or plurality of oligonucleotides or methods of the invention can be used to assess any number of these or other related diseases and disorders.

In some embodiments of the invention, the oligonucleotide or plurality of oligonucleotides and methods of use thereof are useful for characterizing certain diseases or disease states. As desired, a pool of oligonucleotides useful for characterizing various diseases is assembled to create a master pool that can be used to probe useful for characterizing the various diseases. One of skill will also appreciate that pools of oligonucleotides useful for characterizing specific diseases or disorders can be created as well. The sequences provided herein can also be modified as desired so long as the functional aspects are still maintained (e.g., binding to various targets or ability to characterize a phenotype). For example, the oligonucleotides may comprise DNA or RNA, incorporate various non-natural nucleotides, incorporate other chemical modifications, or comprise various deletions or insertions. Such modifications may facilitate synthesis, stability, delivery, labeling, etc, or may have little to no effect in practice. In some cases, some nucleotides in an oligonucleotide may be substituted while maintaining functional aspects of the oligonucleotide. Similarly, 5' and 3' flanking regions may be substituted. In still other cases, only a portion of an oligonucleotide may be determined to direct its functionality such that other portions can be deleted or substituted. Numerous techniques to synthesize and modify nucleotides and polynucleotides are disclosed herein or are known in the art.

In an aspect, the invention provides a kit comprising a reagent for carrying out the methods of the invention provided herein. In a similar aspect, the invention contemplates use of a reagent for carrying out the methods of the invention provided herein. In embodiments, the reagent comprises an oligonucleotide or plurality of oligonucleotides. The oligonucleotide or plurality of oligonucleotides can be those provided herein. The reagent may comprise various other useful components including without limitation microRNA (miR) and messenger RNA (mRNA)), a protein-nucleic acid complex, and various combinations, fragments and/or complexes of any of these. The one or more reagent can be one or more of: a) a reagent configured to isolate a microvesicle, optionally wherein the at least one reagent configured to isolate a microvesicle comprises a binding agent to a microvesicle antigen, a column, a substrate, a filtration unit, a polymer, polyethylene glycol, PEG4000, PEG8000, a particle or a bead; b) at least one oligonucleotide configured to act as a primer or probe in order to amplify, sequence, hybridize or detect the oligonucleotide or plurality of oligonucleotides; c) a reagent configured to remove one or more abundant protein from a sample, wherein optionally the one or more abundant protein comprises at least one of albumin, immunoglobulin, fibrinogen and fibrin; d) a reagent for epitope retrieval; and e) a reagent for PHC visualization.

Detecting Watson-Crick Base Pairing with an Oligonucleotide Probe

The oligonucleotide probes provided by the invention can bind via non-Watson Crick base pairing. However, in some cases, the oligonucleotide probes provided by the invention can bind via Watson Crick base pairing. The oligonucleotide probe libraries of the invention, e.g., as described above, can query both types of binding events simultaneously. For example, some oligonucleotide probes may bind protein antigens in the classical aptamer sense, whereas other oligonucleotide probes may bind tissues, cells, microvesicles or other targets via nucleic acids associated with such targets, e.g., nucleic acid (including without limitation microRNA and mRNA) on the surface of the targets. Such surface bound nucleic acids can be associated with proteins. For example, they may comprise Argonaute-microRNA complexes. The argonaute protein can be Ago1, Ago2, Ago3 and/or Ago4.

In addition to the oligonucleotide probe library approach described herein which relies on determining a sequence of the oligonucleotides (e.g., via sequencing, hybridization or amplification), assays can also be designed to detect Watson Crick base pairing. In some embodiments, these approaches rely on Ago2-mediated cleavage wherein an Ago2-microRNA complex can be used to detected using oligonucleotide probes. For further details, see PCT/US15/62184, filed Nov. 23, 2015, which application is incorporated by reference herein in its entirety.

Tissue ADAPT

As noted herein, the invention provides methods of enriching oligonucleotide libraries against various biological samples, including tissue samples. Tissue samples may be fixed. Fixation may be used in the preparation of histological sections by which biological tissues are preserved from decay, thereby preventing autolysis or putrefaction. The principal macromolecules inside a cell are proteins and nucleic acids. Fixation terminates any ongoing biochemical reactions, and may also increase the mechanical strength or stability of the treated tissues. Thus, tissue fixation can be used to preserve cells and tissue components and to do this in such a way as to allow for the preparation of thin, stained sections. Such samples are available for many biological specimens, e.g., tumor samples. Thus, fixed tissues provide a desirable sample source for various applications of the oligonucleotide probe libraries of the invention. This process may be referred to as "tissue ADAPT."

Tissue ADAPT according to the invention has been used to provide various oligonucleotide probes. In an aspect, the invention provides an oligonucleotide comprising a region corresponding to: a) a variable sequence as described in any one of Examples 19-31; b) a variable sequence as described in any one of Tables 20-23, 25, 27, 38-40, or 45; or c) a sequence listed in any one of SEQ ID NO. 1-206506. In some embodiments, the oligonucleotide further comprises a 5' region with sequence 5'-CTAGCATGACTGCAGTACGT (SEQ ID NO. 4), a 3' region with sequence 5'-CTGTCTCT-TATACACATCTGACGCTGCCGACGA (SEQ ID NO. 5), or both. The invention further provides an oligonucleotide comprising a nucleic acid sequence or a portion thereof that is at least 50, 55, 60, 65, 70, 75, 80, 85, 90, 95, 96, 97, 98, 99 or 100 percent homologous to such oligonucleotide sequences. In a related aspect, the invention provides a plurality of oligonucleotides comprising at least 1, 2, 3, 4, 5, 6, 7, 8, 9, 10, 11, 12, 13, 14, 15, 16, 17, 18, 19, 20, 25, 30, 40, 45, 50, 55, 60, 65, 70, 75, 80, 85, 90, 95, 100, 125, 150, 175, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, or at least 100000 different oligonucleotide sequences as described above.

As described herein, many useful modifications can be made to nucleic acid molecules. In an embodiment, the oligonucleotide or the plurality of oligonucleotides of the invention comprise a DNA, RNA, 2'-O-methyl or phosphorothioate backbone, or any combination thereof. In some embodiments, the oligonucleotide or the plurality of oligonucleotides comprises at least one of DNA, RNA, PNA, LNA, UNA, and any combination thereof. The oligonucleotide or at least one member of the plurality of oligonucleotides can have at least one functional modification selected from the group consisting of DNA, RNA, biotinylation, a non-naturally occurring nucleotide, a deletion, an insertion, an addition, and a chemical modification. In some embodiments, the chemical modification comprises at least one of C18, polyethylene glycol (PEG), PEG4, PEG6, PEG8, PEG12 and digoxygenin.

The oligonucleotide or plurality of oligonucleotides of the invention can be labeled using any useful label such as described herein. For example, the oligonucleotide or plurality of oligonucleotides can be attached to a nanoparticle, liposome, gold, magnetic label, fluorescent label, light emitting particle, biotin moiety, or radioactive label.

Tissue ADAPT provides for the enrichment of oligonucleotide libraries against samples of interest. In an aspect, the invention provides a method of enriching an oligonucleotide library using multiple rounds of positive and negative selection. The method of enriching a plurality of oligonucleotides may comprise: a) performing at least one round of positive selection, wherein the positive selection comprises: i) contacting at least one sample with the plurality of oligonucleotides, wherein the at least one sample comprises tissue; and ii) recovering members of the plurality of oligonucleotides that associated with the at least one sample; b) optionally performing at least one round of negative selection, wherein the negative selection comprises: i) contacting at least one additional sample with the plurality of oligonucleotides, wherein at least one additional sample comprises tissue; ii) recovering members of the plurality of oligonucleotides that did not associate with the at least one additional sample; and c) amplifying the members of the plurality of oligonucleotides recovered in at least one or step (a)(ii) and step (b)(ii), thereby enriching the oligonucleotide library. Various alternatives of these processes are useful and described herein, such as varying the rounds of enrichment, and varying performance or positive and negative selection steps. In an embodiments, the recovered members of the plurality of oligonucleotides in step (a)(ii) are used as the input for the next iteration of step (a)(i). In an embodiment, the recovered members of the plurality of oligonucleotides in step (b)(ii) are used as the input for the next iteration of step (a)(i). The unenriched oligonucleotide library may possess great diversity. For example, the unenriched oligonucleotide library may comprise at least 2, 3, 4, 5, 6, 7, 8, 9, 10, 11, 12, 13, 14, 15, 16, 17, 18, 19, 20, 25, 30, 40, 45, 50, 55, 60, 65, 70, 75, 80, 85, 90, 95, 100, 125, 150, 175, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, $10^6$, $10^7$, $10^8$, $10^9$, $10^{10}$, $10^{11}$, $10^{12}$, $10^{13}$, $10^{14}$, $10^{15}$, $10^{16}$, $10^{17}$, or at least $10^{18}$ different oligonucleotide sequences. In an embodiment, the unenriched oligonucleotide library comprises the naïve F-Trin library as described herein.

In embodiments of the enrichment methods of the invention, the at least one sample and/or at least one additional sample comprise tissue. As desired, such tissue may be fixed using methods described herein or known in the art. The fixed tissue may be archived. The fixed tissue may comprise formalin fixed paraffin embedded (FFPE) tissue. In embodiment, the FFPE tissue comprises at least one of a fixed tissue, unstained slide, bone marrow core or clot, biopsy sample, surgical sample, core needle biopsy, malignant fluid, and fine needle aspirate (FNA). The FFPE tissue can be fixed on a substrate. For example, the substrate can be a glass slide, membrane, or any other useful material.

In some embodiment, the at least one sample and/or the at least one additional sample are fixed on different substrates. As a non-limiting example, the at least one sample is fixed on one glass slide whereas the at least one additional sample is fixed on a different glass slide. As desired, such slides may be from different patients, different tumors, a same tumor at different time points, multiple slices of the same tumor, etc. Alternately, the at least one sample and/or the at least one additional sample is fixed on a single substrate. As a non-limiting example, the at least one sample and at least one additional sample are fixed on a same glass slide, such as a tumor sample and normal adjacent tissue to the tumor. In some embodiments, the at least one sample and/or the at least one additional sample are lysed (see, e.g., Example 29), scraped from a substrate (see, e.g., Example 30), or subjected to microdissection (see, e.g., Example 31). Lysed samples can be arrayed on a substrate. The invention contemplates any useful substrate. In some embodiments, the substrate comprises a membrane. For example, the membrane can be a nitrocellulose membrane.

In various embodiments of the enrichment methods of the invention, the at least one sample and the at least one additional sample differ in a phenotype of interest. The at least one sample and the at least one additional sample can be from different sections of a same substrate. As a non-limiting example, the samples may comprise cancer tissue and normal adjacent tissue from a fixed tissue sample. In such cases, the at least one sample and the at least one additional sample may be scraped or microdissected from the same substrate to facilitate enrichment.

The oligonucleotide library can be enriched for analysis of any desired phenotype. In embodiments, the phenotype comprises a tissue, anatomical origin, medical condition, disease, disorder, or any combination thereof. For example, the tissue can be muscle, epithelial, connective and nervous tissue, or any combination thereof. For example, the anatomical origin can be the stomach, liver, small intestine, large intestine, rectum, anus, lungs, nose, bronchi, kidneys, urinary bladder, urethra, pituitary gland, pineal gland, adrenal gland, thyroid, pancreas, parathyroid, prostate, heart, blood vessels, lymph node, bone marrow, thymus, spleen, skin, tongue, nose, eyes, ears, teeth, uterus, vagina, testis, penis, ovaries, breast, mammary glands, brain, spinal cord, nerve, bone, ligament, tendon, or any combination thereof. As described further below, the phenotype can be related to at least one of diagnosis, prognosis, theranosis, medical condition, disease or disorder.

In various embodiments of the enrichment methods of the invention, the method further comprises determining a target of the enriched members of the oligonucleotide library. Techniques for such determining are provided herein. See, e.g., Examples 9-10, 17 and 19.

Tissue ADAPT further comprises analysis of biological samples. In an aspect, the invention provides a method of characterizing a phenotype in a sample comprising: a) contacting the sample with at least one oligonucleotide or plurality of oligonucleotides; and b) identifying a presence or level of a complex formed between the at least one oligonucleotide or plurality of oligonucleotides and the sample, wherein the presence or level is used to characterize the phenotype. In a related aspect, the invention provides a method of visualizing a sample comprising: a) contacting the sample with at least one oligonucleotide or plurality of oligonucleotides; b) removing the at least one oligonucleotide or members of the plurality of oligonucleotides that do not bind the sample; and c) visualizing the at least one oligonucleotide or plurality of oligonucleotides that bound to the sample. The visualization can be used to characterize a phenotype.

The sample to be characterized can be any useful sample, including without limitation a tissue sample, bodily fluid, cell, cell culture, microvesicle, or any combination thereof. In some embodiments, the tissue sample comprises fixed tissue. The tissue may be fixed using any useful technique for fixation known in the art. Examples of fixation methods include heat fixation, immersion, perfusion, chemical fixation, cross-linked (for example, with an aldehyde such as formaldehyde or glutaraldehyde), precipitation (e.g., using an alcohol such as methanol, ethanol and acetone, and acetic acid), oxidation (e.g., using osmium tetroxide, potassium dichromate, chromic acid, and potassium permanganate), mercurials, picrates, Bouin solution, hepes-glutamic acid buffer-mediated organic solvent protection effect (HOPE), and freezing. In preferred embodiments, the fixed tissue is formalin fixed paraffin embedded (FFPE) tissue. In various embodiments, the FFPE sample comprises at least one of a fixed tissue, unstained slide, bone marrow core or clot, biopsy sample, surgical sample, core needle biopsy, malignant fluid, and fine needle aspirate (FNA).

Any useful technique for identifying a presence or level can be used for applications of tissue ADAPT, including without limitation nucleic acid sequencing, amplification, hybridization, gel electrophoresis, chromatography, or visualization. In some embodiments, the hybridization comprises contacting the sample with at least one labeled probe that is configured to hybridize with at least one oligonucleotide or plurality of oligonucleotides. The at least one labeled probe can be directly or indirectly attached to a label. The label can be, e.g., a fluorescent, radioactive or magnetic label. An indirect label can be, e.g., biotin or digoxigenin. See, e.g., Example 28. In some embodiments, the sequencing comprises next generation sequencing, dye termination sequencing, and/or pyrosequencing of the at least one oligonucleotide or plurality of oligonucleotides. The visualization may be that of a signal linked directly or indirectly to the at least one oligonucleotide or plurality of oligonucleotides. The signal can be any useful signal, e.g., a fluorescent signal or an enzymatic signal. In some embodiments, the enzymatic signal is produced by at least one of a luciferase, firefly luciferase, bacterial luciferase, luciferin, malate dehydrogenase, urease, peroxidase, horseradish peroxidase (HRP), alkaline phosphatase (AP), β-galactosidase, glucoamylase, lysozyme, a saccharide oxidase, glucose oxidase, galactose oxidase, glucose-6-phosphate dehydrogenase, a heterocyclic oxidase, uricase, xanthine oxidase, lactoperoxidase, and microperoxidase. Visualization may comprise use of light microscopy or fluorescent microscopy. Various examples of visualization using polyligand histochemistry (PHC) are provided herein. See Examples 19-31.

In the methods of the invention directed to characterizing or visualizing a sample, the target of at least one of the at least one oligonucleotide or plurality of oligonucleotides may be known. For example, an oligonucleotide may bind a known protein target. In some embodiments, the target of at least one the at least one oligonucleotide or plurality of oligonucleotides is unknown. For example, the at least one oligonucleotide or plurality of oligonucleotides may themselves provide a biosignature or other useful result that does not necessarily require knowledge of the antigens bound by some or all of the oligonucleotides. In some embodiments, the targets of a portion of the oligonucleotides are known whereas the targets of another portion of the oligonucleotides have not been identified.

In the methods of characterizing or visualizing a sample, the at least one oligonucleotide or plurality of oligonucleotides can be as provided herein. The at least one oligonucleotide or plurality of oligonucleotides may have been determined using the enrichment methods of the invention provided herein, e.g., enrichment via tissue ADAPT. For example, the at least one oligonucleotide or plurality of oligonucleotides may comprise nucleic acids may have a sequence or a portion thereof that is at least 50, 55, 60, 65, 70, 75, 80, 85, 90, 95, 96, 97, 98, 99 or 100 percent homologous to an oligonucleotide sequence according to at least one of SEQ ID NOs. 1-206506.

For example, the at least one oligonucleotide or plurality of oligonucleotides may comprise nucleic acids may have a sequence or a portion thereof that is at least 50, 55, 60, 65, 70, 75, 80, 85, 90, 95, 96, 97, 98, 99 or 100 percent homologous to an oligonucleotide sequence according to at least 1, 2, 3, 4, 5, 6, 7, 8, 9, 10, 12, 15, 20 or all of SEQ ID NOs. 2922-2926, 2929-2947 and 2950-2952. In such cases, the phenotype may be, e.g., lung cancer or prostate cancer. See Example 14.

In another example, the at least one oligonucleotide or plurality of oligonucleotides may comprise nucleic acids having a sequence or a portion thereof that is at least 50, 55, 60, 65, 70, 75, 80, 85, 90, 95, 96, 97, 98, 99 or 100 percent homologous to an oligonucleotide sequence according to at least 1, 2, 3, 4, 5, 6, 7, 8, 9, 10, 12, 15, 20 or all of SEQ ID NOs. 2953-2961 and 2971-2979. In such cases, the phenotype may be, e.g., prostate cancer. See Example 17.

In yet another example, the at least one oligonucleotide or plurality of oligonucleotides may comprise nucleic acids having a sequence or a portion thereof that is at least 50, 55, 60, 65, 70, 75, 80, 85, 90, 95, 96, 97, 98, 99 or 100 percent homologous to an oligonucleotide sequence according to at least 1, 2, 3, 4, 5, 6, 7, 8, 9, 10, 12, 15, 20, 25, 30, 35, 40, 50 or all of SEQ ID NOs. 3039-3061. In such cases, the phenotype may be, e.g., HER2 status (+/−). See Example 19.

In still another example, the at least one oligonucleotide or plurality of oligonucleotides may comprise nucleic acids having a sequence or a portion thereof that is at least 50, 55, 60, 65, 70, 75, 80, 85, 90, 95, 96, 97, 98, 99 or 100 percent homologous to an oligonucleotide sequence according to at least 1, 2, 3, 4, 5, 6, 7, 8, 9, 10, 12, 15, 20, 25, 30, 35, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 150,000 or all of SEQ ID NOs. 3062-103061 and 103062-203061. In such cases, the phenotype may be, e.g., response to anti-HER2 therapy, wherein optionally the anti-HER2 therapy comprises trastuzumab. See Examples 20-22.

In an example, the at least one oligonucleotide or plurality of oligonucleotides may comprise nucleic acids having a sequence or a portion thereof that is at least 50, 55, 60, 65, 70, 75, 80, 85, 90, 95, 96, 97, 98, 99 or 100 percent homologous to an oligonucleotide sequence according to at least 1, 2, 3, 4, 5, 6, 7, 8, 9, 10, 12, 15, 20, 25, 30, 35, 40, 50, 60, 70, 80, 90, 100, 200, 300, 400, 500, 600, 700, 800, 900, 1000, 2000, 3000, 4000 or all of SEQ ID NOs. 203064-203067 and 203076-206478. In such cases, the phenotype may be, e.g., response to at least one of FOLFOX and bevacizumab. See Example 24.

In another example, the at least one oligonucleotide or plurality of oligonucleotides may comprise nucleic acids having a sequence or a portion thereof that is at least 50, 55, 60, 65, 70, 75, 80, 85, 90, 95, 96, 97, 98, 99 or 100 percent homologous to an oligonucleotide sequence according to at least 1, 2, 3, 4, 5, 6, 7, 8, 9, 10, 12, 15 or all of SEQ ID NOs. 206491-206506. In such cases, the phenotype may be, e.g., a tissue identity, including without limitation whether the tissue comprises breast, colon, kidney, lung or pancreatic tissue. See Example 29.

In the methods of the invention, including enriching an oligonucleotide library, characterizing a sample or visualizing a sample, the phenotype can be a biomarker status. In some embodiments, the biomarker is selected from Table 4 or FIGS. 26A-B. In some embodiments, the biomarker status comprises at least one of HER2 positive, HER2 negative, EGFR positive, EGFR negative, TUBB3 positive, or TUBB3 negative. See, e.g., Examples 19-23, 24, 26. In some embodiments, the biomarker status comprises expression, copy number, mutation, insertion, deletion or other alteration of at least one of ALK, AR, ER, ERCC1, Her2/Neu, MGMT, MLH1, MSH2, MSH6, PD-1, PD-L1, PD-L1 (22c3), PMS2, PR, PTEN, RRM1, TLE3, TOP2A, TOPO1, TrkA, TrkB, TrkC, TS, and TUBB3. In various embodiments, the biomarker status comprises the presence or absence of at least one of EGFR vIII or MET Exon 14 Skipping. In embodiments, the biomarker status comprises expression, copy number, fusion, mutation, insertion, deletion or other alteration of at least one of ALK, BRAF, NTRK1, NTRK2, NTRK3, RET, ROS1, and RSPO3. In embodiments, the biomarker status comprises expression, copy number, fusion, mutation, insertion, deletion or other alteration of at least one of ABL2, ACSL3, ACSL6, AFF1, AFF3, AFF4, AKAP9, AKT2, AKT3, ALDH2, ALK, APC, ARFRP1, ARHGAP26, ARHGEF12, ARID1A, ARID2, ARNT, ASPSCR1, ASXL1, ATF1, ATIC, ATM, ATP1A1, ATR, AURKA, AURKB, AXIN1, AXL, BAP1, BARD1, BCL10, BCL11A, BCL2L11, BCL3, BCL6, BCL7A, BCL9, BCR, BIRC3, BLM, BMPR1A, BRAF, BRCA1, BRCA2, BRIP1, BUB1B, C11orf30 (EMSY), C2orf44, CACNA1D, CALR, CAMTA1, CANT1, CARD11, CARS, CASC5, CASP8, CBFA2T3, CBFB, CBL, CBLB, CCDC6, CCNB1IP1, CCND1, CCND2, CCND3, CCNE1, CD274 (PDL1), CD74, CD79A, CDC73, CDH11, CDK4, CDK6, CDK8, CDKN1B, CDKN2A, CDX2, CHEK1, CHEK2, CHIC2, CHN1, CIC, CIITA, CLP1, CLTC, CLTCL1, CNBP, CNTRL, COPB1, CREB1, CREB3L1, CREB3L2, CREBBP, CRKL, CRTC1, CRTC3, CSF1R, CSF3R, CTCF, CTLA4, CTNNA1, CTNNB1, CYLD, CYP2D6, DAXX, DDR2, DDX10, DDX5, DDX6, DEK, DICER1, DOT1L, EBF1, ECT2L, EGFR, ELK4, ELL, EML4, EP300, EPHA3, EPHA5, EPHB1, EPS15, ERBB2 (HER2), ERBB3 (HER3), ERBB4 (HER4), ERC1, ERCC2, ERCC3, ERCC4, ERCC5, ERG, ESR1, ETV1, ETV5, ETV6, EWSR1, EXT1, EXT2, EZH2, EZR, FANCA, FANCC, FANCD2, FANCE, FANCG, FANCL, FAS, FBXO11, FBXW7, FCRL4, FGF10, FGF14, FGF19, FGF23, FGF3, FGF4, FGF6, FGFR1, FGFR1OP, FGFR2, FGFR3, FGFR4, FH, FHIT, FIP1L1, FLCN, FLI1, FLT1, FLT3, FLT4, FNBP1, FOXA1, FOXO1, FOXP1, FUBP1, FUS, GAS7, GATA3, GID4 (C17orf39), GMPS, GNA13, GNAQ, GNAS, GOLGA5, GOPC, GPHN, GPR124, GRIN2A, GSK3B, H3F3A, H3F3B, HERPUD1, HGF, HIP1, HMGA1, HMGA2, HNRNPA2B1, HOOK3, HSP90AA1, HSP90AB1, IDH1, IDH2, IGF1R, IKZF1, IL2, IL21R, IL6ST, IL7R, IRF4, ITK, JAK1, JAK2, JAK3, JAZF1, KDM5A, KDR (VEGFR2), KEAP1, KIAA1549, KIF5B, KIT, KLHL6, KMT2A (MLL), KMT2C (MLL3), KMT2D (MLL2), KRAS, KTN1, LCK, LCP1, LGR5, LHFP, LIFR, LPP, LRIG3, LRP1B, LYL1, MAF, MALT1, MAML2, MAP2K1, MAP2K2, MAP2K4, MAP3K1, MCL1, MDM2, MDM4, MDS2, MEF2B, MEN1, MET (cMET), MITF, MLF1, MLH1 (NGS), MLLT1, MLLT10, MLLT3, MLLT4, MLLT6, MNX1, MRE11A, MSH2 (NGS), MSH6 (NGS), MSI2, MTOR, MYB, MYC, MYCN, MYD88, MYH11, MYH9, NACA, NCKIPSD, NCOA1, NCOA2, NCOA4, NF1, NF2, NFE2L2, NFIB, NFKB2, NFKBIA, NIN, NOTCH2, NPM1, NR4A3, NSD1, NT5C2, NTRK1, NTRK2, NTRK3, NUP214, NUP93, NUP98, NUTM1, PALB2, PAX3, PAX5, PAX7, PBRM1, PBX1, PCM1, PCSK7, PDCD1 (PD1), PDCD1LG2 (PDL2), PDGFB, PDGFRA, PDGFRB, PDK1, PER1, PICALM, PIK3CA, PIK3R1, PIK3R2, PIM1, PML, PMS2 (NGS), POLE, POT1, POU2AF1, PPARG, PRCC, PRDM1, PRDM16, PRKAR1A, PRRX1, PSIP1, PTCH1, PTEN (NGS), PTPN11, PTPRC, RABEP1, RAC1, RAD50, RAD51, RAD51B, RAF1, RALGDS, RANBP17, RAP1GDS1, RARA, RB1, RBM15, REL, RET, RICTOR, RMI2, RNF43, ROS1, RPL22, RPL5, RPN1, RPTOR, RUNX1, RUNX1T1, SBDS, SDC4, SDHAF2, SDHB, SDHC, SDHD, SEPT9, SET, SETBP1, SETD2, SF3B1, SH2B3, SH3GL1, SLC34A2, SMAD2, SMAD4, SMARCB1, SMARCE1, SMO, SNX29, SOX10, SPECC1, SPEN, SRGAP3, SRSF2, SRSF3, SS18, SS18L1, STAT3, STAT4, STAT5B, STIL, STK11, SUFU, SUZ12, SYK, TAF15, TCF12, TCF3, TCF7L2, TET1, TET2, TFEB, TFG, TFRC, TGFBR2, TLX1, TNFAIP3, TNFRSF14, TNFRSF17, TOP1, TP53, TPM3, TPM4, TPR, TRAF7, TRIM26, TRIM27, TRIM33, TRIP11, TRRAP, TSC1, TSC2, TSHR, TTL, U2AF1, USP6, VEGFA, VEGFB, VTI1A, WHSC1, WHSC1L1, WIF1, WISP3, WRN, WT1, WWTR1, XPA, XPC, XPO1, YWHAE, ZMYM2, ZNF217, ZNF331, ZNF384, ZNF521, and ZNF703. The biomarker status may comprise expression, copy number, fusion, mutation, insertion, deletion or other alteration of at least one of ABI1, ABL1, ACKR3, AKT1, AMER1 (FAM123B), AR, ARAF, ATP2B3, ATRX, BCL11B, BCL2, BCL2L2, BCOR, BCORL1, BRD3, BRD4, BTG1, BTK, C15orf65, CBLC, CD79B, CDH1, CDK12, CDKN2B, CDKN2C, CEBPA, CHCHD7, CNOT3, COL1A1, COX6C, CRLF2, DDB2, DDIT3, DNM2, DNMT3A, EIF4A2, ELF4, ELN, ERCC1 (NGS), ETV4, FAM46C, FANCF, FEV, FOXL2, FOXO3, FOXO4, FSTL3, GATA1, GATA2, GNA11, GPC3, HEY1, HIST1H3B, HIST1H4I, HLF, HMGN2P46, HNF1A, HOXA11, HOXA13, HOXA9, HOXC11, HOXC13, HOXD11, HOXD13, HRAS, IKBKE, INHBA, IRS2, JUN, KAT6A (MYST3), KAT6B, KCNJ5, KDM5C, KDM6A, KDSR, KLF4, KLK2, LASP1, LMO1, LMO2, MAFB, MAX, MECOM, MED12, MKL1, MLLT11, MN1, MPL, MSN, MTCP1, MUC1, MUTYH, MYCL (MYCL1), NBN, NDRG1, NKX2-1, NONO, NOTCH1, NRAS, NUMA1, NUTM2B, OLIG2, OMD, P2RY8, PAFAH1B2, PAK3, PATZ1, PAX8, PDE4DIP, PHF6, PHOX2B, PIK3CG, PLAG1, PMS1, POU5F1, PPP2R1A, PRF1, PRKDC, RAD21, RECQL4, RHOH, RNF213, RPL10, SEPT5, SEPT6, SFPQ, SLC45A3, SMARCA4, SOCS1, SOX2, SPOP, SRC, SSX1, STAG2, TAL1, TAL2, TBL1XR1, TCEA1, TCL1A, TERT, TFE3, TFPT, THRAP3, TLX3, TMPRSS2, UBR5, VHL, WAS, ZBTB16, and ZRSR2. The biomarker status can be for a biomarker in any one of PCT/US2007/69286, filed May 18, 2007; PCT/US2009/60630, filed Oct. 14, 2009; PCT/2010/000407, filed Feb. 11, 2010; PCT/US12/41393, filed Jun. 7, 2012; PCT/US2013/073184, filed Dec. 4, 2013; PCT/US2010/54366, filed Oct. 27, 2010; PCT/US11/67527, filed Dec. 28, 2011; PCT/US15/13618, filed Jan. 29, 2015; and PCT/US16/20657, filed Mar. 3, 2016; each of which applications is incorporated herein by reference in its entirety. Examples of additional biomarkers that can be incorporated into the methods and compositions of the invention include without limitation those disclosed in International Patent Application Nos. PCT/US2009/62880, filed Oct. 30, 2009; PCT/US2009/006095, filed Nov. 12, 2009; PCT/US2011/26750, filed Mar. 1, 2011; PCT/US2011/031479, filed Apr. 6, 2011; PCT/US11/48327, filed Aug. 18, 2011; PCT/US2008/71235, filed Jul. 25, 2008; PCT/US10/58461, filed Nov. 30, 2010; PCT/US2011/21160, filed Jan. 13, 2011; PCT/US2013/030302, filed Mar. 11, 2013; PCT/US12/25741, filed Feb. 17, 2012; PCT/2008/76109, filed Sep. 12, 2008; PCT/US12/42519, filed Jun. 14, 2012; PCT/US12/50030, filed Aug. 8, 2012; PCT/US12/49615, filed Aug. 3, 2012; PCT/US12/41387, filed Jun. 7, 2012; PCT/US2013/072019, filed Nov. 26, 2013; PCT/US2014/039858, filed May 28, 2013; PCT/IB2013/003092, filed Oct. 23, 2013; PCT/US13/76611, filed Dec. 19, 2013; PCT/US14/53306, filed Aug. 28, 2014; and PCT/US15/62184, filed Nov. 23, 2015; PCT/US16/40157, filed Jun. 29, 2016; PCT/US16/44595, filed Jul. 28, 2016; and PCT/US16/21632, filed Mar. 9, 2016; each of which applications is incorporated herein by reference in its entirety. The methods of the invention can be used to enrich oligonucleotide libraries and analyze samples given any desired biomarker status for which appropriate samples are available.

In the methods of the invention, including enriching an oligonucleotide library, characterizing a sample or visualizing a sample, the phenotype can be a phenotype comprises a disease or disorder. The methods can be employed to assist in providing a diagnosis, prognosis and/or theranosis for the disease or disorder. For example, the enriching may be performed using sample such that the enriched library can be used to assist in providing a diagnosis, prognosis and/or theranosis for the disease or disorder. Similarly, the characterizing may comprise assisting in providing a diagnosis, prognosis and/or theranosis for the disease or disorder. The visualization may also comprise assisting in providing a diagnosis, prognosis and/or theranosis for the disease or disorder. In some embodiments, the theranosis comprises predicting a treatment efficacy or lack thereof, classifying a patient as a responder or non-responder to treatment, or monitoring a treatment efficacy. The theranosis can be directed to any appropriate treatment, e.g., the treatment may comprise at least one of chemotherapy, immunotherapy, targeted cancer therapy, a monoclonal antibody, an anti-HER2 antibody, trastuzumab, an anti-VEGF antibody, bevacizumab, and/or platinum/taxane therapy. In some embodiments, the treatment comprises at least one of afatinib, afatinib+cetuximab, alectinib, aspirin, atezolizumab, bicalutamide, cabozantinib, capecitabine, carboplatin, ceritinib, cetuximab, cisplatin, crizotinib, dabrafenib, dacarbazine, doxorubicin, enzalutamide, epirubicin, erlotinib, everolimus, exemestane+everolimus, fluorouracil, fulvestrant, gefitinib, gemcitabine, hormone therapies, irinotecan, lapatinib, liposomal-doxorubicin, matinib, mitomycin-c, nab-paclitaxel, nivolumab, olaparib, osimertinib, oxaliplatin, palbociclib combination therapy, paclitaxel, palbociclib, panitumumab, pembrolizumab, pemetrexed, pertuzumab, sunitinib, T-DM1, temozolomide docetaxel, temsirolimus, topotecan, trametinib, trastuzumab, vandetanib, and vemurafenib. The hormone therapy can be one or more of tamoxifen, toremifene, fulvestrant, letrozole, anastrozole, exemestane, megestrol acetate, leuprolide, goserelin, bicalutamide, flutamide, abiraterone, enzalutamide, triptorelin, abarelix, and degarelix.

The theranosis can be for a therapy listed in FIGS. 26A-B, or in any one of PCT/US2007/69286, filed May 18, 2007; PCT/US2009/60630, filed Oct. 14, 2009; PCT/2010/000407, filed Feb. 11, 2010; PCT/US12/41393, filed Jun. 7, 2012; PCT/US2013/073184, filed Dec. 4, 2013; PCT/US2010/54366, filed Oct. 27, 2010; PCT/US11/67527, filed Dec. 28, 2011; PCT/US15/13618, filed Jan. 29, 2015; and PCT/US16/20657, filed Mar. 3, 2016; each of which applications is incorporated herein by reference in its entirety. The likelihood of benefit or lack of benefit of these therapies for treating various cancers can be related to a biomarker status. For example, anti-HER2 treatments may be of most benefit for patients whose tumors express HER2, and vice versa. Using appropriate samples for enrichment (e.g., known responders or non-responders), tissue ADAPT may be used to provide improved theranosis as compared to conventional companion diagnostics. See, e.g., Examples 20-22; see also Examples 24, 27.

In the methods of the invention directed to characterizing a sample, the characterizing may comprise comparing the presence or level to a reference. In some embodiments, the reference comprises a presence or level determined in a sample from an individual without a disease or disorder, or from an individual with a different state of a disease or disorder. The presence or level can be that of a visual level, such as an IHC score, determined by the visualizing. As a non-limiting example, the comparison to the reference of at least one oligonucleotide or plurality of oligonucleotides provided by the invention indicates that the sample comprises a cancer sample or a non-cancer/normal sample.

In some embodiments of the methods of the invention, one or more sample comprises a bodily fluid. The bodily fluid can be any useful bodily fluid, including without limitation peripheral blood, sera, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, female ejaculate, sweat, fecal matter, hair oil, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, blastocyl cavity fluid, or umbilical cord blood.

In the methods of the invention, including characterizing a sample or visualizing a sample, the sample can be from a subject suspected of having or being predisposed to a medical condition, disease, or disorder.

In the methods of the invention, including enriching an oligonucleotide library, characterizing a sample or visualizing a sample, the medical condition, the disease or disorder may be a cancer, a premalignant condition, an inflammatory disease, an immune disease, an autoimmune disease or disorder, a cardiovascular disease or disorder, neurological disease or disorder, infectious disease or pain. In some embodiments, the cancer comprises an acute lymphoblastic leukemia; acute myeloid leukemia; adrenocortical carcinoma; AIDS-related cancers; AIDS-related lymphoma; anal cancer; appendix cancer; astrocytomas; atypical teratoid/rhabdoid tumor; basal cell carcinoma; bladder cancer; brain stem glioma; brain tumor (including brain stem glioma, central nervous system atypical teratoid/rhabdoid tumor, central nervous system embryonal tumors, astrocytomas, craniopharyngioma, ependymoblastoma, ependymoma, medulloblastoma, medulloepithelioma, pineal parenchymal tumors of intermediate differentiation, supratentorial primitive neuroectodermal tumors and pineoblastoma); breast cancer; bronchial tumors; Burkitt lymphoma; cancer of unknown primary site; carcinoid tumor; carcinoma of unknown primary site; central nervous system atypical teratoid/rhabdoid tumor; central nervous system embryonal tumors; cervical cancer; childhood cancers; chordoma; chronic lymphocytic leukemia; chronic myelogenous leukemia; chronic myeloproliferative disorders; colon cancer; colorectal cancer; craniopharyngioma; cutaneous T-cell lymphoma; endocrine pancreas islet cell tumors; endometrial cancer; ependymoblastoma; ependymoma; esophageal cancer; esthesioneuroblastoma; Ewing sarcoma; extracranial germ cell tumor; extragonadal germ cell tumor; extrahepatic bile duct cancer; gallbladder cancer; gastric (stomach) cancer; gastrointestinal carcinoid tumor; gastrointestinal stromal cell tumor; gastrointestinal stromal tumor (GIST); gestational trophoblastic tumor; glioma; hairy cell leukemia; head and neck cancer; heart cancer; Hodgkin lymphoma; hypopharyngeal cancer; intraocular melanoma; islet cell tumors; Kaposi sarcoma; kidney cancer; Langerhans cell histiocytosis; laryngeal cancer; lip cancer; liver cancer; lung cancer; malignant fibrous histiocytoma bone cancer; medulloblastoma; medulloepithelioma; melanoma; Merkel cell carcinoma; Merkel cell skin carcinoma; mesothelioma; metastatic squamous neck cancer with occult primary; mouth cancer; multiple endocrine neoplasia syndromes; multiple myeloma; multiple myeloma/plasma cell neoplasm; mycosis fungoides; myelodysplastic syndromes; myeloproliferative neoplasms; nasal cavity cancer; nasopharyngeal cancer; neuroblastoma; Non-Hodgkin lymphoma; nonmelanoma skin cancer; non-small cell lung cancer; oral cancer; oral cavity cancer; oropharyngeal cancer; osteosarcoma; other brain and spinal cord tumors; ovarian cancer; ovarian epithelial cancer; ovarian germ cell tumor; ovarian low malignant potential tumor; pancreatic cancer; papillomatosis; paranasal sinus cancer; parathyroid cancer; pelvic cancer; penile cancer; pharyngeal cancer; pineal parenchymal tumors of intermediate differentiation; pineoblastoma; pituitary tumor; plasma cell neoplasm/multiple myeloma; pleuropulmonary blastoma; primary central nervous system (CNS) lymphoma; primary hepatocellular liver cancer; prostate cancer; rectal cancer; renal cancer; renal cell (kidney) cancer; renal cell cancer; respiratory tract cancer; retinoblastoma; rhabdomyosarcoma; salivary gland cancer; Sézary syndrome; small cell lung cancer; small intestine cancer; soft tissue sarcoma; squamous cell carcinoma; squamous neck cancer; stomach (gastric) cancer; supratentorial primitive neuroectodermal tumors; T-cell lymphoma; testicular cancer; throat cancer; thymic carcinoma; thymoma; thyroid cancer; transitional cell cancer; transitional cell cancer of the renal pelvis and ureter; trophoblastic tumor; ureter cancer; urethral cancer; uterine cancer; uterine sarcoma; vaginal cancer; vulvar cancer; Waldenström macroglobulinemia; or Wilm's tumor. In some embodiments, the premalignant condition comprises Barrett's Esophagus. In some embodiments, the autoimmune disease comprises inflammatory bowel disease (IBD), Crohn's disease (CD), ulcerative colitis (UC), pelvic inflammation, vasculitis, psoriasis, diabetes, autoimmune hepatitis, multiple sclerosis, myasthenia gravis, Type I diabetes, rheumatoid arthritis, psoriasis, systemic lupus erythematosis (SLE), Hashimoto's Thyroiditis, Grave's disease, Ankylosing Spondylitis Sjogrens Disease, CREST syndrome, Scleroderma, Rheumatic Disease, organ rejection, Primary Sclerosing Cholangitis, or sepsis. In some embodiments, the cardiovascular disease comprises atherosclerosis, congestive heart failure, vulnerable plaque, stroke, ischemia, high blood pressure, stenosis, vessel occlusion or a thrombotic event. In some embodiments, the neurological disease comprises Multiple Sclerosis (MS), Parkinson's Disease (PD), Alzheimer's Disease (AD), schizophrenia, bipolar disorder, depression, autism, Prion Disease, Pick's disease, dementia, Huntington disease (HD), Down's syndrome, cerebrovascular disease, Rasmussen's encephalitis, viral meningitis, neurospsychiatric systemic lupus erythematosus (NPSLE), amyotrophic lateral sclerosis, Creutzfeldt-Jacob disease, Gerstmann-Straussler-Scheinker disease, transmissible spongiform encephalopathy, ischemic reperfusion damage (e.g. stroke), brain trauma, microbial infection, or chronic fatigue syndrome. In some embodiments, the pain comprises fibromyalgia, chronic neuropathic pain, or peripheral neuropathic pain. In some embodiments, the infectious disease comprises a bacterial infection, viral infection, yeast infection, Whipple's Disease, Prion Disease, cirrhosis, methicillin-resistant *Staphylococcus aureus*, HIV, HCV, hepatitis, syphilis, meningitis, malaria, tuberculosis, influenza.

In an aspect, the invention provides a kit comprising at least one reagent for carrying out the methods provided by the invention, including enriching an oligonucleotide library, characterizing a sample or visualizing a sample. In a related aspect, the invention provides use of at least one reagent for carrying out the methods provided by the invention, including enriching an oligonucleotide library, characterizing a sample or visualizing a sample. In some embodiments, the at least one reagent comprises an oligonucleotide or a plurality of oligonucleotides provided herein. Additional useful reagents are also provided herein. See, e.g., the protocols provided in the Examples.

The at least one oligonucleotide or plurality of oligonucleotides provided by tissue ADAPT can be used for various purposes. As described above, such oligonucleotides can be used to characterize and/or visualize a sample. As the oligonucleotides are selected to associate with tissues of interest, such associations can also be used for other purposes. In an aspect, the invention provides a method of imaging at least one cell or tissue, comprising contacting the at least one cell or tissue with at least one oligonucleotide or plurality of oligonucleotides provided herein, and detecting the at least one oligonucleotide or the plurality of oligonucleotides in contact with at least one cell or tissue. In a non-limiting example, such method can be used for medical imaging of a tumor or tissue in a patient.

For example, the at least one oligonucleotide or plurality of oligonucleotides may comprise nucleic acids may have a sequence or a portion thereof that is at least 50, 55, 60, 65, 70, 75, 80, 85, 90, 95, 96, 97, 98, 99 or 100 percent homologous to an oligonucleotide sequence according to at least 1, 2, 3, 4, 5, 6, 7, 8, 9, 10, 12, 15, 20 or all of SEQ ID NOs. 2922-2926, 2929-2947 and 2950-2952. In such cases, the imaging may be, e.g., directed to lung or prostate tissue. See Example 14.

In another example, the at least one oligonucleotide or plurality of oligonucleotides may comprise nucleic acids having a sequence or a portion thereof that is at least 50, 55, 60, 65, 70, 75, 80, 85, 90, 95, 96, 97, 98, 99 or 100 percent homologous to an oligonucleotide sequence according to at least 1, 2, 3, 4, 5, 6, 7, 8, 9, 10, 12, 15, 20 or all of SEQ ID NOs. 2953-2961 and 2971-2979. In such cases, the phenotype may be, e.g., prostate cancer. See Example 17.

In yet another example, the at least one oligonucleotide or plurality of oligonucleotides may comprise nucleic acids having a sequence or a portion thereof that is at least 50, 55, 60, 65, 70, 75, 80, 85, 90, 95, 96, 97, 98, 99 or 100 percent homologous to an oligonucleotide sequence according to at least 1, 2, 3, 4, 5, 6, 7, 8, 9, 10, 12, 15, 20, 25, 30, 35, 40, 50 or all of SEQ ID NOs. 3039-3061. In such cases, the imaging may be, e.g., directed to HER2 status of a cell or tissue. See Example 19.

In still another example, the at least one oligonucleotide or plurality of oligonucleotides may comprise nucleic acids having a sequence or a portion thereof that is at least 50, 55, 60, 65, 70, 75, 80, 85, 90, 95, 96, 97, 98, 99 or 100 percent homologous to an oligonucleotide sequence according to at least 1, 2, 3, 4, 5, 6, 7, 8, 9, 10, 12, 15, 20, 25, 30, 35, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 150,000 or all of SEQ ID NOs. 3062-103061 and 103062-203061. In such cases, the imaging may be, e.g., directed to a HER2 status of a cell or tissue. See Examples 20-22.

In an example, the at least one oligonucleotide or plurality of oligonucleotides may comprise nucleic acids having a sequence or a portion thereof that is at least 50, 55, 60, 65, 70, 75, 80, 85, 90, 95, 96, 97, 98, 99 or 100 percent homologous to an oligonucleotide sequence according to at least 1, 2, 3, 4, 5, 6, 7, 8, 9, 10, 12, 15, 20, 25, 30, 35, 40, 50, 60, 70, 80, 90, 100, 200, 300, 400, 500, 600, 700, 800, 900, 1000, 2000, 3000, 4000 or all of SEQ ID NOs. 203064-203067 and 203076-206478. In such cases, the imaging may be, e.g., directed to colorectal cells or tissue. See Example 24.

In another example, the at least one oligonucleotide or plurality of oligonucleotides may comprise nucleic acids having a sequence or a portion thereof that is at least 50, 55, 60, 65, 70, 75, 80, 85, 90, 95, 96, 97, 98, 99 or 100 percent homologous to an oligonucleotide sequence according to at least 1, 2, 3, 4, 5, 6, 7, 8, 9, 10, 12, 15 or all of SEQ ID NOs. 206491-206506. In such cases, the imaging may be, e.g., directed to a tissue, including without limitation breast, colon, kidney, lung or pancreatic tissue. See Example 29.

In the imaging methods provided by the invention, the at least one oligonucleotide or the plurality of oligonucleotides can carry various useful chemical structures or modifications such as described herein. Such modifications can be made to enhance binding, stability, allow detection, or for other useful purposes.

In the imaging methods provided by the invention, the at least one oligonucleotide or the plurality of oligonucleotides can be administered to a subject prior to the detecting. Such method may allow imaging of at least one cell or tissue in the subject. In some embodiments, the at least one cell or tissue comprises neoplastic, malignant, tumor, hyperplastic, or dysplastic cells. In some embodiments, the at least one cell or tissue comprises at least one of lymphoma, leukemia, renal carcinoma, sarcoma, hemangiopericytoma, melanoma, abdominal cancer, gastric cancer, colon cancer, cervical cancer, prostate cancer, pancreatic cancer, breast cancer, or non-small cell lung cancer cells. The at least one cell or tissue can be from any desired tissue or related to desired any medical condition, disease or disorder such as described herein.

As the oligonucleotides provided by tissue ADAPT are selected to associate with tissues of interest, such associations can also be used in therapeutic applications such as targeted drug delivery. The oligonucleotides may provide therapeutic benefit alone or by providing targeted delivery of immunomodulators, drugs and the like. In an aspect, the invention provides a pharmaceutical composition comprising a therapeutically effective amount of a construct comprising the at least one oligonucleotide or the plurality of oligonucleotides as provided herein, or a salt thereof, and a pharmaceutically acceptable carrier, diluent, or both. In some embodiments, the at least one oligonucleotide or plurality of oligonucleotides associates with one or more protein listed in Table 28.

For example, the at least one oligonucleotide or plurality of oligonucleotides may comprise nucleic acids having a sequence or a portion thereof that is at least 50, 55, 60, 65, 70, 75, 80, 85, 90, 95, 96, 97, 98, 99 or 100 percent homologous to an oligonucleotide sequence according to at least 1, 2, 3, 4, 5, 6, 7, 8, 9, 10, 12, 15, 20 or all of SEQ ID NOs. 2922-2926, 2929-2947 and 2950-2952. Such pharmaceutical composition may be useful for therapy related to a cancer, wherein optionally the cancer comprises lung cancer or prostate cancer. See Example 14.

In another example, the at least one oligonucleotide or plurality of oligonucleotides may comprise nucleic acids having a sequence or a portion thereof that is at least 50, 55, 60, 65, 70, 75, 80, 85, 90, 95, 96, 97, 98, 99 or 100 percent homologous to an oligonucleotide sequence according to at least 1, 2, 3, 4, 5, 6, 7, 8, 9, 10, 12, 15, 20 or all of SEQ ID NOs. 2953-2961 and 2971-2979. Such pharmaceutical composition may be useful for therapy related to a cancer, wherein optionally the cancer comprises prostate cancer. See Example 17.

In still another example, the at least one oligonucleotide or plurality of oligonucleotides may comprise nucleic acids having a sequence or a portion thereof that is at least 50, 55, 60, 65, 70, 75, 80, 85, 90, 95, 96, 97, 98, 99 or 100 percent homologous to an oligonucleotide sequence according to at least 1, 2, 3, 4, 5, 6, 7, 8, 9, 10, 12, 15, 20, 25, 30, 35, 40, 50 or all of SEQ ID NOs. 3039-3061. Such pharmaceutical composition may be useful for therapy related to a cancer, wherein optionally the cancer comprises breast cancer. See Example 19.

In yet another example, the at least one oligonucleotide or plurality of oligonucleotides may comprise nucleic acids having a sequence or a portion thereof that is at least 50, 55, 60, 65, 70, 75, 80, 85, 90, 95, 96, 97, 98, 99 or 100 percent homologous to an oligonucleotide sequence according to at least 1, 2, 3, 4, 5, 6, 7, 8, 9, 10, 12, 15, 20, 25, 30, 35, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 150,000 or all of SEQ ID NOs. 3062-103061 and 103062-203061. Such pharmaceutical composition may be useful for therapy related to a cancer, wherein optionally the cancer comprises breast cancer. See Examples 20-22.

In an example, the at least one oligonucleotide or plurality of oligonucleotides may comprise nucleic acids having a sequence or a portion thereof that is at least 50, 55, 60, 65, 70, 75, 80, 85, 90, 95, 96, 97, 98, 99 or 100 percent homologous to an oligonucleotide sequence according to at least 1, 2, 3, 4, 5, 6, 7, 8, 9, 10, 12, 15, 20, 25, 30, 35, 40, 50, 60, 70, 80, 90, 100, 200, 300, 400, 500, 600, 700, 800, 900, 1000, 2000, 3000, 4000 or all of SEQ ID NOs. 203064-203067 and 203076-206478. Such pharmaceutical composition may be useful for therapy related to a cancer, wherein optionally the cancer comprises colorectal cancer. See Example 24.

In yet another example, the at least one oligonucleotide or plurality of oligonucleotides may comprise nucleic acids having a sequence or a portion thereof that is at least 50, 55, 60, 65, 70, 75, 80, 85, 90, 95, 96, 97, 98, 99 or 100 percent homologous to an oligonucleotide sequence according to at least 1, 2, 3, 4, 5, 6, 7, 8, 9, 10, 12, 15 or all of SEQ ID NOs. 206491-206506. Such pharmaceutical composition may be useful for therapy related to a cancer, wherein optionally the cancer comprises a cancer of the breast, colon, kidney, lung or pancreas. See Example 29.

The at least one oligonucleotide or the plurality of oligonucleotides within the pharmaceutical composition can have any useful desired chemical modification. In an embodiment, the at least one oligonucleotide or the plurality of oligonucleotides is attached to a toxin or chemotherapeutic agent. The at least one oligonucleotide or the plurality of oligonucleotides may be comprised within a multipartite construct. The at least one oligonucleotide or the plurality of oligonucleotides can be attached to a liposome or nanoparticle. In some embodiments, the liposome or nanoparticle comprises a toxin or chemotherapeutic agent. In such cases, the at least one oligonucleotide or the plurality of oligonucleotides can be used to target a therapeutic agent to a desired cell, tissue, organ or the like.

In a related aspect, the invention provides a method of treating or ameliorating a disease or disorder in a subject in need thereof, comprising administering the pharmaceutical composition of the invention to the subject. In another related aspect, the invention provides a method of inducing cytotoxicity in a subject, comprising administering the pharmaceutical composition of the invention to the subject. Any useful means of administering can be used, including without limitation at least one of intradermal, intramuscular, intraperitoneal, intravenous, subcutaneous, intranasal, epidural, oral, sublingual, intracerebral, intravaginal, transdermal, rectal, by inhalation, topical administration, or any combination thereof.

The oligonucleotide or plurality of oligonucleotides provided by tissue ADAPT can be used for imaging or therapeutic applications of any desired medical condition, disease or disorder, such as those described herein (see above). As a non-limiting example, the oligonucleotide or plurality of oligonucleotides can be used for imaging of tumors from various anatomical locals, or for treatment of cancers derived from various tissues.

Kits

The invention also provides a kit comprising one or more reagent to carry out the methods of the invention. For example, the one or more reagent can be the one or more aptamer, a buffer, blocker, enzyme, or combination thereof. The one or more reagent may comprise any useful reagents for carrying out the subject methods, including without limitation aptamer libraries, substrates such as microbeads or planar arrays or wells, reagents for biomarker and/or microvesicle isolation (e.g., via chromatography, filtration, ultrafiltration, centrifugation, ultracentrifugation, flow cytometry, affinity capture (e.g., to a planar surface, column or bead), polymer precipitation, and/or using microfluidics), aptamers directed to specific targets, aptamer pools that facilitate detection of a tissue/cell/microvesicle/biomarker population, reagents such as primers for nucleic acid sequencing or amplification, arrays for nucleic acid hybridization, detectable labels, solvents or buffers and the like, various linkers, various assay components, blockers, and the like. The one or more reagent may also comprise various compositions provided by the invention. In an embodiment, the one or more reagent comprises one or more aptamer of the invention. The one or more reagent can comprise a substrate, such as a planar substrate, column or bead. The kit can contain instructions to carry out various assays using the one or more reagent. The one or more reagent may comprise a reagent for performing a PHC assay, including components of enzymatic detection systems and substrates thereof useful for staining a tissue sample.

In an embodiment, the kit comprises an oligonucleotide probe or composition provided herein. The kit can be configured to carry out the methods provided herein. For example, the kit can include an aptamer of the invention, a substrate, or both an aptamer of the invention and a substrate.

In an embodiment, the kit is configured to carry out an assay. For example, the kit can contain one or more reagent and instructions for detecting the presence or level of a biological entity in a biological sample. In such cases, the kit can include one or more binding agent to a biological entity of interest. The one or more binding agent can be bound to a substrate. The one or more binding agent can be modified to allow capture, detection or visualization. For example, the one or more binding agent can be biotinylated or conjugated to digoxigenin.

In an embodiment, the kit comprises a set of oligonucleotides that provide a particular oligonucleotide profile for a biological sample. An oligonucleotide profile can include, without limitation, a profile that can be used to characterize a particular disease or disorder. For example, the disease or disorder can be a proliferative disease or disorder, including without limitation a cancer. In some embodiments, the cancer comprises a breast cancer.

EXAMPLES

Example 1

Aptamer Target Identification

In this Example, aptamers conjugated to microspheres are used to assist in determining the target of two aptamers identified by library screening methods as described above. The general approach is shown in FIG. 9. The approach is used to verify the targets of CAR003, an aptamer identified by library screening to recognize EpCAM. CAR003 is an aptamer candidate identified using the above methodology.

As an RNA aptamer, CAR003 with alternate tail sequence has the following RNA sequence (SEQ ID NO. 3):

```
5'-auccagagug acgcagcagu cuuuucugau ggacacgugg
uggucuagua ucacuaagcc accgugucca-3'
```

In this approach, the sequence of CAR003 is randomly rearranged before linkage to the microspheres. The microspheres are used as controls to bind to targets that are similar but not identical to the intended target molecule.

The protocol used is as follows:

1) The candidate aptamers (here, CAR003) and negative control aptamers (here, randomly arranged CAR003) are synthesized with modifications to allow capture (here, the aptamers are biotinylated) and crosslinking (here, using the Sulfo-SBED Biotin Label Transfer Reagent and Kit, Catalog Number 33073 from Thermo Fisher Scientific Inc., Rockford, Ill., to allow photocrosslinking)

2) Each of the aptamers is individually mixed with microvesicles having the target of interest (here, BrCa cell line microvesicles).

3) After incubation to allow the aptamers to bind target, ultraviolet light is applied to the mixtures to trigger crosslinking of the aptamers with the microvesicle targets.

4) The microvesicles are lysed, thereby releasing the crosslinked aptamer-target complex into solution.

5) The crosslinked aptamer-target complexes are captured from solution using a streptavidin coated substrate.

6) The crosslinked aptamer-target complexes for each aptamer are run individually on SDS-PAGE gel electrophoresis. The captured protein targets are visualized with Coomasie Blue staining.

7) The crosslinking and binding steps may be promiscuous so that multiple bands including the intended target but also random proteins will appear on each of the gels. The intended target will be found in a band that appears on the gel with the candidate aptamer (here, CAR003) but not the related negative control aptamers (here, randomly arranged CAR003). The bands corresponding to the target are excised from the gel.

8) Mass spectrometry (MS) is used to identify the aptamer target from the excised bands.

Example 2

Disease Diagnosis

This example illustrates the use of oligonucleotide probes of the invention to diagnose a proliferative disease.

A suitable quantity of an oligonucleotide or pool of oligonucleotides that bind a BrCa-derived population of microvesicles, such as identified in Example 12 or various Examples below, is synthesized via chemical means known in the art. The oligonucleotides are conjugated to a diagnostic agent suitable for detection, such as a fluorescent moiety, using a conjugation method known in the art.

The composition is applied to microvesicles isolated from blood samples taken from a test cohort of patients suffering from a proliferative disease associated with the overexpression of microvesicles, e.g. breast cancer. The composition is likewise applied to microvesicles isolated from blood samples taken from a negative control cohort, not suffering from a proliferative disease.

The use of appropriate detection techniques (e.g., microbead assay or flow cytometry) on the test cohort samples indicates the presence of disease, while the same techniques applied to the control cohort samples indicate the absence of disease.

The results show that the oligonucleotides of the present invention are useful in diagnosing proliferative diseases.

Example 3

Theranostics

This example illustrates the use of oligonucleotide probes of the present invention to provide a theranosis for a drug for treating a proliferative disease.

A suitable quantity of an oligonucleotide or pool of oligonucleotides that bind breast cancer tissue, such as identified in Examples 19-21 or various Examples below, is synthesized via chemical means known in the art. The probes are conjugated to an agent suitable for detection, such as a biotin moiety, which can then be detected using streptavidin constructs such as streptavidin-horse radish peroxidase using immunohistochemistry (IHC) techniques. The oligonucleotide probe or panel of oligonucleotide probes are within a suitable composition, such as a buffered solution.

Treatment selection. The probes are applied to tumor tissue samples taken from a test cohort of patients suffering from a proliferative disease, e.g. breast cancer, that responded to a certain treatment, e.g., trastuzumab. The probes are likewise applied to tumor tissue taken from a control cohort consisting of patients suffering from the same proliferative disease that did not respond to the treatment. The use of appropriate detection techniques (e.g., IHC) on the test cohort samples indicates that probes which bind the samples are useful for identifying patients that will respond to the treatment, while the same techniques applied to the control cohort samples identifies probes useful for identifying patients that will not respond to the treatment.

Treatment monitoring. In another setting, the probes are applied to tumor tissue samples from a test cohort of patients suffering from a proliferative disease, e.g. breast cancer, prior to or during a course of treatment, such as surgery, radiotherapy and/or chemotherapy. The probes are then applied to tumor tissue samples from the patients over a time course. The use of appropriate detection techniques (e.g., IHC) on the test cohort samples indicates whether the detected population of disease-related cells increases, decreases, or remains steady in concentration over time during the course of treatment. An increase in the population of disease-related cells post-treatment may indicate that the treatment is less effective whereas a decrease in the population of disease-related cells post-treatment may indicate that the treatment has a beneficial effect.

The results show that the oligonucleotide probes of the present invention are useful in theranosing proliferative diseases.

Example 4

Therapeutic Oligonucleotide Probes

This example illustrates the use of oligonucleotide probes of the present invention to treat a proliferative disease.

A suitable quantity of an oligonucleotide or pool of oligonucleotides that bind breast cancer tumor tissue, such as identified in Examples 19-21 or various Examples below, is synthesized via chemical means known in the art. The oligonucleotides are conjugated to a chemotherapeutic agent, such as Doxil, using a conjugation method known in the art. The conjugate is formulated in an aqueous composition.

The composition is administered intravenously, in one or more doses, to a test cohort of subjects suffering from breast cancer. A control cohort suffering from breast cancer is administered a placebo intravenously, according to a corresponding dosage regimen.

Pathological analysis of tumor samples and/or survival indicates that mortality and/or morbidity are improved in the test cohort over the control cohort.

The results show that the oligonucleotides of the present invention are useful in treating proliferative diseases.

Example 5

Oligonucleotide—Sequencing Detection Method

This example illustrates the use of an oligonucleotide pool to detect microvesicles that are indicative of a phenotype of interest. The method makes use of a pool of oligonucleotides that have been enriched against a target of interest that is indicative of a phenotype of interest. The method in this Example allows efficient use of a library of oligonucleotides to preferentially recognize a target entity.

For purposes of illustration, the method is described in the Example with a microvesicle target from a bodily fluid sample. One of skill will appreciate that the method can be extended to other types of target entity (e.g., cells, proteins, various other biological complexes), sample (e.g., tissue, cell culture, biopsy, other bodily fluids) and other phenotypes (other cancers, other diseases, etc) by enriching an aptamer library against the desired input samples.

General workflow:

1) Obtain sample (plasma, serum, urine or any other biological sample) of patients with unknown medical etymology and pre-treating them accordingly to ensure availability of the target of interest (see below). Where the target of interest is a microvesicle population, the microvesicles can be isolated and optionally tethered to a solid support such as a microbead.

2) Expose pre-treated sample to an oligonucleotide pool carrying certain specificity against target of interest. As described herein, an oligonucleotide pool carrying certain specificity against the target of interest can be enriched using various selection schemes, e.g., using non-cancer microvesicles for negative selection and cancer microvesicles for positive selection as described above. DNA or RNA oligonucleotides can be used as desired.

3) Contact oligonucleotide library with the sample.

4) Elute any oligonucleotides bound to the target.

5) Sequence the eluted oligonucleotides. Next generation sequencing methods can be used.

6) Analyze oligonucleotide profile from the sequencing. A profile of oligonucleotides known to bind the target of interest indicates the presence of the target within the input sample. The profile can be used to characterize the sample, e.g., as cancer or non-cancer.

Protocol Variations:

Various configurations of the assay can be performed. Four exemplary protocols are presented for the purposes of the oligonucleotide-sequencing assay. Samples can be any appropriate biological sample. The protocols can be modified as desired. For example, the microvesicles can be isolated using alternate techniques instead or in addition to ultracentrifugation. Such techniques can be disclosed herein, e.g., polymer precipitation (e.g., PEG), column chromatography, and/or affinity isolation.

Protocol 1:

Ultracentrifugation of 1-5 ml bodily fluid samples (e.g., plasma/serum/urine) (120K×g, no sucrose) with two washes of the precipitate to isolate microvesicles.

Measure total protein concentration of recovered sample containing the isolated microvesicles.

Conjugate the isolated microvesicles to magnetic beads (for example MagPlex beads (Luminex Corp. Austin Tex.)).

Incubate conjugated microvesicles with oligonucleotide pool of interest.

Wash unbound oligonucleotides by retaining beads using magnet.

Elute oligonucleotides bound to the microvesicles.

Amplify and purify the eluted oligonucleotides.

Oligonucleotide sequencing (for example, Next generation methods; Ion Torrent: fusion PCR, emulsion PCR, sequencing).

Assess oligonucleotide profile.

Protocol 2:

This alternate protocol does not include a microvesicle isolation step, microvesicles conjugation to the beads, or separate partitioning step. This may present non-specific binding of the oligonucleotides against the input sample.

Remove cells/debris from bodily fluid sample and dilute sample with PBS containing $MgCl_2$ (2 mM).

Pre-mix sample prepared above with oligonucleotide library.

Ultracentrifugation of oligonucleotide/sample mixture (120K×g, no sucrose). Wash precipitated microvesicles.

Recover precipitate and elute oligonucleotides bound to microvesicles.

Amplify and purify the eluted oligonucleotides.

Oligonucleotide sequencing (for example, Next generation methods; Ion Torrent: fusion PCR, emulsion PCR, sequencing).

Assess oligonucleotide profile.

Protocol 3:

This protocol uses filtration instead of ultracentrifugation and should require less time and sample volume.

Remove cells/debris from bodily fluid sample and dilute it with PBS containing $MgCl_2$ (2 mM).

Pre-mix sample prepared above with oligonucleotide library.

Load sample into filter (i.e., 150K or 300K MWCO filter or any other that can eliminate unbound or unwanted oligonucleotides). Centrifuge sample to concentrate. Concentrated sample should contain microvesicles.

Wash concentrate. Variant 1: Dilute concentrate with buffer specified above to the original volume and repeat centrifugation. Variant 2: Dilute concentrate with buffer specified above to the original volume and transfer concentrate to new filter unit and centrifuge. Repeat twice.

Recover concentrate and elute oligonucleotides bound to microvesicles.

Amplify and purify the eluted oligonucleotides.

Oligonucleotide sequencing (for example, Next generation methods; Ion Torrent: fusion PCR, emulsion PCR, sequencing).

Assess oligonucleotide profile.

Protocol 4:

Ultracentrifugation of 1-5 ml bodily fluid sample (120K×g, no sucrose) with 2 washes of the precipitate to isolate microvesicles.

Pre-mix microvesicles with oligonucleotide pool.

Load sample into 300K MWCO filter unite and centrifuge (2000×g). Concentration rate is ~3×.

Wash concentrate. Variant 1: Dilute concentrate with buffer specified above to the original volume and centrifuge. Repeat twice. Variant 2: Dilute concentrate with buffer specified above to the original volume and transfer concentrate to new filter unit and centrifuge. Repeat twice Recover concentrate and elute oligonucleotides bound to microvesicles.

Amplify and purify the eluted oligonucleotides.

Oligonucleotide sequencing (for example, Next generation methods; Ion Torrent: fusion PCR, emulsion PCR, sequencing).

Assess oligonucleotide profile.

In alterations of the above protocols, polymer precipitation is used to isolate microvesicles from the patient samples. For example, the oligonucleotides are added to the sample and then PEG4000 or PEG8000 at 4% or 8% concentration is used to precipitate and thereby isolate microvesicles. Elution, recovery and sequence analysis continues as above.

Example 6

Plasma/Serum Probing with an Oligonucleotide Probe Library

The following protocol is used to probe a plasma or serum sample using an oligonucleotide probe library.

Input Oligonucleotide Library:

Use 2 ng input of oligonucleotide library per sample.

Input oligonucleotide library is a mixture of two libraries, cancer and non-cancer enriched, concentration is 16.3 ng/ul.

Dilute to 0.2 ng/ul working stock using Aptamer Buffer (3 mM $MgCl_2$ in 1×PBS)

Add 10 ul from working stock (equal to 2 ng library) to each optiseal tube

Materials:

PBS, Hyclone SH30256.01, LN: AYG165629, bottle #8237, exp. July 2015

Round Bottom Centrifuge Tubes, Beckman 326820, LN:P91207

OptiSeal Centrifuge tubes and plugs, polyallomer Konical, Beckman 361621, lot #Z10804SCA Ultracentrifuge rotor: 50.4 TI Ultracentrifuge rotor: 50.4 TI, Beckman Canis ID #0478

Protocol:

1 Pre-chill tabletop centrifuge, ultracentrifuge, buckets, and rotor at 4° C.

2 Thaw plasma or serum samples

3 Dilute 1 ml of samples with 1:2 with Aptamer Buffer (3 mM $MgCl_2$ in 1×PBS)

4 Spin at 2000×g, 30 min, 4° C. to remove debris (tabletop centrifuge)

5 Transfer supernatants for all samples to a round bottom conical

6 Spin at 12,000×g, 45 min, 4° C. in ultracentrifuge to remove additional debris.

7 Transfer supernatant about 1.8 ml for all samples into new OptiSeal bell top tubes (uniquely marked).

8 Add 2 ng (in 10 ul) of DNA Probing library to each optiseal tube

9 QS to 4.5 ml with Aptamer Buffer

10 Fix caps onto the OptiSeal bell top tubes

11 Apply Parafilm around caps to prevent leakage

12 Incubate plasma and oligonucleotide probe library for 1 hour at room temperature with rotation 13 Remove parafilm (but not caps)

14 Place correct spacer on top of each plugged tube

15 Mark pellet area on the tubes, insure this marking is facing outwards from center.

16 Spin tubes at 120,000×g, 2 hr, 4° C. (inner row, 33,400 rpm) to pellet microvesicles.

17 Check marking is still pointed away from center.

18 Completely remove supernatant from pellet, by collecting liquid from opposite side of pellet marker and using a 10 ml syringe barrel and 21G2 needle 19 Discard supernatant in appropriate biohazard waste container 20 Add 1 ml of 3 mM MgCl2 diluted with 1×PBS 21 Gentle vortex, 1600 rpm for 5 sec and incubate 5 min at RT.

22 QS to ~4.5 mL with 3 mM Mg Cl2 diluted with 1×PBS

23 Fix caps onto the OptiSeal bell top tubes.

24 Place correct spacer on top of each plugged tube.

25 Mark pellet area on the tubes, insure this marking is facing outwards from center.

26 Spin tubes at 120,000×g, 70 min, 4° C. (inner row 33,400 rpm) to pellet microvesicles 27 Check marking in still pointed away from center.

28 Completely remove supernatant from pellet, by collecting liquid from opposite side of pellet marker and using a 10 ml syringe barrel and 21G2 needle 29 Discard supernatant in appropriate biohazard waste container 30 Add 1 ml of 3 mM MgCl2 diluted with 1×PBS 31 Gentle vortex, 1600 rpm for 5 sec and incubate 5 min at RT.

32 QS to ~4.5 mL with 3 mM Mg Cl2 diluted with 1×PBS

33 Fix caps onto the OptiSeal bell top tubes.

34 Place correct spacer on top of each plugged tube.

35 Mark pellet area on the tubes, insure this marking is facing outwards from center.

36 Spin tubes at 120,000×g, 70 min, 4° C. (inner row 33,400 rpm) to pellet microvesicles 37 Check marking is still pointed away from center.

38 Save an aliquot of the supernatant (100 ul into a 1.5 ml tube)

39 Completely remove supernatant from pellet, by collecting liquid from opposite side of pellet marker and using a 10 ml syringe barrel and 21G2 needle 40 Add 50 ul of Rnase-free water to the side of the pellet 41 Leave for 15 min incubation on bench top 42 Cut top off tubes using clean scissors.

43 Resuspend pellet, pipette up and down on the pellet side

44 Measure the volume, make a note on the volume in order to normalize all samples 45 Transfer the measured resuspended eluted microvesicles with bound oligonucleotides to a Rnase free 1.5 ml Eppendorf tube 46 Normalize all samples to 100 ul to keep it even across samples and between experiments.

Next Generation Sequencing Sample Preparation:

I) Use 50 ul of sample from above, resuspended in 100 ul H2O and containing microvesicle/oligo complexes, as template in Transposon PCR, 14 cycles.

II) AMPure transposon PCR product, use entire recovery for indexing PCR, 10 cycles.

III) Check indexing PCR product on gel, proceed with AMPure if band is visible. Add 3 cylces if band is invisible, check on gel. After purification quantify product with QuBit and proceed with denaturing and diluting for loading on HiSeq flow cell (Illumina Inc., San Diego, Calif.).

IV) 5 samples will be multiplexed per one flow cell. 10 samples per HiSeq.

Example 7

Oligonucleotide Probe Library

This Example presents development of an oligonucleotide probe library to detect biological entities. In this Example, steps were taken to reduce the presence of double stranded oligonucleotides (dsDNA) when probing the patient samples. The data were also generated comparing the effects of 8% and 6% PEG used to precipitate microvesicles (and potentially other biological entities) from the patient samples.

Protocol:

1) Pre-chill tabletop centrifuge at 4° C.

2) Protease inhibition: dissolve 2 tablets of "cOmplete ULTRA MINI EDTA-free EASYpack" protease inhibitor in 1100 ul of $H_2O$ (20× stock of protease inhibitor).

3) Add 50 ul of protease inhibitor to the sample (on top of frozen plasma) and start thawing: 1 ml total ea.

4) To remove cells/debris, spin samples at 10,000×g, 20 min, 4° C. Collect 1 ml supernatant (SN).

5) Mix 1 ml supernatant from step 4 with 1 ml of 2×PBS 6 mM $MgCl_3$, collect 400 ul into 3 tubes (replicates A, B, C) and use it in step 6.

6) Add competitor per Table 5: make dilutions in 1×PBS, 3 mM $MgCl_2$, mix well, pour into trough, pipet using multichannel.

TABLE 5

| | | | | Competitors | | | |
|---|---|---|---|---|---|---|---|
| units | Type of Competitor | Stock Concentration | Intermediate stock concentration | Number of samples | Volume from stock to make intermediate stock, ul | Buffer to make intermediate stock | Final Volume, ul | Final Concentration |
| ng/ul | Salmon DNA | — | 40 | — | — | — | 425.5 | 0.8 |
| ng/ul | tRNA | — | 40 | — | — | — | 425.5 | 0.8 |
| x | S1 | 20 | 0.5 | 280 | 65.5 | 2555.6 | 425.5 | 0.01 |

7) Incubate for 10 min, RT, end-over-end rotation

Pool of 6-3S and 8-3S oligonucleotide probing libraries is ready: 2.76 ng/ul (~185 ng). Save pool stock and dilutions. New pool can be made by mixing 171.2 ul (500 ng) of library 6-3S (2.92 ng/ul) with 190.8 ul (500 ng) of library 8-3S (2.62 ng/ul). Aliquot pooled library into 30 ul and store at −80 C.

Add ssDNA oligonucleotide probing library to the final concentration 2.5 pg/ul for binding. Make dilutions in 1×PBS, 3 mM $MgCl_2$.

TABLE 6

| | | | | Probe library calculations | | | | |
|---|---|---|---|---|---|---|---|---|
| Original stock, ng/ul | Lib Name | Required working stock (ng/ul) | ul from original stock to make working | ul of buffer to make working | Final volume, ul | Number of samples | Volume per sample from working stock | Final concentration (pg/ul) |
| 2.76 | Pooled library 6-3S/8-3S | 0.1 | 26.1 | 694.1 | 720.2 | 60 | 10.9 | 2.5 |

8) Binding: Incubate for 1 h at RT with rotation.
9) Prepare polymer solution: 20% PEG8000 in 1×PBS 3 mM MgCl2 (dilute 40% PEG8000 with 2×PBS with 6 mM MgCl2). Add 20% PEG8000 to sample to the final concentration 6%. Invert few times to mix, incubate for 15 min at 4 C

TABLE 7

PEG calculations

| PEG MW | PEG stock, % | Final conc., % | Final volume, ul | Volume 20% PEG to add, ul | Volume of buffer to adjust final volume, ul | Sample volume before adding PEG | Total samples | Total 20% PEG needed, ml |
| --- | --- | --- | --- | --- | --- | --- | --- | --- |
| 8000 | 20 | 6 | 622.8 | 186.9 | −0.4 | 436.4 | 60 | 11.2 |

10) Spin at 10,000×g for 5 min, RT.
11) Remove SN, add 1 ml 1×PBS, 3 mM MgCl2 and wash pellet by gentle invertion with 1 ml aptamer buffer.
12) Remove buffer, Re-suspend pellets in 100 ul H2O: incubate at RT for 10 min on mixmate 900 rpm to re-suspend.
13) Make sure each sample is re-suspended by pipetting after step 13. Make notes on hardly re-suspendable samples.
14) 50 ul of re-suspended sample to indexing PCR→next generation sequencing (NGS).
15) Keep leftover at 4 C Technical Validation:

The current protocol was tested versus a protocol using 8% PEG8000 to precipitate microvesicles. The current protocol further comprises steps to reduce dsDNA in the oligonucleotide probing libraries.

Figure 5A:
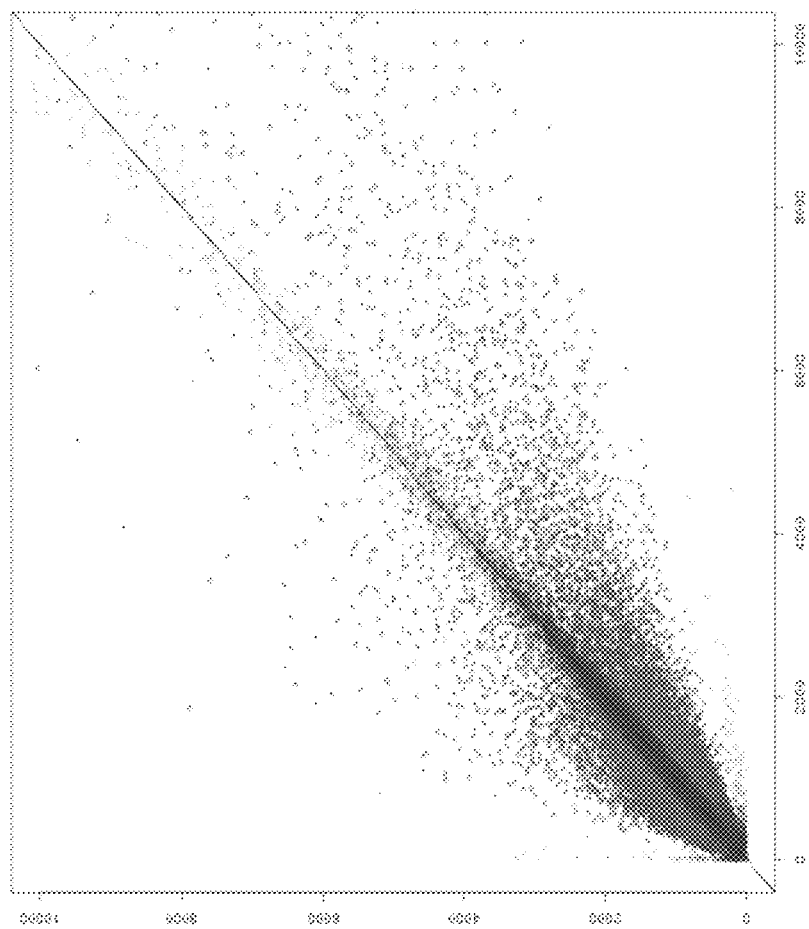

FIG. 5A shows the within sample variance (black) between binding replicates and the between sample variance (grey). Black is on top of grey, thus any observable grey oligo is informative about differences in the biology of two patient samples. This evaluation of Sources of Variance shows that the technical variances is significantly smaller than the biological variance.

Figure 5B:
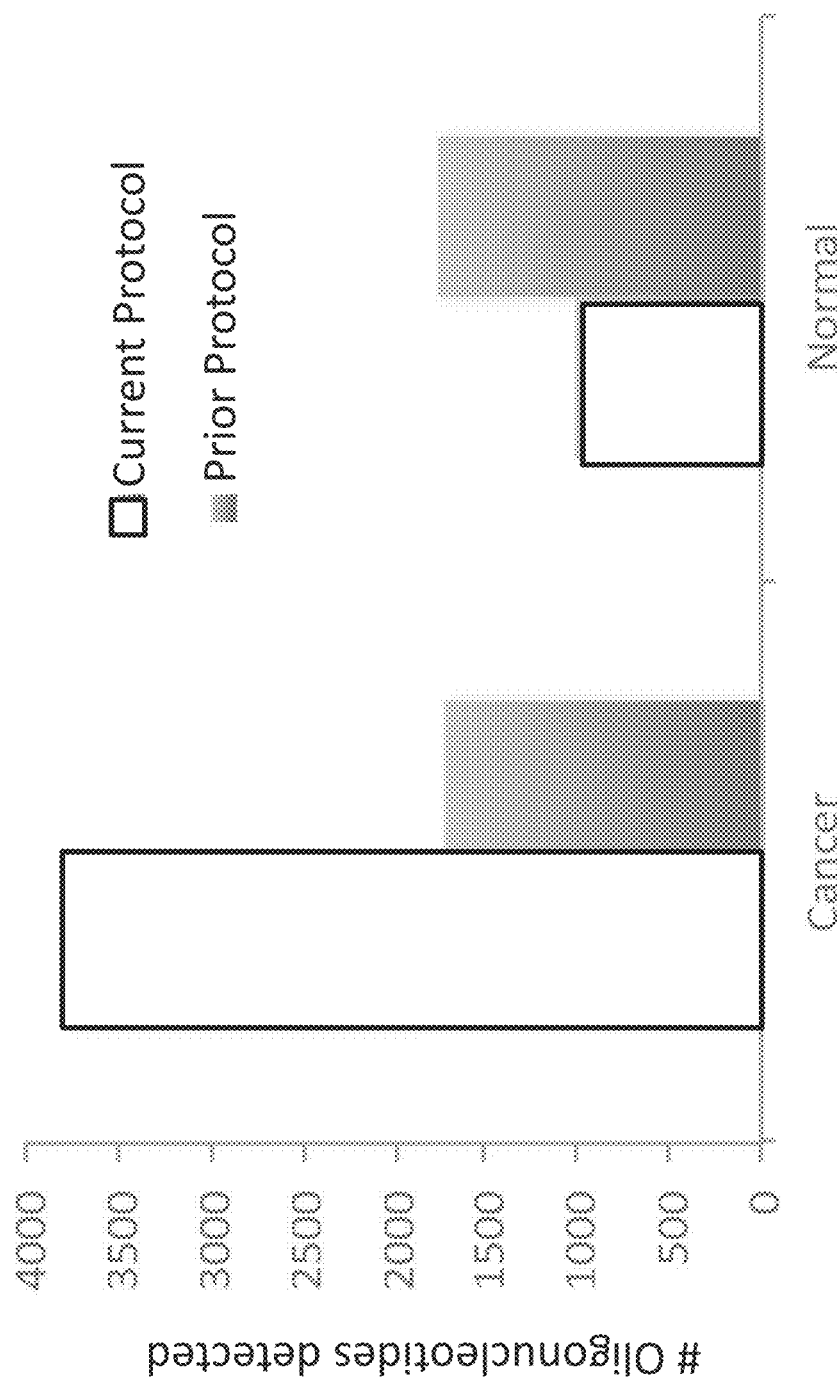

FIG. 5B shows the impact of using a higher proportion of single stranded DNA and PEG 6% isolation (white bars) compared to when there is a higher amount of double stranded DNA and 8% PEG (grey). This data indicates that the protocol in this Example improves biological separation between patients.

The plots in FIG. 5C show the difference between an earlier protocol (PEG 8% with increased dsDNA) and a modified protocol of the Example (PEG 6% no dsDNA). The black is the scatter between replicates (independent binding events) and the grey is the difference between patients. This data shows that the signal to noise increased significantly using the newer protocol.

Patient Testing:

The protocol above was used to test patient samples having the following characteristics:

TABLE 8

Patient characteristics

| Sample Type | Description |
| --- | --- |
| Cancer | Mixed type carcinoma; Malignant; |
| Cancer | Invasive, predominant intraductal component (8500/3) |
| Cancer | Fibrocystic Changes; Invasive lobular carcinoma - 8520/3; Lobular carcinoma in situ - 8520/2; Benign; In situ and grade 3 intraepith; Malignant; Fat necrosis, periductal inflammation, malignant cellsFat necrosis; Inflammation; Benign; |
| Cancer | Invasive, predominant intraductal component (8500/3) |
| Cancer | Mucinous (colloid) adenocarcinoma (8480/3) |
| Cancer | Invasive lobular carcinoma - 8520/3; Microcalcifications; Benign; Malignant; |
| Cancer | Otherfibrocystic changeInvasive, NOS (8500/3) |
| Cancer | Invasive ductal carcinoma, not otherwise specified (NOS) - 8500/3; Malignant; |
| Cancer | Invasive ductal carcinoma, not otherwise specified (NOS) - 8500/3; Malignant; |
| Cancer | Intraductal carcinoma, non-infiltrating, NOS (in situ) (8500/2) |

TABLE 8-continued

Patient characteristics

| Sample Type | Description |
|---|---|
| Cancer | Atypical lobular hyperplasia |
| | Otherfibrocystic changes, inter and intralobular fibrosis, apocrine metaplasia, columnar cell change, microcalcificationsInvasive, NOS (8500/3) |
| Cancer | FibroadenomaInvasive, NOS (8500/3) |
| Cancer | Ductal carcinoma in situ - 8500/2; Invasive ductal carcinoma, not otherwise specified (NOS) - 8500/3; Microcalcifications; Benign; In situ and grade 3 intraepith; Malignant; |
| Cancer | Ductal carcinoma in situ - 8500/2; Invasive lobular carcinoma - 8520/3; Lobular carcinoma in situ - 8520/2; In situ and grade 3 intraepith; Malignant; |
| Cancer | Ductal carcinoma in situ - 8500/2; Invasive ductal carcinoma, not otherwise specified (NOS) - 8500/3; Microcalcifications; Benign; In situ and grade 3 intraepith; Malignant; Focal Micropapillary Features, invasive ductal carcinoma with micropapillary features, invasive ductal carcinoma with mucinous and micropapillary featInvasive ductal carcinoma with micropapillary and mucinous features; Invasive micropapillary carcinoma - 8507/3; Malignant; |
| Cancer | Invasive, predominant intraductal component (8500/3) |
| Cancer | Invasive ductal carcinoma, not otherwise specified (NOS) - 8500/3; Malignant; |
| Cancer | Invasive, NOS (8500/3) |
| Cancer | Infiltrating duct and lobular carcinoma (8522/3) |
| Cancer | Invasive, predominant in situ component (8522/3) |
| Non-Cancer | Otherusual ductal hyperplasia, apocrine metaplasia, microcysts, elastosis |
| Non-Cancer | Otherstromal fibrosis, fibrous cyst wall |
| Non-Cancer | Otherfibrocystic change, stromal fibrosis, cyst formation, microcalcifications, apocrine metaplasia, sclerosing adenosis, usual ductal hyperplasia |
| Non-Cancer | Otherfibrocystic changes, apocrine metaplasia, cystic change, usual ductal hyperplasia |
| Non-Cancer | Otherfibrocystic change, microcalcifications |
| Non-Cancer | Fibroadenoma |
| Non-Cancer | Otherintraductal papilloma, sclerosis, microcalcifications, stromal fibrosis |
| Non-Cancer | Fibroadenoma |
| Non-Cancer | Otherfat necrosis |
| Non-Cancer | Otherstromal fibrosis, microcalcifications |
| Non-Cancer | Otherfibrocystic change, microcystic change, focal secretory features |
| Non-Cancer | Otherstromal fibrosis |
| Non-Cancer | Fibroadenoma Otheradenosis, columnar cell change/hyperplasia, usual ductal hyperplasia |
| Non-Cancer | OtherFNA - insufficient material for diagnosis |
| Non-Cancer | Otherintraductal papilloma |
| Non-Cancer | Otherfibrocystic changes, duct ectasia, usual ductal hyperplasia, apocrine metaplasia, microcalcifications |

Microvesicles (and potentially other biological entities) were precipitated in blood (plasma) samples from the above patients using polymer precipitation with PEG as indicated above. The protocol was used to probe the samples with the oligonucleotide probe libraries. Sequences that bound the PEG precipitated samples were identified using next generation sequencing (NGS).

Figure 5D:
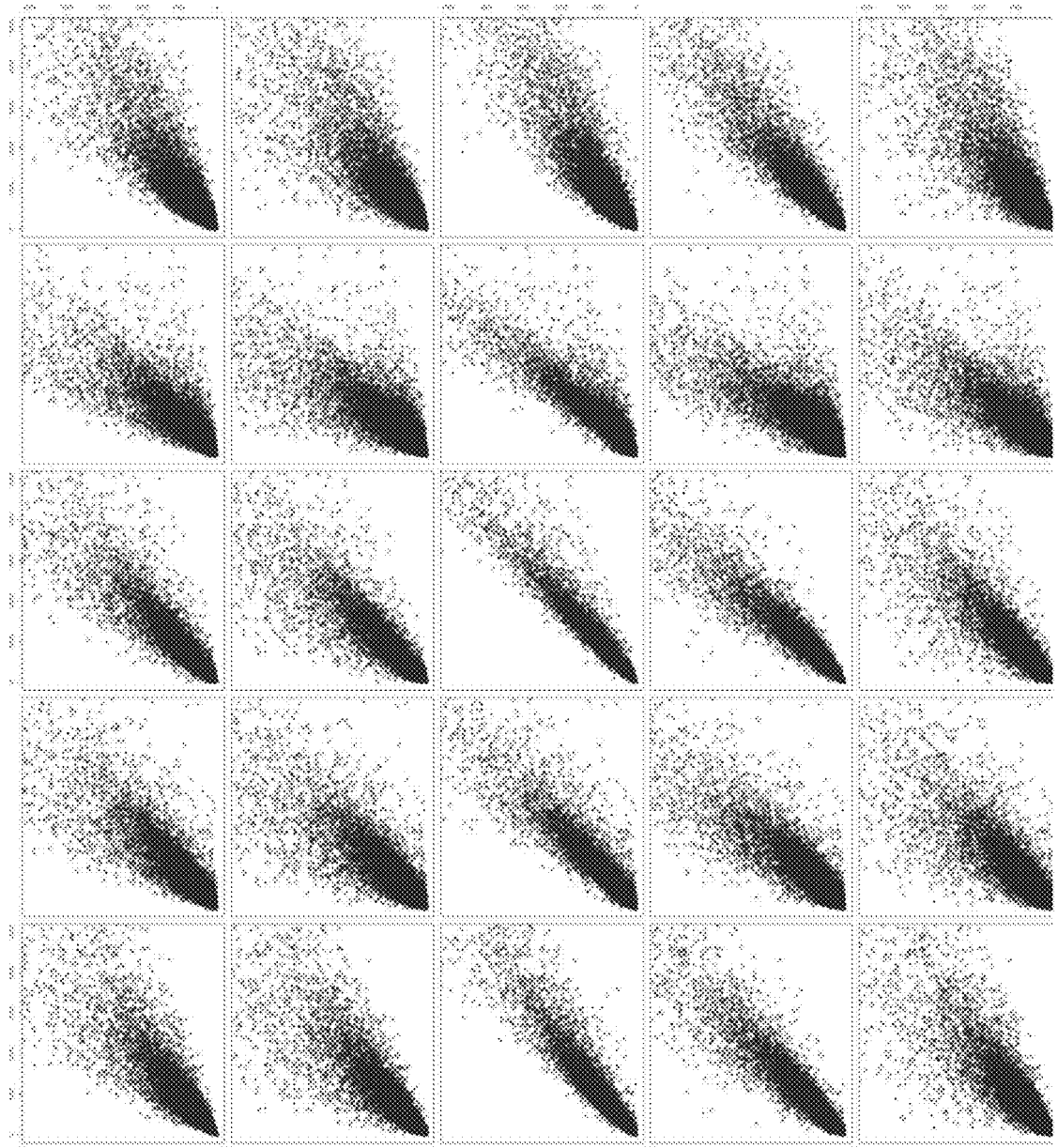

FIG. 5D shows scatter plots of a selection of results from testing the 40 patients listed previously. The spread in the data indicates that large numbers of oligos were detected that differed between samples. The number of significant oligos found is much greater than would be expected randomly as shown in Table 9. The table shows the number of oligonucleotides sorted by copy number detected and p-value. The d-# indicates the number copies of a sequence observed for the data in the rows.

TABLE 9

Expected versus observed sequences

| | Total Number | P-0.1 | P-0.05 | P-0.01 | P-0.005 |
|---|---|---|---|---|---|
| d-50 | 83,632 | 47,020 | 30,843 | 5,934 | 2,471 |
| d-100 | 52,647 | 29,106 | 19,446 | 3,893 | 1,615 |
| d-200 | 28,753 | 14,681 | 9,880 | 2,189 | 914 |
| d-500 | 10,155 | 4,342 | 2,927 | 725 | 315 |
| d-50 | 100.0% | 56.2% | 36.9% | 7.1% | 3.0% |

TABLE 9-continued

Expected versus observed sequences

| | Total Number | P-0.1 | P-0.05 | P-0.01 | P-0.005 |
|---|---|---|---|---|---|
| d-100 | 100.0% | 55.3% | 36.9% | 7.4% | 3.1% |
| d-200 | 100.0% | 51.1% | 34.4% | 7.6% | 3.2% |
| d-500 | 100.0% | 42.8% | 28.8% | 7.1% | 3.1% |
| Maximum expected | 10.0% | 5.0% | 1.0% | 0.5% |

As a control, the cancer and non-cancer samples were randomly divided into two groups. Such randomization of the samples significantly reduced the number of oligos found that differentiate between sample groups. Indeed, there was a 50-fold increase in informative oligos between the cancer/non-cancer grouping versus random grouping. FIG. 5E shows data as in Table 9 and indicates the number of observed informative oligos between the indicated sample groups.

Figure 5F:
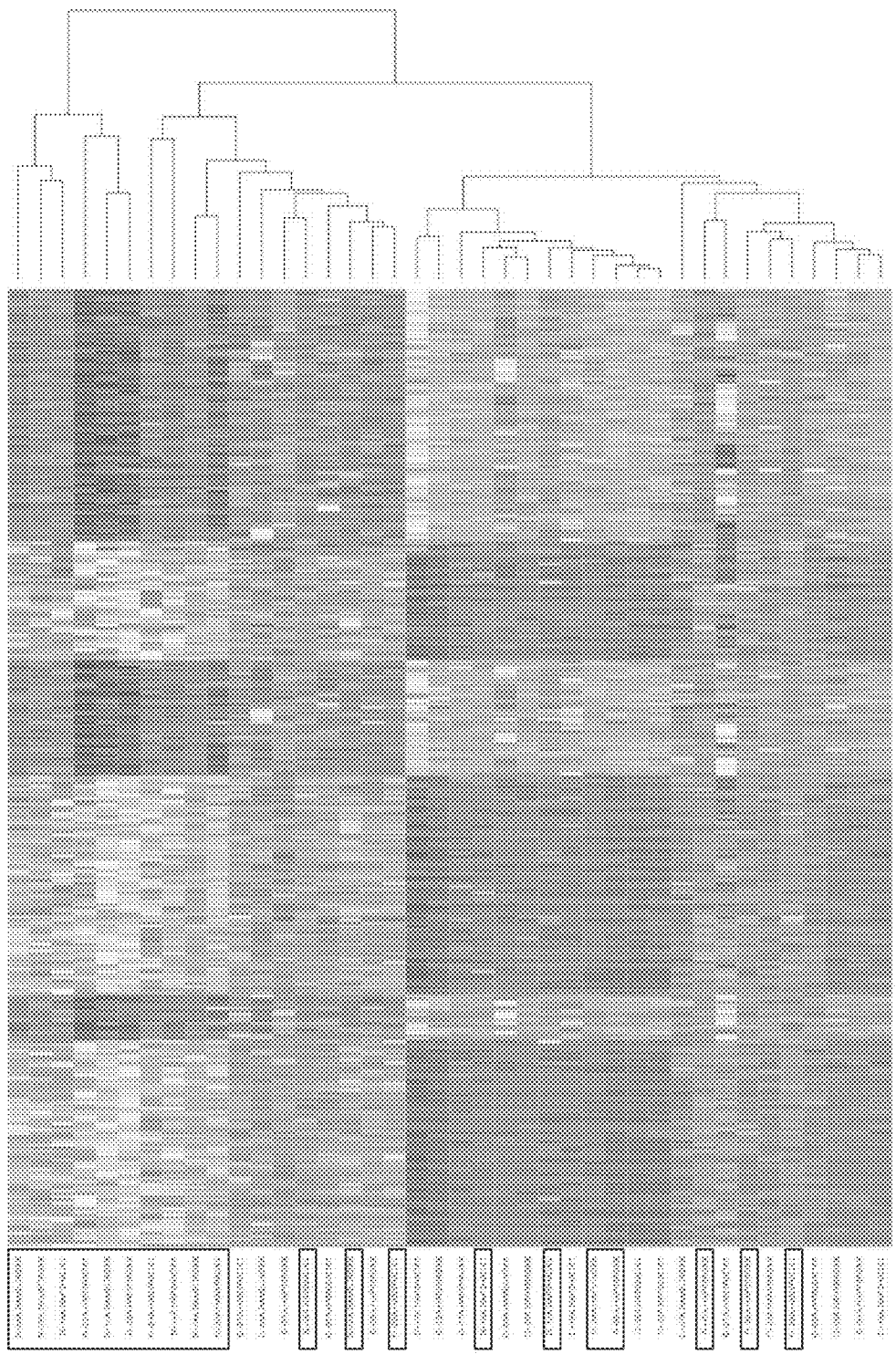
Figure 5G:
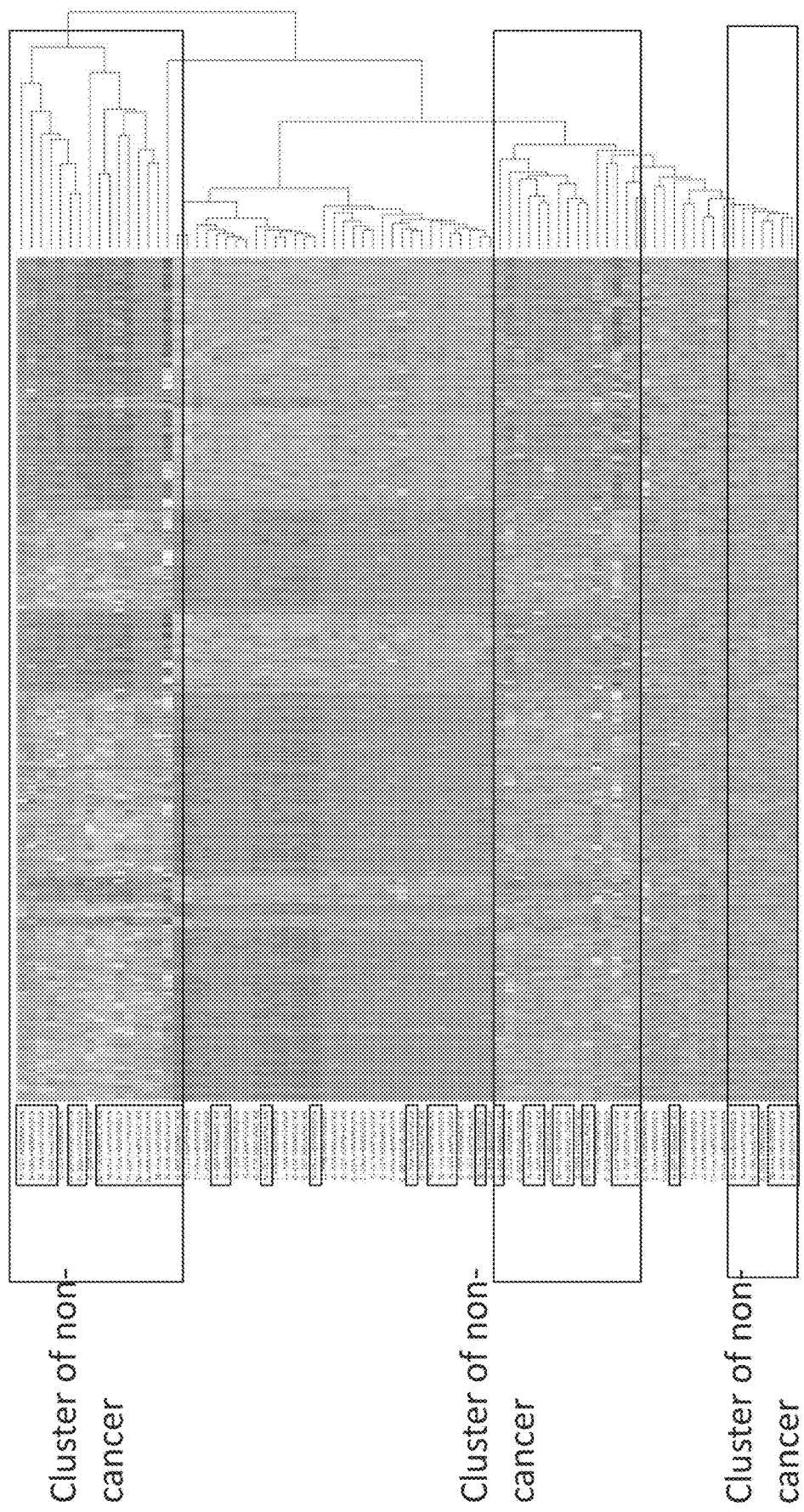

FIG. 5F shows distinct groups of oligos that differentiate between cancer and non-cancer samples. The figure shows a heatmap of the 40 samples tested with oligos selected that had more than 500 copies and p-value less than 0.005. There are clear subpopulations emerging with a distinct non-cancer cohort at the top. The non-cancer samples have boxes around them on the left axis. FIG. 5G is similar and shows results with an additional 20 cancer and 20 non-cancer samples. As shown, analysis with the 80 samples provides the emergence of more distinct and larger clusters.

The data for the additional 80 samples was also used to compare the consistency of informative oligos identified in different screening experiments. Of the 315 informative oligos identified using the first set of 40 patients, 86% of them showed fold-change in a consistent manner when tested on the independent set of 40 patients.

Example 8

Enrichment of Oligonucleotide Probes Using a Balanced Library Design

In this Example, a naïve ADAPT oligonucleotide library was screened to enrich oligonucleotides that identify microvesicles circulating in the blood of breast cancer patients and microvesicles circulating in the blood of healthy, control individuals (i.e., without breast cancer). The input library was the naïve F-TRin-35n-B 8-3s library, which comprises a 5' region (5' CTAG-CATGACTGCAGTACGT (SEQ ID NO. 4)) followed by the random naïve aptamer sequences of 35 nucleotides and a 3' region (5' CTGTCTCTTATACA-CATCTGACGCTGCCGACGA (SEQ ID NO. 5)). The "balanced" design is described in Example 23 of Int'l Patent Publication WO/2015/031694 (Appl. No. PCT/US2014/053306, filed Aug. 28, 2014), which is incorporated by reference herein in its entirety. The working library comprised approximately $2 \times 10^{13}$ synthetic oligonucleotide sequences. The naïve library may be referred to as the "L0 Library" herein.

Figure 12A:
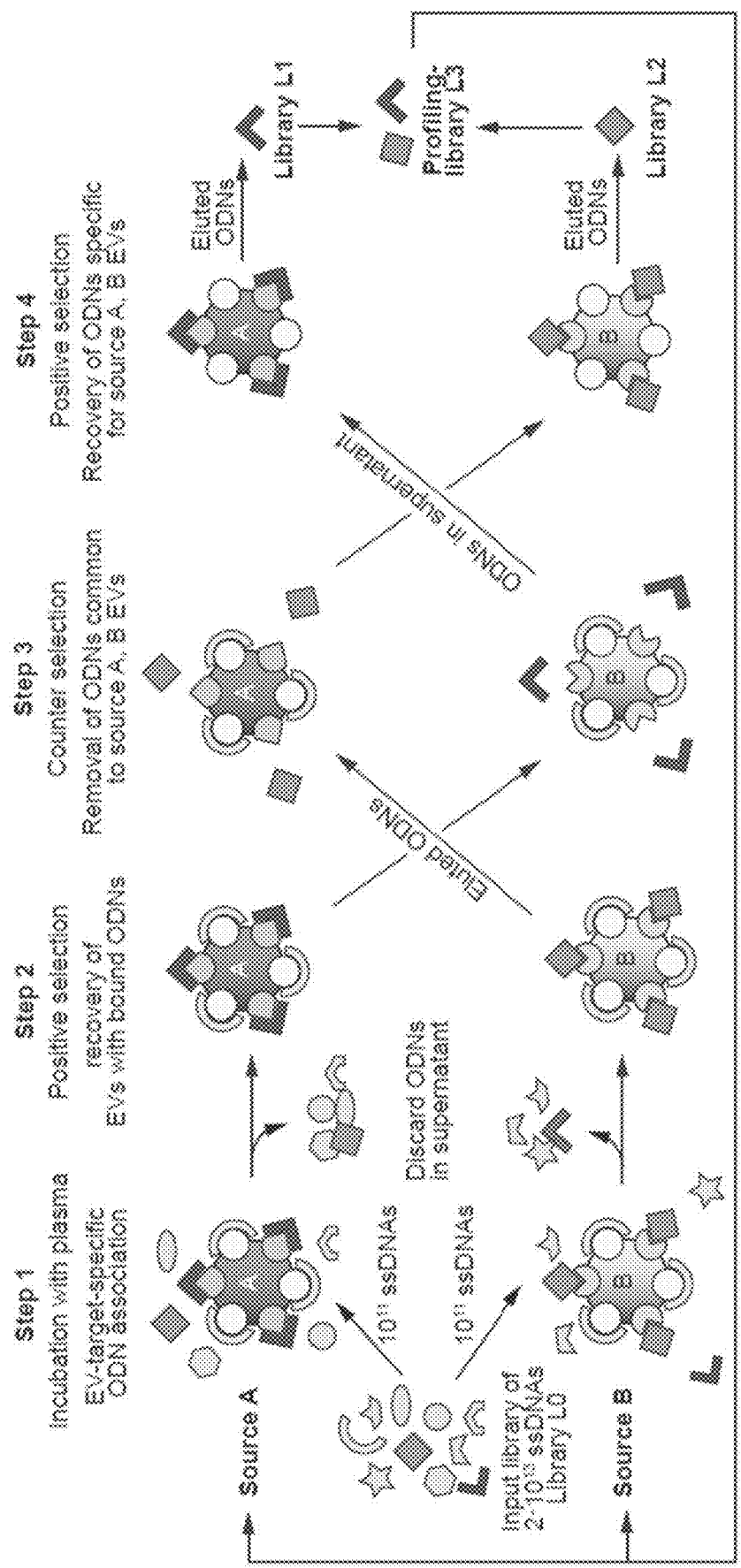
FIGS. 12A-C illustrate enriching a naïve oligonucleotide library with balanced design for oligonucleotides that differentiate between breast cancer and non-cancer microvesicles derived from plasma samples.

The L0 Library was enriched against fractionated plasma samples from breast cancer patients and from healthy (non-breast cancer) controls using the protocol shown in FIG. 12A. In Step 1, an aliquot of approximately $10^{11}$ sequences of PCR-amplified L0 was incubated with pooled blood-plasma from 59 breast cancer patients with positive biopsy (represented by "Source A" in FIG. 12A). In parallel, another aliquot of $10^{11}$ sequences was incubated with pooled blood-plasma from 30 patients with suspected breast cancer who proved negative on biopsy and 30 self declared healthy women (represented by "Source B" in FIG. 12A). In Step 2, microvesicles (extracellular vesicles, "EV") were precipitated using ultracentrifugation (UC) from both L0-samples. The EV-associated oligodeoxynucleotides (ODNs) were recovered from the respective pellets. In Step 3, a counter-selection step (Step 3) was carried out by incubation of each enriched library with plasma from the different cohorts to drive the selection pressure towards enrichment of ODNs specifically associated with each sample cohort. In this step, sequences contained in the EV pellets were discarded. In Step 4, a second positive selection was performed. In this step, the sequences contained in the respective supernatants (sn) from Step 3 were mixed with plasma from another aliquot of each positive control sample-population, and EVs were again isolated. EV-associated ODNs were recovered, representing two single-round libraries called library L1 for positive enrichment of cancer (positive biopsy) patients, and library L2 for the positive enrichment against control patients. In a final step, L1 and L2 were amplified by PCR, reverted to single stranded DNA (ssDNA), and mixed to yield library L3.

This enrichment scheme was iterated two times more using L3 as the input to further reduce the complexity of the profiling library to approximately $10^6$ different sequences. In Step 2, UC was used for partitioning of microvesicles, which may increase the specificity for the EV fraction. In Steps 3 and 4, partitioning was performed using PEG-precipitation. This procedure enriches for ODNs specific for each biological source. Library L3 contains those ODNs that are associated with targets characteristic for EV-populations from both sources, i.e. ODNs acting as aptamers that bind to molecules preferentially expressed in each source. A total of biopsy-positive (n=59), biopsy-negative (n=30), and self-declared normal (n=30) were used in the first round of L3 enrichment, while only the cancer and non-cancer samples were used in the subsequent rounds.

Figure 12C:
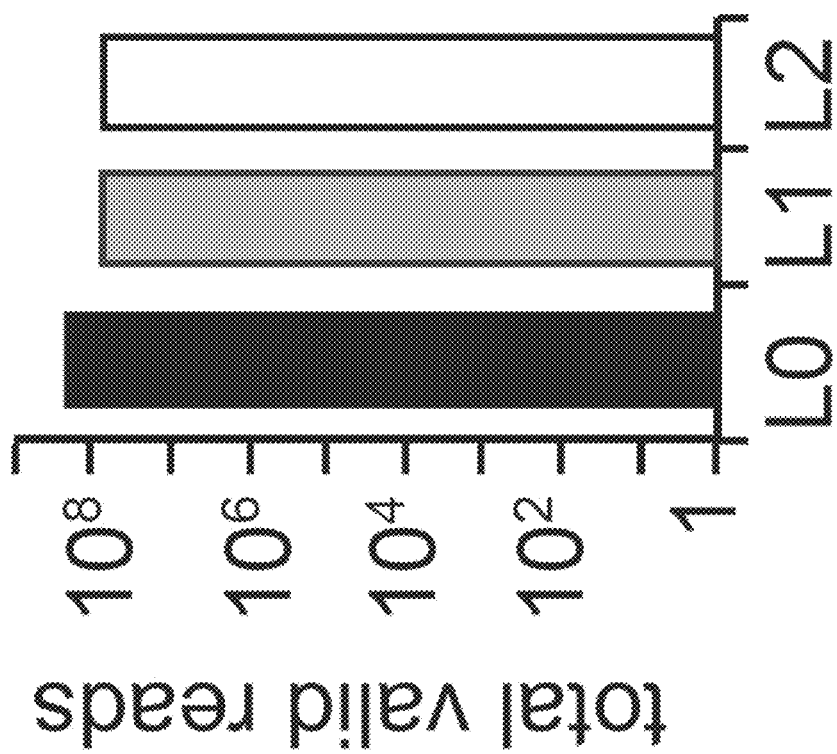
Figure 12B:
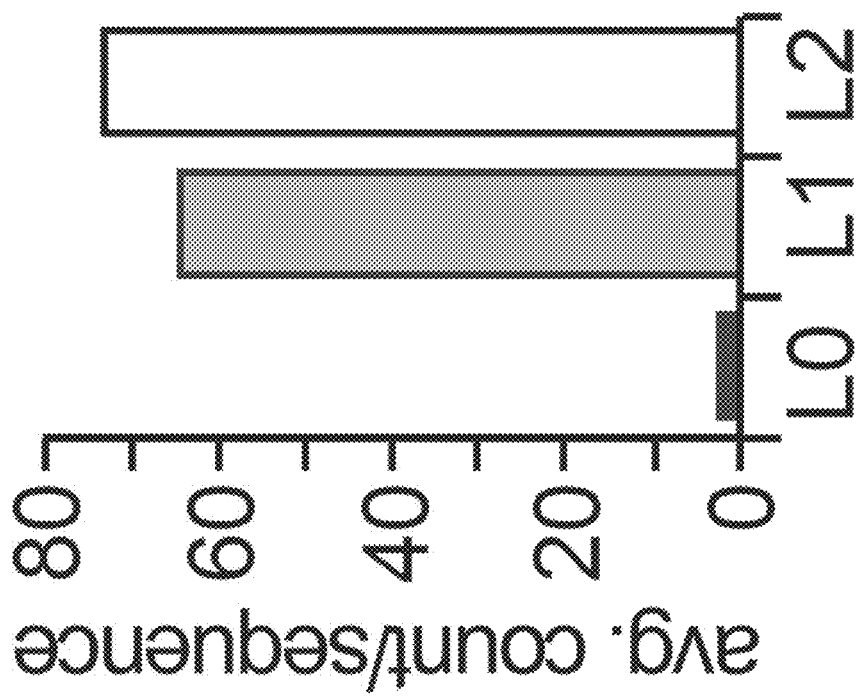

The enriched libraries were characterized using next-generation-sequencing (NGS) to measure copy numbers of sequences contained in each profiling library. NGS of L0 shows that the vast majority of sequences existed in low copy numbers, whereas libraries L1 and L2 showed significantly higher average counts per sequence (FIG. 12B) and a reduced amount of different sequences, with unaltered total valid reads, (FIG. 12C) consistent with an enrichment process.

Example 9

Analysis of ADAPT-Identified Biomarkers

As described herein, e.g., in the section entitled "Aptamer Target Identification," an unknown target recognized by an aptamer can be identified. In this Example, an oligonucleotide probe library (also referred to as Adaptive Dynamic Artificial Poly-ligand Targeting (ADAPT) libraries or Topographical Oligonucleotide Probe "TOP" libraries) was developed as described here and targets of the screened oligonucleotides were determined. This Example used a ADAPT library generated by enriching microvesicles collected from the blood of breast cancer patients and normal controls (i.e., non-cancer individuals). The enrichment protocols are described herein in Example 8.

Materials & Methods
SBED Library Conjugation

A naïve F-TRin-35n-B 8-3s library was enriched against microvesicles from normal female plasma. The naïve unenriched library comprised a 5' region (5' CTAG-CATGACTGCAGTACGT (SEQ ID NO. 4)) followed by the random naïve aptamer sequences of 35 nucleotides and a 3' region (5 CTGTCTCTTATACA-CATCTGACGCTGCCGACGA (SEQ ID NO. 5)). The naïve library may be referred to as the "L0 Library" herein and the enriched library referred to as the "L2 library." See Example 8. The screened library was PCR amplified with a C6-amine sense primer (C6 Amine-5' CTAG-CATGACTGCAGTACGT 3' (SEQ ID NO. 4)) and a 5' phosphorylated anti-sense primer (5' Phos TCGTCGGCAGCGTCA (SEQ ID NO. 6)), the purified product was strand separated and conjugated with sulfo-SBED (Thermo Scientific) according to Vinkenborg et al. (Angew Chem Int Ed Engl. 2012, 51:9176-80) with the following modifications: The reaction was scaled down to 5 μg C6-amine DNA library (8.6 μM) in 25 mM HEPES-KOH, 0.1M NaCl, pH 8.3 and incubated with either 100-fold molar excess of sulfo-SBED or DMSO in a 21 μL volume for 30 min at room temp in the dark. The SBED-conjugated library was immediately separated from the unconjugated library and free sulfo-SBED by injection onto a Waters X-Bridge™ OST C-18 column (4.6 mm×50 mm) and fractionated by HPLC (Agilent 1260 Infinity) with a linear gradient Buffer A: 100 mM TEAA, pH7.0, 0% ACN to 100 mM TEAA, pH7.0, 25% ACN at 0.2 ml/min, 65° C.

There SBED-conjugated fractions were desalted into water with Glen Gel-Pak™ Cartridges and concentrated by speed-vac. SBED conjugation was confirmed by LC-MS and/or a dot blot with streptavidin-HRP detection.

Binding Reaction and Cross-Linking

SBED library functionalization was tested by performing the ADAPT assay with SBED vs DMSO mock conjugated control C6-amine library and sequenced on a HiSeq 2500™ (Illumina Corp.). The aptamer precipitation was performed with forty-eight ADAPT reactions incubated for 1 hr with end-over-end rotation at room temp with a 5 ng input of SBED conjugated library per 200 µL of plasma (pre-spun to remove cellular debris at 10,000×g for 20 min, 4° C.) in 1×PBS, 3 mM MgCl$_2$, 0.01 mM dextran sulfate, 40 ng/µl salmon sperm DNA and 40 ng/µl yeast transfer RNA, and cOmplete ULTRA Mini EDTA-Free™ protease inhibitors (Roche) equivalent to ~240 ng library and 9.6 mls plasma. A duplicate set of 48 reactions was prepared with the DMSO control C6-amine library. Aptamer library-protein complexes were precipitated with incubation in 6% PEG8000 for 15 min at 4° C. then centrifuged at 10,000×g for 5 min. Pellets were washed with 1 ml 1×PBS, 3 mM MgCl2 by gentle inversion to remove unbound aptamers. The washed pellets were resuspended in 100 µL of water and subjected to photo-cross-linking at 365 nm with a hand-held 3UV (254 NM/302 NM/365 NM) lamp, 115 volts (Thermo Scientific) for 10 min on ice with 1-2 cm between the 96-well plate and lamp.

Oligonucleotide Precipitation

Cross-linked reactions were subsequently pooled (~4.8 ml) per library or 4.8 ml of 1×PBS (AP bead only control) and incubated with 10 µL of Prepared Dynabeads® My Oile™ Streptavidin C1 (10 mg/ml) (Life Technologies) (pre-washed with 1×PBS, 0.01% Triton X-100) shaking for 1 hr at room temp. Beads were transferred to an eppendorf tube and lysed for 20 min with lysis buffer (50 mM Tris-HCl, 10 mM MgCl2, 200 mM NaCl, 0.5% Triton X-100, 5% glycerol, pH 7.5) on ice, washed 3 times with wash buffer 1 (10 mM Tris-HCl, 1 mM EDTA, 2M NaCl, 1% Triton X-100), followed by 2 times with wash buffer 2 (10 mM Tris-HCl, 1 mM EDTA, 2M NaCl, 0.01% Triton X-100) as described by Vinkenborg et al. (Angew Chem Int Ed Engl. 2012, 51:9176-80). Cross-linked proteins were eluted by boiling 15 min in 1×LDS sample buffer with reducing agent added (Life Technologies) and loaded on a 4-12% SDS-PAGE gradient gel (Life Technology). Proteins and DNA were detected with double staining with Imperial Blue Protein Stain (Thermo Scientific) followed by Prot-SIL2™ silver stain kit (Sigma) used according to manufacturer's instructions in order to enhance sensitivity and reduce background.

Protein Identification

Protein bands that appeared to differ between the cancer and normal were excised from the gradient gels and subjected to liquid chromatography-tandem mass spectrometry (LC-MS/MS).

Results

Figure 6:
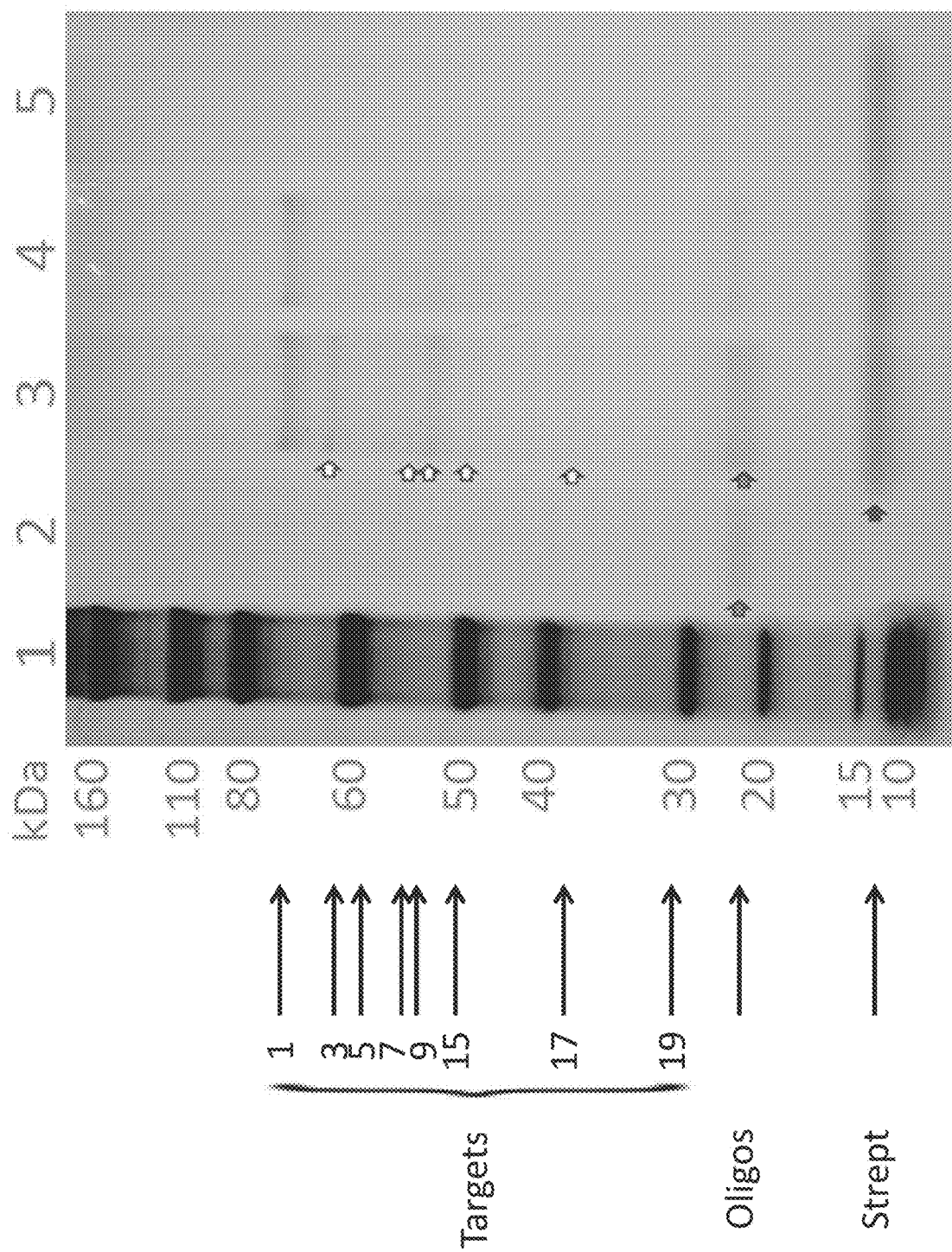
FIG. 6 shows protein targets of oligonucleotide probes run on a silver stained SDS-PAGE gel.

ADAPT protein targets were identified from bands cut from a silver stained SDS-PAGE gel (FIG. 6). Aptamer-SBED protein complexes (lane 3) or Aptamer-DMSO protein complexes (control-lane 4) were precipitated with 6% PEG8000, subjected to UV photo-cross-linking, and pulled-down with Streptavidin coated beads. Eluate was analyzed under reducing conditions by SDS-PAGE and silver staining Aptamer library alone (5 ng) (lane 1) was loaded as a control for migration of the library (second to bottom arrows) and an equal volume of eluate from a bead only sample (lane 4) was loaded as a streptavidin control to control for potential leaching of the streptavidin monomer (bottom arrow) under the harsh elution conditions. Upper arrows ("Targets") indicate specific or more predominant bands identified with the SBED-conjugated library vs. the mock DMSO treated control C6-amine library. Indicated target protein bands were cut out and sent for LC-MS/MS protein identification or indicated DNA library bands were eluted, reamplified and sequenced. The identified proteins are those that appeared as upregulated in the normal samples.

Tables 10-17 list human proteins that were identified in 8 bands excised from the silver stained gel. In all tables the proteins are those identified in the oligo-SBED protein complexes with proteins identified in the corresponding control lanes removed. The band numbers in the tables indicate different bands cut from the gel (FIG. 6). Accession numbers in the table are from the UniProt database (www.uniprot.org). "GN=" is followed by the gene name. Various protein classifications indicated in the Tables 10-17 include Nucleic Acid Binding Proteins (NAB), Tumor suppressors (TS), cell adhesion/cytoskeletal (CA/CK) and abundant plasma proteins (ABP).

TABLE 10

| Band 3 | | |
|---|---|---|
| Accession number | Class | Protein name |
| P02538 | CA/CK | Keratin, type II cytoskeletal 6A GN = KRT6A |
| P15924 | CA/CK | Desmoplakin GN = DSP |
| P04259 | CA/CK | Keratin, type II cytoskeletal 6B GN = KRT6B |
| P60709 | CA/CK | Actin, cytoplasmic 1 GN = ACTB |
| P20930 | CA/CK | Filaggrin GN = FLG |
| P07476 | CA/CK | Involucrin GN = IVL |
| P31947 | TS | 14-3-3 protein sigma GN = SFN |
| Q7Z794 | CA/CK | Keratin, type II cytoskeletal 1b GN = KRT77 |
| P02545 | NAB | Prelamin-A/C GN = LMNA |
| P19012 | CA/CK | Keratin, type I cytoskeletal 15 GN = KRT15 |
| P47929 | CA/CK & TS | Galectin-7 GN = LGALS7 |
| P11142 | | Heat shock cognate 71 kDa protein GN = HSPA8 |
| P58107 | NAB | Epiplakin GN = EPPK1 |
| P08107 | | Heat shock 70 kDa protein 1A/1B GN = HSPA1A |
| Q02413 | CA/CK | Desmoglein-1 GN = DSG1 |
| P06396 | CA/CK | Gelsolin GN = GSN |
| O60814 | NAB | Histone H2B type 1-K GN = HIST1H2BK |
| P68104 | NAB | Elongation factor 1-alpha 1 GN = EEF1A1 |

TABLE 10-continued

Band 3

| Accession number | Class | Protein name |
|---|---|---|
| P05387 | NAB | 60S acidic ribosomal protein P2 GN = RPLP2 |
| Q7RTS7 | CA/CK | Keratin, type II cytoskeletal 74 GN = KRT74 |
| P31946 | TS | 14-3-3 protein beta/alpha GN = YWHAB |
| Q13835 | CA/CK | Plakophilin-1 GN = PKP1 |
| P14923 | CA/CK | function plakoglobin GN = JUP |
| P09651 | NAB | Heterogeneous nuclear ribonucleoprotein A1 GN = HNRNPA1 |
| P07900 | | Heat shock protein HSP 90-alpha GN = HSP90AA1 |
| Q96KK5 | NAB | Histone H2A type 1-H GN = HIST1H2AH |
| P04406- | CA/CK | Glyceraldehyde-3-phosphate dehydrogenase GN = GAPDH |
| P10412 | NAB | Histone H1.4 GN = HIST1H1E |
| P04792 | | Heat shock protein beta-1 GN = HSPB1 |
| Q9NZT1 | | Calmodulin-like protein 5 GN = CALML5 |
| P81605 | | Dermcidin GN = DCD |
| P27348 | TS | 14-3-3 protein theta GN = YWHAQ |
| P55072 | NAB | Transitional endoplasmic reticulum ATPase GN = VCP |
| Q09666 | NAB | Neuroblast differentiation-associated protein AHNAK GN = AHNAK |
| P23246 | NAB | Splicing factor, proline- and glutamine-rich GN = SFPQ |
| Q15149 | CA/CK | Plectin GN = PLEC |
| Q8NC51 | NAB | Plasminogen activator inhibitor 1 RNA-binding protein GN = SERBP1 |
| P07237 | | Protein disulfide-isomerase GN = P4HB |
| O60437 | CA/CK | Periplakin GN = PPL |
| P01717 | ABP | Ig lambda chain V-IV region Hil |
| P55884 | NAB | Eukaryotic translation initiation factor 3 subunit B GN = EIF3B |
| P11021 | | 78 kDa glucose-regulated protein GN = HSPA5 |
| P01024 | | Complement C3 GN = C3 |
| P04350 | CA/CK | Tubulin beta-4A chain GN = TUBB4A |
| P01857 | ABP | Ig gamma-1 chain C region GN = IGHG1 |
| P61247 | NAB | 40S ribosomal protein S3a GN = RPS3A |
| P62937 | | Peptidyl-prolyl cis-trans isomerase A GN = PPIA |
| O15020 | CA/CK | Spectrin beta chain, non-erythrocytic 2 GN = SPTBN2 |
| P30101 | | Protein disulfide-isomerase A3 GN = PDIA3 |
| Q6KB66 | CA/CK | Keratin, type II cytoskeletal 80 GN = KRT80 |
| Q9UJU6 | CA/CK | Drebrin-like protein GN = DBNL |
| P47914 | NAB | 60S ribosomal protein L29 GN = RPL29 |
| P39023 | NAB | 60S ribosomal protein L3 GN = RPL3 |
| A6NMY6 | CA/CK | Putative annexin A2-like protein GN = ANXA2P2 |
| P60174 | CA/CK | Triosephosphate isomerase GN = TPI1 |
| P35241 | CA/CK | Radixin GN = RDX |
| P07305 | NAB | Histone H1.0 GN = H1F0 |
| P15259 | CA/CK | Phosphoglycerate mutase 2 GN = PGAM2 |
| P0CG05 | ABP | Ig lambda-2 chain C regions GN = IGLC2 |
| Q92817 | CA/CK | Envoplakin GN = EVPL |
| P06733 | NAB | MBP-1 of Alpha-enolase GN = ENO1 |
| P22626 | NAB | Heterogeneous nuclear ribonucleoproteins A2/B1 GN = HNRNPA2B1 |
| P62424 | NAB | 60S ribosomal protein L7a GN = RPL7A |
| P60660 | CA/CK | Myosin light polypeptide 6 GN = MYL6 |
| P04083 | NAB | Annexin A1 GN = ANXA1 |
| Q14134 | NAB | Tripartite motif-containing protein 29 GN = TRIM29 |
| P39019 | NAB | 40S ribosomal protein S19 GN = RPS19 |
| Q8WVV4 | CA/CK | Protein POF1B GN = POF1B |
| Q02878 | NAB | 60S ribosomal protein L6 GN = RPL6 |
| Q9Y6X9 | NAB | MORC family CW-type zinc finger protein 2 GN = MORC2 |
| Q9NQC3 | NAB | Reticulon-4 GN = RTN4 |
| Q5T753 | CA/CK | Late cornified envelope protein 1E GN = CA/CK E |

TABLE 11

Band 9

| Accession number | Class | Protein name |
|---|---|---|
| P61626 | | Lysozyme C GN = LYZ |
| Q9HCK1 | NAB | DBF4-type zinc finger-containing protein 2 GN = ZDBF2 |

TABLE 12

Band 1

| Accession number | Class | Protein name |
|---|---|---|
| P01834 | ABP | Ig kappa chain C region GN = IGKC |
| P01765 | ABP | Ig heavy chain V-III region TIL |
| P04003 | NAB | C4b-binding protein alpha chain GN = C4BPA |
| P60709 | CA/CK | Actin, cytoplasmic 1 GN = ACTB |
| Q5T751 | CA/CK | Late cornified envelope protein 1C GN = LCE1C |

TABLE 13

Band 5

| Accession number | Class | Protein name |
|---|---|---|
| P01860 | ABP | Ig gamma-3 chain C region GN = IGHG3 |
| O60902 | NAB | Short stature homeobox protein 2 GN = SHOX2 |

TABLE 14

Band 7

| Accession number | Class | Protein name |
|---|---|---|
| Q04695 | CA/CK | Keratin, type I cytoskeletal 17 GN = KRT17 |
| Q7Z794 | CA/CK | Keratin, type II cytoskeletal 1b GN = KRT77 |
| Q6KB66 | CA/CK | Keratin, type II cytoskeletal 80 GN = KRT80 |
| P01833 | | Polymeric immunoglobulin receptor GN = PIGR |
| P01042 | | Kininogen-1 GN = KNG1 |
| Q02413 | CA/CK | Desmoglein-1 GN = DSG1 |
| P15924 | CA/CK | Desmoplakin GN = DSP |
| Q8TF72 | | Protein Shroom3 GN = SHROOM3 |
| P02671 | ABP | Fibrinogen alpha chain GN = FGA |
| Q5T749 | CA/CK | Keratinocyte proline-rich protein GN = KPRP |
| Q5VZP5 | | Inactive dual specificity phosphatase 27 GN = DUSP27 |
| Q5T751 | CA/CK | Late cornified envelope protein 1C GN = LCE1C |
| Q9UL12 | | Sarcosine dehydrogenase, mitochondrial GN = SARDH |
| P00698 | | Lysozyme C OS = *Gallus gallus* GN = LYZ |
| Q8N114 | | Protein shisa-5 GN = SHISA5 |

TABLE 15

Band 15

| Accession number | Class | Protein name |
|---|---|---|
| P08238 | | Heat shock protein HSP 90-beta GN = HSP90AB1 |
| P68104 | NAB | Elongation factor 1-alpha 1 GN = EEF1A1 |
| P02675 | ABP | Fibrinogen beta chain GN = FGB |
| Q8TF72 | | Protein Shroom3 GN = SHROOM3 |
| P0CG05 | ABP | Ig lambda-2 chain C regions GN = IGLC2 |
| P78386 | CA/CK | Keratin, type II cuticular Hb5 GN = KRT85 |
| Q7Z5Y6 | | Bone morphogenetic protein 8A GN = BMP8A |
| O14633 | CA/CK | Late cornified envelope protein 2B GN = LCE2B |

TABLE 16

Band 17

| Accession number | Class | Protein name |
|---|---|---|
| P02538 | CA/CK | Keratin, type II cytoskeletal 6A GN = KRT6A |
| P01834 | ABP | Ig kappa chain C region GN = IGKC |
| P06702 | | Protein S100-A9 GN = S100A9 |
| P68104 | NAB | Elongation factor 1-alpha 1 GN = EEF1A1 |
| P01024 | | Complement C3 GN = C3 |
| P81605 | | Dermcidin GN = DCD |
| P05109 | | Protein S100-A8 GN = S100A8 |
| Q5T751 | CA/CK | Late cornified envelope protein 1C GN = LCE1C |

TABLE 17

Band 19

| Accession number | Class | Protein name |
|---|---|---|
| P02768 | NAB | Serum albumin GN = ALB |
| P0CG05 | ABP | Ig lambda-2 chain C regions GN = IGLC2 |
| P06702 | | Protein S100-A9 GN = S100A9 |
| P08238 | | Heat shock protein HSP 90-beta GN = HSP90AB1 |
| P60709 | CA/CK | Actin, cytoplasmic 1 GN = ACTB |
| P13647 | CA/CK | Keratin, type II cytoskeletal 5 GN = KRT5 |
| P01616 | ABP | Ig kappa chain V-II region MIL |
| Q86YZ3 | CA/CK | Homerin GN = HRNR |
| P01857 | ABP | Ig gamma-1 chain C region GN = IGHG1 |
| P62805 | NAB | Histone H4 GN = HIST1H4A |
| P59665 | | Neutrophil defensin 1 GN = DEFA1 |
| P61626 | | Lysozyme C GN = LYZ |
| P01024 | ABP | Complement C3 GN = C3 |
| Q8TF72 | | Protein Shroom3 GN = SHROOM3 |
| P83593 | ABP | Ig kappa chain V-IV region STH (Fragment) |
| P01700 | ABP | Ig lambda chain V-I region HA |
| P01877 | ABP | Ig alpha-2 chain C region GN = IGHA2 |
| Q9UL12 | | Sarcosine dehydrogenase, mitochondrial GN = SARDH |
| Q6NXT2 | NAB | Histone H3.3C GN = H3F3C |
| P02788 | NAB | Lactotransferrin GN = LTF |
| P02787 | ABP | Serotransferrin GN = TF |

Certain proteins were identified in multiple bands. For example, IGLC2 was identified in bands 3, 15 and 19 and SHROOM3 was identified in bands 7, 15, 19. This may be due to degradation products, isoforms or the like. These experiments identified 108 proteins (plus 2 lysozyme controls), comprising among others 34 Nucleic Acid Binding Proteins (NAB) where 7 of the 34 are putative tumor suppressors/repressors; 37 cell adhesion/cytoskeletal (CA/CK); and 14 abundant plasma proteins (ABP). All of the tumor suppressors/repressors are DNA/RNA binding proteins. Other proteins comprise chaperones, signaling molecules etc.

The biomarkers in this Example can be used to detect microvesicles that are indicative of cancer or non-cancer samples.

Example 10

Identification of Biomarkers Through Affinity Enrichment with an Enriched Oligonucleotide Library and Mass Spectrometry This Example continues upon the Example above. Identification of protein-protein and nucleic acid-protein complexes by affinity purification mass spectrometry (AP-MS) can be hampered in samples comprising complex mixtures of biological components (e.g., bodily fluids including without limitation blood and derivatives thereof). For example, it may be desirable to detect low abundance protein and nucleic acid-protein complexes in a complex milieu comprising various components that may interact promiscuously with specific binding sites such as high abundance proteins that interact non-specifically with the affinity resin. AP-MS has been used previously to enrich for pre-identified targets of interest using individual DNA or RNA aptamers or specific nucleic acid binding domains. In this Example, an enriched oligonucleotide probing library was used as the affinity reagent. This approach combined with mass spectrometry enables the identification of differentially expressed biomarker from different disease states or cellular perturbations without relying on a priori knowledge of the targets of interest. Such biomarker may comprise proteins, nucleic acids, miRNA, mRNA, carbohydrates, lipid targets, combinations thereof, or other components in a biological system.

The method comprises identification of an enriched oligonucleotide probe library according to the methods of the invention followed by target identification with affinity purification of the bound probing library and mass spectrometry. The members of the enriched oligonucleotide probing library comprise an affinity tag. A biological sample is probed with the oligonucleotide probe library, affinity purification of the oligonucleotide probe library via the affinity tag is performed which will accordingly purify biological entities in complex with various members of the probe library, and read-out of targets that purified with the members of the probe library is performed using liquid chromatography-tandem mass spectrometry (LC-MS/MS) for proteins or oligonucleotide targets (e.g., miRNA or mRNA) with next generation sequencing (NGS). Confirmation of protein targets is performed using quantitative mass spectrometry (MS), e.g., using MRM/SRM or SWATH based methods.

The method of the Example lends itself to various options. For example, any appropriate affinity tags can be used for affinity pull-down, including without limitation anti-sense oligonucleotides, biotin, polyhistidine, FLAG octapeptide (i.e., N-DYKDDDDK-C (SEQ ID NO. 7), where N stands for Amino-terminus and C stands for Carboxy terminus), 3×FLAG, Human influenza hemagglutinin (HA)-tag (i.e., N-YPYDVPDYA-C (SEQ ID NO. 8)), myc-tag (N-EQKLISEEDL-C (SEQ ID NO. 9)), other such as known in the art, and combinations thereof. Similarly, any appropriate enrichment support can be used in addition to the magnetic streptavidin beads exemplified herein, including without limitation other bead systems, agarose beads, planar arrays or column chromatography supports. It follows that the various supports can be coupled with the various affinity reagents appropriate for the oligonucleotide library, including without limitation streptavidin, avidin, anti-His tag antibodies, nickel, and the like. The different affinity tags and supports can be combined as desired. This Example used cross-linking but in certain cases such cross-linking is not necessary and may even be undesirable, e.g., to favor identification of high affinity complex formation. When cross-linking is desired, any appropriate cross-linkers can be used to carry out the invention, including BS2G, DSS, formaldehyde, and the like. Other appropriate cross-linkers and methods are described herein. See, e.g., Section "Aptamer Target Identification." Lysis buffers and wash stringencies can be varied, e.g, depending on whether complexes are cross-linked or not. Less stringent lysis/wash conditions may produce a wider array of potential protein complexes of interest whereas more stringent lysis/wash conditions may favor higher affinity oligo-target complexes and/or targets comprising specific proteins (e.g., by disassociating larger complexes bound to the oligos). One of skill will further appreciate that qualitative and/or quantitative LC-MS/MS may be used for target detection and verification. Similarly, metabolic labeling and label-free approaches may be used for quantitative MS, including without limitation spectral counting, SILAC, dimethyl labeling, TMT labeling, Targeted MS with SRM/MRM or SWATH, and the like.

References

Vickenborg et al. "Aptamer based affinity labeling of proteins", Angew Chem Int. 51(36):9176-80 (2012).

Tacheny, M, Arnould, T., Renard, A. "Mass spectrometry-based identification of proteins interacting with nucleic acids", Journal of Proteomics 94; 89-109 (2013).

Faoro C and Ataide S F. "Ribonomic approaches to study the RNA-binding proteome.", FEBS Lett. 588(20):3649-64 (2014).

Budayeva H G, Cristea, I M, "A mass spectrometry view of stable and transient protein interactions." Adv Exp Med Biol. 806:263-82 (2014).

Example 11

Protocol for Affinity Capture Using Oligonucleotide Probing Library

This Example presents a detailed protocol for the method of affinity capture using an oligonucleotide probing library presented in the Example above.

Protocol:

The oligonucleotide probe library comprises F-TRin-35n-B-8-3s described herein either desthiobiotin labeled or unlabeled library and binding to normal (i.e., non-cancer) female plasma. The oligonucleotide probe library is enriched against the plasma samples as described elsewhere (e.g., in Example 7). The plasma samples are processed separately against the desthiobiotin labeled or unlabeled oligonucleotide libraries. General parameters included the following:

48 normal plasma samples are pooled for enrichment of each oligonucleotide library (Desthiobiotin or Unlabeled)

200 µl input plasma per sample

Ultracentrifugation (UC) is used to pre-clear the samples 5 ng of each aptamer library is added to each sample Binding competitors for all library samples include 0.01× Si (dextran sulfate), 340 ng for tRNA and 340 ng Salmon sperm DNA as described elsewhere herein 6% PEG 8000 is used for precipitation of microvesicles within the samples Affinity purification is performed with C1 Streptavidin beads (MyOne Strptavidin Beads C1-65001, lot 2 ml (10 mg/ml))

Buffers:

Plasma dilution: 6 mM MgCl2 in 2×PBS

Pellet Wash Buffer: 1×PBS, 3 mM MgCl2

PEG Ppt Buffer: 20% Peg8000 in 1×PBS, 3 mM MgCl2

Bead Prep Buffer: 1×PBS containing 0.01% Triton X-100

Lysis Buffer: prepare a 2× stock solution consisting of 100 mM Tris-HCl, 20 mM MgCl2, 400 mM NaCl, 1% Triton X-100, 10% glycerol, pH 7.5. Diluted to 1× with water 1:1 prior to using.

AP Wash buffer 1: 10 mM Tris-HCl, 1 mM EDTA, 2M NaCl, 1% Triton X-100, pH 7.5

AP wash buffer 2: 10 mM Tris-HCL, 1 mM EDTA, 2M NaCl, 0.01% Triton X-100, pH 7.5

Biotin Elution buffer 1: 5 mM Biotin, 20 mM Tris, 50 mM NaCl, pH 7.5

1×LDS, 1× Reducing buffer 2

Reagent/Instrument Prep:

Pre-chill Ultracentrifuge to 4° C.

Protease inhibition: dissolve 2 tablets of "cOmplete ULTRA MINI EDTA-free EASYpack" protease inhibitor in 1100 µl of H2O (20× stock of protease inhibitor).

Plasma Preparation (for each of Desthiobiotin or Unlabeled Oligonucleotide Libraries):

1. Add 50 µl of protease inhibitor to each ml of sample (on top of frozen plasma) in a room temperature (RT) water bath. Will use 20 mls of pooled plasma, so 1100 µl inhibitor.

2. To remove cell/debris, spin samples at 7500×g 20 min, 4° C. in the Ultracentrifuge.

3. Collect the supernatant, pool and measure volume & record.

4. Add an equal volume of 2×PBS, 6 mM $MgCl_2$ to the plasma.

5. Label low-retention eppendorf tubes 1-96.

6. Transfer 400 µl of each sample to eppendorf tubes based on appropriate tube map 7. Using an electronic P200, add competitors: 8.6 µl of 40 ng/µl Salmon sperm DNA; 8.6 µl of 40 ng/µl tRNA; 8.6 µl of 0.5× S1.

8. Incubate at RT with end over end rotation for 10 min.

9. Add 10 µL of appropriate oligo library, mix well. Save any leftover diluted library for gel control (see below).

10. Incubate 1 hr at RT with end over end rotation.

11. Using an electronic repeat P100, add 187 µl of 20% PEG 8000 to sample for a final 6% concentration to the 435.5 µl of sample/oligo library. Invert a few times to mix and incubate for 15 min at 4° C.

12. Spin each sample in table top centrifuge at 10,000×g for 5 min.

13. Remove supernatant and discard, add 1 ml 1×PBS, 3 mM $MgCl_2$ to pellet.

14. Wash pellet by gentle inversion

15. Remove buffer, re-suspend pellets in 100 µl 1×PBS, 3 mM $MgCl_2$: incubate at RT for 10 min on mixmate@900 rpm to re-suspend. Make sure each sample is well re-suspended by pipetting.

16. Pool all desthiobiotin library samples into one 50 ml falcon tube, and the unlabeled library into another, total volume for each should be 4800 µl.

17. Take 10 µL aliquot for the input into AP sample for gel (add 10 µL of 2×LDS buffer w/2× reducing agent.

Affinity Purification:

18. Prepare 10 µL of MyOne Strep-coated Magnetic beads per each condition into a 1.5 ml eppendorf tube and place on a magnetic bead rack. Have a Bead only control as well (n=3)

19. Remove supernatant and wash 1×500 µl with Bead buffer.

20. Discard supernatant

21. Resuspend beads in an equal volume of 1×PBS, 3 mM $MgCl_2$ (equal vol to what was taken out originally=10 µl)

22. Add the 10 µl of beads directly to the 4780 µL from step 19. To Bead only control add PBS.

23. Incubate samples with streptavidin beads 1 hr RT on plate shaker (taped).

24. Place on the large magnetic stand for 1 min and remove supernatant

25. Add 1.5 mL of 1× lysis buffer to the samples (do 3×500 µl with a good rinse of the 50 mL falcon tube for each to collect all the beads) and transfer to a new set of eppendorf tubes.

26. Incubate for 20 min on ice.

27. Place tubes in magnetic bead rack, let equilibrate 1 min and remove the supernatant.

28. Wash the beads with wash buffer #1 via vortexing. Resuspend well.

29. Place tubes on magnetic bead rack, let equilibrate 1 min and remove the supernatant 30. Wash 2 additional times as with wash buffer #1 steps 27-29 (total 3 washes with wash buffer #1)

31. Repeat steps 27-29 (2) additional times with wash buffer #2

32. During the last wash transfer beads to a new eppendorf tube. (to reduce non-specific binding)

33. Do one dry spin to make sure all residual wash buffer is removed.

34. Add 10 µl of Biotin Elution buffer 1 to beads

35. Incubate for 15 minutes at 37° C.

36. Place on magnetic stand for 1 min, collect sup and transfer to a new tube, add 10 µL of 2× LDS, 2× Reducing agent to eluted sample. Save as Elution #1.

37. Add 10 µl of 1×LDS Sample Buffer, 1× Reducing buffer to magnetic beads.

38. Boil the samples for 15 min at 90° C. The boiling time is 15 minutes to essure the streptavidin on the beads unfolds and releases the biotinylated aptamer-protein complex.

39. Place samples on magnetic stand on ice and collect the eluted sample. This is Elution #2. Discard the beads.

40. Gel 1 layout:

Lane 1: 5 ng Desthiobiotin library
Lane 2: 1×LDS
Lane 3: Marker
Lane 4: Desthiobiotin Elution #1
Lane 5: Unlabeled Elution #1
Lane 6: Bead only Elution #1
Lane 7: Desthiobiotin Elution #2
Lane 8: Unlabeled Elution #2
Lane 9: Bead only Elution #2
Lane 10: Input for AP (saved from step 17)

Running Reducing SDS Gel:

Prepare 1×MOPS SDS Running Buffer from 20×MOPS SDS Buffer

Use 10 or 12 well 4-12% Bis Tris gel

Peel off tape seal and place in the gel box. Insert spacer for second gel cassette if needed Fill the inside/upper chamber with running buffer MOPS (1×) and 500 ul Antioxidant Remove the comb carefully, not disturbing the wells Rinse the wells with the running buffer to remove the storage buffer which can interfere with sample running Slowly load samples to each well carefully using L-20 tip Fill the outer/lower chamber with approximately 600 ml of running buffer MOPS (1×)

Place top portion of unit and secure correct electrodes

Run the gel to migrate proteins

100 V constant for samples to move through stack (until all samples line up) for 15 min Increase to 150 V constant for running (until visible sample buffer comes to bottom) for ~1 hr At the end of the run, stop the power supply and remove the gel cassettes from cell Disassemble the gel cassette by with gel knife.

Remove one side of cassette case. Trim off the gel foot and wells (avoid drying gel).

Transfer gel into container filled with Milli Q water and perform a quick wash.

Silver Staining:

Materials:

ProteoSilver TMSilver Stain Kit, Sigma Catalog No. PROT-SIL 1, Lot No. SLBJ0252V Ethanol, Fisher Scientific Catalog No. BP2818-4, Lot No. 142224

Acetic acid, Acros organics Catalog No. 14893-0025, Lot No. B0520036

Water, Sigma Catalog No. W4502, Lot No. RNBD1581

Preparation:

1. Fixing solution. Add 50 ml of ethanol and 10 ml of acetic acid to 40 ml of ultrapure water.

2. 30% Ethanol solution. Add 30 ml of ethanol to 70 ml of ultrapure water.

3. Sensitizer solution. Add 1 ml of ProteoSilver Sensitizer to 99 ml of ultrapure water. The prepared solution should be used within 2 hours. A precipitate may form in the Proteo-Silver Sensitizer. This precipitate will not affect the performance of the solution. Simply allow the precipitate to settle and remove 1 ml of the supernatant.

4. Silver solution. Add 1 ml of ProteoSilver Silver Solution to 99 ml of ultrapure water. The prepared solution should be used within 2 hours.

5. Developer solution. Add 5 ml ProteoSilver Developer 1 and 0.1 ml ProteoSilver Developer 2 to 95 ml of ultrapure water. The developer solution should be prepared immediately (<20 minutes) before use.

6. All steps should be carried out in the hood and waste needs to be collected in toxic designated container.

Procedure

A. Direct Silver Staining

All steps are carried out at room temperature on an orbital shaker at 60 to 70 rpm.

1. Fixing—After electrophoresis of the proteins in the mini polyacrylamide gel, place the gel into a clean tray with 100 ml of the Fixing solution overnight in the hood. Cover tightly.

2. Ethanol wash—Decant the Fixing solution and wash the gel for 10 minutes with 100 ml of the 30% Ethanol solution.

3. Water wash—Decant the 30% Ethanol solution and wash the gel for 10 minutes with 200 ml of ultrapure water.

4. Sensitization—Decant the water and incubate the gel for 10 minutes with 100 ml of the Sensitizer solution.

5. Water wash—Decant the Sensitizer solution and wash the gel twice, each time for 10 minutes with 200 ml of ultrapure water.

6. Silver equilibration—Decant the water and equilibrate the gel for 10 minutes with 100 ml of the Silver solution.

8. Water wash—Decant the Silver solution and wash the gel for 1 to 1.5 minutes with 200 ml of ultrapure water.

9. Gel development—Decant the water and develop the gel with 100 ml of the Developer solution. Development times of 3 to 7 minutes are sufficient to produce the desired staining intensity for most gels. Development times as long as 10 to 12 minutes may be required to detect bands or spots with very low protein concentrations (0.1 ng/mm2)

10. Stop—Add 5 ml of the ProteoSilver Stop Solution to the developer solution to stop the developing reaction and incubate for 5 minutes. Bubbles of $CO_2$ gas will form in the mixture.

11. Storage—Decant the Developer/Stop solution and wash the gel for 15 minutes with 200 ml of ultrapure water. Store the gel in fresh, ultrapure water and take picture for documentation.

Protein Identification

Protein bands of interest were excised from the gradient gels and subjected to liquid chromatography-tandem mass spectrometry (LC-MS/MS) as above.

Example 12

Use of an Oligonucleotide Probe Library to Characterize Breast Cancer Samples

An oligonucleotide probe library comprising approximately 2000 different probe sequences was constructed and used to probe approximately 500 individual breast cancer and non-cancer samples. The probe sequences were derived from different screening experiments and are listed herein in SEQ ID NOs 10-2921. The oligonucleotides listed in these tables were synthesized and pooled together. The samples were plasma samples from 212 breast cancer patients, 177 biopsy confirmed non-cancer patients, and 117 normal control patients (self-reported as non-cancer). The plasma samples were contacted with the oligonucleotide probe library and microvesicles were isolated using PEG precipitation. Oligonucleotides that were recovered with the microvesicles were isolated. Next Generation Sequencing (Illumina HiSeq) was used to identify the isolated sequences for each sample.

Analysis of significance of difference identified 18 aptamers with p-values below 0.01 when compared Cancer/Normal, 15 aptamers with p-values below 0.001 when compared cancer/Non-Cancer, 28 aptamers with p-values below 0.001 when compared Non-Cancer/Normal.

Multi-oligonucleotide panels were next contructed using a cross-validation approach. Briefly, 50 samples were randomly withheld from the sample cohort. The performance of individual oligonucleotides to distinguish the remaining cancers and non-cancer/normals was determined using logistic regression methodology. Additional oligonucleotides were added iteratively and performance was assessed using logistic regression until further performance improvements were no longer obtained with additional oligonucleotides. The approach generally led to panels of approximately 20-100 different probe sequences. The contructed panels were then used to classify the 50 withheld samples and diagnostic performance was assessed using Receiver Operating Curve (ROC) analysis and estimation of the Area under the Curve (AUC).

In approximately 300 rounds of cross-validation, the average AUC was 0.6, thus showing that the average performance was statistically better than random (i.e., AUC of 0.5) and that the probe library could distinguish breast cancer and non-breast cancer/normal patient samples. AUC values as high as 0.8 were observed for particular cross validations. FIGS. 7A-B illustrate a model generated using a training (FIG. 7A) and test (FIG. 7B) set from a round of cross validation. The AUC was 0.803. The variable regions of the sequences used to build this model are shown in Table 18. Another exemplary round of cross-validation is shown in FIGS. 7C-D. The AUC was 0.678.

The SEQ ID NOs. of the sequences used in the model in FIGS. 7A-B are listed in rank in Table 18. The oligonucleotides were synthesized with a 5' region consisting of the sequence (5'-CTAGCATGACTGCAGTACGT (SEQ ID NO. 4)) and a 3' region consisting of the sequence (5'-CTGTCTCTTATACACATCTGACGCTGCCGACGA (SEQ ID NO. 5)) flanking the variable regions.

TABLE 18

| Oligonucleotide Probe Variable Regions Rank Ordered SEQ ID NOs |
|---|
| 88, 1057, 834, 1608, 653, 1090, 2803, 499, 2587, 1082, 237, 2873, 2886, 759, 287, 390, 472, 119, 289, 96, 380, 459, 1226, 1331, 1012, 2542, 1284, 2765, 2528, 334, 1688, 949, 172, 1180, 832, 658, 195, 509, 1015, 538, 465, 696, 41, 954, 2771, 55, 407, 1351, 2524, 2760, 1728, 2600, 1731, 729, 2920, 156, 1322, 1745, 478, 236, 139, 2911, 2013, 1077, 525, 507, 2534, 1041, 1499, 766, 1037, 1143, 912, 1502, 968, 1420 |

The data presented in this Example demonstrate that an oligonucleotide pool comprising members having the variable regions listed in SEQ ID NOs 10-2921, e.g., a pool of probes having the variable regions listed in Table 18, can be used to distinguish plasma from individuals having breast cancer versus plasma from non-breast cancer individuals.

Example 13

Single Stranded DNA (ssDNA) Oligonucleotide Library Preparation for Library Development The preparation of high yield and high quality ssDNA libraries is a critical step in SELEX (Systematic Evolution of Ligands by EXponential enrichment) [1, 2] as well as in other biological applications, such as DNA chips and microarrays [3], and single-stranded conformation polymorphism technique (SSCP) [4]. The standard approach for preparing ssDNA libraries includes PCR amplification to first generate a double stranded (dsDNA) library, followed by ssDNA separation and purification. Several strategies of ssDNA preparation have been developed to date, each with advantages and disadvantages:

Lambda Exonuclease Digestion [2, 5-7]

The dsDNA standard PCR product is followed by Lambda exonuclease to digest the complementary strand and leave the target ssDNA. ssDNA purification is then performed to remove enzymes and unwanted buffer.

Advantages: Regular PCR amplification has high yield in generating dsDNA.

Disadvantages: The purity of final ssDNA is limited by enzyme digestion efficiency. Also dsDNA needs to be purified prior to digestion, together with post-digestion purification there will be two purifications, which results in substantial loss of input material. The digestion usually requires at least 2 hours. The digestion rate may not be consistent.

Asymmetric PCR [8, 9]

The procedure generates target ssDNA as the main product and less dsDNA products and non-target ssDNA. The band corresponding to the target ssDNA is cut from a native gel.

Advantages: The final ssDNA product potentially has high purity.

Disadvantages: Separation of strands is possible in the native gel, but the yield is typically low and the presence of non-target strand cannot be excluded. The yield cannot be increased on denaturing gel because the strands have the same length.

Biotin-Streptavidin Magnetic Beads Separation [10, 11]

The non-target PCR primer is biotinylated so final PCR products are Biotinylated-dsDNA, which can be captured by streptavidin magnetic beads and denatured to release the non-biotin labeled target ssDNA.

Advantages: The final ssDNA product has relatively high purity.

Disadvantages: In most cases, the input library needs to be biotinylated, but it may be difficult to replace or release the captured target strands from streptavidin beads. Post-denaturing purification is required to remove NaOH and/or acid used for neutralization.

Unequal Primer Length PCR [12]

The non-target PCR primer has a chemical modified spacer and a few extra nucleotides following. In the PCR reaction, the DNA polymerase will stop at the spacer, resulting in unequal length of PCR dsDNA product. Then target ssDNA can be cut from a denaturing PAGE gel.

Advantages: The final ssDNA product has high purity because the target ssDNA is not mixed with non-target strands.

Disadvantages: ssDNA cannot be seen on native gel. Requires time consuming denaturing PAGE gel. It may be difficult to denature some dsDNA library, which can limit the final yield.

Indirect Purification Method [13]

The indirect purification strategy combines Asymmetric PCR and Biotin-streptavidin magnetic beads separation. In short, regular PCR is used to generate sufficient template, then asymmetric PCR with excess of target primer and less biotinylated complementary primers, followed by biotin-streptavidin separation.

Advantages: May increase yield and purity of ssDNA product.

Disadvantages: It cannot produce biotinylated target ssDNA library. The process is relatively long and complicated and may be prone to generate mutants of the original sequence.

The invention provides methods of enriching oligonucleotide probe libraries against a target of interest. As the probes comprise ssDNA, the process may comprise PCR amplification then conversion back into ssDNA after each round of enrichment. In this Example, we developed a strategy for preparation of a ssDNA oligonucleotide library. The goals were to develop a process that is efficient and quick, while delivering high quality/purity ssDNA. We aimed to combine PCR and ssDNA prep in one step, remain efficient in the presence of selection buffer, target molecules, other sample components (e.g., highly abundant proteins for plasma samples) and other assay components (e.g., PEG precipitation solution that may be used to precipitate microvesicles). In addition, we desired the method to be able to generate ssDNA library with any modification, including without limitation Biotin.

We have used an optimized version of Lambda exonuclease digestion protocol for preparation of ssDNA oligonucleotide library. However, the digestion yield limits the overall recovery and is not consistent between different library preparations. In some cases, the ssDNA band is hardly visible on the gel following digestion. We have also observed incomplete digestion of dsDNA in the ssDNA product. In this Example, we developed an alternative protocol, termed "ssDNA by Unequal length PRimer Asymmetric PCR," or SUPRA. It lacks disadvantages from the known methods listed above, and provides high quality and yield up to 10× higher yield of ssDNA oligonucleotide library as compared to the previous methods. It is relatively fast and convenient technically, since target ssDNA can be distinguished from non-target DNA on a gel.

Figure 9A:
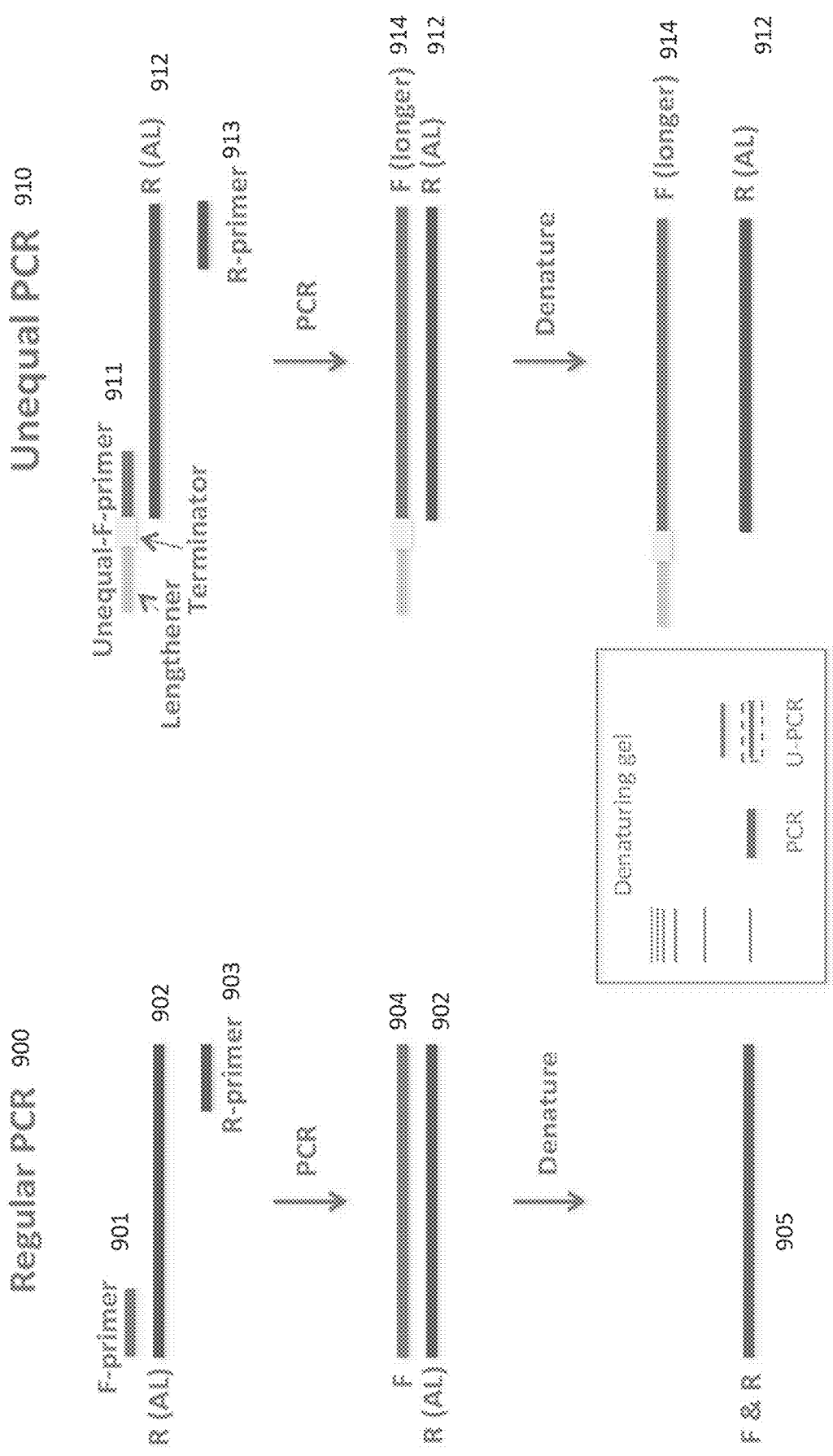
FIGS. 9A-C illustrate SUPRA (SsDNA by Unequal length PRimer Asymmetric PCR), a protocol for single stranded DNA (ssDNA) oligonucleotide library preparation.

A schematic comparing standard PCR 900 and unequal length PCR 910 is shown in FIG. 9A. In regular PCR 900, a forward primer 901 and reverse primer 903 are hybridized with the reverse strand of an aptamer library 902. The PCR reaction is performed, thereby creating equal length forward 904 and reverse strands 902. The strands are denatured in equal length single strands 905. In unequal length PCR 901, a formard primer 911 having a lengthener segment and terminator segment and a reverse primer 913 are hybridized with the reverse strand of an aptamer library 912. The PCR reaction is performed, thereby creating unequal length forward 914 and reverse strands 912. The strands are denatured into unequal length single strands 914 and 912 that can be separated by size, e.g., on a denaturing gel.

The steps of SUPRA include: (i) Modification of regular non-target primer with two Isp9 (Internal Spacer 9; triethylene glycol spacer) as terminator and 32 extra nucleotides (e.g., poly-A) as lengthener. It is referred as Unequal-Forward-Double isp9 primer (UF-D9); (ii) Perform asymmetric PCR, by mixing DNA template, UF-D9 and regular target (reverse) primer at ratio that favors the reverse primer, e.g., 1:37.5. The PCR program has longer elongation step (e.g., 3 min instead of standard 1 min) and more cycles due to linear amplification mode (instead of exponential). The PCR product contains a majority of target ssDNA and small portion of dsDNA. (iii) Mix PCR reaction products 1:1 with denaturing buffer (e.g., 180 mM NaOH and 6 mM EDTA) and denature samples by heating (e.g., 70° C. for 10 min) and cooling (e.g., incubation on ice for 3 min); (iv) Run denatured products in denaturing buffer on an agarose gel stained with SybrGold. The non-target strand, which is longer due to the lengthener, will appear as upper band (if visible) and the target strand (strong lower band) is cut and purified. The process can include optional steps, including without limitation: (v) Weigh the gel pieces and purify ssDNA from the gel pieces (e.g., using the ssDNA Nucleospin kit or the like); (vi) quantification of the yield and native gel can be used to check the purity and yield of final product (e.g., using the ssDNA Qubit kit or the like).

Figure 9B:
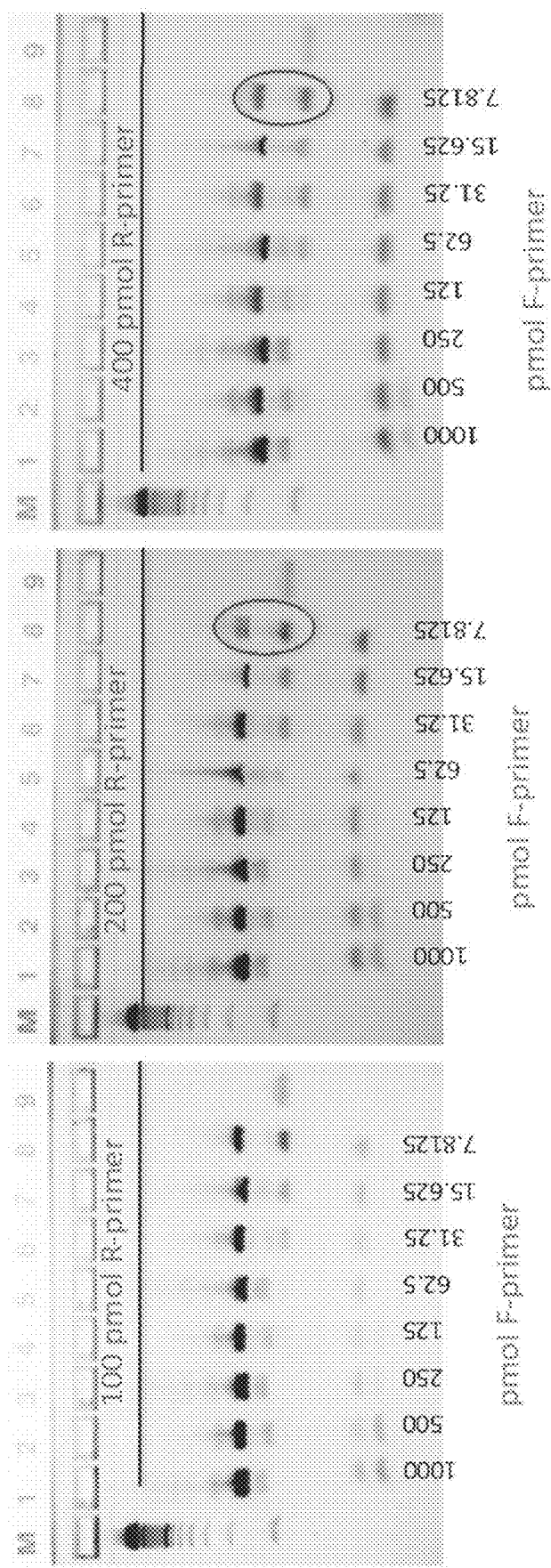

The first step (i) uses a specific design of the forward primer with efficient terminator and lengthener, which creates non-target strand of unequal length. The DNA polymerase used to build the target strand will stop polymerization once it reaches the terminator, and the lengthener facilitates differentiation between the target and non-target strands. In the second step (ii), the ratio between the two primers is shifted toward the reverse primer, to produce a majority of target ssDNA. The ratio, however, should not limit double strand templates production to keep reaction running FIG. 9B is a gel showing titration of forward and reverse primers input in asymmetrical PCR. The optimal condition, at which target strand is clearly visible, is in the range 1:20-1:50 F:R primers ratio. As shown in the figure, the ratio between two primers in asymmetric PCR can affect dsDNA and ssDNA amount in final products. The PCR thermocycler program is also adjusted to provide efficiency in the asymmetric PCR. In the third step (iii), a reliable denaturing method is used to separate target ssDNA to ensure the final yield and high purity.

As desired, the final step (vi) estimates the ratio of residual dsDNA, e.g., using ssDNA Qubit kit. In cases where the yield is not critical, the denaturing steps (iii) and (iv) can be skipped and the PCR products can be directly run on native gel. There will be a dsDNA band, but lower MW target ssDNA band can be distinguished and purified from gel. This is also a way to visualize the target band directly after PCR for a quality check or purification without denaturing. The purity of final product will be the same but yield will be lower.

Figure 9C:

A comparison of native versus denatured gel purification is shown in FIG. 9C. A post-probing oligonucleotide probe library was PCRed using unequal length primers mixed at a ratio of 1:38 (Forward/Reverse). In the figure, the left lane on each gel is a 50 bp molecular weight ladder and the lower band is the reverse primer. The positions of the dsDNA and ss DNA are indicated. A native gel showed the presence of both dsDNA and ssDNA (target strand) (FIG. 9C, panel A). Here, part of the target reverse strand is migrating in dsDNA. Thus, using the native gel, one can purify target ssDNA with moderate recovery. When a higher yield is desired, the PCR products can be run on denaturing agarose gel as described above. This approach provides maximal recovery wherein only target strand is visible, and can be cut from gel and purified (FIG. 9C, panel B). In this case, the reverse strand ssDNA, which is part of the dsDNA on native gel (FIG. 9C, panel A), is denatured and migrates together with other free molecules of target ssDNA strand, while forward strand becomes invisible due to limited amplification.

Compared to standard asymmetric PCR, which has relatively low yield and does not allow to distinguish target and non-target strands on denaturing gel, SUPRA delivers different lengths of target and non-target that can be purified on both native gel and denaturing gels. Compared to unequal primer length PCR, which uses lengthy Urea-PAGE protocol and produces only dsDNA, SUPRA has less dsDNA and free target ssDNA can be cut even from native gel if yield is not critical.

SUPRA has been used in the oligonucleotide probe library enrichment methods provided by the invention. The method is robust. In the presence of enrichment buffer, target/non-target molecules, proteins, exosomes/microvesicles, PEG and other components, SUPRA provides high quality and quantity of the ssDNA oligonucleotide library.

References

1. Comparison of different methods for generation of single-stranded DNA for SELEX processes. Anal. Bioanal. Chem. 2012, 404, 835-842.
2. Upgrading SELEX Technology by Using Lambda Exonuclease Digestion for Single-Stranded DNA Generation. Molecules 2010, 15, 1-11.
3. Tang, K.; Fu, D. J.; Julien, D.; Braun, A.; Cantor, C. R.; Koster, H. Chip-based genotyping by mass spectrometry. Proc. Natl. Acad. Sci. USA 1999, 96, 10016-10020.
4. Kuypers, A. W.; Linssen, P. C.; Willems, P. M.; Mensink, E. J. On-line melting of double-stranded DNA for analysis of single-stranded DNA using capillary electrophoresis. J. Chromatogr. B Biomed. Appl. 1996, 675, 205-211.
5. Higuchi, R. G.; Ochman, H. Production of single-stranded DNA templates by exonuclease digestion following the polymerase chain reaction. Nucleic Acids Res. 1989, 17, 5865.
6. Jones, L. A.; Clancy, L. E.; Rawlinson, W. D.; White, P. A. High-affinity aptamers to subtype 3a hepatitis C virus polymerase display genotypic specificity. Antimicrob. Agents Chemother. 2006, 50, 3019-3027.
7. S. S. Oh, K. Ahmads, M. Cho, Y. Xiao, H. T. Soh, "Rapid, Efficient Aptamer Generation: Kinetic-Challenge Microfluidic SELEX," presented in the 12th Annual UC Systemwide Bioengineering Symposium, June 1315, 2011, Santa Barbara, U.S.A
8. Gyllensten, U. B.; Erlich, H. A. Generation of single-stranded DNA by the polymerase chain reaction and its application to direct sequencing of the HLA-DQA locus. Proc. Natl. Acad. Sci. USA 1988, 85, 7652-7656.
9. Wu, L.; Curran, J. F. An allosteric synthetic DNA. Nucleic Acids Res. 1999, 27, 1512-1516.
10. Espelund, M.; Stacy, R. A.; Jakobsen, K. S. A simple method for generating single-stranded DNA probes labeled to high activities. Nucleic Acids Res. 1990, 18, 6157-6158.
11. A. Paul, M. Avci-Adali, G. Ziemer, H. P. Wendel. Streptavidin-coated magnetic beads for DNA strand separation implicate a multitude of problems during cell-SELEX. Oligonucleotides 2009, 19, 243-254.
12. Williams K., Bartel D. PCR product with strands of unequal length. Nucleic Acids Research, 1995, Vol. 23, No. 20.

13. Indirect purification method provides high yield and quality ssDNA sublibrary for potential aptamer selection. Anal. Biochem. 2015, online available.

Example 14

Oligonucleotide Pools to Characterize Cell Lines

In this Example, an oligonucleotide library was enriched using a combination of cells from different cancer cell lines to create cancer specific pools and against a pool of non-cancer cells. The enrichment is performed to identify cancer specific oligonucleotides and oligonucleotide pools that can be used in various applications, including without limitation diagnostic assays, as drugs or in drug delivery.

Figure 13:
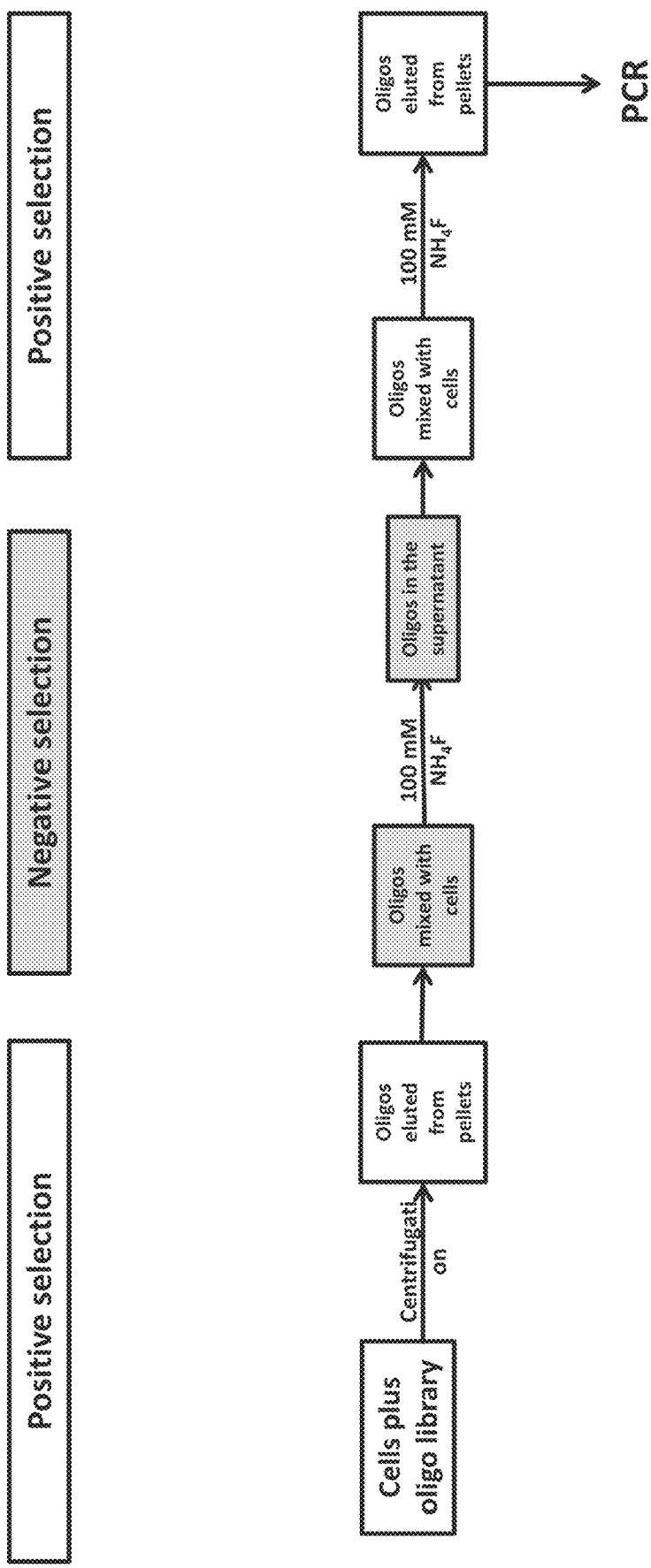
FIG. 13 shows a schematic for enriching an oligonucleotide library against cell lines.

The unscreened library comprised F-Trin-B primers (i.e., 5' CTAGCATGACTGCAGTACGT (SEQ ID NO 4) and 5' CTGTCTCTTATACACATCTGACGCTGCCGACGA (SEQ ID NO 5) as shown above) surrounding a region of randomly generated nucleotides. The enrichment was performed using methodology presented herein. See Examples above. Detailed protocols are below in Examples 15 and 16. One round of enrichment consisted of a series of positive, negative and positive selections before amplification via PCR of the enriched oligonucleotides. See FIG. 13, which shows a diagram of one round of enrichment. The amplified library (PCR) is used as the input into the next round or enrichment. The cell lines used consisted of nine lung cancer lines, five prostate cancer lines and nine non-cancer lines as listed in Table 19.

TABLE 19

| | | Cell Lines | | |
|---|---|---|---|---|
| Indication | Cell Line | Tissue | Disease | Morphology |
| Lung Pool | A549 | Lung | Carcinoma | Epithelial |
| | NCI-H1395 | Lung | Adenocarcinoma | Epithelial |
| | NCI-H1838 | Lung | Adenocarcinoma; Non-Small Cell Lung Cancer | Epithelial |
| | NCI-H1975 | Lung | Adenocarcinoma; Non-Small Cell Lung Cancer | Epithelial |
| | NCI-H2122 | Lung; Derived From Metastatic Site: Pleural Effusion | Adenocarcinoma; Non-Small Cell Lung Cancer | Rounded And Epithelial Cells |
| | NCI-H460 | Lung; Pleural Effusion | Carcinoma; Large Cell Lung Cancer | Epithelial |
| | H69AR | Lung | Carcinoma; Small Cell Lung Cancer | Epithelial |
| | HCC827 | Lung | Adenocarcinoma | Epithelial |
| | NCI-H1688 | Lung; Derived From Metastatic Site: Liver | Carcinoma; Small Cell Lung Cancer | Epithelial |
| Prostate Pool | 22RV1 | Prostate | Carcinoma | Epithelial |
| | DU145 | Prostate; Derived From Metastatic Site: Brain | Carcinoma | Epithelial |
| | LnCaP | Prostate; Derived From Metastatic Site: Left Supraclavicular Lymph Node | Carcinoma | Epithelial |
| | PC3 | Prostate; Derived From Metastatic Site: Bone | Carcinoma | Epithelial |
| | VCaP | Prostate; Derived From Metastatic Site: Vertebral Metastasis | Cancer | Epithelial |
| Non-Cancer Pool | CCD-16Lu | Lung | Normal | Fibroblast |
| | CCD-19Lu | Lung | Normal | Fibroblast |
| | CCD841CoN | Colon | Normal | Epithelial |
| | CCD-18Co | Colon | Normal | Fibroblast |
| | HCC1143BL | B Lymphoblast; Peripheral Blood Lymphocytes | Normal | Lymphoblast |
| | NCI-BL1395 | Peripheral Blood; B Lymphoblast; Epstein-Barr Virus (EBV) Transformed | Normal | Lymphoblast |
| | NCI-BL128 | Peripheral Blood; B Lymphoblast; Epstein-Barr Virus (EBV) Transformed | Normal | Lymphoblast |
| | Primary Prostate Epithelial Cells | Prostate | Normal | Epithelial |
| | PNT2 | Prostate | Normal | Epithelial |

Nine rounds of enrichment were performed against the lung cancer sample pool. The variable regions of the top five most enriched sequences are shown in Table 20. The enriched libraries consisted of the Variable Region as shown in the table inserted between the flanking sequences shown above as 5' CTAGCATGACTGCAGTACGT (SEQ ID NO 4)—[Variable Region]—CTGTCTCTTATACA-CATCTGACGCTGCCGACGA (SEQ ID NO 5). The sequences were also 5' biotinylated. 25 ng of starting library was used in the enrichment. As control sequences, the reverse complements were synthesized as shown in Table 20. These are reverse complements of the entire oligonucleotides including the flanking regions. S1LCa25-R9S1RC-5'biotin and S1LCa25-R9S3RC-5'biotin are the reverse complements of S1LCa25-R9S1-5'biotin and S1LCa25-R9S3-5'biotin, respectively. The reverse complements can be used as negative controls as they should not specifically bind the targets of the enriched sequences.

TABLE 20

Lung Cancer Enriched Oligonucleotides

| | Sequence name | | SEQ ID NO. |
|---|---|---|---|
| | | Variable Region (5'->3') | |
| Most enriched sequences | S1LCa25-R9S1-5'biotin | GGGGTTGTTTTGGGATGCCTTTTTCTCTGTATTTCA | 2922 |
| | S1LCa25-R9S2-5'biotin | GTCCTCGCCCGGGCTTCTGTTTGTTTTTTGGATTCGA | 2923 |
| | S1LCa25-R9S3-5'biotin | AACGCTTGATTTGGGTGGTTGGATTGACCTTTTTATGA | 2924 |
| | S1LCa25-R9S4-5'biotin | TTTTTTATTGGGTGCGCATAGGCGAGTGGTCTCTT | 2925 |
| | S1LCa25-R9S5-5'biotin | TGATTACATCGCCTGTATGGGTTGTTGTTTGTGTC | 2926 |
| | | Full Sequence (5'->3') | |
| Reverse complement sequences | S1LCa25-R9S1RC-5'biotin | TCGTCGGCAGCGTCAGATGTGTATAAGAGACAGTGAAATACAGAGAAAAAGGCATCCCAAAACAACCCCACGTACTGCAGTCATGCTAG | 2927 |
| | S1LCa25-R9S3RC-5'biotin | TCGTCGGCAGCGTCAGATGTGTATAAGAGACAGTCATAAAAAGGTCAATCCAACCACCCAAATCAAGCGTTACGTACTGCAGTCATGCTAG | 2928 |

Nine rounds of enrichment were also performed against the prostate cancer sample pool. The variable regions of various enriched sequences are shown in Table 21. The amount of starting library used in the enrichment is indicated in the table. The libraries consisted of the Variable Region as shown in the table inserted between the flanking sequences (SEQ ID NOs 4-5) as shown above. After the enrichment, the libraries were used to probe the cell pools and NGS was used to determine the identity and counts of the bound sequences. Table 21 shows the counts of sequences in prostate cancer (PCA) or non-PCA and the fold-change between PCA and non-PCA. Probing was performed in triplicate. The sequences in Table 30 had a coefficient of variation (% CV)≤20% across normalized counts for three probing replicates and fold changes cancer/non-cancer≤0.6 or ≥1.4. The average percent variation (% CV) was ~11% for the PCA pools and ~12% for the non-PCA pools.

TABLE 21

Prostate Cancer Enriched Oligonucleotides

| | Variable Region (5'->3') | SEQ ID NO | PCA Average normalized counts | Non-PCA Average normalized counts | Fold Change - Cancer/Non-Cancer |
|---|---|---|---|---|---|
| Enrichment with 5 ng initially | GGTTTTATCGTTTCTTTAGTTGGGTTCTTGGGTGA | 2929 | 475 | 346 | 1.4 |
| | GGATCTTGGTTAGTATTTTTGGTATTTTCTGTGGT | 2930 | 415 | 300 | 1.4 |

TABLE 21-continued

Prostate Cancer Enriched Oligonucleotides

| | Variable Region (5'->3') | SEQ ID NO | PCA Average normalized counts | Non-PCA Average normalized counts | Fold Change - Cancer/Non-Cancer |
|---|---|---|---|---|---|
| | GGATGCTGGTTAGTATTTTGGTATTTTCTGTGGT | 2931 | 564 | 408 | 1.4 |
| | TATTTAGGGGTTGTGGGTCTAATTTTTGTTTGTTCGA | 2932 | 551 | 397 | 1.4 |
| Enrichment with 25 ng initially | TCCTGGTTTCTGGTGGTTTCATTTAGCTTGTTACCTGA | 2933 | 376 | 276 | 1.4 |
| | TCCTGGTTTCTGGTGGTTTAATTTTGCTTGTTACATGA | 2934 | 934 | 687 | 1.4 |
| | TCCTGGTTTCTGGTGGTTTCATTTTGATTGTTACCT GA | 2935 | 2036 | 1485 | 1.4 |
| | TTTGGTTGGTCCATGGGTAAGCTTGGTGATTCTCTTGA | 2936 | 438 | 315 | 1.4 |
| | TCCTGGTTTCTGGTGGTTTCATTTTGCTTGTTACATGA | 2937 | 2194 | 1565 | 1.4 |
| Enrichment with 50 ng initially | ACATGCACTGAGCCCGACACACCCGCCTGAACTAT | 2938 | 361 | 570 | 0.6 |
| | ACTAATTGTTTTGGGGGTAGTTGTTTTTTTTCTGT | 2939 | 3984 | 2893 | 1.4 |
| | GGATCCTGGTTAGTATTTTTGGTATATTCTGTGGT | 2940 | 277 | 201 | 1.4 |
| | TATGTTCTTTTTATTTTAGTGGTTGTGGCCTATCTA | 2941 | 506 | 367 | 1.4 |

The sequences above were 5' biotinylated for capture. As control sequences, reverse complements were synthesized as shown in Table 22. These are reverse complements of the entire oligonucleotides including the flanking regions. S1PCa5-R9S1RC-5'biotin and S1PCa25-R9S1RC-5'biotin are the reverse complements of the complete S1PCa5-R9S1-5'biotin and S1PCa25-R9S1-5'biotin sequences with flanking regions, respectively. The reverse complements can be used as negative controls as they should not specifically bind the targets of the enriched sequences.

TABLE 22

Prostate Cancer Enriched Oligonucleotides

| | Sequence name | Variable Region (5'->3') | SEQ ID NO |
|---|---|---|---|
| Enrichment with 5 ng initially | S1PCa5-R9S1-5'biotin | GGTTTTATCGTTTCTTTAGTTGGGTTCTTGGGTGA | 2942 |
| | S1PCa5-R9S4-5'biotin | TATTTAGGGGTTGTGGGTCTAATTTTTGTTTGTTCGA | 2943 |
| Enrichment with 25 ng initially | S1PCa25-R9S1-5'biotin | TCCTGGTTTCTGGTGGTTTCATTTAGCTTGTTACCTGA | 2944 |
| | S1PCa25-R9S1-5'biotin | TCCTGGTTTCTGGTGGTTTCATTTTGCTTGTTACATGA | 2945 |
| Enrichment with 50 ng initially | S1PCa50-R9S1-5'biotin | ACATGCACTGAGCCCGACACACCCGCCTGAACTAT | 2946 |
| | S1PCa50-R9S3-5'biotin | GGATCCTGGTTAGTATTTTTGGTATATTCTGTGGT | 2947 |
| | | Full Sequence | |
| Reverse complement sequences to 5 ng library | S1PCa5-R9S1RC-5'biotin | /5Biosg/TCGTCGGCAGCGTCAGATGTGTATAAGAGACAGTCACCCAAGAACCCAACTAAAGAAACGATAAAACCACGTACTGCAGTCATGCTAG | 2948 |
| Reverse complement sequences to 25 ng library | S1PCa25-R9S1RC-5'biotin | /5Biosg/TCGTCGGCAGCGTCAGATGTGTATAAGAGACAGTCAGGTAACAAGCTAAATGAAACCACCAGAAACCAGGAACGTACTGCAGTCATGCTAG | 2949 |

Additional sequences as in Table 21 are shown in Table 23. Table 23 includes sequences with % CV>20%, as indicated.

TABLE 23

Additional Prostate Cancer Enriched Oligonucleotides

| | Variable Region (5'->3') | SEQ ID NO | Prostate Cancer Pool | | Non-Cancer Pool | | Fold Change - Cancer/Non-Cancer |
| --- | --- | --- | --- | --- | --- | --- | --- |
| | | | Average normalized counts | % CV | Average normalized counts | % CV | |
| Enrichment with 5 ng initially | AGTTCTTGGGGGTTTTGGTTGG TGCCTTGTATGTTA | 2950 | 670 | 10% | 266 | 41% | 2.5 |
| | AGTTCTTGGGGGTTTTGGTTGT TGCCTTGTCTATTA | 2951 | 11 | 60% | 1 | 0% | 10.7 |
| Enrichment with 25 ng initially | TTGCCGCCCTTTATGGTTTGTT TTTTGCGATGTGGGA | 2952 | 45 | 49% | 8 | 90% | 5.4 |

Assays such as qPCR, cell enzyme linked assay (ELA), confocal microscopy and cell viability assays are performed to verify binding of oligonucleotides to cells and identify potential cell killing properties of certain oligonucleotides.

Example 15

Enrichment Protocol

Re-amplification of original F-TRin-35n-B oligonucleotide library.
Samples for One Round of Enrichment
900,000 cells from pool of Prostate/Lung cell lines (split 3 times in 300,000 each)
900,000 cells from pool of Normal cell lines (split 3 times in 300,000 each)
Preparations
Pre-chill tabletop centrifuge at 4° C.
Bring 300,000 of Prostate/Lung cells to 140 ul with 1×PBS with 3 mM MgCl$_2$ (138.6 ul PBS+1.4 ul 300 mM MgCl$_2$), add competitors listed below and incubate for 20 min with end-over-end rotation.
Mixture of two competitors: Salmon DNA+tRNA.
Competitor salmon DNA: add 800 ng of salmon DNA (Stock 10 ug/ul→Dilute 1:250 with 1×PBS+3 mM MgCl$_2$ [40 ng/ul]→20 ul input).
Competitor tRNA: add 800 ng of tRNA (Stock 10 ug/ul→Dilute 1:250 with 1×PBS+3 mM MgCl$_2$ [40 ng/ul] →20 ul input).
Library/sample incubation (positive selection)
Prepare 5, 25, 50 ng for first round and same corresponding for following rounds of oligonucleotide library in 20 ul of 1×PBS with 3 mM MgCl$_2$. After heating the DNA for 3 min@95 C, put it on ice immediately for 5 min. Add DNA to the blocked cells and incubate them for 30 min at RT, with end-over-end rotation
Spinning Cells
Spin cells from step II at 500×g for 5 min (spin at 4 C) and discard supernatant by pipetting it out.
Re-suspend pellet in 1 ml of 1×PBS+3 mM MgCl$_2$; vortex/mix and centrifuge again at 500×g for 5 min (spin at 4 C)
Repeat the wash one more time.
Re-suspend pellet in 50 ul of water.
Use pellet in step IV.

Oligonucleotide Elution
Add 25 ul of 0.1N NaOH to cells from III, incubate for 10 min at 50 C, mixmate and agitate for 10 sec at 550 rpm→Add 25 ul of 0.1N HCL→Spin at 12000×g for 10 min at 4 C→proceed with NucleoSpin ssDNA purification MAKE SURE TO USE CORRECT BUFFER TO BIND (NTC) ssDNA (number of columns to be identified)→Elute, each column in 20 ul of water (incubation time before elution is 5 min). Add 4 ul of 5×PBS+15 mM MgCl2 solution, before proceeding to the next enrichment.
Library/Sample Incubation (Negative Selection)
Bring 300,000 of Normal cells (depending on number of steps) to 140 ul with 1×PBS with 3 mM MgCl$_2$ (138.6 ul PBS+1.4 ul 300 mM MgCl$_2$) and mix with the mixture of competitors as described above in step I.c (40 ul total), incubate for 20 min with end-over-end rotation. Then, add eluted oligonucleotide libraries (~20 ul) (heat treat 3 min@95 C, put it on ice immediately for 5 min) from step IV and incubate 30 min at RT.
Spinning Cells
Spin cells from step V at 500×g for 5 min (spin at 4 C) and collect supernatant.
Treatment of supernatant with NucleoSpin ssDNA purification. MAKE SURE TO USE CORRECT BUFFER TO BIND (NTC) ssDNA (number of columns to be identified) →Elute, each column in 20 ul of water (incubation time before elution is 5 min).
Add 4 ul of 5×PBS+15 mM MgCl2 solution, before proceeding to the next enrichment.
Library/Sample Incubation (Positive Selection)
Bring 300,000 of Prostate/Lung cells to 140 ul with 1×PBS with 3 mM MgCl$_2$ (138.6 ul PBS+1.4 ul 300 mM MgCl$_2$) and mix with the mixture of competitors as described above in step I.c (40 ul total), incubate for 20 min with end-over-end rotation. Mix with libraries from step VI (heat treat 3 min@95 C, put it on ice immediately for 5 min) and incubate for 30 min at RT with end-over-end rotation.
Spinning Cells
Spin cells from step VII at 500×g for 5 min (spin at 4 C) and discard supernatant by pipetting it out.
Re-suspend pellet in 1 ml of 1×PBS+3 mM MgCl$_2$; vortex/mix and centrifuge again at 500×g for 5 min (spin at 4 C).
Repeat the wash one more time.
Re-suspend pellet in 50 ul of water.
Follow the oligonucleotide elution (IV) and then nucleospin purification to get the ssDNA in 20 ul water.

The ssDNA in water (20 ul) will be used entirely for PCR amplification.

Example 16

Enrichment Protocol

Samples for one round of enrichment
900,000 cells from pool of Prostate/Lung cell lines (split 3 times in 300,000 each)
900,000 cells from pool of Normal cell lines (split 3 times in 300,000 each)
No cells enrichment for every library input

TABLE 24

Buffers

| Exp. ID | Buffers |
|---|---|
| B1 | PBS + 3 mM MgCl2 |
| B2 | PBS + 3 mM MgCl2 + 0.5% F-127 + 0.5% PEG4000 |
| B3 | PBS + 3 mM MgCl2 + 0.5% F-127 + 1 mg/ml HSA |

Or the titers of buffer with F-127 and H SA-F-127@0.5, 1 and 2%
Cells are available in 1×PBS+3 mM MgCl2 buffer and need to be transferred.

I. Preparations
Pre-chill tabletop centrifuge at 4° C.
Transfer 300,000 cancer cells—140 ul into 3 fresh tubes. Spin at 500×g for 5 mins. Remove the supernatant buffer and add 70 ul of the buffer B2.
Add competitors listed below and incubate for 20 min with end-over-end rotation.
Mixture of two competitors:
a. Competitor salmon DNA: add 800 ng of salmon DNA (Stock 10 ug/ul→Dilute 1:125 with B2 [80 ng/ul]→10 ul input). b. Competitor t-RNA: add 800 ng of tRNA (Stock 10 ug/ul→Dilute 1:125 with B2 [80 ng/ul]→10 ul input).
Bring up the volume to 180 ul with 90 ul of Buffer B2, for the blocking.

II. Library/Sample Incubation (Positive Selection)
Prepare 5/25/50 ng of F-TRin-35n-B Starting Library for first round in 20 ul of buffer B2. After heating the DNA for 3 min@95 C, put it on ice immediately for 5 min. Add DNA to the blocked cells and incubate them for 30 min at RT, with end-over-end rotation.

III. Spinning Cells
Spin cells from step II at 500×g for 5 min at 4 C and discard supernatant by pipetting it out.
Re-suspend pellet in 1 ml of B2; vortex and centrifuge again at 500×g for 5 min at 4 C.
Repeat the wash one more time. (Additional Wash)
Re-suspend pellet in 30 ul of buffer B2.
Use pellet in step IV.

IV. Oligonucleotide Elution
Add 10 ul of 0.25N NaOH to cells from III, incubate for 10 min at 50 C, mix-mate and agitate for 5-10 sec at 550 rpm→Add 10 ul of 0.25N HCL→Spin at 16000×g for 10 min at 4 C. Collect the supernatant; this will be used as library for the next step.

V. Library/Sample Incubation (Negative Selection)
Transfer 300,000 normal cells—140 ul into 3 fresh tubes. Spin@500×g for 5 mins. Remove the supernatant buffer and add 70 ul of the buffer B2.

Mix with the mixture of competitors (10 ul of Salmon sperm DNA@80 ng/ul+10 ul of Yeast t-RNA@80 ng/ul), bring up the volume to 150 ul (add 60 ul) of Buffer B2, incubate for 20 min with end-over-end rotation. Then, add eluted oligonucleotide libraries (~50 ul) (heat treat for 3 min@95 C, put it on ice immediately for 5 min) from step IV and incubate 30 min at RT.

VI. Spinning Cells
Spin cells from step V at 500×g for 5 min at 4 C and collect supernatant as library for next step (200 ul).

VII. Library/Sample Incubation (Positive Selection)
Transfer 300,000 cancer cells—140 ul into 3 fresh tubes. Spin at 500×g for 5 mins. Remove the supernatant buffer and add 70 ul of the buffer B2.
Mix with the mixture of competitors (10 ul of Salmon sperm DNA@80 ng/ul+10 ul of Yeast t-RNA@80 ng/ul), incubate for 20 min with end-over-end rotation. Mix with libraries from step VI (heat treat 3 min@95 C, put it on ice immediately for 5 min) and incubate for 30 min at RT with end-over-end rotation (total 290 ul).

VIII. Spinning Cells
Spin cells from step VII at 500×g for 5 min at 4 C and discard supernatant by pipetting it out.
Re-suspend pellet in 1 ml of B2; vortex and centrifuge again at 500×g for 5 min at 4 C.
Repeat the wash one more time. (Additional Wash)
Re-suspend pellet in 50 ul of water; it will be used entirely for PCR amplification.

Example 17

Oligonucleotide Pools to Characterize Cell Line Microvesicles

In this Example, an oligonucleotide library was enriched using microvesicles shed from various cancer cell lines. The enrichment is performed as in Example 14 as above except that the sample comprised microvesicles as opposed to cells. This method can be performed to identify disease specific oligonucleotides and oligonucleotide pools that can be used in various applications, including without limitation diagnostic assays, as drugs or in drug delivery.

Figure 14A:
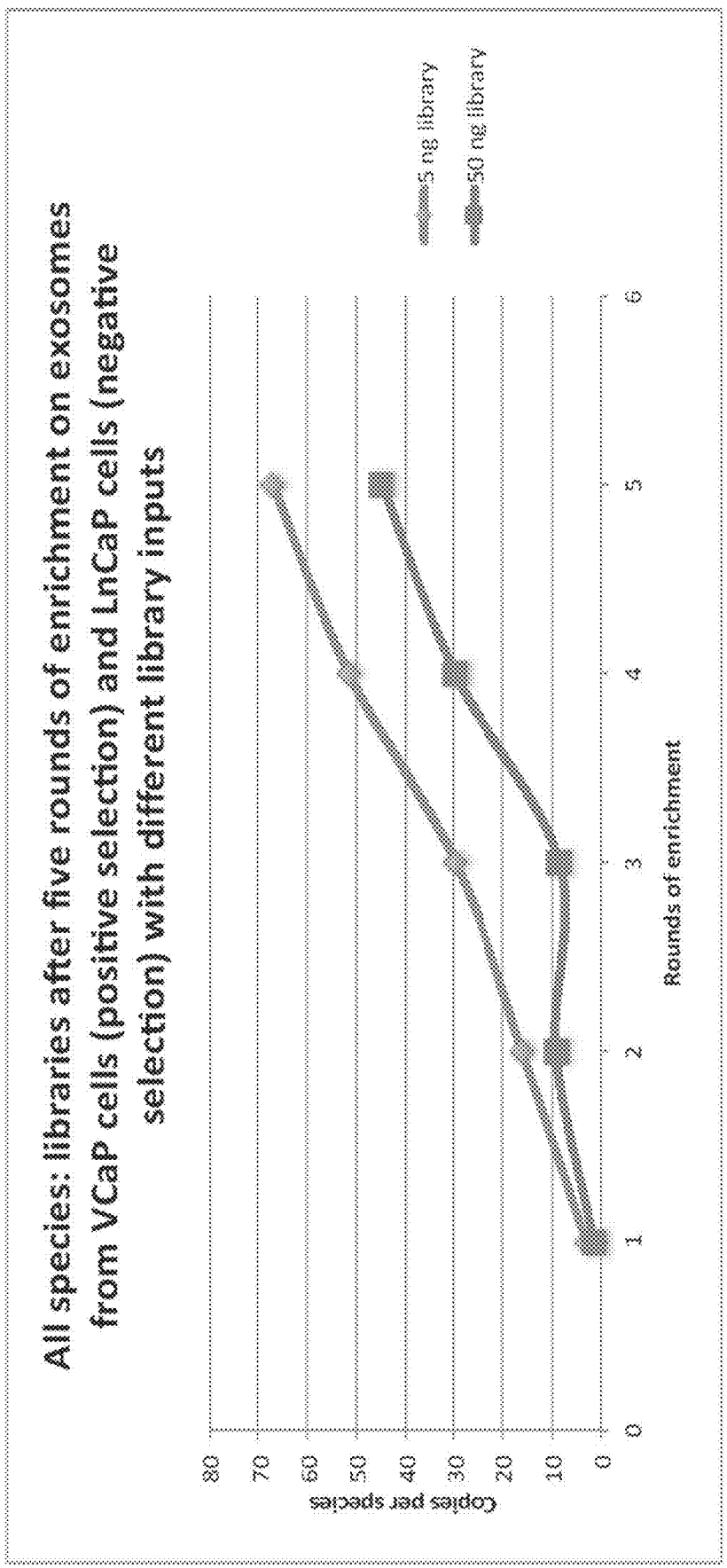
FIGS. 14A-C show oligonucleotide probes that recognize microvesicles (exosomes) shed by prostate cancer cell lines.
Figure 14B:
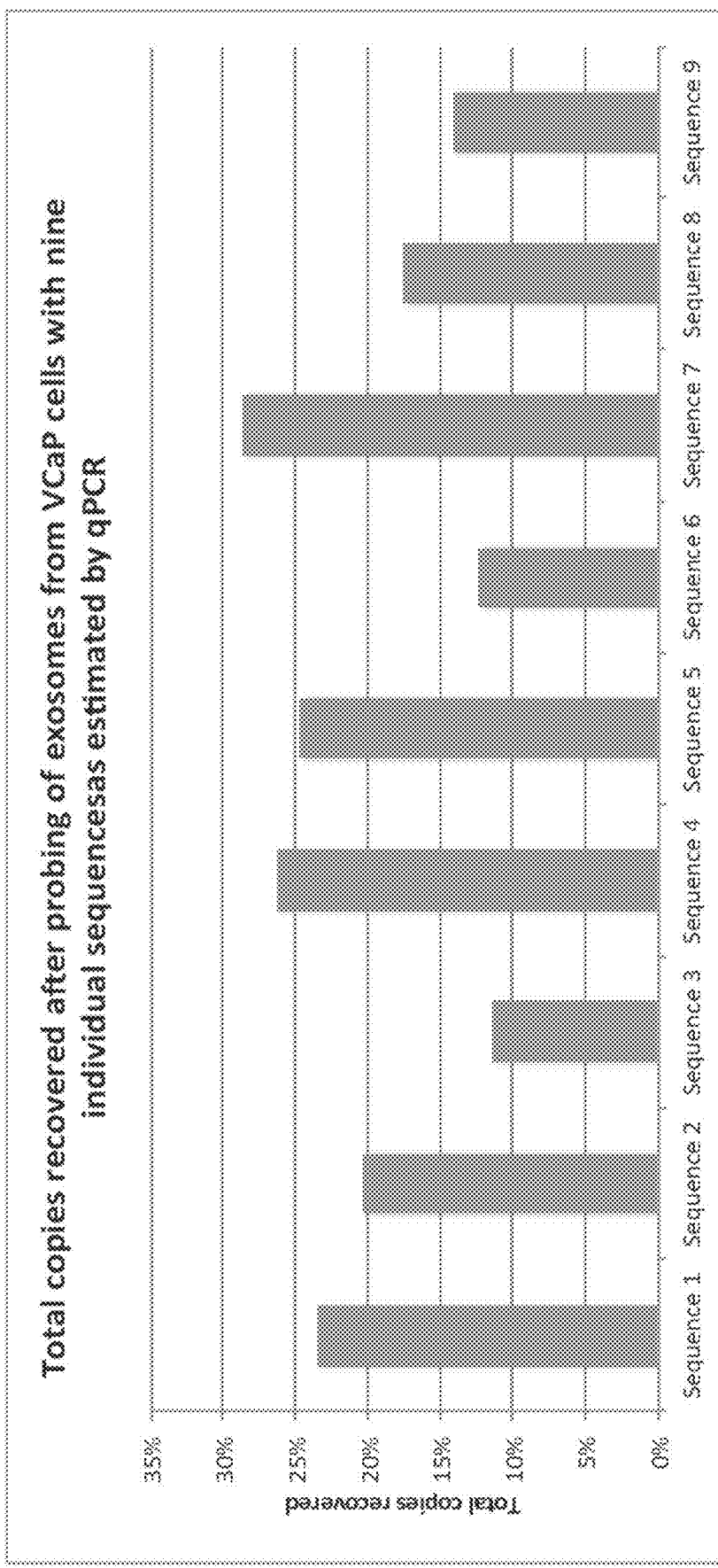

The unscreened library comprised F-Trin-B primers (i.e., 5' CTAGCATGACTGCAGTACGT (SEQ ID NO 4) and 5' CTGTCTCTTATACACATCTGACGCTGCCGACGA (SEQ ID NO 5)) flanking a random variable region. Enrichment was performed on microvesicles from cell lines as described further in Example 18 below. FIG. 14A shows copies per species of five rounds of enrichment on exosomes from VCaP and LNCaP cells as indicated in the figure. Positive selection was performed on VCAP microvesicles shed from VCAP cells and negative selection was performed on LNCaP microvesicles shed from LNCaP cells. The figure shows that the copies numbers of various oligonucleotide probe species increased with each round, indicating that the oligonucleotide probe library is being enriched with those species. The variable regions of several enriched oligonucleotide probes are shown in Table 25. The probes are 5' biotinylated. These probes are from the enrichment performed with 5 ng library on exosomes from VCaP and LnCaP cells. Table 25 shows nine sequences with fold changes of at least 4.0-fold elevated in VCaP versus LNCaP. Each sequence also had averaged normalized counts of at least 500 for probing on VCaP exosomes. Fold changes are shown in the table. FIG. 14B shows copies recovered after probing (see Example below for protocol) with the nine oligonucleotide probes in the table. Also as shown in the table, the reverse complement of the entire probe sequences (i.e., including the F-Trin-B primers shown above) are used as controls.

TABLE 25

Variable Regions of Oligonucleotide probes

| Variable Regions (5'->3') | SEQ ID NO | Fold Change (VCaP / LNCaP) |
|---|---|---|
| ATATGGGGTTTATGGGGATGGTGTTATGGGTGGAATGA | 2953 | 5.4 |
| ATGGGGAGGGGGGTAGGCTGTCTTAATTGGTGGTT | 2954 | 4.3 |
| ATTAATGGGTGGGGGGTTTAGCTTGATGTGGGTTGTGA | 2955 | 4.0 |
| GAATGGGGGATACTGTTAGTGTGGGTCTGGGGGT | 2956 | 6.7 |
| GGGGGGGGCTTTTTATGGTTTCTGGGGGACCTGCT | 2957 | 4.9 |
| GGTGATGAATTAAATGGGGGGGGTATCAAGTGTGGA | 2958 | 6.5 |
| TACTTAATTGGGGGGGGGATTCTGTTTTGTCTCT | 2959 | 6.2 |
| TAGCCTTTGGGGGTTGTTTTGGGGGATTGGGTTGTTGA | 2960 | 6.3 |
| TAGTGACTACGGGTATGGGGATTGGGGGTTTGGTTTGA | 2961 | 4.5 |

| Reverse Complements (5'->3') | SEQ ID NO |
|---|---|
| /5Biosg/TCGTCGGCAGCGTCAGATGTGTATAAGAGACAGTCATTCCACCCATAACACCA TCCCCATAAACCCCATATACGTACTGCAGTCATGCTAG | 2962 |
| /5Biosg/TCGTCGGCAGCGTCAGATGTGTATAAGAGACAGAACCACCAATTAAGACAGCC TACCCCCCTCCCCATACGTACTGCAGTCATGCTAG | 2963 |
| /5Biosg/TCGTCGGCAGCGTCAGATGTGTATAAGAGACAGTCACAACCCACATCAAGCTA AACCCCCCACCCATTAATACGTACTGCAGTCATGCTAG | 2964 |
| /5Biosg/TCGTCGGCAGCGTCAGATGTGTATAAGAGACAGACCCCCAGACCCACACTAAC AGTATCCCCCCATTCACGTACTGCAGTCATGCTAG | 2965 |
| /5Biosg/TCGTCGGCAGCGTCAGATGTGTATAAGAGACAGAGCAGGTCCCCCAGAAACCA TAAAAAGCCCCCCCCACGTACTGCAGTCATGCTAG | 2966 |
| /5Biosg/TCGTCGGCAGCGTCAGATGTGTATAAGAGACAGTCCACACTTGATACCCCCCC CATTTAATTCATCACCACGTACTGCAGTCATGCTAG | 2967 |
| /5Biosg/TCGTCGGCAGCGTCAGATGTGTATAAGAGACAGAGAGACAAAACAGAATCCCC CCCCCCAATTAAGTAACGTACTGCAGTCATGCTAG | 2968 |
| /5Biosg/TCGTCGGCAGCGTCAGATGTGTATAAGAGACAGTCAACAACCCAATCCCCCAA AACAACCCCCAAAGGCTAACGTACTGCAGTCATGCTAG | 2969 |
| /5Biosg/TCGTCGGCAGCGTCAGATGTGTATAAGAGACAGTCAAACCAAACCCCCAATCC CCATACCCGTAGTCACTAACGTACTGCAGTCATGCTAG | 2970 |

Figure 14C:
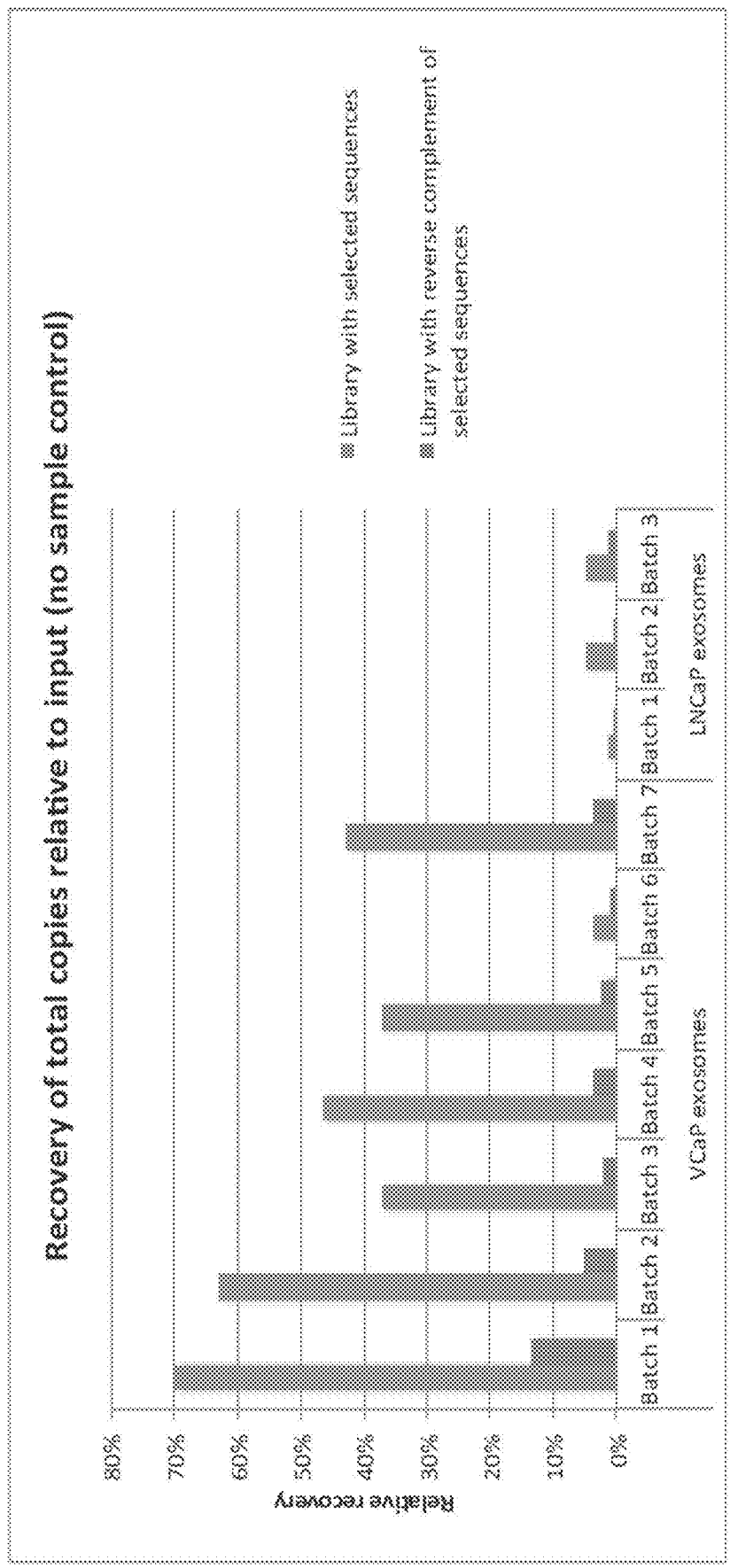

FIG. 14C shows higher recovery on six out of seven batches of isolated VCaP exosomes compared to exosomes from LNCaP cells as seen by probing with a library of the nine individual DNA sequences in Table 25. The figure also shows probing with the reverse complement controls. As expected, these sequences showed little recovery with the exosomes as compared to the oligonucleotide probe sequences with variable regions SEQ ID NOs 2953-2961.

Several proteins have been identified by probing of exosomes from VCaP cells with an aptamer having variable region 5'-TACTTAATTGGGGGGGGGGAT-TCTGTTTTGTCTCT-3' (i.e., SEQ ID NO 2959) followed by pull downs and analysis by mass spectrometry. See Example 9 for methodology. Exemplary results are shown in Table 26. These experiments identified key proteins in the regulation of exosome biogenesis (ESCRT, Syntenin) and endocytic trafficking (chemokine CXCL11) overexpressed in Cancer. The ESCRT machinery (ESCRT-0, I, II and III) participates in exosomes biogenesis and the proteins have been observed to be overexpressed in human cancers. See, e.g, Kowal et al., Biogenesis and secrection of exosomes, Current Opinion in Cell Biology, 2014, 29:116-125; Hurley and Hanson, Membrane budding and scission by the ESCRT machinery: it's all in the neck, Nat Rev Mol Cell Biol, 2010 11:556-566; Raiborg and Stenmark, The ESCRT machinery in endosomal sorting of ubiquitylated membrane proteins, Nature 2009 458: 45-52, all of which proteins are incorporated by reference herein in their entirety. The experiments further identified cold shock proteins whose miRNA suppression sensitizes cells to chemotherapeutic agents.

TABLE 26

Proteins from VCaP exosomes pulled down with Sequence 7

| Accession | Description | Cellular role |
|---|---|---|
| O14625 | C-X-C motif chemokine 11 GN = CXCL11 (also Interferon-inducible T-cell alpha chemoattractant (I-TAC)) | chemokine that is overexpressed in blood and tissue of men with advanced prostate adenocarcinomas |
| Q92616 | Translational activator GCN1 GN = GCN1 | |
| Q9H444 | Charged multivesicular body protein 4b GN = CHMP4B | ESCRT-III; membrane scission |
| Q14767 | Latent-transforming growth factor beta-binding protein 2 GN = LTBP2 | |
| P26599-3 | Isoform 3 of Polypyrimidine tract-binding protein 1 GN = PTBP1 (also Heterogeneous nuclear ribonucleoprotein I (hnRNP I)) | cancer associated splicing factor |
| P98179 | RNA-binding protein 3 GN = RBM3 | part of ESCRT-III; membrane scission; cold shock protein. Knock-down has been shown to enhance chemotherapeutic cell killing of prostate cells |
| O43633 | Charged multivesicular body protein 2a GN = CHMP2A | |
| P62888 | 60S ribosomal protein L30 GN = RPL30 | |
| Q9UK41-2 | Isoform 2 of Vacuolar protein sorting-associated protein 28 homolog GN = VPS28 | part of ESCRT-I; membrane budding with ESCRT-II |
| O60884 | DnaJ homolog subfamily A member 2 GN = DNAJA2 | |
| Q14011-3 | Isoform 3 of Cold-inducible RNA-binding protein GN = CIRBP (A18 hnRNP) | cold shock protein. Knock-down has been shown to enhance chemotherapeutic cell killing of prostate cells |
| Q8N684-3 | Cleavage and polyadenylation specificity factor subunit 7 GN = CPSF7 | |
| P05109 | Protein S100-A8 GN = S100A8 | |
| P05386 | 60S acidic ribosomal protein P1 GN = RPLP1 | |
| Q7LBR1 | Charged multivesicular body protein 1b GN = CHMP1B | associated to ESCRT-III; regulation of membrane scission and ESCRT-III disassembly |
| O00560-1 | Syntenin-1 GN = SDCBP | adaptor protein that binds to syndecans and ALIX which interacts with multiple ESCRT proteins |

Negative controls from the above enrichment with 5 ng library on exosomes from VCaP and LnCaP cells were also identified. Several are shown in Table 27. The Table shows 3 sequences with fold changes of at least 4.0 higher on LNCaP exosomes and 2 sequences with fold changes of 1 (indicating no fold change between VCaP and LNCaP exosomes). The variable regions are shown in Table 27. Also as shown in the table, the reverse complement of the entire probe sequences (i.e., including the F-Trin-B primers shown above) are used as controls.

TABLE 27

| Variable Regions of Oligonucleotide probes | | |
|---|---|---|
| Variable Regions (5'→3') | SEQ ID NO. | Fold change (VCaP/LNCaP) |
| TCCGTTTATCTACTTTTCCGGTACTGTTCCCGTTT | 2971 | 0.2 |
| ATCGCGTCGCCCCCGGATATTATTGTTTCTTGTTC | 2972 | 0.2 |
| TTGCTTGCCCGGCCATAAACACGATCTTGTTCTCTA | 2973 | 0.2 |
| GATACGGTCTTTGGTGCTTGTGTGAATCTATGGGTGA | 2974 | 1.0 |
| TCCTGGTTTCTGGTGGTTTATTTAGCTTGTTACCTGA | 2975 | 1.0 |
| AGTGGGTGGTGGGTTCGGTTTGCTTGGTTCCCTGTTGA | 2976 | |
| ATTGAGGTGGTTTTGAGGTGGGCTATCTGAGGGAT | 2977 | |
| GGGGGGGGCTTTTTATGGTTTCTGGGGGACCTGCT | 2978 | |
| ATATGGGGTTTATGGGGATGGTGTTATGGGTGGAATGT | 2979 | |

| Reverse Complements (5'→3') | SEQ ID NO |
|---|---|
| /5Biosg/TCGTCGGCAGCGTCAGATGTGTATAAGAGACAGAAACGGGAACAGTACCGGAAAAGTAGATAAACGGAACGTACTGCAGTCATGCTAG | 2980 |
| /5Biosg/TCGTCGGCAGCGTCAGATGTGTATAAGAGACAGGAACAAGAAACAATAATATCCGGGGGCGACGCGATACGTACTGCAGTCATGCTAG | 2981 |
| /5Biosg/TCGTCGGCAGCGTCAGATGTGTATAAGAGACAGTAGAGAACAAGATCGTGTTTATGGCCGGGCAAGCAAACGTACTGCAGTCATGCTAG | 2982 |

TABLE 27-continued

Variable Regions of Oligonucleotide probes

| | |
|---|---|
| /5Biosg/TCGTCGGCAGCGTCAGATG<br>TGTATAAGAGACAGTCACCCCATAGAT<br>TCACACAAGCACCAAAGACCGTATCAC<br>GTACTGCAGTCATGCTAG | 2983 |
| /5Biosg/TCGTCGGCAGCGTCAGATG<br>TGTATAAGAGACAGTCAGGTAACAAGC<br>TAAATAAACCACCAGAAACCAGGAACG<br>TACTGCAGTCATGCTAG | 2984 |
| /5Biosg/TCGTCGGCAGCGTCAGATG<br>TGTATAAGAGACAGTCAACAGGGAACC<br>AAGCAAACCGAACCCACCACCCACTAC<br>GTACTGCAGTCATGCTAG | 2985 |
| /5Biosg/TCGTCGGCAGCGTCAGATG<br>TGTATAAGAGACAGATCCCTCAGATAG<br>CCCACCTCAAAACCACCTCAATACGTA<br>CTGCAGTCATGCTAG | 2986 |
| /5Biosg/TCGTCGGCAGCGTCAGATG<br>TGTATAAGAGACAGAGCAGGTCCCCA<br>GAAACCATAAAAAGCCCCCCCCACGTA<br>CTGCAGTCATGCTAG | 2987 |
| /5Biosg/TCGTCGGCAGCGTCAGATG<br>TGTATAAGAGACAGACATTCCACCCAT<br>AACACCATCCCCATAAACCCCATATAC<br>GTACTGCAGTCATGCTAG | 2988 |

Assays such as qPCR, cell enzyme linked assay (ELA), confocal microscopy and cell viability assays are performed to verify binding of oligonucleotides to cells and identify potential cell killing properties of certain oligonucleotides.

Example 18

Enrichment Protocol for Microvesicles

Samples:
Experiment 1: (F98 cells: Organism: Rattus norvegicus; Cell Type: Glioblastoma; Tissue: brain; Disease: undifferentiated malignant glioma)
25 ug of microvesicles from transfected F98 cells (EGFR+) for each positive step
25 ug of microvesicles from parental F98 cells for each negative step
Experiment 2: (Prostate Cancer cell lines)
25 ug of microvesicles from VCaP cells for each positive step
25 ug of microvesicles from LnCaP cells for each negative step
Controls:
Reaction buffer with no microvesicles for each positive and negative step
Reaction buffer: 1×PBS+3 mM MgCl2+0.5% F127+1 mg/ml HSA
Sample preparation: prepare 25 ug of microvesicles in 35 ul 1×PBS and add 35 ul of 1×PBS+6 mM MgCl2+1% F127+2 mg/ml HSA to obtain 25 ug of microvesicles in 70 ul of 1×PBS+3 mM MgCl2+0.5% F127+1 mg/ml HSA
Enrichment Scheme:
First round: only positive step
Second round: positive step→negative step→positive step
Third round: positive step→negative step→positive step
Fourth round: positive step→negative step→positive step Each round ends with PCR followed by purification of ssDNA after gel electrophoresis
I. Preparations
a) Pre-chill tabletop centrifuge at 4° C.
b) Add competitors as listed below to each 25 ug of transfected F98 or VCaP microvesicles in 70 ul reaction buffer and incubate for 20 min with shaking at 500 rpm on mixmate.
c) Mixture of two competitors:
Competitor salmon DNA: add 800 ng of salmon DNA (Stock 10 ug/ul→Dilute 1:125 with reaction buffer [80 ng/ul]→10 ul input).
Competitor t-RNA: add 800 ng of tRNA (Stock 10 ug/ul→Dilute 1:125 with reaction buffer [80 ng/ul]→10 ul input).
d) Bring the volume to 180 ul with 90 ul of reaction buffer, for the blocking.
II. Library/Sample Incubation (Positive Selection)
Prepare 5 ng and 50 ng of F-TRin-35n-B Starting Library for first round in 20 ul of reaction buffer. After heating the DNA for 3 min@95 C, put it on ice immediately for 5 min. Add DNA to the blocked cells and incubate them for 30 min at RT, with end-over-end rotation.
III. Precipitation Protocol with 6% PEG8000
a) Use microvesicles from step II as sample.
b) Add 200 ul of 12% PEG8000 to 200 ul of sample.
c) Leave sample on ice for 30 min.
d) Spin at 16000×g for 10 min and discard supernatant.
e) Re-suspend pellet in 200 ul reaction buffer and centrifuge again at 16000×g for 10 min
f) Re-suspend pellet in 30 ul of reaction buffer.
g) First round: go straight to PCR. Following rounds: go to IV.
IV. Oligonucleotide Probe Elution
Add 10 ul of 0.25N NaOH to cells from III, incubate for 10 min at 50 C, mix-mate and agitate for 5-10 sec at 550 rpm→Add 10 ul of 0.25 N HCL→Spin at 16000×g for 10 min at 4 C. Collect the supernatant; this will be used as library for the next step.
V. Library/Sample Incubation (Negative Selection)
To each 25 ug of parental F98 or LnCaP exosomes in 70 ul reaction buffer add the mixture of competitors (10 ul of Salmon sperm DNA@80 ng/ul+10 ul of Yeast t-RNA@80 ng/ul), bring the volume to 150 ul by addition of 60 ul reaction buffer and incubate for 20 min with shaking at 500 rpm on mixmate. Then add eluted oligonucleotide probe libraries (~50 ul) (heat treat for 3 min@95 C, incubate on ice immediately for 5 min) from step IV and incubate 30 min at room temperature (RT).
VI. Precipitation protocol with 6% PEG8000 (using sample from III)
a) Use microvesicles/DNA mixture from step V.
b) Add 200 ul of 12% PEG8000 to 200 ul of sample.
c) Leave sample on ice for 30 min.
d) Spin at 16000×g for 10 min and collect supernatant.
VII. Library/Sample Incubation (Positive Selection)
To each 25 ug of transfected F98 or VCaP exosomes in 70 ul reaction buffer add the mixture of competitors (10 ul of Salmon sperm DNA@80 ng/ul+10 ul of Yeast t-RNA@80 ng/ul) and incubate for 20 min with shaking at 500 rpm on mixmate. Then, add oligonucleotide probe libraries (~400 ul) (heat treat for 3 min@95 C, put it on ice immediately for 5 min) from step VI and incubate 30 min at RT (total volume of 490 ul).
VIII. Precipitation Protocol with 6% PEG8000
a) Use microvesicles from step VII as sample.
b) Add 490 ul of 12% PEG8000 to 490 ul of sample.

c) Leave sample on ice for 30 min.
d) Spin at 16000×g for 10 min and discard supernatant.
e) Re-suspend pellet in 200 ul reaction buffer and centrifuge again at 16000×g for 10 min
f) Re-suspend pellet in 30 ul of reaction buffer.
g) Go to PCR.
Probing Exosomes can be probed with the enriched oligonucleotide probe libraries. For these experiments, exosomes are contacted with ssDNA enriched oligonucleotide probe libraries, precipitated with 6% PEG8000, and the co-precipitated oligonucleotide probes are amplified by qPCR.

Example 19

Oligonucleotide Enrichment on HER2+ Tissue Samples

Receptor tyrosine-protein kinase erbB-2 (ERBB2) is a protein encoded by the ERBB2 gene, which is also frequently called HER2 (human epidermal growth factor receptor 2) or HER2/neu. About 20% of breast cancers overexpress the HER2 gene, which causes cells to receive improper signals to grow and divide. HER2+ cancers tend to be aggressive and fast-growing. For individuals with HER2+ breast cancers, the anti-HER2 monoclonal antibody trastuzumab (trade name Herceptin) has been shown to dramatically reduce the risk of recurrence.

Figure 15A:
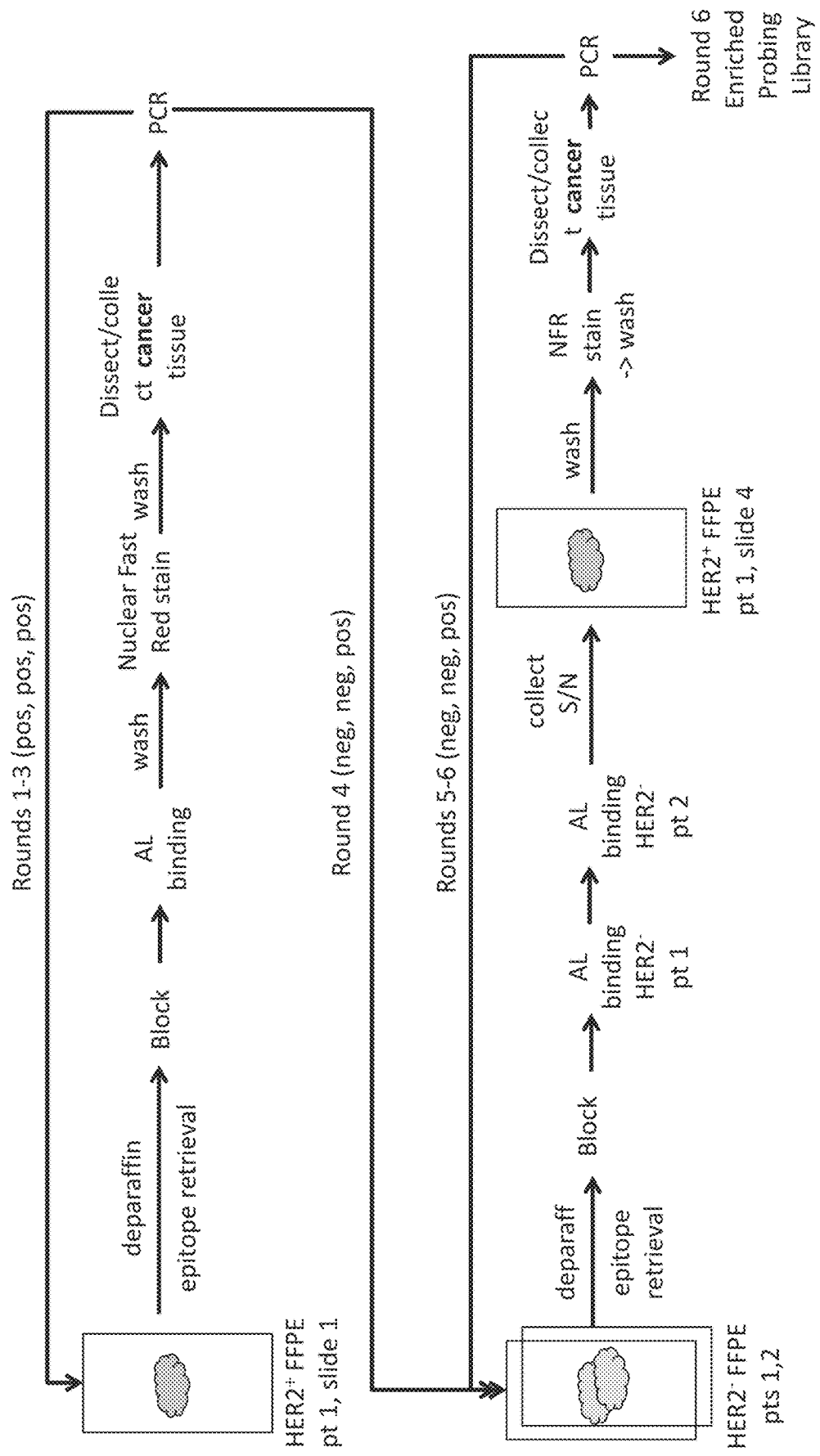
Figure 15B:
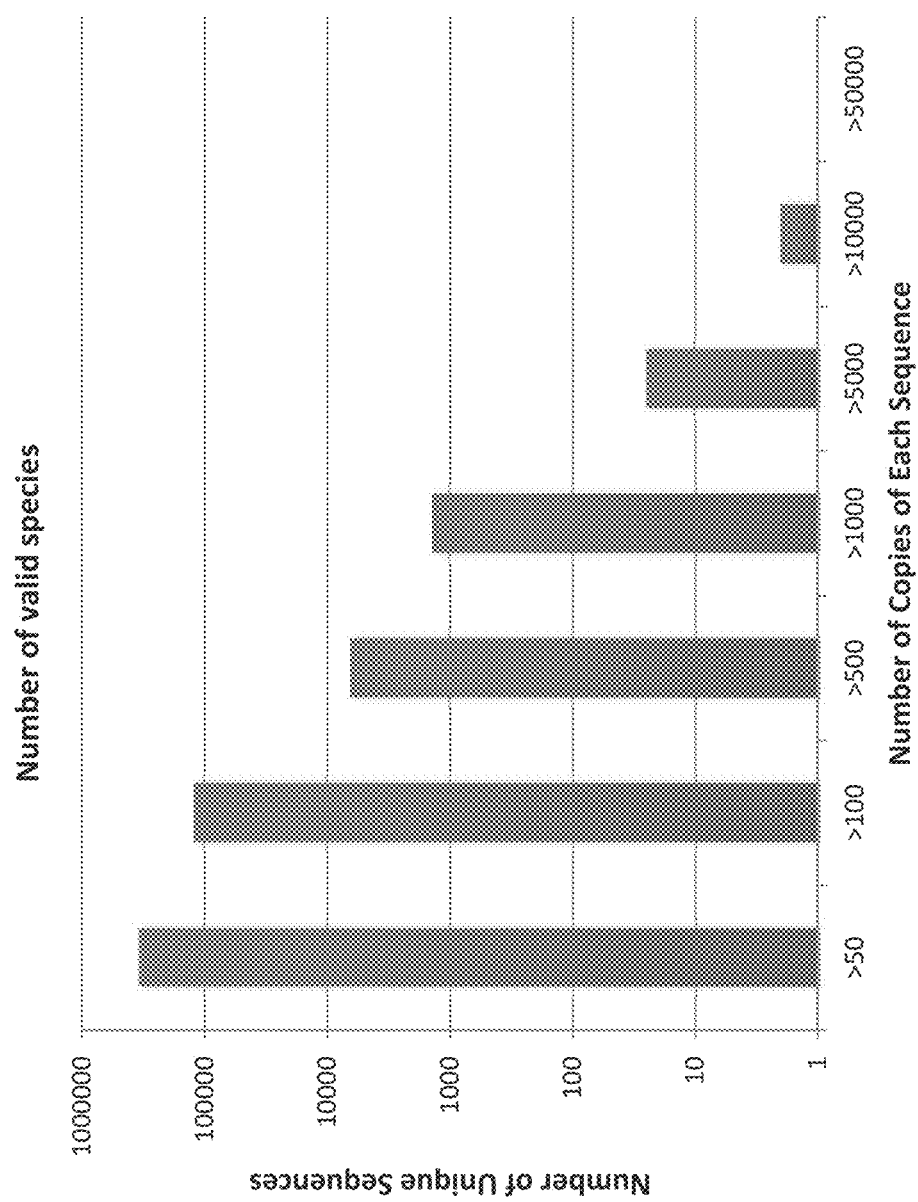

In this Example, we enriched a naïve F-Trin-B oligonucleotide probe library against HER2 positive (HER2+) fixed tissue samples. The probe library is as described herein, i.e., each member has a 5' primer CTAGCATGACTGCAGTACGT (SEQ ID NO 4) and a 3' primer CTGTCTCTTATACACATCTGACGCTGCCGACGA (SEQ ID NO 5) surrounding a variable region. Enrichment was performed as described herein using six rounds of selection against FFPE (fresh frozen paraffin embedded) tissue from five patients with HER2+ invasive breast cancer (the HER2+ cohort) and six patients with HER2− invasive breast cancer (the HER2− cohort). HER2 status was determined by IHC assay. The blocking buffer used during selection comprised Salmon sperm DNA, tRNA, F127 polymer, and BSA protein. The enrichment scheme is detailed in FIG. 15A. As indicated in the figure, rounds 1-3 were performed using positive selection only (i.e., to enrich binders to the HER2+ samples). Rounds 4-6 used both positive selection against the HER2+ samples and negative selection against the HER2− samples. The enriched library at the end of round 6 was used in further studies as the Enriched Probing Library. Attributes of the Enriched Probing Library are shown in FIG. 15B, wherein the number of unique valid sequences is plotted against the numbers of copies of each sequence, as determined by NGS. The Enriched Probing Library comprised $3.6 \times 10^7$ unique sequences. The variable regions of the 50 most prevalent sequences are listed in order of highest prevalence to lower prevalence in SEQ ID NOs 2989-3038.

The Enriched Probing Library was used to stain HER2+ and HER2− breast cancer tissue. FIG. 15C shows representative staining of a HER2+ tumor sample after no enrichment (Round 0, "R0" in the figure, left panel) or after the six rounds of enrichment (post-Round 6, "R6" in the figure, right panel). As seen in the figure, much higher amounts of stain were observed with the enriched R6 probe library as compared to the naïve R0 library. Similarly, FIG. 15D shows representative staining of a HER2− tumor sample after no enrichment (R0, left panel) or after the six rounds of enrichment (R6, right panel). As seen in the figure, little to no staining was observed with either the enriched R6 probe library or the naïve R0 library.

Figure 15E:
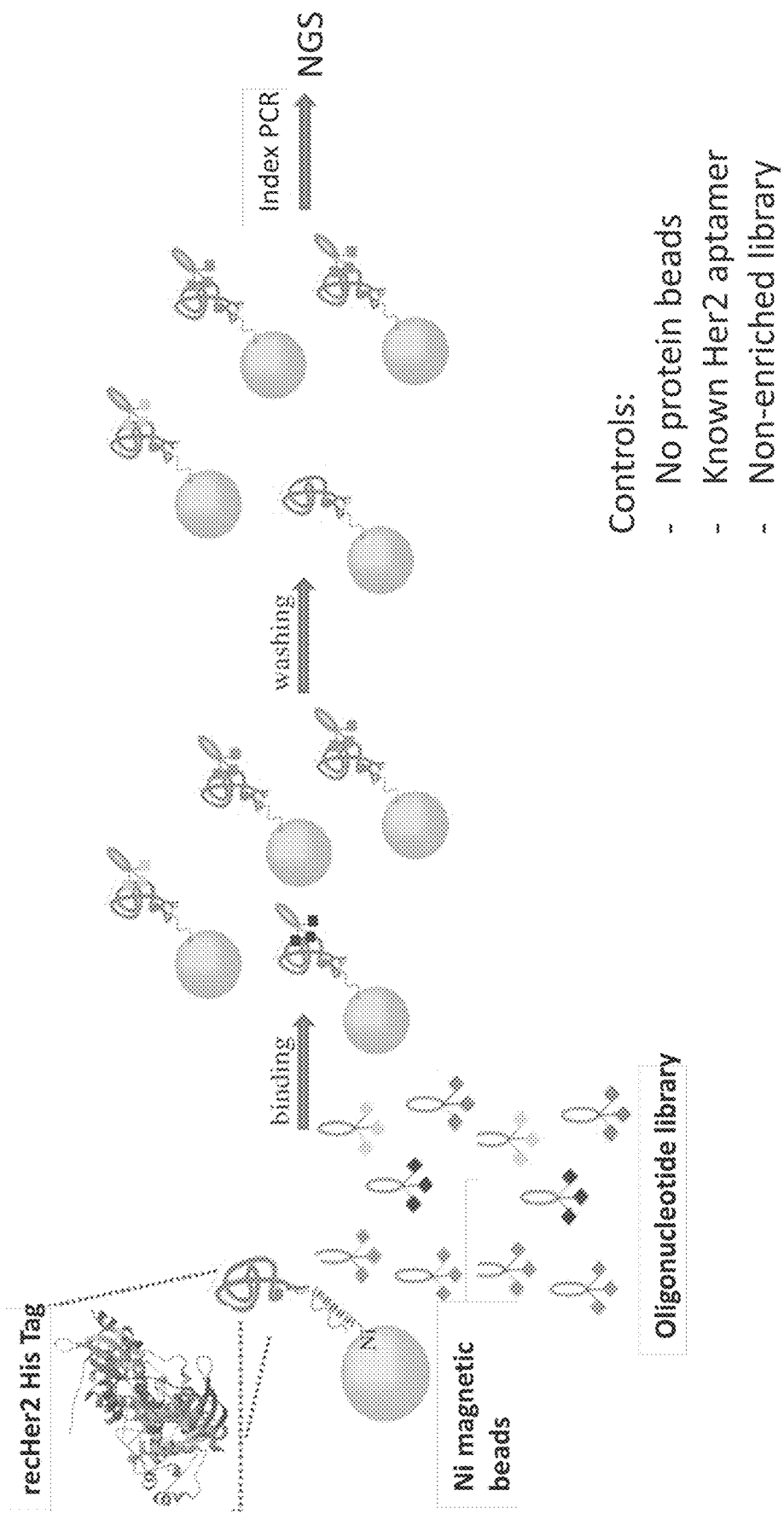

To identify specific members of the Enriched Probing Library that bind HER2, the experimental plan outlined in FIG. 15E was performed. Recombinant HER2 caning a histadine tag ("recHer2 His Tag") was conjugated to magnetic beads ("Ni magnetic beads"). The beads were mixed with the Enriched Probing Library ("Oligonucleotide library") and allowed to incubate to allow binding of probes to the HER2 beads. The bound beads were washed and probe binders were recovered and identified by next generation sequencing (NGS) Similar experiments were performed with negative controls to filter out probes that bind assay components, including No protein beads and Non-enriched library. A known HER2 aptamer was used as a positive control. The experiments were performed twice and a number of filters were applied, such as sequences that appeared in both sets of binding experiments and did not bind the protein beads. With all controls filtered out, there were 404 sequences remaining. The variable regions of the most prevalent sequences, ordered by prevalence, are listed as SEQ ID NOs 3039-3061. These sequences are ordered individually and used in an immunoassay format to identify HER2 binders.

We next explored targets of the R6 library. The R6 library and the unenriched R0 library were amplified with a Biotin-C3-C6-amine primer. The libraries were TBE gel purified, conjugated with the amine reactive diazirine crosslinker, Sulfo-NHS-SS-Diazirine (Sulfo-SDAD) (sulfosuccinimidyl 2-[(4,4'-azipentanamido)ethyl]-1,3'-dithioproprionate) (Thermo Scientific) and purified by HPLC to remove the unconjugated oligonucleotides. The SDAD conjugated library was then qualified for staining HER2+ or HER2− FFPE tissue slides compared to the biotinylated library used for enrichment as detailed above.

Binding of the conjugated library was done under similar conditions used for the selection on HER2+ or HER2− tissue on a Ventana Discovery Ultra instrument (Ventana Medical Systems, Tucson, Ariz.). One set of slides for each tissue (HER2+ or HER2) were stained with the R6 library, the R0 library, or no library to assess the level of specific binding. In parallel, nine slides per condition was removed prior to detection with Streptavidin-horse radish peroxidase (Strept-HRP) and were subjected to photo-crosslinking 2 cm above the slide at 365 nm with a handheld UV light for 10 minutes on ice. Slides were then scraped into QProteome buffer without beta-mercaptoethanol added (Qiagen) and extracted according to manufacturer's instructions. Detergent was removed with HiPPR detergent removal columns (Thermo Fisher Scientific) and protein concentration was then determined with the BCA assay. Cross-linked protein-aptamer complexes were then affinity purified from 200 µg of FFPE tissue lysate by incubation with 10 µL of Dynabeads® MyOne™ Streptavidin C1 (Thermo Scientific) for 30 mins at room temperature, washed twice with 1×TBS, washed twice with high stringency wash buffer (10 mM Tris, 2M NaCl, 1 mM EDTA, 1% Triton X-100), followed by two washes with low stringency wash buffer to remove the NaCl, resuspended in 1×PBS and eluted by boiling in 1× lauryl dodecyl sulfate (LDS) with reducing agent. Reducing the samples transfers the crosslinker from the aptamer to the protein targets. The reduced samples were run under reducing conditions in a 4-12% SDS-PAGE gel at 150 volts for 15 min. The entire lane was excised and subjected to in-gel trypsin digestion. Alkylation with iodoacetamide was replaced with Iodoacetyl Tandem Mass Tag™ (iodoTMT;

Thermo Fisher Scientific) to facilitate identification of cross-linked targets by LC-MS/MS.

Results for one HER2+ case are shown in Table 28. These results were filtered to remove proteins that also cross-linked with the unenriched R0 library. Background binding with the R0 library appeared to be most prevalent in the nucleus. The table indicates whether the identified proteins have been reported in association with HER2 or breast cancer (BrCa) or a clinical trial (for any indication), or have been used or suggested as a drug target for any indication. References are noted in brackets.

TABLE 28

Targets of R6 Identified for One HER2+ Tissue Sample

| Accession | Gene ID | Description | Her2 or BrCa related? | Drug Target | Clinical Trial |
|---|---|---|---|---|---|
| P60709 | ACTB | Actin, cytoplasmic 1 | Her2 and ATPase2 in actin rich membrane domains [1] | | |
| P14618 | PKM | Pyruvate kinase PKM | Early marker for response to trastuzumab therapy-tumor M2-PK (alias for PKM) determination in the plasma of patients with metastasized breast cancer could be a helpful tool for monitoring therapeutic success. Dichloroacetate (DCA, an inhibitor of the mitochondrial pyruvate dehydrogenase kinase) was able to depolarize cancer (but not normal) mitochondria and induce apoptosis in cancer but not normal tissues [2] | Yes | Yes |
| P17858-1 | PFKL | ATP-dependent 6-phosphofructokinase, liver type | pentose phosphate pathway gene; hexokinase-2, a key mediator of aerobic glycolysis, and the downstream proteins PFKL and ENO1; activated by p53 [3] | Yes | Yes |
| P25705-1 | ATP5A1 | ATP synthase subunit alpha, mitochondrial | Ectopic ATP synthase is a drug target for breast cancer; ATP synthase inhibitor citreoviridin [4], [5] | Yes | Yes |
| P06576 | ATP5B | ATP synthase subunit beta, mitochondrial | Ectopic ATP synthase is a drug target for breast cancer; ATP synthase inhibitor citreoviridin [4], [5] | Yes | Yes |
| P47914 | RPL29 | 60S ribosomal protein L29 | up in MCF-7 with treated with recombinant bromelain vs untreated MCF-7 [6] | Yes | |
| P62917 | RPL8 | 60S ribosomal protein L8 | The RPL8 antigen may represent a relevant vaccine target for patients with melanoma, glioma, and breast carcinoma whose tumors express this protein [7] | Yes | |
| Q8TEJ3 | SH3RF3 | SH3 domain-containing RING finger protein 3 | E3 ligase activity; anti-apoptotic regulator for the c-Jun N-terminal kinase (JNK) pathway [8], [9] | Yes | |
| P21802 | FGFR2 | Fibroblast growth factor receptor 2 | Target for triple negative Bca therapies. Gain of function mutations in FGFRs were also identified in a variety of human cancers such as myeloproliferative syndromes, lymphomas, prostate and breast cancers as well as other malignant diseases [10], [11] | Yes | Yes |
| P02675 | FGB | Fibrinogen beta chain | High plasma fibrinogen is correlated with poor response to trastuzumab treatment in HER2 positive breast cancer [12] | Yes | Yes |
| O60506 | SYNCRIP | Heterogeneous nuclear ribonucleoprotein Q | Component of the hepatocyte exosomal machinery controlling microma sorting | ? | |

References in Table 28

[1] Jeong et al., PMCA2 regulates HER2 protein kinase localization and signaling and promotes HER2-mediated breast cancer, PNAS, E282-E290 (pub'd online Jan. 4, 2016).

[2] Hoopmann et al., Tumor M2 pyruvate kinase—determination in breast cancer patients receiving trastuzumab therapy. Cancer Lett. 2002 Dec. 10; 187(1-2):223-8.

[3] Liu et al, Comprehensive Proteomics Analysis Reveals Metabolic Reprogramming of Tumor-Associated Macrophages Stimulated by the Tumor Microenvironment. J Proteome Res. 2017 Jan. 6; 16(1):288-297.

[4] Chang et al., Combination therapy targeting ectopic ATP synthase and 26S proteasome induces ER stress in breast cancer cells, Cell Death and Disease (2014) 5, e1540

[5] Pan et al., ATP synthase ecto-a-subunit: a novel therapeutic target for breast cancer, Journal of Translational Medicine 2011, 9:211

[6] Fouz et al., Gene expression analysis in MCF-7 breast cancer cells treated with recombinant bromelain. Appl Biochem Biotechnol. 2014 August; 173(7):1618-39.

[7] Swoboda, et al., Shared MHC Class II—Dependent Melanoma Ribosomal Protein L8 Identified by Phage Display. Cancer Res 2007; 67: (8). Apr. 15, 2007

[8] Karkkainen et al., POSH2 is a RING finger E3 ligase with Rac1 binding activity through a partial CRIB domain. FEBS Lett. 2010 Sep. 24; 584(18):3867-72

[9] Wilhelm et al., Sh3rf2/POSHER protein promotes cell survival by ring-mediated proteasomal degradation of the c-Jun N-terminal kinase scaffold POSH (Plenty of SH3s) protein. J Biol Chem. 2012 Jan. 13; 287(3):2247-56.

[10] Eswarakumar et al., Cellular signaling by fibroblast growth factor receptors. Cytokine Growth Factor Rev. 2005 April; 16(2):139-49

[11] Wang and Guda. Integrative exploration of genomic profiles for triple negative breast cancer identifies potential drug targets. Medicine (Baltimore). 2016 July; 95(30): e4321.

[12] Liu et al., High Plasma Fibrinogen is Correlated With Poor Response to Trastuzumab Treatment in HER2 Positive Breast Cancer, Medicine. 94(5) February 2015.

[13] Santangelo et al., The RNA-Binding Protein SYNCRIP Is a Component of the Hepatocyte Exosomal Machinery Controlling MicroRNA Sorting. Cell Rep. 2016 Oct. 11; 17(3):799-808.

This Example presents an approach wherein oligonucleotide probes can be identified using tissue sample input. The resulting oligonucleotides can be used to identify HER2+ tissue samples and distinguish HER2− tissues. General applications of this approach include without limitation identifying predictive biomarkers and identifying drug targets. In this specific case, oligonucleotide probes are identified that indicate aggressive phenotype (i.e., HER2+ tumors are known to be aggressive) but that can be targeted by anti-HER2 treatments. We also identified certain targets of the R6 library in a HER2+ breast cancer sample and specifically identified several drug targets. Moreover, the oligonucleotides themselves can be used to target these proteins, and thus comprise drug candidates at the same time they identify drug targets.

This approach in this Example can be used for any other appropriate biomarkers.

Example 20

Oligonucleotide Enrichment on Tissue Samples to Identify Drug Responders

Figure 16A:
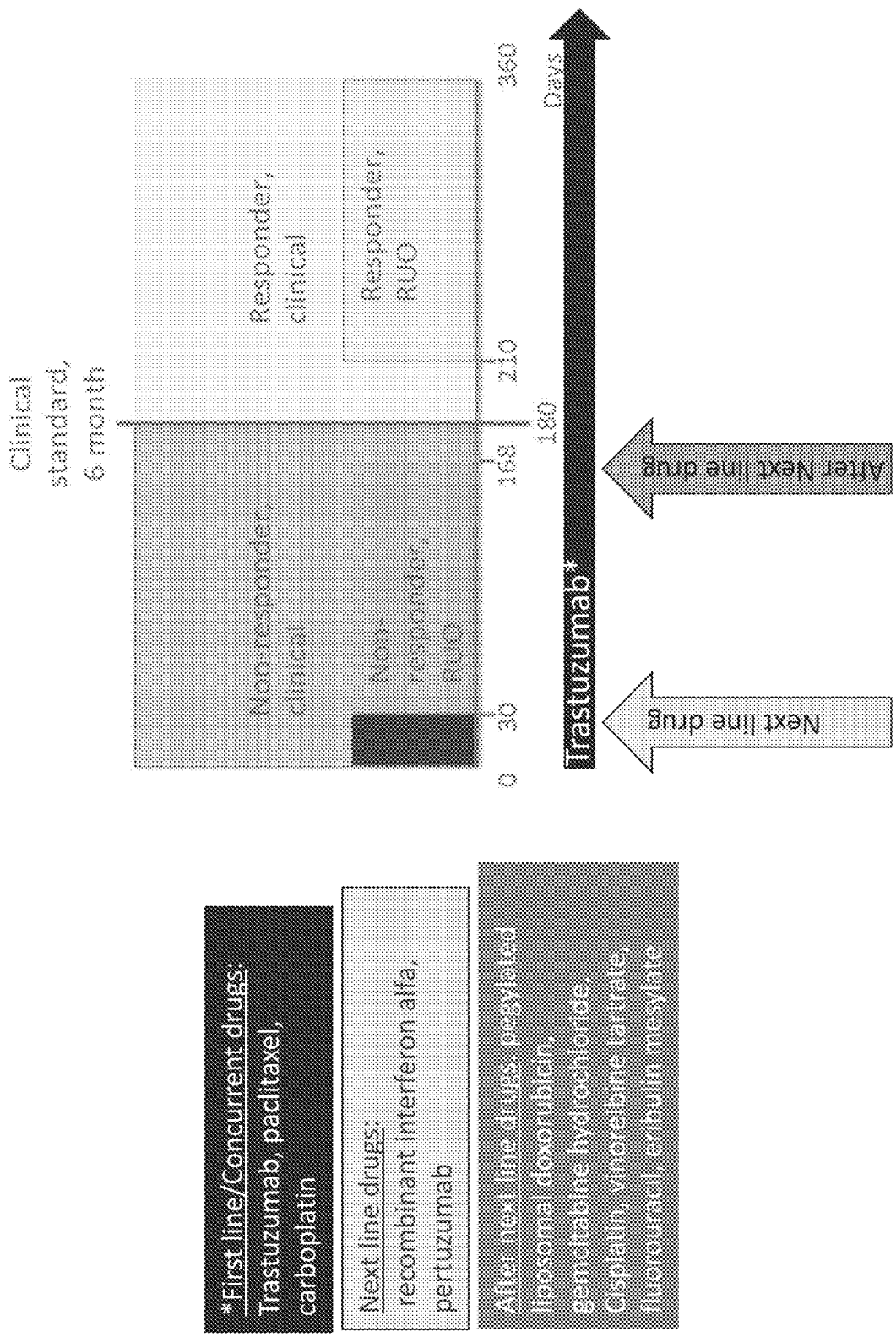

This Example follows the work presented in Example 19 above. The task was to develop an oligonucleotide library capable of distinguishing Breast Cancer (BCa) patients that respond or not to trastuzumab treatment. Often administered together with various chemotherapeutic agents, trastuzumab alone shows efficacy in some patients (<20%) that overexpress HER2 as determined by IHC assay. For purposes of this Example, responders and non-responders are based upon each patient's time-to-next-treatment ("TNT" or "TTNT") as a proxy for response. FIG. 16A illustrates treatment schemes for BCa along with a timeline differentiating between responders and non-responders. As shown the non-responders are treated with another chemotherapy treatment within six months of initiation of treatment with trastuzamab. The resulting oligonucleotides can be used to predict response and direct therapy to proper population of patients.

Figure 16B:
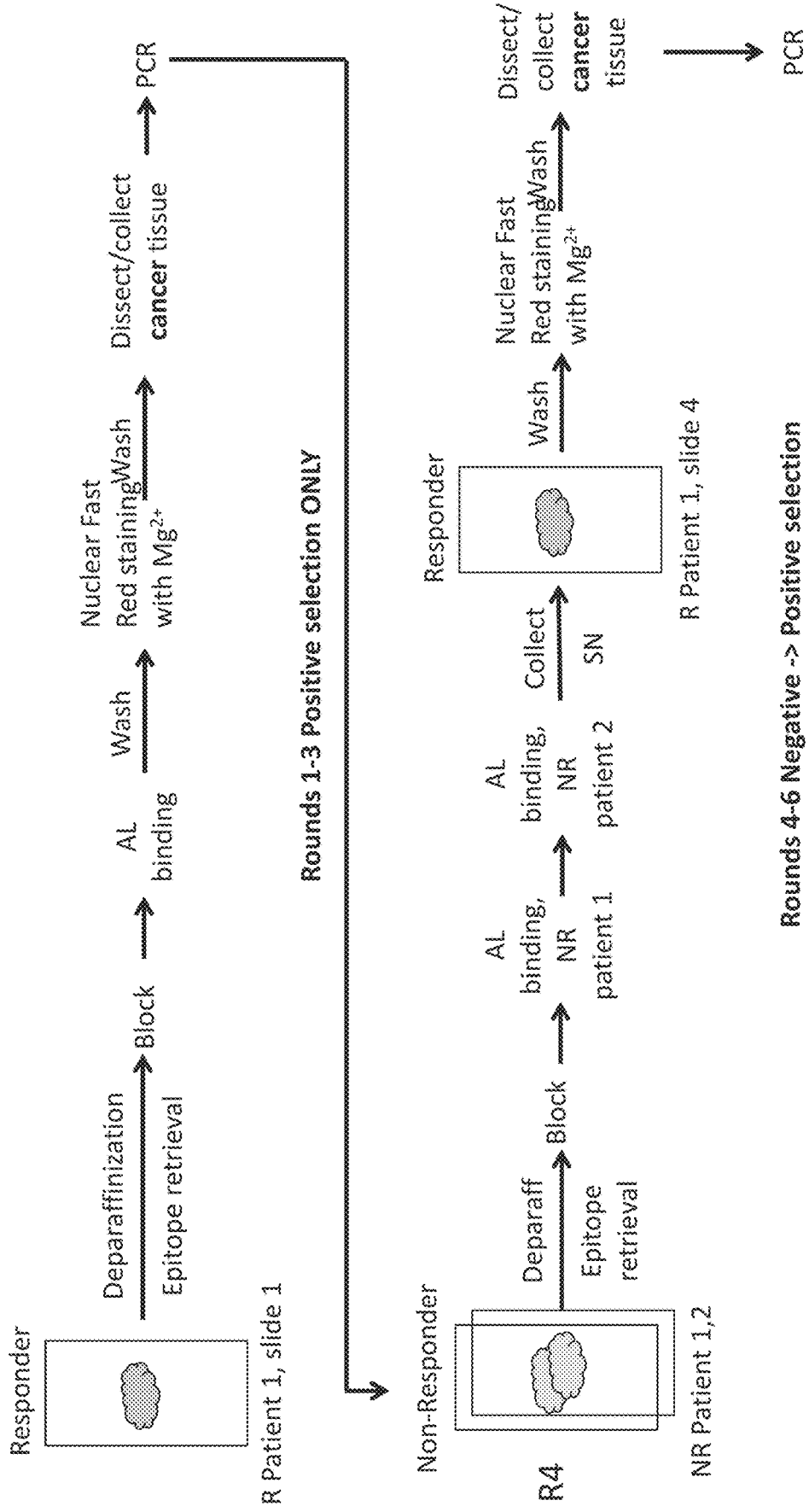

Methodology was similar to that described above in Example 19. A general scheme for enrichment of the naïve F-trin-35 library is shown in FIG. 16B (AL=aptamer library). In the figure, responders are shown as positive samples for selection, but enrichments were similarly performed with non-responders as the positive samples for enrichment. Six rounds of enrichment were performed. 17 enriched oligonucleotide libraries were obtained, wherein eight libraries were trained towards non-responder and nine libraries were trained toward responders. The 17 libraries are referred to as libraries A-S.

Figure 16E:
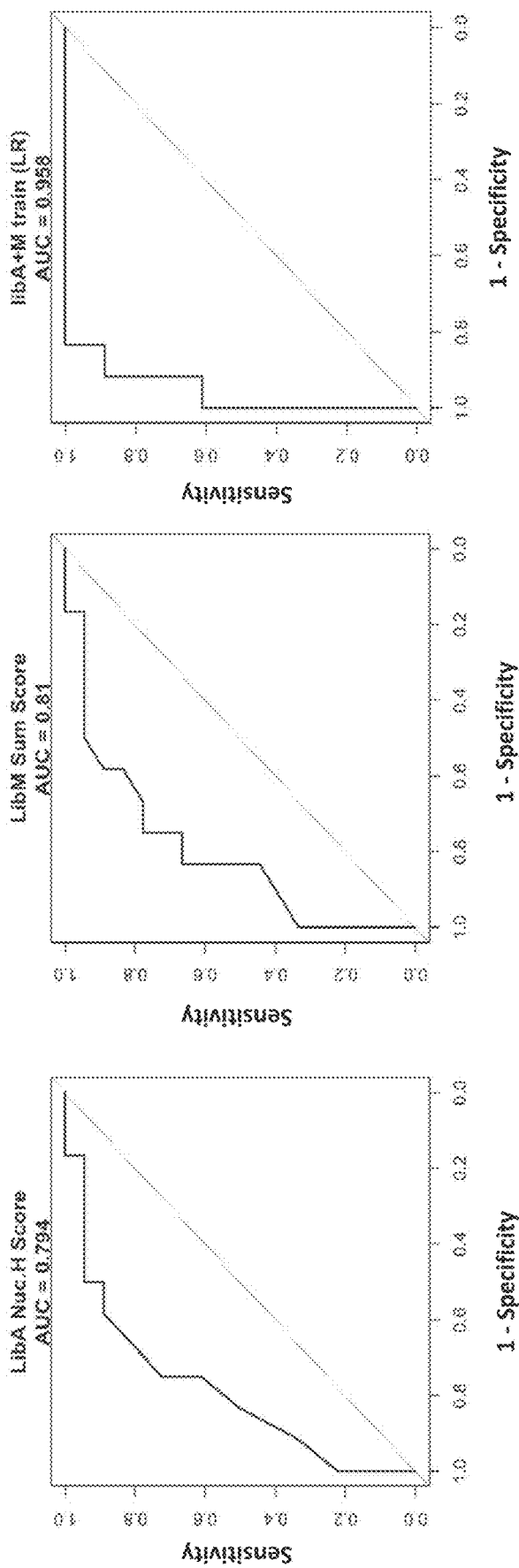
Figure 16F:
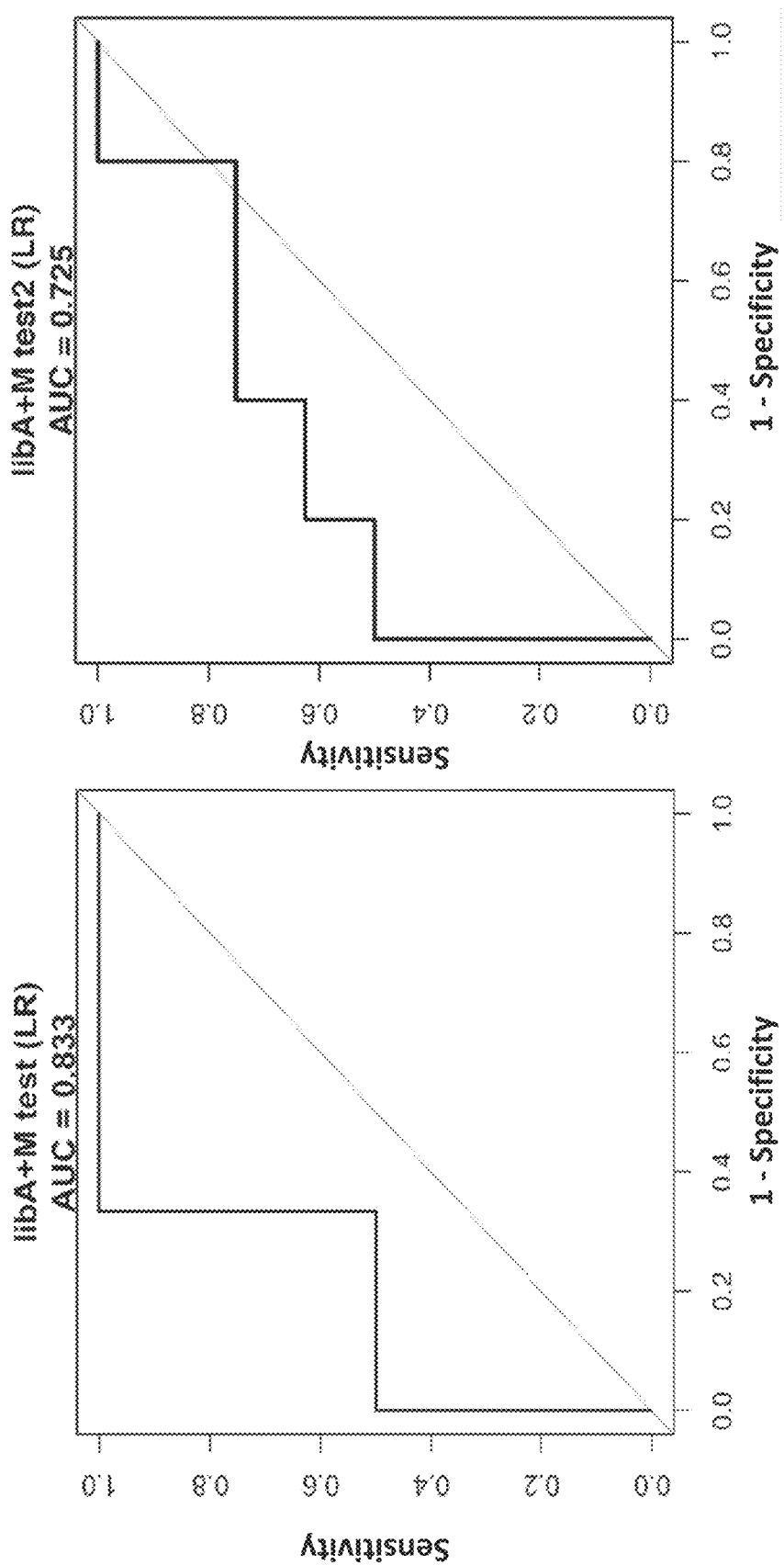

The libraries were trained on a set of 20 non-responders and 20 responders. Given this patient cohort, responders were defined as patients treated for 212 days and up with trastuzamab and non-responders were defined as those treated for 8-119 days with trastuzumab. FIG. 16C shows staining of non-responder and responder samples using oligonucleotide probe library A sorted by staining intensity. As can be observed in the figure, staining was more prevalent in the non-responder samples Summary results for staining the training samples the Non-responder selected library A and responder selected library M are shown in FIG. 16D. The variable regions of the 100000 most prevalent sequences in library A are included herein as SEQ ID NOs. 3062-103061, ordered by prevalence. The variable regions of the 100000 most prevalent sequences in library M are included herein as SEQ ID NOs. 103062-203061, also ordered by prevalence. ROC curves generated for each library separately and the combined A & M libraries are shown in FIG. 16E. Joint performance was determined using logistic regression. Several non-responder samples without sufficient slides were removed from these data. As shown in FIG. 16E, the trained library A and library M had excellent performance for distinguishing the responder and non-responder samples. As a control, library A was used to stain slides from breast cancer cases that were not treated with trastuzumab. No differential staining patterns were observed (data not shown). FIG. 16F shows results of using the trained libraries to classify two small test sets with significant AUC values as shown. The combined AUC was 0.78, which indicates clinical utility.

Thus, the oligonucleotide probe libraries can be used to identify trastuzumab responder tissues instead of only HER2+ tissues per currently available companion diagnostics.

As in Example 19 above, targets are identified that are responsible for the response (or its absence) to trastuzumab and which can be used to develop more efficient treatment.

Example 21

Polyligand Profiling Differentiates Cancer Patients According to their Benefit of Treatment Patient response to specific cancer treatment is dependent upon subtle differences in tumor systems states that can be difficult to access. Highly multiplexed measurement techniques can be advantageous to assess these perturbations. In this Example, we used polyligand profiling with oligonucleotide probe libraries as described herein to perform such analysis. We generated two single-stranded oligodeoxynucleotide probe libraries that distinguish between tumor tissue from breast cancer patients who either did or did not derive benefit from trastuzumab-based regimens. Testing of an independent sample set verified the ability of the libraries to differentiate patients, as assessed by calculating AUC values from ROC curves in comparison to standard HER2-immunohistochemical scoring. Kaplan-Meier plots confirmed that outcomes were in accordance with test results: Test-positive patients had a median duration of 604 days of trastuzumab treatment, whereas test-negative patients had a median duration of 129 days of trastuzumab treatment. Thus, this Example demonstrates use of polyligand profiling to classify distinct clinical outcomes.

Precision oncology seeks to adapt the treatment of individual cancer patients to the specific mutations and unique molecular interaction networks of each tumor. The genomic complexity and heterogeneity of the underlying molecular signatures is vast and each tumor can have its unique profile, even within the same patient (1-3). Patients that benefit from specific treatment regimens often differ from those that do not in features other than merely the expression status of single or small numbers of biomarkers. Consequently, the current paradigms for precision oncology rely on three major pillars: First, the identification of mutations by DNA/RNA sequencing in patients' tumors; second, the quantification of known biomarkers in tumor tissue; third, the identification of new biomarkers and master regulator genes. However, based on the limited success of several recent clinical trials, the prospect and potential of precision oncology has recently been challenged (4, 5). Thus, limitations have become evident and call for a paradigm-shift to facilitate the identification of patients who will or will not benefit from a particular cancer treatment (6-8) and the development of improved companion diagnostic tests (CDx) (9). Because single or small numbers of biomarkers may not always adequately predict treatment benefit, in these cases a more effective CDx would simultaneously access the multitude of intricate molecular features that underlie the vastly complex and currently largely unpredictable phenotype of drug response. Accessing the phenotypic diversity conferred by tumor heterogeneity and the changes in the tumor microenvironment that are induced by tumor cells may require identification of subtle variations in the underlying molecular interaction network, or interactome, the complexity of which is estimated to consist of several hundred thousand, or even millions of multi-molecular complexes (10). Such identification may benefit from an unbiased, hypothesis-free approach to access informative and highly complex molecular characteristics, a challenge that could require an equal or greater number of potential detector molecules.

Here we report one approach to achieve this comprehensive goal: polyligand profiling. In this Example, we assessed the ability of polyligand profiling to differentiate between patients who do or do not derive benefit from a particular cancer treatment, which may also be referred to as responders or non-responders, respectively. We then compare polyligand profiling to immunohistochemical (IHC) analysis of HER2, one of the most successful and widely applied CDx. Her2 is overexpressed in fifteen to thirty percent of human breast cancers (11, 12). Because HER2 amplification is associated with increased tumor cell proliferation and poor prognosis, patients with HER2 positive (HER2+) breast cancer are candidates for treatment with trastuzumab. However, only 30% of patients with HER2+ breast cancer benefit from trastuzumab mono-therapy (13). Trastuzumab (Herceptin) is a monoclonal antibody that binds human epidermal growth factor receptor 2 (HER2, ErbB2) and inhibits its function (14-16).

Materials and Methods for the experiments described in this Example are provided in Example 22 below. Clinical information for patients included in this Example is provided in Tables 29-32. In the tables, "CPP" stands for cyclophosphamide. All samples were breast carcinomas.

TABLE 29

| Patient Information: Training toward Non-Benefiters (NB) | | | | | | | |
|---|---|---|---|---|---|---|---|
| Enrichment case ID | TTNT | HER2 ISH | HER2 IHC | First line regimen | Next line regimen | Additional treatments | Clinical |
| TL-NB+ | 158 | + | + | carboplatin paclitaxel trastuzumab | recombinant interferon alfa-2b pertuzumab | pegylated liposomal doxorubicin hydrochloride gemcitabine hydrochloride cisplatin vinorelbine tartrate fluorouracil eribulin mesylate | Diagnosis: Ultrasound-guided core biopsy, right breast: Infiltrating carcinoma involving all cores. Stage: Unknown Grade: 3/Poorly differentiated |
| TL-NB− | 335 | + | + | carboplatin docetaxel trastuzumab | | | Diagnosis: Left breast, lumpectomy: Invasive ductal carcinoma. Stage: I Grade: 2/Moderately differentiated |
| TL-NB− | 280 | + | + | carboplatin paclitaxel trastuzumab | ado-trastuzumab emtansine | | Diagnosis: Left breast and axilla (modified mastectomy): Invasive |

TABLE 29-continued

Patient Information: Training toward Non-Benefiters (NB)

| Enrichment case ID | TTNT | HER2 ISH | HER2 IHC | First line regimen | Next line regimen | Additional treatments | Clinical |
|---|---|---|---|---|---|---|---|
| | | | | | | | ductal carcinoma, poorly differentiated. Stage: IIIC Grade: 3/Poorly differentiated |
| Alt. lib. 1+ | 119 | − | − | trastuzumab vinorelbine tartrate | eribulin mesylate | trastuzumab nab-paclitaxel | |
| Alt. lib. 1− | 321 | − | − | trastuzumab vinorelbine tartrate | | | |
| Alt. lib. 1− | 225 | + | + | trastuzumab vinorelbine tartrate | ado-trastuzumab emtansine | docetaxel pertuzumab nab-paclitaxel | |
| Alt. lib. 2+ | 21 | + | + | trastuzumab | docetaxel carboplatin | | |
| Alt. lib. 2− | 294 | + | + | trastuzumab | carboplatin gemcitabine hydrochloride | ado-trastuzumab emtansine | |
| Alt. lib. 2− | 349 | + | − | trastuzumab | | | |
| Alt. lib. 3+ | 15 | + | + | trastuzumab | docetaxel | carboplatin nab-paclitaxel | |
| Alt. lib. 3− | 294 | + | + | trastuzumab | carboplatin gemcitabine hydrochloride | ado-trastuzumab emtansine | |
| Alt. lib. 3− | 349 | + | − | trastuzumab | | | |
| Alt. lib. 4+ | 109 | + | + | paclitaxel pertuzumab trastuzumab | cyclophosphamide doxorubicin hydrochloride | | |
| Alt. lib. 4− | 263 | + | + | docetaxel pertuzumab trastuzumab | | | |
| Alt. lib. 4− | 217 | − | +/− | nab-paclitaxel pertuzumab trastuzumab | letrozole fulvestrant | | |
| Alt. lib. 5+ | 56 | − | +/− | nab-paclitaxel pertuzumab trastuzumab | carboplatin gemcitabine hydrochloride | ado-trastuzumab emtansine eribulin mesylate | |
| Alt. lib. 5− | 263 | + | + | docetaxel pertuzumab trastuzumab | | | |
| Alt. lib. 5− | 217 | − | +/− | nab-paclitaxel pertuzumab trastuzumab | letrozole fulvestrant | | |
| Alt. lib. 6+ | 56 | + | +/− | trastuzumab vinorelbine tartrate | carboplatin | ado-trastuzumab emtansine trastuzumab fulvestrant cyclophosphamide methotrexate fluorouracil leuprolide acetate docetaxel gemcitabine hydrochloride | |
| Alt. lib. 6− | 321 | − | − | trastuzumab vinorelbine tartrate | | | |
| Alt. lib. 6− | 225 | + | + | trastuzumab vinorelbine tartrate | ado-trastuzumab emtansine | docetaxel pertuzumab nab-paclitaxel | |
| Alt. lib. 7+ | 69 | n.p. | − | docetaxel pertuzumab trastuzumab | leuprolide acetate | docetaxel | |
| Alt. lib. 7− | 263 | + | + | docetaxel pertuzumab trastuzumab | | | |
| Alt. lib. 7− | 217 | − | +/− | nab-paclitaxel pertuzumab trastuzumab | letrozole fulvestrant | | |

TABLE 30

| Enrichment case ID | TTNT | HER2 ISH | HER2 IHC | First line regimen | Next line regimen | Additional treatments | Clinical |
|---|---|---|---|---|---|---|---|
| Patient Information: Training toward Benefiters (B) | | | | | | | |
| Alt. lib. 8+ | 364 | + | + | trastuzumab vinorelbine tartrate | ado-trastuzumab emtansine | | |
| Alt. lib. 8− | 33 | + | + | trastuzumab vinorelbine tartrate | docetaxel | | |
| Alt. lib. 8− | 85 | − | − | trastuzumab vinorelbine tartrate | docetaxel | docetaxel investigational agent cyclophosphamide fluorouracil | |
| Alt. lib. 9+ | 369 | − | Equivocal | trastuzumab | docetaxel pertuzumab | ado-trastuzumab emtansine | |
| Alt. lib. 9− | 56 | n.p. | + | trastuzumab | leuprolide acetate | vinorelbine tartrate eribulin mesylate bevacizumab nab-paclitaxel ado-trastuzumab emtansine trastuzumab | |
| Alt. lib. 9− | 20 | − | − | trastuzumab | nab-paclitaxel | vinorelbine tartrate gemcitabine hydrochloride | |
| TL-B+ | 371 | + | + | carboplatin docetaxel trastuzumab | | | Diagnosis: Left breast, lumpectomy: Infiltrating ductal carcinoma, poorly differentiated/grade 3. Stage: IIIA Grade: 3/Poorly differentiated |
| TL-B− | 42 | + | + | carboplatin nab-paclitaxel trastuzumab | pegylated liposomal doxorubicin hydrochloride | cyclophosphamide | Diagnosis: Right breast mass, excision: Multifocal invasive ductal carcinoma. Stage: IV Grade: 3/Poorly differentiated |
| TL-B− | 91 | + | + | carboplatin docetaxel trastuzumab | letrozole | | Diagnosis: Breast, left, Mammotome biopsy: Infiltrating ductal carcinoma, no special type. High combined histologic grade (3, 3, 2). Stage: I Grade: 3/Poorly differentiated |
| Alt. lib. 10+ | 406 | + | + | trastuzumab | | | |
| Alt. lib. 10− | 56 | n.p. | + | trastuzumab | leuprolide acetate | vinorelbine tartrate eribulin mesylate bevacizumab nab-paclitaxel ado-trastuzumab emtansine trastuzumab | |
| Alt. lib. 10− | 20 | − | − | trastuzumab | nab-paclitaxel | vinorelbine tartrate gemcitabine hydrochloride | |
| Alt. lib. 11+ | 598 | + | + | trastuzumab vinorelbine tartrate | vinorelbine tartrate trastuzumab | trastuzumab gemcitabine hydrochloride docetaxel pertuzumab eribulin mesylate | |
| Alt. lib. 11− | 33 | + | + | trastuzumab vinorelbine tartrate | docetaxel | | |
| Alt. lib. 11− | 85 | − | − | trastuzumab vinorelbine tartrate | docetaxel | docetaxel investigational agent cyclophosphamide fluorouracil | |
| Alt. lib. 12+ | 604 | − | − | carboplatin docetaxel trastuzumab | gemcitabine hydrochloride | | |

TABLE 30-continued

Patient Information: Training toward Benefiters (B)

| Enrichment case ID | TTNT | HER2 ISH | HER2 IHC | First line regimen | Next line regimen | Additional treatments | Clinical |
|---|---|---|---|---|---|---|---|
| Alt. lib. 12− | 42 | + | + | carboplatin nab-paclitaxel trastuzumab | pegylated liposomal doxorubicin hydrochloride | cyclophosphamide | |
| Alt. lib. 12− | 91 | + | + | carboplatin docetaxel trastuzumab | letrozole | | |
| Alt. lib. 13+ | 623 | + | + | nab-paclitaxel trastuzumab | gemcitabine hydrochloride | ado-trastuzumab emtansine | |
| Alt. lib. 13− | 67 | + | + | docetaxel trastuzumab | pertuzumab | fulvestrant | |
| Alt. lib. 13− | 70 | +/− | − | paclitaxel trastuzumab | nab-paclitaxel | cyclophosphamide doxorubicin hydrochloride docetaxel pertuzumab ado-trastuzumab emtansine docetaxel trastuzumab pertuzumab | |
| Alt. lib. 14+ | 391 | + | + | trastuzumab | | | |
| Alt. lib. 14− | 56 | n.p. | + | trastuzumab | leuprolide acetate | vinorelbine tartrate eribulin mesylate bevacizumab nab-paclitaxel ado-trastuzumab emtansine trastuzumab | |
| Alt. lib. 14− | 20 | − | − | trastuzumab | nab-paclitaxel | vinorelbine tartrate gemcitabine hydrochloride | |
| Alt. lib. 15+ | 1202 | − | − | paclitaxel trastuzumab | nab-paclitaxel gemcitabine hydrochloride | | |
| Alt. lib. 15− | 67 | + | + | docetaxel trastuzumab | pertuzumab | fulvestrant | |
| Alt. lib. 15− | 70 | +/− | − | paclitaxel trastuzumab | nab-paclitaxel | cyclophosphamide doxorubicin hydrochloride docetaxel pertuzumab ado-trastuzumab emtansine docetaxel trastuzumab pertuzumab | |

TABLE 31

Patient Information: Test Herceptin TTNT

| ID | Type | Diagnosis | TTNT | Censored | First line | Next line | Stage | Grade | Specimen cite | Age | HER2 IHC | HER2 ISH | ER |
|---|---|---|---|---|---|---|---|---|---|---|---|---|---|
| ALx-R-18 | R | Mid chest wall, biopsy: Poorly differentiated carcinoma, involving dermis and subcutaneous fibroadipose tissue. | 219 | Y | trastuzumab nab-paclitaxel | | IV | Grade 3/Poorly differentiated | Chest, NOS | 58 | NA | + | − |
| ALx-NR-10 | NR | Liver; biopsy: Malignant epithelial neoplasm, consistent within metastatic invasive lobular carcinoma. | 78 | N | gemcitabine hydrochloride trastuzumab docetaxel | carboplatin | IV | Unknown | Liver | 52 | − | − | − |
| ALx-R-20 | R | Left breast mass, excision: Invasive ductal carcinoma, grade 3. | 391 | Y | trastuzumab | | Unknown | Grade 3/Poorly differentiated | Breast | 60 | + | + | + |
| ALx-R-10 | R | Breast, left, 3 o'clock, 7 cm from nippled (ultrasound guided core biopsy): Invasive ductal carcinoma. | 287 | Y | gemcitabine hydrochloride carboplatin trastuzumab | | Unknown | Grade 3/Poorly differentiated | Breast | 52 | − | +/− | + |
| ALx-R-19 | R | Mass, left axilla, needle biopsy: Invasive adenocarcinoma, morphologically consistent with recurrent breast carcinoma. | 321 | Y | trastuzumab vinorelbine tartrate | | IV | Grade 3/Poorly differentiated | Connective & Soft Tissue | 46 | − | − | + |
| ALx-R-14 | R | Left breast, mastectomy: In situ intraductal and infiltrating duct carcinoma. Tumor emboli in dermal lymphatics of skin and nipple. | 765 | N | fulvestrant carboplatin docetaxel trastuzumab | | IV | Grade 3/Poorly differentiated | Breast | 65 | − | +/− | + |
| ALx-NR-20 | NR | Lymph node, right axillary (needle core biopsy): Metastatic high-grade carcinoma, consistent with breast primary. | 70 | N | trastuzumab paclitaxel | nab-paclitaxel | IV | Grade 3/ Poorly differentiated | Lymph Nodes | 40 | − | +/− | + |
| ALx-NR-18 | NR | Liver mass, biopsy: Metastatic adenocarcinoma, compatible with breast primary. | 67 | N | trastuzumab docetaxel | pertuzumab | IV | Grade 2/Moderately differentiated | Liver | 63 | + | + | + |
| ALx-R-5 | R | Left breast, 2:00, lumpectomy: Infiltrating ductal carcinoma, moderately differentiated, grade II/III. | 339 | Y | CPP docetaxel trastuzumab | | I | Grade 2/Moderately differentiated | Breast | 52 | + | + | + |
| ALx-NR-7 | NR | Right supraclavicular lymph node: Single lymph node (3 cm), replaced by metastatic carcinoma. | 56 | N | trastuzumab nab-paclitaxel pertuzumab | gemcitabine hydrochloride carboplatin | IIIC | Unknown | Lymph Nodes | 47 | +/− | − | + |
| ALx-R-4 | R | Liver, partial hepatectomy, section 5: Metastatic invasive mammary carcinoma. | 294 | N | trastuzumab | gemcitabine hydrochloride carboplatin | IV | Unknown | Liver | 54 | + | + | + |
| ALx-R-16 | R | Right breast, 8:00 N + 10, biopsy: Invasive ductal carcinoma, no | 272 | N | trastuzumab docetaxel | fulvestrant | IV | Grade 2/Moderately differentiated | Breast | 49 | − | − | + |

TABLE 31-continued

Patient Information: Test Herceptin TTNT

| ID | Type | Diagnosis | TTNT | Censored | First line | Next line | Stage | Grade | Specimen cite | Age | HER2 IHC | HER2 ISH | ER |
|---|---|---|---|---|---|---|---|---|---|---|---|---|---|
| ALx-R-8 | R | special type (1.1 cm). Breast, right, core biopsy: Infiltrating ductal carcinoma. | 238 | Y | carboplatin trasnizumab | | I | Grade 3/Poorly differentiated | Breast | 55 | + | + | – |
| ALx-R-17 | R | Left breast mass, core biopsy: Poorly differentiated infiltrating ductal carcinoma. | 623 | N | trastuzumab nab-paclitaxel | gemcitabine hydrochloride | Unknown | Grade 3/Poorly differentiated | Breast | 46 | + | + | – |
| ALx-R-9 | R | Left breast mastectomy: Invasive lobular carcinoma. | 604 | N | carboplatin docetaxel trasnizumab | gemcitabine hydrochloride | IIIC | Grade 2/Moderately differentiated | Breast | 82 | – | – | + |
| ALx-R-15 | R | Left breast mass: Infiltrating ductal carcinoma, Nottingham combined histologic grade III. | 406 | Y | trasnizumab | | IV | Grade 3/Poorly differentiated | Breast, NOS | 35 | + | + | + |
| ALx-NR-9 | NR | Metastatic carcinoma involving one out of seventeen (1/17) axillary lymph nodes. | 82 | N | trasnizumab pertazumab trastuzumab docetaxel | CPP doxorubicin hydrochloride | I | Grade 2/Moderately differentiated | Axillary lymph node | 46 | + | + | – |
| ALx-R-11 | R | Right breast, "masses" at 10 and 2 o'clock positions, resection: Invasive lobular carcinoma. | 1202 | N | trasnizumab paclitaxel | gemcitabine hydrochloride nab-paclitaxel | IV | Grade 3/Poorly differentiated | Breast, NOS | 79 | – | – | + |
| ALx-R-7 | R | Peritoneal mass, needle core biopsy: Metastatic carcinoma, with morphologic and immunohistochemical features consistent with the patient's known breast center. | 369 | N | trasnizumab | pertuzumab docetaxel | II | Grade 3/Poorly differentiated | Breast, NOS | 52 | +/– | – | – |
| ALx-NR-14 | NR | | 69 | N | trasnizumab docetaxel pertuzumab | leuprolide acetate | IV | Unknown | Peritoneal cavity | 35 | – | – | + |
| ALx-R-13 | R | Skin, "lesion" on right anterior chest w all, excisional biopsy: Metastatic carcinoma of mammary origin with prominent apocrine features. | 598 | N | trasnizumab vinorelbine tartrate | trasnizumab vinorelbine tartrate | IV | Grade 3/Poorly differentiated | Skin of chest wall | 62 | + | + | – |
| ALx-R-1 | R | Left axillary sentinel nodes, left breast: Invasive ductal carcinoma. Nottingham grade 3. | 301 | Y | fluorouracil CPP methotrexate trasnizumab | | Unknown | Grade 3/Poorly differentiated | Breast, NOS | 66 | +/– | +/– | – |
| ALx-NR-12 | NR | Right chest wall mass excision: Invasive ductal carcinoma, grade 2. | 109 | N | trasnizumab paclitaxel pertuzumab | CPP doxorubicin hydrochloride | I | Grade 2/Moderately differentiated | Chest wall, NOS | 53 | + | + | – |
| ALx-R-6 | R | Breast, right, mastectomy: Infiltrating mammary carcinoma with mixed ductal and lobular phenotype. | 291 | Y | trasnizumab docetaxel CPP | | II | Grade 2/Moderately differentiated | Breast, NOS | 56 | – | – | + |
| ALx-NR-11 | NR | Right adrenalectomy: Adenocarcinoma, consistent with | 56 | N | vinorelbine tartrate | carboplatin | IV | Unknown | Adrenal gland, | 54 | +/– | + | + |

TABLE 31-continued

Patient Information: Test Herceptin TTNT

| ID | Type | Diagnosis | TTNT | Censored | First line | Next line | Stage | Grade | Specimen site | Age | HER2 IHC | HER2 ISH | ER |
|---|---|---|---|---|---|---|---|---|---|---|---|---|---|
| ALx-NR-4 | NR | metastatic mammary carcinoma. Lymph node, right axillary, excision: Metastatic adenocarcinoma consistent with breast primary. | 113 | N | trastuzumab nab-paclitaxel carboplatin pertuzumab trastuzumab | capecitabine | IIIA | Grade 1/Well differentiated | Axillary lymph node NOS | 51 | +/− | − | − |
| ALx-R-41 | R | Left breast, simple mastectomy: Invasive ductal carcinoma, Nottingham grade III. | 190 | Y | pertuzumab docetaxel carboplatin trastuzumab | | II | Grade 3/Poorly differentiated | Breast, NOS | 34 | +/− | − | + |
| ALx-R-42 | R | Right breast, core biopsy: Infiltrating ductal carcinoma. | 196 | Y | trastuzumab pertuzumab docetaxel | | I | Grade 3/Poorly differentiated | Breast | 52 | − | − | + |
| ALx-R-43 | R | Right breast, simple mastectomy: Recurrent invasive grade 3 ductal carcinoma. | 375 | Y | trastuzumab docetaxel carboplatin trastuzumab | | II | Grade 3/Poorly differentiated | Breast | 41 | + | + | − |
| ALx-R-44 | R | Left breast scar revision: Invasive poorly-differentiated ductal carcinoma. | 334 | Y | trastuzumab | | IV | Unknown | Liver | 64 | − | + | + |
| ALx-R-45 | R | | 406 | Y | trastuzumab fulvestrant | | I | Grade 3/Poorly differentiated | Breast | 54 | − | + | + |
| ALx-R-47 | R | Left breast inframammary crease: Metastatic carcinoma involving dermal lymphovascular spaces. | 546 | Y | trastuzumab | | I | Unknown | Skin | 55 | + | + | − |
| ALx-R-48 | R | Left breast and axillary contents, modified radical mastectomy: Invasive ductal carcinoma. | 856 | Y | trastuzumab | | IV | Grade 3/Poorly differentiated | Axillary lymph node | 40 | − | +/− | − |
| ALx-R-49 | NR | Liver, biopsy: Metastatic carcinoma. | 106 | N | trastuzumab | bevacizumab carboplatin | IV | Grade 3/Poorly differentiated | Liver | 46 | + | + | + |
| ALx-R-50 | R | Skin, left breast, biopsy: Dermal intralymphatic tumor, consistent with inflammatory carcinoma. | 186 | N | trastuzumab | vinorelbine tartrate | I | Unknown | Connective & Soft Tissue | 41 | + | + | − |
| ALx-R-51 | R | Right axillary/pectoral tumor, excision: Infiltrating ductal carcinoma involving subcutaneous fibroadipose tissue and adjoining skeletal muscle. | 196 | N | trastuzumab | vinorelbine tartrate trastuzumab | I | Grade 3/Poorly differentiated | Connective & Soft Tissue | 55 | + | + | + |
| ALx-R-52 | NR | Liver, segment VI, partial resection: Consistent with metastatic mammary carcinoma. | 80 | N | trastuzumab pertuzumab fulvestrant | octreotide acetate | IV | Unknown | Liver | 46 | + | + | − |
| ALx-R-53 | R | Right liver lobe, partial lobectomy: Metastatic carcinoma, consistent with breast primary. | 190 | N | trastuzumab | fulvestrant | IV | Unknown | Liver | 63 | − | − | + |
| ALx-R-54 | R | Left breast mass: Infiltrating duct | 433 | N | leuprolide acetate | paclitaxel | IV | Grade 3/Poorly differentiated | Breast | 44 | | QNS | |

TABLE 31-continued

Patient Information: Test Herceptin TTNT

| ID | Type | Diagnosis | TTNT | Censored | First line | Next line | Stage | Grade | Specimen cite | Age | HER2 IHC | HER2 ISH | ER |
|---|---|---|---|---|---|---|---|---|---|---|---|---|---|
| | | carcinoma with lobular features, grade 3. | | | docetaxel trastuzumab pertuzumab | | | | | | | | |
| ALx-R-55 | R | Pelvic mass, biopsy: Metastatic carcinoma. | 183 | N | trastuzumab vinorelbine tartrate | nab-paclitaxel | IV | Unknown | Pelvis, NOS | 42 | +/− | + | + |
| ALx-R-56 | R | Liver, needle biopsy (SS-13-01227): Mild steatosis and cholestasis. | 250 | N | trastuzumab pertuzumab docetaxel | ado-trastuzumab emtansine | IV | Unknown | Liver | 68 | + | + | − |
| ALx-R-57 | NR | Breast, left, simple mastectomy: Residual infiltrative mammary carcinoma with ductal and lobular features. | 49 | N | trastuzumab | ado-trastuzumab emtansine | II | Grade 2/Moderately differentiated | Breast, NOS | 44 | + | + | − |
| ALx-R-58 | NR | SU-12-02676: Right breast (lumpectomy): Residual poorly differentiated adenocarcinoma, multifocal. | 154 | N | trastuzumab | docetaxel | Unknown | Grade 3/Poorly differentiated | Breast, NOS | 41 | − | − | − |
| ALx-R-59 | NR | Right axillary mass: High grade infiltrating ductal carcinoma. | 128 | N | trastuzumab | docetaxel | Unknown | Grade 3/Poorly differentiated | Breast, NOS | 62 | + | + | − |
| ALx-R-60 | NR | Bone, right distal femur tumor, excision: Metastatic adenocarcinoma, compatible with breast primary. | 129 | N | trastuzumab | pertuzumab docetaxel | IV | Unknown | Femur | 51 | + | + | + |

TABLE 32

| ID | Type | Diagnosis | TTNT | Censored | First line | Next line | Stage | Grade | Specimen cite | Age | HER2 IHC | HER2 ISH | ER |
|---|---|---|---|---|---|---|---|---|---|---|---|---|---|
| PI-1 | NR | Right breast and medial portion of inframammary bridge, simple mastectomy: Infiltrating ductal carcinoma, grade 2 (Nottingham classification). | 22 | N | docetaxel | CPP | Unknown | NA | Breast | 73 | − | − | − |
| PI-2 | R | Left masectomy breast tissue: Invasive mammary carcinoma. | 822 | Y | nab-paclitaxel fluorouracil | | IIIA | Grade 2/Moderately differentiated | Breast | 49 | − | − | + |
| PI-3 | R | Right breast (simple mastectomy): Infiltrating ductal carcinoma | 461 | N | nab-paclitaxel bevacizumab carboplatin | gemcitabine hydrochloride | II | Grade 3/Poorly differentiated | Breast | 43 | − | − | + |
| PI-4 | NR | Lymph node from left neck (biopsy): Metastatic poorly differentiated carcinoma involving one out of one lymph node' (1/1). | 21 | N | nab-paclitaxel | eribulin mesylate | Unknown | NA | Lymph Nodes | 40 | − | +/− | + |
| PI-5 | NR | Right axillary lymph node (biopsy): Metastatic carcinoma. | 40 | N | docetaxel | doxorubicin hydrochloride CPP | I | Unknown | Lymph Nodes | 43 | − | − | − |
| PI-6 | NR | Liver "mass" (percutaneous needle core biopsies): Metastatic adenocarcinoma, consistent with breast primary. | 29 | N | carboplatin nab-paclitaxel bevacizumab | gemcitabine hydrochloride | IV | Grade 2/Moderately differentiated | Liver | 47 | − | others | − |
| PI-7 | NR | Touch preps and core biopsy, left iliac crest: Positive for malignancy. | 84 | N | nab-paclitaxel | patupilone | IV | Unknown | Bones & Joints | 60 | − | − | + |
| PI-8 | NR | Breast, left, 12-3:00: Invasive lobular carcinoma, pleomorphic type. | 62 | N | docetaxel CPP | doxorubicin hydrochloride | II | Grade 3/Poorly differentiated | Breast | 62 | − | − | + |
| PI-9 | NR | Mass, retroperitoneum; biopsy: Metastatic carcinoma, consistent with breast primary. | 59 | N | nab-paclitaxel | patupilone | IV | Unknown | Retroperitoneum & Peritoneum | 55 | − | − | + |
| PI-10 | NR | Left breast (182 grams), simple mastectomy: Infiltrating ductal carcinoma. | 98 | N | paclitaxel | CPP doxorubicin hydrochloride fluorouracil | II | Grade 3/Poorly differentiated | Breast | 39 | − | − | − |
| PI-11 | NR | Left breast, simple mastectomy: Infiltrating lobular carcinoma. | 70 | N | docetaxel patupilone | fluorouracil | IV | Grade 2/Moderately differentiated | Breast | 44 | − | − | + |
| PI-12 | R | Lymph nodes, right axillary, excision: Metastatic adenocarcinoma consistent with breast primary involving one of three lymph nodes (1/3). | 402 | N | paclitaxel bevacizumab nab-paclitaxel | gemcitabine hydrochloride | IV | Grade 2/Moderately differentiated | Lymph Nodes | 56 | − | − | − |
| PI-13 | R | Ascites fluid, cytology: Metastatic adenocarcinoma, consistent with lobular breast carcinoma. | 631 | N | gemcitabine hydrochloride docetaxel | gemcitabine hydrochloride | IV | Unknown | Peritoneal Fluid | 70 | − | − | + |
| PI-14 | NR | Left breast, needle biopsies: | 56 | N | nab- | doxorubicin | IIIA | Grade 3/Poorly | Breast | 62 | − | − | − |

TABLE 32-continued

Patient Information: Test Platinum/Taxane TTNT

| ID | Type | Diagnosis | TTNT | Censored | First line | Next line | Stage | Grade | Specimen cite | Age | HER2 IHC | HER2 ISH | ER |
|---|---|---|---|---|---|---|---|---|---|---|---|---|---|
| PI-15 | R | Invasive ductal carcinoma, grade 3 (of 3). Core needle biopsy, left lateral breast/axillary lymph node mass: Metastatic poorly differentiated adenocarcinoma, morphologically and immunohistochemically compatible with primary ductal breast origin. | 449 | N | paclitaxel CPP epirubicin hydrochloride paclitaxel | paclitaxel hydrochloride CPP eribulin mesylate | IV | Grade 3/Poorly differentiated | Lymph Nodes | 73 | – | – | – |
| PI-16 | R | Right breast mass, excision: Invasive ductal carcinoma. | 343 | N | doxorubicin hydrochloride CPP docetaxel | gemcitabine hydrochloride | II | Grade 3/Poorly differentiated | Breast | 44 | – | – | – |
| PI-17 | NR | Supraclavicular node left: Lymph node totally replaced by metastatic carcinoma, consistent with primary breast carcinoma. The tumor extends completely through the node capsule to the surrounding fatty tissues. | 99 | N | docetaxel carboplatin | gemcitabine hydrochloride | IV | Unknown | Lymph Nodes | 57 | – | – | – |
| PI-18 | R | Chest wall mass, right posterior, biopsy: Metastatic carcinoma, favor mammary primary. | 341 | N | carboplatin docetaxel | eribulin mesylate | IV | Grade 2/Moderately differentiated | Connective & Soft Tissue | 80 | +/– | – | + |
| PI-19 | NR | Reamings, hip, right, biopsy: Metastatic poorly differentiated carcinoma consistent with breast origin. | 105 | N | paclitaxel carboplatin bevacizumab | gemcitabine hydrochloride | IV | Grade 3/Poorly differentiated | Bones & Joints | 64 | – | – | – |
| PI-20 | R | Right breast, 10 o'clock, lumpectomy: Infiltrating ductal adenocarcinoma. | 674 | Y | CPP docetaxel | | IIIA | Grade 3/Poorly differentiated | Breast | 69 | – | – | + |
| PI-21 | NR | Liver, needle biopsies: Metastatic carcinoma morphologically consistent with breast primary. | 21 | N | docetaxel | doxorubicin hydrochloride | IV | Grade 2/Moderately differentiated | Liver | 45 | +/– | – | + |
| PI-22 | NR | Left breast lumpectomy, 2 o'clock: Infiltrating ductal adenocarcinoma, Elston grade III, 4 cm maximum dimension, present 1 mm from the inferior margin. | 49 | N | docetaxel CPP | gemcitabine hydrochloride | IIIC | Grade 3/Poorly differentiated | Breast | 71 | – | – | – |
| PI-23 | R | Left breast mass, additional margins left breast, axillary contents, and additional axillary contents: Invasive lobular carcinoma. | 686 | Y | docetaxel therapeutic immune globulin CPP | | II | Grade 3/Poorly differentiated | Breast | 72 | – | – | – |
| PI-24 | NR | Breast, right, Mammotome biopsy: Infiltrating ductal carcinoma, no special type | 22 | N | nab-paclitaxel carboplatin | pegylated liposomal doxonibicin hydrochloride | I | Grade 3/Poorly differentiated | Breast, NOS | 43 | – | – | – |
| PI-25 | NR | Duodenum, biopsy: Poorly-differentiated carcinoma, compatible with metastatic | 63 | N | carboplatin gemcitabine hydrochloride | capecitabine | IV | Grade 3/Poorly differentiated | Duodenum | 31 | +/– | – | – |

TABLE 32-continued

Patient Information: Test Platinum/Taxane TTNT

| ID | Type | Diagnosis | TTNT | Censored | First line | Next line | Stage | Grade | Specimen site | Age | HER2 IHC | HER2 ISH | ER |
|---|---|---|---|---|---|---|---|---|---|---|---|---|---|
| PI-26 | NR | mammary carcinoma. Right breast mass core needle biopsies (image directed): Infiltrating duct carcinoma, high grade (grade 3). | 106 | N | paclitaxel | | IV | Grade 3/Poorly differentiated | Breast, NOS | 56 | − | − | − |
| PI-27 | NR | Right breast mass: Invasive ductal carcinoma. Nottingham grade 3. | 43 | N | carboplatin docetaxel | methotrexate | Unknown | NA | Breast, NOS | 59 | − | − | − |
| PI-28 | NR | Left breast, modified radical mastectomy with level I/II node dissection: 3.5 cm poorly differentiated invasive ductal carcinoma with focal necrosis and foci of high grade ductal carcinoma in situ (comedo type). | 70 | N | carboplatin | Methotrexate fluorouracil | IIIA | Grade 3/Poorly differentiated | Breast, NOS | 61 | − | − | − |
| PI-29 | NR | Left breast mass, left breast core biopsy: Infiltrating ductal carcinoma. | 70 | N | nab-paclitaxel carboplatin | gemcitabine hydrochloride | Unknown | Grade 3/Poorly differentiated | Breast, NOS | 53 | − | − | − |
| PI-30 | NR | Left breast Mammotome biopsy: Infiltrating carcinoma. | 83 | N | nab-paclitaxel carboplatin | pegylated liposomal doxorubicin hydrochloride | II | Grade 3/Poorly differentiated | Breast, NOS | 58 | − | − | − |
| PI-31 | NR | Right breast segment, segmental mastectomy: Poorly-differentiated invasive ductal carcinoma. | 22 | N | carboplatin docetaxel | CPP | II | Grade 3/Poorly differentiated | Breast, NOS | 62 | − | − | − |
| PI-32 | NR | Right neck node, core biopsy: Metastatic poorly differentiated adenocarcinoma. | 58 | N | nab-paclitaxel | eribulin mesylate | Unknown | NA | Connective, subcutaneous and other soft tissues of head, face and neck | 45 | NA | NA | − |
| PI-33 | NR | | 28 | N | carboplatin gemcitabine hydrochloride | pemetrexed disodium | IIIA | Grade 3/Poorly differentiated | Breast, NOS | 57 | − | − | − |
| PI-34 | R | Breast, left, core biopsy: Invasive carcinoma, grade 2 (of 3). | 630 | N | carboplatin | pegylated liposomal doxorubicin hydrochloride | IV | Grade 2/Moderately differentiated | Breast, NOS | 78 | − | − | − |
| PI-35 | NR | Left breast and axilla, modified radical mastectomy: Invasive ductal carcinoma. | 80 | N | carboplatin gemcitabine hydrochloride | pegylated liposomal doxorubicin hydrochloride | IIIC | Grade 3/Poorly differentiated | Breast, NOS | 75 | − | − | − |
| PI-36 | NR | Left breast biopsy: Infiltrating ductal carcinoma. High combined histologic grade (3, 3, 3). | 91 | N | nab-paclitaxel carboplatin | pegylated liposomal doxorubicin hydrochloride | Unknown | Grade 3/Poorly differentiated | Breast, NOS | 50 | − | − | − |
| PI-37 | NR | T9 bone, core biopsy: Metastatic carcinoma, compatible with breast primary. | 56 | N | bevacizumab paclitaxel | CPP doxorubicin | IV | Unknown | Bone, NOS | 45 | +/− | − | + |
| PI-38 | NR | Breast, left 2:00 N10 | 40 | N | carboplatin | doxorubicin hydrochloride | I | Grade 3/Poorly | Breast, NOS | 46 | − | − | − |

TABLE 32-continued

Patient Information: Test Platinum/Taxane TTNT

| ID | Type | Diagnosis | TTNT | Censored | First line | Next line | Stage | Grade | Specimen cite | Age | HER2 IHC | HER2 ISH | ER |
|---|---|---|---|---|---|---|---|---|---|---|---|---|---|
| | | (ultrasound-guided, vacuum-assisted biopsy): Invasive ductal carcinoma, grade 3. | | | paclitaxel | hydrochloride CPP | | differentiated | | | | | |
| PI-39 | NR | Right breast, mastectomy: Infiltrating ductal carcinoma. | 63 | N | docetaxel carboplatin | Fluorouracil CPP | II | Grade 3/Poorly differentiated | Breast, NOS | 83 | − | − | − |
| PI-40 | NR | Left breast mass, core biopsy: Infiltrating ductal carcinoma. | 84 | N | paclitaxel | CPP doxorubicin hydrochloride | IV | Grade 3/Poorly differentiated | Breast, NOS | 37 | − | − | − |
| PI-41 | NR | Breast, left (biopsies): Infiltrating ductal carcinoma, grade 2. | 73 | N | gemcitabine hydrochloride carboplatin | doxorubicin hydrochloride CPP | IV | Grade 2/Moderately differentiated | Breast, NOS | 56 | +/− | − | − |

In this Example, we subjected a library of $10^{13}$ unique single-stranded DNA oligodeoxynucleotides (ssODNs; which may also be referred to as aptamers or oligonucleotide probes herein) (17, 18) to several rounds of positive and negative selection in situ for subsets of sequences that preferentially bind to formalin-fixed and paraffin-embedded (FFPE) tumor tissue slices from breast cancer patients who did or did not derive benefit from regimens containing trastuzumab. We refer to this process as library training. Each patient's time to next therapy (TTNT), i.e. the time that elapsed until trastuzumab-based treatment changed defined whether a patient belonged to the group that derived benefit from trastuzumab containing treatment (B) or to the group that did not (NB) (19). The definition of treatment benefit (B) and no benefit (NB) by TTNT is consistent with recently published FDA guidance (20). For the purpose of library training, cases with TTNT greater than 180 days were considered as B and cases with TTNT fewer than 180 days were considered NB. In total, 8 NB cases (see Table 29) and 9 B-cases (see Table 30) were used for the training of 17 different libraries. Among them were two best-performing trained libraries, TL-B and TL-NB (see "Enrichment case ID" in Tables 29-30), which we employed to generate a predictive assay based on polyligand profiling that differentiates B from NB patients.

Figure 17A:
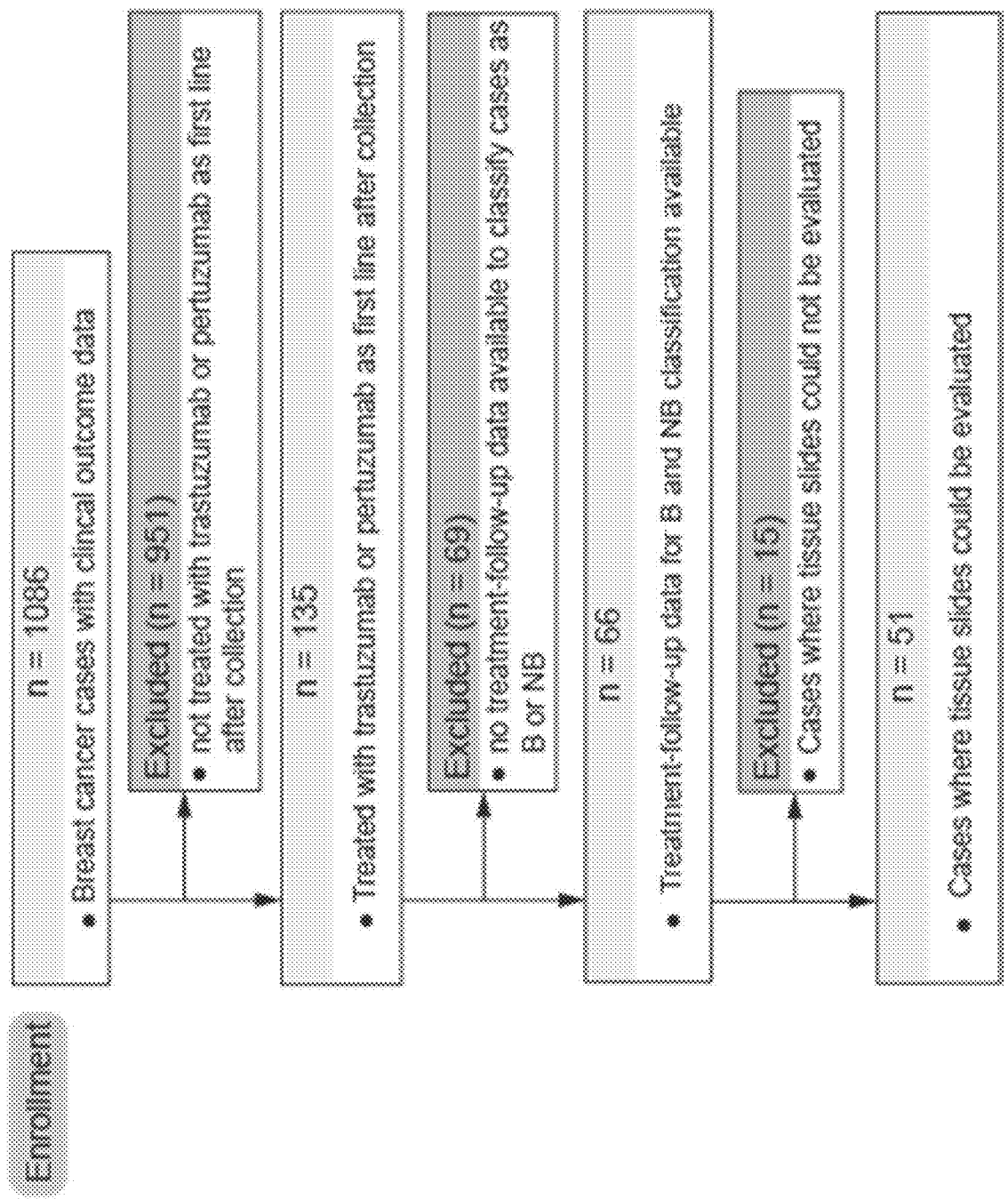
FIGS. 17A-P show oligonucleotide probes that distinguish trastuzamab responder breast cancer tissue samples.
Figure 17B:
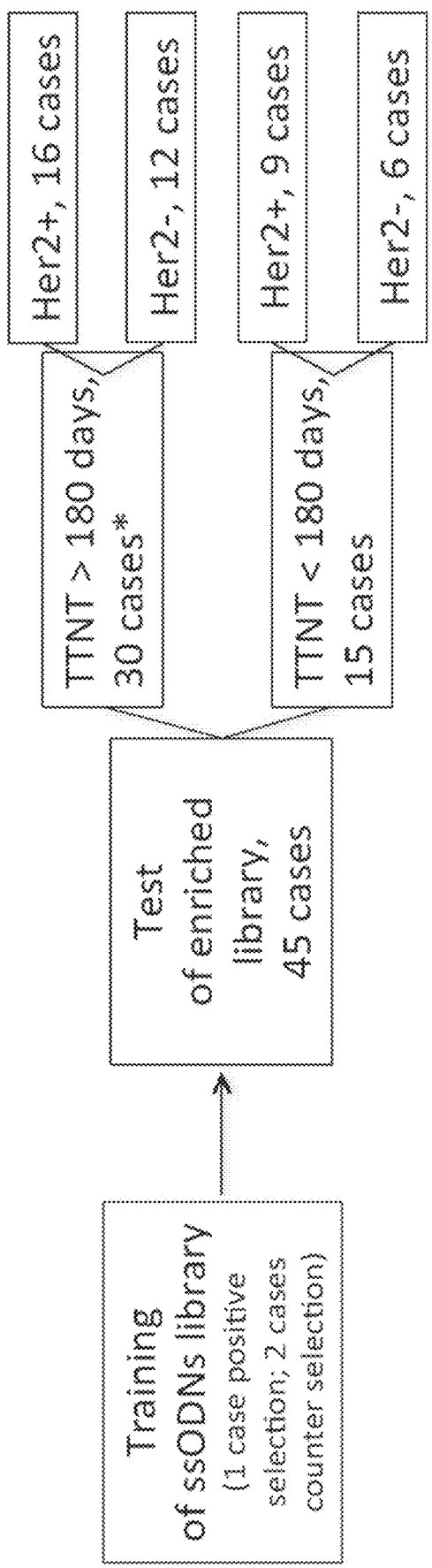

FIGS. 17A-B show the rationale for the selection of patients (FIG. 17A) and the workflow of the training and testing procedure of the ssODN library, including the number of cases used in each step (FIG. 17B). Clinical information for each of the patients included in this process, such as tumor anatomical site, treatment, hormonal status, etc. is provided in Tables 29-32. The starting library was subjected to positive selection using one NB case (rounds 1-6) and negative selection using two B cases (rounds 4-6) to generate TL-NB, and vice versa for generating TL-B. In Tables 29-30, the cases are grouped in triads. For example, positive selection was performed using NB case, TL-NB+, and negative selection in the same enrichment was performed using the two B cases just below identified as TL-NB- and TL-NB-. For addition details of the selection schemes and protocols, see FIG. 17C and Example 22. Testing readout is based on polyligand-histochemistry ("PHC") staining of FFPE slides from cases independent of those used for training. All tissue samples used for training and testing were collected prior to treatment to ensure that library training is independent of molecular changes in the tumor tissue that occur as a result of treatment.

Figure 17C:
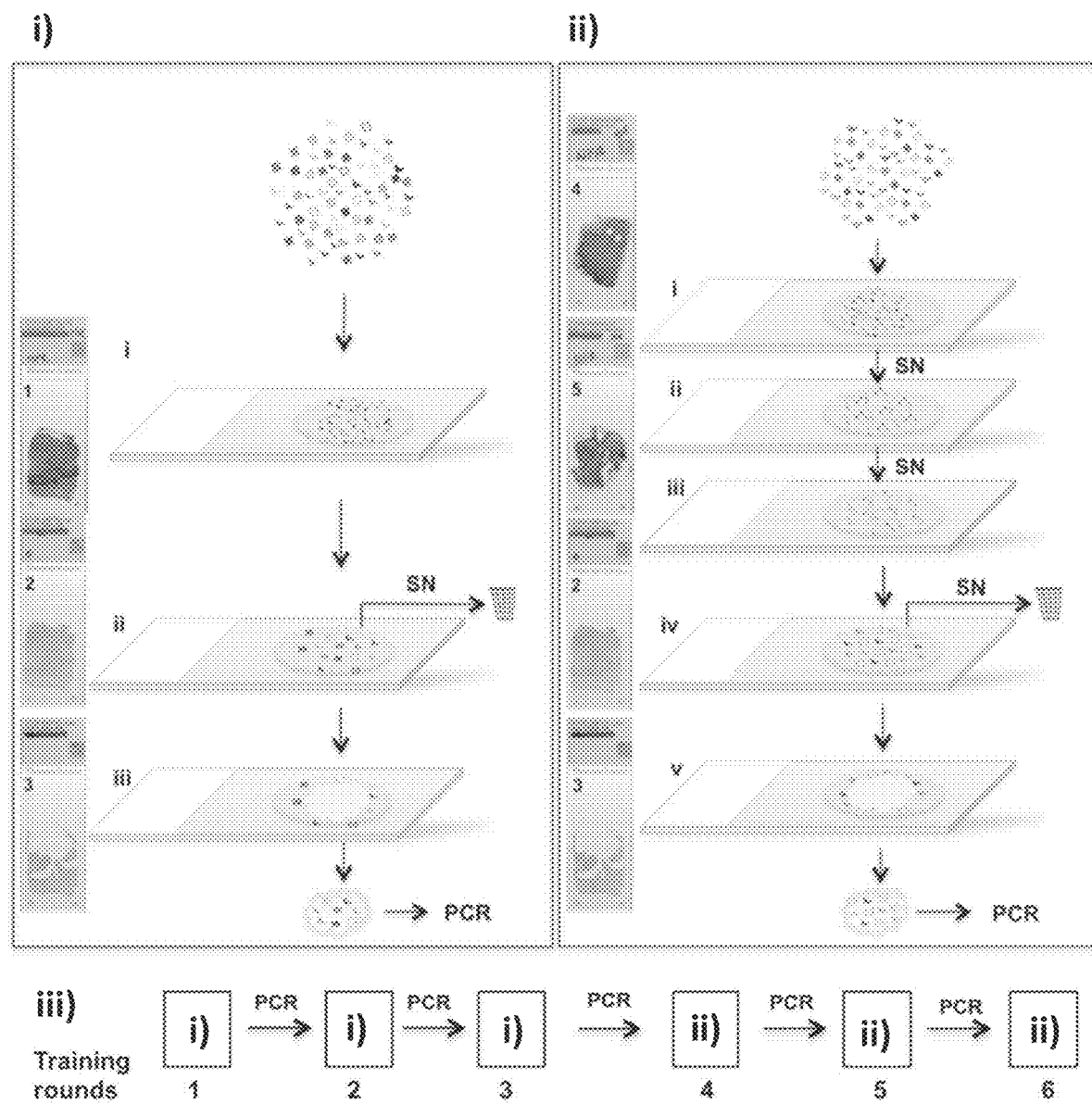
Figure 17D:
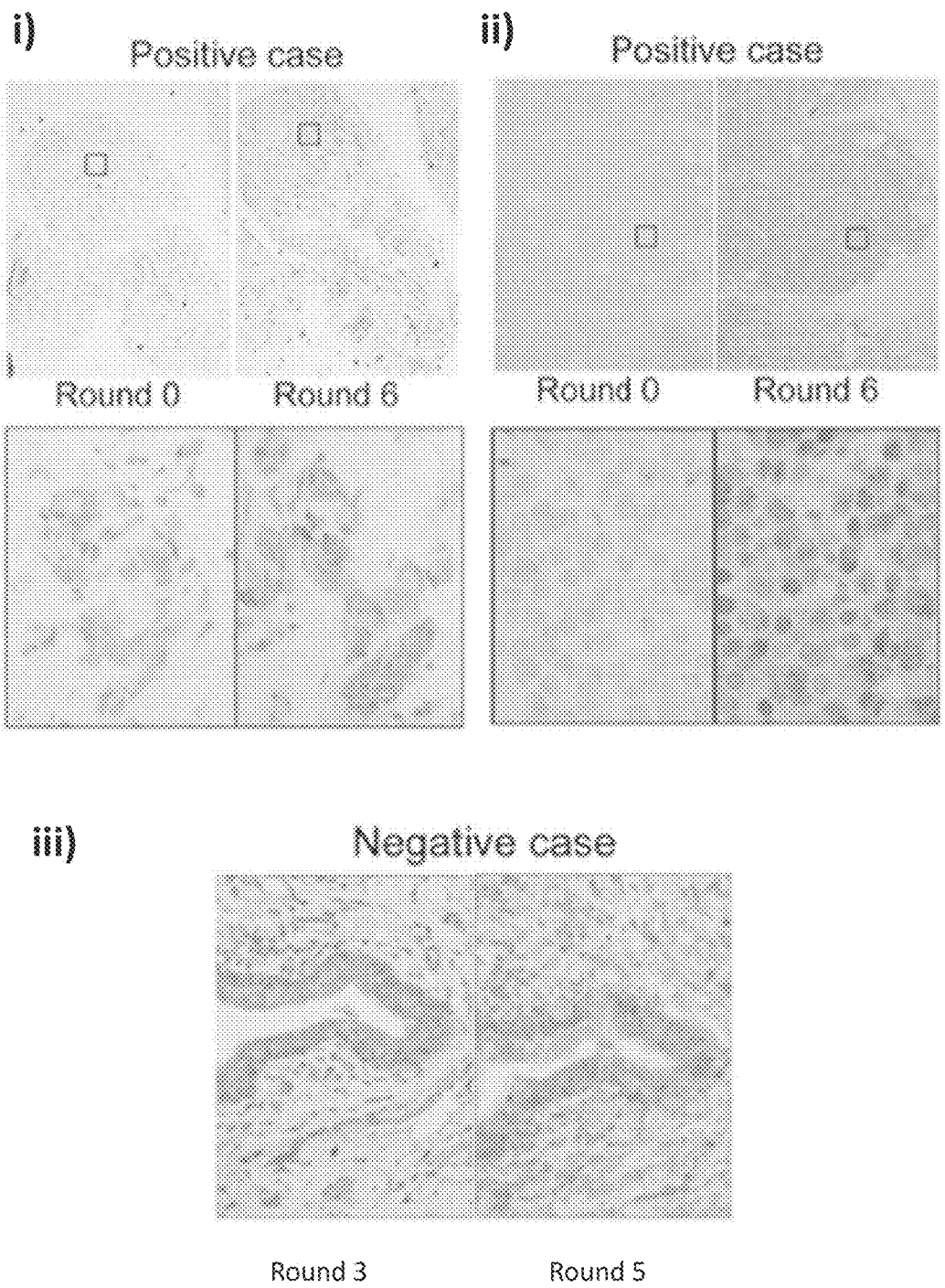

FIG. 17C provides an overview of the procedure for ssODN library training FIG. 17Ci outlines positive training steps towards a library that identifies non-benefitting (NB) cases: (i) incubation of the ssODN library with the NB tissue; (ii) removal of unbound sequences, (iii) dissection of tumor tissue and recovery of the subset of sequences, specific to the NB cancer tissue. SN: supernatant. Recovered ssODNs were amplified by PCR, converted to ssODNs and used for the next training round. The slide images on the left show tissue appearance: Slide 1) Hematoxylin and eosin (H&E) staining of NB tissue (tumor area outlined in green); Slide 2) Nuclear Fast Red (NFR) stained tissue after partitioning before dissection; Slide 3) Remaining normal tissue after dissection of cancer tissue with bound ssODNs. FIG. 17Cii outlines training steps with additional counter-selection steps on benefit (B) cases: (i) incubation of the ssODN library with the 1st B tissue; (ii) incubation of the supernatant from (i) with the 2nd B case; (iii) incubation of the supernatant from (ii) with the NB case from A; (iv) and (v) correspond to the steps (ii) and (iii) in A. The slide images on the left show tissue appearance: Slide 4) Hematoxylin and eosin (H&E) staining of 1st B tissue (tumor area outlined in green); Slide 5) Hematoxylin and eosin (H&E) staining of 2nd B tissue (tumor area outlined in green); Slides 2 and 3 are the same as in FIG. 17Ci. FIG. 17Ciii outlines the entire ssODN library training, which is comprised of three training rounds as shown in FIG. 17Ci (indicated "i)"); followed by three training rounds as shown in FIG. 17Cii (indicated "ii)"). FIG. 17Di shows staining of the tissue from the NB-case that was used during the selection process with untrained library (round 0), compared to the trained TL-NB library (round 6; upper panel: 4×, lower panel: 20×). FIG. 17Dii shows staining of tissue from an NB case not used during the selection process with untrained library (round 0), compared to the trained library TL-NB (round 6; upper panel: 4×, lower panel: 20×). FIG. 17Diii shows staining of the tissue from the responder case employed for counter selection in the training of TL-NB, using the output ssODNs from round 3 (left), compared to the output ssODNs from round 5 (right).

In more detail, the training library for non-benefiting patients TL-NB was obtained by incubating the starting library directly with FFPE-fixed breast tumor tissue from a trastuzumab NB-patient. After one hour of incubation (step i), non-binding ssODNs were removed by washing (step ii), followed by a dissection of the tumor tissue away from normal adjacent tissue (step iii) and asymmetric PCR-amplification of ssODNs bound to the dissected tumor tissue. See FIG. 17Ci and Example 22. These positive selection steps were performed a total of three times on serial tissue sections of the same case (rounds 1-3; FIG. 17Ci, iii). The ssODN-library from the third round of enrichment was then subjected to two consecutive counter-selection steps by incubating with FFPE tissue from two trastuzumab B-patients. The supernatant from the second counter-selection step, i.e. the library that is depleted of ssODNs that are associated with binding to B-tumor tissue, was transferred to a new tissue section from the original NB-patient's tumor for one final positive selection step as described above and the subset of bound ssODNs was PCR-amplified (FIG. 17Cii). The negative-negative-positive steps were performed a total of three times (SELEX rounds 4-6; FIG. 17Ciii). A comparison of the staining intensities of the unselected library with that of the round 6 TL-NB library on the NB case used for the selection showed a significant increase of staining for the enriched library (FIG. 17Di, round 6), whereas no or weak staining was seen for the unselected library (FIG. 17Di, round 0). Similar staining was observed on a separate NB case not used for the library training (FIG. 17Dii). Not unexpectedly, staining intensity was also high when the PCR-amplified library from round 3 (the enriched library before counter selection) was applied to a B case (FIG. 17Diii, left panel). However, after round 5 a notable decrease in staining intensity was observed for TL-NB applied to the same B case, indicating that the counter-selection steps were effective (FIG. 17Diii, right panel). Thus, TL-NB shows high staining intensities on NB tissue, while it stains the B-case used for counter selection with considerably weaker intensity. TL-NB was therefore suitable for PHC staining on an independent test-set.

To test whether we could also train a random library for a set of ssODNs that preferentially stain B-cases, we carried out a separate enrichment process in the opposite direction, using B-cases for positive, and NB-cases for counter-selection. The resulting trained library, TL-B, showed preferential staining of B-cases compared to the NB-cases or the untrained starting library. FIG. 17E shows staining of library TL-B on B and NB tissues. FIG. 17Ei shows staining of tissue from a B case not used during the selection process with untrained library (round 0), compared to the trained library TL-B (round 6; upper panel: 4×, lower panel: 20×) FIG. 17Eii shows staining of the tissue of a patient who did not derive benefit from trastuzumab-based regimens (NB) by polyligand-histochemistry (PHC), using the library enriched on a benefiting case (B) at round 4, compared to TL-B after round 6.

Taken together, the PHC staining characteristics observed with TL-NB and TL-B indicate sufficient selection pressure and successful enrichment toward their targeted phenotypes. The variable regions of the 100000 most prevalent sequences in the NB selected enrichment (library TL-NB) are included herein as SEQ ID NOs. 3062-103061, ordered by prevalence. The variable regions of the 100000 most prevalent sequences in the B selected enrichment (library TL-B) are included herein as SEQ ID NOs. 103062-203061, also ordered by prevalence.

Figure 17F:
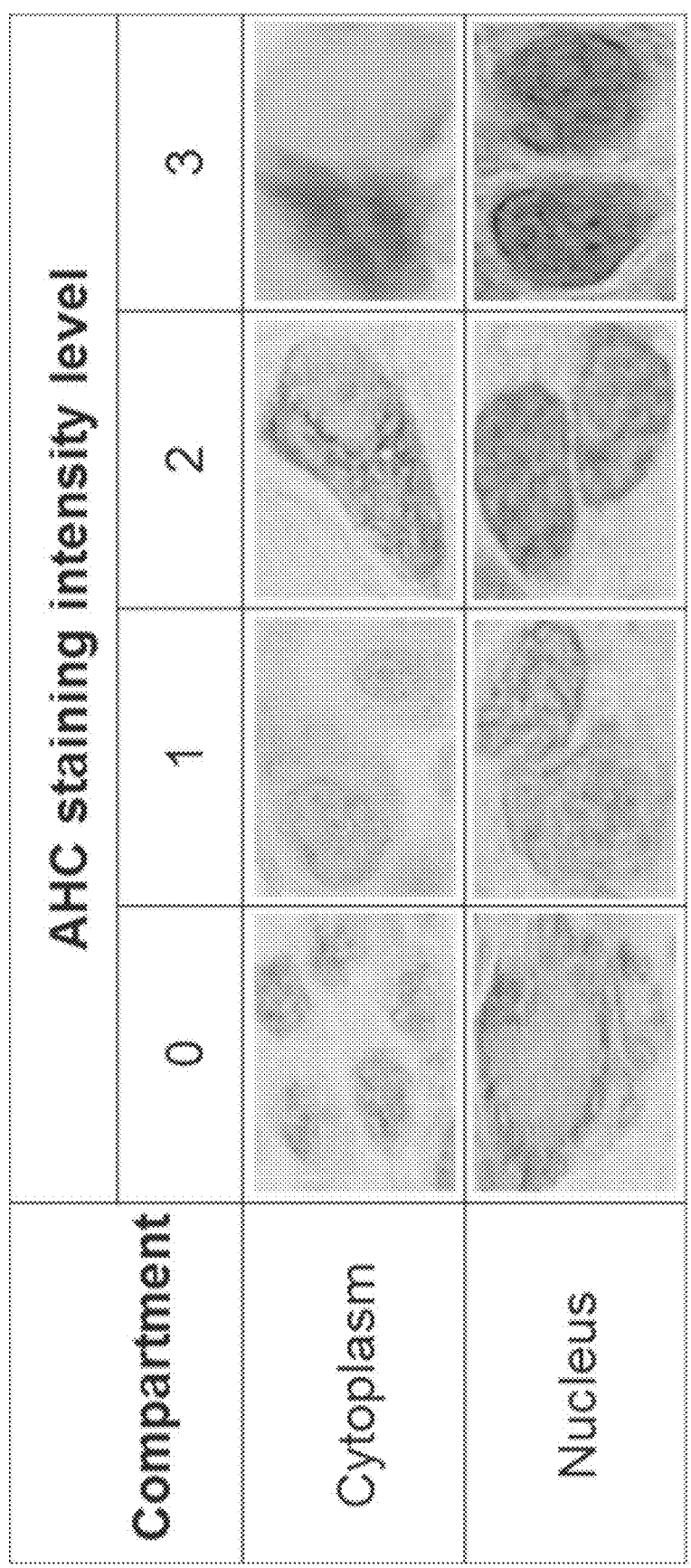
Figure 17G:
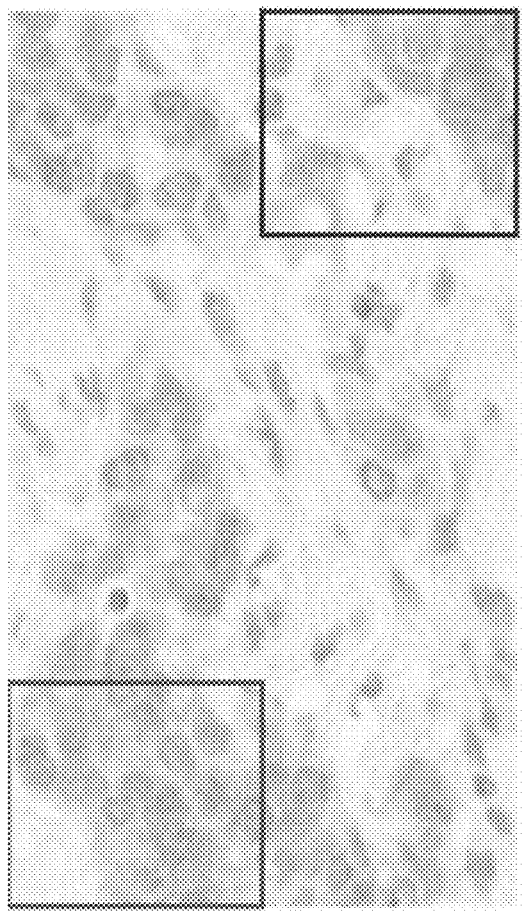
Figure 17H:
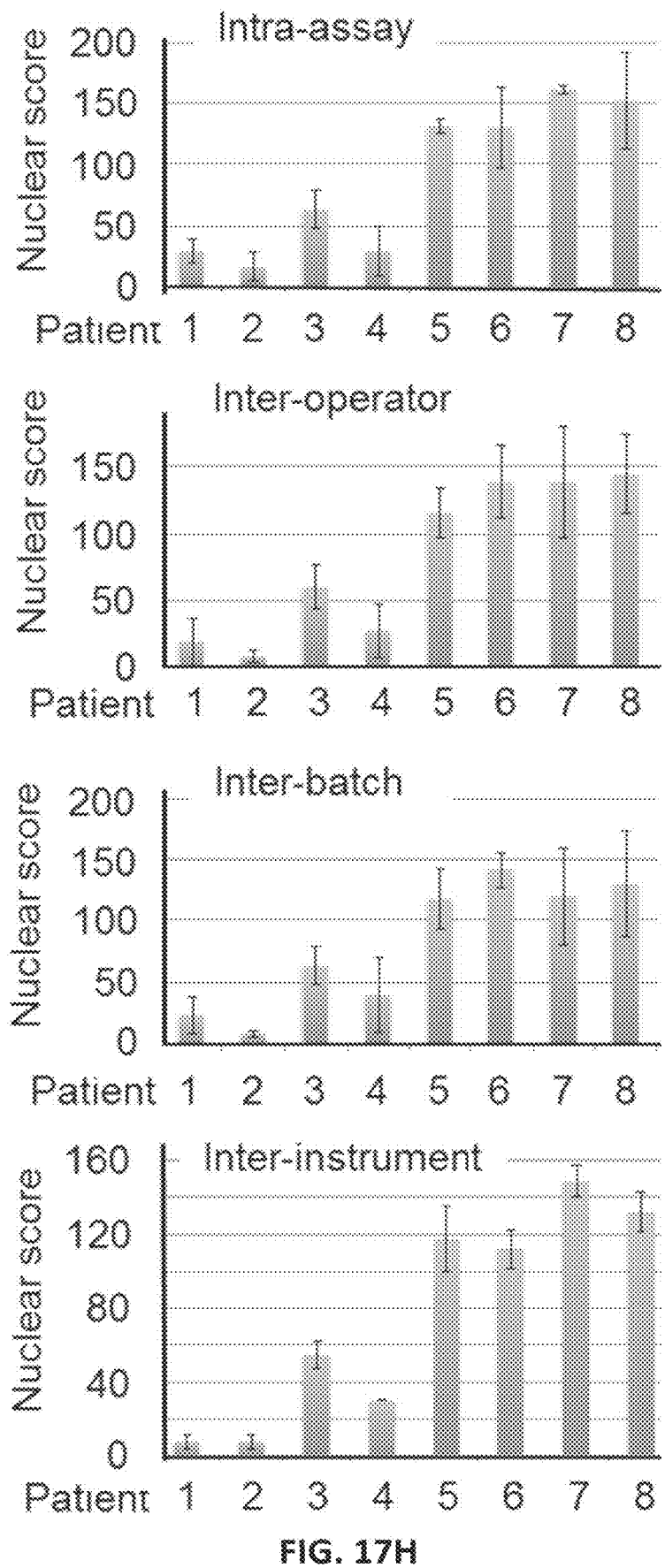
Figure 17I:
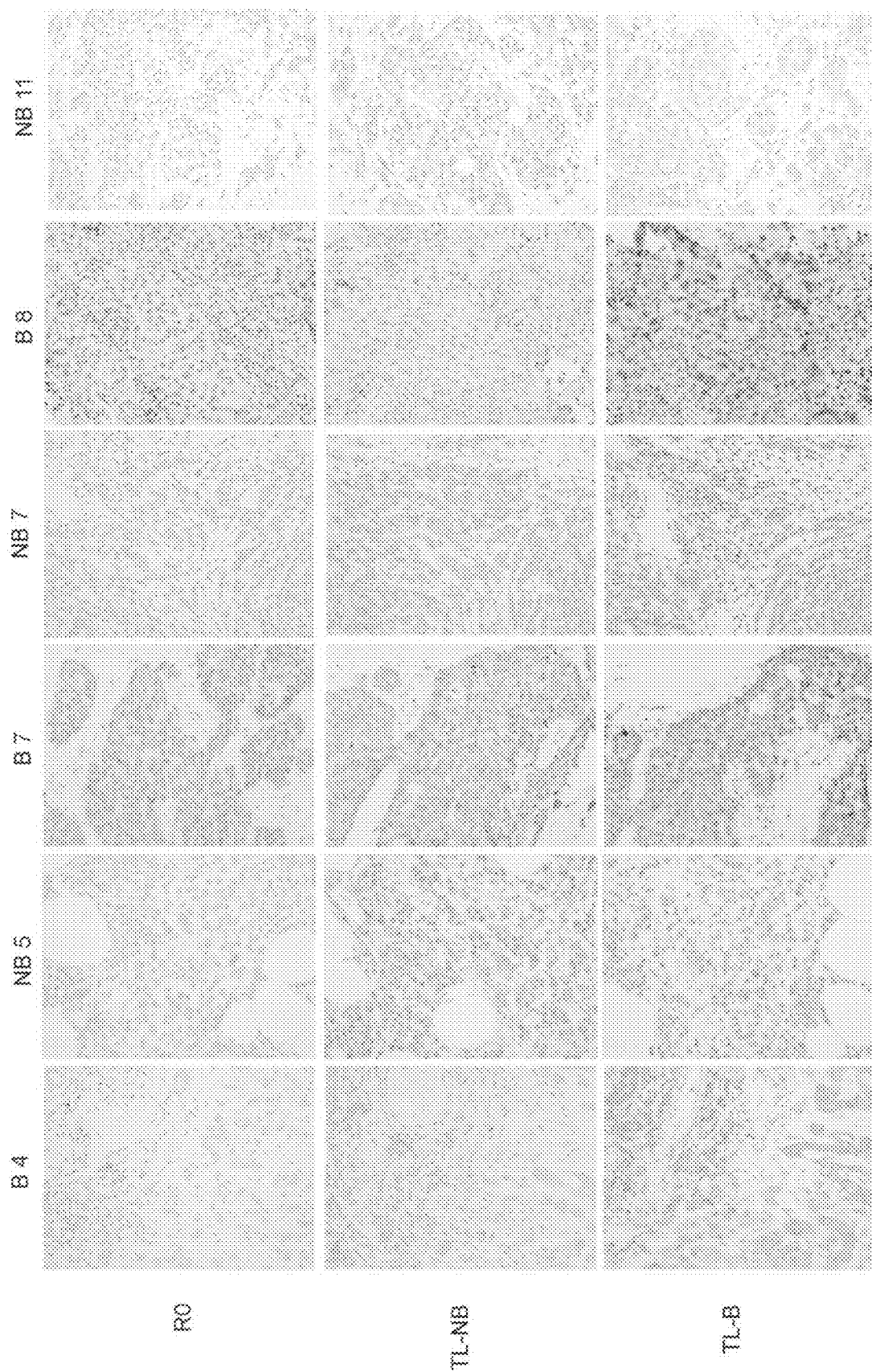
Figure 17J:
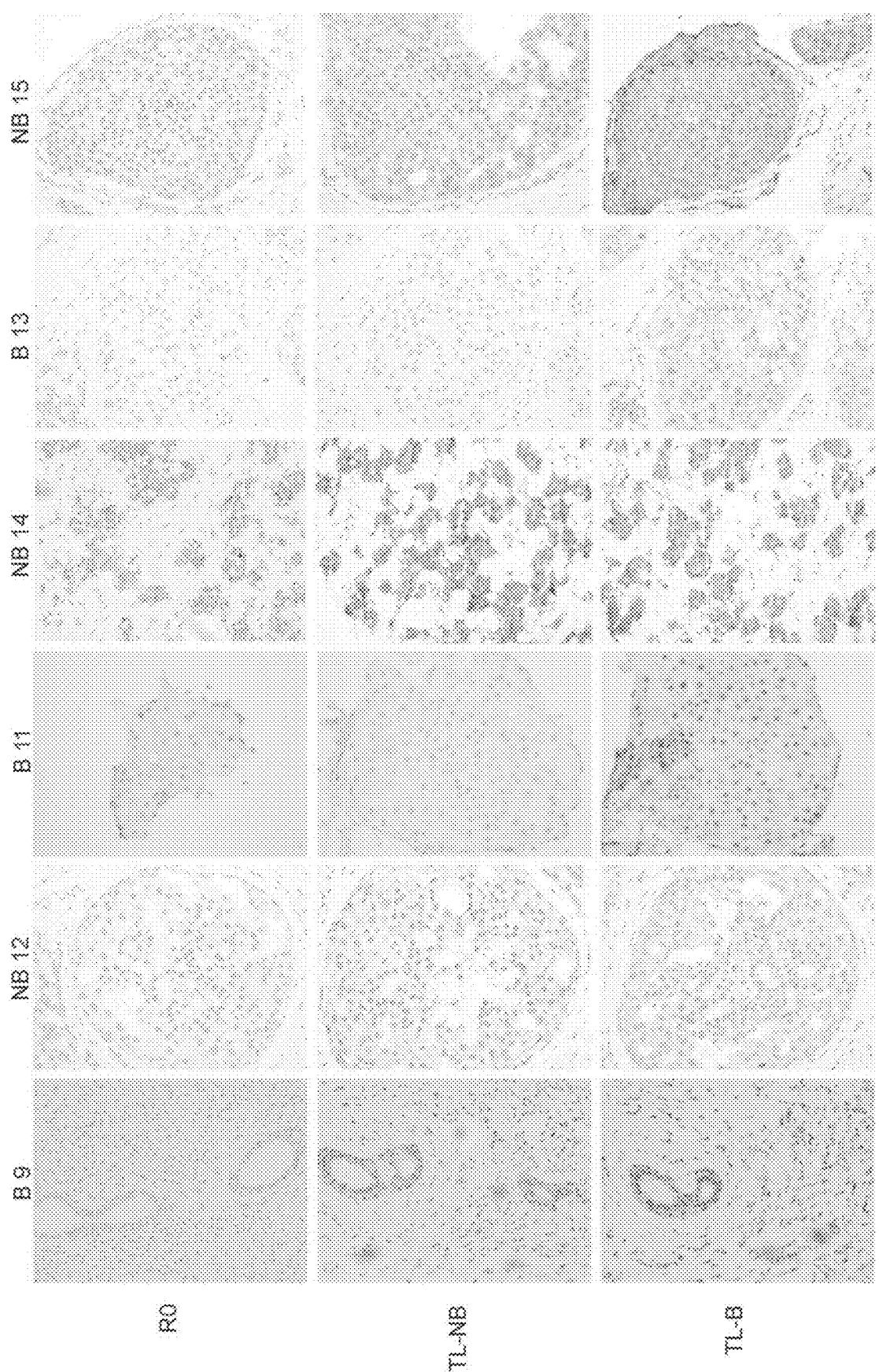
Figure 17K:
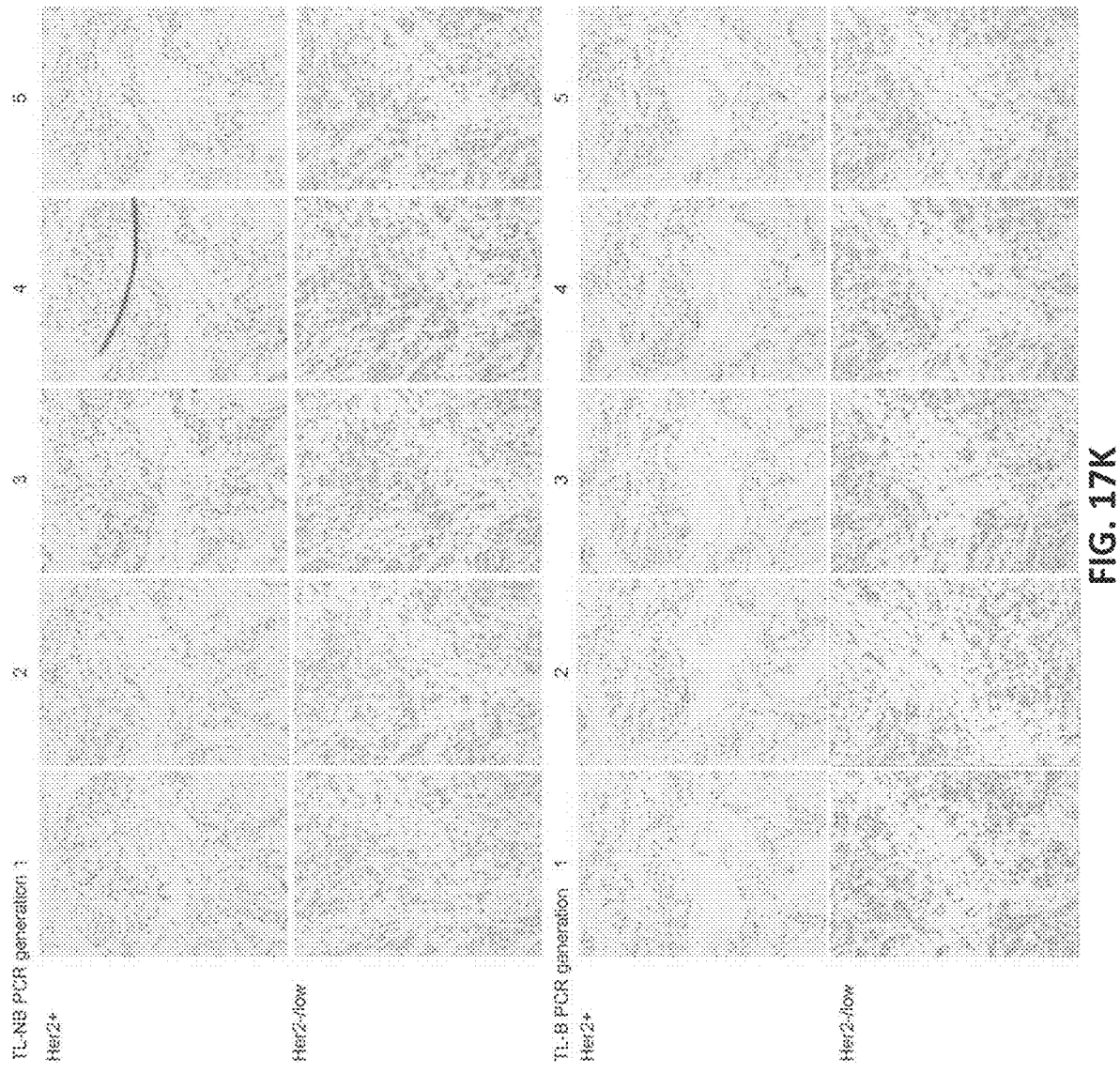
Figure 17L:
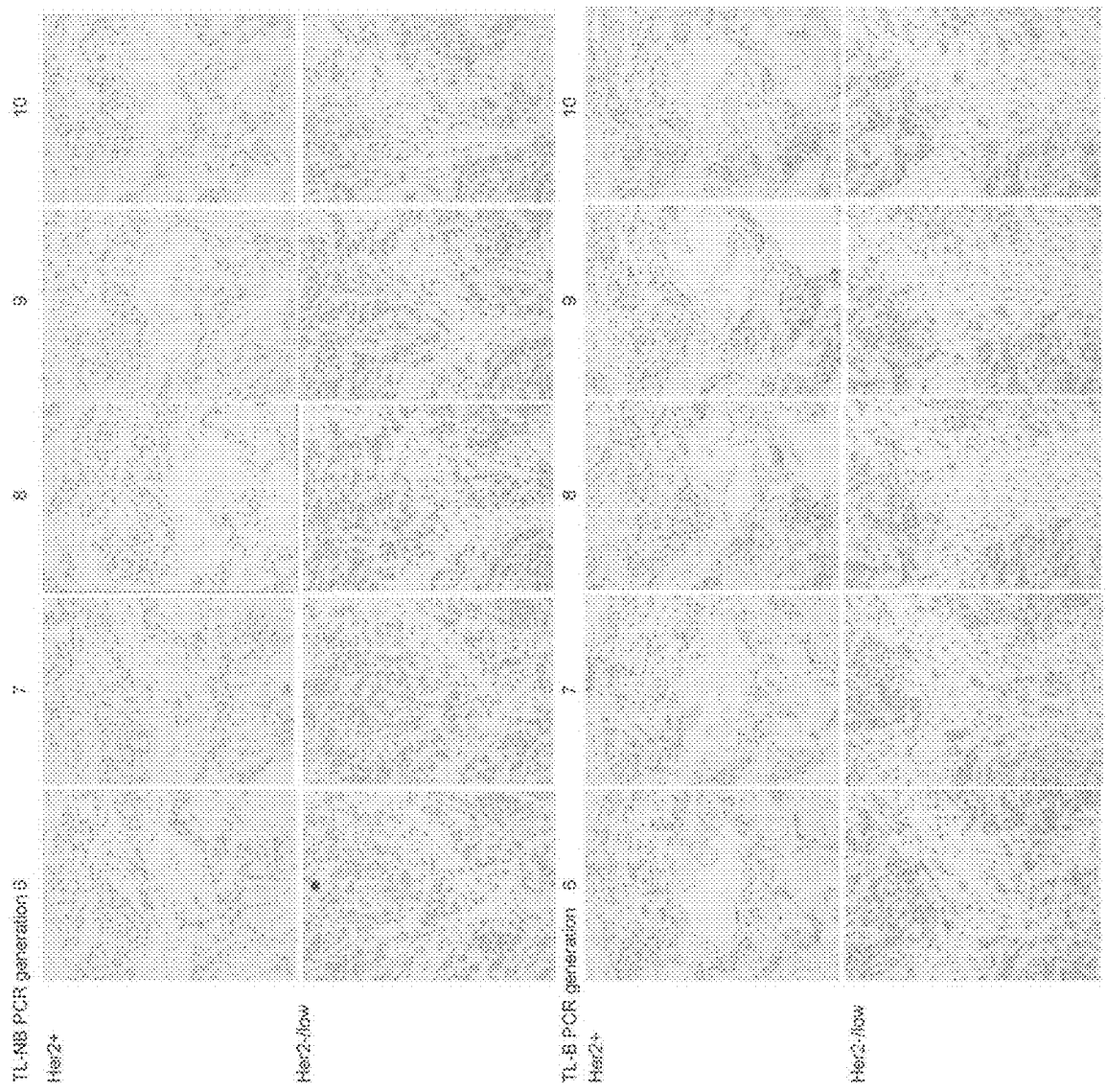

To evaluate the performance of TL-NB and TL-B on cases independent from those used for training, we verified that histological H-scoring of the tissue staining intensity obtained with the trained libraries can be employed for the quantitative comparison of the cases, similar to standard pathological practice for IHC (2l). The scoring for both cytoplasmic and nuclear staining was performed by a board-certified pathologist who was blinded to the patient outcomes. Protocols are found in FIGS. 17F-H and Example 22 and scoring results are shown in Tables 33-36. Examples of PHC staining intensity levels in the cytoplasm and the nuclei of breast cancer FFPE tissue ranging from 0 to 3 are shown in FIG. 17F. See also FIGS. 17I-J, which show polyligand histochemistry (PHC) staining profiles comparison of the non-enriched starting library (R0) and enriched libraries TL-NB and TL-B on patients not benefiting (NB) and benefiting (B) from trastuzumab containing treatment. The view areas are matched in each row between libraries within each panel. The library R0 usually exhibits little to no staining, while the enriched libraries can be scored from 1+ to 3+. Library TL-NB, which was enriched toward a trastuzumab non-benefiting case exhibits stronger intensity on NB cases, except for NB-15. Library TL-B, which was enriched toward a Trastuzumab responder case, exhibits stronger intensity on the B cases. The magnification in FIGS. 17I-J is 20×. The histological scores were calculated by standard methods by determining the percentages of cells on the entire tissue, classified to fall within each PHC intensity level in the cytoplasm and the nucleus. See FIG. 17G and Example 22. To evaluate staining and scoring reproducibility, we selected cases that showed weak and strong staining with TL-NB and then scored nuclear staining (22) between technical replicates (FIG. 17H, first panel "Intra-assay"), different operators (FIG. 17H, second panel "Inter-operator"), different batches of library (FIG. 17H, third panel :Inter-batch"), and different instruments (FIG. 17H, fourth panel "Inter-instrument"). The classification of four strongly and weakly staining cases was consistent and independent of these variables, indicating that the staining and scoring is reproducible. To further assess the technical reproducibility of PCR amplified versions of TL-NB and TL-B, both libraries were amplified for up to ten PCR-generations. See FIGS. 17K-L, which show technical reproducibility of the staining with libraries TL-NB and TL-B resulting from different PCR-generations 1-5 (FIG. 17K), and 6-10 (FIG. 17L). Examples from two different cases (Her2+ and Her2−/low) at 20× magnifications are shown. For each PCR generation, an aliquot (0.4 ng) of each preceding library generation was amplified for 10 PCR cycles. Each PCR generation of TL-NB and TL-B was then used for the staining of consecutive tissue sections from the same NB patient for TL-NB and the same B patient for TL-B. Each PCR generation of TL-NB and TL-B was used for the staining of consecutive tissue sections from the same NB patient for TL-NB and the same B patient for TL-B. No significant difference in the staining was observed from generation to generation, indicating highly robust performance of both libraries after excessive PCR amplification.

TABLE 33

| Histological Scoring, TL-NB, Trastuzamab TTNT | | | | | | | | | | | |
|---|---|---|---|---|---|---|---|---|---|---|---|
| Case ID in | Her2 | Nuclear | | | | Cytoplasmic | | | | Nuclear | Cytoplasmic | Total |
| the test set | status | 0 | 1 | 2 | 3 | 0 | 1 | 2 | 3 | score | score | score |
| ALx-R-42 | Neg | 80 | 0 | 20 | 0 | 0 | 100 | 0 | 0 | 40 | 100 | 140 |
| ALx-R-53 | Neg | 20 | 80 | 0 | 0 | 0 | 100 | 0 | 0 | 80 | 100 | 180 |
| ALx-R-41 | Neg | 5 | 10 | 85 | 0 | 0 | 100 | 0 | 0 | 180 | 100 | 280 |
| ALx-R-55 | Neg | 30 | 60 | 10 | 0 | 0 | 100 | 0 | 0 | 80 | 100 | 180 |
| ALx-R-58 | Pos | 30 | 40 | 30 | 0 | 0 | 70 | 30 | 0 | 100 | 130 | 230 |
| ALx-R-60 | Pos | 15 | 30 | 55 | 0 | 100 | 0 | 0 | 0 | 140 | 0 | 140 |
| ALx-R-59 | Pos | 20 | 50 | 30 | 0 | 30 | 50 | 20 | 0 | 110 | 90 | 200 |
| ALx-R-50 | Neg | 100 | 0 | 0 | 0 | 30 | 70 | 0 | 0 | 0 | 70 | 70 |
| ALx-R-51 | Pos | 5 | 90 | 5 | 0 | 0 | 100 | 0 | 0 | 100 | 100 | 200 |
| ALx-R-43 | Pos | 1 | 20 | 79 | 0 | 0 | 100 | 0 | 0 | 178 | 100 | 278 |
| ALx-NR-4 | Neg | 10 | 90 | 0 | 0 | 0 | 100 | 0 | 0 | 90 | 100 | 190 |
| ALx-NR-7 | Neg | 60 | 40 | 0 | 0 | 80 | 20 | 0 | 0 | 40 | 20 | 60 |
| ALx-NR-9 | Pos | 20 | 80 | 0 | 0 | 0 | 100 | 0 | 0 | 80 | 100 | 180 |
| ALx-NR-10 | Neg | 30 | 40 | 30 | 0 | 0 | 60 | 40 | 0 | 100 | 140 | 240 |
| ALx-NR-11 | Pos | 50 | 40 | 10 | 0 | 30 | 70 | 0 | 0 | 60 | 70 | 130 |
| ALx-NR-12 | Pos | 20 | 50 | 30 | 0 | 0 | 100 | 0 | 0 | 110 | 100 | 210 |
| ALx-NR-14 | Neg | 10 | 0 | 80 | 10 | 0 | 100 | 0 | 0 | 190 | 100 | 290 |
| ALx-NR-18 | Pos | 60 | 20 | 20 | 0 | 0 | 90 | 10 | 0 | 60 | 110 | 170 |
| ALx-NR-20 | Neg | 90 | 10 | 0 | 0 | 0 | 80 | 20 | 0 | 10 | 120 | 130 |
| ALx-R-1 | Neg | 40 | 60 | 0 | 0 | 5 | 20 | 75 | 0 | 60 | 170 | 230 |
| ALx-R-4 | Pos | 100 | 0 | 0 | 0 | 0 | 40 | 60 | 0 | 0 | 160 | 160 |
| ALx-R-5 | Pos | 60 | 40 | 0 | 0 | 5 | 85 | 10 | 0 | 40 | 105 | 145 |
| ALx-R-6 | Neg | 10 | 60 | 30 | 0 | 10 | 90 | 0 | 0 | 120 | 90 | 210 |
| ALx-R-7 | Neg | 40 | 60 | 0 | 0 | 100 | 0 | 0 | 0 | 60 | 0 | 60 |
| ALx-R-8 | Pos | 95 | 5 | 0 | 0 | 99 | 1 | 0 | 0 | 5 | 1 | 6 |

TABLE 33-continued

Histological Scoring, TL-NB, Trastuzamab TTNT

| Case ID in the test set | Her2 status | Nuclear 0 | 1 | 2 | 3 | Cytoplasmic 0 | 1 | 2 | 3 | Nuclear score | Cytoplasmic score | Total score |
|---|---|---|---|---|---|---|---|---|---|---|---|---|
| ALx-R-9  | Neg | 50  | 50  | 0  | 0 | 50 | 50  | 0  | 0 | 50  | 50  | 100 |
| ALx-R-10 | Neg | 60  | 40  | 0  | 0 | 0  | 80  | 20 | 0 | 40  | 120 | 160 |
| ALx-R-11 | Neg | 90  | 10  | 0  | 0 | 30 | 70  | 0  | 0 | 10  | 70  | 80  |
| ALx-R-13 | Pos | 90  | 10  | 0  | 0 | 90 | 10  | 0  | 0 | 10  | 10  | 20  |
| ALx-R-14 | Neg | 90  | 10  | 0  | 0 | 10 | 90  | 0  | 0 | 10  | 90  | 100 |
| ALx-R-15 | Pos | 100 | 0   | 0  | 0 | 10 | 85  | 5  | 0 | 0   | 95  | 95  |
| ALx-R-16 | Pos | 100 | 0   | 0  | 0 | 0  | 100 | 0  | 0 | 0   | 100 | 100 |
| ALx-R-17 | Neg | 100 | 0   | 0  | 0 | 10 | 50  | 40 | 0 | 0   | 130 | 130 |
| ALx-R-18 | Pos | 15  | 85  | 0  | 0 | 0  | 80  | 20 | 0 | 85  | 120 | 205 |
| ALx-R-19 | Neg | 95  | 5   | 0  | 0 | 10 | 90  | 0  | 0 | 5   | 90  | 95  |
| ALx-R-20 | Pos | 50  | 40  | 10 | 0 | 20 | 70  | 10 | 0 | 60  | 90  | 150 |
| ALx-R-45 | Neg | 20  | 60  | 20 | 0 |    |     |    |   | 100 | 0   | 100 |
| ALx-R-44 | Neg | 80  | 20  | 0  | 0 |    |     |    |   | 20  | 0   | 20  |
| ALx-R-48 | Neg | 0   | 60  | 40 | 0 |    |     |    |   | 140 | 0   | 140 |
| ALx-R-47 | Neg | 0   | 100 | 0  | 0 |    |     |    |   | 100 | 0   | 100 |
| ALx-R-54 | Pos | 100 | 0   | 0  | 0 |    |     |    |   | 0   | 0   | 0   |
| ALx-R-56 | Pos | 20  | 70  | 10 | 0 |    |     |    |   | 90  | 0   | 90  |
| ALx-R-52 | Neg | 20  | 80  | 0  | 0 |    |     |    |   | 80  | 0   | 80  |
| ALx-R-57 | Pos | 0   | 50  | 50 | 0 |    |     |    |   | 150 | 0   | 150 |
| ALx-R-49 | Pos | 90  | 10  | 0  | 0 |    |     |    |   | 10  | 0   | 10  |

TABLE 34

Histological Scoring, TL-NB, Platinum/Taxane TTNT

| Case ID in the test set | Her2 status | Nuclear 0 | 1 | 2 | 3 | Cytoplasmic 0 | 1 | 2 | 3 | Nuclear score | Cytoplasmic score | Total score |
|---|---|---|---|---|---|---|---|---|---|---|---|---|
| Pl-1  | Neg | 5  | 45 | 50 | 0 | 0   | 100 | 0  | 0 | 145 | 100 | 245 |
| Pl-2  | Pos | 70 | 30 | 0  | 0 | 10  | 70  | 20 | 0 | 30  | 110 | 140 |
| Pl-3  | Neg | 10 | 55 | 35 | 0 | 0   | 100 | 0  | 0 | 125 | 100 | 225 |
| Pl-4  | Neg | 30 | 70 | 0  | 0 | 0   | 100 | 0  | 0 | 70  | 100 | 170 |
| Pl-5  | Neg | 45 | 50 | 5  | 0 | 0   | 100 | 0  | 0 | 60  | 100 | 160 |
| Pl-6  | Pos | 20 | 40 | 40 | 0 | 0   | 100 | 0  | 0 | 120 | 100 | 220 |
| Pl-7  | Neg | 60 | 30 | 10 | 0 | 10  | 90  | 0  | 0 | 50  | 90  | 140 |
| Pl-8  | Pos | 35 | 45 | 20 | 0 | 0   | 70  | 30 | 0 | 85  | 130 | 215 |
| Pl-9  | Pos |    |    |    |   |     |     |    |   | 0   | 0   | 0   |
| Pl-10 | Neg | 0  | 10 | 90 | 0 | 100 | 0   | 0  | 0 | 190 | 0   | 190 |
| Pl-11 | Pos | 5  | 90 | 5  | 0 | 0   | 100 | 0  | 0 | 100 | 100 | 200 |
| Pl-12 | Neg | 20 | 40 | 40 | 0 | 10  | 90  | 0  | 0 | 120 | 90  | 210 |
| Pl-13 | Pos | 50 | 40 | 10 | 0 | 0   | 100 | 0  | 0 | 60  | 100 | 160 |
| Pl-14 | Pos | 80 | 20 | 0  | 0 | 50  | 50  | 0  | 0 | 20  | 50  | 70  |
| Pl-15 | Neg |    |    |    |   |     |     |    |   | 0   | 0   | 0   |
| Pl-16 | Neg | 20 | 80 | 0  | 0 | 0   | 60  | 40 | 0 | 80  | 140 | 220 |
| Pl-17 | Neg | 20 | 80 | 0  | 0 | 100 | 0   | 0  | 0 | 80  | 0   | 80  |
| Pl-18 | Neg |    |    |    |   |     |     |    |   | 0   | 0   | 0   |
| Pl-19 | Neg |    |    |    |   |     |     |    |   | 0   | 0   | 0   |
| Pl-20 | Neg | 10 | 90 | 0  | 0 | 0   | 100 | 0  | 0 | 90  | 100 | 190 |
| Pl-21 | Pos | 5  | 10 | 85 | 0 | 100 | 0   | 0  | 0 | 180 | 0   | 180 |
| Pl-22 | Pos | 60 | 30 | 10 | 0 | 70  | 30  | 0  | 0 | 50  | 30  | 80  |
| Pl-23 | Neg | 10 | 30 | 60 | 0 | 10  | 90  | 0  | 0 | 150 | 90  | 240 |
| Pl-24 | Pos | 5  | 70 | 25 | 0 | 0   | 100 | 0  | 0 | 120 | 100 | 220 |
| Pl-25 | Pos |    |    |    |   |     |     |    |   | 0   | 0   | 0   |
| Pl-26 | Pos | 10 | 80 | 10 | 0 | 0   | 80  | 20 | 0 | 100 | 120 | 220 |
| Pl-27 | Neg | 10 | 70 | 20 | 0 | 20  | 80  | 0  | 0 | 110 | 80  | 190 |
| Pl-28 | Pos | 35 | 40 | 25 | 0 | 0   | 60  | 40 | 0 | 90  | 140 | 230 |
| Pl-29 | Pos | 3  | 67 | 30 | 0 | 0   | 100 | 0  | 0 | 127 | 100 | 227 |
| Pl-30 | Pos | 10 | 80 | 10 | 0 | 10  | 90  | 0  | 0 | 100 | 90  | 190 |
| Pl-31 | Pos | 20 | 60 | 20 | 0 | 0   | 100 | 0  | 0 | 100 | 100 | 200 |
| Pl-32 | Neg | 20 | 80 | 0  | 0 | 0   | 80  | 20 | 0 | 80  | 120 | 200 |
| Pl-33 | Neg | 40 | 60 | 0  | 0 | 100 | 0   | 0  | 0 | 60  | 0   | 60  |
| Pl-34 | Pos | 70 | 30 | 0  | 0 | 20  | 60  | 20 | 0 | 30  | 100 | 130 |
| Pl-35 | Pos | 50 | 50 | 0  | 0 | 10  | 90  | 0  | 0 | 50  | 90  | 140 |
| Pl-36 | Pos | 80 | 10 | 10 | 0 | 0   | 100 | 0  | 0 | 30  | 100 | 130 |
| Pl-37 | Neg | 20 | 10 | 70 | 0 | 30  | 70  | 0  | 0 | 150 | 70  | 220 |
| Pl-38 | Neg | 30 | 60 | 10 | 0 | 10  | 90  | 0  | 0 | 80  | 90  | 170 |
| Pl-39 | Pos | 10 | 90 | 0  | 0 | 0   | 100 | 0  | 0 | 90  | 100 | 190 |
| Pl-40 | Neg | 60 | 35 | 5  | 0 | 20  | 80  | 0  | 0 | 45  | 80  | 125 |
| Pl-41 | Neg | 5  | 45 | 50 | 0 | 0   | 80  | 20 | 0 | 145 | 120 | 265 |

TABLE 35

Histological Scoring, TL-B, Trastuzamab TTNT

| Case ID in the test set | Her2 status | Nuclear 0 | Nuclear 1 | Nuclear 2 | Nuclear 3 | Cytoplasmic 0 | Cytoplasmic 1 | Cytoplasmic 2 | Cytoplasmic 3 | Nuclear score | Cytoplasmic score | Total score |
|---|---|---|---|---|---|---|---|---|---|---|---|---|
| ALx-R-42 | Neg | 35 | 45 | 20 | 0 | 0 | 100 | 0 | 0 | 85 | 100 | 185 |
| ALx-R-53 | Neg | 30 | 70 | 0 | 0 | 0 | 100 | 0 | 0 | 70 | 100 | 170 |
| ALx-R-41 | Neg | 10 | 80 | 10 | 0 | 10 | 90 | 0 | 0 | 100 | 90 | 190 |
| ALx-R-55 | Neg | 90 | 10 | 0 | 0 | 0 | 100 | 0 | 0 | 10 | 100 | 110 |
| ALx-R-58 | Pos | 20 | 80 | 0 | 0 | 0 | 100 | 0 | 0 | 80 | 100 | 180 |
| ALx-R-60 | Pos | 10 | 40 | 50 | 0 | 10 | 90 | 0 | 0 | 140 | 90 | 230 |
| ALx-R-59 | Pos | 15 | 85 | 0 | 0 | 0 | 100 | 0 | 0 | 85 | 100 | 185 |
| ALx-R-50 | Neg | 50 | 50 | 0 | 0 | 0 | 100 | 0 | 0 | 50 | 100 | 150 |
| ALx-R-51 | Pos | 5 | 95 | 0 | 0 | 0 | 100 | 0 | 0 | 95 | 100 | 195 |
| ALx-R-43 | Pos | 5 | 45 | 50 | 0 | 5 | 95 | 0 | 0 | 145 | 95 | 240 |
| ALx-NR-4 | Neg | 25 | 65 | 10 | 0 | 0 | 90 | 10 | 0 | 85 | 110 | 195 |
| ALx-NR-7 | Neg | 70 | 30 | 0 | 0 | 100 | 0 | 0 | 0 | 30 | 0 | 30 |
| ALx-NR-9 | Pos | 40 | 60 | 0 | 0 | 0 | 100 | 0 | 0 | 60 | 100 | 160 |
| ALx-NR-10 | Neg | 80 | 10 | 10 | 0 | 10 | 80 | 10 | 0 | 30 | 100 | 130 |
| ALx-NR-11 | Pos | 90 | 10 | 0 | 0 | 10 | 90 | 0 | 0 | 10 | 90 | 100 |
| ALx-NR-12 | Pos | 10 | 20 | 70 | 0 | 0 | 100 | 0 | 0 | 160 | 100 | 260 |
| ALx-NR-14 | Neg | 50 | 20 | 30 | 0 | 10 | 20 | 70 | 0 | 80 | 160 | 240 |
| ALx-NR-18 | Pos | 88 | 10 | 2 | 0 | 2 | 88 | 10 | 0 | 14 | 108 | 122 |
| ALx-NR-20 | Neg | 80 | 20 | 0 | 0 | 20 | 50 | 30 | 0 | 20 | 110 | 130 |
| ALx-R-1 | Neg | 10 | 10 | 80 | 0 | 0 | 90 | 10 | 0 | 170 | 110 | 280 |
| ALx-R-4 | Pos | 20 | 80 | 0 | 0 | 0 | 60 | 40 | 0 | 80 | 140 | 220 |
| ALx-R-5 | Pos | 20 | 40 | 40 | 0 | 0 | 60 | 40 | 0 | 120 | 140 | 260 |
| ALx-R-6 | Neg | 5 | 35 | 60 | 0 | 0 | 100 | 0 | 0 | 155 | 100 | 255 |
| ALx-R-7 | Neg | 10 | 45 | 45 | 0 | 0 | 80 | 20 | 0 | 135 | 120 | 255 |
| ALx-R-8 | Pos | 10 | 25 | 25 | 40 | 0 | 40 | 60 | 0 | 195 | 160 | 355 |
| ALx-R-9 | Neg | 5 | 35 | 60 | 0 | 0 | 100 | 0 | 0 | 155 | 100 | 255 |
| ALx-R-10 | Neg | 5 | 95 | 0 | 0 | 0 | 100 | 0 | 0 | 95 | 100 | 195 |
| ALx-R-11 | Neg | 2 | 30 | 68 | 0 | 0 | 100 | 0 | 0 | 166 | 100 | 266 |
| ALx-R-13 | Pos | 93 | 5 | 2 | 0 | 25 | 75 | 0 | 0 | 9 | 75 | 84 |
| ALx-R-14 | Neg | 10 | 80 | 10 | 0 | 0 | 50 | 50 | 0 | 100 | 150 | 250 |
| ALx-R-15 | Pos | 20 | 20 | 60 | 0 | 0 | 80 | 20 | 0 | 140 | 120 | 260 |
| ALx-R-16 | Pos | 10 | 60 | 30 | 0 | 0 | 20 | 80 | 0 | 120 | 180 | 300 |
| ALx-R-17 | Neg | 70 | 30 | 0 | 0 | 0 | 50 | 50 | 0 | 30 | 150 | 180 |
| ALx-R-18 | Pos | 5 | 15 | 80 | 0 | 0 | 0 | 100 | 0 | 175 | 200 | 375 |
| ALx-R-19 | Neg | 100 | 0 | 0 | 0 | 10 | 20 | 70 | 0 | 0 | 160 | 160 |
| ALx-R-20 | Pos | 20 | 50 | 30 | 0 | 0 | 100 | 0 | 0 | 110 | 100 | 210 |
| ALx-R-45 | Pos | 50 | 40 | 10 | 0 | 10 | 70 | 20 | 0 | 60 | 110 | 170 |
| ALx-R-44 | Neg | 0 | 50 | 50 | 0 | 80 | 20 | 0 | 0 | 150 | 20 | 170 |
| ALx-R-48 | Neg | 20 | 70 | 10 | 0 | 0 | 100 | 0 | 0 | 90 | 100 | 190 |
| ALx-R-47 | Pos | 0 | 100 | 0 | 0 | 0 | 100 | 0 | 0 | 100 | 100 | 200 |
| ALx-R-54 | Neg | 100 | 0 | 0 | 0 | 0 | 100 | 0 | 0 | 0 | 100 | 100 |
| ALx-R-56 | Neg | 60 | 40 | 0 | 0 | 0 | 70 | 30 | 0 | 40 | 130 | 170 |
| ALx-R-52 | Pos | 20 | 80 | 0 | 0 | 10 | 60 | 30 | 0 | 80 | 120 | 200 |
| ALx-R-57 | Pos | 0 | 100 | 0 | 0 | 0 | 100 | 0 | 0 | 100 | 100 | 200 |
| ALx-R-49 | Neg | 95 | 5 | 0 | 0 | 30 | 70 | 0 | 0 | 5 | 70 | 75 |

TABLE 36

Histological Scoring, TL-B, Platinum/Taxane TTNT

| Case ID in the test set | Her2 status | Nuclear 0 | Nuclear 1 | Nuclear 2 | Nuclear 3 | Cytoplasmic 0 | Cytoplasmic 1 | Cytoplasmic 2 | Cytoplasmic 3 | Nuclear score | Cytoplasmic score | Total score |
|---|---|---|---|---|---|---|---|---|---|---|---|---|
| Pl-1 | Neg | 5 | 95 | 0 | 0 | 0 | 80 | 20 | 0 | 95 | 120 | 215 |
| Pl-2 | Pos | 80 | 20 | 0 | 0 | 20 | 80 | 0 | 0 | 20 | 80 | 100 |
| Pl-3 | Neg | 5 | 95 | 0 | 0 | 0 | 100 | 0 | 0 | 95 | 100 | 195 |
| Pl-4 | Neg | 10 | 90 | 0 | 0 | 0 | 100 | 0 | 0 | 90 | 100 | 190 |
| Pl-5 | Neg | 60 | 39 | 1 | 0 | 0 | 100 | 0 | 0 | 41 | 100 | 141 |
| Pl-6 | Pos |  |  |  |  |  |  |  |  | 0 | 0 | 0 |
| Pl-7 | Neg | 70 | 30 | 0 | 0 | 70 | 30 | 0 | 0 | 30 | 30 | 60 |
| Pl-8 | Pos | 80 | 20 | 0 | 0 | 60 | 40 | 0 | 0 | 20 | 40 | 60 |
| Pl-9 | Pos |  |  |  |  |  |  |  |  | 0 | 0 | 0 |
| Pl-10 | Neg | 0 | 50 | 50 | 0 | 0 | 100 | 0 | 0 | 150 | 100 | 250 |
| Pl-11 | Pos | 5 | 95 | 0 | 0 | 0 | 100 | 0 | 0 | 95 | 100 | 195 |
| Pl-12 | Neg | 30 | 70 | 0 | 0 | 30 | 70 | 0 | 0 | 70 | 70 | 140 |
| Pl-13 | Pos | 30 | 40 | 30 | 0 | 0 | 100 | 0 | 0 | 100 | 100 | 200 |
| Pl-14 | Pos | 90 | 10 | 0 | 0 | 40 | 60 | 0 | 0 | 10 | 60 | 70 |
| Pl-15 | Neg |  |  |  |  |  |  |  |  | 0 | 0 | 0 |
| Pl-16 | Neg | 5 | 95 | 0 | 0 | 0 | 100 | 0 | 0 | 95 | 100 | 195 |
| Pl-17 | Neg | 50 | 50 | 0 | 0 | 0 | 100 | 0 | 0 | 50 | 100 | 150 |

TABLE 36-continued

Histological Scoring, TL-B, Platinum/Taxane TTNT

| Case ID in the test set | Her2 status | Nuclear 0 | 1 | 2 | 3 | Cytoplasmic 0 | 1 | 2 | 3 | Nuclear score | Cytoplasmic score | Total score |
|---|---|---|---|---|---|---|---|---|---|---|---|---|
| Pl-18 | Neg | | | | | | | | | 0 | 0 | 0 |
| Pl-19 | Neg | | | | | | | | | 0 | 0 | 0 |
| Pl-20 | Neg | 10 | 90 | 0 | 0 | 70 | 30 | 0 | 0 | 90 | 30 | 120 |
| Pl-21 | Pos | 5 | 45 | 50 | 0 | 0 | 100 | 0 | 0 | 145 | 100 | 245 |
| Pl-22 | Pos | 50 | 50 | 0 | 0 | 40 | 60 | 0 | 0 | 50 | 60 | 110 |
| Pl-23 | Neg | 20 | 80 | 0 | 0 | 0 | 80 | 0 | 0 | 80 | 80 | 160 |
| Pl-24 | Pos | 20 | 70 | 10 | 0 | 20 | 40 | 40 | 0 | 90 | 120 | 210 |
| Pl-25 | Pos | | | | | | | | | 0 | 0 | 0 |
| Pl-26 | Pos | 60 | 40 | 0 | 0 | 0 | 60 | 40 | 0 | 40 | 140 | 180 |
| Pl-27 | Neg | 0 | 50 | 50 | 0 | 0 | 100 | 0 | 0 | 150 | 100 | 250 |
| Pl-28 | Pos | 5 | 95 | 0 | 0 | 0 | 40 | 60 | 0 | 95 | 160 | 255 |
| Pl-29 | Pos | 0 | 5 | 95 | 0 | 0 | 100 | 0 | 0 | 195 | 100 | 295 |
| Pl-30 | Pos | 5 | 95 | 0 | 0 | 5 | 95 | 0 | 0 | 95 | 95 | 190 |
| Pl-31 | Pos | 5 | 85 | 10 | 0 | 0 | 100 | 0 | 0 | 105 | 100 | 205 |
| Pl-32 | Neg | 50 | 50 | 0 | 0 | 0 | 70 | 30 | 0 | 50 | 130 | 180 |
| Pl-33 | Neg | 40 | 60 | 0 | 0 | 0 | 100 | 0 | 0 | 60 | 100 | 160 |
| Pl-34 | Pos | 100 | 0 | 0 | 0 | 100 | 0 | 0 | 0 | 0 | 0 | 0 |
| Pl-35 | Pos | 10 | 85 | 5 | 0 | 0 | 100 | 0 | 0 | 95 | 100 | 195 |
| Pl-36 | Pos | 30 | 60 | 10 | 0 | 20 | 75 | 5 | 0 | 80 | 85 | 165 |
| Pl-37 | Neg | 20 | 20 | 60 | 0 | 100 | 0 | 0 | 0 | 140 | 0 | 140 |
| Pl-38 | Neg | 50 | 40 | 10 | 0 | 0 | 100 | 0 | 0 | 60 | 100 | 160 |
| Pl-39 | Pos | 30 | 70 | 0 | 0 | 20 | 70 | 10 | 0 | 70 | 90 | 160 |
| Pl-40 | Neg | 60 | 40 | 0 | 0 | 0 | 100 | 0 | 0 | 40 | 100 | 140 |
| Pl-41 | Neg | 20 | 80 | 0 | 0 | 0 | 50 | 50 | 0 | 80 | 150 | 230 |

With two libraries in hand that reciprocally show preferential staining for either B or NB cases, we tested use fo PHC scores for the differentiation and prediction of responders and non-responders to trastuzumab-based regimens in the 45 independent test cases. See FIG. 17A. We assessed the PHC scores of TL-B and TL-NB by receiver operating characteristic (ROC) curves, and calculated area under the curve (AUC) values (FIGS. 17Mi-ii). For TL-NB, an AUC value of 0.703 was obtained based on the scoring of the nucleus (22) (FIG. 17Mi), whereas TL-B yielded an AUC value of 0.688 (FIG. 17Mii) based on the scoring of both nucleus and cytoplasm. These AUC values from the individual libraries indicate that TL-NB and TL-B provide reliable information that distinguishes the NB and B phenotypes. To predict the patient's response to trastuzumab-based regimens with a multivariate method that uses PHC scores from both TL-NB and TL-B staining, a logistic regression model was developed. Specifically, the binary outcome of benefit- or non-benefit status was used as the dependent variable; the staining scores of TL-NB and TL-B, respectively, were treated as independent variables. We then assessed the performance of the model by ROC curve analysis. As a result, by combining the data from the two libraries, the AUC-value increased to 0.804, indicating improved performance due to the reciprocal nature of the training schemes (FIG. 17Miii, indicated by AUC=0.804). The statistical reliability of this analysis was further verified by 10-fold cross validation (CV), which resulted in an AUC value of 0.760 (FIG. 17Miii, indicated by AUC=0.760). We then compared these PHC-based NB and B classifications with those predicted by HER2 immunohistochemistry scoring of the same 45 cases test set (FIG. 17Miii, indicated by AUC=0.410). The HER2 IHC results yielded an AUC value of 0.410, indicating that TL-NB and TL-B outperformed conventional HER2 IHC in classifying trastuzumab B and NB cases in this cohort.

Figure 17N:
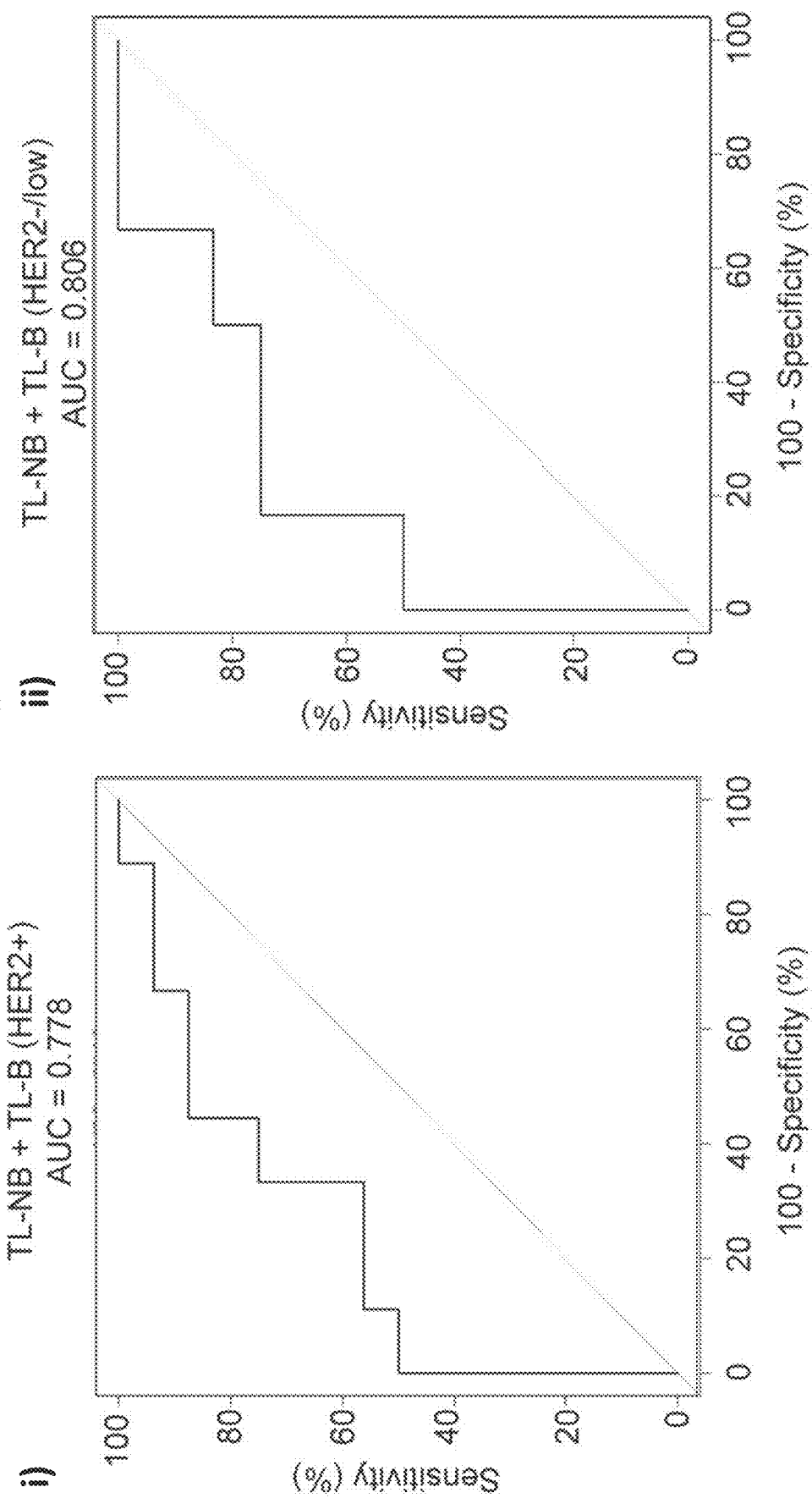

TL-NB and TL-B were able to effectively classify B and NB patients that had low levels of HER2-expression by IHC with an AUC value of 0.8. FIG. 17N shows the receiver operating characteristic (ROC) curves for differentiation between patients, benefiting and not from trastuzumab-based regimens, using combined histological scores from libraries TL NB and TL B polyligand histochemistry (PHC) staining in the test set of 45 cases, shown separately in the group of HER2+ cases (A) and in the group of HER2−/low cases (B). Hence, the ability of the libraries to differentiate NB from B-cases does not depend solely on the HER2 status.

Figure 17O:
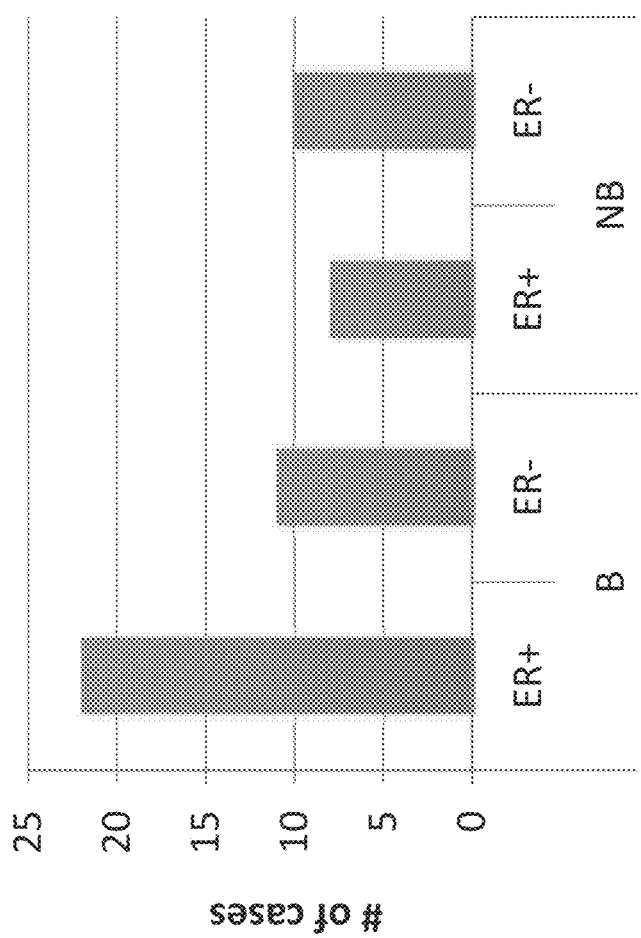

To determine whether TL-NB and TL-B were revealing information about response to trastuzumab-based regimens and not only classifying patients with a favorable prognosis regardless of trastuzumab treatment, we stained FFPE tumor tissues from an independent cohort of 33 patients who were treated with a platinum/taxane combination without trastuzumab. Like all other samples in this study, the samples from this non-trastuzumab cohort were collected prior to treatment. The AUC of the combined libraries on 33 HER2-cases independent from the test set who received platinum/taxane combination therapy instead of trastuzumab was 0.302 (FIG. 17Miii, indicated by AUC=0.302), indicating that the performance of TL-NB and TL-B relate to the molecular profile determining the response to the presence of trastuzumab in the treatment regimens. Moreover, trastuzumab has been reported to be substantially less effective in estrogen receptor (ER)-positive breast cancer (23, 24), but we found that the ER status of all cases enrolled in our study showed no correlation with the benefit from trastuzumab-based therapy. See FIG. 17O, which shows that in the tested population, benefit from trastuzumab does not correlate with hormonal status. ER status for the patients in this Example is shown in Tables 31-32. Taken together, these data indicate that the application of these libraries to the 45-cases test-set classifies patients with benefit from patients without benefit from trastuzumab-containing treatment with high accuracy, regardless of their HER2-status.

Figure 17P:
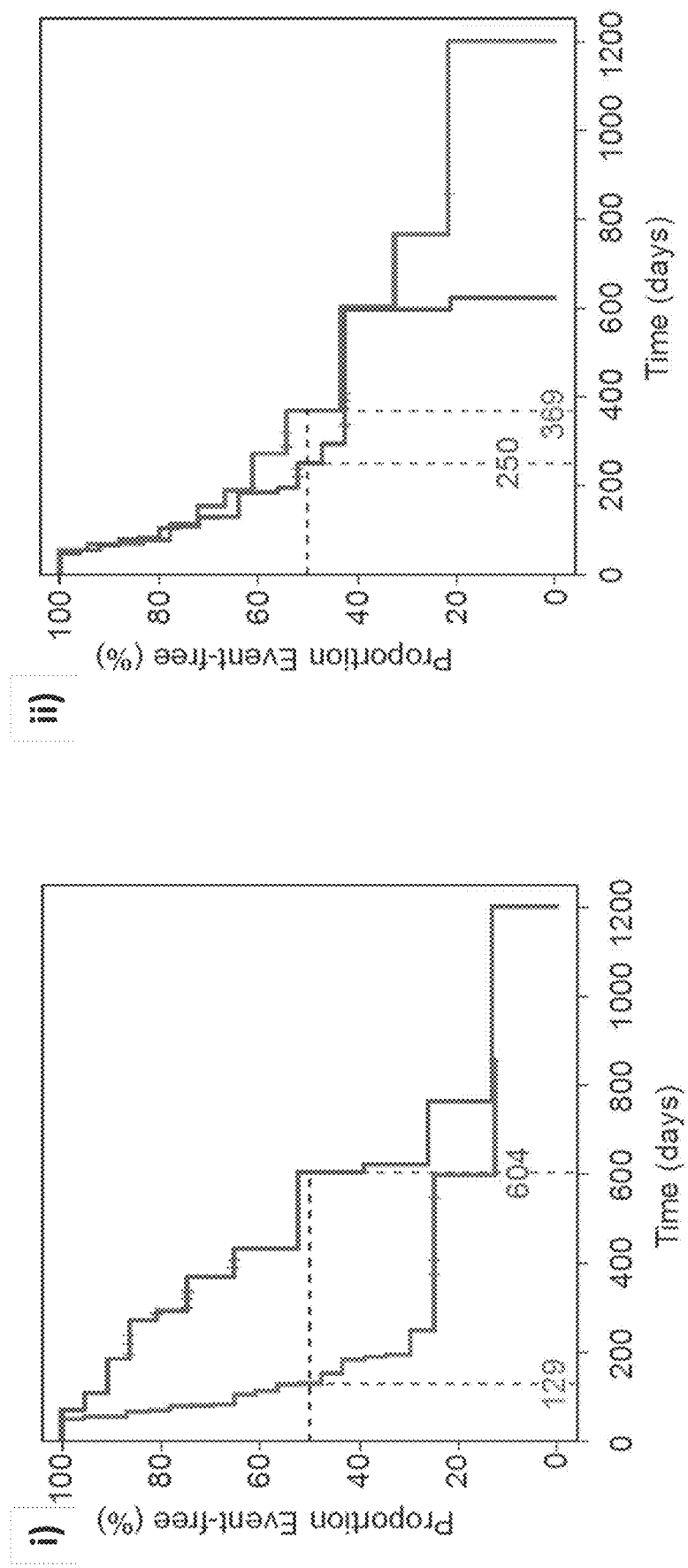

We next sought to evaluate the ability of PHC to select the fraction of patients that benefit from trastuzumab-based regimens for more than 180 days. FIG. 17Pi-ii show Kaplan-Meier curves of trastuzumab-treated breast cancer patients stratified by polyligand profiling. In FIG. 17Pi, the shortest distance between the ROC curves to point (specificity and sensitivity=100%) determines the cutoff of test positive and negative, and is represented as dot on the line indicated by AUC=0.804 in FIG. 17Miii (Sensitivity: 66.6%; Specificity: 86.7%). An "event" was defined as the time point (days) at which a patient either deceased from cancer or at which trastuzumab-based treatment changed. Median time of benefit is 604 days for patients tested positive ((FIG. 17Pi, upper curve), n=22, event=11) and 129 days for patients tested negative ((FIG. 17Pi, lower curve), n=23, event=18). HR=0.320, 95% CI: 0.146-0.703; log-rank p=0.003. The small vertical lines mark cases that were censored due to absence of treatment follow-up data. See Table 32. FIG. 17Pii shows the Kaplan-Meier curve of trastuzumab-treated breast cancer patients stratified by tumors' HER2 status. HER2 status of patients with both HER2 IHC and HER2 ISH test results was determined according to the following rules. 1. HER2 positive, if any test shows positive result; else 2, HER2−/low, if any test shows negative result; else 3, NA, if both test show equivalent result. Median time of benefit was 250 days for HER2 positive cases ((FIG. 17Pii, lower curve, n=25, event=16), and 369 days for HER2−/low cases ((FIG. 17Pii, upper curve; n=18, event=12). HR=1.39, 95% CI: 0.62-3.13; log-rank p=0.418. Accordingly, the resulting Kaplan-Meier curves show that cases with positive test results exhibited a significantly longer TTNT (FIG. 17Pi, upper curve) than those tested negative (FIG. 17Pi, lower curve). The median event-free time, i.e. the time that elapsed before the treatment regimens changed, increased from 129 days for the test-negative to 604 days for the test-positive cases. For comparison, we analyzed the prognostic value based on the tumors' HER2 status as determined by IHC. In this case, the KM-curves did not reveal any significant difference in TTNT between patients that were HER2+ or Her2−/low (FIG. 17Pii). These data indicate that polyligand profiling can be employed to generate a predictive assay that differentiates between patients that benefit from a certain treatment regimens from those that do not.

In this Example, we demonstrated a prototypical polyligand profiling approach with potential to improve patient stratification for cancer therapy. The approach was applied to train the libraries TL-B and TL-NB for classifying trastuzumab response by TTNT. Polyligand profiling is not limited to this condition and will be applicable for differentiating a wide variety of phenotypes depending on the question at hand and the availability of suitable samples. Previous studies have used morphology-based enrichment of ssODN libraries on cancer tissues (see herein, references 25, 26) in order to identify new biomarkers. In this study, to account for the heterogeneity of molecular composition and the complex interactomes that reflect intra- and inter-tumoral variability it is reasonable that library training as introduced here enriches for a complex variety of ligands.

Without optimization, the PHC-test developed in this Example outperformed the standard HER2 IHC in differentiating the patients in this cohort who benefit from trastuzumab-based treatment from those that do not. See FIGS. 17M, P and related discussion above. These data indicate that the PHC-test can provide a CDx, in this case one that aims at identifying the 50-70% of HER2+ patients who will not benefit from trastuzumab. Conversely, it has been reported that 16-45% of patients with breast cancer who express low levels of Her2 derived benefit from adjuvant trastuzumab in combination chemotherapy (27-29). The data shown in FIGS. 17M, P indicate that a CDx based on polyligand profiling also has the potential to identify the patients who benefit from trastuzumab-containing regimens from the group expressing low levels of Her2.

Polyligand profiling allows accessing the molecular information that is reflected by the perturbations within the vast diversity of biological complexes that constitute cellular interactomes within or among tumors. In addition to predicting patients with benefit or without benefit from a given drug treatment regimens, the PHC approach can advance precision oncology in additional ways. For example, when applied to existing therapies as well as to new compounds in clinical trials polyligand profiling could reduce the administration of toxic therapies that are ineffective, and thereby could increase the success rate of new drugs.

References cited in this Example, all incorporated by reference herein in their entirety.
1. D. Hanahan, R. A. Weinberg, Hallmarks of cancer: the next generation. Cell 144, 646-674 (2011).
2. M. Gerlinger et al., Intratumor heterogeneity and branched evolution revealed by multiregion sequencing. N Engl J Med 366, 883-892 (2012).
3. L. A. Garraway, E. S. Lander, Lessons from the cancer genome. Cell 153, 17-37 (2013).
4. V. Prasad, Perspective: The precision-oncology illusion. Nature 537, S63 (2016).
5. V. Prasad, T. Fojo, M. Brada, Precision oncology: origins, optimism, and potential. Lancet Oncol 17, e81-86 (2016).
6. G. L. Klement et al., Future paradigms for precision oncology. Oncotarget 7, 46813-46831 (2016).
7. R. Kurzrock, F. J. Giles, Precision oncology for patients with advanced cancer: the challenges of malignant snowflakes. Cell Cycle 14, 2219-2221 (2015).
8. J. Shrager, J. M. Tenenbaum, Rapid learning for precision oncology. Nat Rev Clin Oncol 11, 109-118 (2014).
9. M. J. Duffy, J. Crown, Companion biomarkers: paving the pathway to personalized treatment for cancer. Clin Chem 59, 1447-1456 (2013).
10. M. P. Stumpf et al., Estimating the size of the human interactome. Proc Natl Acad Sci USA 105, 6959-6964 (2008).
11. Z. Mitri, T. Constantine, R. O'Regan, The HER2 Receptor in Breast Cancer: Pathophysiology, Clinical Use, and New Advances in Therapy. Chemother Res Pract 2012, 743193 (2012).
12. H. J. Burstein, The distinctive nature of HER2-positive breast cancers. N Engl J Med 353, 1652-1654 (2005).
13. R. Bartsch, C. Wenzel, G. G. Steger, Trastuzumab in the management of early and advanced stage breast cancer. Biologics 1, 19-31 (2007).
14. I. Petak, R. Schwab, L. Orfi, L. Kopper, G. Keri, Integrating molecular diagnostics into anticancer drug discovery. Nat Rev Drug Discov 9, 523-535 (2010).
15. D. J. Slamon et al., Human breast cancer: correlation of relapse and survival with amplification of the HER-2/neu oncogene. Science 235, 177-182 (1987).
16. J. Horton, Trastuzumab use in breast cancer: clinical issues. Cancer Control 9, 499-507 (2002).
17. M. Famulok, J. S. Hartig, G. Mayer, Functional aptamers and aptazymes in biotechnology, diagnostics, and therapy. Chem. Rev. 107, 3715-3743 (2007).
18. M. Famulok, G. Mayer, Aptamer modules as sensors and detectors. Acc Chem Res 44, 1349-1358 (2011).

19. TTNT is a FDA-approved clinical endpoint that is robustly captured by electronic medical record systems and therefore is generally available.
20. U.S. Department of Health and Human Services Food and Drug Administration Center for Drug Evaluation and Research (CDER), Guidance for industry: clinical trial endpoints for the approval of cancer drugs and biologics.
21. Z. Gatalica, S. M. Lele, B. A. Rampy, B. A. Norris, The expression of Fhit protein is related inversely to disease progression in patients with breast carcinoma. Cancer 88, 1378-1383 (2000).
22. TL-NB staining of the cytoplasm was not informative for the differentiation of B and NB cases.
23. L. Lousberg, J. Collignon, G. Jerusalem, Resistance to therapy in estrogen receptor positive and human epidermal growth factor 2 positive breast cancers: progress with latest therapeutic strategies. Ther Adv Med Oncol 8, 429-449 (2016).
24. S. Loi et al., Effects of Estrogen Receptor and Human Epidermal Growth Factor Receptor-2 Levels on the Efficacy of Trastuzumab: A Secondary Analysis of the HERA Trial. JAMA Oncol 2, 1040-1047 (2016).
25. H. Wang et al., Morph-X-Select: Morphology-based tissue aptamer selection for ovarian cancer biomarker discovery. Biotechniques 61, 249-259 (2016).
26. S. Li et al., Identification of an aptamer targeting hnRNP A1 by tissue slide-based SELEX. J Pathol 218, 327-336 (2009).
27. S. Paik, C. Kim, N. Wolmark, HER2 status and benefit from adjuvant trastuzumab in breast cancer. N Engl J Med 358, 1409-1411 (2008).
28. S. Ithimakin et al., HER2 drives luminal breast cancer stem cells in the absence of HER2 amplification: implications for efficacy of adjuvant trastuzumab. Cancer Res 73, 1635-1646 (2013).
29. clinicaltrials.gov/ct2/show/NCT01275677?term=NSABP+B01275647&rank=01275671.

Example 22

Polyligand Profiling Materials and Methods

This Example provides Materials and Methods used in Example 21 above.

FFPE Tissue Cases

The study was performed with Western Institutional Review Board approval, 45 CFR 46.101(b)(4).

This study included cases from women with invasive breast cancer that received trastuzumab-based treatment first line after tissue collection with a sufficient number of properly fixed and embedded slides available. Cases with in situ cancer, improperly fixed or crushed tissue sections were not included in this study. Cases with incomplete staining (i.e. insufficient coverage of the tissue with binding solution) and other technical problems with the assay performance were excluded from analysis.

Serial tissue sections of 51 patients with breast cancer that had time-to-next treatment (TTNT) data from trastuzumab therapy were used for training of the ssODN libraries and testing of TL-NB and TL-B. A separate group of 33 cases that had TTNT data from platinum-taxane treatment was used as a control set to evaluate the specificities of TL-NB and TL-B towards trastuzumab-based TTNT. Excised tissue containing both tumor and normal parts, was formalin-fixed, paraffin-embedded and serially sectioned (4 µm). Haematoxylin and eosin (H&E) staining was performed for 1-2 slides of each case and served for initial pathological diagnosis. Pre-treatment of the FFPE tissue slides before the enrichment included incubating slides at 60° C. for 1.5 h, followed by automated deparaffinization and epitope retrieval on the Ventana UltraView Autostainer (Ventana Medical Systems, Inc., Tuscon, Ariz.). Specifically, deparaffinization at 72° C. for 24 min, dehydration by ethanol, epitope retrieval at 90° C. for 36 min and 100° C. for 4 min (pH 8), followed by peroxidase inhibition ($H_2O_2$, $1\% \le x < 5\%$) and washing slides with detergent (Dawn 1-00; P&G Professional, The Procter & Gamble Company, Cincinnati, Ohio) to remove residual liquid coverslip. For testing of the enriched libraries, deparaffinization was performed manually, by incubation at 60° C. for 1.5 hour, followed by epitope retrieval on PT-Linker (Dako, Agilent Technologies, Santa Clara, Calif.) at 97° C. for 20 min, pH 9.

Treatment regimens and pathological diagnoses for 84 cases can be found in Tables 29-32. A subset of 3 non-benefiting (NB) breast cancer cases and 3 benefiting (B) breast cancer cases was selected for enrichment. Patients who stayed on their initially prescribed trastuzumab therapy for at least 181 days were classified as B; patients whose treatment changed within 180 days were classified as NB. Clinical information for the training cases can be found in Tables 29-30. For enrichment purposes, tissue areas with breast carcinoma were utilized as positive selection targets, while adjacent non-malignant tissue as well as carcinoma tissue from patients with alternative response was used as counter selection targets.

ssDNA Library Design and Reproduction with Unequal Length Primers Asymmetrical PCR The random ssDNA library (naïve F-TRin-35n-B 8-3s library) contains 35 random nucleotides flanked by constant regions. Specifically, the naïve library comprises a 5' region (5' CTAGCATGACTGCAGTACGT (SEQ ID NO. 4)) followed by a random naïve oligonucleotide sequence of 35 nucleotides and a 3' region (5' CTGTCTCTTATACACATCTGACGCTGCCGACGA (SEQ ID NO. 5)). This library was synthesized at Integrated DNA Technologies (IDT, Coralville, Iowa, USA), pooled in equimolar amounts and PCR amplified to add biotin to the 5'-end. The library constant regions are complimentary to primers: reverse: 5'-Biosg-CTAGCATGACTGCAGTACGT-3' (SEQ ID NO. 4) and forward: 5'-AAAAAAAAAAAAAAAAAAAAAAAAAAAAAAAAAA (SEQ ID NO. 203062)/iSp9//iSp9/TCGTCGGCAGCGTCA-3' (SEQ ID NO. 203063)), which were used in asymmetric PCR to generate majority of the target strand. The internal spacers iSp9 (Internal triethylene glycol Spacer, IDT) of the forward primer prevented extension of the complimentary strand, while the addition of poly-A tail resulted in longer length of forward strands, allowing for size separation and target strand ssDNA recovery following gel excision from 4% denaturing agarose E-gels with final purification by gel extraction column (Nucleospin, MACHEREY-NAGEL GmbH & Co. KG, Düren, Del.). Biotinylated antisense library was used for enrichment. Asymmetric PCR mixture (100 µl) contained 5× Q5 PCR buffer, 0.2 mM dNTPs, 0.08 µM of forward primer, 30 µM of reverse primer, 0.01 pmol template (of pure library) or 57 µl of post-dissection solution containing library/tissue (after enrichment) and 2U of Q5 Hot Start High-Fidelity DNA polymerase (New England Biolabs, Ipswich, Mass.). PCR program included initial denaturation at 98° C. for 30 sec, followed by cycle of denaturation, annealing (60° C. for 30 sec) and extension (72° C. for 3 min), and final extension was at 72° C. for 5 min. For pure library 15 cycles of amplification were performed, for libraries during enrichment number of cycles varies between 15 and 30 depends on the recovery. Asymmetric PCR products were mixed with denaturing buffer (180 mM NaOH, 6 mM EDTA), heated at 70° C. for 10 min, cooled down on ice for 3 min, loaded ~20 µl on 4% agarose SYBRGold gel (E-GEL EX Gels, G401004, Life Technologies), separated for 15 min. Single stranded reverse strand was cut, gel pieces were combined with NTC buffer (Nucleospin, Macherey-Nagel), melted at 50° C. for 5-10 min until all pieces got molten. 700 µl of melted agarose was loaded onto Nucleospin column and then followed standard procedure for ssDNA purification. Purified DNA was eluted with 30 µl of NE buffer.

FFPE Tissue Slide-Based SELEX

Enrichment of ssODNs libraries toward Trastuzumab response was performed according to the scheme in FIG. 17C. Treatment regimens for enrichment cases can be found in Table 29-30. In the enrichment of each library, first three rounds were performed on positive cases only, followed by additional three rounds with two counter selections cases and one positive case. For positive selection, 400 µl of blocking buffer (0.8 ng/ul Salmon DNA (Life Technologies, Thermo Fisher Scientific Inc., Waltham, Mass., USA), 0.8 ng/µl tRNA (Life Technologies), 1 µg/µl HSA (Sigma), 0.5% F127 (Thermo Fisher) and 3 mM $MgCl_2$ in 1×PBS) was mixed with 90 µl of ssODN library solution (7 pmol for round 1, 3.5 pmol for following rounds in 1×PBS, 3 mM $MgCl_2$) on top of the Agilent gasket slide (Agilent Technologies, Santa Clara, Calif.). FFPE tissue slide, after deparaffinization and epitope retrieval, was mounted on top of the gasket slide containing binding cocktail and incubated for 1 hour in Agilent microarray hybridization chambers with rotation at RT. After incubation, slides were washed by dipping into 2×750 ml washing buffer (1×PBS, 3 mM $MgCl_2$) buffer, 3 dips into each jar. Next, 490 µl of nuclear fast red (NFR), supplemented with 3 mM $MgCl_2$, was added to the slide for 45 s and washed by 6 times dipping in 750 ml washing buffer. Based on the initial pathological diagnosis from corresponding H&E slides, cancer areas were dissected and transferred into 180 µl water, which served as a template for asymmetric PCR with unequal length primers to generate single stranded library for next round (see protocol above). Remaining normal tissue served for internal counter selection. This protocol was repeated for 3 rounds. For negative selection, binding cocktail was added directly to the tissue of counter selection slides and incubated for 1 hour in humidity chamber. After incubation, maximum volume of supernatant was collected. Additionally, 50 µl of blocking buffer was applied to collect the unbound ssODNs. Combined supernatant was added to the $2^{nd}$ counter selection slide and incubated for 1 hour. After incubation supernatant was collected the same way as before and applied to the slide from positive case for another hour incubation, done this time in the Agilent microarray hybridization chamber. The following steps, washing, staining and PCR, were the same as described above.

Polyligand-Histochemistry (PHC) Screening of the Enriched Libraries

Staining of FFPE tissue slides with enriched libraries was performed on Dako Autostainer. After baking slides at 60° C. for 1.5 hour, epitope retrieval was done on Dako PT-Linker at pH9, 98° C., 22 min. The staining on Dako Autostainer includes 5 min peroxidase inhibition with 450 µl of solution, containing disodium hydrogenorthophosphate 5%<=x<7%, $H_2O_2$ 3%<=x<5%, phosphoric acid, monosodium salt, monohydrate 1%<=x<2%, 1 hour incubation with 450 ul of binding cocktail (3.5 pmol of enriched library, 0.65 ng/µl Salmon DNA, 0.65 ng/µl tRNA, 10% BlockAid (Life Technologies), 30 min incubation with 450 µl of Streptavidin Poly-HRP, supplemented with 3 mM $MgCl_2$, 10 min staining with DAB solution, supplemented with 3 mM $MgCl_2$, followed by 5 min incubation with 450 µl of Hematoxylin (2 ng/µl final conc.). Rinsing with 1×PBS, 3 mM $MgCl_2$ buffer was done between each step. Finally, the stained slides were dehydrated with ethanol, xylene and covered by coverslip for long-term storage. Microscopy was done on Olympus BX41 (Olympus Corporation of the Americas, Center Valley, Pa., USA).

Histological scores for both nuclear and cytoplasmic staining were calculated as sum between intensity levels (1, 2 and 3) multiplied by the percentage of the cells with this particular intensity.

Statistical Analysis

Firstly, the ability of each single library to classify Trastuzumab responders and non-responders was assessed by ROC curves and AUCs. See, e.g., FIGS. 17J-K. To predict the patient's response to trastuzumab therapy with a multivariate method using PHC scores from both library TL-NB and TL-B staining, a logistic regression model was developed. Specifically, a binary outcome of responder/non-responder was used as the response variable, and staining scores of libraries TL-NB and TL-B were treated as independent variables (FIG. 17J (C), solid line labeled AUC=0.804). A 10-fold cross-validation was conducted to assess the generalizability of the model's prediction performance, in which the data set was randomly split into 10 equal parts exclusively. A logistic regression model was built on 9 parts, and subsequently tested on the 1 hold-out part. This process was iterated throughout the 10 parts, and only the predicted probability was collected for further assessment (FIG. 17J (C), dashed line labeled AUC=0.760).

The end points of time to next treatment (TTNT) were defined as either the time of next non-trastuzumab treatment or death. Patients without the next non-trastuzumab treatment or death information were censored at the last contact date (see vertical marks in the Kaplan-Meier curves (FIG. 17M). A Cox-PH model was fitted using either tumors' HER2 status or PHC test results as the independent variable. Median survival time was calculated from the Kaplan-Meier estimate. The Log-rank test was performed to evaluate the significance of TTNT survival between groups. All analysis was conducted using the "survival" r package.

Example 23

Alternate Oligonucleotide Probe Assay Classifies Outcomes of Breast Cancer Patients Treated with Trastuzumab-Based Therapy Background: Although trastuzumab is a highly effective targeted therapy, approximately 50% of patients with HER2+ breast cancers do not benefit from trastuzumab-based regimens. We developed a poly-ligand aptamer-based approach that outperforms traditional HER2 testing in its ability to classify patients likely to derive benefit from trastuzumab.

Methods: A library of $10^{13}$ biotinylated ssDNA oligodeoxynucleotides (ssODN) was incubated on FFPE tissue slides of patients who either benefitted (B) or did not benefit (NB) from trastuzumab-based therapies based on time to next treatment. Unbound ssODNs were discarded and bound ssODNs were retained for two subsequent rounds of positive selection. Starting at round 4, the partially enriched library was applied to cases representing the alternate phenotype (NB for B and vice versa) for negative selection and supernatant containing unbound ssODNs was collected and retained. Libraries obtained after two more rounds of negative selection were used as probes to stain and score 30 B and 15 NB independent cases by Polyligand Histochemistry (PHC). The ability of the trained libraries to classify patients who benefitted from trastuzumab-based treatment was assessed by calculating AUC values from ROC curves. Kaplan-Meier (KM) plots were used to compare outcomes with test results. [001117] Results: Two libraries effectively classified B and NB groups (ROC AUC of 0.8). In contrast, standard HER2 IHC yielded an AUC of 0.4. Median duration of trastuzumab treatment was 604 days for test-positive patients and 129 days for test-negative patients (HR=0.320, 95% CI:0.146-0.703; log-rank p=0.003), indicating that PHC scoring was highly effective for classifying distinct clinical outcomes. By HER2 status alone (IHC), median duration of trastuzumab treatment of 250 days for HER2+ cases and 369 days for HER2−/low cases (HR=1.39, 95% CI: 0.62-3.13; log-rank p=0.418).

Conclusions: These results indicate that polyligand profiling provides a high-performance systems biology approach to generating predictive assays that can be used to identify patients more or less likely to benefit from targeted therapies such as trastuzumab.

Example 24

Selection of Aptamers on FFPE Tissue from Individuals Diagnosed with Colorectal Cancer and Treated with FOLFOX and Bevacizumab Bevacizumab is a recombinant humanized monoclonal antibody that blocks angiogenesis by inhibiting vascular endothelial growth factor A (VEGF-A). VEGF-A is a chemical signal that stimulates angiogenesis in a variety of diseases, especially in cancer. Bevacizumab, sold under the trade name Avastin, was approved by the FDA in February 2004 for use in metastatic colorectal cancer (CRC) when used with standard chemotherapy treatment (as first-line treatment) and with 5-fluorouracil-based therapy for second-line metastatic colorectal cancer. FOLFOX is a chemotherapy regimen for treatment of colorectal cancer, made up of three drugs: 1) FOL—Folinic acid (leucovorin); 2) F—Fluorouracil (5-FU); and 3) OX—Oxaliplatin (Eloxatin). FOLFOX and bevacizumab may be used as first-line treatment for metastatic CRC.

Figure 18B:
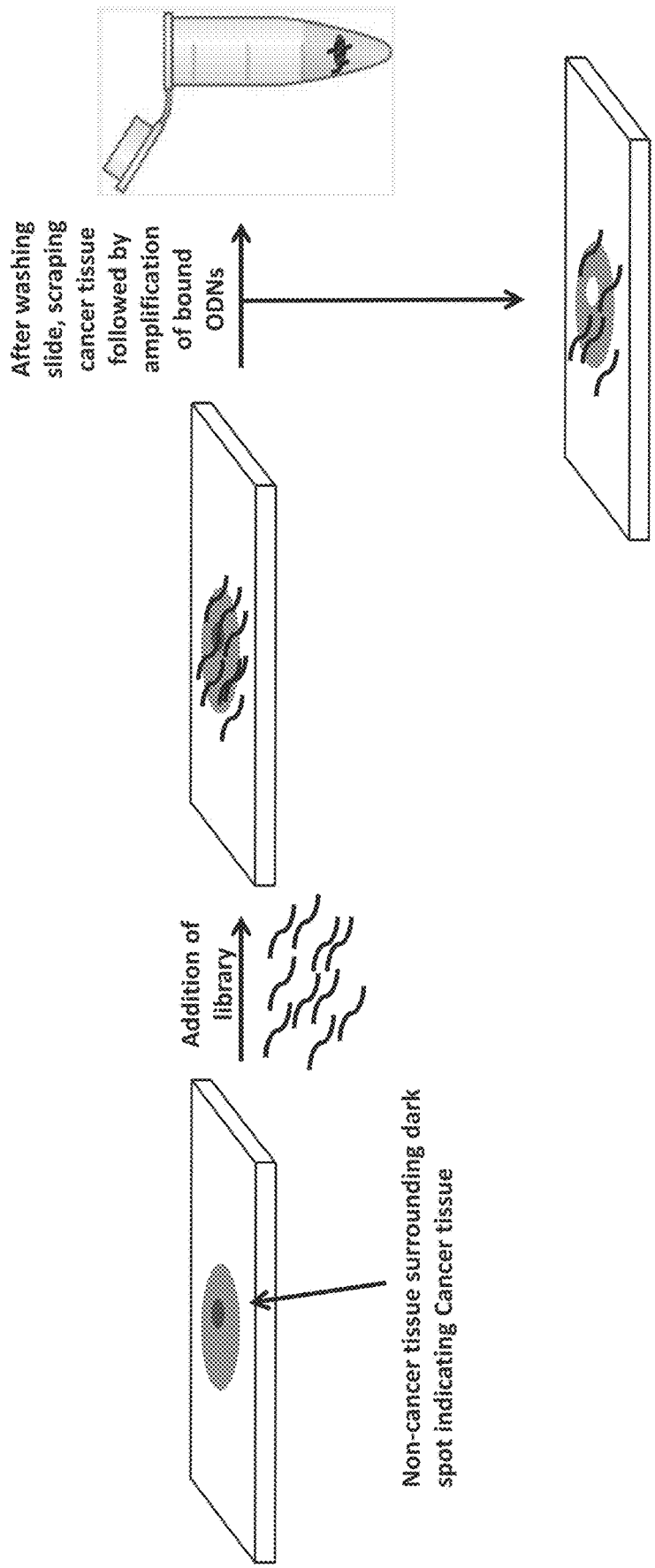
Figure 18C:
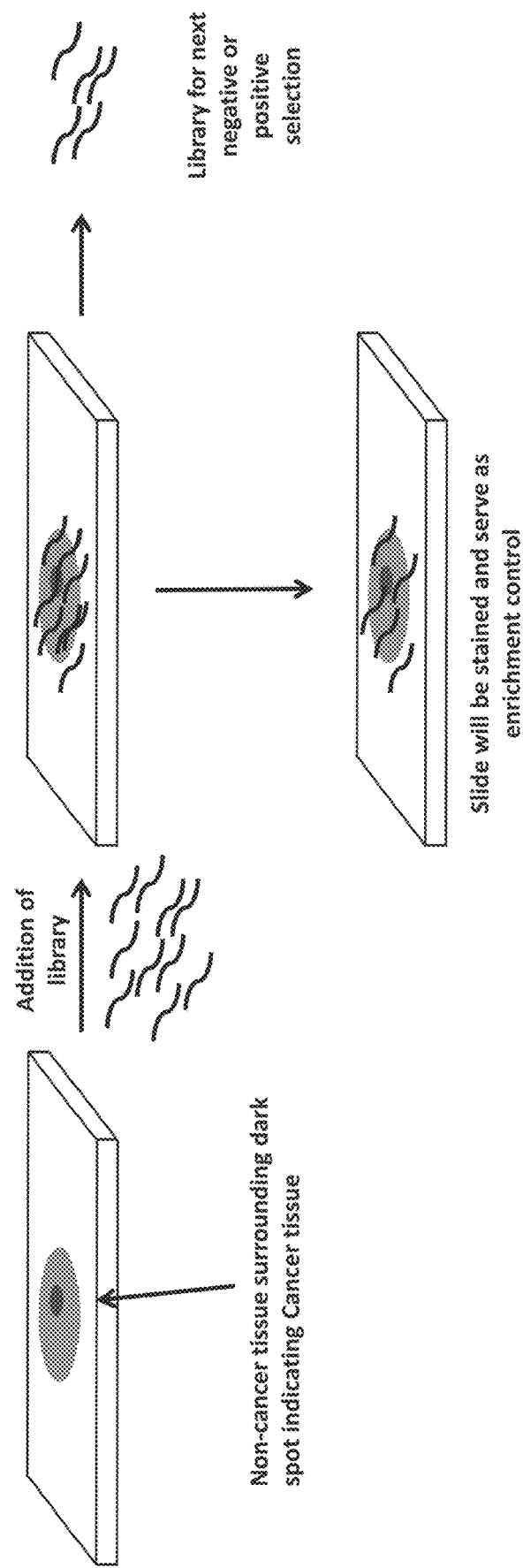

Currently, there is no good way to predict efficacy of FOLFOX with Bevacizumab as a treatment in cancer therapy. The goal of this Example was the development of oligonucleotide probe libraries that can be used in an assay that predicts the response to a combinational therapy with FOLFOX/bevacizumab in individuals diagnosed with colorectal cancer. The approach taken is similar to Examples 19-20 above. Briefly, the selection of oligonucleotide probes was performed on FFPE CRC tissue samples. Patients were divided into two cohorts based on the time they have stayed on FOLFOX (TNT; time to next treatment): responder and non-responder. A non-responder stayed on FOLFOX for a maximum of 124 days while a responder was on this treatment for at least 241 days. Bevacizumab treatment varied from patient to patient. It might have started at the same time as FOLFOX or later and ended at the same time, earlier or later than FOLFOX. An enrichment scheme is outlined in FIG. 18A with positive and negative selection steps illustrated in FIG. 18B and FIG. 18C, respectively.

Six rounds of positive selection of 7 enrichments for responder and 4 enrichments for non-responders were performed, creating 11 pools of enriched oligonucleotide probes. Counter selection was performed for responder cases on the non-responder samples and vice versa. An exemplary set of slides is shown in FIGS. 18D-E, which shows staining of an FFPE sample used for positive selection in enrichment "M" stained with H&E (FIG. 18D) or the probe library M (FIG. 18E). The figure shows staining for cancer tissue; tumor site: colon; specimen: colon. The slides are shown at 20× magnification. Table 37 shows results of staining intensity of the indicated tissue samples with the indicated probe library.

TABLE 37

| Enriched oligonucleotide probes | | | | |
|---|---|---|---|---|
| | Enriched Probe Library | Specimen used for positive selection | Cancer | Non-Cancer |
| Non-responder | A | Rectum | ++ | − |
| | C | Colon | +++ | No data |
| | E | | +++ | No data |
| | F | | ++ | + |
| Responder | G | | ++ | ++ |
| | H | | ++ | − |
| | I | | +++ | +++ |
| | J | | +++ | + |
| | K | | ++ | ++ |
| | L | | ++ | + |
| | M | | +++ | + |

Figure 18F:
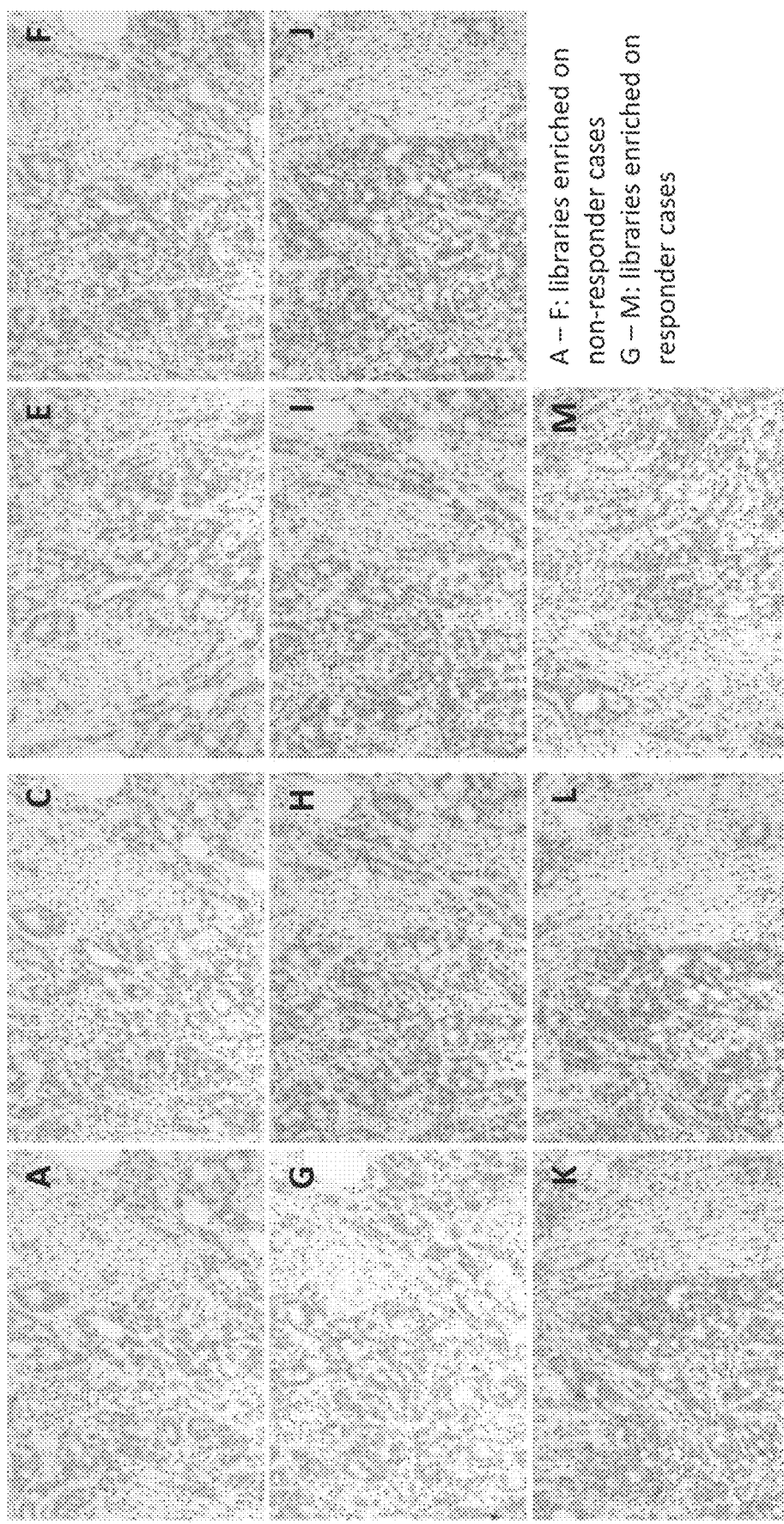
Figure 18G:
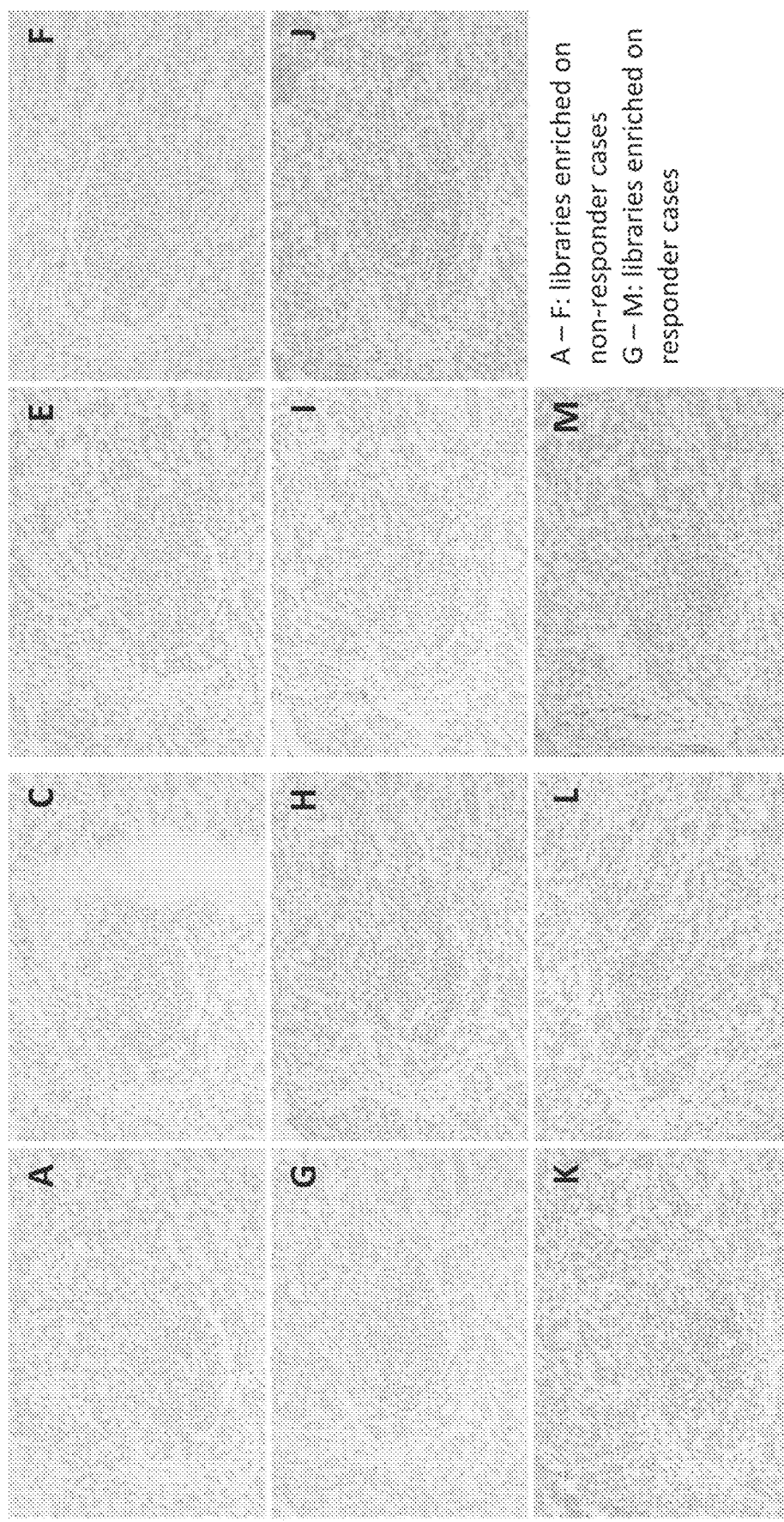

To test the enriched libraries, one non-responder case and 5 responder cases that were not part of the enrichment were stained with all 11 libraries. In addition, the cases used for positive selection were stained with the corresponding libraries. Exemplary results for staining of one test sample, Sample 2, are shown in FIGS. 18F-G. The sample characteristics include: Responder; tumor site: descending colon; specimen: descending colon. FIG. 18F shows staining of a cancer sample from the Sample 2 slide. The library (A-M) are indicated over each slide in the figure. As shown, slightly darker staining was observed in slides H-M as compared to the others. FIG. 18G shows staining of non-cancer tissue from the Sample 2 slide. In this setting, staining was lighter and of similar intensity across all samples.

Another set of enrichment experiments was performed on a fixed sample comprising tumor tissue from an individual considered to be a responder to bevacizumab. For positive selection, the oligonucleotide probe library was binding to the entire tissue on the slide but only the cancer tissue was scraped off the slide, then the library was recovered from the scraped tissue and amplified. After three such rounds, three rounds of two steps of negative selection (tissue from two individuals not responding to Avastin) and one positive selection as before were performed. Round 7 included one more positive selection. For round 8, the enrichment strategy was altered. Instead of doing enrichment of tissue fixed to slides, the cancer tissue and the non-cancer tissue were scraped and separated in different tubes. To perform enrichments in tubes, we used centrifugation at 100,000×g to separate the tissue from unbound library. Four rounds of enrichment on scraped cancer tissue with counter selection on scraped non-cancer tissue were performed. The library after 12 rounds was used for probing and selection of aptamer that bound stronger to cancer relative to non-cancer tissue. Four sequences recovered from the enrichment are shown in Table 38. The table indicates the variable region of the identified sequences along with the full length sequence with 5' region CTAGCATGACTGCAGTACGT (SEQ ID NO 4) and a 3' region CTGTCTCTTATACACATCTGACGCTGCCGACGA (SEQ ID NO 5) surrounding the variable region. These sequences can be used to identify, e.g., by staining, cancer tissue from a responder to bevacizumab. In the table, the sequences with name comprising "RC" are the reverse complement sequences used as non-binding controls.

TABLE 38

Oligonucleotide probes that bind bevacizumab responder cancer tissue

| Variable Region (5'->3') | SEQ ID NO | Seq name | Full sequence (5'->3') | SEQ ID NO |
|---|---|---|---|---|
| GCTTCCCGC AACCGTCCT ACCCATCCT ACGCCTCC | 203064 | 5825D-R12c-S1-5'biotin | /5Biosg/CTAGCATGACTGCAGTACGTGC TTCCCGCAACCGTCCTACCCATCCTACGCC TCCCTGTCTCTTATACACATCTGACGCTGC CGACGA | 203068 |
|  |  | 5825D-R12c-S1RC-5'biotin | /5Biosg/TCGTCGGCAGCGTCAGATGTGT ATAAGAGACAGGGAGGCGTAGGATGGGTAG GACGGTTGCGGGAAGCACGTACTGCAGTCA TGCTAG | 203069 |
| TGGTCACCG CTTCCGCTG GTACGCCCC ACCCCATAA | 203065 | 5825D-R12c-S2-5'biotin | /5Biosg/CTAGCATGACTGCAGTACGTTG GTCACCGCTTCCGCTGGTACGCCCCACCCC ATAACTGTCTCTTATACACATCTGACGCTG CCGACGA | 203070 |
|  |  | 5825D-R12c-S2RC-5'biotin | /5Biosg/TCGTCGGCAGCGTCAGATGTGT ATAAGAGACAGTTATGGGGTGGGGCGTACC AGCGGAAGCGGTGACCAACGTACTGCAGTC ATGCTAG | 203071 |
| ACCTAGCTG CTCCCTACT CCCTTCTTA TGTACATTA | 203066 | 5825D-R12c-S3-5'biotin | /5Biosg/CTAGCATGACTGCAGTACGTAC CTAGCTGCTCCCTACTCCCTTCTTATGTAC ATTACTGTCTCTTATACACATCTGACGCTG CCGACGA | 203072 |
|  |  | 5825D-R12c-S3RC-5'biotin | /5Biosg/TCGTCGGCAGCGTCAGATGTGT ATAAGAGACAGTAATGTACATAAGAAGGGA GTAGGGAGCAGCTAGGTACGTACTGCAGTC ATGCTAG | 203073 |
| TTCATGCTG TTCCATGAC CTCCACATT TCTCACGCT GA | 203067 | 5825D-R12c-S4-5'biotin | /5Biosg/CTAGCATGACTGCAGTACGTTT CATGCTGTTCCATGACCTCCACATTTCTCA CGCTGACTGTCTCTTATACACATCTGACGC TGCCGACGA | 203074 |
|  |  | 5825D-R12c-S4RC-5'biotin | /5Biosg/TCGTCGGCAGCGTCAGATGTGT ATAAGAGACAGTCAGCGTGAGAAATGTGGA GGTCATGGAACAGCATGAAACGTACTGCAG TCATGCTAG | 203075 |

Additional sequences were determined after round 9 above. Tissue from responder cancer (i.e., cancer tissue from responder patients), responder non-cancer (i.e., non-cancer tissue from responder patients), non-responder cancer (i.e., cancer tissue from non-responder patients) and non-responder non-cancer (i.e., non-cancer tissue from non-responder patients) were scraped and bound oligonucleotides were sequenced. The fold changes between the non-responder cancer and other tissues were calculated after normalization of read counts from the sequencing to the tissue sizes. Table 39 shows fold changes for the non-responder cancer over the other three tissue types as indicated. The table indicates the variable region of the identified sequences. The full length sequences comprised 5' region CTAGCATGACTGCAGTACGT (SEQ ID NO 4) and a 3' region CTGTCTCTTATACACATCTGACGCTGCCGACGA (SEQ ID NO 5) surrounding the variable region. Any appropriate flanking sequences can be used. In Table 40, the complete sequences for the first six variable regions in Table 39 along with the complete sequences with flanking regions. These sequences can be used to identify, e.g., by staining, cancer tissue from a responder to bevacizumab. The variables regions of additional sequences with fold changes of at least 100% in one comparison are listed in SEQ ID NOs. 203114-206478. In Table 40, the sequences with name comprising "RC" are the reverse complement sequences and can be used as non-binding controls. The sequences in Table 40 are further shown labeled with digoxigenin (DIG). Anti-digoxigenin antibodies with high affinities and specificity can be used in a variety of biological immuno-assays, e.g., to visualize the oligonucleotide staining as described herein. Both biotin and digoxigenin labeling can be used in such applications, in addition to any other such useful labeling systems. Any desired number or combination of the sequences in Table 39 can be used to create oligonucleotide probes such as in Table 40.

TABLE 39

Sequences with fold-change differences between bevacizumab non-responders and responders

| Variable Sequence 5'->3' | SEQ ID NO | Sample Type/Fold changes | | |
|---|---|---|---|---|
| | | Responder, Cancer | Non-responder, non-cancer | Responder, non-cancer |
| ATATGCGATGCTAGCTCGAAGCGTGTGCAGTCCCT | 203076 | 2 | 4 | 2 |
| GTCCAGCTCGCAATTACACTAGTTTGCCAGTAAAAG | 203077 | 3 | 4 | 3 |
| TCCGGAGTCCATAAGACTACGGATAGCTTTGACCG | 203078 | 3 | 3 | 9 |
| CATGCACATCGCGTTTCGGAAACAAAAGTGTAGATA | 203079 | 2 | 3 | 4 |
| CCACACGACGTGTGACCTCGGATTCCTCATACACT | 203080 | 2 | 3 | 3 |
| ACTGGGTACTTGAATCATTGTCGCATTTCCCTATT | 203081 | 4 | 3 | 11 |
| CGTAGTTAAGACGCCTCAAGACACATACGGCTTGAA | 203082 | 0 | 49 | 0 |
| TCATGACCGAGTAACGACCGACCCACATATCCGC | 203083 | 1 | 37 | 2 |
| GTTGGCTCCCTCTAGCATATCCCCACTAGCTGG | 203084 | 1 | 26 | 1 |
| CGCCCACTCTTGTTGTTACCGTGCTGTCCTCGGTC | 203085 | 1 | 22 | 1 |
| GCATGTGTGGTTTCCCCAGCGCACTCGAGACGACT | 203086 | 0 | 22 | 1 |
| GAAAAGTCAGACTTTTGAAGGATTGTGCTGGAACT | 203087 | 1 | 20 | 1 |
| GAACATGAAGCATCGAAAGCACTTCACGTAGATTCGA | 203088 | 1 | 17 | 0 |
| TTGTGGATTCAAGCGGTCACCACTATGCCAACTTCCA | 203089 | 1 | 14 | 1 |
| CCACCTTTTCCACCCATTCCAGGATAGTCGCCCACGA | 203090 | 0 | 13 | 0 |
| GTTCGGATGCCCACAGCCCGTTAAGGTATTTTCACGA | 203091 | 0 | 11 | 0 |
| TTGTGGGGACGTATGAGCAGATCCATGCGCGCCA | 203092 | 0 | 9 | 1 |
| AGATCTCCGGTACGCCACCGGCGATACCGATTCAG | 203093 | 1 | 9 | 1 |
| GTAACCCGATTTTCACGGCCGACCGCATACGCGCC | 203094 | 0 | 8 | 1 |
| GCTAGACACTTACAGTGACGTTACTGTCTTGAGCT | 203095 | 0 | 8 | 1 |
| GGACATTCAGGTGTCGCTCATCCAAAGCTACGTGC | 203096 | 1 | 7 | 6 |
| GTTATCGCACTGAAAAGTAATTCCTTGTATACTCT | 203097 | 1 | 7 | 1 |
| GCAAAGGATCCTGGTTGGGCACTTTGTTCCTTTCC | 203098 | 0 | 7 | 0 |
| ACCCACTAGGAGGTCGTTAAAGGATAGTTGTAAACTCA | 203099 | 2 | 7 | 2 |
| TCTTGCCTCTGTATGAGCGAGAACTTCTCGCGCGTTCA | 203100 | 1 | 7 | 1 |
| GTCAGTCCCTGGAGTCCATGTGCTTTACCGCCGTC | 203101 | 0 | 7 | 0 |
| GAAAGACAACACGTATACATCCCTGAGCCACCCACGA | 203102 | 0 | 6 | 0 |
| CCATTGCTCTTACACCGCCTGTCCTTACGGTTGTGGA | 203103 | 1 | 6 | 4 |
| TGTTTGCCGATCTCTCATCTGGAGGAACGGGGCA | 203104 | 0 | 6 | 1 |
| GTAGTATGTTCTCTTTACTGCGACATGAGTTTCGGTCA | 203105 | 1 | 6 | 1 |
| CGTCACGACACCTACACAAAGCCGCACTCCCTCTGGA | 203106 | 1 | 6 | 1 |
| GTATGGTTAACACCAATTACCGGATCCGTAGATTCA | 203107 | 0 | 6 | 0 |
| AACAATACCACAGTGGATGCTACCAGTCCCATTAT | 203108 | 1 | 6 | 1 |
| GACCCGTTTTGTCGTTGTATTGATATGGTACGTCTTGA | 203109 | 1 | 6 | 1 |
| AAATCGCGACCGGGACAGTGCCGATATTTTTCACG | 203110 | 0 | 6 | 1 |
| CTATCCGATGCTACCACTGTTTGAAATCAACAGCC | 203111 | 1 | 6 | 0 |

TABLE 39-continued

Sequences with fold-change differences between bevacizumab non-responders and responders

| Variable Sequence 5'->3' | SEQ ID NO | Sample Type/Fold changes | | |
|---|---|---|---|---|
| | | Responder, Cancer | Non-responder, non-cancer | Responder, non-cancer |
| CTTCATTCGGTTCGGCCGTTCGAACACACTTGTCCCA | 203112 | 1 | 6 | 1 |
| GCTAATGCTCGGTGAGGATCGAGCTCCGGTGCCTC | 203113 | 1 | 6 | 1 |

TABLE 40

Oligonucleotide probes that bind bevacizumab responder cancer tissue

| Variable Region SEQ ID NO | Seq name | Full sequence (5'->3') | SEQ ID NO |
|---|---|---|---|
| 203076 | 5825C-R9-S1-5'DIG | /5DIG/CTAGCATGACTGCAGTACGTATATGCGATGCT AGCTCGAAGCGTGTGCAGTCCCTCTGTCTCTTATACAC ATCTGACGCTGCCGACGA | 206479 |
| | 5825C-R9-S1-RC-5'DIG | /5DIG/TCGTCGGCAGCGTCAGATGTGTATAAGAGACA GAATAGGGAAATGCGACAATGATTCAAGTACCCAGTAC GTACTGCAGTCATGCTAG | 206480 |
| 203077 | 5825C-R9-S2-5'DIG | /5DIG/CTAGCATGACTGCAGTACGTGTCCAGCTCGCA ATTACACTAGTTTGCCAGTAAAAGCTGTCTCTTATACA CATCTGACGCTGCCGACGA | 206481 |
| | 5825C-R9-S2-RC-5'DIG | /5DIG/TCGTCGGCAGCGTCAGATGTGTATAAGAGACA GAGGGACTGCACACGCTTCGAGCTAGCATCGCATATAC GTACTGCAGTCATGCTAG | 206482 |
| 203078 | 5825C-R9-S3-5'DIG | /5DIG/CTAGCATGACTGCAGTACGTTCCGGAGTCCAT AAGACTACGGATAGCTTTGACCGCTGTCTCTTATACAC ATCTGACGCTGCCGACGA | 206483 |
| | 5825C-R9-S3-RC-5'DIG | /5DIG/TCGTCGGCAGCGTCAGATGTGTATAAGAGACA GTATCTACACTTTTGTTTCCGAAACGCGATGTGCATGA CGTACTGCAGTCATGCTAG | 206484 |
| 203079 | 5825C-R9-S4-5'DIG | /5DIG/CTAGCATGACTGCAGTACGTCATGCACATCGC GTTTCGGAAACAAAAGTGTAGATACTGTCTCTTATACA CATCTGACGCTGCCGACGA | 206485 |
| | 5825C-R9-S4-RC-5'DIG | /5DIG/TCGTCGGCAGCGTCAGATGTGTATAAGAGACA GAGTGTATGAGGAATCCGAGGTCACACGTCGTGTGGAC GTACTGCAGTCATGCTAG | 206486 |
| 203080 | 5825C-R9-S5-5'DIG | /5DIG/CTAGCATGACTGCAGTACGTCCACACGACGTG TGACCTCGGATTCCTCATACACTCTGTCTCTTATACAC ATCTGACGCTGCCGACGA | 206487 |
| | 5825C-R9-S5-RC-5'DIG | /5DIG/TCGTCGGCAGCGTCAGATGTGTATAAGAGACA GCTTTTACTGGCAAACTAGTGTAATTGCGAGCTGGACA CGTACTGCAGTCATGCTAG | 206488 |
| 203081 | 5825C-R9-S6-5'DIG | /5DIG/CTAGCATGACTGCAGTACGTACTGGGTACTTG AATCATTGTCGCATTTCCCTATTCTGTCTCTTATACAC ATCTGACGCTGCCGACGA | 206489 |
| | 5825C-R9-S6-RC-5'DIG | /5DIG/TCGTCGGCAGCGTCAGATGTGTATAAGAGACA GCGGTCAAAGCTATCCGTAGTCTTATGGACTCCGGAAC GTACTGCAGTCATGCTAG | 206490 |

Example 25

Background Optimization and Automation

In this Example, we optimized fixed tissue staining with oligonucleotide probe libraries as in the experiments described in the Examples above. For example, such optimization was performed to reduce non-specific background staining with enriched oligonucleotide probe libraries when using polyligand histochemistry (PHC). Certain conditions were found to address non-specific background staining. Certain changes in the staining protocols are shown in Table 41. The "New" and "New+" improved protocols were optimized and automated using the Ventana Discovery platform. In the table, BA refers to BlockAid Blocking Solution (Thermo Fisher Scientific), and PBS refers to phosphate buffered saline. As seen from the table, the blocking conditions are more stringent in the New and New+ protocols.

TABLE 41

Background optimization conditions

| | Original Protocol | New Protocol | New+ Protocol |
|---|---|---|---|
| Permeabilization | No | Yes (0.1% Triton-100 for 10 mins) | Yes (0.1% Triton-100 for 10 mins) |
| Deparaffinization | 69° C. for 32 mins | 69° C. for 32 mins | 69° C. for 32 mins |
| Antigen Retrieval | 95° C. for 32 mins | 95° C. for 32 mins | 95° C. for 32 mins |
| Library cocktail | 10% BA (no Triton) | 25% BA (0.01% Triton) | 25% BA (0.01% Triton) |
| Rinses | 1 rinse | 4 rinses | 4 rinses |
| Str-HRP + MgCl$_2$ | In PBS | In PBS | In 25% BA |

The complete protocol is as follows. Examples of staining various tissues will follow. Reagents are shown in Table 42. The equipment is a Ventana Discovery Autostainer.

TABLE 42

Raw Materials

| Reagent | Vendor | cat # |
|---|---|---|
| Salmon DNA | Life Tech | 15632-011 |
| tRNA | Life Tech | AM7119 |
| BlockAid | Life Tech | B10710 |
| Streptavidin Poly-HRP | Life Tech | 21140 |
| MgCl2 | Affymetrix | 78641 |
| Hyclone PBS | V.W.R. International | SH30256.01 |
| Sigma PBS Packet | Sigma-Aldrich | P3813 |
| H2O | Sigma-Aldrich | W4502 |
| Molecular Grade Water | Life Tech | 10977-015 |
| DAB Buffer | Dako | SM803 |

Reagent Preparation

Step 1: Permeabilization of all slides immediately prior to epitope retrieval. Completely immerse slides in 0.1% Triton X 100 in 1×PBS, incubate for 10 mins at room temperature (RT).

Step 2: Wash the slide by dipping 10× in 750 mL 1×PBS (1Liter copling jar).

Step 3: Prepare Competitor/Block/Aptamer Library cocktail. In Table 43, the SA-poly HRP cocktail is shown. SA-poly HRP refers to Streptavidin Poly-HRP conjugate, which is biotin-binding protein conjugated with polymers of horseradish peroxidase that enables signal amplification and detection of biotinylated binding agents (e.g., antibodies or aptamers) for IHC and other methods.

TABLE 43

SA-poly HRP cocktail

| Reagent | Stock Concentration | Cocktail Concentration | Volume from stock, ul | Final Concentration |
|---|---|---|---|---|
| H2O | — | — | 0.00 | |
| SA-poly HRP, x | 250 | 4 | 384.0 | 1.00 |
| PBS, x | 20 | 4 | 4800.0 | 1.00 |
| MgCl2, mM | 1000 | 12 | 288.0 | 3.00 |
| BlockAid, % | 100 | 77.2 | 18528.0 | 19.30 |

The biotinylated oligonucleotide probe library is mixed with MgCl$_2$ prior to addition to the Competitor/Block master mix shown in Table 44:

TABLE 44

Block/Aptamer master mix

| Reagent | Stock Concentration | Intermediate stock (in H20) | Cocktail Concentration | Volume of stock to make cocktail, ul | Final Concentration |
|---|---|---|---|---|---|
| H$_2$O | | | | 72.5 | |
| Triton, % | 100 | 1 | 0.03 | 14.2 | 0.01 |
| Salmon DNA, ng/ul | — | 300 | 1.96 | 3.1 | 0.65 |
| tRNA, ng/µl | — | 300 | 1.96 | 3.1 | 0.65 |
| BlockAid, % | 100 | — | 75.00 | 354.4 | 25.00 |
| MgCl$_2$, mM | 1000 | — | 9.00 | 4.3 | 3.00 |
| PBS, x | 20 | — | 0.00 | 0.0 | 0.00 |
| Oligo library ng/µl | 15 | — | 0.67 | 21.0 | 0.22 |

Staining

Step 4: Aptohistochemistry on Ventana Discovery autostainer

Deparaffinization and Epitope Retrieval

All Slides: Apply corresponding block/aptamer solution 150 µl (Table 44), incubate for 1 h@RT (300 µl of Running buffer will be added automatically)

All Slides: Apply 100 µl of SA-HRP+MgCl$_2$+19% BA SA-poly HRP cocktail (Table 43)

Apply DAB buffer

Apply Hematoxylin

Post Staining

Step 5: Pour off liquid coverslip and use paper towel to wick off residual oil from edge of glass.

Step 6: Standard coverslipping.

Step 7: Score slide staining.

Tissue staining

Figure 19A:
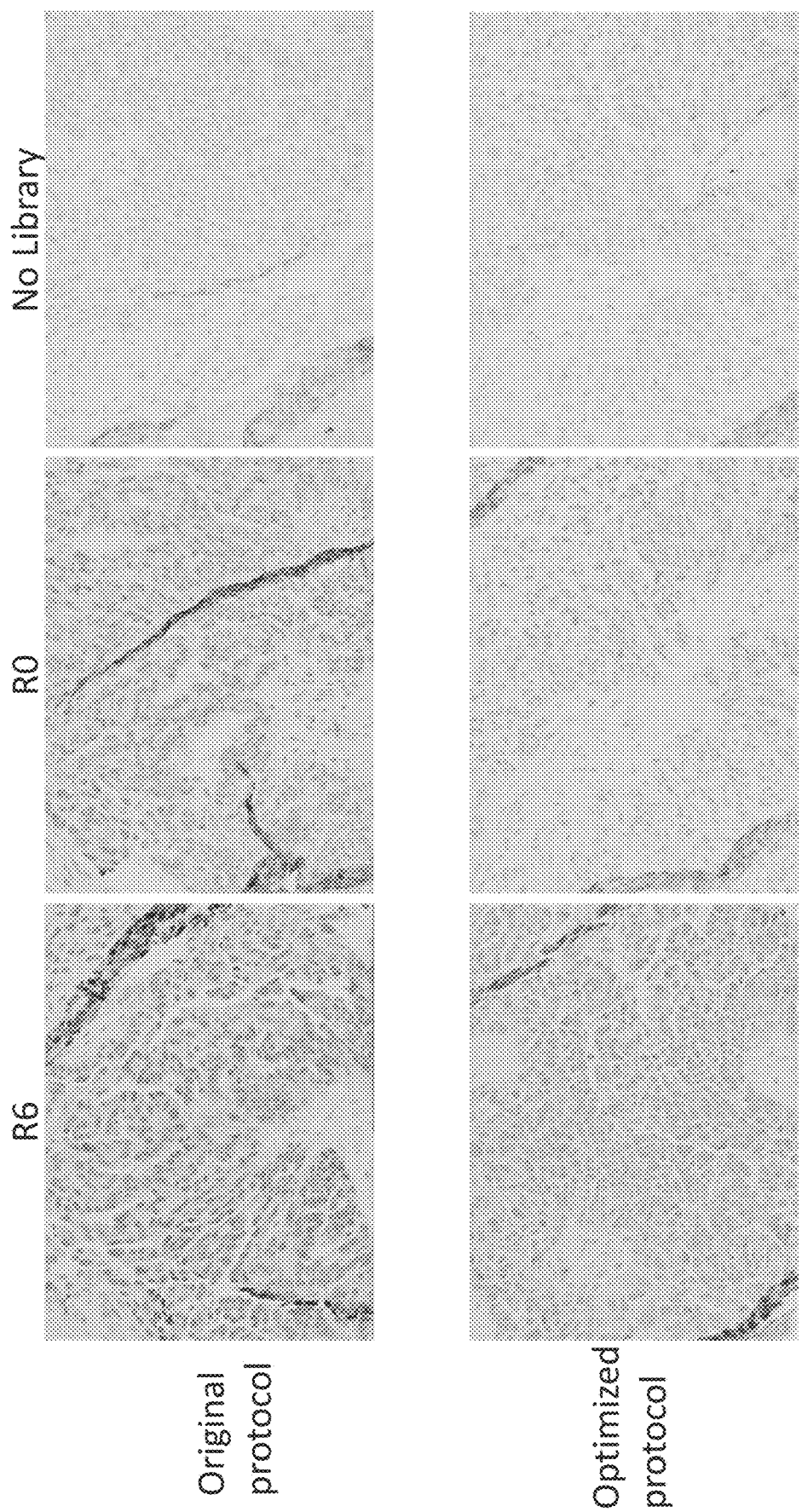
FIGS. 19A-K show background optimization of oligonucleotide probe staining of fixed tissue samples.
Figure 19B:
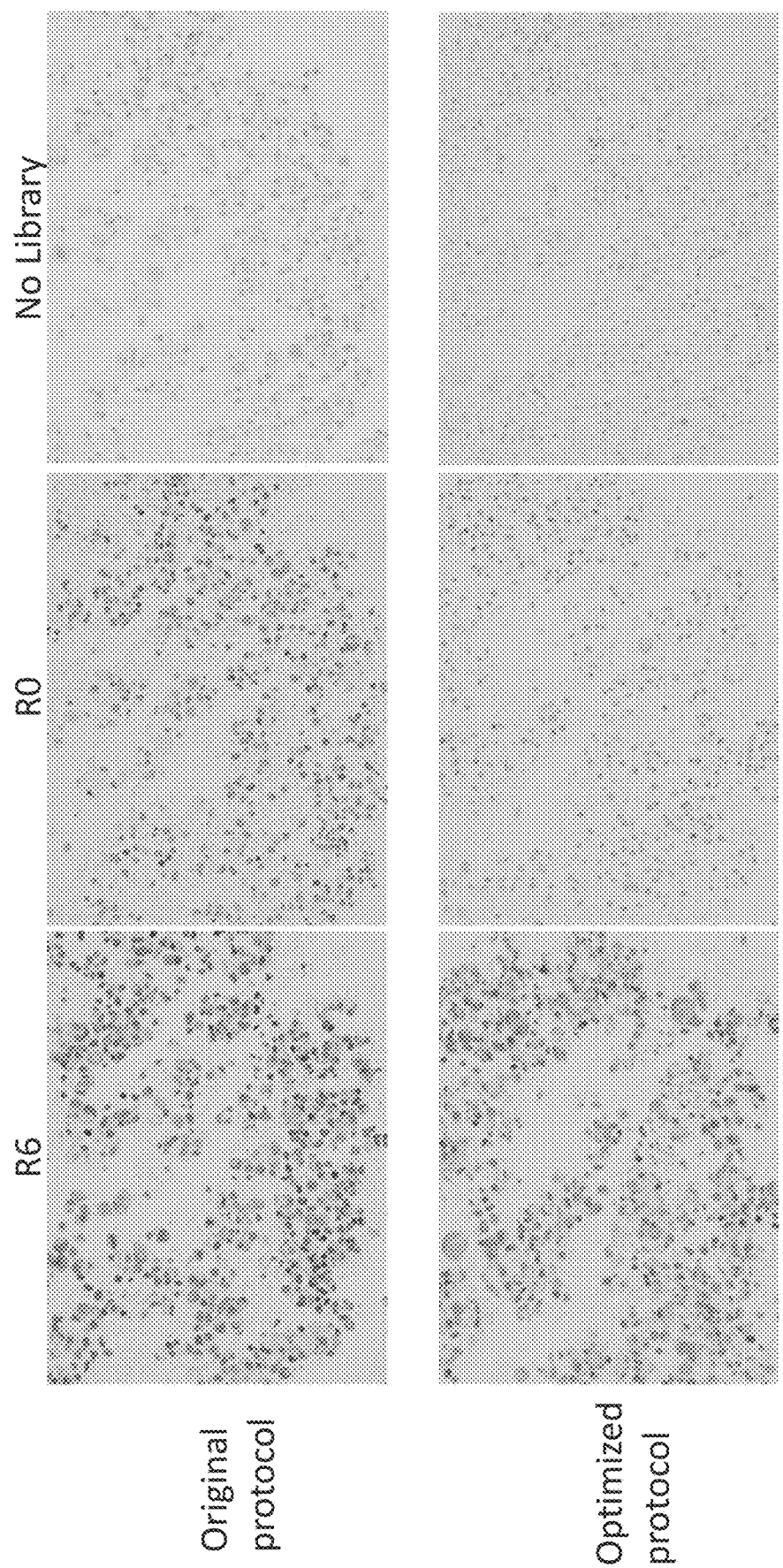
Figure 19C:
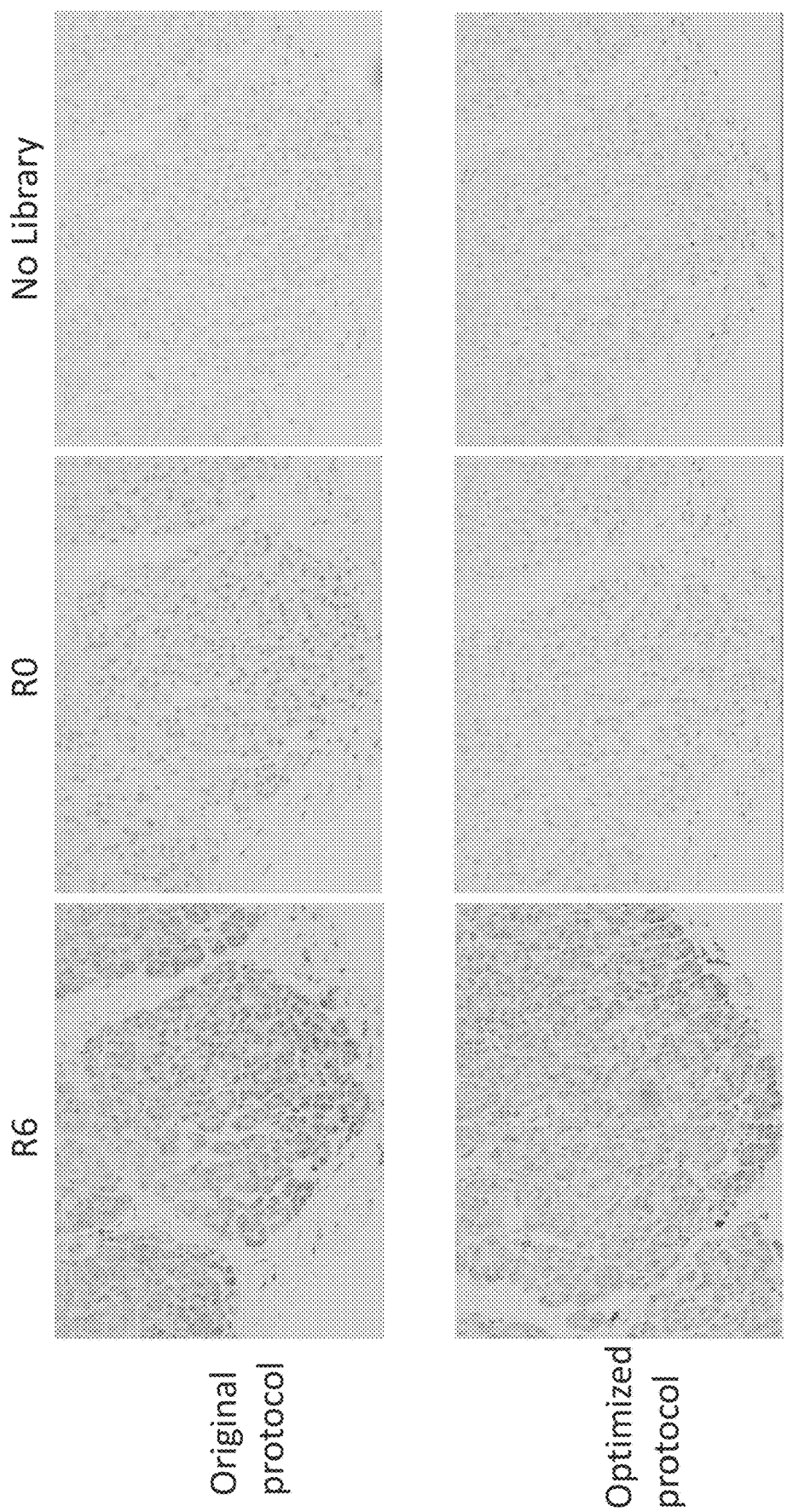
Figure 19D:
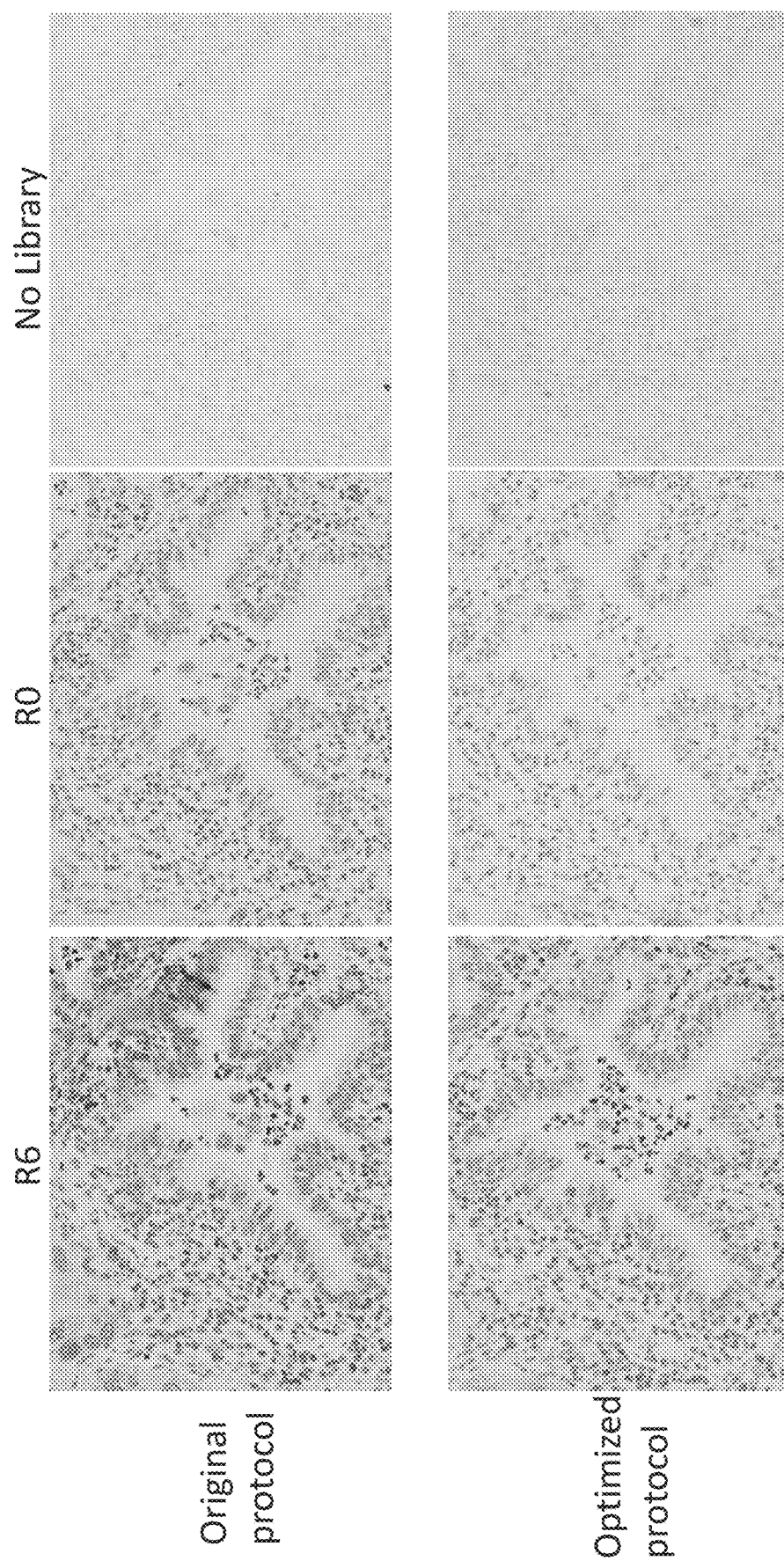
Figure 19E:
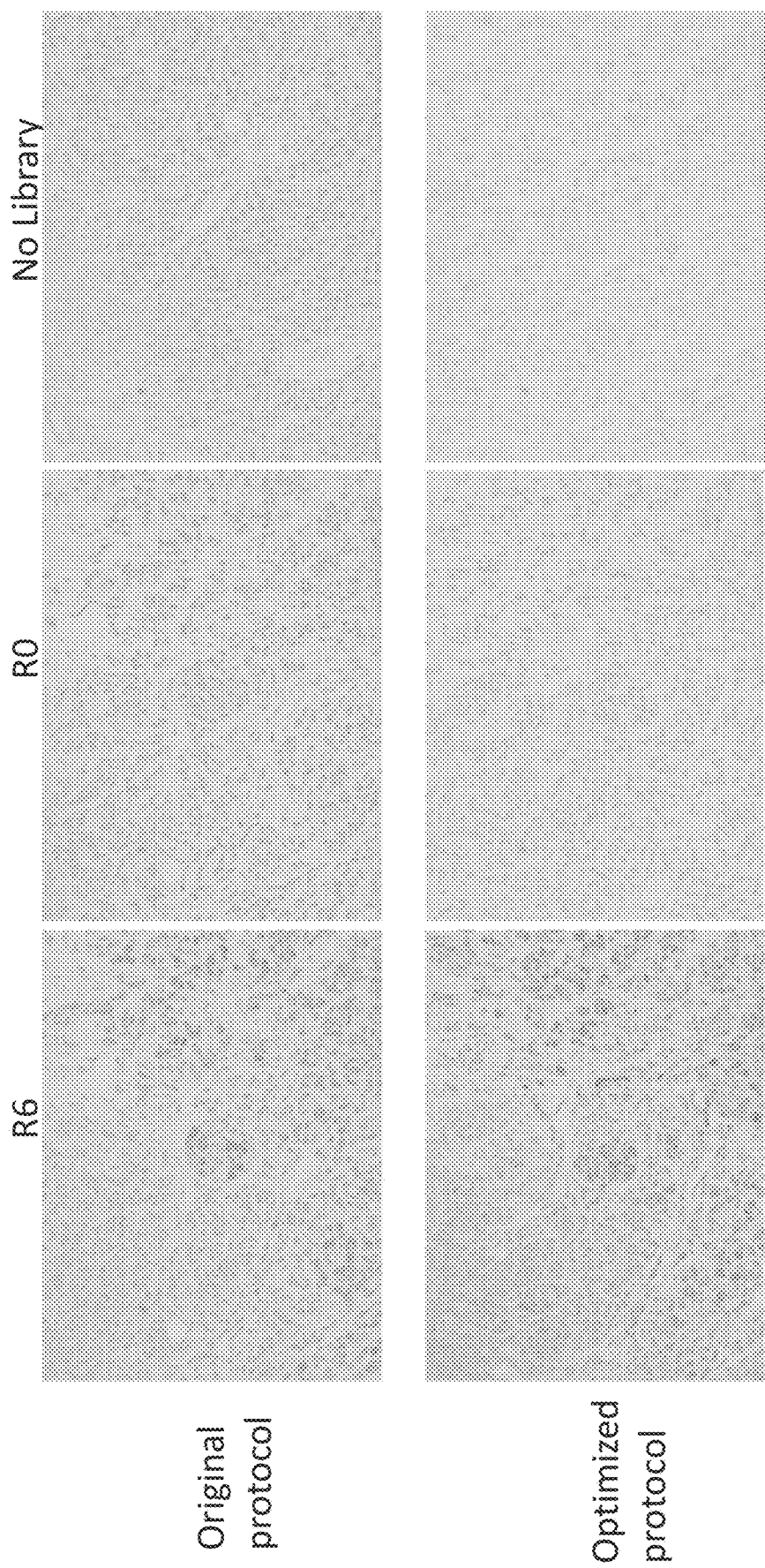
Figure 19F:
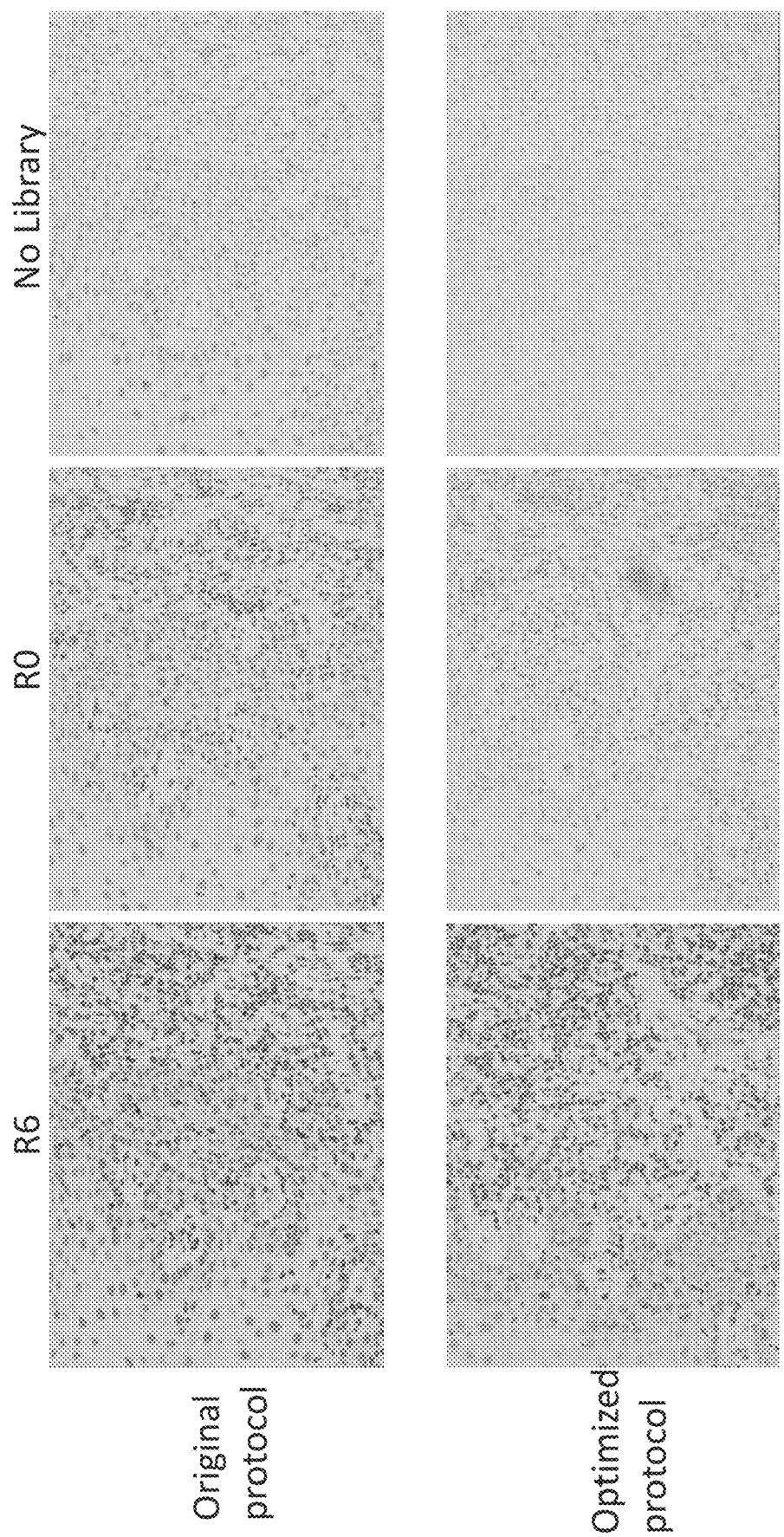
Figure 19G:
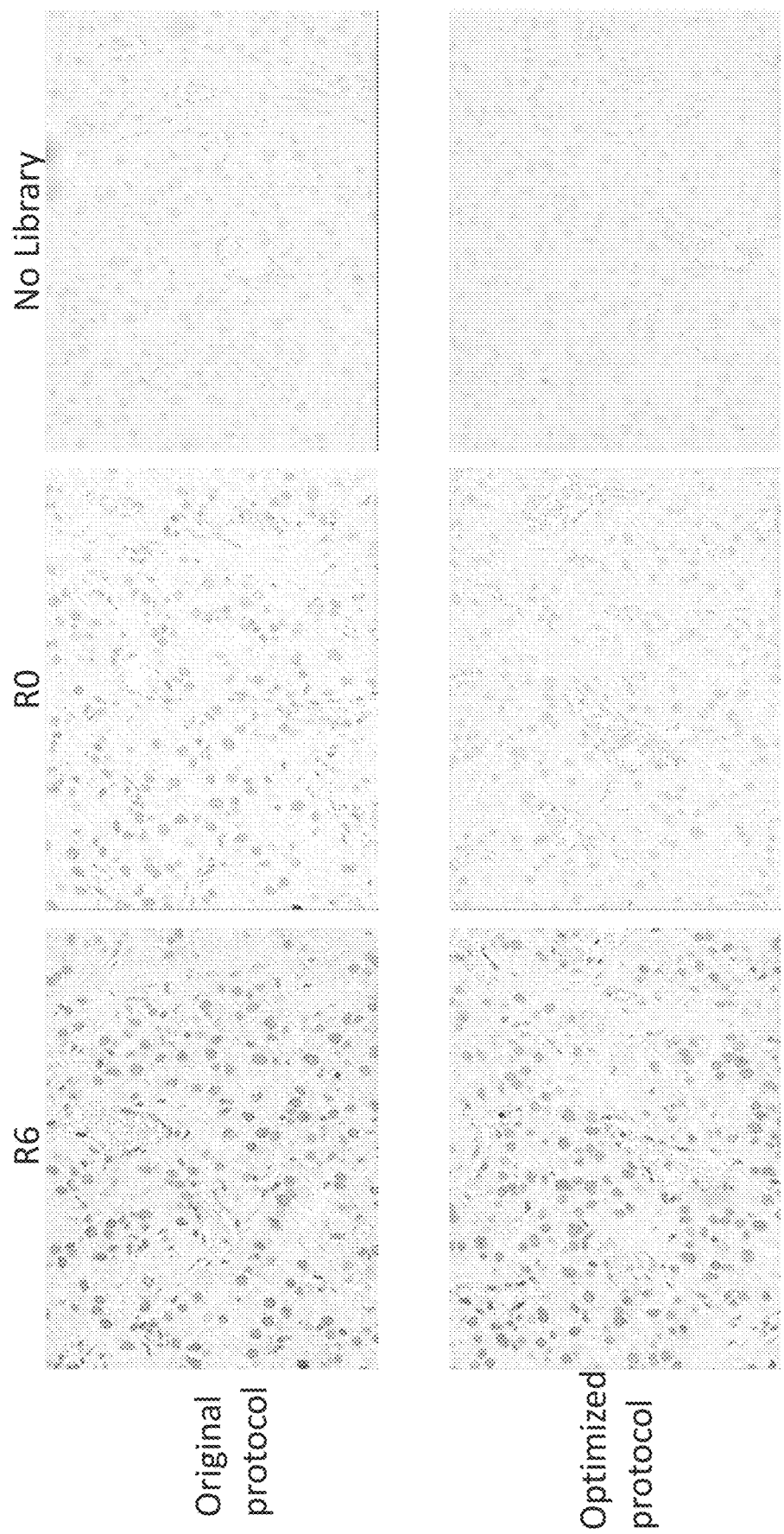
Figure 19H:
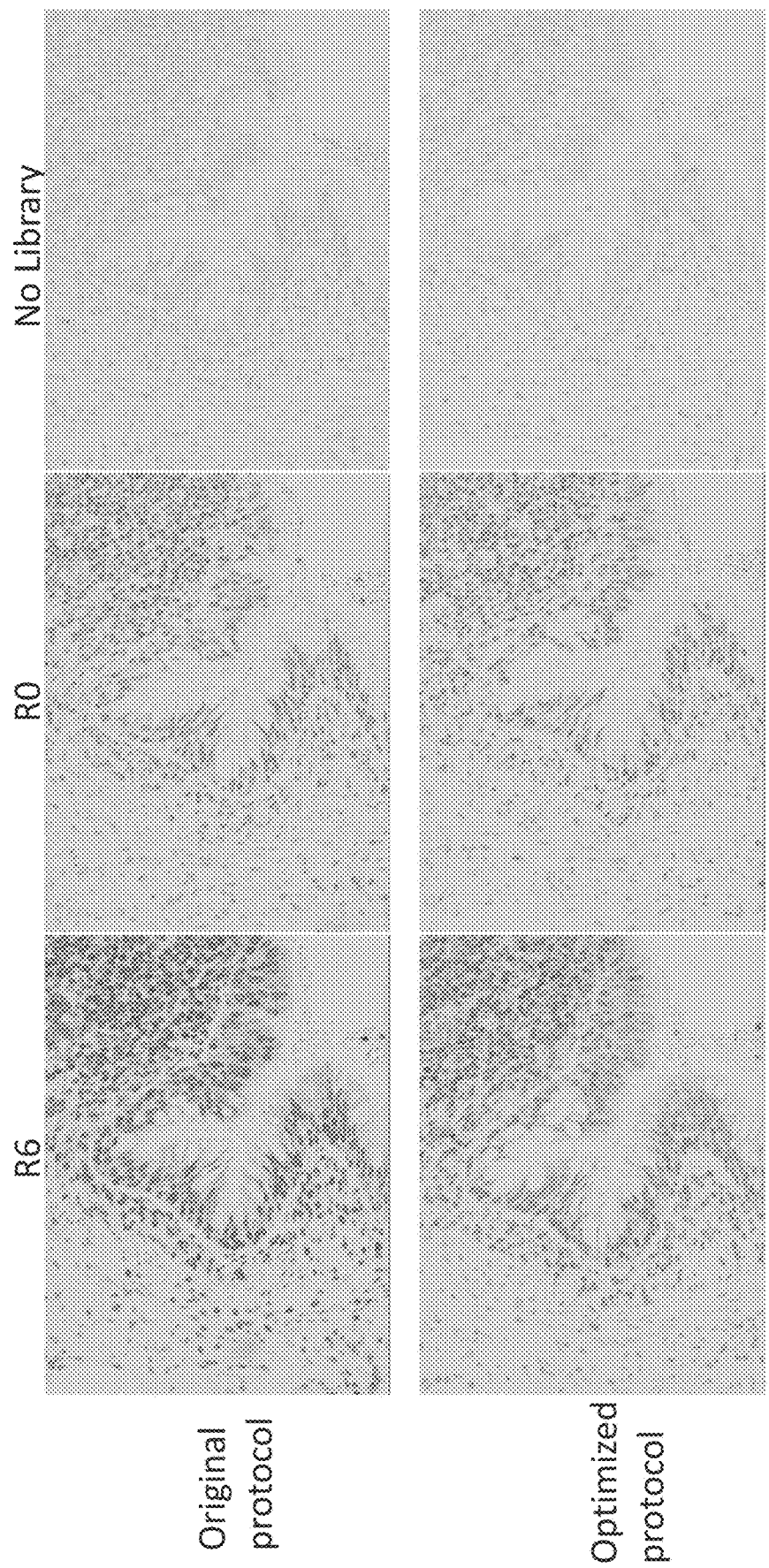
Figure 19I:
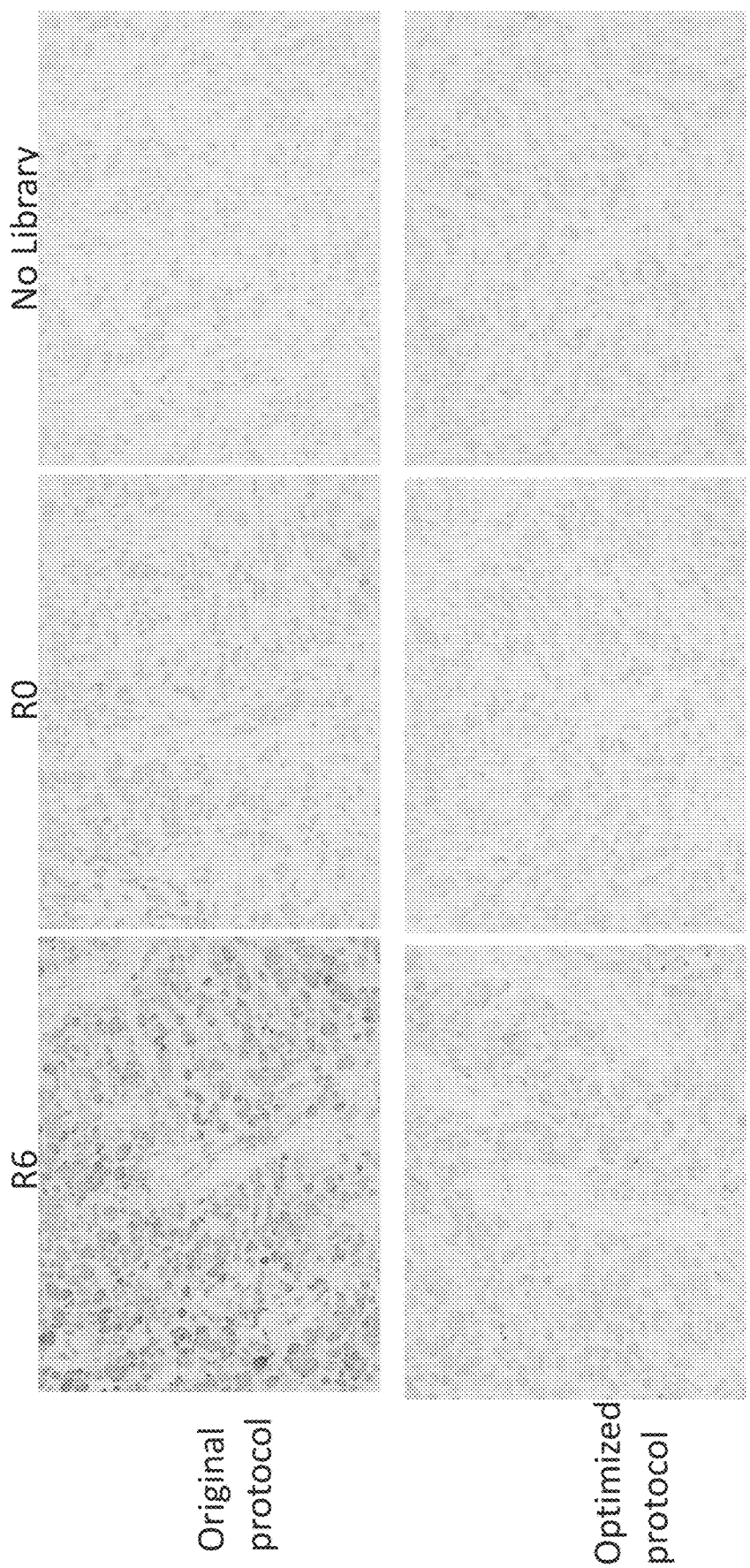
Figure 19J:
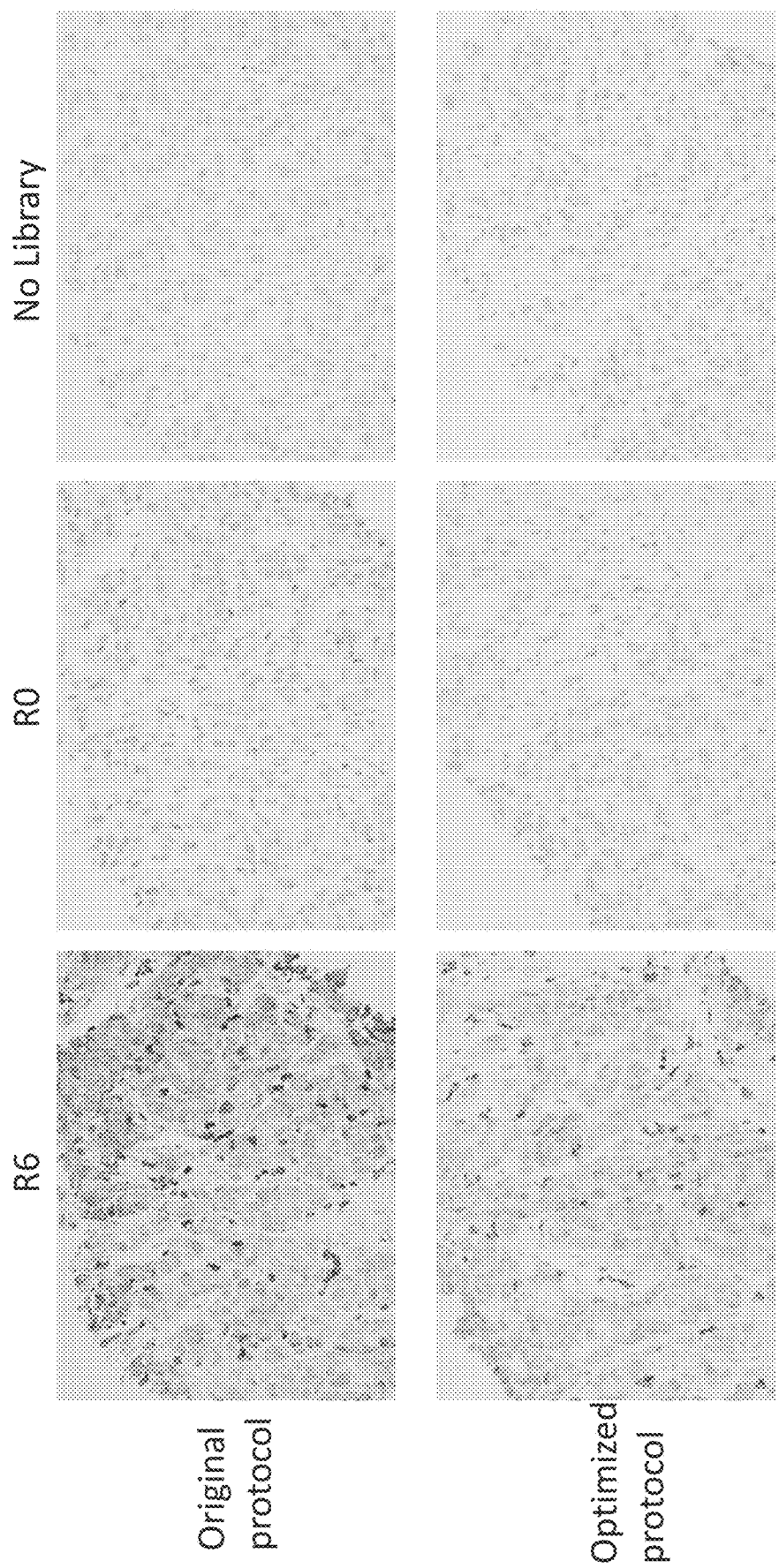
Figure 19K:
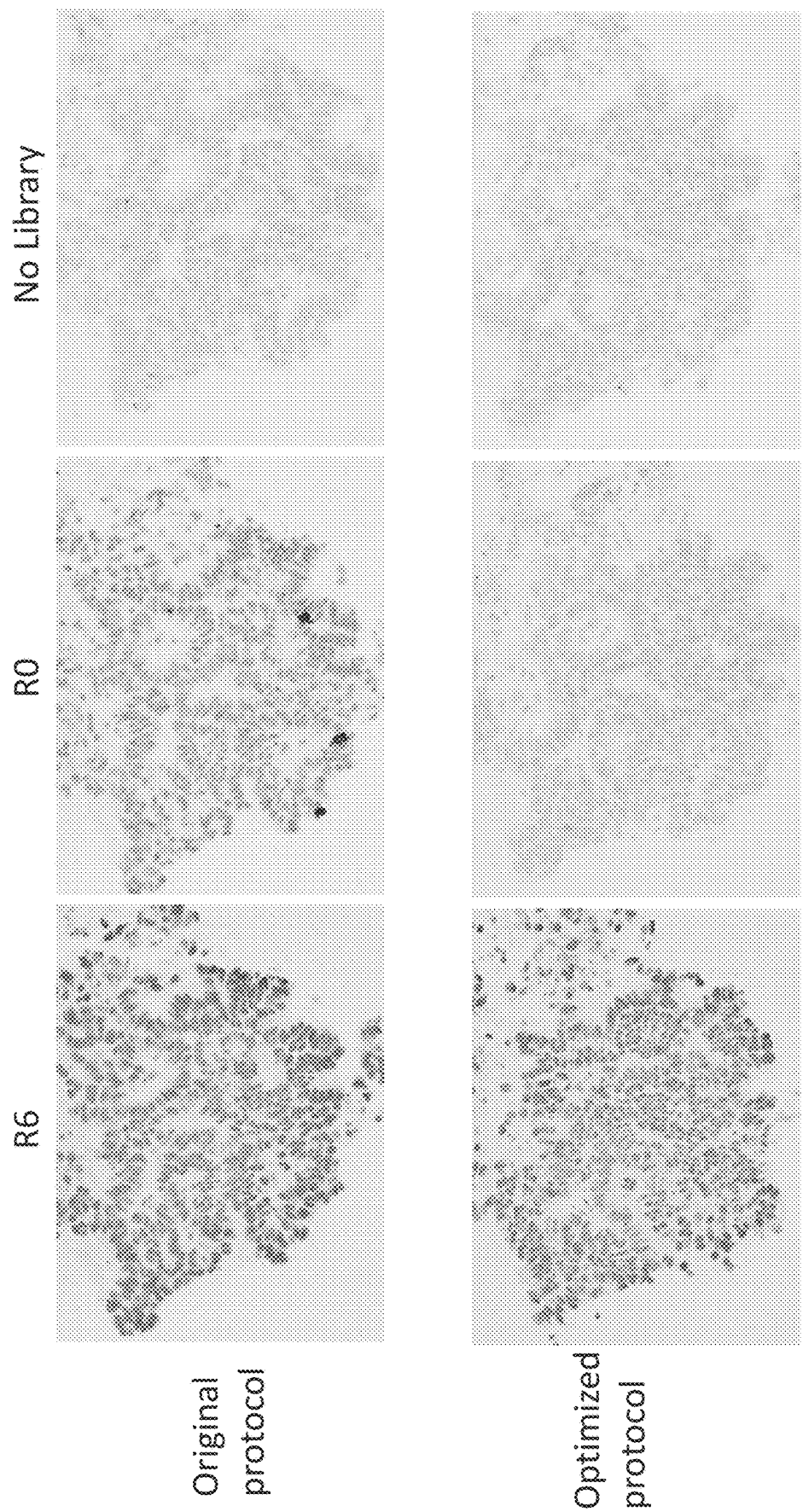

The protocol above was used to stain fixed tissues from various anatomical locales, including tumor samples from ovarian, breast, pancreatic, bladder, melanoma, head & neck, kidney, non-small cell lung (NSCLC), glioblastoma (GBM), hepatocellular carcinoma (HCC) and colon origin. The oligonucleotide probe library used was the R6 library from HER2+ breast tissue enrichment in Example 19. The unenriched library (R0) was used as a control. Accordingly, the probe library was not optimized for each tissue but nonetheless provided discernible staining in various tissues as shown in FIGS. 19A-K. The figures show H&E stained slides with the original protocol and the optimized protocol presented in this Example FIG. 19A shows results for ovarian cancer samples. The darkest staining of all samples was observed with the original protocol, though discernible brown stain was observed in the No Library sample that was absent any oligonucleotide probes. With the optimized library, staining was most evident with R6 and no brown staining was observed in the No Library sample. Without being bound by theory, the staining observed in the absence of probe library with the original protocol may be derived from non-specific binding of the SA-HRP, or in some cases due to endogenous biotin. Qualitatively similar results were observed with breast cancer tissue (FIG. 19B), pancreatic cancer tissue (FIG. 19C), bladder cancer tissue (FIG. 19D), melanoma tissue (FIG. 19E), head and neck cancer tissue (FIG. 19F), kidney cancer cancer tissue (FIG. 19G), NSCLC tissue (FIG. 19H), GBM tissue (FIG. 19I), HCC tissue (FIG. 19J), and colon cancer tissue (FIG. 19K). With melanoma and GBM tissues, slight staining was observed in the optimized no library samples, but this staining was nonetheless noticeably reduced as compared to the original no library samples. With the NCSLC and colon tissues, little staining was observed in the no library samples under either set of conditions.

Example 26

Oligonucleotide Probe Enrichment on TUBB3+ Pancreatic Cancer Tissue

In this Example, we used the FFPE tissue enrichment protocol developed in the Examples above (see, e.g., Examples 21-22 and 25) to enrich a naïve oligonucleotide probe library against TUBB3+ pancreatic cancer tissue samples.

Figure 20B:
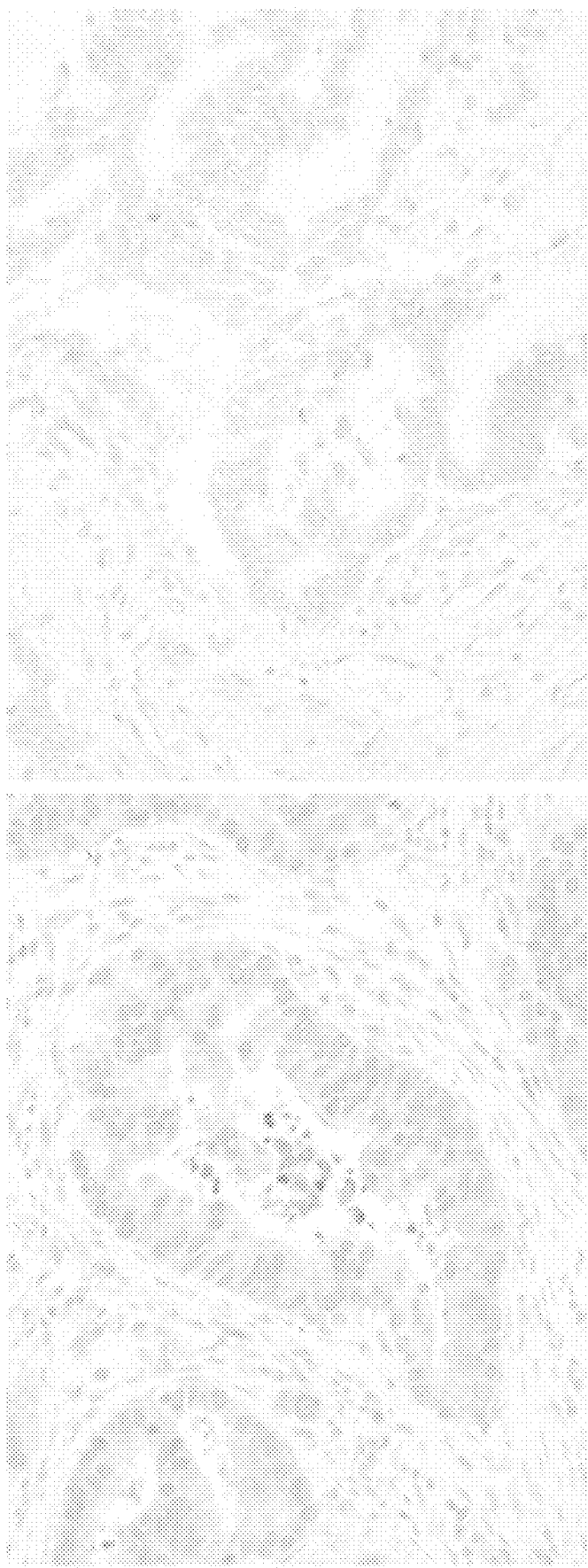

The random ssDNA library (naïve F-TRin-35n-B 8-3s library) contains 35 random nucleotides flanked by constant regions. Specifically, the naïve library comprises a 5' region (5' CTAGCATGACTGCAGTACGT (SEQ ID NO. 4)) followed by a random naïve oligonucleotide sequence of 35 nucleotides and a 3' region (5' CTGTCTCTTATACA-CATCTGACGCTGCCGACGA (SEQ ID NO. 5)). The samples were pancreatic FFPE tissue samples with TUBB3 status confirmed by conventional IHC. Seven rounds of enrichment were performed. We initially performed enrichment with the full protocol from Example 25 but no enrichment was observed. Without being bound by theory, it is likely the optimized protocol in Example 25 is too stringent as it was optimized for probing and not enrichment. Thus, the optimized protocol was adapted for the enrichment process as shown in FIG. 20A. In this scheme, enrichment was performed according to the order P→P→P→(N→P)→(N→P)→(N→P)→P, where "P" ("Pos" in FIG. 20A) refers to positive selection against TUBB3+ samples and "N" ("Neg" in FIG. 20A) refers to negative selection against TUBB3− samples. The enrichment was performed with low stringency in early rounds using the conditions as shown in FIG. 20A. For example, the figure shows that the concentration of detergent (Triton X100) and blocking agents (BlockAid) were increased in later rounds of enrichment. Further as indicated in the figure, staining as described in Example 25 was performed after later rounds of enrichment to observe the enrichment process. An example in shown in FIG. 20B, where much higher levels of brown stain are observed in the Positive sample as compared to the Negative sample.

Figure 20C:
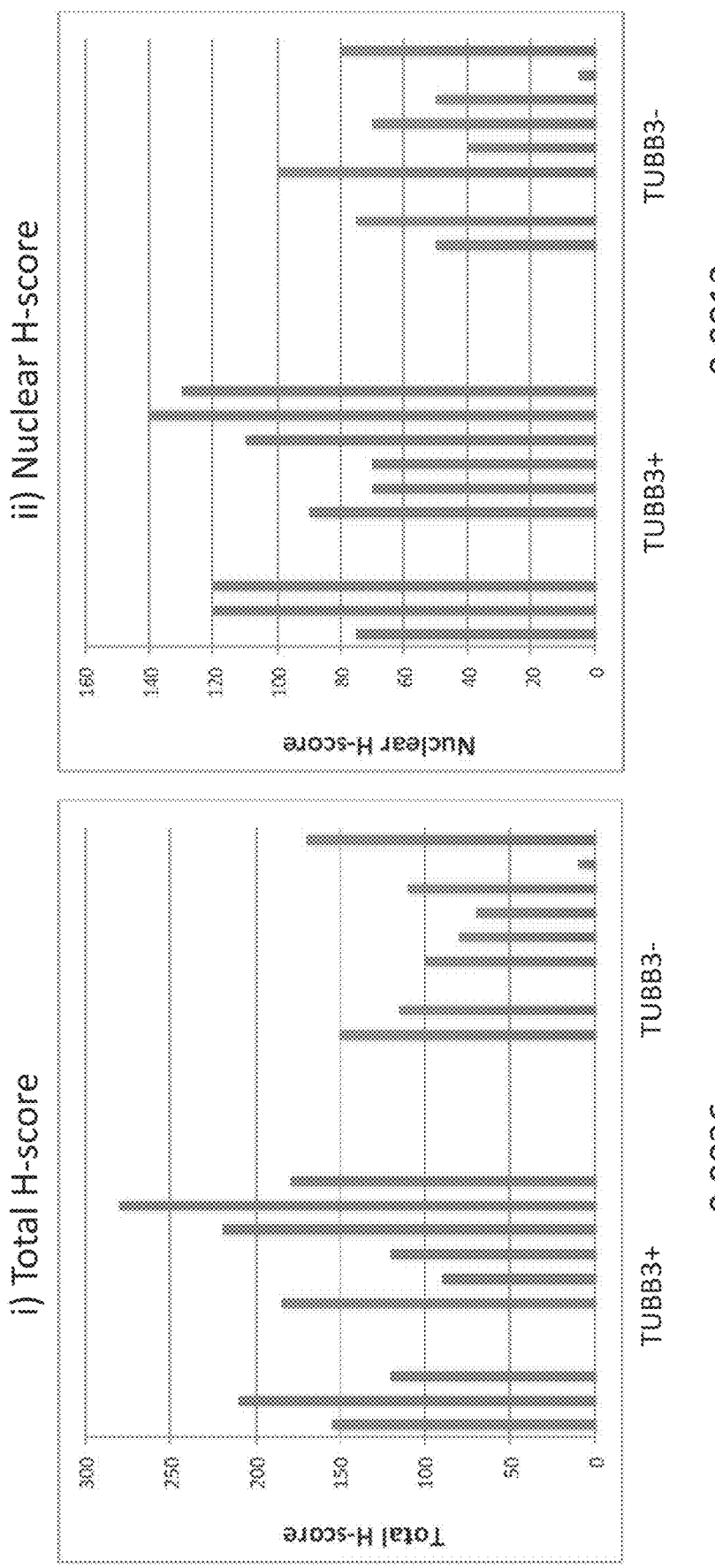

The final enriched library after seven rounds of enrichment is referred to as the TUBB3− R7 library. The TUBB3− R7 library was used to probe nine TUBB3+ and nine TUBB3− pancreatic cancer tissue slides that were not used in the enrichment process (i.e., non-enrichment cases) Staining intensity was determined by blinded pathologists. H-Scores (i.e., [1×(% cells 1+)+2×(% cells 2+)+3×(% cells 3+)]) were calculated based on the staining intensity for both overall slide staining and nuclear staining Results are shown in FIG. 20C, which plots total (i) or nuclear (ii) H-score for the indicated groups of samples (i.e., TUBB3+ or TUBB3−). The p-values for the differences between the groups are indicated beneath each plot. The H-Scores were also used to generate ROC plots and calculate ROC AUC values, as shown in FIG. 20D. This figure provides plots for total (i) or nuclear (ii) ROC curves. The AUC value for total (i) was 0.843 and the AUC value for nuclear (ii) was 0.889. Thus, in both cases the TUBB3−R7 library had very high performance at differentiating TUBB3+ and TUBB3− pancreatic cancer tissue specimens.

In Example 19, we presented an oligonucleotide probe library that was able to distinguish HER2+ and HER2− breast cancer samples. Similarly, in this Example, we developed an oligonucleotide probe library that was able to distinguish TUBB3+ and TUBB3− pancreatic cancer samples.

Example 27

TTNT for Platinum/Taxane Treatment in Ovarian Cancer

In this Example, we used the FFPE tissue enrichment protocol as in Example 26 to enrich a naïve oligonucleotide probe library against ovarian cancer tissue samples that were considered as responders or non-responders to platinum/taxane treatment. Responder (benefit)/non-responder (non-benefit) status was determined using time-to-next-treatment (TTNT) after platinum/taxane treatment, also known as drug free interval (DFI), as described in Examples 20-22. For this Example, non-responders were those with DFI<6 months and responders were those with DFI>6 months.

Figure 21B:
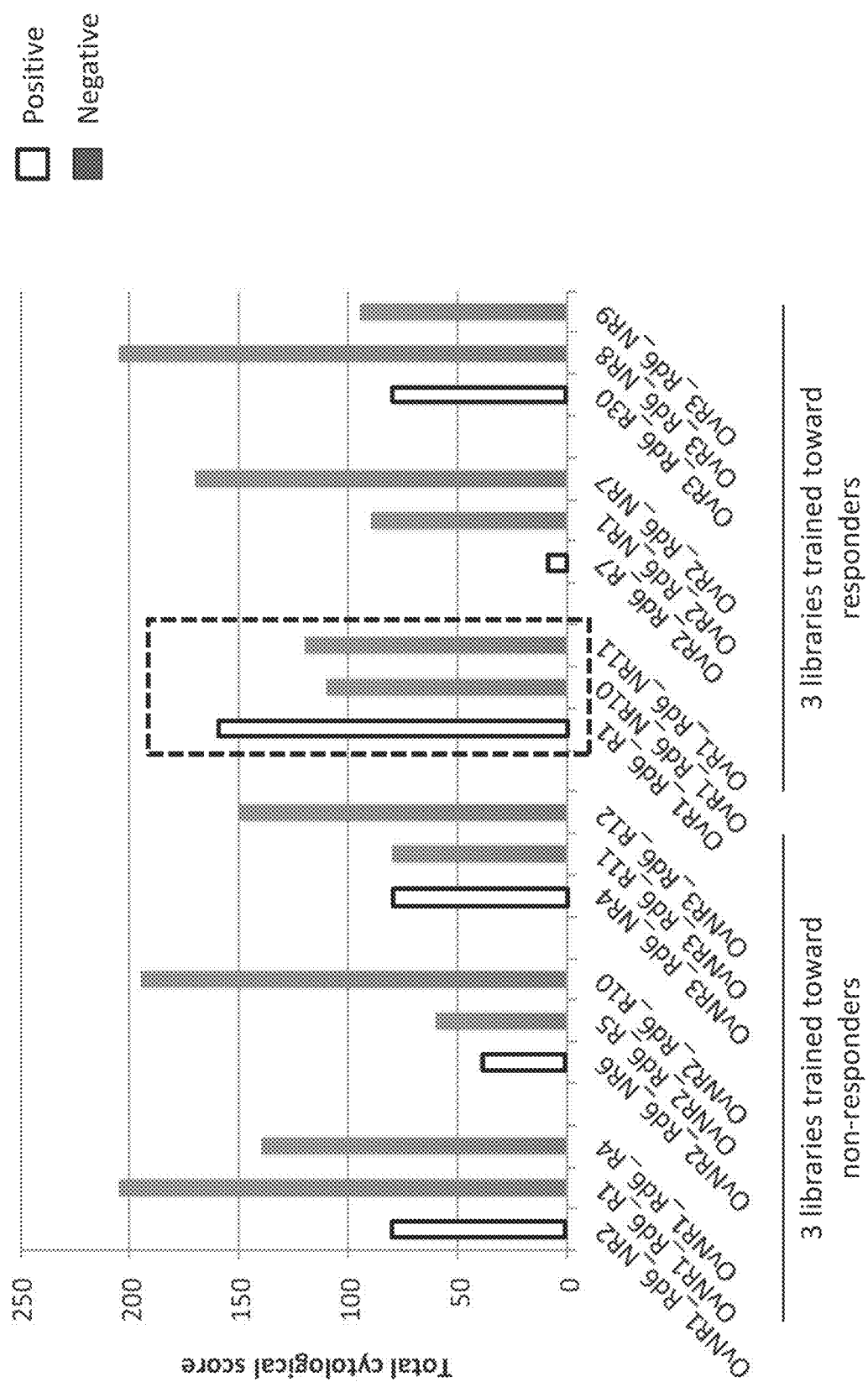

Methodology was similar to that in Example 26 with modifications described here. The enrichment process is outlined in FIG. 21A. Enrichment was performed according to the order P→P→P→(2N*→P)→(2N*→P)→(2N*→P, where "P" ("Pos" in FIG. 21A) refers to positive selection against responder tissue samples, "N" ("Neg" in FIG. 21A) refers to negative selection against non-responder tissue samples, and * indicates that two negative slides were used in parallel, the supernatants were pooled and the probes were purified with Streptavidin beads before PCR. The reverse process was also performed, wherein positive selection was against non-responder tissue samples and negative selection was against responder tissue samples. As in Example 26, more stringent conditions were used in later rounds of enrichment. See FIG. 21A for enrichment conditions. FIG. 21B shows examples of staining with six enriched libraries, three libraries trained toward non-responders and three trained toward responders, as indicated. The library in FIG. 21B showed the expected staining pattern with greater staining in the positive enrichment cases (here responders). This library will be used to probe non-enrichment ovarian cancer samples that benefit/respond or not from platinum/taxane treatment as described above.

Example 28

Detection of Oligonucleotide Probe Binding to Tissue Samples

Protocols similar to the Examples above were used to enrich the naïve F-TRin-35n-B 8-3s library against FFPE kidney tissue slides. The biotinylated library after 6 rounds of enrichment was used to probe fixed kidney tissue similar to Example 25. Slides were also probed with biotinylated unenriched F-TRin-35n-B 8-3s library as a control. The oligonucleotide probe binding was visualized as above using Streptavidin-horse radish peroxidase (SA-HRP) (Life Technologies, cat #11207733910). Despite stringent probing conditions, notable levels of background staining seen with the unenriched library control. In this Example, we used an alternative staining protocol to visualize oligonucleotide probe binding to the kidney samples.

Without being bound by theory, we examined whether non-specific binding of SA-HRP to the samples could be responsible and developed an alternate visualization methodology. Biotin-avidin/streptavidin biological assays have many desirable characteristics such as well known methods and reagents, do not require antibodies due to the strong and specific biotin-avidin binding, and streptavidin beads are available for pull down experiments/immunoprecipitation. However, in some cases endogenous biotin in the tissue could lead to problematic background binding. In this Example, we tested a digoxigenin (DIG) modified oligonucleotide library with anti-DIG-HRP antibody detection. Unlike biotin, digoxigenin is a steroid found exclusively in the flowers and leaves of certain plants.

Figure 22A:
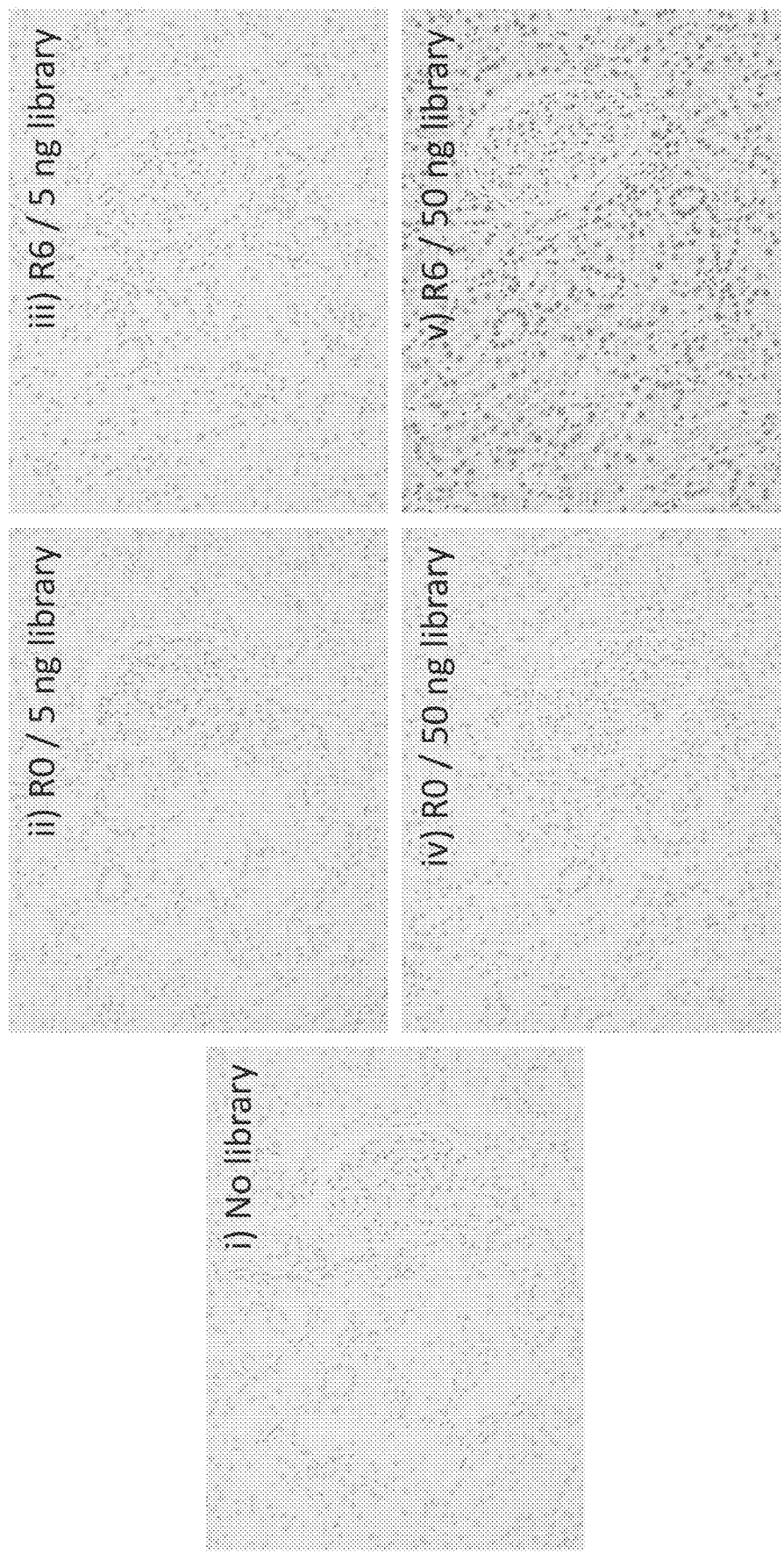

FIG. 22A show staining of kidney FFPE slides using the indicated DIG modified oligonucleotide libraries and anti-DIG-HRP antibody detection. FIG. 22Ai shows a no-library control, FIG. 22Aii shows staining with 5 ng of the unenriched (R0) library, FIG. 22Aiii shows staining with 5 ng of the round (R6) library, FIG. 22Aiv shows staining with 50 ng of the unenriched (R0) library, and FIG. 22Av shows staining with 50 ng of the round 6 (R6) library. All images were taken at a 20× magnification. In the figures, no brown staining was observed with no-library control (FIG. 22Ai) and 5 ng R0 samples (FIG. 22Aii). Only slight staining was observed with the 50 ng R0 samples (FIG. 22Aiv). More staining was observed with the 5 ng R6 samples (FIG. 22Aiii), and strong stain was observed when using 50 ng of the R6 library (FIG. 22Av). These data indicate that the DIG modified oligonucleotide libraries were effective at eliminating background staining observed with the biotin modified oligonucleotide libraries in the fixed kidney tissue samples used in this study.

We also examined whether the incubation times during enrichment would influence the enrichment process. Four different enrichments were performed against kidney tissue wherein the library incubation time during enrichment was varied at 30 min, 1 h, 2 h, and 3 h. We then performed anti-DIG staining with 50 ng of libraries from six rounds of enrichment under each of the incubation conditions. We found that incubation time correlated with staining intensity: the longer the incubation time the stronger the staining See FIG. 22B, which shows slides from six rounds of enrichment with incubation times of 30 min (FIG. 22Bi), 1 h (FIG. 22Bii), 2 h (FIG. 22Biii), and 3 h (FIG. 22Biv).

Example 29

On-Slide Oligonucleotide Probe Enrichment Against FFPE Tissue Lysate

In certain instances, such as in the experiments described above in Examples 19-28, paraffin blocks comprising tumor samples, or multiple slides comprising sections from such blocks are available. In such cases, multiple slides from a single sample, including without limitation multiple sections from a tumor, can be used for oligonucleotide probe library enrichment and/or probing. In this Example, we developed a method for on-slide oligonucleotide probe enrichment against FFPE tissue lysate. Lysates from FFPE tissue slides were arrayed onto nitrocellulose film slides for enrichment and analysis. Such alternate methods may prove beneficial in certain cases, e.g., where limited samples are available, such as a single FFPE tissue slide per patient or tumor sample.

Figure 23A:
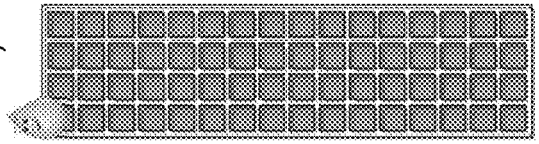

Methodology 2300 is outlined in FIG. 23A. As shown, 1 µL of 2.5 µg/µl FFPE lysate is arrayed onto nitrocellulose film slides (AVID Film Slide+64-well ProPlate; Grace Bio-Labs, Bend, Oreg.) 2301. The slides are air dried overnight (O/N) at 4° C. 2302. The slides are washed six times in wash buffer comprising 50 µl of 1×PBS, 3 mM MgCl$_2$ 2303. The naïve F-Trin library as described herein is added in various concentrations (0.1/0.5/2.5 ng) to certain wells in 20 µl with blocking buffer comprising 1×PBS (pH 7.4), 3 mM MgCl$_2$, 1% HSA, 0.5% F127, 8 ng/µl Salmon Sperm DNA and 8 ng/µl Yeast tRNA 2304. The library is incubated on the film slides for 1 hour at room temperature (RT) with shaking at 100 rpm. After incubation, the film slides are washed five times with wash buffer 2305. The wells of the film slides are scraped with a pipet tip and transferred to 30 µl H$_2$O 2306. Oligonucleotides recovered in the scraping are amplified by asymmetric PCR as described herein and single stranded oligonucleotide probes (ssDNA) are purified 2307. For the desired number of rounds of enrichment, 0.1/0.5/2.5 ng of the previous round's enriched library in blocking solution is added to fresh film slides 2308. After incubation, the oligonucleotide probes that bound to the sample are recovered and amplified as in round 1 2309. The recovered library was sequenced using next-generation sequencing 2310 after round 3.

The above procedure was performed on film slides arrayed with lysates from FFPE tissue slides from human subjects with various anatomical origins, including breast, colon, kidney, lung and pancreas. After three rounds of enrichment, the "Rd3" libraries were sequenced as described above 2310. In all cases, the largest number of sequences was observed in the samples incubated with 0.1 ng of oligonucleotide library.

Three more rounds of enrichment were performed as above with breast & pancreas FFPE lysates. In one set of enrichments, the methodology 2300 was as above. The library resulting from six rounds of positive selection on lysate from breast tissue is referred to as the Br_Rd6_Lib. In a next set of enrichments, the methodology 2300 was as above with addition of a competitor tissue lysate during incubation 2304. For this step in rounds 4-6, we added 0.1/0.5/2.5 ng of the 0.1 ng Rd3 library from a different tissue's enrichment in 80 µl of blocking buffer. For example, the Rd3 library from the breast lysate enrichments was incubated with breast and pancreatic lysates at the same time. The sequences bound to the breast lysate were retained, while sequences bound to pancreatic lysate were discarded. The library resulting from six rounds of positive selection on lysate from breast tissue wherein the last three rounds of enrichment included competition with lysates from pancreas tissue is referred to as the Br_Rd6+_Lib.

Figure 23B:
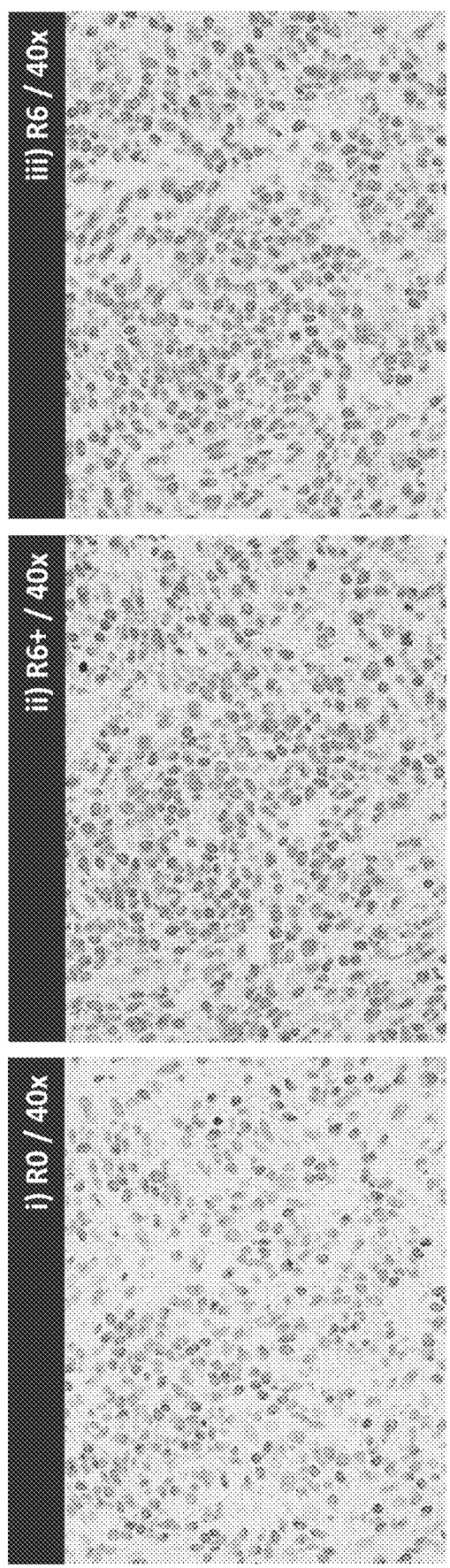

After enrichment, we used the Br_Rd6_Lib and Br_Rd6+_Lib as well as starting naïve F-TRin library (i.e., Rd0) to stain normal breast, colon, kidney and lung tissue slides. Slides were stained generally as described in Example 40 above using a SA-HRP system using 50 ng of library per slide. We observed higher level of staining when probing breast tissue with the Br_Rd6_Lib and Br_Rd6+_Lib oligonucleotide probe libraries than with the Rd0 naïve control. Representative results are shown in FIG. 23B. Some background staining was observed in the Rd0 slides (FIG. 23Bi) but much higher levels of staining with the Br_Rd6+_Lib (FIG. 23Bii) and Br_Rd6_Lib slides (FIG. 23Biii).

The above results demonstrated oligonucleotide probe library enrichment with selection on FFPE tissue lysate bound to film slides. We further showed that the enriched aptamers can stain FFPE tissue slides. See, e.g., FIG. 23B. This approach has utility if the amount of working material is limited and has the ability to perform competitive selection using the same library against multiple targets.

We next selected certain high abundance and high fold-change oligonucleotide aptamers from the Rd6_Lib and Br_Rd6+_Lib oligonucleotide probe libraries for use in on-slide staining of normal breast tissue. As controls for the staining experiments, we used oligonucleotides with complement sequences in the variable regions. The selected sequences were synthesized with 5'-biotin. Each group of sequences was pooled at a final concentration of 10 ng/µL. For example, eight probes with high abundance sequences selected from the Br_Rd6_Lib and Br_Rd6+_Lib library were combined in a single tube and the eight corresponding reverse complement oligonucleotides were pooled in a separate tube. We applied 25 ng, 50 ng or 100 ng of each oligonucleotide pools to the tissue slides for staining Normal breast tissue slides from the same block as those used for lysate preparation were used for staining Slides were pretreated for 10 minutes in 0.1% Triton X-100 and rinsed in distilled $H_2O$. Epitope retrieval was performed at 96° C. for 45 minutes. The staining protocol is as described in this Example above using a streptavidin-HRP system. The selected sequences are shown in Table 45. The table indicates the variable region of the identified sequences. The full length sequences comprised 5' region 5'-CTAG-CATGACTGCAGTACGT (SEQ ID NO 4) and a 3' region 5'-CTGTCTCTTATACACATCTGACGCTGCCGACGA (SEQ ID NO 5) surrounding the variable region.

TABLE 45

Sequences Selected for Staining

| Criteria | Variable Sequence (5'->3') | SEQ ID NO |
|---|---|---|
| High Abundance (Br_Rd6_Lib and Br_Rd6+_Lib) | GGGGGCCCCTTTTGTTTTCTTTTTGTTATTTTTGC | 206491 |
| | GGCTTCCTGGGGGTTTTTGTAATTGTATTTTCTGTTGA | 206492 |
| | ACCCTTTAGGTGTTTTTTTTGGTTTTCATTTTTTA | 206493 |
| | TTCGCCGTTTTTGTTTTGTTGTCTTAGGTTACCTC | 206494 |
| High Abundance (Br_Rd6_Lib) | TGCTGGGTGGTTTGTTTTTTTATTTGGTGCATTCT | 206495 |
| | GCCGTGATTCATTTGAGGGTTCCTTGTTTGATTTTA | 206496 |
| | TTAGGTATGCCACGTGCCTAATTGGGGTTTTTGTTTGA | 206497 |
| | TGTCATCTCACCTAACCACACAACCTACTACCTCA | 206498 |
| High Fold-Difference (Br_Rd6_Lib and Br_Rd6+_Lib) | TTCAATCTACACTGGTATTTCGCCTCCTCGCTGGGTGA | 206499 |
| | GGTCCTCCGGCGCATATTCCTTACCGTAAATTATA | 206500 |
| | TTGTTTCCAACTCTTGAATTTCTTGGTACTTGTCCA | 206501 |
| | TGGACTCTCTCCTCTGCCTCTGTGATAGCGGTTTTTGA | 206502 |
| High Fold-Difference (Br_Rd6_Lib) | CTTGAATTCCCATGTCTCTCCTGCCCCCCTCACTA | 206503 |
| | TTCTGAGGCTCACCACTTTGCACAAACTTTTCACCGA | 206504 |
| | GGGTTTATTCTGCTTATCCTTTCGTTTTCTTGTTGA | 206505 |
| | ATGCCACCACTGATCGCTAAGTTACCCCAACTGTTTGA | 206506 |

We observed greater staining the higher the input of probes. Thus, probing with 100 ng of the oligonucleotide probes yielded the highest level staining, albeit with the highest levels of background staining Representative results are shown in FIG. 23C and FIG. 23D (both are 20× magnifications). FIG. 23C shows results for probing with 100 ng pools of eight sequences selected by abundance (i.e., first eight sequences in Table 45), which shows the most staining intensity. FIG. 23D shows results for probing with 25 ng pools of eight sequences selected by high fold change (i.e., last eight sequences in Table 45), which shows lower staining intensity but also reduced background with the negative controls. In both figures, the left most panel (i) shows slides stained with these oligonucleotides wherein the right panel (ii) shows the staining with their reverse complements.

Example 30

Oligonucleotide Probe Enrichment on Scraped Tissue

As another alternate enrichment scheme, in this Example we performed oligonucleotide probe library enrichment in an Eppendorf tube on tissue scraped from an FFPE slide. As in Example 29, this approach may be beneficial in certain scenarios, including without limitation when limited tissue is available, such as a single FFPE slide.

We started with the naïve F-Trin library described herein. Positive selection was performed on colon cancer tissue samples with negative selection on non-cancer tissue from the same slide. Regions of cancer and non-cancer tissue were determined by a pathologist. Selected regions were scraped from the slide then placed in an Eppendorf tube. Three rounds of enrichment were performed with positive selection against cancer tissue. Five more rounds of enrichment were performed with positive selection against cancer tissue and negative selection on non-cancer tissue. In these experiments, separation of unbound library was performed by ultracentrifugation. For example, positive selection was performed by incubating the oligonucleotide probes with tumor tissue, and collecting oligonucleotides that co-precipitated with the tissue during ultracentrifugation. Similarly, negative selection was performed by incubating the oligonucleotide probes with non-cancer tissue, then collecting the supernatant after ultracentrifugation.

We used the library enriched after eight rounds (the "R8" library) to stain fixed tissue from four colon cancer cases used in the enrichment process. We used the unenriched library ("R0") as control Staining was performed with the Ventana Discovery system as in Example 25 using 50 ng of library per slide with an SA-HRP system. We compared staining intensity on cancer and non-cancer regions from a single slide. See FIG. 24A. The figure shows staining with the R0 control library on cancer tissue (i), the R8 enriched library on cancer tissue (ii), the R0 control library on non-cancer tissue (iii), and the R8 enriched library on non-cancer tissue (iv). As shown in the figure, the strongest staining was observed on cancer tissue with enriched (round 8) library Minimal staining was observed on non-cancer tissue with enriched (round 8) library. Finally, no staining was observed on any tissue with the unenriched (round 0) library. These results indicate the enrichment process was effective to generate an oligonucleotide probe library that can distinguish colon cancer tissue.

Figure 24B:
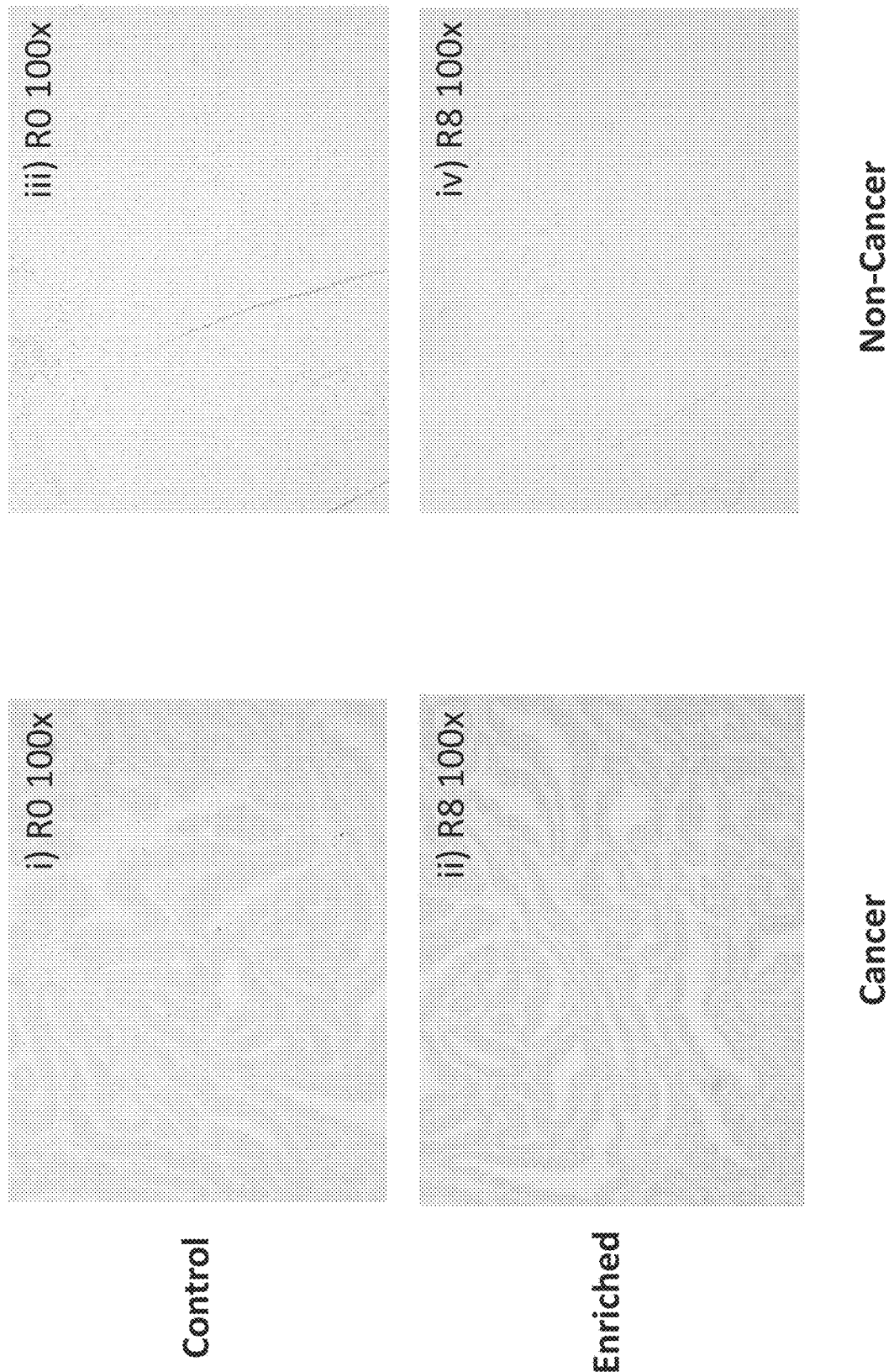

We also used the R8 library to stain fixed tissue from four colon cancer cases that were not used in the enrichment process. Representative results are shown in FIG. 24B. The figure shows staining with the R0 control library on cancer tissue (i), the R8 enriched library on cancer tissue (ii), the R0 control library on non-cancer tissue (iii), and the R8 enriched library on non-cancer tissue (iv). As shown in the figure, the strongest staining was observed on cancer tissue with enriched (round 8) library. For three cases we observed no staining on non-cancer tissue with the enriched (round 8) library, whereas one case showed slight staining. In addition, we observed no staining on any tissue with unenriched (round 0) library, whereas the same case that showed slight staining with the R8 library on non-cancer tissue also showed slight staining with the R0 library as well. These results indicate that the enriched oligonucleotide probe library can distinguish colon cancer tissue with high accuracy as we observed no false negatives and one potential false positive with this sample set.

Example 31

Oligonucleotide Probe Enrichment Using Microdissection

Laser capture microdissection (LCM), also called microdissection, laser microdissection (LMD), or laser-assisted microdissection (LMD or LAM), is a method for isolating specific cells of interest from microscopic regions of tissue/cells/organisms. In this Example, we used LCM as a method to extract tissue for oligonucleotide probe enrichment as described herein. The method comprises dissection on a microscopic scale with the help of a laser. LCM technology can harvest the cells of interest directly or can isolate specific cells by cutting away unwanted cells to give histologically pure enriched cell populations. A laser is coupled into a microscope and focuses onto the tissue on the slide. By movement of the laser an element is cut out and separated from the adjacent tissue.

An extraction process follows the cutting process. In one such method, a sticky surface is pressed onto the sample, which is then torn out. This extracts the desired region, but can also remove particles or unwanted tissue on the surface. In another method, a plastic membrane is melted onto the sample, which is then torn out. The membrane is heated with a laser to melt it to the sample. This method may also extract undesired debris. Extraction can also occur without contact. In one such approach, the sample is transported by laser pressure and gravity (gravity-assisted microdissection). In another approach, a cap coated with an adhesive is positioned directly on the thinly cut tissue section, the section itself resting on a thin membrane (e.g., polyethylene naphtalene). A laser gently heats the adhesive on the cap fusing it to the underlying tissue and another laser cuts through tissue and underlying membrane. The membrane-tissue entity now adheres to the cap and the cells on the cap can be used in downstream applications (DNA, RNA, protein analysis).

FFPE samples are commonly fixed to glass slides. We found that not all LCM methods are appropriate for oligonucleotide probe enrichment with such samples. For example, LCM after epitope retrieval but before addition of the oligonucleotide probe library is problematic because the sample should not be dehydrated after epitope retrieval. LCM before epitope retrieval can be problematic with heat induced epitope retrieval if the transfer film doesn't hold up during the standard heat epitope retrieval. For example, we tested sample extraction using the CapSure® Macro LCM Caps and the ArcturusXT Microdissection System from ThermoFisher Scientific (Waltham, Mass.) and found that standard heated epitope retrieval conditions (95° C.) may either melt or destroy the capture film.

Figure 25B:
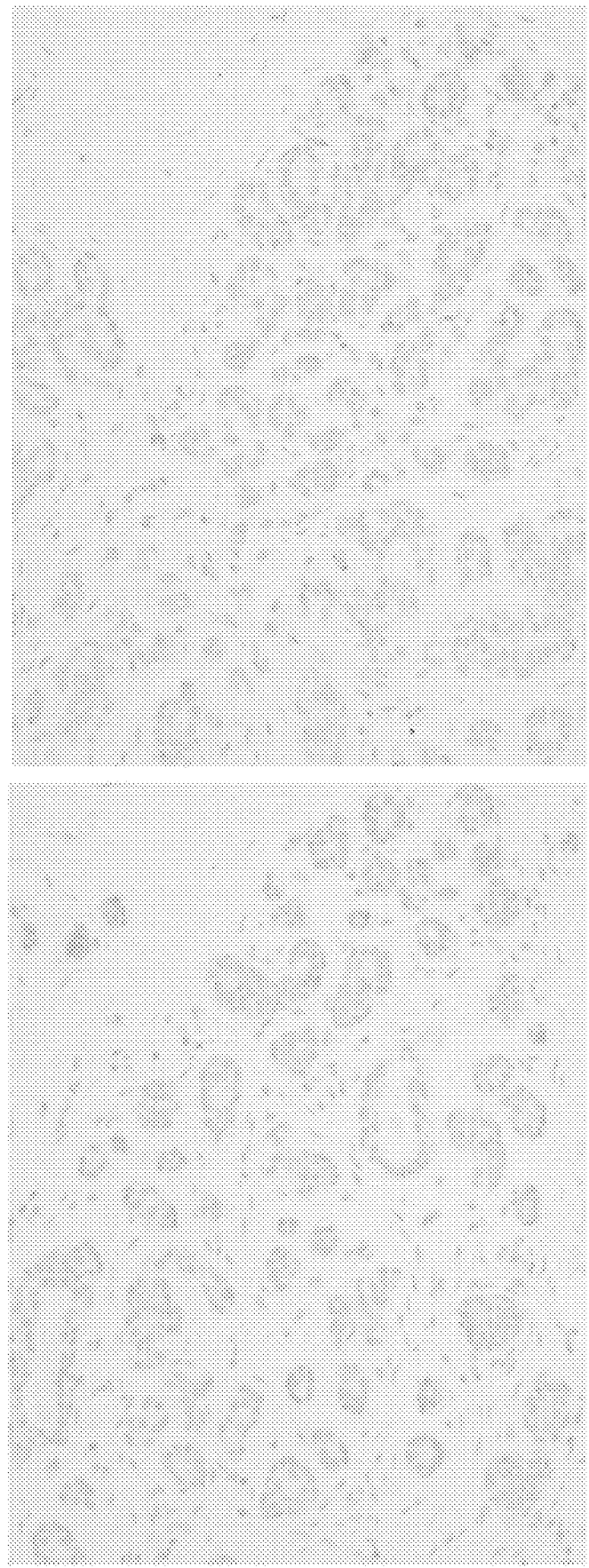

To address such issues, we performed four rounds of enrichment starting with the naïve F-Trin library described herein on breast tissue attached to LCM SureCaps with epitope retrieval at 75° C. We used the resulting R4 oligonucleotide probe library to stain fixed breast tissue using the Dako platform as in Example 19, with epitope retrieval at 75° C. or 97° C. with between one and three wash steps after addition of library. With epitope retrieval at 75° C. and one wash step (i.e., least stringent wash conditions), no staining was observed. Epitope retrieval at 97° C. and one wash step produced the strongest staining with the enriched library (R4). Under these conditions, we obtained slightly less staining with R0 library and minimal background with a no DNA control. Conditions including epitope retrieval at 97° C. and stringent three wash steps resulted in the strongest staining with enriched library (R4) and slightly less staining with the R0 library Minimal background was found the no DNA control but clearly less than with one wash step. We then tested both the Dako and Ventana IHC systems for staining of fixed breast tissue. See Examples 19 and 25, respectively. We performed library inputs titers (Dako: 50 ng, 25 ng and 12 ng; Ventana: 50 ng and 25 ng) in combination with a stringent staining protocol, comprising 25% BlockAid in library, 19% BlockAid in SA-HRP, 0.01% Triton X-100 and four washes after addition of library. When using the Dako system, we observed stronger staining with the R4 library than the unenriched R0 library with all library inputs (i.e., 50 ng, 25 ng and 12 ng). Representative results are shown in FIG. 25A, which shows the samples stained with 50 ng of the R4 library (FIG. 25Ai) or R0 control (FIG. 25Aii). When using the Ventana system, we also observed stronger staining with the R4 library than the unenriched R0 library with both library inputs (i.e., 50 ng and 25 ng). Representative results are shown in FIG. 25B, which shows the samples stained with 25 ng of the R4 library (FIG. 25Bi) or R0 control (FIG. 25Bii). Under these conditions, background staining was minimal with the R0 control.

These results demonstrate enrichment of an oligonucleotide probe library using microdissected FFPE tissue samples. As with Example 30, this approach may provide more pure samples, e.g., by dissecting purely cancer cells for analysis. As with Examples 30-31, approach may also prove beneficial under some conditions such as when limited sample is available. And as in Example 30, cancer and non-cancer samples can be extracted from a single slide.

Although preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11332748B2). An electronic copy of the "Sequence Listing" will also be available from the USPTO upon request and payment of the fee set forth in 37 CFR 1.19(b)(3).

What is claimed is:

1. A method of enriching an oligonucleotide library comprising a plurality of oligonucleotides, the method comprising:
   (a) performing at least one round of positive selection, wherein the positive selection comprises:
   (i) contacting at least one sample with the plurality of oligonucleotides, wherein the at least one sample comprises tissue; and
   (ii) recovering members of the plurality of oligonucleotides that associated with the at least one sample;
   (b) performing at least one round of negative selection, wherein the negative selection comprises:
   (i) contacting at least one additional sample with the plurality of oligonucleotides, wherein at least one additional sample comprises tissue;
   (ii) recovering members of the plurality of oligonucleotides that did not associate with the at least one additional sample; and
   (c) amplifying the members of the plurality of oligonucleotides recovered in at least one or step (a)(ii) and step (b)(ii),
   wherein the tissue in the at least one sample in step a(i) and/or the tissue in the at least one additional sample in step b(i) is lysed, or scraped from a substrate thereby enriching the oligonucleotide library.

2. The method of claim 1, wherein the recovered members of the plurality of oligonucleotides in step (a)(ii) are used as the input for the next iteration of step (a)(i).

3. The method of claim 1, wherein the recovered members of the plurality of oligonucleotides in step (b)(ii) are used as the input for the next iteration of step (a)(i).

4. The method of claim 1, wherein the unenriched oligonucleotide library comprises a plurality of oligonucleotide aptamers, wherein each aptamer sequence comprises a 5' region (5' CTAGCATGACTGCAGTACGT (SEQ ID NO. 4)) followed by a random naïve aptamer sequence of 35 nucleotides and a 3' region (5' CTGTCTCTTATACACATCTGACGCTGCCGACGA (SEQ ID NO. 5)).

5. The method of claim 1, wherein the at least one sample and/or at least one additional sample comprise fixed tissue.

6. The method of claim 5, wherein the fixed tissue comprises formalin fixed paraffin embedded (FFPE) tissue.

7. The method of claim 6, wherein the FFPE tissue comprises at least one of a fixed tissue, unstained slide, bone marrow core or clot, biopsy sample, surgical sample, core needle biopsy, malignant fluid, and fine needle aspirate (FNA).

8. The method of claim 7, wherein the FFPE tissue is fixed on a substrate.

9. The method of claim 8, wherein the at least one sample and/or the at least one additional sample are fixed on different substrates.

10. The method of claim 8, wherein the at least one sample and/or the at least one additional sample is fixed on a single substrate.

11. The method of claim 1, wherein the at least one sample and the at least one additional sample differ in a phenotype of interest.

12. The method of claim 11, wherein the at least one sample and the at least one additional sample are from different sections of a same substrate.

13. The method of claim 12, wherein the at least one sample and the at least one additional sample are scraped from the same substrate.

14. The method of claim 11, wherein the phenotype comprises a tissue, anatomical origin, medical condition, disease, disorder, or any combination thereof.

15. The method of claim 14, wherein the tissue comprises muscle, epithelial, connective and nervous tissue, or any combination thereof.

16. The method of claim 11, wherein the phenotype comprises the presence of or likelihood of developing a tumor, neoplasm, or cancer, or characterizing the tumor, neoplasm, or cancer.

17. The method of claim 1, further comprising determining a target of the enriched members of the oligonucleotide library.

18. The method of claim 1, further comprising one or more washing steps.

19. The method of claim 1, further comprising epitope retrieval prior to (a).

* * * * *